US011066480B2

(12) United States Patent
Spriggs et al.

(10) Patent No.: US 11,066,480 B2
(45) Date of Patent: Jul. 20, 2021

(54) ANTI-MUC16 ANTIBODIES AND USES THEREOF

(71) Applicant: MEMORIAL SLOAN KETTERING CANCER CENTER, New York, NY (US)

(72) Inventors: David Spriggs, New York, NY (US); Alberto Fernandez-Tejada, Logrono (ES); Dharmarao Thapi, Bayside Hills, NY (US)

(73) Assignee: MEMORIAL SLOAN KETTERING CANCER CENTER, New York, NY (US)

( * ) Notice: Subject to any disclaimer, the term of this patent is extended or adjusted under 35 U.S.C. 154(b) by 542 days.

(21) Appl. No.: 15/558,694

(22) PCT Filed: Mar. 16, 2016

(86) PCT No.: PCT/US2016/022643
§ 371 (c)(1),
(2) Date: Sep. 15, 2017

(87) PCT Pub. No.: WO2016/149368
PCT Pub. Date: Sep. 22, 2016

(65) Prior Publication Data

US 2018/0112008 A1 Apr. 26, 2018

Related U.S. Application Data

(60) Provisional application No. 62/134,402, filed on Mar. 17, 2015.

(51) Int. Cl.

| | |
|---|---|
| ***A61K 39/395*** | (2006.01) |
| ***C07K 16/30*** | (2006.01) |
| ***C07K 14/47*** | (2006.01) |
| ***A01K 67/027*** | (2006.01) |
| ***A61K 39/00*** | (2006.01) |
| ***A61P 35/00*** | (2006.01) |
| ***C07K 16/28*** | (2006.01) |

(52) U.S. Cl.
CPC ...... *C07K 16/3092* (2013.01); *A01K 67/0275* (2013.01); *A61K 39/0011* (2013.01); *A61K 39/00117* (2018.08); *A61P 35/00* (2018.01); *C07K 14/4727* (2013.01); *C07K 16/2809* (2013.01); *A01K 2217/052* (2013.01); *A01K 2217/15* (2013.01); *A01K 2217/203* (2013.01); *A01K 2227/105* (2013.01); *A01K 2267/0331* (2013.01); *C07K 2317/24* (2013.01); *C07K 2317/31* (2013.01); *C07K 2317/33* (2013.01); *C07K 2317/34* (2013.01); *C07K 2317/56* (2013.01); *C07K 2317/565* (2013.01); *C07K 2317/622* (2013.01); *C07K 2317/73* (2013.01); *C07K 2317/76* (2013.01); *C07K 2317/77* (2013.01); *C07K 2317/92* (2013.01); *C12N 2800/30* (2013.01)

(58) Field of Classification Search
None
See application file for complete search history.

(56) References Cited

U.S. PATENT DOCUMENTS

| | | | |
|---|---|---|---|
| 4,816,397 | A | 3/1989 | Boss et al. |
| 4,816,567 | A | 3/1989 | Cabilly et al. |
| 4,946,778 | A | 8/1990 | Ladner et al. |
| 4,975,369 | A | 12/1990 | Beavers et al. |
| 4,978,745 | A | 12/1990 | Schoemaker et al. |
| 5,057,313 | A | 10/1991 | Shih et al. |
| 5,225,539 | A | 7/1993 | Winter |
| 5,475,092 | A | 12/1995 | Chari et al. |
| 5,545,806 | A | 8/1996 | Lonberg et al. |
| 5,569,825 | A | 10/1996 | Lonberg et al. |
| 5,585,499 | A | 12/1996 | Chan et al. |
| 5,625,126 | A | 4/1997 | Lonberg et al. |
| 5,736,137 | A | 4/1998 | Anderson et al. |
| 5,846,545 | A | 12/1998 | Chari et al. |
| 5,976,818 | A | 11/1999 | O'Brien |
| 6,333,410 | B1 | 12/2001 | Chan et al. |
| 6,340,701 | B1 | 1/2002 | Chari et al. |
| 6,372,738 | B2 | 4/2002 | Chari et al. |
| 6,429,295 | B1 | 8/2002 | Carr Perez et al. |
| 7,202,346 | B2 | 4/2007 | Payne et al. |
| 7,227,002 | B1 | 6/2007 | Kufer et al. |
| 7,501,123 | B2 | 3/2009 | Roschke et al. |
| 7,585,952 | B2 | 9/2009 | D'Alessio et al. |
| 7,632,925 | B2 | 12/2009 | Kufer et al. |
| 7,662,387 | B2 | 2/2010 | Law et al. |

(Continued)

FOREIGN PATENT DOCUMENTS

| | | |
|---|---|---|
| JP | 2006/502110 | 1/2006 |
| RU | 2412947 C2 | 2/2011 |

(Continued)

OTHER PUBLICATIONS

Almagro & Fransson, Frontiers in Bioscience 2008; 13:1619-33 (Year: 2008).*
De Genstetal., Dev Comp Immunol 2006; 30:187-98 (Year: 2006).*
Yoshinaga et al., J. Biochem 2008; 143:593-601. (Year: 2006).*
Padlan et al. (PNAS 1989, 86:5938-5942) (Year: 1989).*
Lamminmaki et al. (JBC 2001,276:36687-36694) (Year: 2001).*
Ahmad et al., "Galectin-3 precipitates as a pentamer with synthetic multivalent carbohydrates and forms heterogeneous cross-linked complexes." J Biol Chem 279, 10841-10847 (2004).

(Continued)

*Primary Examiner* — Meera Natarajan
(74) *Attorney, Agent, or Firm* — Foley & Lardner LLP

(57) ABSTRACT

Provided herein are compositions, methods, and uses involving antibodies that immunospecifically bind glycosylated forms of MUC16, a tethered mucin protein. Also provided herein are uses and methods for managing, treating, or preventing disorders, such as cancer.

51 Claims, 67 Drawing Sheets

Figure 1A:
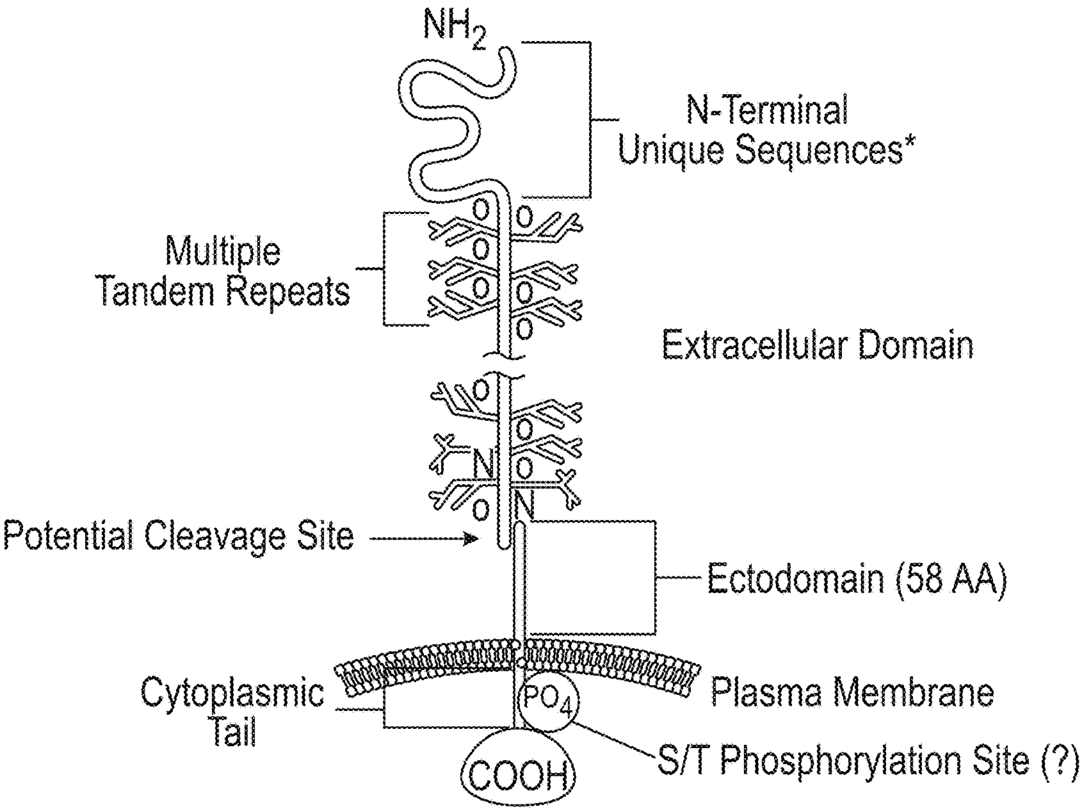

Specification includes a Sequence Listing.

(56) References Cited

U.S. PATENT DOCUMENTS

| | | | |
|---|---|---|---|
| 7,666,425 | B1 | 2/2010 | Bander |
| 7,959,923 | B2 | 6/2011 | You et al. |
| 9,169,328 | B2 | 10/2015 | Spriggs et al. |
| 9,790,283 | B2 | 10/2017 | Spriggs et al. |
| 2004/0057952 | A1 | 3/2004 | Payne et al. |
| 2004/0162413 | A1 | 8/2004 | Watkins et al. |
| 2006/0094069 | A1 | 5/2006 | Robertson et al. |
| 2018/0230231 | A1 | 8/2018 | Spriggs et al. |

FOREIGN PATENT DOCUMENTS

| | | | |
|---|---|---|---|
| WO | WO 1990/013678 | | 11/1990 |
| WO | WO 1992/022653 | | 12/1992 |
| WO | WO 2004/005470 | A2 | 1/2004 |
| WO | WO 2006/034488 | A2 | 3/2006 |
| WO | WO 2008/141044 | | 11/2008 |
| WO | WO 2011/119979 | A1 | 9/2011 |
| WO | WO 2015/006043 | A1 | 1/2015 |
| WO | WO 2016/149368 | A1 | 9/2016 |

OTHER PUBLICATIONS

Badgwell and Bast, "Early detection of ovarian cancer." *Dis Markers,* 23(5-6):397-410 (2007).

Bafna et al., "MUC4, a multifunctional transmembrane glycoprotein, induces oncogenic transformation of NIH3T3 mouse fibroblast cells." *Cancer Res.,* 68(22):9231-9238 (2008).

Barber et al., "Chimeric NKG2D receptor-bearing T cells as immunotherapy for ovarian cancer." *Cancer Res.,* 67(10):5003-5008 (2007).

Barber et al., "Immunotherapy with chimeric NKG2D receptors leads to long-term tumor-free survival and development of host antitumor immunity in murine ovarian cancer." *J Immunol.,* 180(1):72-78 (2008).

Bast et al., "A radioimmunoassay using a monoclonal antibody to monitor the course of epithelial ovarian cancer." *N Eng J Med.,* 309(15):883-887 (1983).

Bast et al., "A radioimmunoassay using a monoclonal antibody to monitor the course of epithelial ovarian cancer." N Engl J Med 309: 883-887 (1983).

Bast et al., "New tumor markers: CA125 and beyond." *Int J Gynecol Cancer,* 15 Suppl 3:274-281 (2005).

Bast et al., "Reactivity of a monoclonal antibody with human ovarian carcinoma." *J Clin Invest.,* 68(5):1331-1337 (1981).

Bellone et al., "Generation of CA125-specific cytotoxic 1' lymphocytes in human leukocyte antigen-A2.1-positive healthy donors and patients with advanced ovarian cancer." *Am J Obstet Gynecol.,* 200(1):75 e71-10 (2009).

Berek, "Immunotherapy of ovarian cancer with antibodies: a focus on oregovomab." *Expert Opin Biol Ther.,* 4(7):1159-1165 (2004).

Berek, "Immunotherapy of ovarian cancer with antibodies: a focus on oregovomab." *Expert Opinion on Biological Therapy,* 4(7):1159-1165 (2004).

Bernsel and Von Heijne, "Improved membrane protein topology prediction by domain assignments." *Protein Sci.,* 14(7):1723-1728 (2005).

Blalock et al., 2007, "Functions of MUC16 in Corneal Epithelial Cells", *Investigative Ophthalmology Visual Science,* vol. 48, No. 10, pp. 4509-4518.

Blalock et al., 2008, "Release of Membrane-Associated Mucins from Ocular Surface Epithelia", *Investigative Ophthalmology & Visual Science,* vol. 49, No. 5, pp. 1564-1871.

Borghouts et al., "Current strategies for the development of peptide-based anti-cancer therapeutics." *J Pept Sci.,* 11(11):713-726 (2005).

Brand et al., 2006, "Prospect for anti-HER2 receptor therapy in breast cancer", *Anticancer Research,* 26:463-70.

Brentjens and Sadelain, "Somatic cell engineering and the immunotherapy of leukemias and lymphomas." *Adv Pharmacol,* 51:347-370 (2004).

Brentjens et al., "Eradication of systemic B-cell tumors by genetically targeted human T lymphocytes co-stimulated by CD80 and interleukin-15." *Nat Med.,* 9(3):279-286 (2003).

Brentjens et al., "Genetically targeted T cells eradicate systemic acute lymphoblastic leukemia xenografts." *Clin Cancer Res.,* 13(18 Pt 1):5426-5435 (2007).

Brentjens, "A Phase I trial for the treatment of chemo-refractory chronic lymphocytic leukemia with CD19-targeted autologous T cells." *Molecular Therapy* 16:S15 (2008).

Burton and Mascola, "Antibody responses to envelope glycoproteins in HIV-1 infection." *Nat Immunol* 16, 571-576 (2015).

Carpenito et al., "Control of large, established tumor xenografts with genetically retargeted human T cells containing CD28 and CD137 domains." *Proc Natl Acad Sci., USA,* 106(9):3360-3365 (2009).

Chang et al., "A novel peptide enhances therapeutic efficacy of liposomal anti-cancer drugs in mice models of human lung cancer." *PLoS One,* 4(1):e4171 (2009).

Cheon et al., "CA125/MUC16 is dispensable for mouse development and reproduction." PLoS One 4: e4675 (2009).

Cole et al., "The EBV-hybridoma technique and its application to human lung cancer." in *Monoclonal Antibodies and Cancer Therapy* (Sell, Ed.), pp. 77-96, Alan R. Liss, Inc. (1985).

Corrales et al. "Conjunctival mucin mRNA expression in contact lens wear." Optom Vis Sci 86: 1051-1058 (2009).

Cote et al., "Generation of human monoclonal antibodies reactive with cellular antigens." *Proc Natl. Acad Sci., USA,* 80(7):2026-2030 (1983).

Curiel et al., "Specific recruitment of regulatory T cells in ovarian carcinoma fosters immune. privilege and predicts reduced survival." *Nat Med.,* 10(9):942-949 (2004).

Daly et al., "Recognition of human colon cancer by T cells transduced with a chimeric receptor gene." *Cancer Gene Ther.,* 7(2):284-291 (2000).

David and Reisfeld, "Protein iodination with solid state lactoperoxidase." *Biochemistry,.* 13(5):1014-1021 (1974).

Davies et al., "MUC16 is produced in tracheal surface epithelium and submucosal glands and is present in secretions from normal human airway and cultured bronchial epithelial cells." *Int J Biochem Cell Biol.,* 39(10):1943-1954 (2007).

Debat et al., "Overpassing an aberrant Vkappa gene to sequence an anti-idiotypic abzyme with beta-lactamase-like activity that could have a linkage with autoimmune diseases." *FASEB,* 15:815-822 (2001).

Doenecke et al., "Rapid amplification of cDNA ends (RACE) improves the PCR-based isolation of immunoglohulin variable region genes from murine and human lymphoma cells and cell lines." *Leukemia,* 11(10):1787-1792 (1997).

Duraisamy et al., :Distinct evolution of the human carcinoma-associated transmembrane mucins, MUC1, MUC4 and MUC16. Gene 373: 28-34 (2006).

Elofsson and Von Heijne, "Membrane protein structure: prediction versus reality." *Annu Rev BioChem.,* 76:125-140 (2007).

Faisal et al., "Leptasome-entrapped leptospiral antigens conferred significant higher levels of protection than those entrapped with PC-liposomes in a hamster model." *Vaccine,* 27(47):6537-6545.

Fendrick et al., "CA125 phosphorylation is associated with its secretion from the WISH human amnion cell line." *Tumour Biol.,* 18(5):278-289 (1997).

Fendrick et al., "Characterization of CA 125 synthesized by the human epithelial amnion WISH cell line." *Tumour Biol.,* 14(5):310-318 (1993).

Fernandez-Tejada et al., "Chemical synthesis of the β-subunit of human luteinizing (hLH) and chorionic gonadotropin (hCG) glycoprotein hormones." J Am Chem Soc 136, 8450-8458 (2014).

Finney et al., "Activation of resting human primary T cells with chimeric receptors: costimulation from CD28, inducible costimulator, CD134, and CD137 in series with signals from the TCR zeta chain." *J Immunol.,* 172(1): 104-113 (2004).

Fritsche and Bast, "CA 125 in ovarian cancer: advances and controversy." *Clin Chem.,* 44(7):1379-1380 (1998).

(56) References Cited

OTHER PUBLICATIONS

GenBank Accession No. AJ277812.1, "Mus musculus partial mRNA for immunoglobulin kappa light chain variable region (IGKV gene)." URL: http://www.ncbi.nlm.nih.gov/nuccore/7711058 (2001).
Giannakouros et al., "Transformation of NIH3T3 mouse fibroblast cells by MUC16 mucin (CA125) is driven by its cytoplasmic tail." *International Journal of Oncology,* 46(1):91-98 (2014).
Gong et al., "Cancer patient T cells genetically targeted to prostate-specific membrane antigen specifically lyse prostate cancer cells and release cytokines in response to prostate-specific membrane antigen." *Neoplasia,* 1(2):123-127 (1999).
Govindarajan and Gipson, "Membrane-tethered mucins have multiple functions on the ocular surface." Exp Eye Res 90: 655-663 (2010).
Granovsky et al., "Suppression of tumor growth and metastasis in Mgat5-deficient mice." Nat Med 6, 306-312 (2000).
Greenwood and Hun Ier, "Preparation of iodine-131 labelled human growth hormone of high specific activity." *Nature,* 194:495-496 (1962).
Gubbels et al., "Mesothelin-MUC16 binding is a high affinity, N-glycan dependent interaction that facilitates peritoneal metastasis of ovarian tumors." *Molecular Cancer,* 5(1):50 (2006).
Habib-Agahi et al., "4-1BBL costimulation retrieves CD28 expression in activated T cells." *Cell Immunol.,* 256(1-2):39-46 (2009).
Habib-Agahi et al., "Co-stimulation with 4-1BB ligand allows extended T-cell proliferation, synergizes with CD80/CD86 and can reactivate anergic T cells." *Int Immunol.,* 19(12):1383-1394 (2007).
Habib-Agahi et al., "Co-stimulation with 4-1BB ligand allows extended T-cell proliferation, synergizes with CD80/CD86 and can reactivate anergic T cells." *Int Immunol.,* 19(12):1383-1394, Sup. List (2007).
Habib-Agahi et al., "Co-stimulation with 4-1BB ligand allows extended T-cell proliferation, synergizes with CD80/CD86 and can reactivate anergic T cells." *Int Immunol.,* 19(12):1383-1394, Sup. Fig. 1 (2007).
Habib-Agahi et al., "Co-stimulation with 4-1BB ligand allows extended T-cell proliferation, synergizes with CD80/CD86 and can reactivate anergic T cells." *Int Immunol* 19(12):1383-1394, Sup. Fig. 2 (2007).
Hamanishi et al., "Programmed cell death 1 ligand 1 and tumor-infiltrating CD8+ T lymphocytes arc prognostic factors of human ovarian cancer." *Proc Natl Acad Sci., USA,* 104(9):3360-3365 (2007).
Harris et al., "A comparison of the metastatic pattern of infiltrating lobular carcinoma and infiltrating duct carcinoma of the breast." *Br J Cancer,* 50(1):23-30 (1984).
Hedvat et al., "Application of tissue microarray technology to the study of non-Hodgkin's and Hodgkin's lymphoma." *Hum Pathol.,* 33(10):968-974 (2002).
High et al., "Sec61p is adjacent to nascent type I and type II signal-anchor proteins during their membrane insertion." *J Cell Biol.,* 121(4):743-750 (1993).
Hirabayashi et al., "Oligosaccharide specificity of galectins: a search by frontal affinity chromatography." Biochim Biophys Acta 1572, 232-254 (2002).
Hollingsworth and Swanson, "Mucins in cancer: protection and control of the cell surface." *Nat Rev Cancer,* 4(1):45-60 (2004).
Hollyman et al., "Manufacturing validation of biologically functional T cells targeted to CD19 antigen for autologous adoptive cell therapy." *J Immuno Ther.,* 32(2):169-180 (2009).
Huang et al., "MUC1 cytoplasmic domain coactivates Wnt target gene transcription and confers transformation." *Cancer Biol. Ther.,* 2(6):702-706 (2003).
Huang et al.,"MUC1 oncoprotein blocks glycogen synthase kinase 3beta-mediated phosphorylation and degradation of beta-catenin." Cancer Res 65: 10413-10422 (2005).
Hung et al., "Antigen-specific immunotherapy of cervical and ovarian cancer." *Immunol Rev.,* 222:43-69 (2008).
Huse et al., "Generation of a large combinatorial library of the immunoglobulin repertoire in phage lambda." *Science,* 246(4935):1275-1281 (1989).
Huwyler et al., "Tumor targeting using liposomal antineoplastic drugs." *Int J Nanomedicine,* 3(1):21-29 (2008).
Hwu et al., "In vivo antitumor activity of T cells redirected with chimeric antibody/T-cell receptor genes." *Cancer Res.,* 55(15):3369-3373 (1995).
Imai et al., "Chimeric receptors with 4-1BB signaling capacity provoke potent cytotoxicity against acute lymphoblastic leukemia." *Leukemia,* 18(4):676-684 (2004).
International Search Report for International Application No. PCT/US2016/022643, dated Sep. 5, 2016.
International Search Report for International Application No. PCT/US2011/030025, dated Feb. 8, 2012.
Invitation to Pay Additional Fees, and, Where Applicable, Protest Fee, with Communication Relating to the Results of the Partial International Search for PCT/US2016/022643, dated Jun. 30, 2016.
Jensen et al., "Engineered CD20-specific primary human cytotoxic T lymphocytes for targeting B-cell malignancy." *Cytotherapy,* 5(2):131-138 (2003).
Kabawat et al., "Tissue distribution of a coelomic-epithelium-related antigen recognized by the monoclonal antibody OC125." Int J Gynecol Pathol 2: 275-285 (1983).
Kaneko et al., "A binding domain on mesothelin for CA125/MUC16." *J Biol Chem,* 284(6):3739-3749 (2009).
Kershaw et al., "A phase I study on adoptive immunotherapy using gene-modified T cells for ovarian cancer." *Clin Cancer Res.,* 12(20 Pt 1):6106-6115 (2006).
Kershaw et al., "Dual-specific T cells combine proliferation and antitumor activity." *Nat Biotechnol.,* 20(12):1221-1227 (2002).
Kochenderfer et al., "Construction and preclinical evaluation of an anti-CD19 chimeric antigen receptor." *J ImmunoTher.,* 32(7):689-702 (2009).
Kohler and Milstein, "Continuous cultures of fused cells secreting antibody of predefined specificity." *Nature,* 256(5517):495-497 (1975).
Kononen et al., "Tissue microarrays for high-throughput molecular profiling of tumor specimens." *Nat Med.,* 4(7):844-847 (1998).
Kozbor and Roder, "Comparison of the specific IgM and IgG antibody response in humans induced by antigen (tetanus toxoid) or a polyclonal activator (EBV) in vitro." *Int Arch Allergy Appl Immunol.,* 72(3):260-266 (1983).
Krivak et al., "A Gynecologic Oncology Group Study of serum CA-125 levels in patients with stage III optimally debulked ovarian cancer treated with intraperitoneal compared to intravenous chemotherapy: an analysis of patients enrolled in GOG 172." *Gynecol Oncol.,* 115(1):81-85 (2009).
Lajoie et al., "Plasma membrane domain organization regulates EGFR signaling in tumor cells." J Cell Biol 179, 341-356 (2007).
Lamers et al., "Gene-modified T cells for adoptive immunotherapy of renal cell cancer maintain transgene-specific immune functions in vivo." *Cancer Immunol ImmunoTher.,* 56(12):1875-1883 (2007).
Lamers et al., "Treatment of metastatic renal cell carcinoma with autologous T-lymphocytes genetically retargeted against carbonic anhydrase IX: first clinical experience." *J Clin Oncol.,* 24(13):e20-22 (2006).
Latouche and Sadelain, "Induction of human cytotoxic T lymphocytes by artificial antigen-presenting cells." *Nat Biotechnol.,* 18(4):405-409 (2000).
Lau et al., "Complex N-glycan number and degree of branching cooperate to regulate cell proliferation and differentiation." Cell 129, 123-134 (2007).
Leffers et al., "Prognostic significance of tumor-infiltrating T-lymphocytes in primary and metastatic lesions of advanced stage ovarian cancer." *Cancer Immunol ImmunoTher.,* 58(3):449-459 (2009).
Leffers et al., "Survival of ovarian cancer patients overexpressing the tumour antigen p53 is diminished in case of MHC class I down-regulation." *Gynecol Oncol.,* 110(3):365-373 (2008).
Li et al. "Human DF3/MUC1 carcinoma-associated protein functions as an oncogene." Oncogene 22: 6107-6110 (2003).

(56) References Cited

OTHER PUBLICATIONS

Li et al., "4-1BB (CD137) ligand enhanced anti-tumor immune response against mouse forestomach carcinoma in vivo." *Cell Mol Immunol.*, 5(5):379-384 (2008).
Li et al., "Interaction of human MUC1 and beta-catenin is regulated by Lck and ZAP-70 in activated Jurkat T cells." *Biochem Biophys Res Commun.*, 315(2):471-476 (2004).
Liu et al., A genetically defined model for human ovarian cancer. Cancer Res 64: 1655-1663 (2004).
Lloyd & Yin, "Synthesis and secretion of the ovarian cancer antigen CA 125 by the human cancer cell line NIH:OVCAR-3." Tumour Biol 22: 77-82 (2001).
Lolli et al., "The glycopeptides CSF114(G1c) detects serum antibodies in multiple sclerosis." *Journal of Neuroimmunology,* 167(1-2):131-137 (2005).
Loskog et al., "Addition of the CD28 signaling domain to chimeric T-cell receptors enhances. chimeric T-cell resistance to T regulatory cells." *Leukemia,* 20(10):1819-1828 (2006).
Maher et al., "Human T-lymphocyte cytotoxicity and proliferation directed by a single chimeric. TCRzeta /CD28 receptor." *Nat Biotechnol.*, 20(1):70-75 (2002).
Marcos-Silva et al., "A novel monoclonal antibody to a defined peptide epitope in MUC16." *Glycobiology,* 25(11):1172-1182 (2015).
Marcos-Silva et al., "Characterization of Binding Epitopes of CA125 Monoclonal Antibodies." *Journal of Proteome Research,* 13(7):3349-3359 (2014).
Markwell and Fox, "Surface-specific iodination of membrane proteins of viruses and eucaryotic cells using 1,3,4,6-tetrachloro-3alpha,6alpha-diphenylglycoluril." *Biochemistry,* 17(22):4807-4817 (1978).
Mascola & Haynes, "HIV-1 neutralizing antibodies: understanding nature's pathways.". Immunol Rev 254, 225-244 (2013).
Mazal et al. "Monoclonal antibodies toward different Tn-amino acid backbones display distinct recognition patterns on human cancer cells. Implications for effective immuno-targeting of cancer.". Cancer Immunol. Immunother. 62, 1107-1122 (2013).
Moeller et al., "A functional role for CD28 costimulation in tumor recognition by single-chain receptor-modified T cells." *Cancer Gene Ther.*, 11(5):371-379 (2004).
Moore et al., "Current stale of biomarker development for clinical application in epithelial ovarian cancer." *Gynecol Oncol.*, 116(2):240-245 (2010).
Nakada et al., "Epitopic structure of Tn glycophorin A for an anti-Tn antibody (MLS 128)." Proc. Natl. Acad. Sci. USA 90, 2495-2499 (1993).
Nap et al., "Immunohistochemical characterization of 22 monoclonal antibodies against the CA125 antigen: 2nd report from the ISOBM TD-1 Workshop." *Tumour Biol.*, 17(6):325-331 (1996).
Nelson, "The impact of T-cell immunity on ovarian cancer outcomes." *Immunol Rev.*, 222:101-116 (2008).
Nustad et al., "Epitopes on CA 125 from cervical mucus and ascites fluid and characterization of six new antibodies. Third report from the ISOBM TD-1 workshop." *Tumour Biol.*, 23(5):303-314 (2002).
Nygren, "Conjugation of horseradish peroxidase to $F_{ab}$ fragments with different homobifunctional and heterobifunctional cross-linking reagents. A comparative study." *Journal of Histochemistry & Cytochemistry,* 30(5):407-412 (1982).
O'Brien et al., "More than 15 years of CA 125: what is known about the antigen, its structure and its function." *Int J Biol Markers,* 13(4):188-195 (1998).
O'Brien et al., "The CA 125 gene: a newly discovered extension of the glycosylated N-terminal domain doubles the size of this extracellular superstructure." *Tumour Biol.*, 23(3):154-169 (2002).
O'Brien et al., "The CA 125 gene: an extracellular superstructure dominated by repeat sequences." *Tumour Biol.*, 22(6):348-366 (2001).
Orlandi et al., "Cloning immunoglobulin variable domains for expression by the polymerase chain reaction." *Proc Natl Acad Sci., USA,* 86(10):3833-3837 (1989).
Osinaga et al., "Analysis of the fine specificity of Tn-binding proteins using synthetic glycopeptide epitopes and a biosensor based on surface plasmon resonance spectroscopy." *FEBS Lett.* 469, 24-28 (2000).
Pain and Surolia. "Preparation of protein A-peroxidase monoconjugate using a heterobifunctional reagent, and its use in enzyme immunoassays." *J Immunol Methods,* 40(2):219-230 (1981).
Parker et al., "Expansion and characterization of T cells transduced with a chimeric receptor against ovarian cancer." *Hum Gene Ther.*, 11(17):2377-2387 (2000).
Partridge et al., "Regulation of cytokine receptors by Golgi N-glycan processing and endocytosis." Science 306, 120-124 (2004).
Ponnusamy et al., "MUC4 activates HER2 signalling and enhances the motility of human ovarian cancer cells." *Br J Cancer,* 99(3):520-526 (2008).
Pule et al., "Virus-specific T cells engineered to coexpress tumor-specific receptors: persistence and antitumor activity in individuals with neuroblastoma." *Nat Med.*, 14(11):1264-1270 (2008).
Quintas-Cardama et al., "Multifactorial optimization of gammaretroviral gene transfer into human T lymphocytes for clinical application." *Hum Gene Ther.*, 18(12):1253-1260 (2007).
Ramsauer et al., "Muc4/sialomucin complex, the intramembrane ErbB2 ligand, translocates ErbB2 to the apical surface in polarized epithelial cells." J Biol Chem 278: 30142-30147 (2003).
Ramsauer et al., "MUC4-ErbB2 complex formation and signaling in polarized CACO-2 epithelial cells indicate that Muc4 acts as an unorthodox ligand for ErbB2." *Mol Biol Cell* 17(7):2931-2941 (2006).
Rao et al., "Antibodies Against Specific MUC16 Glycosylation Sites Inhibit Ovarian Cancer Growth." ACS Chem Biol. 12(8):2085-2096. Epub Jun. 28, 2017.
Rao et al., "Dual-fluorescence isogenic high-content screening for MUC16/CA125 selective agents." Mol Cancer Ther 10: 1939-1948 (2011).
Rao et al., "Expression of the Carboxy-Terminal Portion of MUC16/CA125 Induces Transformation and Tumor Invasion." *PLoS One,* 10(5):e0126633 (2015).
Rao et al., "Novel Monoclonal Antibodies Against the Proximal (Carboxy-Terminal) Portions of MUC16." *Applied Immunohistochemistry & Molecular Morphology,* 18(5):462-472 (2010).
Raspollini et al., "Tumour-infiltrating gamma/delta T-lymphocytes are correlated with a brief disease-free interval in advanced ovarian serous carcinoma." *Ann Oncol.*, 16(4):590-596 (2005).
Ren et al., "Human MUC1 carcinoma-associated protein confers resistance to genotoxic anticancer agents." *Cancer Cell,* 5(2):163-175 (2004).
Ren et al., "MUC1 oncoprotein is targeted to mitochondria by heregulin-induced activation of c-Src and the molecular chaperone HSP90." *Oncogene,* 25(1):20-31 (2006).
Riviere et al., "Effects of retroviral vector design on expression of human adenosine deaminase in murine hone marrow transplant recipients engrafted with genetically modified cells." *Proc Natl Acad Sci., USA,* 92(15):6733-6737 (1995).
Rosen et al., "Potential markers that complement expression of CA125 in epithelial ovarian cancer." *Gynecol Oncol.*, 99(2):267-277 (2005).
Rustin et al., "Use of CA-125 in clinical trial evaluation of new therapeutic drugs for ovarian cancer." *Clin Cancer Res.*, 10(11):3919-3926 (2004).
Sadelain et al., "Targeting tumours with genetically enhanced T lymphocytes." *Nat Rev Cancer,* 3(1):35-45 (2003).
Sadelain et al., "The promise and potential pitfalls of chimeric antigen receptors." *Curr Opin Immunol.*, 21(2):215-223 (2009).
Salih et al., "Constitutive expression of functional 4-1BB (CD137) ligand on carcinoma cells." *J Immunol.*, 165(5):2903-2910 (2000).
Santos et al., "Sensitive in vivo imaging of T cells using a membrane-bound *Gaussia princeps* luciferase." *Nat Med.*, 15(3):338-344 (2009).
Sato et al., "Intraepithelial CD8+ tumor-infiltrating lymphocytes and a high CD8+/regulatory T cell ratio are associated with favorable prognosis in ovarian cancer." *Proc Natl Acad Sci., USA,* 102(51):18538-18543 (2005).

(56) References Cited

OTHER PUBLICATIONS

Savoldo et al., "Epstein Barr virus specific cytotoxic T lymphocytes expressing the anti-CD3Ozeta artificial chimeric T-cell receptor for immunotherapy of Hodgkin disease." *Blood,* 110(7):2620-2630 (2007).
Scholler & Urban. "CA125 in ovarian cancer. Biomark." Med. 1, 513-523 (2007).
Seelenmeyer et al., "The cancer antigen CA125 represents a novel counter receptor for galectin-1." J Cell Sci. 116(Pt 7): 1305-1318 (2003).
Shinoda et al., Kruppel-like factor 5 causes cartilage degradation through transactivation of matrix metalloproteinase 9. J Biol Chem 283: 24682-24689 (2008).
Singer, "The structure and insertion of integral proteins in membranes." *Annu Rev Cell Biol.,* 6:247-296, A: pp. 247-268 (1990).
Singer, "The structure and insertion of integral proteins in membranes." *Annu Rev Cell Biol.,* 6:247-296, B: pp. 269:296 (1990).
Singh et al., "Clinical potential of mucins in diagnosis, prognosis, and therapy of ovarian cancer." *Lancet Oncol.,* 9(11):1076-1085 (2008).
Song et al., "Peptide ligand-mediated liposome distribution and targeting to EGFR expressing tumor in vivo." *Int J Pharm.,* 363(1-2):155-161 (2008).
Sorensen et al., "Chemoenzymatically synthesized multimeric Tn/STn MUC1 glycopeptides elicit cancer-specific anti-MUC1 antibody responses and override tolerance." *Glycobiology,* 16(2):96-107 (2006).
Soslow, "Histologic subtypes of ovarian carcinoma: an overview." *Int J Gynecol Pathol.,* 27(2):161-174 (2008).
Stephan et al., "T cell-encoded CD8O and 4-1BBL induce auto- and transcostimulation, resulting in tumor rejection." *Nat Med.,* 13(12):1440-1449 (2007).
Strausberg et al., "Generation and initial analysis of more than 15,000 full-length human and mouse cDNA sequences." Proc Natl Acad Sci USA 99: 16899-16903 (2002).
Strome et al., 2007, "A mechanistic perspective of monoclonal antibodies in cancer therapy beyond target-related effects.", *The Oncologist,* 12:1084-95.
Sun et al., "Quality of life for patients with epithelial ovarian cancer." *Nat Clin Pract Oncol,* 4(1):18-29 (2007).
Taylor et al., Integrative genomic profiling of human prostate cancer. (2010) Cancer Cell 18: 11-22 (2010).
TCGA "Comprehensive genomic characterization defines human glioblastoma genes and core pathways." Nature 455: 1061-1068 (2008).
Thapi et al., "Abstract 3045: Glycosylation dependence in MUC16/CA125 expression in ovarian cancer." Proceedings: AACR 104th Annual Meeting 2013; Apr. 6-10, 2013; Washington, DC; DOI: 10.1158/1538-7445.AM2013-3045 Published Apr. 2013.
Till et al., "Adoptive immunotherapy for indolent non-Hodgkin lymphoma and mantle cell lymphoma using genetically modified autologous CD20-specific T cells." *Blood,* 112(6):2261-2271 (2008).
Tomsova et al., "Prognostic significance of CD3+ tumor-infiltrating lymphocytes in ovarian carcinoma." *Gynecol Oncol.,* 108(2):415-420 (2008).
Ventura et al., Activation of the MEK-56 pathway in high-grade ovarian cancers. (2010) Appl Immunohistochem Mol Morphol 18: 499-508 (2010).
Voinea and Simionescu, "Designing of 'intelligent' liposomes for efficient delivery of drugs." *J Cell Mol Med.,* 6(4):465-474 (2002).
Wan et al., "Expression of co-stimulator 4-1BB molecule in hepatocellular carcinoma and adjacent non-tumor liver tissue, and its possible role in tumor immunity." *World J Gastroenterol.,* 10(2):195-199 (2004).
Wang et al., "A T cell-independent antitumor response in mice with bone marrow cells retrovirally transduced with an antibody/Fc-gamma chain chimeric receptor gene recognizing a human ovarian cancer antigen." *Nat Med.,* 4(2):168-172 (1998).
Wang et al., "Abstract 141: MUC16/CA125 and Epithelial Growth Factor Receptor functionality in ovarian cancer." Proceedings: AACR 106th Annual Meeting 2015; Apr. 18-22, 2015; Philadelphia,. PA; DOI: 10.1158/1538-7445.AM2015-141 Published Aug. 2015.
Wang et al., "An advance in the chemical synthesis of homogeneous N-linked glycopolypeptides by convergent aspartylation." Angew. Chem. Int. Ed. 51, 11571-11575 (2012).
Wang et al., "Universal PCR amplification of mouse immunoglobulin gene variable regions: the design of degenerate primers and an assessment of the effect of DNA polymerase 3' to 5' exonuclease activity." *J Immunol Methods,* 233(1-2):167-177 (2000).
Westwood et al., "Adoptive transfer of T cells modified with a humanized chimeric receptor gene. inhibits growth of Lewis-Y-expressing tumors in mice." *Proc Natl Acad Sci., USA,* 102(52):19051-19056 (2005).
Wilkie et al., "Retargeting of human T cells to tumor-associated MUC1: the evolution of a chimeric antigen receptor." *J Immunol.,* 180(7):4901-4909 (2008).
Wolf et al., "The expression of the regulatory T cell-specific forkhead box transcription factor FoxP3 is associated with poor prognosis in ovarian cancer." *Clin Cancer Res.,* 11(23):8326-8331 (2005).
Woo et al., "Regulatory CD4(+)CD25(+) T cells in tumors from patients with early-stage non-small cell lung cancer and late-stage ovarian cancer." *Cancer Res.,* 61(12):4766-4772 (2001).
Written Opinion of the International Searching Authority for International Application No. PCT/US2016/022643, dated Sep. 5, 2016.
Written Opinion of the International Searching Authority for International Application No. PCT/US2011/030025, dated Feb. 8, 2012.
Xing & Orsulic, "A mouse model for the molecular characterization of brcal-associated ovarian carcinoma." Cancer Res 66: 8949-8953 (2006).
Yin and Lloyd, "Molecular cloning of the CA125 ovarian cancer antigen: identification as a new mucin, MUC16." *J. Biol Chem.,* 276(29):27371-27375 (2001).
Yin et al., "Ovarian cancer antigen CA125 is encoded by the MUC16 mucin gene." *Int J Cancer,* 98(5):737-740 (2002).
Zhang et al., "Intratumoral T cells, recurrence, and survival in epithelial ovarian cancer." *N Engl J Med.,* 348(3):203-213 (2003).
Zorn et al., "The prognostic value of pretreatment CA 125 in patients with advanced ovarian carcinoma: a Gynecologic Oncology Group study." Cancer 115: 1028-1035 (2009).
Alper et al., "Epidermal growth factor receptor signaling and the invasive phenotype of ovarian carcinoma cells." J Natl Cancer Inst 93, 1375-1384 (2001).
Bast et al., "CA125: the past and the future." Int. J. Biol. Markers 13, 179-187 (1998).
Mazzoletti & Broggini, PI3K/AKT/mTOR Inhibitors in Ovarian Cancer. Curr Med Chem 17: 4433-4447 (2010).
Park, "The extracellular portion of the MUC16 cytoplasmic domain is detectable in ovarian carcinoma using a novel monoclonal antibody, 4H11." *Modern pathology,* 0893-3952 (21 (suppl. 1)):217A-218A (Jan. 1, 2008).
Heller and Vendatraman, "Resampling procedures to compare two survival distributions in the presence of right censored data." Biometrics 52: 1204-1213 (1996).
Cohen-Anisfeld and Lansbury, "A practical, convergent method for glycopeptide synthesis." J. Am. Chem. Soc. 115, 10531-10537 (1993).
Likhosherstov et al., "A new simple synthesis of amino sugar β-d-glycosylamines." Carbohydr. Res. 146, C1-C5 (1986).
Dondelinger et al., "Understanding the Significance and Implications of Antibody Numbering and Antigen-Binding Surface/Residue Definition," *Front. Immunol.,* 9:1-15 (2008).
Finkelstein et al. eds., *Protein Physics: A Course of Lectures, 4th Edition,* Academic Press, Cambridge, MA, p. 23 (2012).
Pule et al., "Artificial T-cell receptors," *Cytotherapy,* 5(3):211-226 (2003).
Sun et al., "Metabolic and Functional Profiling of the Normal Rat Retina," *J Comp Neurol,* 505:92-113 (2007).
Yarilin, "Immunology Basics," Education material for students of medical universities, Moscow, *Medicine,* pp. 172-174 (1999) (English translation only).

(56) References Cited

OTHER PUBLICATIONS

Diamond et al., "Somatic mutation of the T15 heavy chain gives rise to an antibody with autoantibody specificity," *Proc. Natl. Acad. Sci. USA,* 81:5841-5844 (1984).
Kang et al., "Antibody redesign by chain shuffling from random combinatorial immunoglobulin libraries," *Proc. Natl. Acad. Sci. USA,* 88:11120-11123 (1991).
Ohno et al., "Antigen-binding specificities of antibodies are primarily determined by seven residues of $V_H$," *Proc. Natl. Acad. Sci. USA,* 82:2945-2949 (1985).
Rudikoff et al., "Single amino acid substitution altering antigen-binding specificity," *Proc. Natl. Acad. Sci. USA,* 79:1979-1983 (1982).
Sadelain et al., "The basic principles of chimeric antigen receptor design," *Cancer Discovery,* 3:388-398 (2013).
Sikkink et al., "Biochemical and aggregation analysis of Bence Jones proteins from different light chain diseases," *Amyloid,* 15(1):29-39 (2008).
H Debat, "Mus musculus partial mRNA for immunoglobulin kappa light chain variabl—AJ277812.1", (Mar. 26, 2001), URL: http://www.ncbi.nlm.nih.gov/nuccore/7711058, (Jun. 14, 2016).
Studnicka et al., 1994, "Human-engineered monoclonal antibodies retain full specific binding activity by preserving non-CDR complementarity-modulating residues", Protein Eng, 7(6):804-814.

* cited by examiner

| 1547 WELSQL----TGVDSLC 1776 | 1777NFSPLAR--TGNSDLP1834 | 1835FWAVILIGLAGLL GLITCLICGVLV1859 | 1860TTRRRKKEGEYNVQQQ CPGYYQSHLDLEDLQ1890 |
|---|---|---|---|
| FIRST TANDEM REPEAT (230 AA) | ECTODOMAIN (58 AA) | TRANSMEMBRANE (25 AA) | CYTOPLASMIC TAIL (31 AA) |

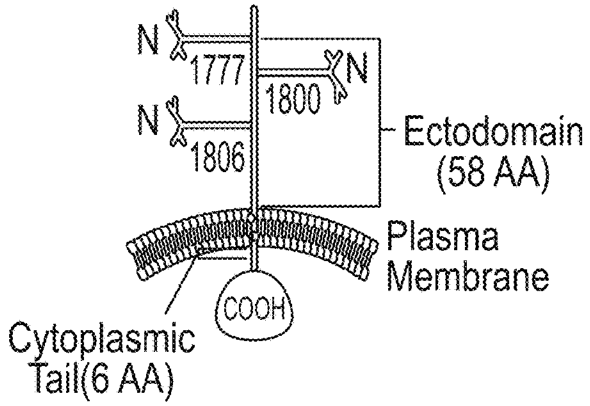

MUC16$^{c86}$
Internal Deletion

MUC16$^{c86}$

| | | |
|---|---|---|
| NFSPLARRVDRVAIYEEFLRM TRNGTQLQNFTLDRSSVLVD 1777 GYSPNRNEPLTGNSDLP1834 | 1835FWAVILIGLAGLL GLITCLICG1856^^^ | ^^1885DLEDLQ1890 |
| Ectodomain 58 aa | Transmembrane 22 aa | Cytoplasmic 6 aa |

FIG. 1E

MUC16$^{3(N▸A)c114}$

| | | |
|---|---|---|
| AFSPLARRVDRVAIYEEFLRM TRAGTQLQAFTLDRSSVLVD 1777 GYSPNRNEPLTGNSDLP1834 | 1835FWAVILIGLAGLL GLITCLICGVLV1859 | 1860TTRRRKKEGEYNVQQQ CPGYYQSHLDLEDLQ1890 |
| 3(N▸A)Mutated Ectodomain 58 aa | Transmembrane 25 aa | Cytoplasmic Tail 31 aa |

FIG. 1F

Fig. 2A 3T3 Transfectant *in vitro* Growth
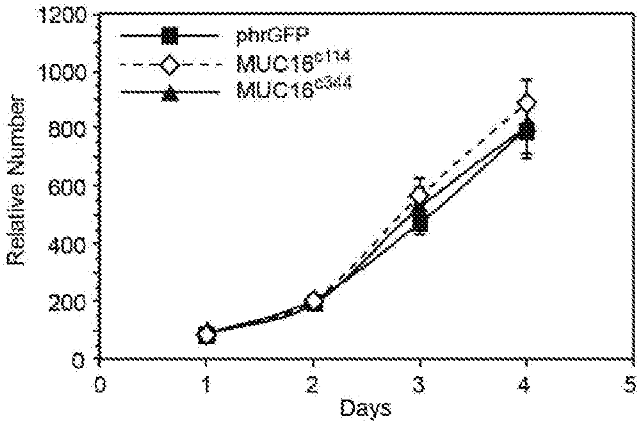
Fig. 2B A2780 Transfectant *in vitro* Growth
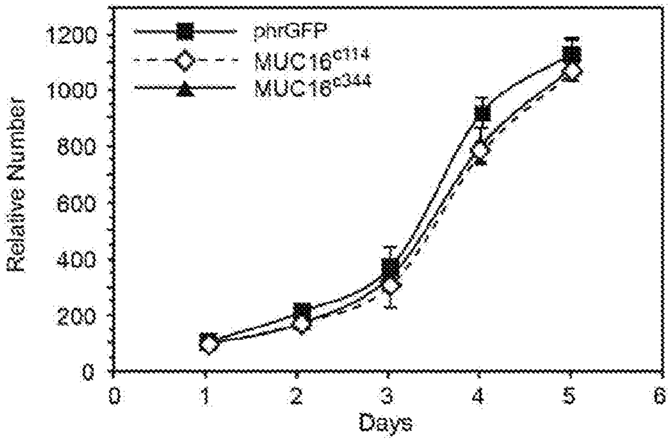
Fig. 2C 3T3 Transfectant *in vitro* Growth
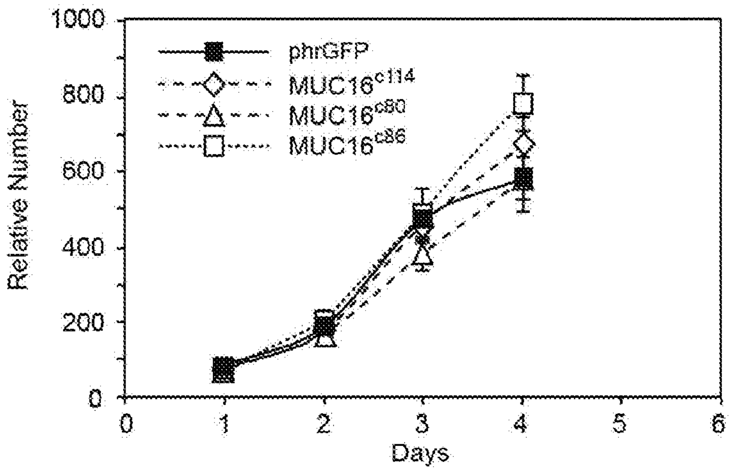

Fig. 3A
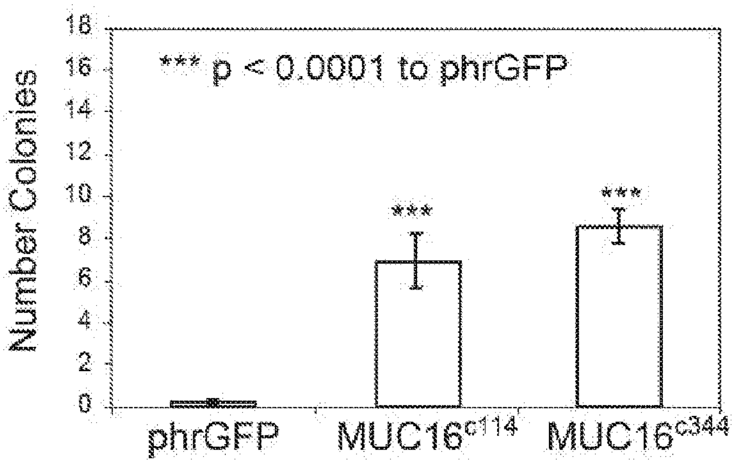
Fig. 3B 3T3 Transfectant Matrigel Invasion
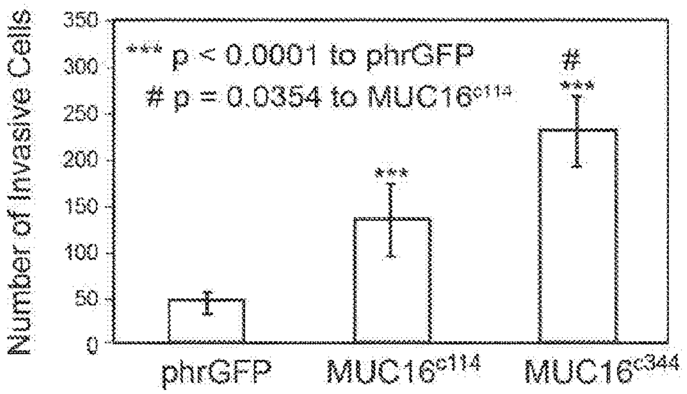
Fig. 3C
| Symbol | 3T3 phr vs $MUC16^{c114}$ | | 3T3 phr vs $MUC16^{c344}$ | |
|---|---|---|---|---|
| | p value | Fold Change | p value | Fold Change |
| CXCL12 | 0.0008 | 10.74 | 0.0071 | 3.48 |
| NF2 | 0.0075 | -1.31 | 0.0317 | -1.28 |
| FN1 | 0.0166 | -3.06 | 0.0377 | -2.20 |
| CTBP1 | 0.0283 | -1.76 | 0.2043 | -1.36 |
| SMAD4 | 0.0324 | -2.42 | 0.1759 | -1.34 |
| CDH11 | 0.0790 | 2.73 | 0.0057 | 9.25 |
| MMP2 | 0.1634 | 1.43 | 0.0445 | 1.86 |
| MMP9 | 0.7675 | 1.03 | 0.0315 | 1.12 |

Oncogene Activation

3T3 Transfectant Xenograft Growth

Ectodomain MUC16$^{c57-c114}$ Construct (58 aa) pFUSE-hIgG1-Fc2

NFSPLARRVDRVAIYEEFLRMTRNGTQLQNFTLDRSSVLVDGYSPNRNEPLTGNSDLP-pFUSE-hIgG1-Fc2

$^{117-244}$LGALS3 Sugar Binding Protein (128 aa)

PYNLPLPGGVVPRMLITILGTVKPNANRIALDFQRGNDVAFHFNPRFNENNRRVIVCNTKLDNNWGRE
ERQSVFPFESGKPFKIQVLVEPDHFKVAVNDAHLLQYNHRVKKLNEISKLGISGDIDLTS - pFUSE-hIgG1-Fc2

MUC16 Transcript Number

| Observed m/z | Charge State | Structural Assignment | | Mass [M+Na]$^+$ | Intensity/ Charge State | Glycan % |
|---|---|---|---|---|---|---|
| 1142 | 1 | M2N2F |  | 1142 | 1.02E+03 | 32.47% |
| 1170 | 1 | M3N2 |  | 1171 | 3.56E+02 | 11.33% |
| 1346 | 1 | M3N2F | 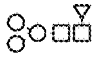 | 1345 | 4.18E+02 | 13.30% |
| 1376 | 1 | M4N2 |  | 1376 | 1.91E+02 | 6.08% |
| 1580 | 1 | M5N2 |  | 1580 | 3.78E+02 | 12. 03% |
| 1784 | 1 | M6N2 | 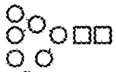 | 1784 | 8.68E+01 | 2.76% |
| 1988 | 1 | M7N2 | 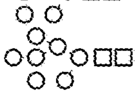 | 1988 | 3.70E+01 | 1.18% |
| 1134 | 2 | GAL2NMBN2F | 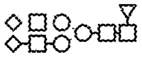 | 2244 | 1.91E+02 | 6.06% |
| 1228 | 2 | NEUAc1 GaL2N2MBN2 |  | 2431 | 1.50E+02 | 4.76% |
| 1316 | 2 | NEUAc1 GaL2N2MBN2F | 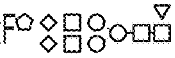 | 2605 | 1.65E+02 | 5.25% |
| 1408 | 2 | NEUAc2GaL2N2MBN2 |  | 2792 | 7.70E+01 | 2.45% |
| 1496 | 2 | NEUAc1 GaL2MBN2F | 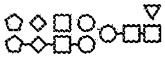 | 2966 | 7.30E+01 | 2.32% |
| | | | | Total | 3.14E+03 | 100.00% |
Figure Legend
▽ Fucose □ N-acetylglucosamin ○ Mannose
◇ Galactose ⬠ N-acetylneuraminic acid
FIG. 13A KLH–15-mer(chitobiose)[C-G25–V38]

KLH–18-mer(chitobiose)$_2$[C-T22–V38]

| | 15 VS 15S PEPTIDES | | | | | | | | | | | 18 VS 18S PEPTIDES | | | | | | | | | | | | STICK ELISAY BY |
|---|---|---|---|---|---|---|---|---|---|---|---|---|---|---|---|---|---|---|---|---|---|---|---|---|
| | ELISA ON 12/24/13 SUPS FROM TIME OF FREEZING | | | | | ELISA DURING FUSION SCREEN (ELISA PERFORMED ON DIFFERENT DAYS) | | | | | | ELISA ON 12/24/13 SUPS FROM TIME OF FREEZING | | | | | ELISA DURING FUSION SCREEN (ELISA PERFORMED ON DIFFERENT DAYS) | | | | | | | |
| ID | DILUTION | 15 | 15S | 15S / 15 RATIO | FOLD OVER TB | DILUTON | 15 | 15S | 15S / 15 RATIO | FOLD OVER TB | ELISAS AGREE | DILUTION | 18 | 18S | 18S / 15 RATIO | FOLD OVER TB | DILUTION | 18 | 18S | 18S / 15 RATIO | FOLD OVER TB | ELISAS AGREE | | |
| 4H11 | NEAT | 0.02 | 0.02 | ... | ... | | | | | | | NEAT | 0.02 | 0.02 | ... | ... | | | | | | | | |
| 9B11 | NEAT | 0.02 | 0.02 | ... | ... | | | | | | | NEAT | 0.02 | 0.02 | ... | ... | | | | | | | | |
| TB | 1:1000 | 0.72 | 0.29 | 0.40 | ... | | | | | | | 1:1000 | 0.81 | 0.77 | 1.95 | ... | | | | | | | | |
| II 01B05 | 400 | 0.34 | 0.47 | 1.38 | 3.46 | 400 | 0.55 | 0.52 | 0.95 | 1.11 | NO | 400 | 0.47 | 0.60 | 1.28 | 1.34 | 400 | 0.43 | 0.78 | 1.81 | 1.29 | YES | | |
| II 02E01 | 400 | 0.42 | 0.37 | 0.88 | 2.20 | 400 | 0.31 | 0.22 | 0.71 | 0.83 | NO | 400 | 0.37 | 0.47 | 1.27 | 1.34 | 400 | 0.28 | 0.51 | 1.82 | 1.30 | YES | | |
| II 04G02 | 80 | 0.38 | 0.05 | 0.13 | 0.33 | 40 | 0.87 | 0.51 | 0.59 | 0.84 | YES | 80 | 0.34 | 0.33 | 0.97 | 1.02 | 80 | 0.37 | 0.61 | 1.65 | 1.24 | NO | | |
| II 07B02 | 400 | 0.44 | 0.25 | 0.57 | 1.42 | 200 | 0.77 | 0.80 | 1.04 | 1.22 | ? | 400 | 0.33 | 0.51 | 1.55 | 1.63 | 400 | 0.53 | 0.92 | 1.74 | 1.24 | ? | | |
| II 09A06 | 100 | 0.96 | 0.31 | 0.32 | 1.81 | 100 | 0.61 | 0.40 | 0.66 | 1.18 | ? | 100 | 1.00 | 0.92 | 0.92 | 0.97 | 400 | 0.25 | 0.37 | 1.48 | 1.56 | NO | YES/? | |
| II 09G09 | 400 | 0.51 | 0.27 | 0.53 | 1.32 | 200 | 0.47 | 0.31 | 0.66 | 1.77 | ? | 400 | 0.50 | 0.62 | 1.24 | 1.31 | 400 | 0.24 | 0.52 | 2.17 | 1.37 | YES | | |
| II 09H07 | 200 | 0.71 | 0.21 | 0.30 | 0.74 | 200 | 0.51 | 0.30 | 0.59 | 1.06 | ? | 200 | 0.62 | 0.69 | 1.11 | 1.17 | 200 | 0.40 | 0.51 | 1.28 | 1.34 | ? | ?/YES | |
| II 10C06 | 400 | 0.41 | 0.26 | 0.63 | 1.59 | 100 | 0.62 | 0.49 | 0.79 | 1.42 | YES | 400 | 0.38 | 0.56 | 1.47 | 1.55 | 400 | 0.25 | 0.37 | 1.48 | 1.56 | YES | | |
| II 12H08 | 200 | 0.68 | 0.26 | 0.38 | 0.96 | 200 | 0.37 | 0.18 | 0.49 | 1.31 | NO | 200 | 0.68 | 0.76 | 1.12 | 1.18 | 400 | 0.17 | 0.36 | 2.12 | 1.34 | ? | YES/? | |
| II 13A07 | 400 | 0.26 | 0.14 | 0.54 | 1.35 | 200 | 0.51 | 0.53 | 1.04 | 1.22 | YES | 400 | 0.23 | 0.34 | 1.48 | 1.56 | 400 | 0.23 | 0.53 | 2.30 | 1.54 | YES | | |
| II 15A08 | 400 | 0.59 | 0.25 | 0.42 | 1.06 | 400 | 0.33 | 0.19 | 0.58 | 1.55 | NO | 400 | 0.60 | 0.67 | 1.12 | 1.18 | 400 | 0.30 | 0.59 | 1.97 | 1.24 | ? | DOUBLE YES | |
| II 16C05 | 400 | 0.62 | 0.23 | 0.37 | 1.93 | 100 | 0.58 | 0.45 | 0.78 | 1.40 | NO | 400 | 0.63 | 0.68 | 1.08 | 1.14 | 400 | 0.24 | 0.36 | 1.50 | 1.58 | NO | | |
| II 18C06 | 400 | 0.44 | 0.14 | 0.32 | 1.80 | 200 | 0.70 | 0.29 | 0.41 | 1.11 | ? | 400 | 0.45 | 0.55 | 1.22 | 1.29 | 400 | 0.39 | 0.54 | 1.64 | 1.17 | ? | | |
| II 19C11 | 400 | 0.30 | 0.10 | 0.33 | 1.83 | 400 | 0.16 | 0.19 | 1.19 | 1.39 | NO | 400 | 0.20 | 0.36 | 1.80 | 1.89 | 400 | 0.38 | 0.47 | 1.24 | 0.88 | NO | YES/? | |
| II 21C03 | 200 | 0.73 | 0.36 | 0.49 | 1.23 | 200 | 0.40 | 0.33 | 0.83 | 1.49 | YES | 200 | 0.72 | 0.78 | 1.11 | 1.17 | 200 | 0.34 | 0.48 | 1.41 | 1.49 | ? | | |
| II 21G12 | 50 | 0.99 | 0.32 | 0.32 | 0.81 | 50 | 0.62 | 0.30 | 0.48 | 0.87 | YES | 50 | 0.92 | 0.88 | 0.96 | 1.01 | 50 | 0.31 | 0.46 | 1.48 | 1.56 | NO | | |
| II 06H10 | 50 | 0.30 | 0.32 | 1.07 | 2.67 | 50 | 0.16 | 0.25 | 1.56 | 4.19 | YES | 50 | 0.28 | 0.33 | 1.13 | 1.24 | 50 | 0.13 | 0.26 | 2.00 | 1.26 | YES | DOUBLE YES | |
| II 16H08 | 20 | 0.12 | 0.16 | 1.33 | 3.33 | 20 | 0.11 | 0.26 | 2.36 | 3.81 | YES | 20 | 0.06 | 0.14 | 2.33 | 2.46 | 60 | 0.13 | 0.33 | 2.54 | 1.92 | YES | DOUBLE YES | |
| II 21F08 | 20 | 0.20 | 0.28 | 1.40 | 3.50 | 40 | 0.14 | 0.34 | 2.43 | 3.91 | YES | 20 | 0.09 | 0.25 | 2.78 | 2.92 | 20 | 0.1 7 | 0.43 | 2.53 | 1.91 | YES | DOUBLE YES | |

FIG. 14

Fig. 22A

N-glycans listed in this table were detected through total ion mapping (M: Mannose, N: N-acethyglucosamine, F: fucose, Gal: Galactose, NeuAc: N-acethylneuraminic acid)

| Structural assignment | | Mass $[M+Na]^+$ | Intensity/Charge state | Glycan % |
|---|---|---|---|---|
| M2N2F | 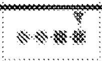 | 1142 | $0.10 \times 10^{-2}$ | 32.47% |
| M3N2 | 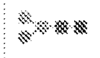 | 1171 | $3.56 \times 10^{-2}$ | 11.33% |
| M3N2F |  | 1345 | $4.18 \times 10^{-2}$ | 13.30% |
| M4N2 | 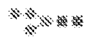 | 1376 | $1.91 \times 10^{-2}$ | 6.08% |
| M5N2 | 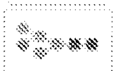 | 1580 | $3.78 \times 10^{-2}$ | 12.03% |
| M6N2 | 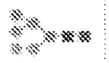 | 1784 | $0.87 \times 10^{-2}$ | 2.76% |
| M7N2 | 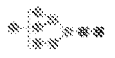 | 1988 | $0.37 \times 10^{-2}$ | 1.18% |
| Gal2N2M3N2F | 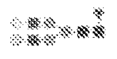 | 2244 | $1.91 \times 10^{-2}$ | 6.06% |
| NeuAc1Gal2N2M3N2 | 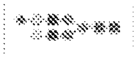 | 2431 | $1.50 \times 10^{-2}$ | 4.76% |
| NeuAc1Gal2N2M3N2F | 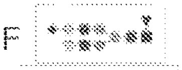 | 2605 | $1.65 \times 10^{-2}$ | 5.25% |
| NeuAc2Gal2N2M3N2 | 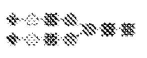 | 2792 | $0.77 \times 10^{-2}$ | 2.45% |
| NeuAc2Gal2N2M3N2F | 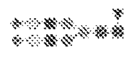 | 2966 | $0.73 \times 10^{-2}$ | 2.32% |
| | | Total | $3.14 \times 10^{-3}$ | 100.00% |

▼ Fucose ■ N-acetylglucosamin ● Mannose

● Galactose ◆ N-acetylneuraminic acid

GlcNAc$_2$(Chitobiose)

$MaN_3GlcNAc_2$

Fig. 23A
| Peptides | Structure | Blank | 4H11 | Anti-glycosylated-MUC16 ectodomain antibodies | | | |
|---|---|---|---|---|---|---|---|
| | | | | 7B12 | 10C6 | 18C6 | 19C11 |
| MUC16 unrelated peptide 18mer | | 0.013 | 0.045 | 0.04 | 0.03 | 0.02 | 0.03 |
| MUC16 unrelated 18mer + GlcNAc2 |  | 0.014 | 0.038 | 0.03 | 0.03 | 0.02 | 0.03 |
| MUC16 15mer | | 0.021 | 0.049 | 1.206 | 0.543 | 1.061 | 1.167 |
| MUC16 15mer + GlcNAc2 |  | 0.019 | 0.06 | 1.323 | 0.573 | 1.442 | 1.514 |
| MUC16 18mer | | 0.032 | 0.076 | 1.09 | 1.06 | 1.01 | 0.98 |
| MUC16 18mer + GlcNAc1 |  | 0.042 | ND | 1.03 | 1.01 | 0.95 | 0.96 |
| MUC16 18mer + GlcNAc2 |  | 0.029 | 0.063 | 1.06 | 1.13 | 1.06 | 1.10 |
| MUC16 18mer + GlcNAc2-Trimannose |  | 0.035 | ND | 1.05 | 0.99 | 0.89 | 0.99 |
| MUC16 18mer + GlcNAc2-FUCOSE1 |  | 0.044 | ND | 1.10 | 1.08 | 1.03 | 1.01 |
| MUC16 Nonglycosylated Peptide2 | | 0.029 | 2.139 | 0.02 | 0.02 | 0.02 | 0.03 |

p55-mer[N1-S55]

GlcNAc$_2$-55-mer $Man_3GlcNAc_2$-55-mer p15-mer[C-G25-V38]

GlcNAc$_2$-15-mer p18-mer[C-T22-V38]

$(GlcNAc_2)_2$-18-mer

GlcNAc$_2$-15-mer-KLH $(GlcNAc_2)_2$-18-mer-KLH

ANTI-MUC16 ANTIBODIES AND USES THEREOF

This application is a national stage of International Patent Application No. PCT/US2016/022643, filed on Mar. 16, 2016, which claims the benefit of U.S. Provisional Application No. 62/134,402, filed on Mar. 17, 2015, which is incorporated by reference herein in its entirety.

This application incorporates by reference a Sequence Listing submitted with this application as a text file entitled "Sequence_Listing_13542-016-228.txt" created on Mar. 14, 2016 and having a size of 375 Kbytes.

1. FIELD

Provided herein are compositions, methods, and uses involving antibodies that immunospecifically bind to MUC16, a tethered mucin protein, and modulate expression and/or activity of MUC16 for managing, treating, or preventing disorders, such as cancer.

2. BACKGROUND

Mucins are important biomolecules for cellular homeostasis and protection of epithelial surfaces. Changes to expression of mucins in ovarian cancer might be exploited in diagnosis, prognosis and treatment (Singh A P, et al. Lancet Oncol 2008; 9(11): 1076-85). MUC16 is one such mucin which is over expressed on most ovarian carcinomas and is an established surrogate serum marker (CA-125) for the detection and progression of ovarian cancers (Badgwell D, et al., Dis Markers 2007; 23(5-6):397410; Bast R C, Jr, et al., Int J Gynecol Cancer 2005; 15 Suppl 3:274-81; Fritsche H A, et al., Clin Chem 1998; 44(7):1379-80; and Krivak T C, et al., Gynecol Oncol 2009; 115(1):81-5). MUC16 is a highly glycosylated mucin composed of a large cleaved and released domain, termed CA-125, consisting of multiple repeat sequences, and a retained domain (MUC-CD) which includes a residual non-repeating extracellular fragment, a transmembrane domain, and a cytoplasmic tail (O'Brien T J, et al. Tumour Biol 2001; 22(6):348-66). Since the antigen is otherwise only expressed at low levels in the uterus, endometrium, fallopian tubes, ovaries, and serosa of the abdominal and thoracic cavities, MUC16 is a potentially attractive target for immune-based therapies.

However, the fact that most of the extracellular domain of MUC16 is cleaved and secreted limits the utility of MUC16 as a target antigen on ovarian carcinomas. In fact, to date, most reported MUC16 monoclonal antibodies bind to epitopes present on the large secreted CA-125 fraction of the glycoprotein, with none known to bind to the retained extra-cellular fraction (MUC-CD) of the antigen (Bellone S, Am J Obstet Gynecol 2009; 200(1):75 el-10, Berek J S. Expert Opin Biol Ther 2004; 4(7): 1159-65; O'Brien T J, et al. Int J Biol Markers 1998; 13(4): 188-95). Thus, the generation of new antibodies to the non-shed region of MUC16 are needed for diagnostic and therapeutic approaches.

3. SUMMARY

Provided are antibodies and antigen-binding fragments thereof, and polypeptides including such antibodies or antigen-binding fragments, such as fusion proteins, conjugates, and/or chimeric antigen receptors, as well as cells expressing the same. Among the antibodies and antigen-binding fragments are those that specifically bind to epitopes of a MUC16 protein. Such antibodies are referred to herein as "MUC16 Glycosylation Antibodies". Such epitopes are typically epitopes within or substantially within an extracellular portion of a MUC16 molecule, generally a non-shed form of MUC16; in some embodiments, the epitope is not within, or the antibody or fragment does not bind to, a tandem repeat region of MUC16 and/or a secreted form of MUC16. In some embodiments, the epitope is within or includes residues within MUC16c114, and typically includes one or more glycosylated residues or glycosylation sites therein. In some embodiments, the epitope includes one or more glycosylation sites, such as sites for N-glycosylation. In some aspects, the epitope includes an asparagine residue corresponding to Asn1806 or Asn1800 of the MUC16 sequence set forth in SEQ ID NO: 150 (and/or a glycosylated form(s) thereof); in some aspects, the epitope includes an asparagine residue corresponding to Asn1806 of SEQ ID NO: 150, but does not include an asparagine residue corresponding to Asn1800 of SEQ ID NO: 150; in some aspects, the epitope includes an asparagine residue corresponding to Asn1800 of SEQ ID NO: 150, but does not include an asparagine residue corresponding to Asn1806 of SEQ ID NO: 150. In some of any of such embodiments, such one or more asparagine is glycosylated, such as N-glycosylated. In some embodiments, the antibody or antigen-binding fragment binds to an epitope within or that includes residues within SEQ ID NO: 131; binds to an epitope within or that includes residues within SEQ ID NO: 130, or a combination thereof; in some embodiments, the antibody or fragment does not immunospecifically bind within a region of MUC16 corresponding to SEQ ID NO: 168, or within residues 2-19 of SEQ ID NO: 168.

In some embodiments, the provided antibodies or antigen-binding fragments include one or more complementarity determining regions (CDRs) corresponding to CDRs of the heavy chain and/or the light chain of an antibody sequence, such as a MUC16-glycosylation site-targeted antibody sequence, described herein, such as of the antibody designated 18C6, of the antibody designated 10C6, and/or of the antibody designated 19C11. In some embodiments, the antibody or fragment has a heavy chain CDR3 (HCDR3) having a sequence corresponding to an HCDR3 of one of the heavy chain sequences provided herein, such as of the heavy chain sequences of the antibody designated 18C6, of the antibody designated 10C6, of the antibody designated 19C11, and/or of the antibody designated 7B12. In some aspects, the HCDR3 has a sequence selected from among IGTAQATDALDY (SEQ ID NO:105), GTAQATDALD (SEQ ID NO:111); $X_{18}$RIGTAQATDALDY (SEQ ID NO:117), wherein $X_{18}$ is T, A, or S; SEQ ID NO: 5; SEQ ID NO: 25; SEQ ID NO: 45; SEQ ID NO: 65; and SEQ ID NO: 85; SEQ ID NO: 31, 51, 71, and 91; SEQ ID NO: 17; SEQ ID ON: 37; SEQ ID NO: 57; SEQ ID NO: 77; and SEQ ID NO: 97.

In some embodiments, the provided antibodies or antigen-binding fragments include a heavy chain CDR1 (HCDR1) having a sequence corresponding to an HCDR1 of one of the heavy chain sequences provided herein, such as of the heavy chain sequences of the antibody designated 18C6, of the antibody designated 10C6, of the antibody designated 19C11, and/or of the antibody designated 7B12. In some aspects, the HCDR1 has a sequence selected from among T$X_1$GMGVG (SEQ ID NO:103), wherein $X_1$ is L or V, sequence GFSL$X_8$T$X_9$GM (SEQ ID NO:109), wherein $X_8$ is N or S, and wherein $X_9$ is L or V, GFSL$X_{15}$T$X_{16}$GMG (SEQ ID NO:115), wherein $X_{15}$ is N or S, and $X_{16}$ is V or L, and the sequence set forth as SEQ ID NO: 3; and the sequence set forth as SEQ ID NO: 9; and the sequence set forth as SEQ ID NO: 15; and the sequence set forth in any of SEQ ID NOs: 23, 43, 63, 83; and the sequence set forth in any of SEQ ID NOs: 29, 49, 69, and 89; and the sequence set forth in any of SEQ ID NOs: 35, 55, 75, and 95.

In some embodiments, the provided antibodies or antigen-binding fragments include a heavy chain CDR2 (HCDR2) having a sequence corresponding to an HCDR2 of one of the heavy chain sequences provided herein, such as of the heavy chain sequences of the antibody designated 18C6, of the antibody designated 10C6, of the antibody designated 19C11, and/or of the antibody designated 7B12. In some aspects, the HCDR2 has a sequence selected from among HIWWDD$X_2$DKYY$X_3$PALKS (SEQ ID NO:104), wherein $X_2$ is E or absent, and $X_3$ is Y or N; WDD$X_{10}$ (SEQ ID NO:110), wherein $X_{10}$ is E or absent; IWWDD$X_{17}$DK (SEQ ID NO:116), wherein $X_{17}$ is E or absent; the sequence set forth as SEQ ID NO: 4; the sequence set forth as SEQ ID NO: 10; and the sequence set forth as SEQ ID NO: 16; and the sequence set forth in any of SEQ ID NOs: 24, 44, 64, 84; and the sequence set forth in any of SEQ ID NOs: 30, 50, 70, 90; and the sequence set forth in any of SEQ ID NOs: 36, 56, 76, 96.

In some embodiments, including any of the aforementioned embodiments, the provided antibodies or antigen-binding fragments include, e.g., further include, a light chain CDR3 (LCDR3) having a sequence corresponding to an LCDR3 of one of the light chain sequences provided herein, such as of the light chain sequences of the antibody designated 18C6, of the antibody designated 10C6, of the antibody designated 19C11, and/or of the antibody designated 7B12. In some aspects, the LCDR3 has a sequence selected from among MQ$X_6$LE$X_7$PLT (SEQ ID NO:108), wherein $X_6$ is G or S and wherein $X_7$ is H or Y; $X_{13}$LE$X_{14}$PL (SEQ ID NO:114) wherein $X_{13}$ is G or S, and wherein $X_{14}$ is H or Y; and MQSLEYPLT (SEQ ID NO:120); a sequence selected from among SEQ ID NOs: 8, 28, 48, 68, and 88; a sequence selected from among SEQ ID NOs: 14, 34, 54, 74, and 94; and a sequence selected from among SEQ ID NOs: 20, 4, 60, 80, and 100.

In some embodiments, including any of the aforementioned embodiments, the provided antibodies or antigen-binding fragments include, e.g., further include, a light chain CDR1 (LCDR1) having a sequence corresponding to an LCDR1 of one of the light chain sequences provided herein, such as of the light chain sequences of the antibody designated 18C6, of the antibody designated 10C6, of the antibody designated 19C11, and/or of the antibody designated 7B12. In some aspects, the LCDR1 has a sequence selected from among RSSKSL$X_4$$X_5$SNGNTYLY (SEQ ID NO:106); SKSL$X_{11}$$X_{12}$SNGNTY (SEQ ID NO:112), wherein $X_{11}$ is L or R, and wherein $X_{12}$ is H or K; KSL$X_{19}$$X_{20}$SNGNTY (SEQ ID NO:118), wherein $X_{19}$ is V or L, and wherein $X_{20}$ is H or K; a sequence selected from among SEQ ID NOs: 6, 26, 46, 66, and 86; a sequence selected from among SEQ ID NOs: 12, 32, 52, 72, and 92; and a sequence selected from among SEQ ID NOs: 18, 38, 58, 78, and 98.

In some embodiments, including any of the aforementioned embodiments, the provided antibodies or antigen-binding fragments include, e.g., further include, a light chain CDR2 (LCDR2) having a sequence corresponding to an LCDR2 of one of the light chain sequences provided herein, such as of the light chain sequences of the antibody designated 18C6, of the antibody designated 10C6, of the antibody designated 19C11, and/or of the antibody designated 7B12. In some aspects, the LCDR2 has a sequence selected from among YMSNLAS (SEQ ID NO:107); YMS (SEQ ID NO:113); and the sequence set forth in any of SEQ ID NOs: 7, 27, 47, 67, 87; 13, 33, 53, 73, 93, 19, 39, 59, 79, 99, 119.

Among the antibodies and antigen-binding fragments of any of the embodiments are those having (a) a VH complementarity determining region (CDR)1 comprising the amino acid sequence T$X_1$GMGVG (SEQ ID NO:103), wherein $X_1$ is L or V; (b) a VH CDR2 comprising the amino acid sequence HIWWDD$X_2$DKYY$X_3$PALKS (SEQ ID NO:104), wherein $X_2$ is E or absent, and $X_3$ is Y or N; and (c) a VH CDR3 comprising the amino acid sequence IGTAQATDALDY (SEQ ID NO:105).

Among the antibodies and antigen-binding fragments of any of the embodiments are those having (a) a VH CDR1 comprising the amino acid sequence GFSL$X_8$T$X_9$GM (SEQ ID NO:109), wherein $X_8$ is N or S, and wherein $X_9$ is L or V; (b) a VH CDR2 comprising the amino acid sequence WDD$X_{10}$ (SEQ ID NO:110), wherein $X_{10}$ is E or absent; and (c) a VH CDR3 comprising the amino acid sequence GTAQATDALD (SEQ ID NO:111).

Among the antibodies and antigen-binding fragments of any of the embodiments are those having (a) a VH CDR1 comprising the amino acid sequence GFSL$X_{15}$T$X_{16}$GMG (SEQ ID NO:115), wherein $X_{15}$ is N or S, and $X_{16}$ is V or L; (b) a VH CDR2 comprising the amino acid sequence IWWDD$X_{17}$DK (SEQ ID NO:116), wherein $X_{17}$ is E or absent; and (c) a VH CDR3 comprising the amino acid sequence $X_{18}$RIGTAQATDALDY (SEQ ID NO:117), wherein $X_{18}$ is T, A, or S.

Among the antibodies and antigen-binding fragments of any of the embodiments are those having a VH CDR1 comprising the amino acid sequence of SEQ ID NO:3, a VH CDR2 comprising the amino acid sequence of SEQ ID NO:4, and a VH CDR3 comprising the amino acid sequence of SEQ ID NO:5; a VH CDR1 comprising the amino acid sequence of SEQ ID NO:9, a VH CDR2 comprising the amino acid sequence of SEQ ID NO:10, and a VH CDR3 comprising the amino acid sequence of SEQ ID NO:11; a VH CDR1 comprising the amino acid sequence of SEQ ID NO:15, a VH CDR2 comprising the amino acid sequence of SEQ ID NO:16, and a VH CDR3 comprising the amino acid sequence of SEQ ID NO:17; a VH CDR1 comprising the amino acid sequence of SEQ ID NO:23, a VH CDR2 comprising the amino acid sequence of SEQ ID NO:24, and a VH CDR3 comprising the amino acid sequence of SEQ ID NO:25; a VH CDR1 comprising the amino acid sequence of SEQ ID NO:29, a VH CDR2 comprising the amino acid sequence of SEQ ID NO:30, and a VH CDR3 comprising the amino acid sequence of SEQ ID NO:31; a VH, which comprises a VH CDR1 comprising the amino acid sequence of SEQ ID NO:35, a VH CDR2 comprising the amino acid sequence of SEQ ID NO:36, and a VH CDR3 comprising the amino acid sequence of SEQ ID NO:37; a VH CDR1 comprising the amino acid sequence of SEQ ID NO:43, a VH CDR2 comprising the amino acid sequence of SEQ ID NO:44, and a VH CDR3 comprising the amino acid sequence of SEQ ID NO:45; a VH, which comprises a VH CDR1 comprising the amino acid sequence of SEQ ID NO:49, a VH CDR2 comprising the amino acid sequence of SEQ ID NO:50, and a VH CDR3 comprising the amino acid sequence of SEQ ID NO:51; a VH CDR1 comprising the amino acid sequence of SEQ ID NO:55, a VH CDR2 comprising the amino acid sequence of SEQ ID NO:56, and a VH CDR3 comprising the amino acid sequence of SEQ ID NO:57; a VH CDR1 comprising the amino acid sequence of SEQ ID NO:63, a VH CDR2 comprising the amino acid sequence of SEQ ID NO:64, and a VH CDR3 comprising the amino acid sequence of SEQ ID NO:65; a VH CDR1 comprising the amino acid sequence of SEQ ID NO:69, a VH CDR2 comprising the amino acid sequence of SEQ ID NO:70, and a VH CDR3 comprising the amino acid sequence of SEQ ID NO:71; a VH CDR1 comprising the amino acid sequence of SEQ ID NO:75, a VH CDR2 comprising the amino acid sequence of SEQ ID NO:76, and a VH CDR3 comprising the amino acid sequence of SEQ ID NO:77; a VH CDR1 comprising the amino acid sequence of SEQ ID NO:83, a VH CDR2 comprising the amino acid sequence of SEQ ID NO:84, and a VH CDR3 comprising the amino acid sequence of SEQ ID NO:85; a VH CDR1 comprising the amino acid sequence of SEQ ID NO:89, a VH CDR2 comprising the amino acid sequence of SEQ ID NO:90, and a VH CDR3 comprising the amino acid sequence of SEQ ID NO:91; a VH, which comprises a VH CDR1 comprising the amino acid sequence of SEQ ID NO:95, a VH CDR2 comprising the amino acid sequence of SEQ ID NO:96, and a VH CDR3 comprising the amino acid sequence of SEQ ID NO:97.

Among the antibodies and antigen-binding fragments of any of the embodiments are those having (a) a VL CDR1 comprising the amino acid sequence RSSKSLX$_4$X$_5$SNGNTYLY (SEQ ID NO:106), wherein X$_4$ is R or L, and X$_5$ is K or H; (b) a VL CDR2 comprising the amino acid sequence YMSNLAS (SEQ ID NO:107); and (c) a VL CDR3 comprising the amino acid sequence MQX$_6$LEX$_7$PLT (SEQ ID NO:108), wherein X$_6$ is G or S, and X$_7$ is H or Y.

Among the antibodies and antigen-binding fragments of any of the embodiments are those having (a) a VL CDR1 comprising the amino acid sequence SKSLX$_{11}$X$_{12}$SNGNTY (SEQ ID NO:112), wherein X$_{11}$ is L or R, and X$_{12}$ is H or K; (b) a VL CDR2 comprising the amino acid sequence YMS (SEQ ID NO:113); and (c) a VL CDR3 comprising the amino acid sequence X$_{13}$LEX$_{14}$PL (SEQ ID NO:114), wherein X$_{13}$ is G or S, and X$_{14}$ is H or Y.

Among the antibodies and antigen-binding fragments of any of the embodiments are those having a VL CDR1 comprising the amino acid sequence KSLX$_{19}$X$_{20}$SNGNTY (SEQ ID NO:118), wherein X$_{19}$ is V or L, and X$_{20}$ is H or K; (b) a VL CDR2 comprising the amino acid sequence YMS (SEQ ID NO:119); and (c) a VL CDR3 comprising the amino acid sequence MQSLEYPLT (SEQ ID NO:120).

Among the antibodies and antigen-binding fragments of any of the embodiments are those having a VL CDR1 comprising the amino acid sequence of SEQ ID NO:26, a VL CDR2 comprising the amino acid sequence of SEQ ID NO:27, and a VL CDR3 comprising the amino acid sequence of SEQ ID NO:28; or a VL CDR1 comprising the amino acid sequence of SEQ ID NO:32, a VL CDR2 comprising the amino acid sequence of SEQ ID NO:33, and a VL CDR3 comprising the amino acid sequence of SEQ ID NO:34; or a VL CDR1 comprising the amino acid sequence of SEQ ID NO:38, a VL CDR2 comprising the amino acid sequence of SEQ ID NO:39, and a VL CDR3 comprising the amino acid sequence of SEQ ID NO:40; or a VL CDR1 comprising the amino acid sequence of SEQ ID NO:46, a VL CDR2 comprising the amino acid sequence of SEQ ID NO:47, and a VL CDR3 comprising the amino acid sequence of SEQ ID NO:48; or a VL CDR1 comprising the amino acid sequence of SEQ ID NO:52, a VL CDR2 comprising the amino acid sequence of SEQ ID NO:53, and a VL CDR3 comprising the amino acid sequence of SEQ ID NO:54; or a VL CDR1 comprising the amino acid sequence of SEQ ID NO:58, a VL CDR2 comprising the amino acid sequence of SEQ ID NO:59, and a VL CDR3 comprising the amino acid sequence of SEQ ID NO:60; or a VL CDR1 comprising the amino acid sequence of SEQ ID NO:86, a VL CDR2 comprising the amino acid sequence of SEQ ID NO:87, and a VL CDR3 comprising the amino acid sequence of SEQ ID NO:88; or a VL CDR1 comprising the amino acid sequence of SEQ ID NO:92, a VL CDR2 comprising the amino acid sequence of SEQ ID NO:93, and a VL CDR3 comprising the amino acid sequence of SEQ ID NO:94; or a VL CDR1 comprising the amino acid sequence of SEQ ID NO:98, a VL CDR2 comprising the amino acid sequence of SEQ ID NO:99, and a VL CDR3 comprising the amino acid sequence of SEQ ID NO:100; or a VL CDR1 comprising the amino acid sequence of SEQ ID NO:6, a VL CDR2 comprising the amino acid sequence of SEQ ID NO:7, and a VL CDR3 comprising the amino acid sequence of SEQ ID NO:8; or a VL CDR1 comprising the amino acid sequence of SEQ ID NO:12, a VL CDR2 comprising the amino acid sequence of SEQ ID NO:13, and a VL CDR3 comprising the amino acid sequence of SEQ ID NO:14; or a VL CDR1 comprising the amino acid sequence of SEQ ID NO:18, a VL CDR2 comprising the amino acid sequence of SEQ ID NO:19, and a VL CDR3 comprising the amino acid sequence of SEQ ID NO:20; or a VL CDR1 comprising the amino acid sequence of SEQ ID NO:66, a VL CDR2 comprising the amino acid sequence of SEQ ID NO:67, and a VL CDR3 comprising the amino acid sequence of SEQ ID NO:68; or a VL CDR1 comprising the amino acid sequence of SEQ ID NO:72, a VL CDR2 comprising the amino acid sequence of SEQ ID NO:73, and a VL CDR3 comprising the amino acid sequence of SEQ ID NO:74; or a VL CDR1 comprising the amino acid sequence of SEQ ID NO:78, a VL CDR2 comprising the amino acid sequence of SEQ ID NO:79, and a VL CDR3 comprising the amino acid sequence of SEQ ID NO:80.

Among the antibodies and antigen-binding fragments of any of the embodiments are those having (a) (i) a VH comprising a VH CDR1 comprising the amino acid sequence TX$_1$GMGVG (SEQ ID NO:103), wherein X$_1$ is L or V; a VH CDR2 comprising the amino acid sequence HIWWDDX$_2$DKYYX$_3$PALKS (SEQ ID NO:104), wherein X$_2$ is E or absent, and X$_3$ is Y or N; and a VH CDR3 comprising the amino acid sequence IGTAQATDALDY (SEQ ID NO:105); and (ii) a VL comprising a VL CDR1 comprising the amino acid sequence RSSKSLX$_4$X$_5$SNGNTYLY (SEQ ID NO:106), wherein X$_4$ is R or L, and X$_5$ is K or H; a VL CDR2 comprising the amino acid sequence YMSNLAS (SEQ ID NO:107); and a VL CDR3 comprising the amino acid sequence MQX$_6$LEX$_7$PLT (SEQ ID NO:108), wherein X$_6$ is G or S, and X$_7$ is H or Y; or (b) (i) a VH comprising a VH CDR1 comprising the amino acid sequence GFSLX$_8$TX$_9$GM (SEQ ID NO:109), wherein X$_8$ is N or S, and wherein X$_9$ is L or V; a VH CDR2 comprising the amino acid sequence WDDX$_{10}$ (SEQ ID NO:110), wherein X$_{10}$ is E or absent; and a VH CDR3 comprising the amino acid sequence GTAQATDALD (SEQ ID NO:111); and (ii) a VL comprising a VL CDR1 comprising the amino acid sequence SKSLX$_{11}$X$_{12}$SNGNTY (SEQ ID NO:112), wherein X$_{11}$ is L or R, and X$_{12}$ is H or K; a VL CDR2 comprising the amino acid sequence YMS (SEQ ID NO:113); and a VL CDR3 comprising the amino acid sequence X$_{13}$LEX$_{14}$PL (SEQ ID NO:114), wherein X$_{13}$ is G or S, and X$_{14}$ is H or Y; or (c) (i) a VH CDR1 comprising the amino acid sequence GFSLX$_{15}$TX$_{16}$GMG (SEQ ID NO:115), wherein X$_{15}$ is N or S, and X$_{16}$ is V or L; a VH CDR2 comprising the amino acid sequence IWWDDX$_{17}$DK (SEQ ID NO:116), wherein X$_{17}$ is E or absent; and a VH CDR3 comprising the amino acid sequence $X_{18}$RIGTAQATDALDY (SEQ ID NO:117), wherein $X_{18}$ is T, A, or S; and (ii) a VL comprising a VL CDR1 comprising the amino acid sequence KSL$X_{19}X_{20}$SNGNTY (SEQ ID NO:118), wherein $X_{19}$ is V or L, and $X_{20}$ is H or K; a VL CDR2 comprising the amino acid sequence YMS (SEQ ID NO:119); and a VL CDR3 comprising the amino acid sequence MQSLEYPLT (SEQ ID NO:120); or (d) (i) a VH comprising a VH CDR1 comprising the amino acid sequence of SEQ ID NO:23, a VH CDR2 comprising the amino acid sequence of SEQ ID NO:24, and a VH CDR3 comprising the amino acid sequence of SEQ ID NO:25; and (ii) a VL comprising a VL CDR1 comprising the amino acid sequence of SEQ ID NO:26, a VL CDR2 comprising the amino acid sequence of SEQ ID NO:27, and a VL CDR3 comprising the amino acid sequence of SEQ ID NO:28; or (e) (i) a VH comprising a VH CDR1 comprising the amino acid sequence of SEQ ID NO:29, a VH CDR2 comprising the amino acid sequence of SEQ ID NO:30, and a VH CDR3 comprising the amino acid sequence of SEQ ID NO:31; and (ii) a VL comprising a VL CDR1 comprising the amino acid sequence of SEQ ID NO:32, a VL CDR2 comprising the amino acid sequence of SEQ ID NO:33, and a VL CDR3 comprising the amino acid sequence of SEQ ID NO:34; or (f) (i) a VH comprising a VH CDR1 comprising the amino acid sequence of SEQ ID NO:35, a VH CDR2 comprising the amino acid sequence of SEQ ID NO:36, and a VH CDR3 comprising the amino acid sequence of SEQ ID NO:37; and (ii) a VL comprising a VL CDR1 comprising the amino acid sequence of SEQ ID NO:38, a VL CDR2 comprising the amino acid sequence of SEQ ID NO:39, and a VL CDR3 comprising the amino acid sequence of SEQ ID NO:40; or (g) (i) a VH comprising a VH CDR1 comprising the amino acid sequence of SEQ ID NO:43, a VH CDR2 comprising the amino acid sequence of SEQ ID NO:44, and a VH CDR3 comprising the amino acid sequence of SEQ ID NO:45; and (ii) a VL comprising a VL CDR1 comprising the amino acid sequence of SEQ ID NO:46, a VL CDR2 comprising the amino acid sequence of SEQ ID NO:47, and a VL CDR3 comprising the amino acid sequence of SEQ ID NO:48; or (h) (i) a VH comprising a VH CDR1 comprising the amino acid sequence of SEQ ID NO:49, a VH CDR2 comprising the amino acid sequence of SEQ ID NO:50, and a VH CDR3 comprising the amino acid sequence of SEQ ID NO:51; and (ii) a VL comprising a VL CDR1 comprising the amino acid sequence of SEQ ID NO:52, a VL CDR2 comprising the amino acid sequence of SEQ ID NO:53, and a VL CDR3 comprising the amino acid sequence of SEQ ID NO:54; or (i) (i) a VH comprising a VH CDR1 comprising the amino acid sequence of SEQ ID NO:55, a VH CDR2 comprising the amino acid sequence of SEQ ID NO:56, and a VH CDR3 comprising the amino acid sequence of SEQ ID NO:57; and (ii) a VL comprising a VL CDR1 comprising the amino acid sequence of SEQ ID NO:58, a VL CDR2 comprising the amino acid sequence of SEQ ID NO:59, and a VL CDR3 comprising the amino acid sequence of SEQ ID NO:60; or (j) (i) a VH comprising a VH CDR1 comprising the amino acid sequence of SEQ ID NO:83, a VH CDR2 comprising the amino acid sequence of SEQ ID NO:84, and a VH CDR3 comprising the amino acid sequence of SEQ ID NO:85; and (ii) a VL comprising a VL CDR1 comprising the amino acid sequence of SEQ ID NO:86, a VL CDR2 comprising the amino acid sequence of SEQ ID NO:87, and a VL CDR3 comprising the amino acid sequence of SEQ ID NO:88; or (k) (i) a VH comprising a VH CDR1 comprising the amino acid sequence of SEQ ID NO:89, a VH CDR2 comprising the amino acid sequence of SEQ ID NO:90, and a VH CDR3 comprising the amino acid sequence of SEQ ID NO:91; and (ii) a VL comprising a VL CDR1 comprising the amino acid sequence of SEQ ID NO:92, a VL CDR2 comprising the amino acid sequence of SEQ ID NO:93, and a VL CDR3 comprising the amino acid sequence of SEQ ID NO:94; or (l) (i) a VH comprising a VH CDR1 comprising the amino acid sequence of SEQ ID NO:95, a VH CDR2 comprising the amino acid sequence of SEQ ID NO:96, and a VH CDR3 comprising the amino acid sequence of SEQ ID NO:97 and (ii) a VL comprising a VL CDR1 comprising the amino acid sequence of SEQ ID NO:98, a VL CDR2 comprising the amino acid sequence of SEQ ID NO:99, and a VL CDR3 comprising the amino acid sequence of SEQ ID NO:100; or (m) (i) a VH comprising a VH CDR1 comprising the amino acid sequence of SEQ ID NO:3, a VH CDR2 comprising the amino acid sequence of SEQ ID NO:4, and a VH CDR3 comprising the amino acid sequence of SEQ ID NO:5; and (ii) a VL comprising a VL CDR1 comprising the amino acid sequence of SEQ ID NO:6, a VL CDR2 comprising the amino acid sequence of SEQ ID NO:7, and a VL CDR3 comprising the amino acid sequence of SEQ ID NO:8; or (n) (i) a VH comprising a VH CDR1 comprising the amino acid sequence of SEQ ID NO:9, a VH CDR2 comprising the amino acid sequence of SEQ ID NO:10, and a VH CDR3 comprising the amino acid sequence of SEQ ID NO:11; and (ii) a VL comprising a VL CDR1 comprising the amino acid sequence of SEQ ID NO:12, a VL CDR2 comprising the amino acid sequence of SEQ ID NO:13, and a VL CDR3 comprising the amino acid sequence of SEQ ID NO:14; or (o) (i) a VH comprising a VH CDR1 comprising the amino acid sequence of SEQ ID NO:15, a VH CDR2 comprising the amino acid sequence of SEQ ID NO:16, and a VH CDR3 comprising the amino acid sequence of SEQ ID NO:17; and (ii) a VL comprising a VL CDR1 comprising the amino acid sequence of SEQ ID NO:18, a VL CDR2 comprising the amino acid sequence of SEQ ID NO:19, and a VL CDR3 comprising the amino acid sequence of SEQ ID NO:20; or (p) (i) a VH comprising a VH CDR1 comprising the amino acid sequence of SEQ ID NO:63, a VH CDR2 comprising the amino acid sequence of SEQ ID NO:64, and a VH CDR3 comprising the amino acid sequence of SEQ ID NO:65; and (ii) a VL comprising a VL CDR1 comprising the amino acid sequence of SEQ ID NO:66, a VL CDR2 comprising the amino acid sequence of SEQ ID NO:67, and a VL CDR3 comprising the amino acid sequence of SEQ ID NO:68; or (q) (i) a VH comprising a VH CDR1 comprising the amino acid sequence of SEQ ID NO:69, a VH CDR2 comprising the amino acid sequence of SEQ ID NO:70, and a VH CDR3 comprising the amino acid sequence of SEQ ID NO:71; and (ii) a VL comprising a VL CDR1 comprising the amino acid sequence of SEQ ID NO:72, a VL CDR2 comprising the amino acid sequence of SEQ ID NO:73, and a VL CDR3 comprising the amino acid sequence of SEQ ID NO:74; or (r) (i) a VH comprising a VH CDR1 comprising the amino acid sequence of SEQ ID NO:75, a VH CDR2 comprising the amino acid sequence of SEQ ID NO:76, and a VH CDR3 comprising the amino acid sequence of SEQ ID NO:77; and (ii) a VL comprising a VL CDR1 comprising the amino acid sequence of SEQ ID NO:78, a VL CDR2 comprising the amino acid sequence of SEQ ID NO:79, and a VL CDR3 comprising the amino acid sequence of SEQ ID NO:80.

Among the antibodies and antigen-binding fragments of any of the embodiments are those having: (a) (i) a VH comprising the amino acid sequence of QV$X_{21}$LKESGPG$X_{22}$LQPSQTLSLTCSFSGFSL$X_{23}$T$X_{24}$ GMGVGW$X_{25}$RQ$X_{26}$SGKGLEWLAHIWWDD$X_{27}$DKY-Y$X_{28}$PALKSRLTIS$X_{29}X_{30}X_{31}$SKNQVFLKI$X_{32}$NV$X_{33}$ TADX$_{34}$ATYYCX$_{35}$RIGTAQATDALDYWGQGTSVTVSS (SEQ ID NO:101), wherein $X_{21}$ is T or N, $X_{22}$ is I or K, $X_{23}$ is N or S, $X_{24}$ is V or L, $X_{25}$ is S or I, $X_{26}$ is P or S, $X_{27}$ is E or absent, $X_{28}$ is N or Y, $X_{29}$ is K or R, $X_{30}$ is A or D, $X_{31}$ is T or S, $X_{32}$ is V or A, $X_{33}$ is G or D, $X_{34}$ is T, I, or S, and $X_{35}$ is T, S, or A; and (ii) a VL comprising the amino acid sequence of DIVMTQAAPSX$_{36}$X$_{37}$VTPGESVSISCRSSKSLX$_{38}$X$_{39}$SNGNTYLYWFLQRPGQSPQRLIYYMSNLASGVPDRFSGRGSGTDFTLX$_{40}$SRVEAX$_{41}$DVGVYYCMQX$_{42}$LEX$_{43}$PLTFGGGTKLEIK (SEQ ID NO:102), wherein $X_{36}$ is I or V, $X_{37}$ is P or S, $X_{38}$ is R or L, $X_{39}$ is K or H, $X_{40}$ is R or K, $X_{41}$ is E or G, $X_{42}$ is S or G, and $X_{43}$ is Y or H; or (b) (i) a VH comprising the amino acid sequence of SEQ ID NO:1; and (ii) a VL comprising the amino acid sequence of SEQ ID NO:2; or (c) (i) a VH comprising the amino acid sequence of SEQ ID NO:21; and (ii) a VL comprising the amino acid sequence of SEQ ID NO:22; or (d) (i) a VH comprising the amino acid sequence of SEQ ID NO:41; and (ii) a VL comprising the amino acid sequence of SEQ ID NO:42; or (e) (i) a VH comprising the amino acid sequence of SEQ ID NO:61; and (ii) a VL comprising the amino acid sequence of SEQ ID NO:62; or (f) (i) a VH comprising the amino acid sequence of SEQ ID NO:81; and (ii) a VL comprising the amino acid sequence of SEQ ID NO:82.

Also among the provided antibodies or antigen-binding fragments are those having at least 90, 95, 96, 97, 98, 99, or 100% identity with the VH and/or VL sequence(s) of any such antibodies and/or of any of the antibodies set forth in Tables 1 and 2. Also among the provided antibodies and fragments thereof are those that compete for binding to MUC16 and/or an epitope thereof with any of such antibodies.

Also provided are fusion proteins, such as chimeric molecules, and/or conjugates, comprising any of the antibodies, such as chimeric antigen receptors (CARs) containing such antibodies or fragments, and cells expressing such molecules. Also provided are humanized versions of any such antibodies.

In some embodiments, provided herein is an antibody or an antigen-binding fragment thereof, wherein the antibody (a) immunospecifically binds to a cell recombinantly expressing a first form of MUC16, which first form is glycosylated, and wherein the amino acid sequence of the first form is SEQ ID NO:133; (b) lacks immunospecific binding to a cell recombinantly expressing a second form of MUC16, which second form is unglycosylated, and wherein the amino acid sequence of the second form is SEQ ID NO:139; and (c) inhibits matrigel invasion in vitro of cells recombinantly expressing said first form of MUC16. In certain embodiments, (i) the cell recombinantly expressing the first form of MUC16 is a SKOV3 cell; (ii) the cell recombinantly expressing the second form of MUC16 is a SKOV3 cell; and (iii) the cells in step (c) are SKOV3 cells. In a specific embodiment, the antibody lacks immunospecific binding to a cell recombinantly expressing a third form of MUC16, which third form is glycosylated, and wherein the amino acid sequence of the third form is SEQ ID NO:139. In certain embodiments, (i) the cell recombinantly expressing the first form of MUC16 is a SKOV3 cell; (ii) the cell recombinantly expressing the second form of MUC16 is a SKOV3 cell; and (iii) the cells in step (c) are SKOV3 cells. In certain embodiments, (i) the cell recombinantly expressing the first form of MUC16 is a SKOV3 cell; (ii) the cell recombinantly expressing the second form of MUC16 is a SKOV3 cell; (iii) the cell recombinantly expressing the third form of MUC16 is a SKOV3 cell; and (iv) the cells in step (c) are SKOV3 cells.

Also provided herein is an antibody or an antigen-binding fragment thereof, wherein the antibody (a) immunospecifically binds to a cell recombinantly expressing a first form of MUC16, which first form is glycosylated, and wherein the amino acid sequence of the first form is SEQ ID NO:133; (b) lacks immunospecific binding to a cell recombinantly expressing a third form of MUC16, which third form is glycosylated, and wherein the amino acid sequence of the second form is SEQ ID NO:139; and (c) inhibits matrigel invasion in vitro of cells recombinantly expressing said first form of MUC16. In certain embodiments, (i) the cell recombinantly expressing the first form of MUC16 is a SKOV3 cell; (ii) the cell recombinantly expressing the third form of MUC16 is a SKOV3 cell; and (iii) the cells in step (c) are SKOV3 cells.

In certain embodiments the antibody or antigen-binding fragment thereof immunospecifically binds to an epitope comprising N-glycosylated asparagine 1806 of SEQ ID NO: 150.

In certain embodiments, the antibody or antigen-binding fragment thereof immunospecifically binds to the amino acid sequence CTRNGTQLQNFTLDRSSV (SEQ ID NO:130), wherein amino acid residue number 4 (N4) and amino acid residue number 10 (N10) of CTRNGTQLQNFTLDRSSV (SEQ ID NO: 130) are glycosylated. In certain embodiments, the antibody or antigen-binding fragment thereof immunospecifically binds to the amino acid sequence CGTQLQNFTLDRSSV (SEQ ID NO:131), wherein amino acid residue number 7 (N7) of CGTQLQNFTLDRSSV (SEQ ID NO:131) is glycosylated. In certain embodiments, the glycosylation consists of an N-linked chitobiose.

In certain embodiments, the antibody or antigen-binding fragment thereof is internalized into a cell expressing the first form of MUC16 upon contacting the cell with the antibody or antigen-binding fragment. In certain embodiments, the cell is a SKOV3 cell that recombinantly expresses the first form of MUC16.

In certain embodiments, the antibody or antigen-binding fragment thereof inhibits growth of a tumor that expresses a glycosylated form of MUC16.

In certain embodiments, the antibody is a monoclonal antibody.

In certain embodiments, the antibody or antigen-binding fragment thereof comprises a heavy chain variable region (VH), which comprises (a) a VH complementarity determining region (CDR)1 comprising the amino acid sequence TX$_1$GMGVG (SEQ ID NO:103), wherein $X_1$ is L or V; (b) a VH CDR2 comprising the amino acid sequence HIWWDDX$_2$DKYYX$_3$PALKS (SEQ ID NO:104), wherein $X_2$ is E or absent, and $X_3$ is Y or N; and (c) a VH CDR3 comprising the amino acid sequence IGTAQATDALDY (SEQ ID NO:105).

In certain embodiments, the antibody or antigen-binding fragment thereof comprises a VH, which comprises (a) a VH CDR1 comprising the amino acid sequence GFSLX$_8$TX$_9$GM (SEQ ID NO:109), wherein $X_8$ is N or S, and wherein $X_9$ is L or V; (b) a VH CDR2 comprising the amino acid sequence WDDX$_{10}$ (SEQ ID NO:110), wherein $X_{10}$ is E or absent; and (c) a VH CDR3 comprising the amino acid sequence GTAQATDALD (SEQ ID NO:111).

In certain embodiments, the antibody or antigen-binding fragment thereof comprises a VH, which comprises (a) a VH CDR1 comprising the amino acid sequence GFSL$X_{15}$T$X_{16}$GMG (SEQ ID NO:115), wherein $X_{15}$ is N or S, and $X_{16}$ is V or L; (b) a VH CDR2 comprising the amino acid sequence IWWDD$X_{17}$DK (SEQ ID NO: 116), wherein $X_{17}$ is E or absent; and (c) a VH CDR3 comprising the amino acid sequence $X_{18}$RIGTAQATDALDY (SEQ ID NO:117), wherein $X_{18}$ is T, A, or S.

In certain embodiments, the antibody or antigen-binding fragment thereof comprises a VH, which comprises a VH CDR1 comprising the amino acid sequence of SEQ ID NO:3, a VH CDR2 comprising the amino acid sequence of SEQ ID NO:4, and a VH CDR3 comprising the amino acid sequence of SEQ ID NO:5.

In certain embodiments, the antibody or antigen-binding fragment thereof comprises a VH, which comprises a VH CDR1 comprising the amino acid sequence of SEQ ID NO:9, a VH CDR2 comprising the amino acid sequence of SEQ ID NO:10, and a VH CDR3 comprising the amino acid sequence of SEQ ID NO:11.

In certain embodiments, the antibody or antigen-binding fragment thereof comprises a VH, which comprises a VH CDR1 comprising the amino acid sequence of SEQ ID NO:15, a VH CDR2 comprising the amino acid sequence of SEQ ID NO:16, and a VH CDR3 comprising the amino acid sequence of SEQ ID NO:17.

In certain embodiments, the antibody or antigen-binding fragment thereof comprises a VH, which comprises a VH CDR1 comprising the amino acid sequence of SEQ ID NO:23, a VH CDR2 comprising the amino acid sequence of SEQ ID NO:24, and a VH CDR3 comprising the amino acid sequence of SEQ ID NO:25.

In certain embodiments, the antibody or antigen-binding fragment thereof comprises a VH, which comprises a VH CDR1 comprising the amino acid sequence of SEQ ID NO:29, a VH CDR2 comprising the amino acid sequence of SEQ ID NO:30, and a VH CDR3 comprising the amino acid sequence of SEQ ID NO:31.

In certain embodiments, the antibody or antigen-binding fragment thereof comprises a VH, which comprises a VH CDR1 comprising the amino acid sequence of SEQ ID NO:35, a VH CDR2 comprising the amino acid sequence of SEQ ID NO:36, and a VH CDR3 comprising the amino acid sequence of SEQ ID NO:37.

In certain embodiments, the antibody or antigen-binding fragment thereof comprises a VH, which comprises a VH CDR1 comprising the amino acid sequence of SEQ ID NO:43, a VH CDR2 comprising the amino acid sequence of SEQ ID NO:44, and a VH CDR3 comprising the amino acid sequence of SEQ ID NO:45.

In certain embodiments, the antibody or antigen-binding fragment thereof comprises a VH, which comprises a VH CDR1 comprising the amino acid sequence of SEQ ID NO:49, a VH CDR2 comprising the amino acid sequence of SEQ ID NO:50, and a VH CDR3 comprising the amino acid sequence of SEQ ID NO:51.

In certain embodiments, the antibody or antigen-binding fragment thereof comprises a VH, which comprises a VH CDR1 comprising the amino acid sequence of SEQ ID NO:55, a VH CDR2 comprising the amino acid sequence of SEQ ID NO:56, and a VH CDR3 comprising the amino acid sequence of SEQ ID NO:57.

In certain embodiments, the antibody or antigen-binding fragment thereof comprises a VH, which comprises a VH CDR1 comprising the amino acid sequence of SEQ ID NO:63, a VH CDR2 comprising the amino acid sequence of SEQ ID NO:64, and a VH CDR3 comprising the amino acid sequence of SEQ ID NO:65.

In certain embodiments, the antibody or antigen-binding fragment thereof comprises a VH, which comprises a VH CDR1 comprising the amino acid sequence of SEQ ID NO:69, a VH CDR2 comprising the amino acid sequence of SEQ ID NO:70, and a VH CDR3 comprising the amino acid sequence of SEQ ID NO:71.

In certain embodiments, the antibody or antigen-binding fragment thereof comprises a VH, which comprises a VH CDR1 comprising the amino acid sequence of SEQ ID NO:75, a VH CDR2 comprising the amino acid sequence of SEQ ID NO:76, and a VH CDR3 comprising the amino acid sequence of SEQ ID NO:77.

In certain embodiments, the antibody or antigen-binding fragment thereof comprises a VH CDR1 comprising the amino acid sequence of SEQ ID NO:83, a VH CDR2 comprising the amino acid sequence of SEQ ID NO:84, and a VH CDR3 comprising the amino acid sequence of SEQ ID NO:85.

In certain embodiments, the antibody or antigen-binding fragment thereof comprises a VH, which comprises a VH CDR1 comprising the amino acid sequence of SEQ ID NO:89, a VH CDR2 comprising the amino acid sequence of SEQ ID NO:90, and a VH CDR3 comprising the amino acid sequence of SEQ ID NO:91.

In certain embodiments, the antibody or antigen-binding fragment thereof comprises a VH, which comprises a VH CDR1 comprising the amino acid sequence of SEQ ID NO:95, a VH CDR2 comprising the amino acid sequence of SEQ ID NO:96, and a VH CDR3 comprising the amino acid sequence of SEQ ID NO:97.

In certain embodiments, the antibody or antigen-binding fragment thereof comprises a VH comprising the amino acid sequence of QV$X_{21}$LKESGPG$X_{22}$LQPSQTLSLTCSFSG-FSL$X_{23}$T$X_{24}$GMGVGW$X_{25}$RQ$X_{26}$SGKGLEWLAHIW-WDD$X_{27}$DKYY$X_{28}$PALKSRLTIS$X_{29}X_{30}X_{31}$SKNQVFL-KI$X_{32}$NV$X_{33}$TAD$X_{34}$ATYYC$X_{35}$RIGTAQATDALDYW-GQGTSVTVSS (SEQ ID NO:101), wherein $X_{21}$ is T or N, $X_{22}$ is I or K, $X_{23}$ is N or S, $X_{24}$ is V or L, $X_{25}$ is S or I, $X_{26}$ is P or S, $X_{27}$ is E or absent, $X_{28}$ is N or Y, $X_{29}$ is K or R, $X_{30}$ is A or D, $X_{31}$ is T or S, $X_{32}$ is V or A, $X_{33}$ is G or D, $X_{34}$ is T, I, or S, and $X_{35}$ is T, S, or A.

In certain embodiments, the antibody or antigen-binding fragment thereof comprises a VH comprising the amino acid sequence of SEQ ID NO:1.

In certain embodiments, the antibody or antigen-binding fragment thereof comprises a VH comprising the amino acid sequence of SEQ ID NO:21.

In certain embodiments, the antibody or antigen-binding fragment thereof comprises a VH comprising the amino acid sequence of SEQ ID NO:41.

In certain embodiments, the antibody or antigen-binding fragment thereof comprises a VH comprising the amino acid sequence of SEQ ID NO:61.

In certain embodiments, the antibody or antigen-binding fragment thereof comprises a VH comprising the amino acid sequence of SEQ ID NO:81.

In certain embodiments, the antibody or antigen-binding fragment thereof comprises a light chain variable region (VL), which comprises (a) a VL CDR1 comprising the amino acid sequence RSSKSL$X_4X_5$SNGNTYLY (SEQ ID NO:106), wherein $X_4$ is R or L, and $X_5$ is K or H; (b) a VL CDR2 comprising the amino acid sequence YMSNLAS (SEQ ID NO:107); and (c) a VL CDR3 comprising the amino acid sequence MQ$X_6$LE$X_7$PLT (SEQ ID NO:108), wherein $X_6$ is G or S, and $X_7$ is H or Y.

In certain embodiments, the antibody or antigen-binding fragment thereof comprises a VL, which comprises (a) a VL CDR1 comprising the amino acid sequence SKSL$X_{11}X_{12}$SNGNTY (SEQ ID NO: 112), wherein $X_{11}$ is L or R, and $X_{12}$ is H or K; (b) a VL CDR2 comprising the amino acid sequence YMS (SEQ ID NO:113); and (c) a VL CDR3 comprising the amino acid sequence $X_{13}LEX_{14}PL$ (SEQ ID NO:114), wherein $X_{13}$ is G or S, and $X_{14}$ is H or Y.

In certain embodiments, the antibody or antigen-binding fragment thereof comprises a VL, which comprises (a) a VL CDR1 comprising the amino acid sequence $KSLX_{19}X_{20}SNGNTY$ (SEQ ID NO:118), wherein $X_{19}$ is V or L, and $X_{20}$ is H or K; (b) a VL CDR2 comprising the amino acid sequence YMS (SEQ ID NO:119); and (c) a VL CDR3 comprising the amino acid sequence MQSLEYPLT (SEQ ID NO:120).

In certain embodiments, the antibody or antigen-binding fragment thereof comprises a light chain variable region (VL), which comprises a VL CDR1 comprising the amino acid sequence of SEQ ID NO:26, a VL CDR2 comprising the amino acid sequence of SEQ ID NO:27, and a VL CDR3 comprising the amino acid sequence of SEQ ID NO:28.

In certain embodiments, the antibody or antigen-binding fragment thereof comprises a VL, which comprises a VL CDR1 comprising the amino acid sequence of SEQ ID NO:32, a VL CDR2 comprising the amino acid sequence of SEQ ID NO:33, and a VL CDR3 comprising the amino acid sequence of SEQ ID NO:34.

In certain embodiments, the antibody or antigen-binding fragment thereof comprises a VL, which comprises a VL CDR1 comprising the amino acid sequence of SEQ ID NO:38, a VL CDR2 comprising the amino acid sequence of SEQ ID NO:39, and a VL CDR3 comprising the amino acid sequence of SEQ ID NO:40.

In certain embodiments, the antibody or antigen-binding fragment thereof comprises a VL, which comprises a VL CDR1 comprising the amino acid sequence of SEQ ID NO:46, a VL CDR2 comprising the amino acid sequence of SEQ ID NO:47, and a VL CDR3 comprising the amino acid sequence of SEQ ID NO:48.

In certain embodiments, the antibody or antigen-binding fragment thereof comprises a VL, which comprises a VL CDR1 comprising the amino acid sequence of SEQ ID NO:52, a VL CDR2 comprising the amino acid sequence of SEQ ID NO:53, and a VL CDR3 comprising the amino acid sequence of SEQ ID NO:54.

In certain embodiments, the antibody or antigen-binding fragment thereof comprises a VL, which comprises a VL CDR1 comprising the amino acid sequence of SEQ ID NO:58, a VL CDR2 comprising the amino acid sequence of SEQ ID NO:59, and a VL CDR3 comprising the amino acid sequence of SEQ ID NO:60.

In certain embodiments, the antibody or antigen-binding fragment thereof comprises a VL, which comprises a VL CDR1 comprising the amino acid sequence of SEQ ID NO:86, a VL CDR2 comprising the amino acid sequence of SEQ ID NO:87, and a VL CDR3 comprising the amino acid sequence of SEQ ID NO:88.

In certain embodiments, the antibody or antigen-binding fragment thereof comprises a VL, which comprises a VL CDR1 comprising the amino acid sequence of SEQ ID NO:92, a VL CDR2 comprising the amino acid sequence of SEQ ID NO:93, and a VL CDR3 comprising the amino acid sequence of SEQ ID NO:94.

In certain embodiments, the antibody or antigen-binding fragment thereof comprises a VL, which comprises a VL CDR1 comprising the amino acid sequence of SEQ ID NO:98, a VL CDR2 comprising the amino acid sequence of SEQ ID NO:99, and a VL CDR3 comprising the amino acid sequence of SEQ ID NO:100.

In certain embodiments, the antibody or antigen-binding fragment thereof comprises a VL, which comprises a VL CDR1 comprising the amino acid sequence of SEQ ID NO:6, a VL CDR2 comprising the amino acid sequence of SEQ ID NO:7, and a VL CDR3 comprising the amino acid sequence of SEQ ID NO:8.

In certain embodiments, the antibody or antigen-binding fragment thereof comprises a VL, which comprises a VL CDR1 comprising the amino acid sequence of SEQ ID NO:12, a VL CDR2 comprising the amino acid sequence of SEQ ID NO:13, and a VL CDR3 comprising the amino acid sequence of SEQ ID NO:14.

In certain embodiments, the antibody or antigen-binding fragment thereof comprises a VL, which comprises a VL CDR1 comprising the amino acid sequence of SEQ ID NO:18, a VL CDR2 comprising the amino acid sequence of SEQ ID NO:19, and a VL CDR3 comprising the amino acid sequence of SEQ ID NO:20.

In certain embodiments, the antibody or antigen-binding fragment thereof comprises a VL, which comprises a VL CDR1 comprising the amino acid sequence of SEQ ID NO:66, a VL CDR2 comprising the amino acid sequence of SEQ ID NO:67, and a VL CDR3 comprising the amino acid sequence of SEQ ID NO:68.

In certain embodiments, the antibody or antigen-binding fragment thereof comprises a VL, which comprises a VL CDR1 comprising the amino acid sequence of SEQ ID NO:72, a VL CDR2 comprising the amino acid sequence of SEQ ID NO:73, and a VL CDR3 comprising the amino acid sequence of SEQ ID NO:74.

In certain embodiments, the antibody or antigen-binding fragment thereof comprises a VL, which comprises a VL CDR1 comprising the amino acid sequence of SEQ ID NO:78, a VL CDR2 comprising the amino acid sequence of SEQ ID NO:79, and a VL CDR3 comprising the amino acid sequence of SEQ ID NO:80.

In certain embodiments, the antibody or antigen-binding fragment thereof comprises a VL comprising the amino acid sequence of $DIVMTQAAPSX_{36}X_{37}VTPGESVSISC$-$RSSKSLX_{38}X_{39}SNGNTYLYWFLQRPGQSPQRLIYYM$-$SNLASGVPDRFSGRGSGTDFTLX_{40}ISRVEAX_{41}DVG$-$VYYCMQX_{42}LEX_{43}PLTFGGGTKLEIK$ (SEQ ID NO:102), wherein $X_{36}$ is I or V, $X_{37}$ is P or S, $X_{38}$ is R or L, $X_{39}$ is K or H, $X_{40}$ is R or K, $X_{41}$ is E or G, $X_{42}$ is S or G, and $X_{43}$ is Y or H.

In certain embodiments, the antibody or antigen-binding fragment thereof comprises a VL comprising the amino acid sequence of SEQ ID NO:22.

In certain embodiments, the antibody or antigen-binding fragment thereof comprises a VL comprising the amino acid sequence of SEQ ID NO:42.

In certain embodiments, the antibody or antigen-binding fragment thereof comprises a VL comprising the amino acid sequence of SEQ ID NO:82.

In certain embodiments, the antibody or antigen-binding fragment thereof comprises a VL comprising the amino acid sequence of SEQ ID NO:2.

In certain embodiments, the antibody or antigen-binding fragment thereof comprises a VL comprising the amino acid sequence of SEQ ID NO:62.

In certain embodiments, the antibody comprises human-derived heavy and light chain constant regions. In certain embodiments, the heavy chain constant region has an isotype selected from the group consisting of gamma1, gamma2, gamma3, and gamma4. In certain embodiments, the light chain constant region has an isotype selected from the group consisting of kappa and lambda.

In certain embodiments, the antibody or antigen-binding fragment thereof is humanized. In certain embodiments, the antibody or antigen-binding fragment thereof is a humanized form of a rodent antibody.

In certain embodiments, the antibody is an immunoglobulin comprising two identical heavy chains and two identical light chains. In certain embodiments, the immunoglobulin is an IgG.

Also provided herein is an antibody conjugate comprising an antibody or antigen-binding fragment thereof provided herein conjugated to an agent. In certain embodiments, the agent is an imaging agent or a cytotoxic agent.

In certain embodiments, the antibody or antigen-binding fragment thereof is a bispecific antibody. In certain embodiments, the bispecific antibody immunospecifically binds CD3. In certain embodiments, the bispecific antibody comprises an immunoglobulin that immunospecifically binds MUC16, wherein the light chain of the immunoglublin is conjugated via a peptide linker to a single chain variable fragment (scFv) that immunospecifically binds CD3. Also provided herein is a bispecific antibody conjugate comprising a bispecific antibody provided herein conjugated to an agent. In certain embodiments, the agent is an imaging agent or a cytotoxic agent.

In certain embodiments, the antigen-binding fragment thereof is a single chain variable fragment (scFv). Also provided herein is a scFv conjugate comprising a scFv provided herein conjugated to an agent. In certain embodiments, the agent is an imaging agent or a cytotoxic agent.

Also provided herein are fusion proteins, chimeric molecules, and conjugates comprising the antibodies and antigen-binding fragments. Provided are chimeric antigen receptors (CARs) including one or more of any of the provided antibodies or antigen-binding fragments thereof, such as a CAR comprising any of the scFvs provided herein or a scFv conjugate provided herein; and/or CARs comprising antigen-binding domains that compete for binding to MUC16 therewith.

Also provided herein is an antibody heavy chain or an antigen-binding portion thereof. Among the provided antibodies and antigen-binding fragments thereof are those having heavy chains and/or antigen-binding portions thereof such as VH regions thereof; also provided are such heavy chains and antigen-binding portions thereof. In some embodiments, the heavy chain or antigen-binding portion thereof comprises a VH, which comprises (a) a VH CDR1 comprising the amino acid sequence $TX_1GMGVG$ (SEQ ID NO:103), wherein $X_1$ is L or V; (b) a VH CDR2 comprising the amino acid sequence $HIWWDDX_2DKYYX_3PALKS$ (SEQ ID NO:104), wherein $X_2$ is E or absent, and $X_3$ is Y or N; and (c) a VH CDR3 comprising the amino acid sequence IGTAQATDALDY (SEQ ID NO:105); wherein, optionally, an antibody or antigen-binding fragment thereof comprising the antibody heavy chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO: 139; and (iii) inhibits matrigel invasion in vitro of cells recombinantly expressing said first form of MUC16.

In some embodiments, the heavy chain or antigen-binding portion thereof comprises a VH, which comprises (a) a VH CDR1 comprising the amino acid sequence $GFSLX_8TX_9GM$ (SEQ ID NO:109), wherein $X_8$ is N or S, and $X_9$ is L or V; (b) a VH CDR2 comprising the amino acid sequence $WDDX_{10}$ (SEQ ID NO: 110), wherein $X_{10}$ is E or absent; and (c) a VH CDR3 comprising the amino acid sequence GTAQATDALD (SEQ ID NO:111); wherein, optionally, an antibody or antigen-binding fragment thereof comprising the antibody heavy chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16.

In some embodiments, the heavy chain or antigen-binding portion thereof comprises a VH, which comprises (a) a VH CDR1 comprising the amino acid sequence $GFSLX_{15}TX_{16}GMG$ (SEQ ID NO:115), wherein $X_{15}$ is N or S, and $X_{16}$ is V or L; (b) a VH CDR2 comprising the amino acid sequence $IWWDDX_{17}DK$ (SEQ ID NO:116), wherein $X_{17}$ is E or absent; and (c) a VH CDR3 comprising the amino acid sequence $X_{18}RIGTAQATDALDY$ (SEQ ID NO:117), wherein $X_{18}$ is T, A, or S; wherein, optionally, an antibody or antigen-binding fragment thereof comprising the antibody heavy chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16.

In some embodiments, the heavy chain or antigen-binding portion thereof comprises a VH, which comprises a VH CDR1 comprising the amino acid sequence of SEQ ID NO:3, a VH CDR2 comprising the amino acid sequence of SEQ ID NO:4, and a VH CDR3 comprising the amino acid sequence of SEQ ID NO:5, wherein, optionally, an antibody or antigen-binding fragment thereof comprising the antibody heavy chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16.

In some embodiments, the heavy chain or antigen-binding portion thereof comprises a VH, which comprises a VH CDR1 comprising the amino acid sequence of SEQ ID NO:9, a VH CDR2 comprising the amino acid sequence of SEQ ID NO:10, and a VH CDR3 comprising the amino acid sequence of SEQ ID NO:11, wherein, optionally, an antibody or antigen-binding fragment thereof comprising the antibody heavy chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii)

inhibits matrigel invasion in vitro of cells recombinantly expressing said first form of MUC16.

In some embodiments, the heavy chain or antigen-binding portions thereof comprises a VH, which comprises a VH CDR1 comprising the amino acid sequence of SEQ ID NO:15, a VH CDR2 comprising the amino acid sequence of SEQ ID NO:16, and a VH CDR3 comprising the amino acid sequence of SEQ ID NO:17, wherein, optionally, an antibody or antigen-binding fragment thereof comprising the antibody heavy chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16.

In some embodiments, the heavy chain or antigen-binding portion thereof comprises a VH, which comprises a VH CDR1 comprising the amino acid sequence of SEQ ID NO:23, a VH CDR2 comprising the amino acid sequence of SEQ ID NO:24, and a VH CDR3 comprising the amino acid sequence of SEQ ID NO:25, wherein, optionally, an antibody or antigen-binding fragment thereof comprising the antibody heavy chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16.

In some embodiments, the heavy chain or antigen-binding portion thereof comprises a VH, which comprises a VH CDR1 comprising the amino acid sequence of SEQ ID NO:29, a VH CDR2 comprising the amino acid sequence of SEQ ID NO:30, and a VH CDR3 comprising the amino acid sequence of SEQ ID NO:31, wherein, optionally, an antibody or antigen-binding fragment thereof comprising the antibody heavy chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16.

In some embodiments, the heavy chain or antigen-binding portion thereof comprises a VH, which comprises a VH CDR1 comprising the amino acid sequence of SEQ ID NO:35, a VH CDR2 comprising the amino acid sequence of SEQ ID NO:36, and a VH CDR3 comprising the amino acid sequence of SEQ ID NO:37, wherein, optionally, an antibody or antigen-binding fragment thereof comprising the antibody heavy chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16.

In some embodiments, the heavy chain or antigen-binding portion thereof comprises a VH, which comprises a VH CDR1 comprising the amino acid sequence of SEQ ID NO:43, a VH CDR2 comprising the amino acid sequence of SEQ ID NO:44, and a VH CDR3 comprising the amino acid sequence of SEQ ID NO:45, wherein, optionally, an antibody or antigen-binding fragment thereof comprising the antibody heavy chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16.

In some embodiments, the heavy chain or antigen-binding portion thereof comprises a VH, which comprises a VH CDR1 comprising the amino acid sequence of SEQ ID NO:49, a VH CDR2 comprising the amino acid sequence of SEQ ID NO:50, and a VH CDR3 comprising the amino acid sequence of SEQ ID NO:51, wherein, optionally, an antibody or antigen-binding fragment thereof comprising the antibody heavy chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16.

In some embodiments, the heavy chain or antigen-binding portion thereof comprises a VH, which comprises a VH CDR1 comprising the amino acid sequence of SEQ ID NO:55, a VH CDR2 comprising the amino acid sequence of SEQ ID NO:56, and a VH CDR3 comprising the amino acid sequence of SEQ ID NO:57, wherein, optionally, an antibody or antigen-binding fragment thereof comprising the antibody heavy chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16.

In some embodiments, the heavy chain or antigen-binding portion thereof comprises a VH, which comprises a VH CDR1 comprising the amino acid sequence of SEQ ID NO:63, a VH CDR2 comprising the amino acid sequence of SEQ ID NO:64, and a VH CDR3 comprising the amino acid sequence of SEQ ID NO:65, wherein, optionally, an antibody or antigen-binding fragment thereof comprising the antibody heavy chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16.

In some embodiments, the heavy chain or antigen-binding portion thereof comprises a VH, which comprises a VH CDR1 comprising the amino acid sequence of SEQ ID NO:69, a VH CDR2 comprising the amino acid sequence of SEQ ID NO:70, and a VH CDR3 comprising the amino acid sequence of SEQ ID NO:71, wherein, optionally, an antibody or antigen-binding fragment thereof comprising the antibody heavy chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16.

In some embodiments, the heavy chain or antigen-binding portion thereof comprises a VH, which comprises a VH CDR1 comprising the amino acid sequence of SEQ ID NO:75, a VH CDR2 comprising the amino acid sequence of SEQ ID NO:76, and a VH CDR3 comprising the amino acid sequence of SEQ ID NO:77, wherein, optionally, an antibody or antigen-binding fragment thereof comprising the antibody heavy chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16.

In some embodiments, the heavy chain or antigen-binding portion thereof comprises a VH, which comprises a VH CDR1 comprising the amino acid sequence of SEQ ID NO:83, a VH CDR2 comprising the amino acid sequence of SEQ ID NO:84, and a VH CDR3 comprising the amino acid sequence of SEQ ID NO:85, wherein, optionally, an antibody or antigen-binding fragment thereof comprising the antibody heavy chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16.

In some embodiments, the heavy chain or antigen-binding portion thereof comprises a VH, which comprises a VH CDR1 comprising the amino acid sequence of SEQ ID NO:89, a VH CDR2 comprising the amino acid sequence of SEQ ID NO:90, and a VH CDR3 comprising the amino acid sequence of SEQ ID NO:91, wherein, optionally, an antibody or antigen-binding fragment thereof comprising the antibody heavy chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16.

In some embodiments, the heavy chain or antigen-binding portion thereof comprises a VH, which comprises a VH CDR1 comprising the amino acid sequence of SEQ ID NO:95, a VH CDR2 comprising the amino acid sequence of SEQ ID NO:96, and a VH CDR3 comprising the amino acid sequence of SEQ ID NO:97, wherein, optionally, an antibody or antigen-binding fragment thereof comprising the antibody heavy chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16.

In some embodiments, the heavy chain or antigen-binding portion thereof comprises a VH comprising the amino acid sequence of $QVX_{21}LKESGPGX_{22}LQPSQTLSLTCSFSGFSLX_{23}TX_{24}GMGVGWX_{25}RQX_{26}SGKGLEWLAHIWWDDX_{27}DKYYX_{28}PALKSRLTISX_{29}X_{30}X_{31}SKNQVFLKIX_{32}NVX_{33}TADX_{34}ATYYCX_{35}RIGTAQATDALDYWGQGTSVTVSS$ (SEQ ID NO:101), wherein $X_{21}$ is T or N, $X_{22}$ is I or K, $X_{23}$ is N or S, $X_{24}$ is V or L, $X_{25}$ is S or I, $X_{26}$ is P or S, $X_{27}$ is E or absent, $X_{28}$ is N or Y, $X_{29}$ is K or R, $X_{30}$ is A or D, $X_{31}$ is T or S, $X_{32}$ is V or A, $X_{33}$ is G or D, $X_{34}$ is T, I, or S, and $X_{35}$ is T, S, or A, wherein, optionally, an antibody or antigen-binding fragment thereof comprising the antibody heavy chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO: 139; and (iii) inhibits matrigel invasion in vitro of cells recombinantly expressing said first form of MUC16.

In some embodiments, the heavy chain or antigen-binding portion thereof comprises a VH comprising the amino acid sequence of SEQ ID NO: 1, wherein, optionally, an antibody or antigen-binding fragment thereof comprising the antibody heavy chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16.

In some embodiments, the heavy chain or antigen-binding portion thereof comprises a VH comprising the amino acid sequence of SEQ ID NO:21, wherein, optionally, an antibody or antigen-binding fragment thereof comprising the antibody heavy chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO: 139; and (iii) inhibits matrigel invasion in vitro of cells recombinantly expressing said first form of MUC16.

In some embodiments, the heavy chain or antigen-binding portion thereof comprises a VH comprising the amino acid sequence of SEQ ID NO:41, wherein, optionally, an antibody or antigen-binding fragment thereof comprising the antibody heavy chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO: 139; and (iii) inhibits matrigel invasion in vitro of cells recombinantly expressing said first form of MUC16.

In some embodiments, the heavy chain or antigen-binding portion thereof comprises a VH comprising the amino acid sequence of SEQ ID NO:61, wherein, optionally, an antibody or antigen-binding fragment thereof comprising the antibody heavy chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO: 139; and (iii) inhibits matrigel invasion in vitro of cells recombinantly expressing said first form of MUC16.

In some embodiments, the heavy chain or antigen-binding portion thereof comprises a VH comprising the amino acid sequence of SEQ ID NO:81, wherein, optionally, an antibody or antigen-binding fragment thereof comprising the antibody heavy chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO: 139; and (iii) inhibits matrigel invasion in vitro of cells recombinantly expressing said first form of MUC16.

In certain embodiments, the antibody heavy chain or antigen-binding portion thereof comprises a human-derived heavy chain constant region. In certain embodiments, the heavy chain constant region has an isotype selected from the group consisting of gamma1, gamma2, gamma3, and gamma4. In certain embodiments, the antibody heavy chain is humanized. In certain embodiments, the antibody heavy chain is a humanized form of a rodent heavy chain.

Also provided herein is an antibody heavy chain conjugate comprising an antibody heavy chain provided herein, wherein said antibody heavy chain is conjugated to an agent. In certain embodiments, the agent is an imaging agent or a cytotoxic agent.

Among the provided antibodies and antigen-binding fragments thereof are those having light chains and/or portions thereof such as VL regions thereof, also provided are such light chains and antigen-binding portions thereof. In some embodiments, the light chain or antigen-binding portion thereof comprises a VL, which comprises (a) a VL CDR1 comprising the amino acid sequence RSSKSLX$_4$X$_5$SNGNTYLY (SEQ ID NO:106), wherein X$_4$ is R or L, and X$_5$ is K or H; (b) a VL CDR2 comprising the amino acid sequence YMSNLAS (SEQ ID NO:107); and (c) a VL CDR3 comprising the amino acid sequence MQX$_6$LEX$_7$PLT (SEQ ID NO:108), wherein X$_6$ is G or S, and X$_7$ is H or Y, wherein, optionally, an antibody or antigen-binding fragment thereof comprising the antibody light chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16.

In some embodiments, the light chain or antigen-binding portion thereof comprises a VL, which comprises (a) a VL CDR1 comprising the amino acid sequence SKSLX$_{11}$X$_{12}$SNGNTY (SEQ ID NO: 112), wherein X$_{11}$ is L or R, and X$_{12}$ is H or K; (b) a VL CDR2 comprising the amino acid sequence YMS (SEQ ID NO:113); and (c) a VL CDR3 comprising the amino acid sequence X$_{13}$LEX$_{14}$PL (SEQ ID NO:114), wherein X$_{13}$ is G or S, and X$_{14}$ is H or Y, wherein, optionally, an antibody or antigen-binding fragment thereof comprising the antibody light chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO: 139; and (iii) inhibits matrigel invasion in vitro of cells recombinantly expressing said first form of MUC16.

In some embodiments, the light chain or antigen-binding portion thereof comprises a VL, which comprises (a) a VL CDR1 comprising the amino acid sequence KSLX$_{19}$X$_{20}$SNGNTY (SEQ ID NO:118), wherein X$_{19}$ is V or L, and X$_{20}$ is H or K; (b) a VL CDR2 comprising the amino acid sequence YMS (SEQ ID NO:119); and (c) a VL CDR3 comprising the amino acid sequence MQSLEYPLT (SEQ ID NO:120), wherein, optionally, an antibody or antigen-binding fragment thereof comprising the antibody light chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16.

In some embodiments, the light chain or antigen-binding portion thereof comprises a VL, which comprises a VL CDR1 comprising the amino acid sequence of SEQ ID NO:6, a VL CDR2 comprising the amino acid sequence of SEQ ID NO:7, and a VL CDR3 comprising the amino acid sequence of SEQ ID NO:8, wherein, optionally, an antibody or antigen-binding fragment thereof comprising the antibody light chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16.

In some embodiments, the light chain or antigen-binding portion thereof comprises a VL, which comprises a VL CDR1 comprising the amino acid sequence of SEQ ID NO:12, a VL CDR2 comprising the amino acid sequence of SEQ ID NO:13, and a VL CDR3 comprising the amino acid sequence of SEQ ID NO:14, wherein, optionally, an antibody or antigen-binding fragment thereof comprising the antibody light chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16.

In some embodiments, the light chain or antigen-binding portion thereof comprises a VL, which comprises a VL CDR1 comprising the amino acid sequence of SEQ ID NO:18, a VL CDR2 comprising the amino acid sequence of SEQ ID NO:19, and a VL CDR3 comprising the amino acid sequence of SEQ ID NO:20, wherein, optionally, an antibody or antigen-binding fragment thereof comprising the antibody light chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16.

In some embodiments, the light chain or antigen-binding portion thereof comprises a VL, which comprises a VL CDR1 comprising the amino acid sequence of SEQ ID NO:26, a VL CDR2 comprising the amino acid sequence of SEQ ID NO:27, and a VL CDR3 comprising the amino acid sequence of SEQ ID NO:28, wherein, optionally, an antibody or antigen-binding fragment thereof comprising the antibody light chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16.

In some embodiments, the light chain or antigen-binding portion thereof comprises a VL, which comprises a VL CDR1 comprising the amino acid sequence of SEQ ID NO:32, a VL CDR2 comprising the amino acid sequence of SEQ ID NO:33, and a VL CDR3 comprising the amino acid sequence of SEQ ID NO:34, wherein, optionally, an antibody or antigen-binding fragment thereof comprising the antibody light chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16.

In some embodiments, the light chain or antigen-binding portion thereof comprises a VL, which comprises a VL CDR1 comprising the amino acid sequence of SEQ ID NO:38, a VL CDR2 comprising the amino acid sequence of SEQ ID NO:39, and a VL CDR3 comprising the amino acid sequence of SEQ ID NO:40, wherein, optionally, an antibody or antigen-binding fragment thereof comprising the antibody light chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16.

In some embodiments, the light chain or antigen-binding portion thereof comprises a VL, which comprises a VL CDR1 comprising the amino acid sequence of SEQ ID NO:46, a VL CDR2 comprising the amino acid sequence of SEQ ID NO:47, and a VL CDR3 comprising the amino acid sequence of SEQ ID NO:48, wherein, optionally, an antibody or antigen-binding fragment thereof comprising the antibody light chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16.

In some embodiments, the light chain or antigen-binding portion thereof comprises a VL, which comprises a VL CDR1 comprising the amino acid sequence of SEQ ID NO:52, a VL CDR2 comprising the amino acid sequence of SEQ ID NO:53, and a VL CDR3 comprising the amino acid sequence of SEQ ID NO:54, wherein, optionally, an antibody or antigen-binding fragment thereof comprising the antibody light chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16.

In some embodiments, the light chain or antigen-binding portion thereof comprises a VL, which comprises a VL CDR1 comprising the amino acid sequence of SEQ ID NO:58, a VL CDR2 comprising the amino acid sequence of SEQ ID NO:59, and a VL CDR3 comprising the amino acid sequence of SEQ ID NO:60, wherein, optionally, an antibody or antigen-binding fragment thereof comprising the antibody light chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16.

In some embodiments, the light chain or antigen-binding portion thereof comprises a VL, which comprises a VL CDR1 comprising the amino acid sequence of SEQ ID NO:66, a VL CDR2 comprising the amino acid sequence of SEQ ID NO:67, and a VL CDR3 comprising the amino acid sequence of SEQ ID NO:68, wherein, optionally, an antibody or antigen-binding fragment thereof comprising the antibody light chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16.

In some embodiments, the light chain or antigen-binding portion thereof comprises a VL, which comprises a VL CDR1 comprising the amino acid sequence of SEQ ID NO:72, a VL CDR2 comprising the amino acid sequence of SEQ ID NO:73, and a VL CDR3 comprising the amino acid sequence of SEQ ID NO:74, wherein, optionally, an antibody or antigen-binding fragment thereof comprising the antibody light chain or antigen-binding portion thereof (i) immunospecifically binds to a cell recombinantly expressing a first form of MUC16, which first form is glycosylated, and wherein the amino acid sequence of the first form is SEQ ID NO: 133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16.

In some embodiments, the light chain or antigen-binding portion thereof comprises a VL, which comprises a VL CDR1 comprising the amino acid sequence of SEQ ID NO:78, a VL CDR2 comprising the amino acid sequence of SEQ ID NO:79, and a VL CDR3 comprising the amino acid sequence of SEQ ID NO:80, wherein, optionally, an antibody or antigen-binding fragment thereof comprising the antibody light chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16.

In some embodiments, the light chain or antigen-binding portion thereof comprises a VL, which comprises a VL CDR1 comprising the amino acid sequence of SEQ ID NO:86, a VL CDR2 comprising the amino acid sequence of SEQ ID NO:87, and a VL CDR3 comprising the amino acid sequence of SEQ ID NO:88, wherein, optionally, an antibody or antigen-binding fragment thereof comprising the antibody light chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16.

In some embodiments, the light chain or antigen-binding portion thereof comprises a VL, which comprises a VL CDR1 comprising the amino acid sequence of SEQ ID NO:92, a VL CDR2 comprising the amino acid sequence of SEQ ID NO:93, and a VL CDR3 comprising the amino acid sequence of SEQ ID NO:94, wherein, optionally, an antibody or antigen-binding fragment thereof comprising the antibody light chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16.

In some embodiments, the light chain or antigen-binding portion thereof comprises a VL, which comprises a VL CDR1 comprising the amino acid sequence of SEQ ID NO:98, a VL CDR2 comprising the amino acid sequence of SEQ ID NO:99, and a VL CDR3 comprising the amino acid sequence of SEQ ID NO:100, wherein, optionally, an antibody or antigen-binding fragment thereof comprising the antibody light chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16.

In some embodiments, the light chain or antigen-binding portion thereof comprises a VL comprising the amino acid sequence of DIVMTQAAPS$X_{36}X_{37}$VTPGESVSISCRSSKSL$X_{38}X_{39}$SNGNTYLYWFLQRPGQSPQRLIYY MSNLASGVPDRFSGRGSGTDFTL$X_{40}$ISRVEA$X_{41}$DVGVYYCMQ$X_{42}$LE$X_{43}$PLTFGGGTKLEIK (SEQ ID NO: 102), wherein $X_{36}$ is I or V, $X_{37}$ is P or S, $X_{38}$ is R or L, $X_{39}$ is K or H, $X_{40}$ is R or K, $X_{41}$ is E or G, $X_{42}$ is S or G, and $X_{43}$ is Y or H, wherein, optionally, an antibody or antigen-binding fragment thereof comprising the antibody light chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16.

In some embodiments, the light chain or antigen-binding portion thereof comprises a VL comprising the amino acid sequence of SEQ ID NO:2, wherein, optionally, an antibody or antigen-binding fragment thereof comprising the antibody light chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16.

In some embodiments, the light chain or antigen-binding portion thereof comprises a VL comprising the amino acid sequence of SEQ ID NO:22, wherein, optionally, an antibody or antigen-binding fragment thereof comprising the antibody light chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16.

In some embodiments, the light chain or antigen-binding portion thereof comprises a VL comprising the amino acid sequence of SEQ ID NO:42, wherein, optionally, an antibody or antigen-binding fragment thereof comprising the antibody light chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16.

In some embodiments, the light chain or antigen-binding portion thereof comprises a VL comprising the amino acid sequence of SEQ ID NO:62, wherein, optionally, an antibody or antigen-binding fragment thereof comprising the antibody light chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16.

In some embodiments, the light chain or antigen-binding portion thereof comprises a VL comprising the amino acid sequence of SEQ ID NO:82, wherein, optionally, an antibody or antigen-binding fragment thereof comprising the antibody light chain or antigen-binding portion thereof (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16.

In certain embodiments, the antibody light chain or antigen-binding portion thereof comprises a human-derived light chain constant region. In certain embodiments, the light chain constant region has an isotype selected from the group consisting of kappa and lambda. In certain embodiments, the antibody light chain is humanized. In certain embodiments, the antibody light chain is a humanized form of a rodent antibody.

Also provided herein is an antibody light chain conjugate comprising an antibody light chain provided herein conjugated to an agent. In certain embodiments, the agent is an imaging agent or a cytotoxic agent.

Also provided herein is a fusion protein comprising an antibody light chain provided herein conjugated via a peptide linker to a scFv. In certain embodiments, the scFv binds CD3.

Also provided herein is a cell, such as an immune cell, such as a T cell, which recombinantly expresses one or more of the molecules provided herein such as a CAR provided herein.

Also provided herein is a polynucleotide comprising nucleic acid sequences encoding a scFv provided herein. Also provided herein is a polynucleotide comprising nucleic acid sequences encoding a scFv, or conjugate thereof, provided herein. Also provided herein is a polynucleotide comprising nucleic acid sequences encoding a CAR provided herein. Also provided herein is a polynucleotide comprising nucleic acid sequences encoding an antibody heavy chain, or antigen-binding portion thereof, provided herein. Also provided herein is a polynucleotide comprising nucleic acid sequences encoding an antibody heavy chain conjugate provided herein. Also provided herein is a polynucleotide comprising nucleic acid sequences encoding an antibody light chain, or antigen-binding portion thereof, provided herein. Also provided herein is a polynucleotide comprising nucleic acid sequences encoding an antibody light chain conjugate provided herein. Also provided herein is a polynucleotide comprising nucleic acid sequences encoding the fusion protein provided herein. A polynucleotide comprising nucleic acid sequences encoding (a) an antibody heavy chain, or antigen-binding portion thereof, provided herein or an antibody heavy chain conjugate provided herein; and (b) an antibody light chain, or antigen-binding portion thereof, provided herein, an antibody light chain conjugate provided herein, or a fusion protein provided herein.

Also provided herein is a vector comprising a polynucleotide provided herein operably linked to a promoter. Also provided herein is a vector comprising (a) a first polynucleotide provided herein operably linked to a first promoter; and (b) a second polynucleotide provided herein operably linked to a second promoter.

Also provided herein is an ex vivo cell comprising a polynucleotide provided herein operably linked to a promoter. Also provided herein is an ex vivo cell comprising a polynucleotide provided herein operably linked to a promoter. Also provided herein is an ex vivo cell comprising a vector provided herein. Also provided herein is an ex vivo cell comprising one or more polynucleotides encoding an antibody or antigen-binding fragment thereof of provided herein operably linked to a promoter.

Also provided herein is a method of producing an antibody heavy chain, or antigen-binding portion thereof, comprising culturing a cell provided herein under conditions such that a polynucleotide is expressed by the cell to produce an antibody heavy chain, or antigen-binding portion thereof, or antibody heavy chain conjugate encoded by the polynucleotide.

Also provided herein is a method of producing an antibody light chain, or antigen-binding portion thereof, comprising culturing a cell provided herein under conditions such that a polynucleotide is expressed by the cell to produce the antibody light chain, or antigen-binding portion thereof, antibody light chain conjugate, or fusion protein encoded by the polynucleotide.

Also provided herein is a method of producing an antibody or antigen-binding fragment thereof comprising culturing an ex vivo cell provided herein under conditions such that a polynucleotide operably linked to a first promoter and a polynucleotide operably linked to a second promoter are expressed by the cell to produce (i) an antibody heavy chain or an antibody heavy chain conjugate encoded by the polynucleotide; and (ii) an antibody light chain, an antibody light chain conjugate, or a fusion protein encoded by the polynucleotide.

Also provided herein is a pharmaceutical composition comprising: a therapeutically effective amount of an antibody or antigen-binding fragment thereof provided herein, an antibody conjugate provided herein, a bispecific antibody provided herein, a bispecific antibody conjugate provided herein, a scFv, a scFv conjugate provided herein, a CAR provided herein, an antibody heavy chain, or antigen-binding portion thereof, provided herein, an antibody heavy chain conjugate provided herein, an antibody light chain, or antigen-binding portion thereof, provided herein, an antibody light chain conjugate provided herein, a fusion protein provided herein, or a T cell provided herein; and a pharmaceutically acceptable carrier.

Also provided herein is a method of treating cancer in a patient in need thereof, comprising administering to said patient the pharmaceutical composition provided herein. In certain embodiments, the cancer is a cancer of the lung, pancreas, breast, uterine, fallopian tube, or primary peritoneum. In certain embodiments, the cancer is a cancer of the ovary. In certain embodiments, the patient is a human patient. In specific embodiments, the method is a combination therapy method, further comprising administering a therapeutically effective amount of an additional therapeutic agent to the patient.

In a specific embodiment of the combination therapy method, the pharmaceutical composition comprises a therapeutically effective amount of a first antibody that is an antibody or antigen-binding fragment thereof described herein, wherein the antibody or antigen-binding fragment thereof recognizes an epitope in MUC16 that comprises N-glycosylated Asn1806 of SEQ ID NO: 150 but does not comprise N-glycosylated Asn1800 of SEQ ID NO: 150, wherein the additional therapeutic agent is a second antibody or antigen-binding fragment thereof, wherein the second antibody or antigen-binding fragment thereof recognizes an epitope in MUC16 that comprises N-glycosylated Asn1806 of SEQ ID NO: 150 and also comprises N-glycosylated Asn1800 of SEQ ID NO: 150. In a specific embodiment, the first antibody or antigen-binding fragment thereof is identified by (i) its ability to immunospecifically bind a cell recombinantly expressing a first form of MUC16, which first form of MUC16 is glycosylated, and wherein the amino acid sequence of the first form is SEQ ID NO: 133; (ii) its lack of immunospecific binding to a cell recombinantly expressing a third form of MUC16, which third form is glycosylated, wherein the amino acid sequence of the third form is SEQ ID NO: 139; and (iii) its ability to immunospecifically bind a cell recombinantly expressing a fourth form of MUC16, which fourth form is glycosylated, and wherein the amino acid sequence of the fourth form is SEQ ID NO: 152, and wherein the cell recombinantly expressing the first form of MUC16, the cell recombinantly expressing the third form of MUC16, and the cell recombinantly expressing the fourth form of MUC16 are of the same cell type, and wherein the second antibody or antigen-binding fragment thereof is identified by (i) its ability to immunospecifically bind to a cell recombinantly expressing a first form of MUC16, which first form is glycosylated, and wherein the amino acid sequence of the first form is SEQ ID NO: 133; and (ii) its lack of immunospecific binding to a cell recombinantly expressing a fifth form of MUC16, which fifth form is glycosylated, and wherein the amino acid sequence of the fifth form is SEQ ID NO: 172, wherein the cell recombinantly expressing the first form of MUC16 is the same type of cell as the cell recombinantly expressing the fifth form of MUC16.

In a specific embodiment of the combination therapy method, the pharmaceutical composition comprises a therapeutically effective amount of a first antibody or antigen-binding fragment thereof that is an antibody or antigen-binding fragment thereof described herein, wherein the antibody or antigen-binding fragment thereof recognizes an epitope in MUC16 that comprises N-glycosylated Asn1806 of SEQ ID NO: 150 but does not comprise N-glycosylated Asn1800 of SEQ ID NO: 150, wherein the additional therapeutic agent is a therapeutically effective amount of a second antibody or antigen-binding fragment thereof, wherein the second antibody or antigen-binding fragment thereof recognizes an epitope in MUC16 that comprises N-glycosylated Asn1800 of SEQ ID NO: 150 but does not comprise N-glycosylated Asn1806 of SEQ ID NO: 150. In a specific embodiment, the first antibody or antigen-binding fragment thereof is identified by (i) its ability to immunospecifically bind a cell recombinantly expressing a first form of MUC16, which first form of MUC16 is glycosylated, and wherein the amino acid sequence of the first form is SEQ ID NO: 133; (ii) its lack of immunospecific binding to a cell recombinantly expressing a third form of MUC16, which third form is glycosylated, and wherein the amino acid sequence of the third form is SEQ ID NO: 139; and (iii) its ability to immunospecifically bind a cell recombinantly expressing a fourth form of MUC16, which fourth form is glycosylated, and wherein the amino acid sequence of the fourth form is SEQ ID NO: 152, wherein the cell recombinantly expressing the first form of MUC16, the cell recombinantly expressing the third form of MUC16, and the cell recombinantly expressing the fourth form of MUC16 are of the same cell type, and wherein the second antibody or antigen-binding fragment thereof is identified by (i) its ability to immunospecifically bind to a cell recombinantly expressing a first form of MUC16, which first form is glycosylated, and wherein the amino acid sequence of the first form is SEQ ID NO:133; (ii) its ability to immunospecifically bind to a cell recombinantly expressing a third form of MUC16, which third form of MUC16 is glycosylated, and wherein the amino acid sequence of the third form is SEQ ID NO: 139; and (iii) its lack of immunospecific binding to a cell recombinantly expressing a fourth form of MUC16, wherein the amino acid sequence of the fourth form is SEQ ID NO:152; and, wherein the cell recombinantly expressing the first form of MUC16, the cell recombinantly expressing the third form of MUC16, and the cell recombinantly expressing the fourth form of MUC16 are of the same type of cell.

Also provided herein is an immunogenic glycopeptide comprising one or more glycosylation sites, wherein (i) the immunogenic glycopeptide is 10 to 60 amino acid residues, 10 to 30 amino acid residues, 15 to 25 amino acid residues, 15 to 20 amino acid residues, or 15 to 18 amino acid residues in length, and (ii) at least one of the one or more glycosylation sites is linked with a carbohydrate. In certain embodiments, the immunogenic glycopeptide comprises one, two, or three glycosylation sites. In certain embodiments, the immunogenic glycopeptide comprises a glycosylation site that is linked with a carbohydrate. In certain embodiments, the immunogenic glycopeptide comprises two glycosylation sites that are each linked with a carbohydrate. In certain embodiments, the carbohydrate is an N- or O-linked carbohydrate. In certain embodiments, the carbohydrate is a monosaccharide, a disaccharide, a trisaccharide, a tetrasaccharide, or a pentasaccharide. In certain embodiments, the carbohydrate is a disaccharide. In certain embodiments, the disaccharide is a chitobiose.

In certain embodiments, the N-terminus of the immunogenic glycopeptide is acetylated. In certain embodiments, the C-terminus of the glycopeptide is in the form of an N-methylcarboxamide derivative. In certain embodiments, the immunogenic glycopeptide is conjugated to an immunogenic carrier protein. In certain embodiments, the immunogenic carrier protein is keyhole limpet hemocyanin.

In certain embodiments, the immunogenic glycopeptide is 15 to 18 amino acid residues in length. In certain embodiments, the immunogenic glycopeptide comprises a glycosylation site that is linked with a chitobiose. In certain embodiments, the immunogenic glycopeptide comprises two glycosylation sites that are each linked with a chitobiose.

In certain embodiments, the immunogenic glycopeptide is 18 amino acid residues in length. In certain embodiments, the immunogenic glycopeptides comprises two glycosylation sites that are each linked with a chitobiose.

In certain embodiments, the immunogenic glycopeptides is 15 amino acid residues in length. In certain embodiments, the immunogenic glycopeptide comprises a glycosylation site that is linked with a chitobiose.

In certain embodiments, the immunogenic glycopeptide comprises an at least 10 amino acid portion of the amino acid sequence of SEQ ID NO: 150, wherein at least one of the one or more glycosylation sites is in said portion of the amino acid sequence.

In certain embodiments, the immunogenic glycopeptide comprises the amino acid sequence of SEQ ID NO:129.

In certain embodiments, the immunogenic glycopeptide comprises a glycosylation site at the $30^{th}$ residue (Asn) of SEQ ID NO: 129 that is linked with a chitobiose.

In certain embodiments, the immunogenic glycopeptide comprises a glycosylation site at the $30^{th}$ residue (Asn) of SEQ ID NO: 129 that is linked with a $Man_3GlcNAc_2$ moiety.

In certain embodiments, the immunogenic glycopeptide comprises the amino acid sequence of SEQ ID NO: 130. In certain embodiments, the immunogenic glycopeptides comprises two glycosylation sites at the $4^{th}$ residue (Asn) and the $10^{th}$ residue (Asn) of SEQ ID NO: 130 that are each linked with a chitobiose.

In certain embodiments, the immunogenic glycopeptide comprises the amino acid sequence of SEQ ID NO: 131. In certain embodiments, the immunogenic glycopeptides comprises a glycosylation site at the $7^{th}$ residue (Asn) of SEQ ID NO: 131 that is linked with a chitobiose.

Also provided herein is a method of generating an antibody or an antigen-binding fragment thereof that specifically binds to a glycol-protein, comprising immunizing a subject with an immunogenic glycopeptide comprising one or more glycosylation sites, wherein (i) the immunogenic glycopeptide is 10 to 60 amino acid residues, 10 to 30 amino acid residues, 15 to 25 amino acid residues, 15 to 20 amino acid residues, or 15 to 18 amino acid residues in length, (ii) the immunogenic glycopeptide comprises an at least 10 amino acid portion of the amino acid sequence of the glycoprotein, (iii) at least one of the one or more glycosylation sites is linked with a carbohydrate, and (iv) at least one of the one or more glycosylation sites is in said portion of the amino acid sequence. In certain embodiments, the antibody or antigen-binding fragment thereof lacks specific binding to a non-glycosylated form of the glycoprotein. In certain embodiments, the subject is a goat, a sheep, a donkey, a chicken, a guinea pig, a rat, a rabbit, or a mouse. In certain embodiments, the subject is a rat, a rabbit, or a mouse. In certain embodiments, the subject is a mouse. In certain embodiments, the immunogenic glycopeptide comprises one, two, or three glycosylation sites. In some embodiments of the method the immunogenic glycopeptide comprises a glycosylation site that is linked with a carbohydrate. In certain embodiments, the immunogenic glycopeptide comprises two glycosylation sites that are each linked with a carbohydrate. In certain embodiments, the carbohydrate is an N- or O-linked carbohydrate. In certain embodiments, the carbohydrate is a monosaccharide, a disaccharide, a trisaccharide, a tetrasaccharide, or a pentasaccharide. In certain embodiments, the carbohydrate is a disaccharide. In certain embodiments, the disaccharide is a chitobiose. In certain embodiments, the N-terminus of the immunogenic glycopeptide is acetylated. In certain embodiments, the C-terminus of the glycopeptide is in the form of an N-methylcarboxamide derivative. In certain embodiments, the immunogenic glycopeptide is conjugated to an immunogenic carrier protein. In certain embodiments, the immunogenic carrier protein is keyhole limpet hemocyanin. In certain embodiments, the immunogenic glycopeptide is 15 to 18 amino acid residues in length. In certain embodiments, the immunogenic glycopeptide comprises a glycosylation site that is linked with a chitobiose. In certain embodiments, the immunogenic glycopeptide comprises two glycosylation sites that are each linked with a chitobiose. In certain embodiments, the immunogenic glycopeptide is 18 amino acid residues in length. In certain embodiments, the immunogenic glycopeptide comprises two glycosylation sites that are each linked with a chitobiose. In certain embodiments, the immunogenic glycopeptide is 15 amino acid residues in length. In certain embodiments, the immunogenic glycopeptide comprises a glycosylation site that is linked with a chitobiose. In certain embodiments, the glycoprotein comprises the amino acid sequence of SEQ ID NO: 150. In certain embodiments, the immunogenic glycopeptide comprises the amino acid sequence of SEQ ID NO:129. In certain embodiments, the immunogenic glycopeptide comprises a glycosylation site at the $30^{th}$ residue (Asn) of SEQ ID NO: 129 that is linked with a chitobiose. In certain embodiments, the immunogenic glycopeptide comprises a glycosylation site at the $30^{th}$ residue (Asn) of SEQ ID NO:129 that is linked with a $Man_3GlcNAc_2$ moiety. In certain embodiments, the immunogenic glycopeptide comprises the amino acid sequence of SEQ ID NO: 130. In certain embodiments, the immunogenic glycopeptide comprises two glycosylation sites at the $4^{th}$ residue (Asn) and the $10^{th}$ residue (Asn) of SEQ ID NO:130 that are each linked with a chitobiose. In certain embodiments, the immunogenic glycopeptide comprises the amino acid sequence of SEQ ID NO: 131. In certain embodiments, the immunogenic glycopeptide comprises a glycosylation site at the $7^{th}$ residue (Asn) of SEQ ID NO: 131 that is linked with a chitobiose.

Also provided herein are antibodies and antigen-binding fragments thereof which immunospecifically bind to MUC16 and which have VH, VL, VH CDR, and/or VL CDR sequences of an antibody described herein (e.g., 10C6, 7B12, 19C11, 16C5, or 18C6), as well as conjugates (e.g., to imaging or cytotoxic agents) thereof.

4. BRIEF DESCRIPTIONS OF FIGURES

Figure 1B:
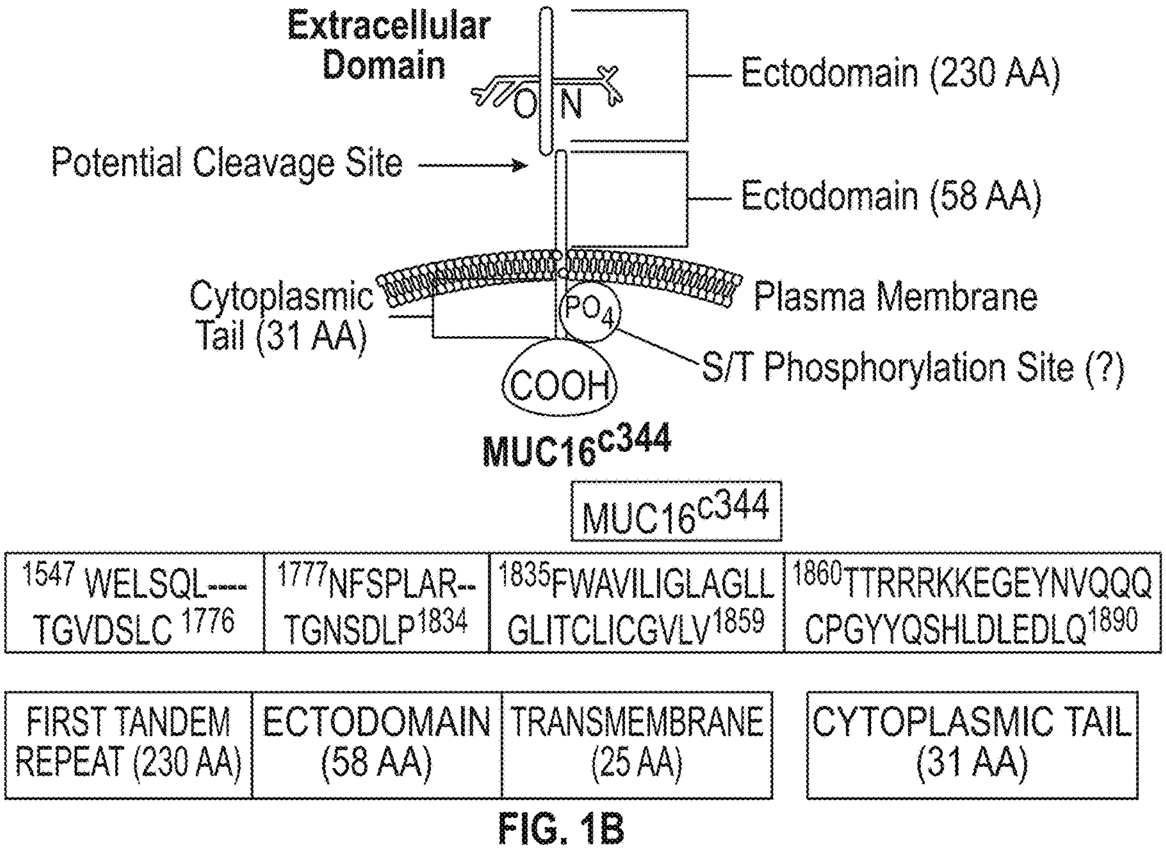
Figure 1C:
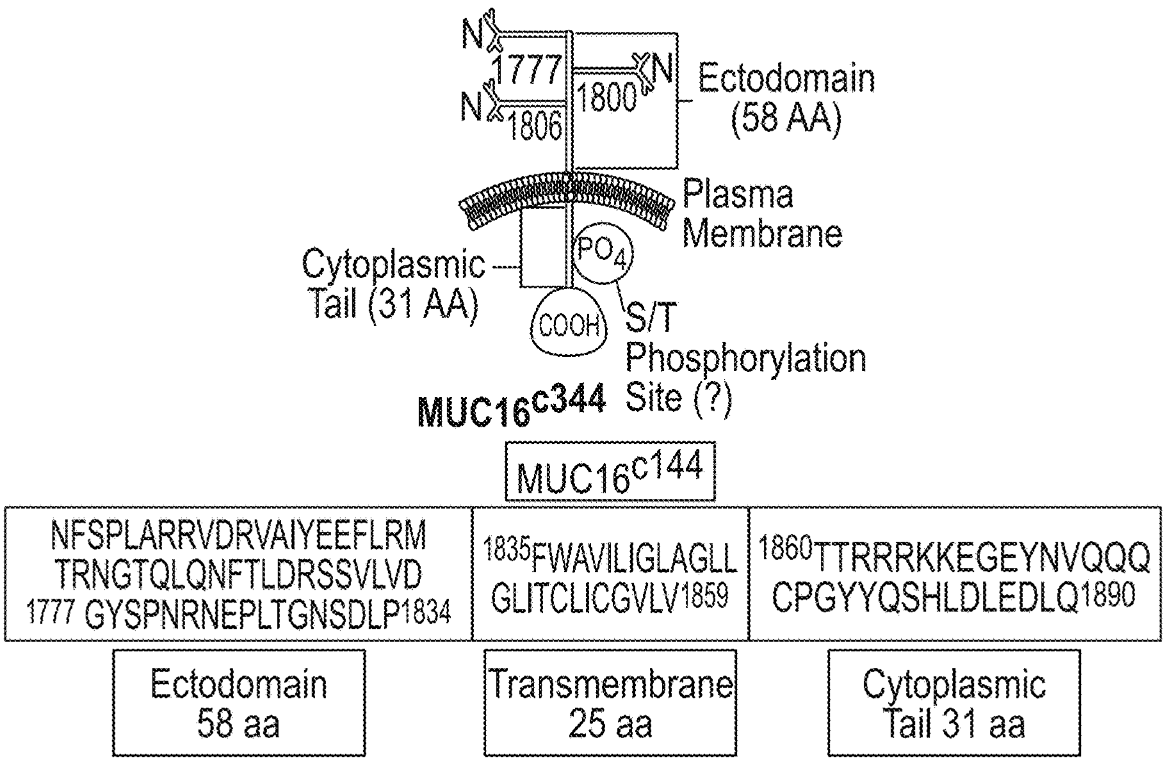
Figure 1D:
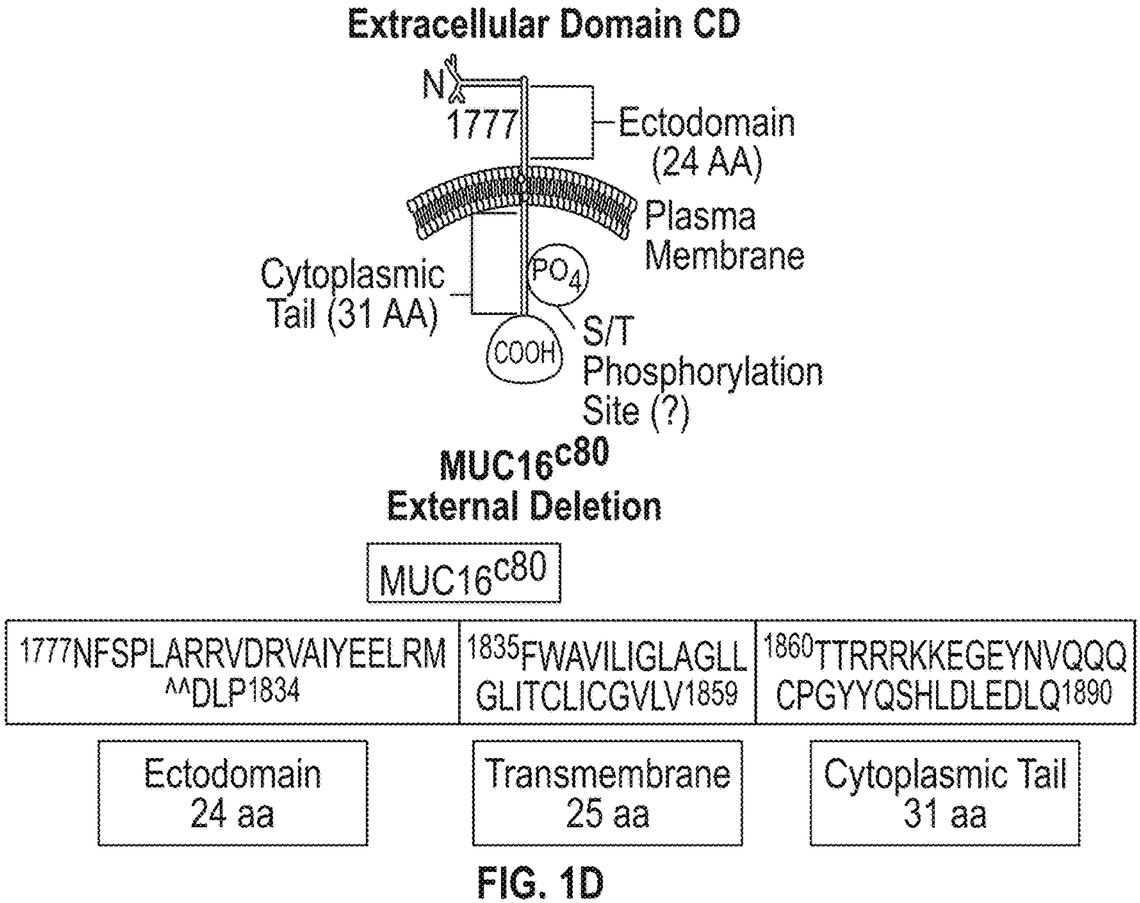
Figure 1G:
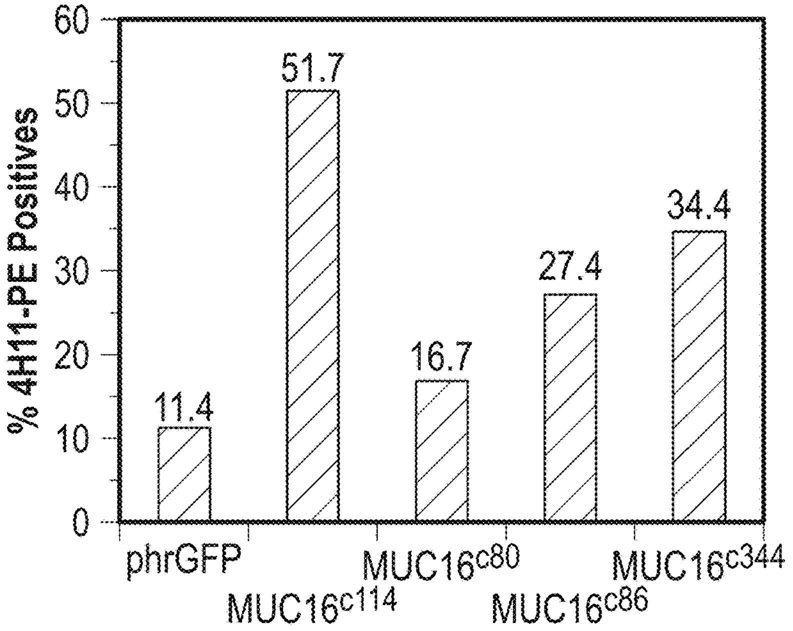
Figure 1H:
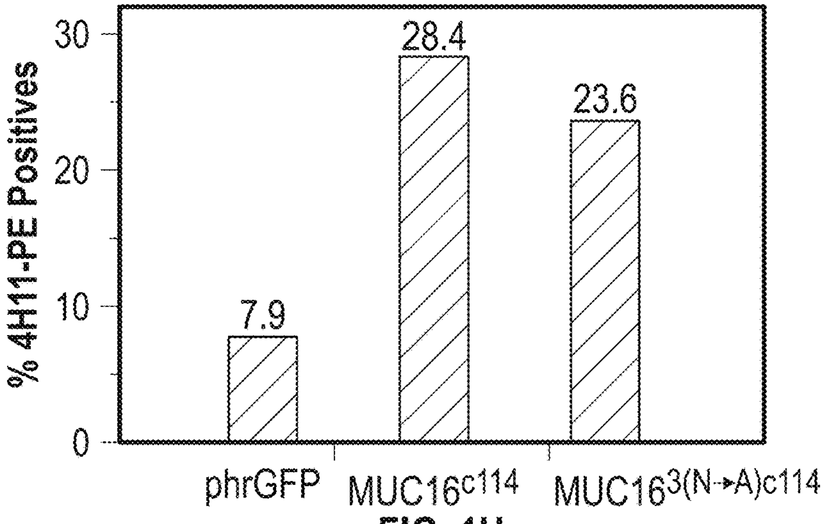
Figure 1I:
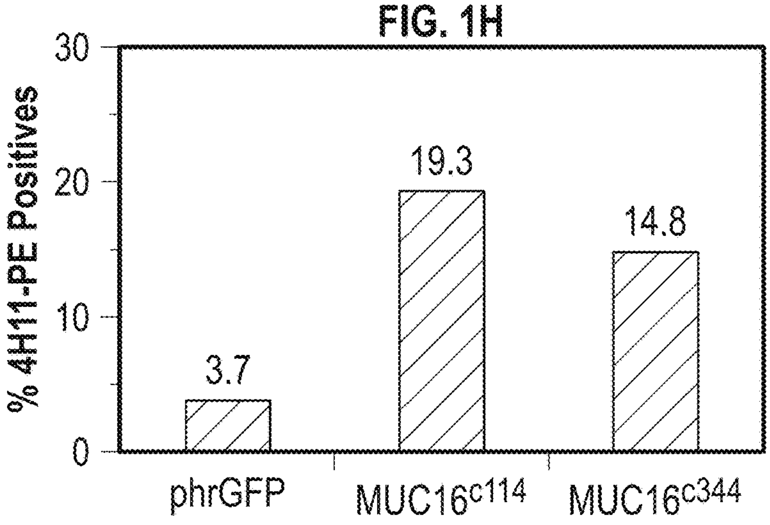

FIG. 1A-FIG. 1I. MUC16 constructs. FIG. 1A: Schematic illustration of MUC16. FIG. 1B: Top: Schematic illustration of $MUC16^{c344}$. Bottom: Linear representation of the truncated $MUC16^{c344}$ construct. The amino acid sequence of the N-terminus of the first tandem repeat is as set forth in SEQ ID NO: 155. The amino acid sequence of the C-terminus of the first tandem repeat is as set forth in SEQ ID NO: 156. The amino acid sequence of the N-terminus of the ectodomain is as set forth in SEQ ID NO: 157. The amino acid sequence of the C-terminus of the ectodomain is as set forth in SEQ ID NO: 158. FIG. 1C: Top: Schematic illustration of $MUC16^{c114}$. Bottom: Linear representation of $MUC16^{c114}$. The amino acid sequence of the ectodomain is as set forth in SEQ ID NO: 161. The amino acid sequence of the transmembrane is as set forth in SEQ ID NO: 159. The amino acid sequence for the cytoplasmic tail is as set forth in SEQ ID NO: 160. FIG. 1D: Top: Schematic illustration of $MUC16^{c80}$. Bottom: Linear representation of the $MUC16^{c80}$. The amino acid sequence of the ectodomain is as set forth in SEQ ID NO: 162. The amino acid sequence of the transmembrane is as set forth in SEQ ID NO: 159. The amino acid sequence of the cytoplasmic cail is as set forth in SEQ ID NO: 159. FIG. 1E: Top: Schematic illustration of $MUC16^{c86}$. Bottom: Linear representation of the $MUC16^{c86}$ The amino acid sequence of the ectodomain is as set forth in SEQ ID NO: 163. The amino acid sequence of the transmembrane domain is as set forth in SEQ NO: 164. The amino acid sequence of the cytoplasmic domain is SEQ ID NO: 165. FIG. 1F: Linear representation of the $MUC16^{c114\text{-}N123}$. The amino acid sequence of 3(N→A) Mutated Ectodomain 58 aa is as set forth in SEQ ID NO: 166. The amino acid sequence of the transmembrane domain is as set forth in SEQ ID NO: 159. The amino acid sequence of the cytoplasmic domain is as set forth in SEQ ID NO: 160. FIG. 1G, FIG. 1H, and FIG. 1I depict the percent of cells detected by 4H11 via FACS analysis, wherein the cell lines express the indicated MUC16 constructs.

FIG. 2A-FIG. 2C. In vitro growth curves for MUC16 transfectants. FIG. 2A depicts in vitro growth curves for $MUC16^{c114}$ and $MUC16^{c344}$ cell lines, as compared to the control cell line (phrGFP), in 3T3 cells. FIG. 2B depicts in vitro growth curves for $MUC16^{c114}$ and $MUC16^{c344}$ cell lines, as compared to the control cell line (phrGFP), in A2780 cells. FIG. 2C depicts in vitro growth curves for $MUC16^{c114}$, $MUC16^{c80}$, and $MUC16^{c86}$ cell lines, as compared to the control cell line (phrGFP), in 3T3 cells.

Figure 3D:
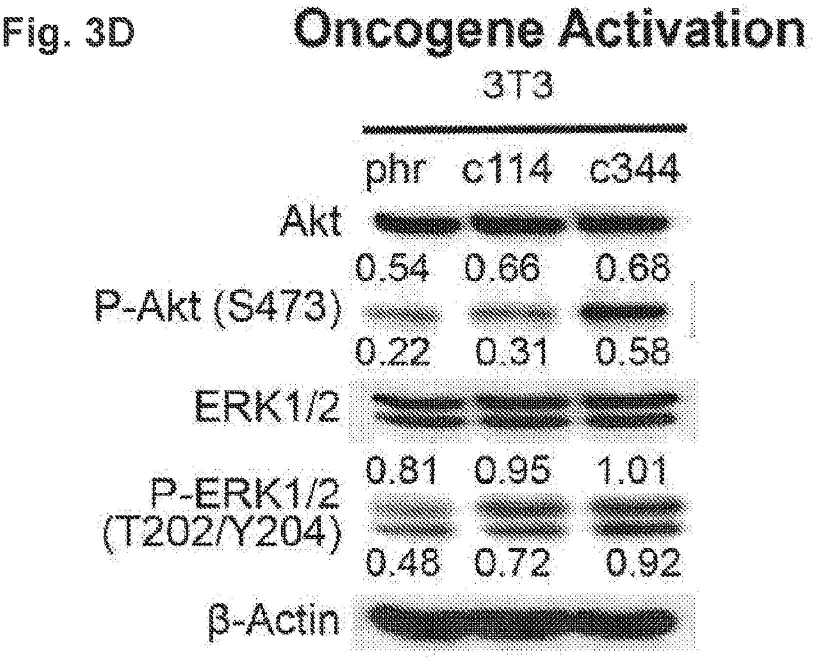
Figure 3E:
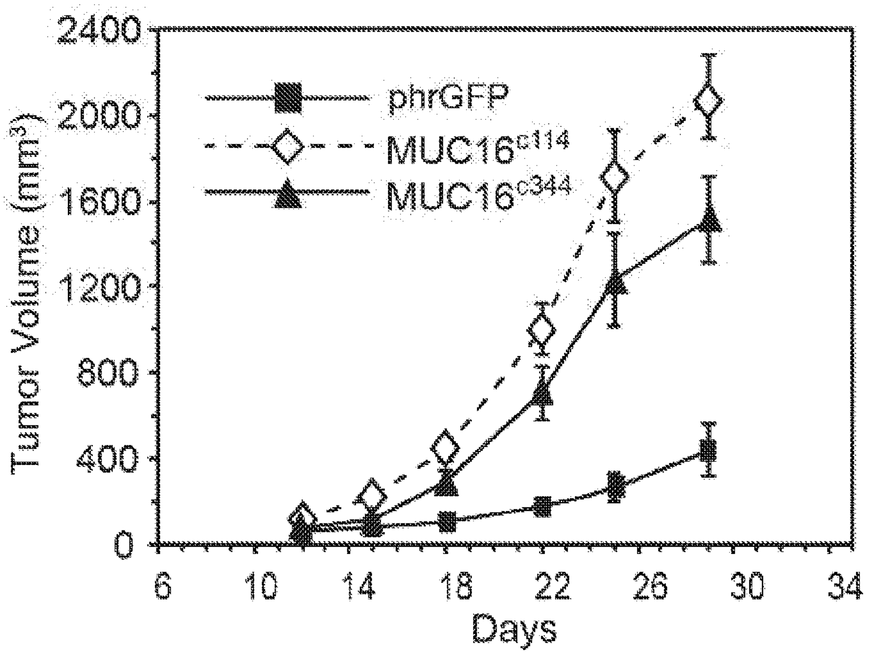

FIG. 3A-FIG. 3E. Effect of MUC16 in 3T3 cells. FIG. 3A depicts soft agar growth of 3T3 transfectants in 60 mm dishes. After 14 days, colonies were counted and plotted. Data shown in the table represent one of three similar experiments (*p<0.0001) compared to soft agar growth of cells expressing the phrGFP control vector. FIG. 3B depicts matrigel invasion assay for 3T3 cell lines following stable transfections with either phrGFP control vector or with $MUC16^{c114}$ or $MUC16^{c344}$ carboxy-terminus constructs. Each assay was performed two or more times in triplicate and counted by hand. Both $MUC16^{c114}$ and $MUC16^{c344}$ cell lines were significantly more invasive (*p<0.0001) compared to invasion of cells expressing the phrGFP vector control and the results with the $MUC16^{c344}$ cell line was significantly different from the results with the $MUC16^{c114}$ cell line ((# p=0.0354). FIG. 3C depicts the expression of metastasis and invasion genes induced by $MUC16^{c114}$ and $MUC16^{c344}$ expression. A SuperArray panel of 80 invasion/metastasis gene transcripts was examined for MUC16-construct-positive and vector only cell lines. The expression of selected chemotactic, adhesion, and invasion transcripts was measured in 3T3 $MUC16^{c114}$ or 3T3-$MUC16^{c344}$ cell lines (each of three triplicates was examined in duplicate and compared to the phr vector only controls by chi square testing). The p value for each transcript, adjusted for repeated measures, is shown in the table. All genes with changes at the p<0.05 or below level are included. FIG. 3D: Transfected 3T3 cells were examined for activation of the ERK/AKT signaling pathways compared to the vector only controls. Phosphorylation of ERK1/2 (pT202/Y204) and AKT (S473) was increased following expression of the $MUC16^{c114}$ and $MUC16^{c344}$ constructs, as compared to the expression of the phr vector. Activation of both pathways was seen in each of the cell lines. B-actin normalized densitometry quantification values are shown below each western blot in the figure. FIG. 3E depicts MUC16-construct-positive tumor growth in athymic nude mice. Two million tumor cells were introduced into the flank of 15 nu/nu mice, and the mice were observed for tumor formation. Tumors were measured by calipers twice weekly. The differences in mean tumor volume were significantly greater for mice bearing MUC16-construct-positive tumors (both lines p<0.0001 compared to cells expressing the phrGFP control vector).

Figure 4B:
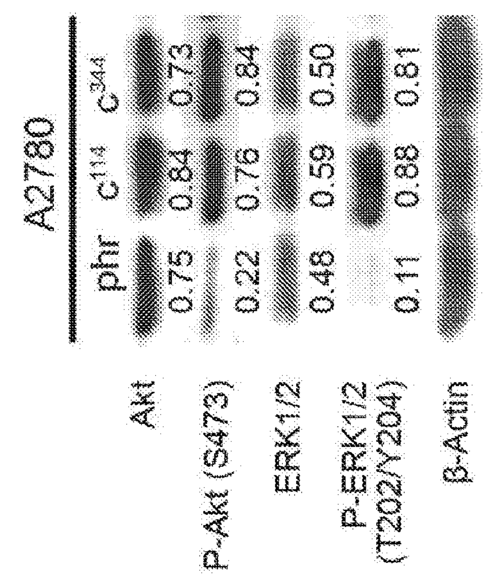
Figure 4A:
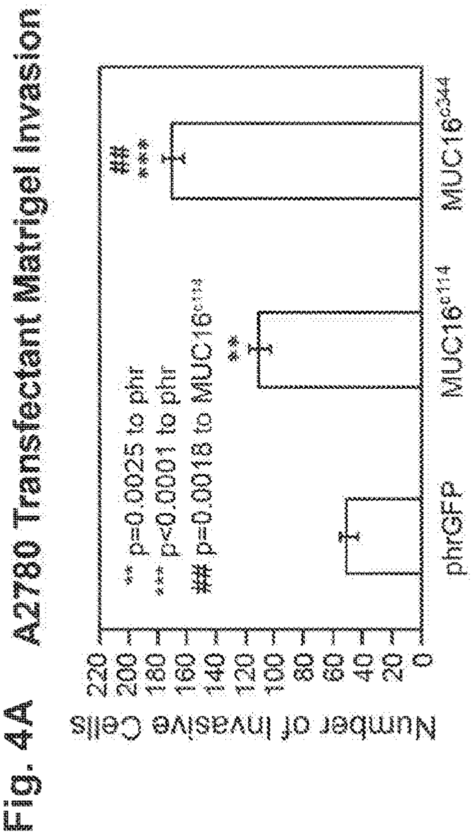
Figure 4C:
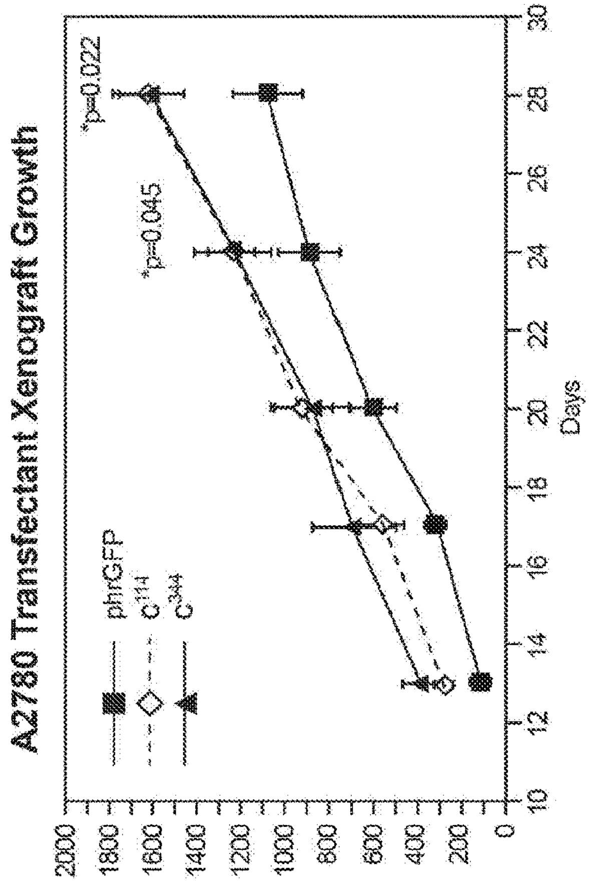

FIG. 4A-FIG. 4C. Oncogenic properties of MUC16 fragments. FIG. 4A depicts matrigel invasion assay for A2780 cell lines transfected either phrGFP control vector or with MUC16 carboxy-terminus expression vectors, $MUC16^{c114}$ or $MUC16^{c344}$. Each assay was performed two or more times in triplicate and counted by hand. Results were compared to matrigel invasion of cells expressing phrGFP control vector or $MUC16^{c114}$. $MUC16^{c114}$ or $MUC16^{c34}$ cell lines showed significant matrigel invasion relative to phrGFP vector control, and the results with the $MUC16^{c344}$ cell line was significantly different from the results with the $MUC16^{c114}$ cell line (##p=0.0018). FIG. 4B depicts the effect of MUC16 expression on ERK/AKT signaling. A2780 cells were examined for activation of the ERK/AKT signaling pathways. Phosphorylation of ERK1/2 (pT202/Y204) and AKT (S473) was increased following expression of each of the MUC16 expression constructs. Both pathways were activated in each of the cell lines. β-actin normalized densitometry quantification values are shown below each western blot in the figure. FIG. 4C depicts MUC16-construct-positive tumor growth in athymic nude mice. Two million tumor cells were introduced into the flank of 15 nu/nu mice, and the mice were observed for tumor formation. Tumors were measured by calipers twice weekly. The differences in mean tumor volume were significantly greater for mice bearing any of the $MUC16^{c114}$- or $MUC16^{c344}$-positive tumors at day 28, as indicated in the figure.

Figure 5A:
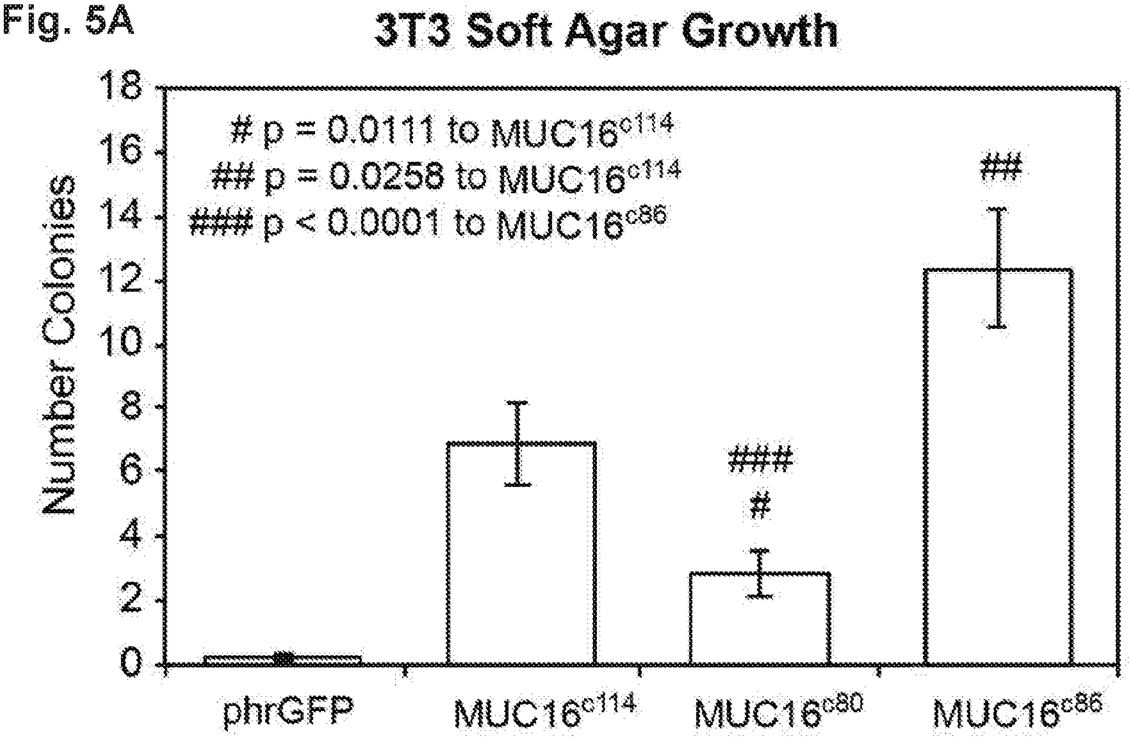
Figure 5B:
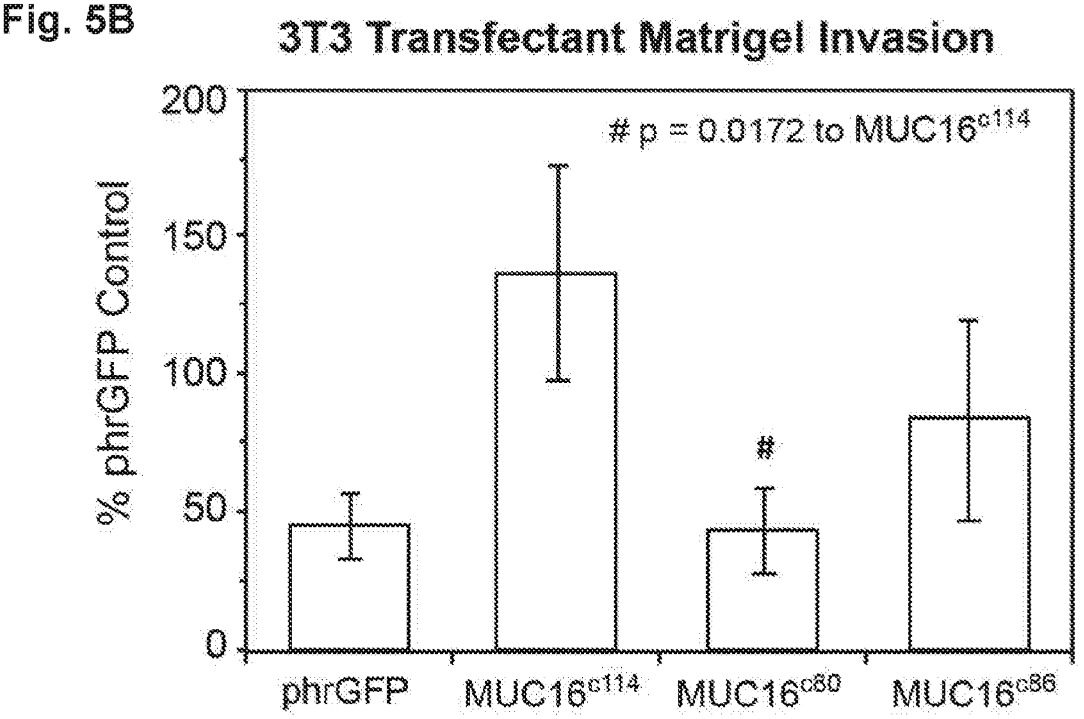
Figure 5C:
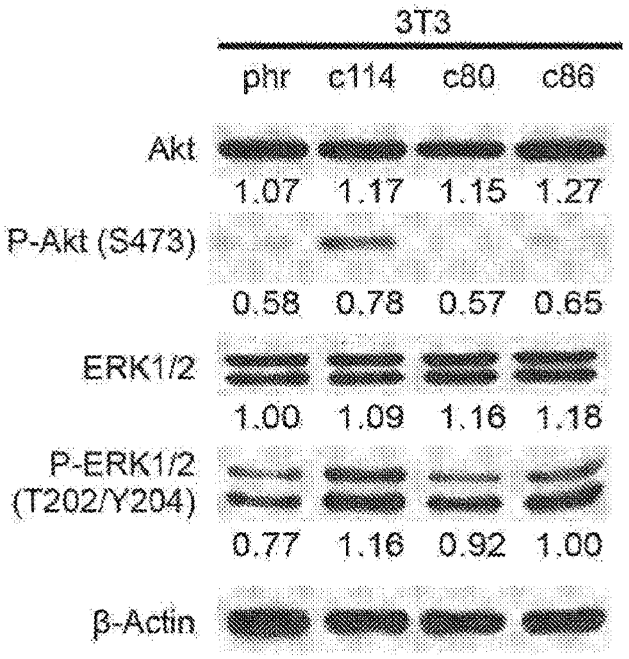
Figure 5D:
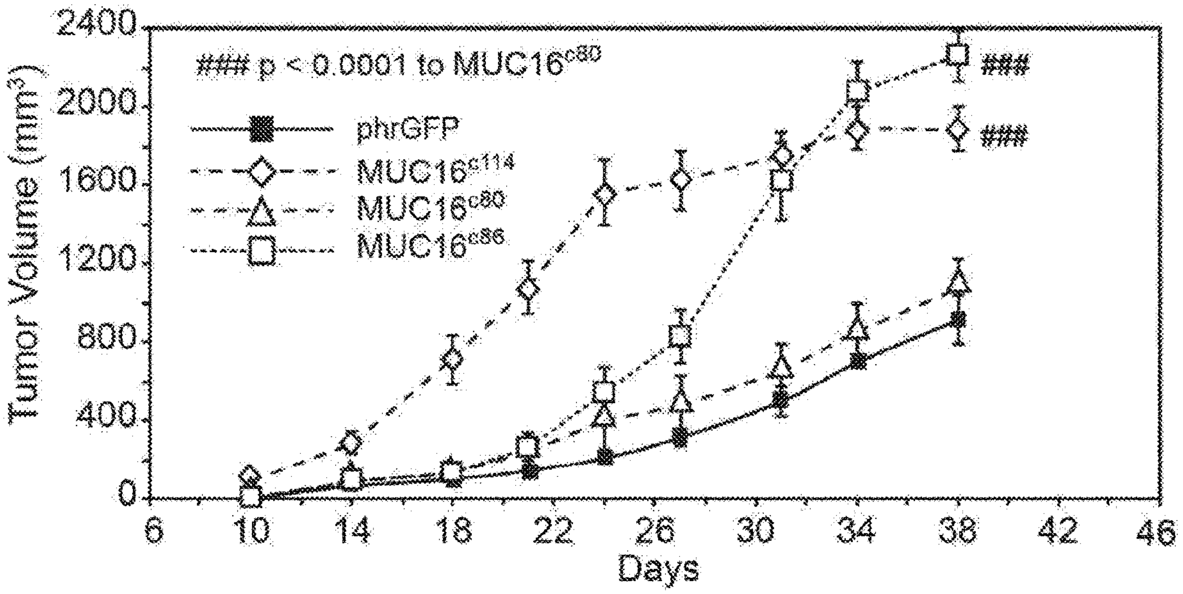

FIG. 5A-FIG. 5D: Effects of truncated $MUC16^{c114}$ variants. FIG. 5A: Soft agar growth. 3T3 transfectants expressing either internal or external domain portions of $MUC16^{c114}$ were layered on soft agar, as described in Section 6.1.2. Colonies were counted and plotted. The data shown represent one of three experiments. Soft agar growth rates for $MUC16^{c80}$ and $MUC16^{c86}$ were significantly different compared to the growth rate for $MUC16^{c114}$ (# p=0.0111 and ## p=0.0258, respectively), whereas a higher level of significance was seen with the growth rate for $MUC16^{80}$ transfectant compared to the growth rate for MUC16$^{c86}$ transfectant (### p<0.0001). FIG. 5B depicts matrigel invasion assay for 3T3 cell lines transfected either phrGFP control vector or with MUC16 carboxy-terminus constructs. Each assay was performed two or more times in triplicate and counted by hand. Invasion of the MUC16$^{c80}$ transfectant cells was significant (# p=0.0172) as compared to invasion of the MUC16$^{c114}$ cell line. FIG. 5C depicts the effect of MUC16 expression on ERK/AKT signaling. Transfected 3T3 cells were examined for activation of the ERK/AKT signaling pathways. Phosphorylation of ERK1/2 (pT202/Y204) and AKT (S473) was increased following MUC16$^{c114}$; however, the signals were lower in cells transfected with MUC16$^{c80}$ or MUC16$^{c86}$ constructs. β-Actin normalized densitometry quantification values are shown below each western blot in the figure. FIG. 5D depicts MUC16-construct-positive tumor growth in athymic nude mice. Two million tumor cells were introduced into the flank of 20 nu/nu mice, and the mice were observed for tumor formation. Tumors were measured by calipers twice weekly. The differences in mean tumor volume were significantly greater for mice bearing MUC16+ tumors. 3T3 MUC16$^{c114}$ and 3T3 MUC16$^{c86}$ transfectants were significantly different compared to MUC16$^{c80}$ transfectants (### p<0.0001).

Figure 6A:
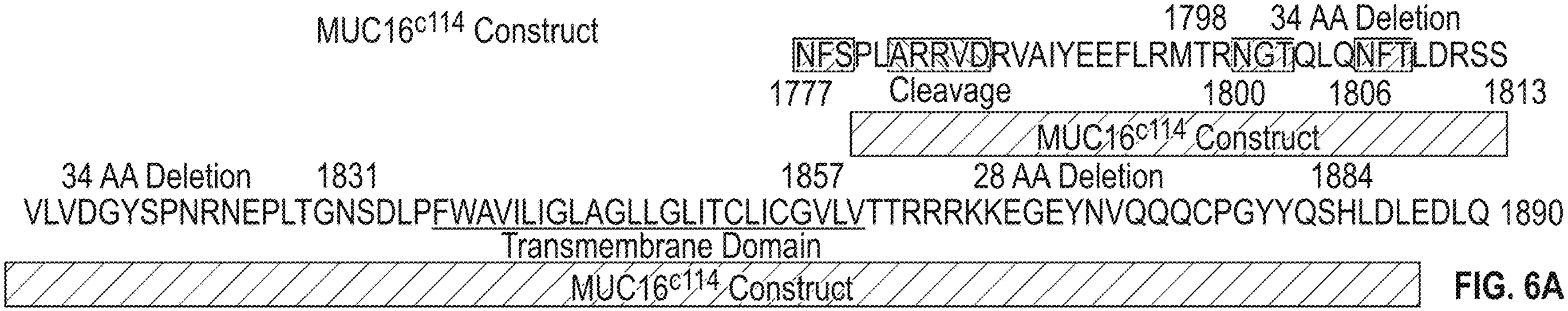
Figure 6B:
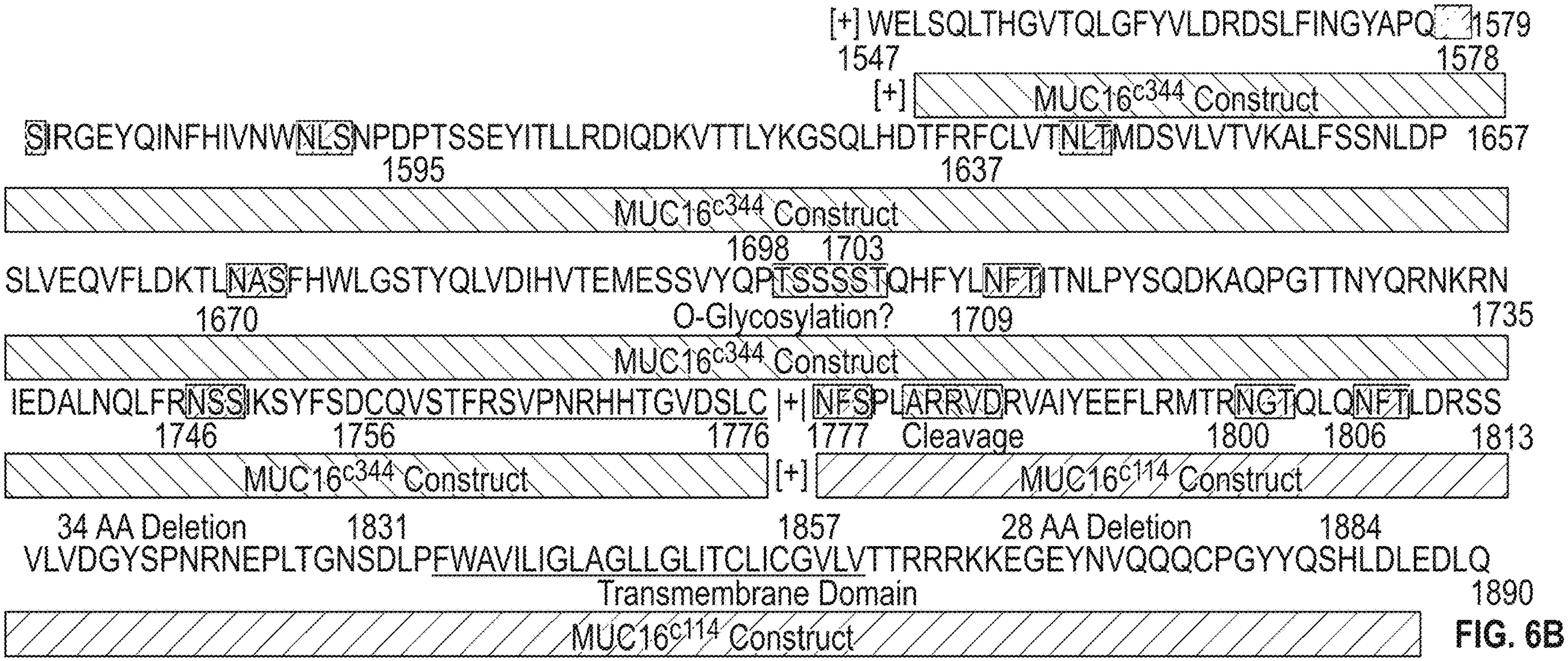

FIG. 6A-FIG. 6B. Amino acid sequence for MUC16$^{c114}$ (amino acid residues 1777 to 1890 (SEQ ID NO: 133), FIG. 6A) and MUC16$^{c344}$ (amino acid residues 1547 to 1890 (SEQ ID NO: 132), FIG. 6B). The N- and O-glycosylation sites are highlighted and the transmembrane domain (amino acid residues 1835 to 1859) is underlined and labeled "Transmembrane Domain." Amino acid residues 1857-1884 represent the 28 amino acid internal domain deletion present in the MUC16$^{c86}$ construct (see, FIG. 1). Amino acid residues 1798-1831 represent the 34 amino acid ectodomain deletion present in the MUC16$^{c80}$ construct (see, FIG. 1).

Figure 7A:
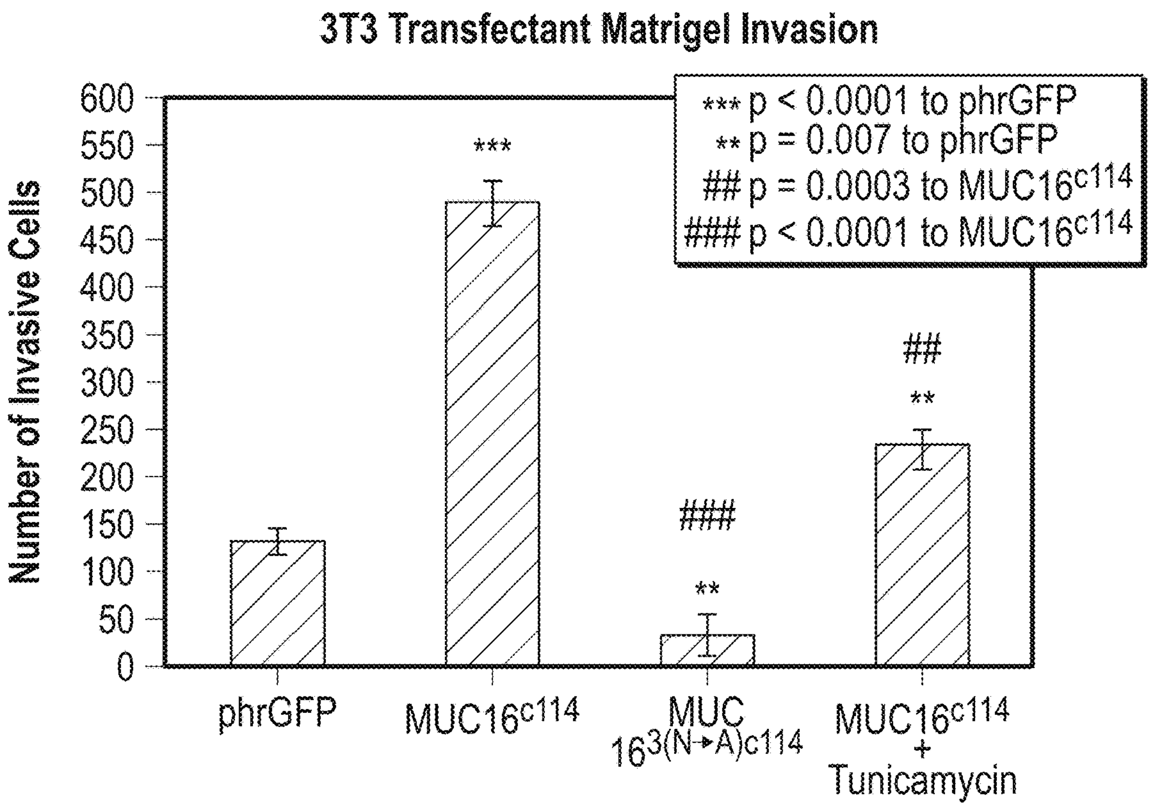
Figure 7B:
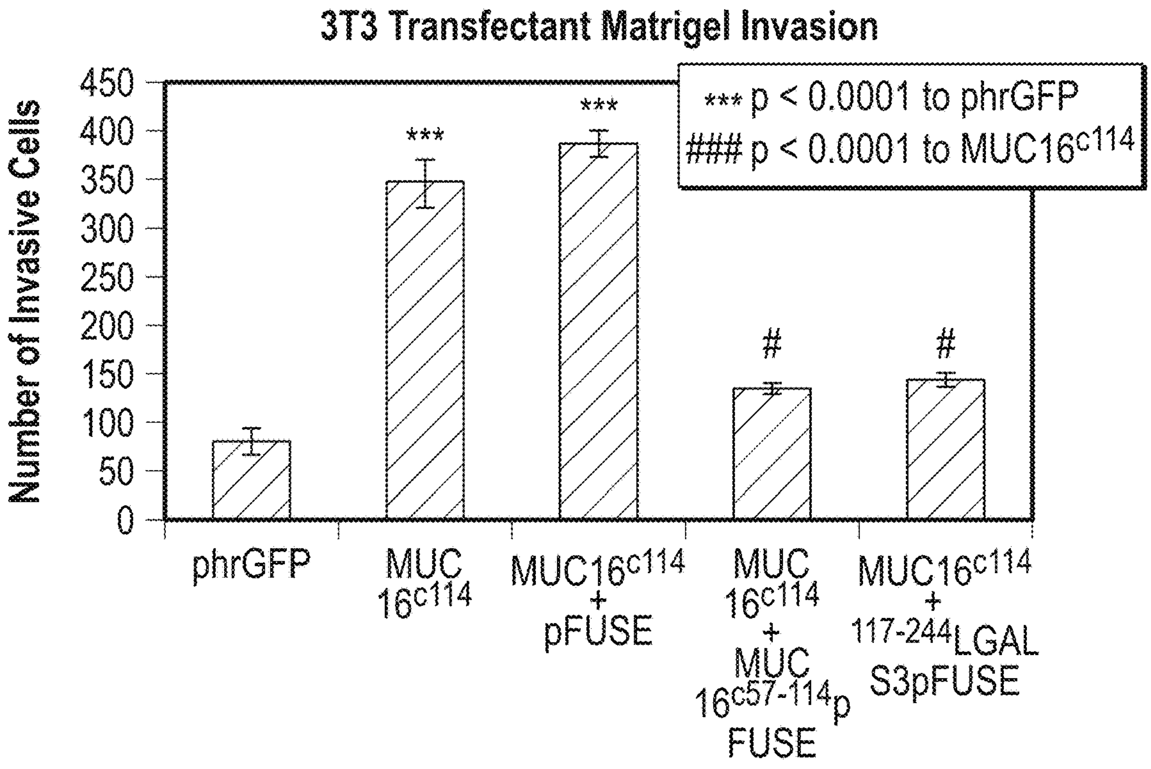
Figure 7C:
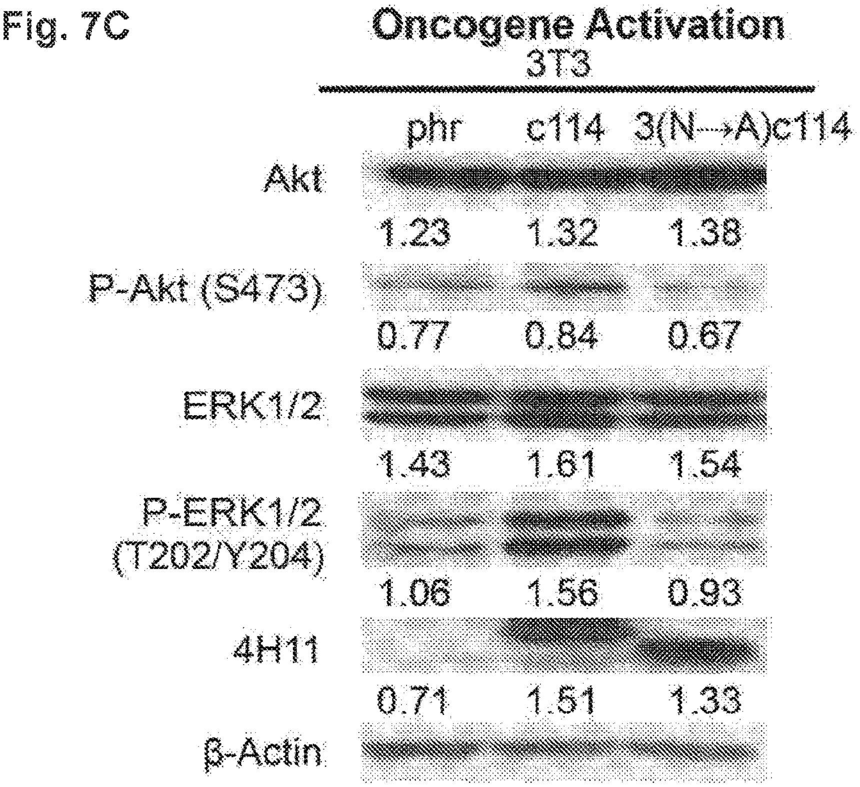
Figure 7D:
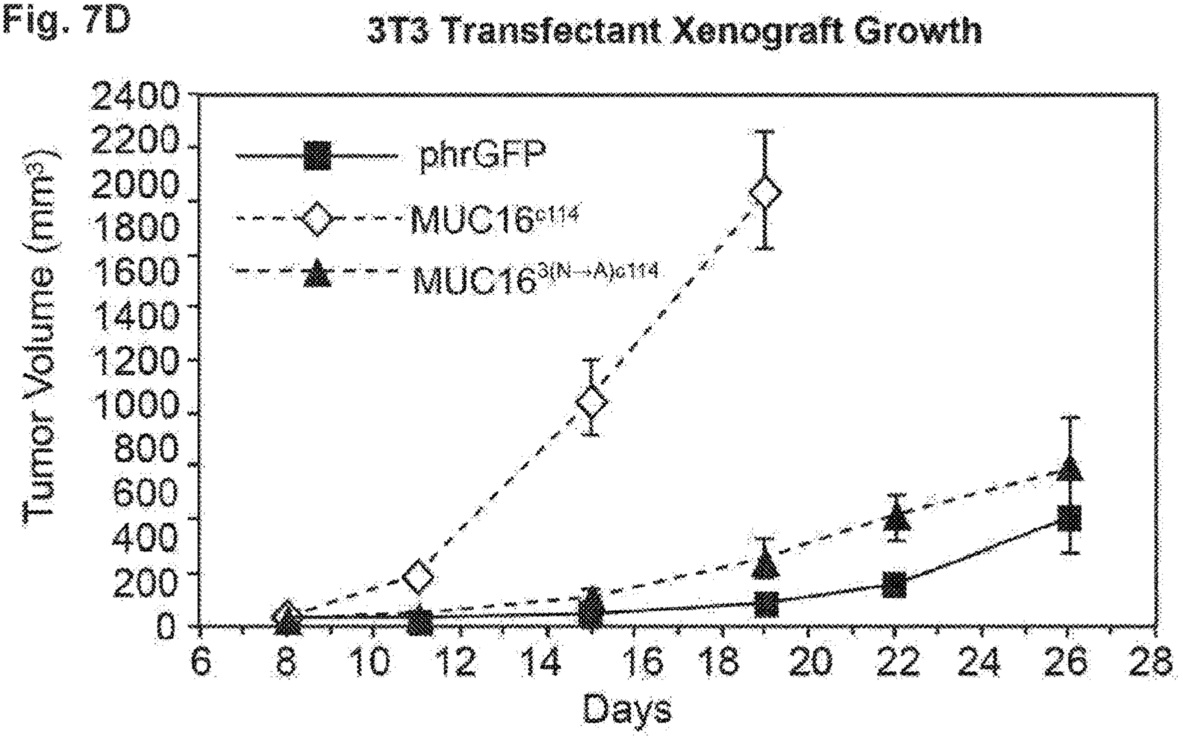
Figure 7E:
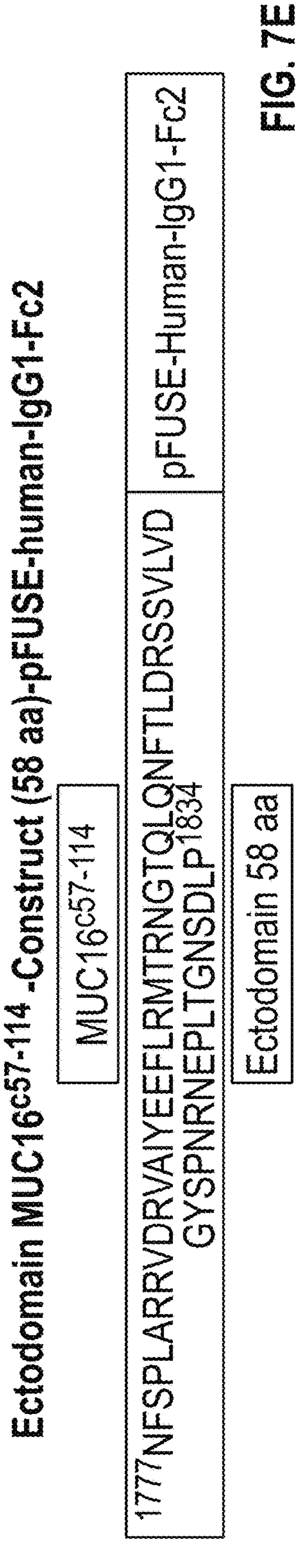
Figure 7F:
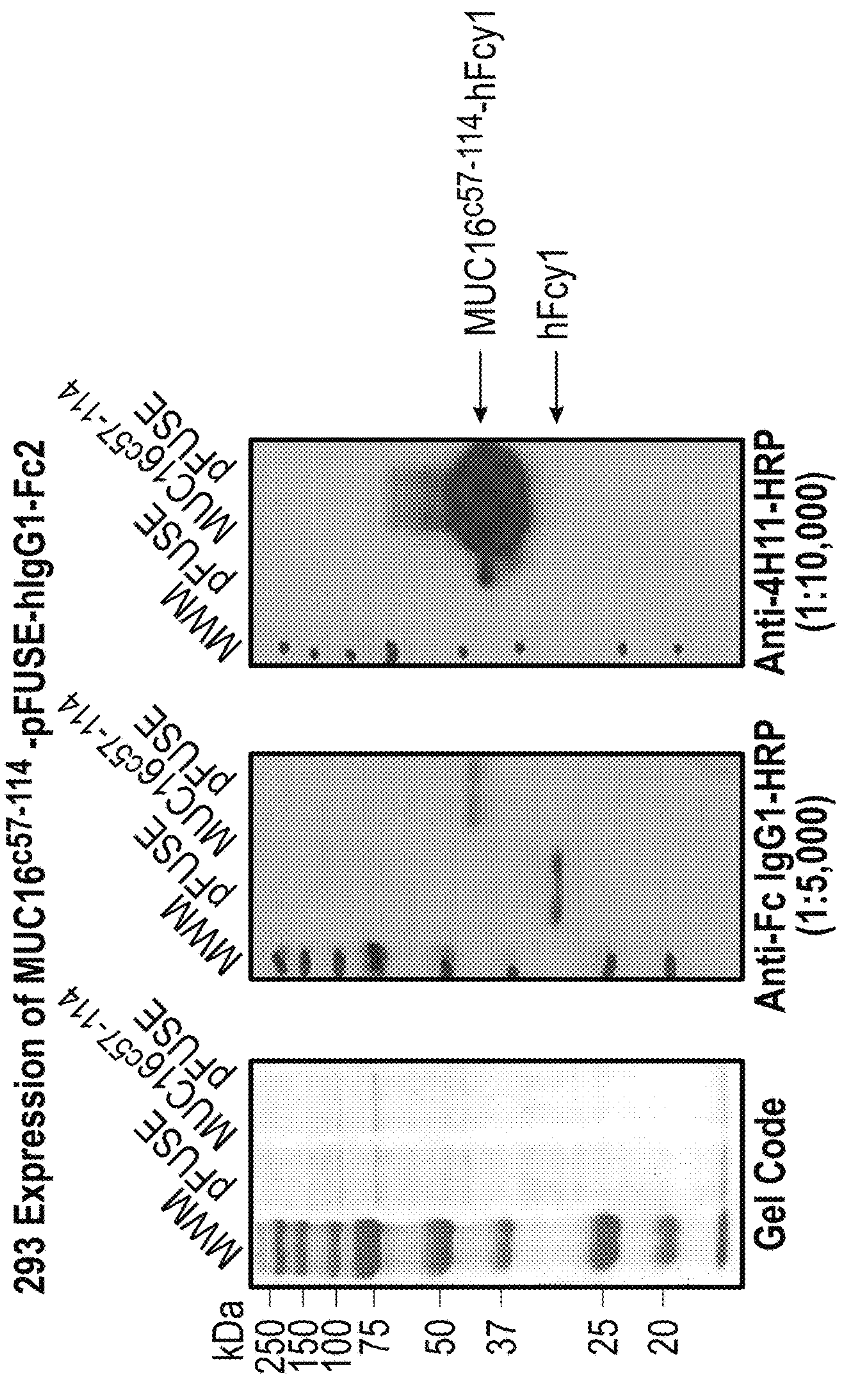
Figure 7G:
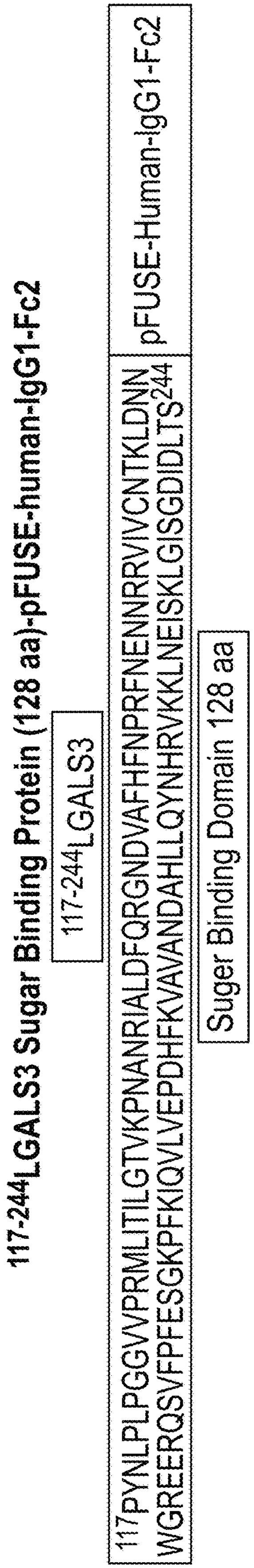
Figure 7H:
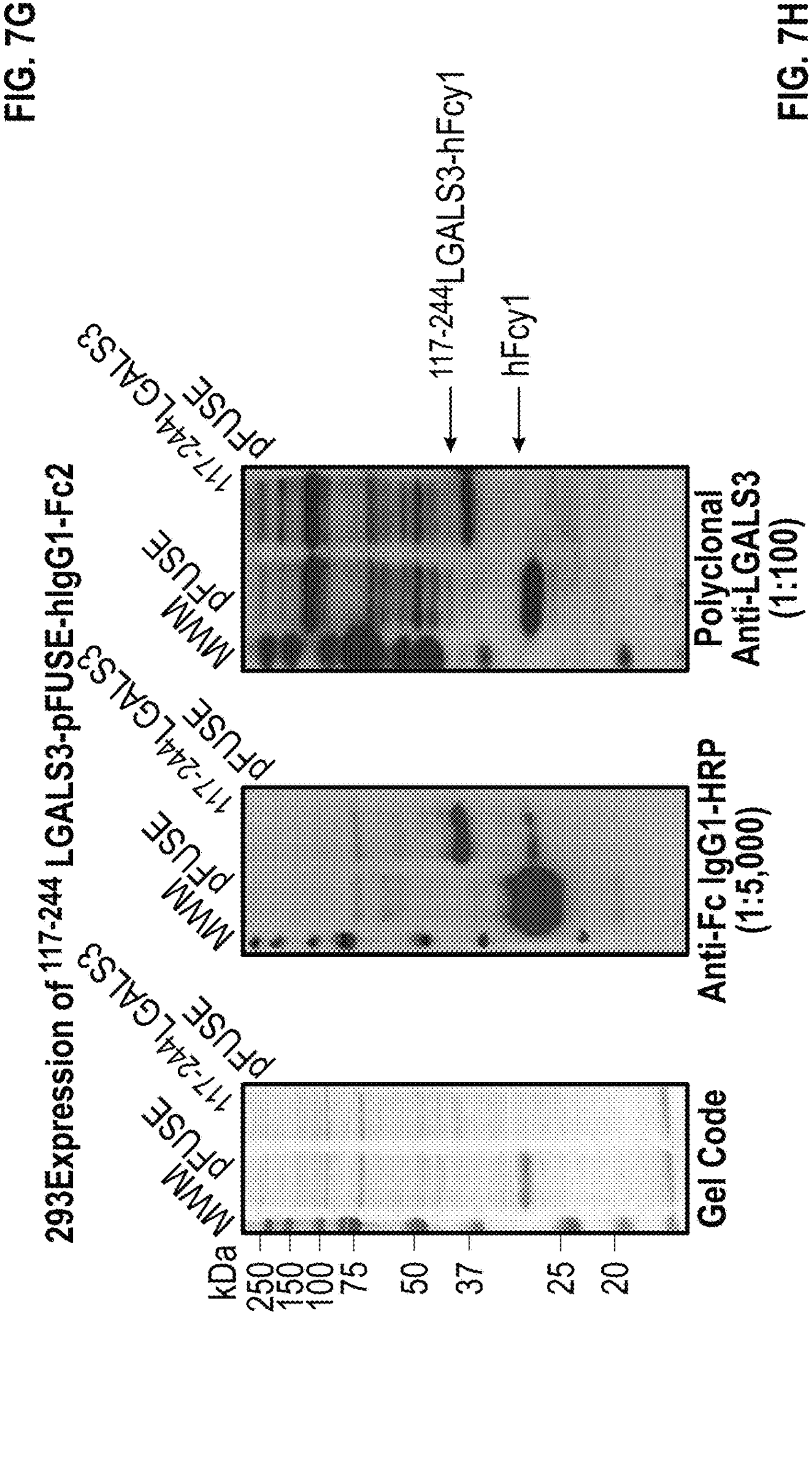

FIG. 7A-FIG. 7H. Effect of N-Glycosylation on MUC16 transformation. FIG. 7A depicts matrigel invasion assay for 3T3 cell lines transfected with phrGFP control vector or MUC16$^{c114}$ or MUC16$^{c114\text{-}N123}$ and MUC16$^{c114}$ treated with 0.1 μg/mL Tunicamycin. Results with the MUC16$^{c114}$ cell line was significantly different (### p<0.0001) than results with the phrGFP vector control cell line. Results with the MUC16$^{c114\text{-}N123}$ cell line were significantly different (p=0.007) compared to results with the phrGFP vector control cell line. Treatment with the N-glycosylation inhibitor Tunicamycin significantly inhibited matrigel invasion compared to the untreated MUC16$^{c114}$ (p=0.004). FIG. 7B depicts matrigel invasion assay for 3T3 transfected cell lines compared to phrGFP control vector. 3T3 cells transfected with MUC16$^{c114}$ were treated with media alone, or treated with 5 μg/mL of control pFUSE hIgG1-Fc2 fusion protein, or with 5 μg/mL of MUC16$^{c57\text{-}c114}$-pFUSE hIgG1-Fc2 fusion protein or with 5 g/mL of $^{117\text{-}244}$LGALS3-pFUSE hIgG1-Fc2 fusion protein as detailed in FIG. 8. The MUC16$^{c114}$ cell line was much more invasive than the control 3T3 cells (*p<0.0001) expressing phrGFP vector control and this was unaffected by exposure to pFUSE vector only protein. In contrast, the MUC16$^{c114}$ cell line treated with MUC16$^{57\text{-}c114}$-pFUSE hIgG1-Fc2 fusion protein or $^{117\text{-}244}$LGALS3-pFUSE hIgG1-Fc2 fusion protein demonstrated significant inhibition of matrigel invasion compared to MUC16$^{c114}$ control cells. FIG. 7C depicts the effect of MUC16 expression on ERK/AKT signaling. Transfected 3T3 cells were also examined for activation of the ERK/AKT signaling pathways. Phosphorylation of ERK1/2 (pT202/Y204) and AKT (S473) was increased in the 3T3 transfected with MUC16$^{c114}$; however, the effect was diminished in 3T3 cells transfected with the MUC16$^{c114\text{-}N123}$ vector ("MUC16$^{c114\text{-}N123}$" and "MUC16$^{3(N\text{-}>>A)c114}$" are used herein interchangeably). Despite mutations the 3 asparagine to alanine mutations, western blot with an anti-MUC16 antibody (4H11 mAb) showed a higher signal than either the phrGFP vector control or the native MUC16$^{c114}$-transfected cells, indicating that the high levels of MUC16$^{3(N\text{-}>A)c114}$ protein is expressed in the transfected 3T3 cells. As used herein, "4H11" refers to the monoclonal anti-MUC16 antibody designated as 4H11 in Rao et al. Appl. Immunohistochem Mol Morphol, 2010, 18(5):462-72 and in International Patent Application Publication No. WO 2011/119979. FIG. 7D depicts MUC16-construct-positive tumor growth in athymic nude mice. Two million tumor cells were introduced into the flank of 20 nu/nu mice, and the mice were observed for tumor formation. Tumors were measured by calipers twice weekly. The differences in mean tumor volume were significantly greater for mice bearing MUC16$^{c114}$ tumors (p<0.0001). Results with the 3T3-MUC16$^{c114}$ transfectant were highly significant as compared to results with the phrGFP control vector cell line (*p<0.0001). However, MUC16$^{c114\text{-}N123}$ 3T3 transfectants did not show any significance over phrGFP vector control 3T3 cells indicating that the mutations of N-glycosylation dramatically decreased tumor growth and invasion. FIG. 7E depicts the linear representation of the MUC16$^{c57\text{-}114}$-pFUSE-human-IgG1-Fc2 construct. The amino acid sequence of the ectodomain is as set forth in SEQ ID NO: 161. FIG. 7F depicts protein levels of MUC16$^{c57\text{-}114}$-pFUSE-human-IgG1-Fc2 construct determined by the indicated antibodies. FIG. 7G depicts the linear representation of the $^{117\text{-}244}$LGALS3-pFUSE-human-IgG1-Fc2 construct. The amino acid sequence of the sugar binding domain is as set forth in SEQ ID NO: 167. FIG. 7**H depicts protein levels of $^{17\text{-}244}$LGALS3-pFUSE-human-IgG1-Fc2 construct determined by the indicated antibodies.

Figures 8, 9A:
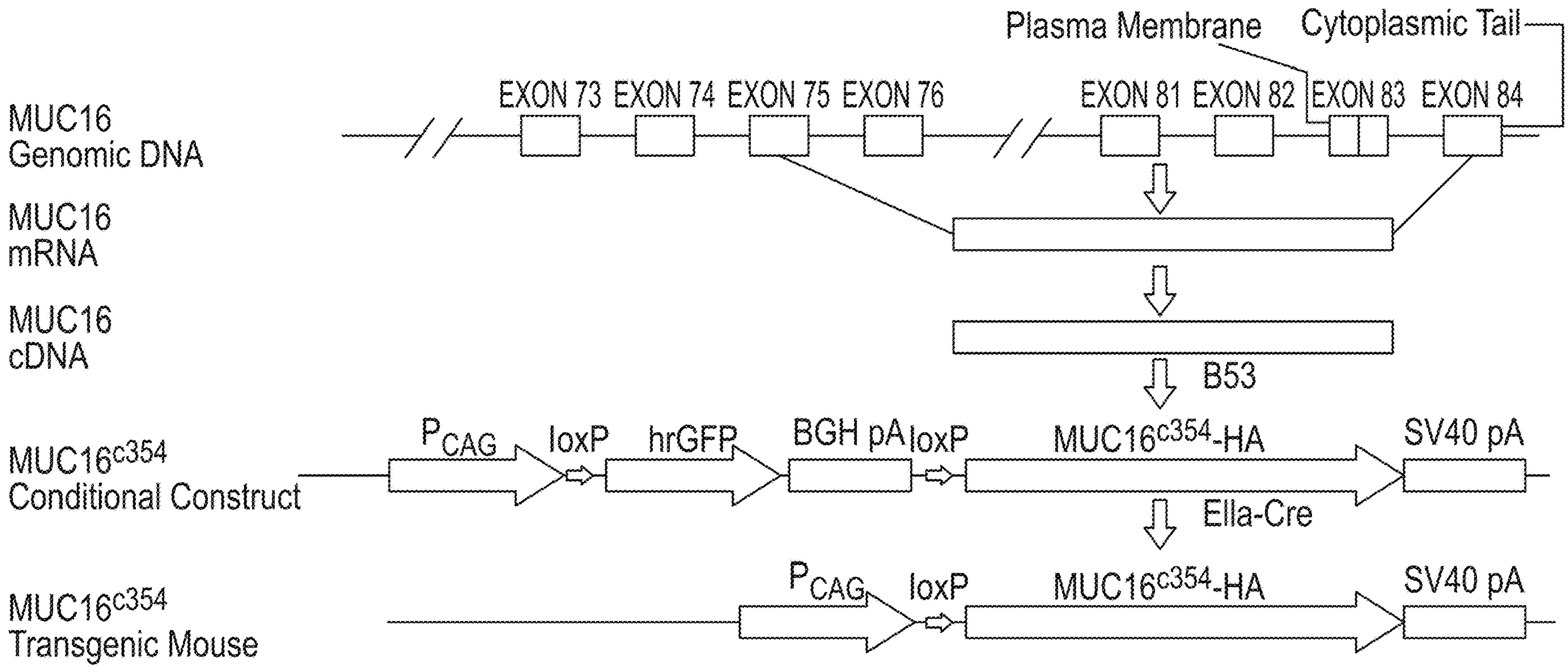

FIG. 8. Sequence for the ectodomain-MUC16$^{57\rightarrow c114}$ (SEQ ID NO: 161; amino acid residues 1777-1834 of MUC16) amino acid sequence inserted into the pFUSE-hIgG1-Fc2 vector to construct the MUC16$^{57\text{-}c114}$pFUSE as a sham receptor and the $^{117\text{-}244}$LGALS3 amino acid sequence (SEQ ID NO: 167) inserted into pFUSE-hIgG1-Fc2, resulting in the $^{117\text{-}244}$LGALS3pFUSE vector.

Figure 9B:
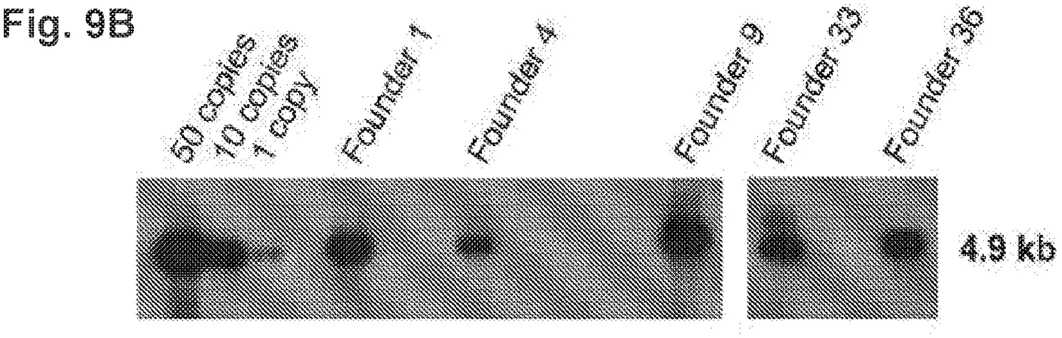
Figure 9C:
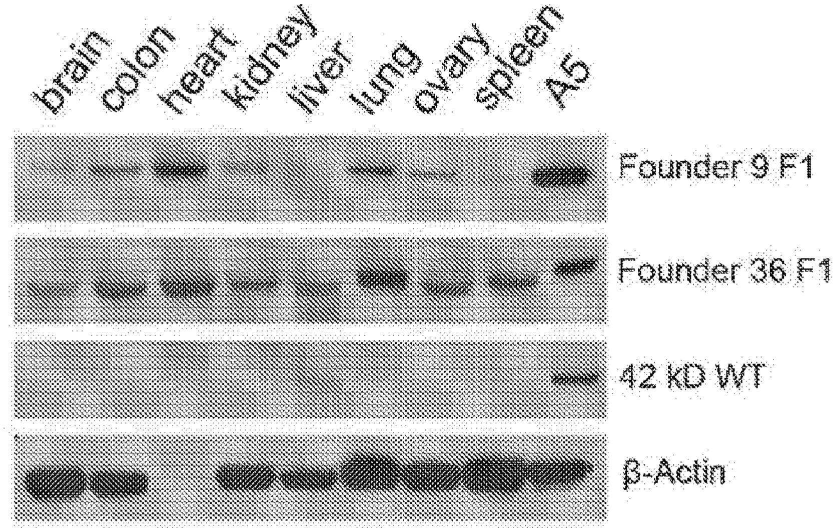
Figure 9D:
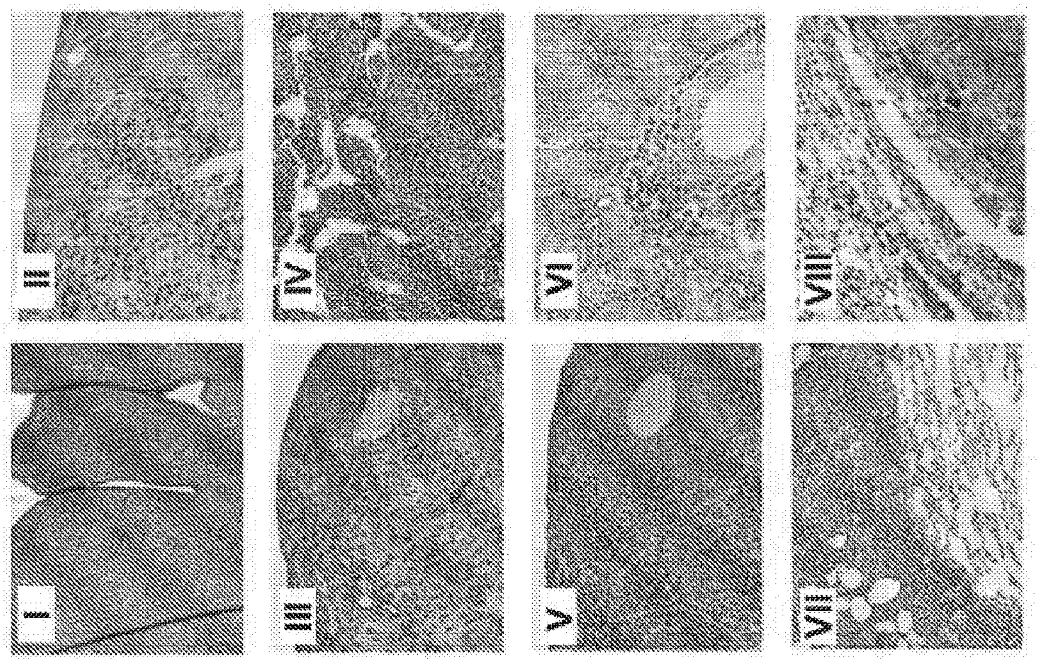
Figure 9E:
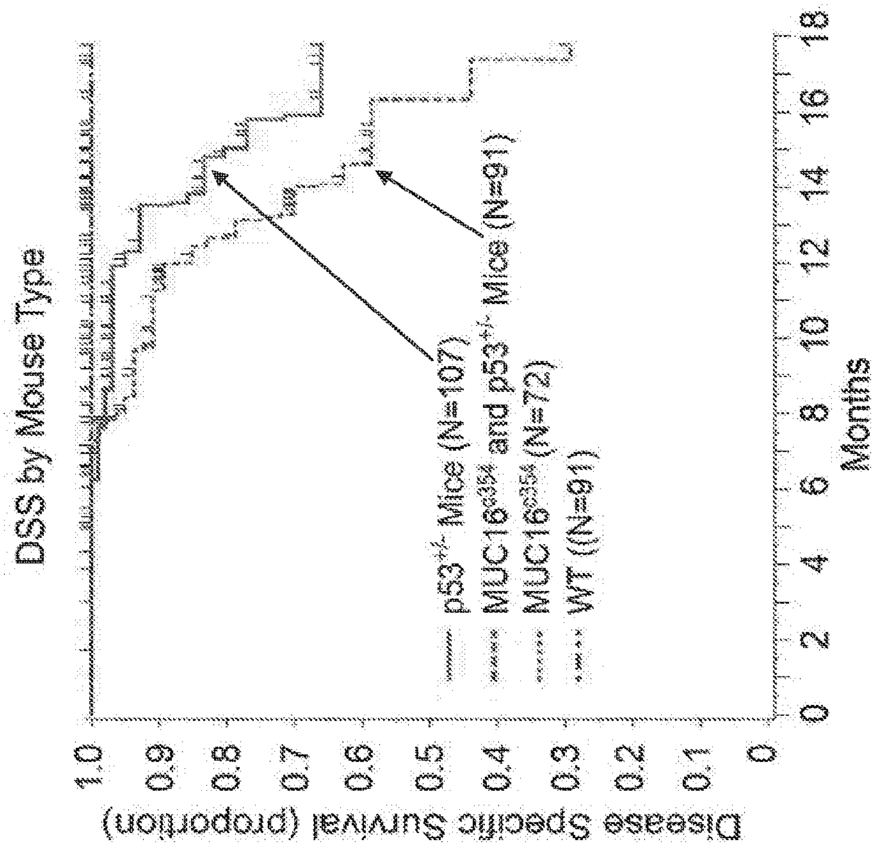

FIG. 9A-FIG. 9E. MUC16c354 transgenic mice. FIG. 9A depicts the strategy for the MUC16$^{c354}$ conditional construct. A CMV early enhancer plus the chicken β actin promoter (CAG) was used to drive the transcription of hrGFP between two loxPs and the downstream MUC16$^{c354}$ sequence. FIG. 9B: Southern blot shows 12 candidates of MUC16$^{c354}$ positive founders among 99 animals after microinjection procedure. FIG. 9C: Western blot with anti-MUC16 antibody, 4H11, was used to identify founders 9 (~50 copies) and 36 (~10 copies) for MUC16$^{c354}$ mouse colony development; A5 is a positive control from a stable transfected SKOV3 with MUC16$^{c354}$. FIG. 9D: Histological analyses of tumors from double MUC16$^{c354}$:p53+/− transgenic mice. Multiple sarcomas and lymphomas were identified in the double MUC16$^{c354}$:p53+/− transgenic mice. Sections were stained with hematoxylin and eosin (H&E). Tumor include histocytic sarcoma in uterus (I, Scale bar: 100 μm), liver (II, Scale bar: 50 μm), ovary (III, Scale bar: 50 μm) and bone marrow (IV, Scale bar: 50 μm) as well as lymphoma in ovary (V, Scale bar: 50 μm), kidney (VI, Scale bar: 50 μm), and lung (VII, Scale bar: 50 μm) with carcinoma in the lung (VIII, Scale bar: 50 μm). FIG. 9E: Transgenic mouse cancer specific Kaplan-Meier Survival Curves: the MUC16$^{c354}$ mice showed no spontaneous tumor development over the first 18 months, similar to the wild type (WT). However, when $MUC16^{c354}$ mice were crossed with p53+/− mice, the double transgenic $MUC16^{c354}$: p53+/− mice showed a significantly worse overall survival due to spontaneous tumor development compared to either the p53+/− mice (p<0.014) or the $MUC16^{c354}$ mice.

Figure 10:
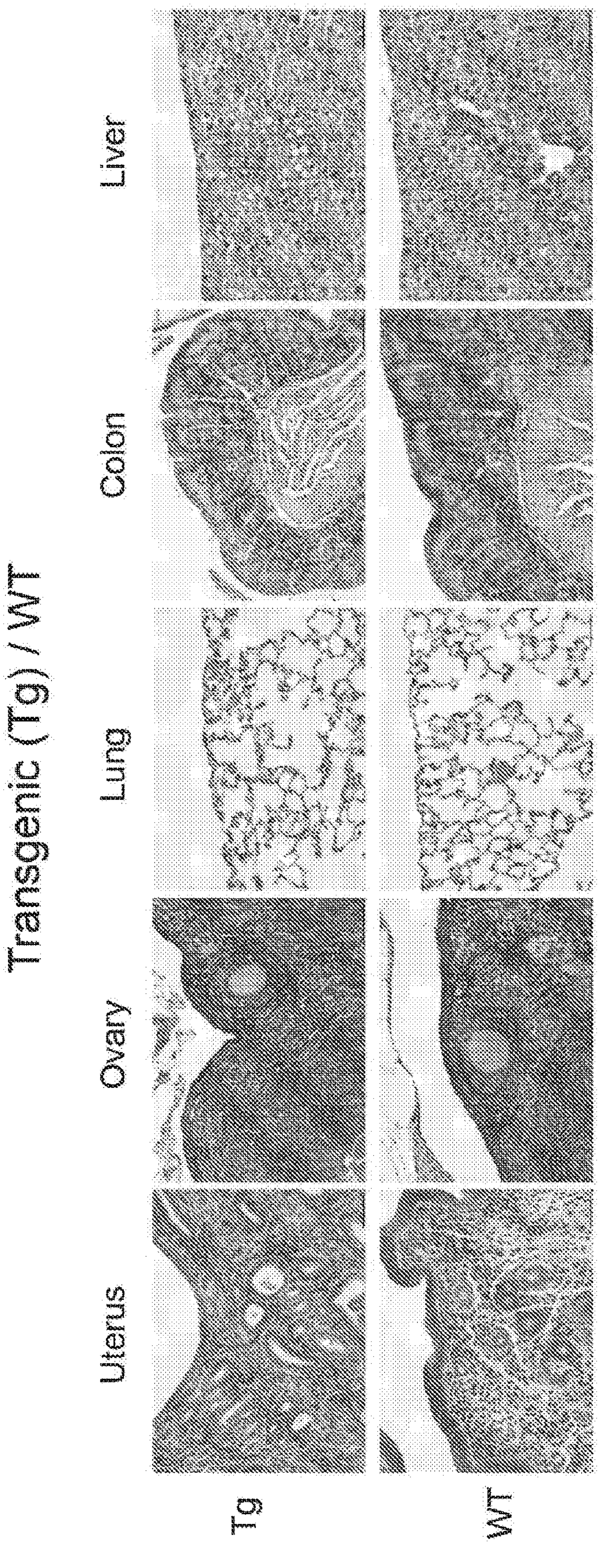

FIG. 10. Representative tissue histological from 12 months old male and female $MUC16^{c354}$ transgenic mice. Tissue sections were stained with hematoxylin and eosin (H&E, Scale bar: 50 μm). Uterine endometrial hyperplasia was observed with similar incidence and severity in both genotypes (here only shown in the transgenic animal). The ovary, lung, colon and liver of transgenic animals (Tg) were similar to the parental line (wild type, WT).

Figure 11A:
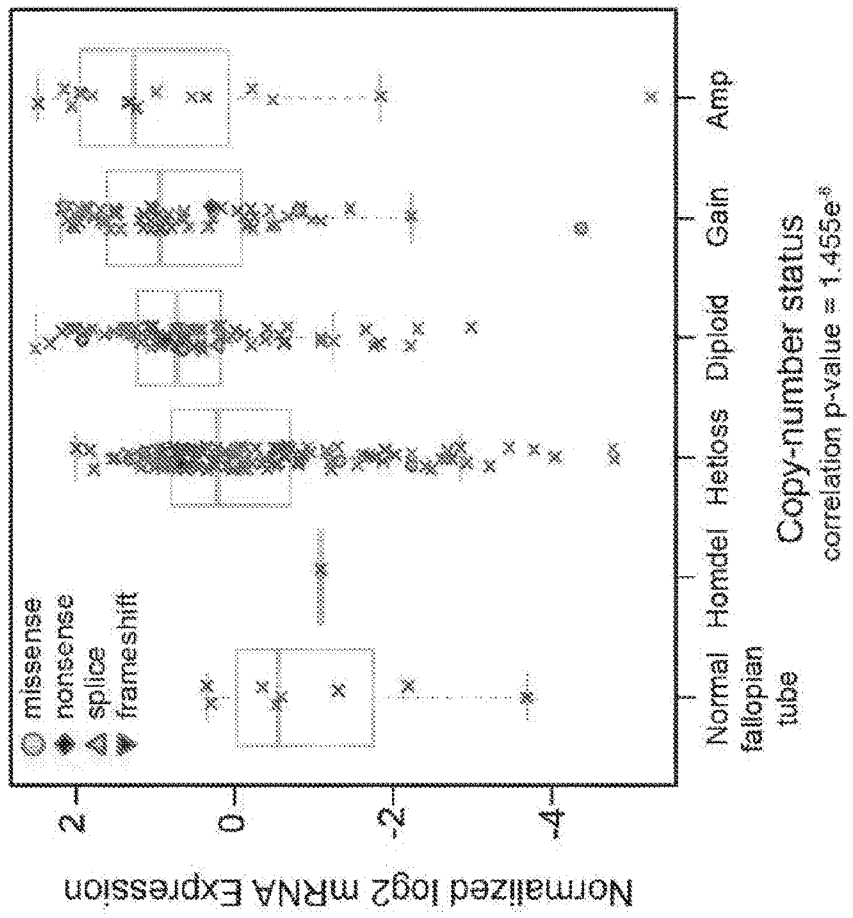
Figure 11B:
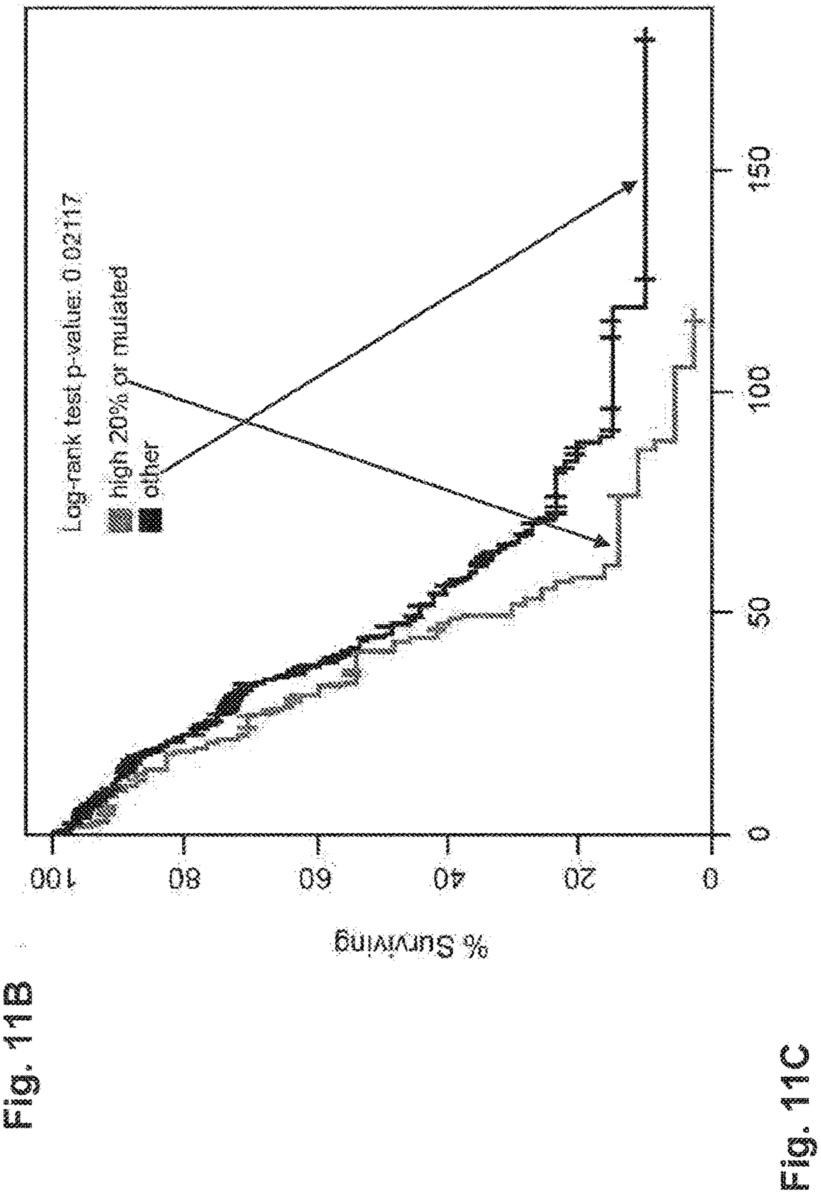
Figure 11C:

FIG. 11A-FIG. 11C. Impact of MUC16 in human ovarian cancer. FIG. 11A depicts MUC16 transcript numbers. FIG. 11B: The quintile of patients with the highest MUC16 expression, combined with the 18 patients with identified MUC16 mutations, have a significantly (p=0.02117) worse survival when compared to the patients with lower MUC16 expression in a Kaplan-Meier analysis. FIG. 11C depicts the relationship of MUC16 genetic alterations with PI3K mutational events in ovarian cancer.

Figure 12A:
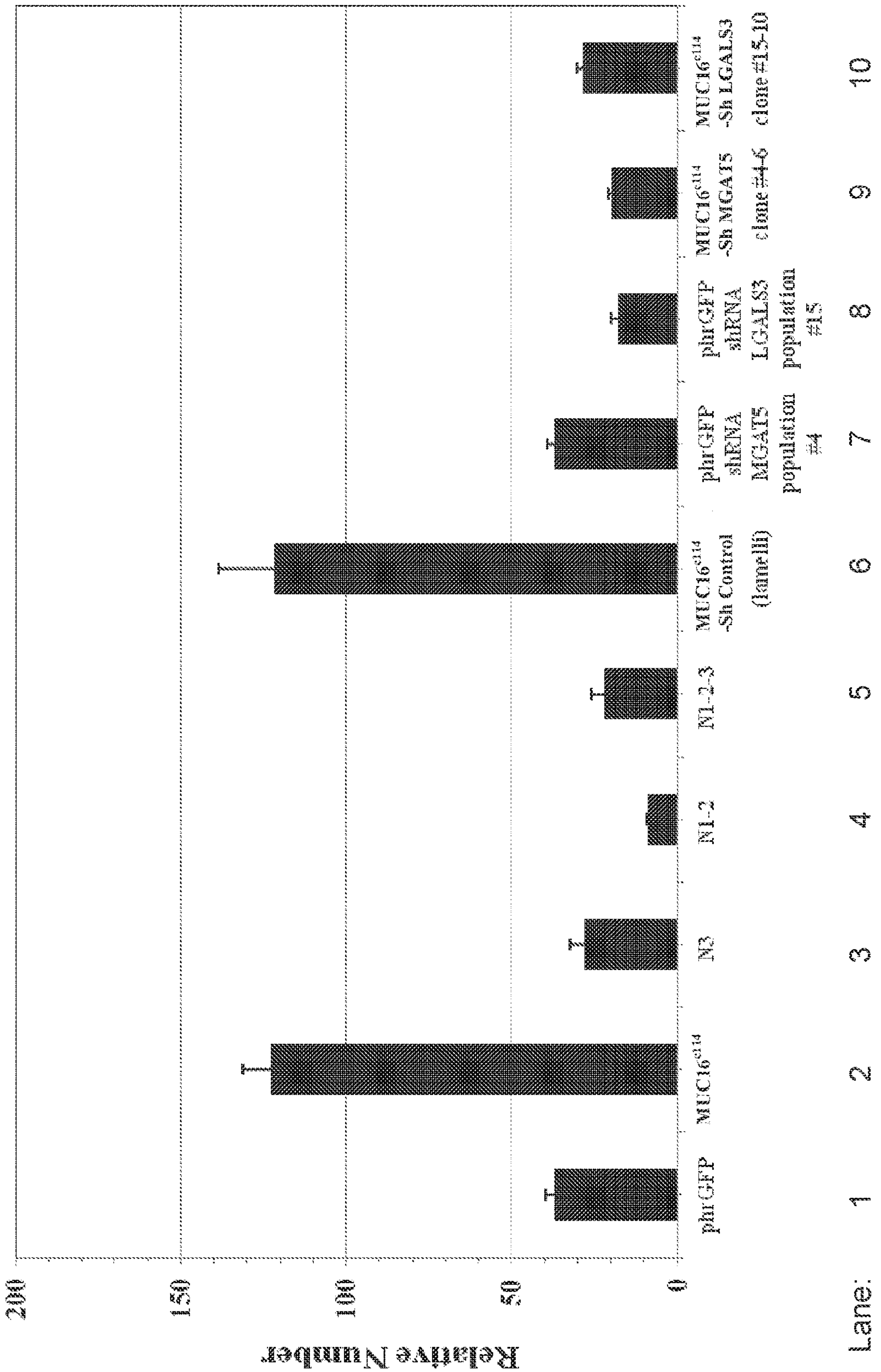
Figure 12B:
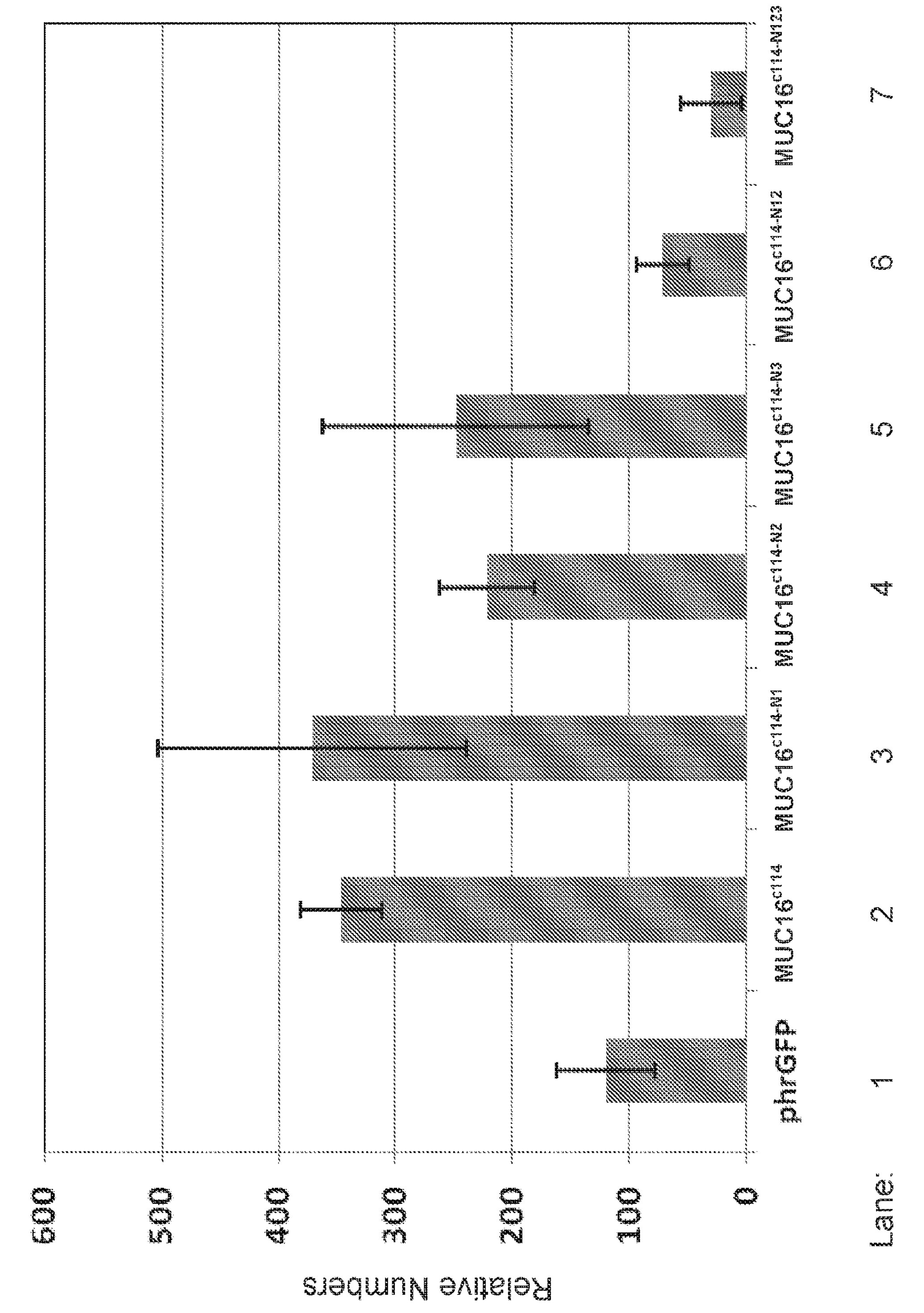
Figure 12C:
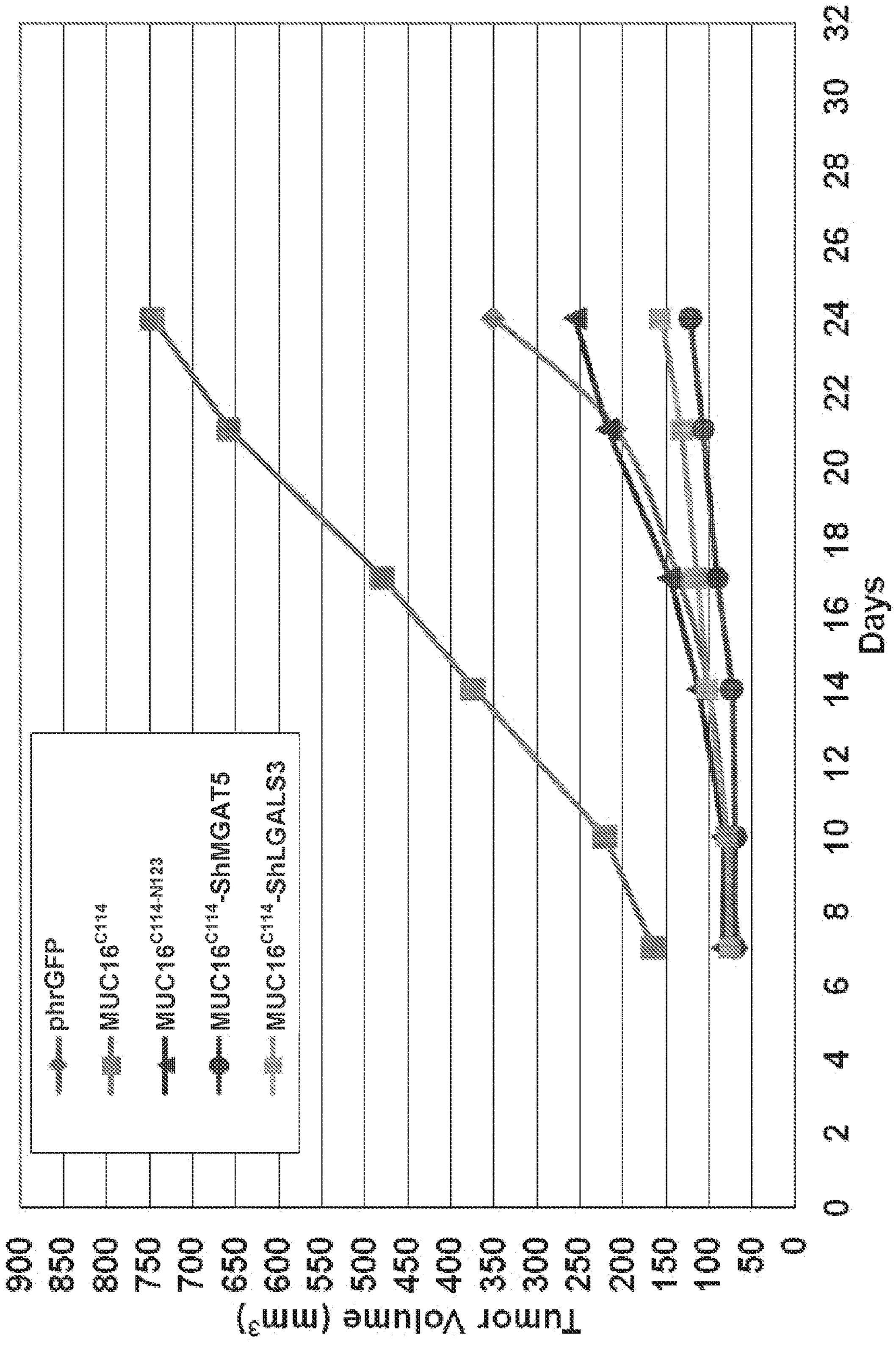

FIG. 12A-FIG. 12C. Glycosylation requirements for MUC16 matrigel invasion. FIG. 12A depicts matrigel invasion assay for SKOV3 transfected cell lines. phrGFP refers to SKOV3 cells expressing a control vector. $MUC16^{c114}$ refers to SKOV3 cells expressing $MUC16^{c114}$. N3 refers to SKOV3 cells expressing $MUC16^{c114\text{-}N3}$. N1-2 refers to SKOV3 cells expressing $MUC16^{c114\text{-}N12}$. N1-2-3 refers to SKOV3 cells expressing $MUC16^{c114\text{-}N123}$. $MUC16^{114}$-shControl refers to SKOV-3 cells expressing $MUC16^{c114}$ and a control shRNA. phrGFP shRNA MGAT population #4 refers to SKOV3 cells expressing a control vector and shRNA against MGAT5. phrGFP shRNA LGALS3 population #15 refers to SKOV3 cells expressing a control vector and shRNA against LGALS3. $MUC16^{c114}$-shMGAT5 refers to SKOV3 cells expressing $MUC16^{c114}$ and an shRNA against MGAT5. $MUC16^{c114}$-shLGALS3 refers to SKOV3 cells expressing $MUC16^{c114}$ and an shRNA against LGALS3. FIG. 12B depicts matrigel invasion assay for 3T3 cells expressing the control vector, phrGFP, or the indicated $MUC16^{c114}$ constructs. FIG. 12C depicts the tumor growth, as determined by tumor volume, in athymic nude mice implanted with SKOV3 cells expressing the indicated constructs.

Figure 13B:
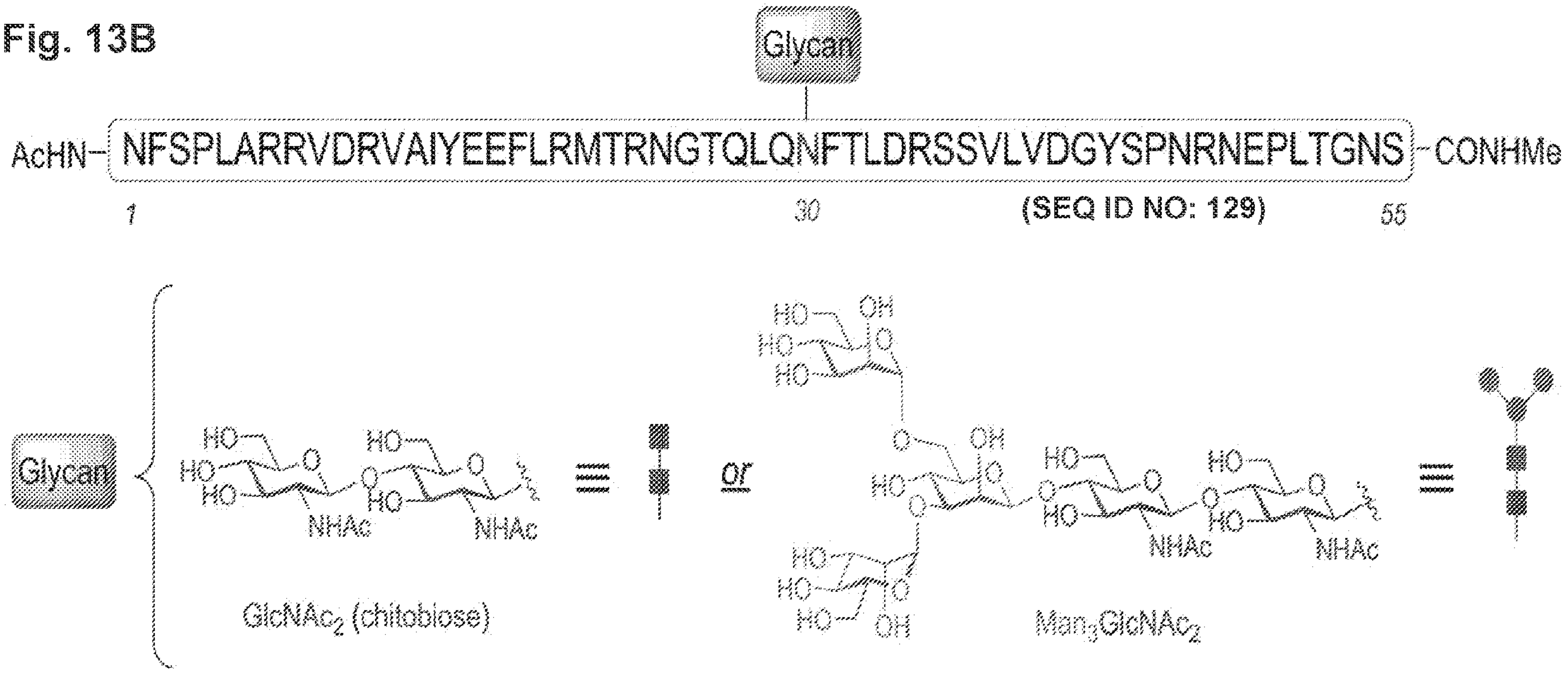
Figure 13C:
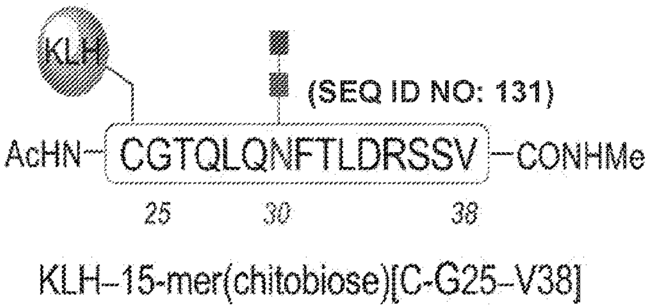
Figure 13D:
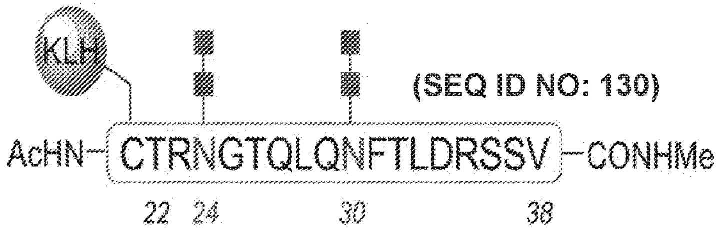

FIG. 13A-FIG. 13D. MUC16 glycosylation patterns and peptides. FIG. 13A depicts the N-linked profiling of SKOV3 cells expressing $MUC16^{c114\text{-}N12}$. Triangles represent fucose. Squares represent N-acetylglucosamine. Grey circles represent mannose. White circles represent galactose. Diamonds represent N-acethylneuramic acid. FIG. 13B depicts the 55-mer (SEQ ID NO:129) immunogen. FIG. 13C depicts the 15-mer (SEQ ID NO:131) immunogen. FIG. 13D depicts the 18-mer (SEQ ID NO:130) immunogen.

FIG. 14 provides a detailed ELISA analysis of the relative reactivity of bioreactive supernatants comprising MUC16 Glycosylation Antibodies with glycosylated and unglycosylated antigens for both the 15 mer and the 18 mer used as immunogens and screening antigen targets.

Figure 15A:
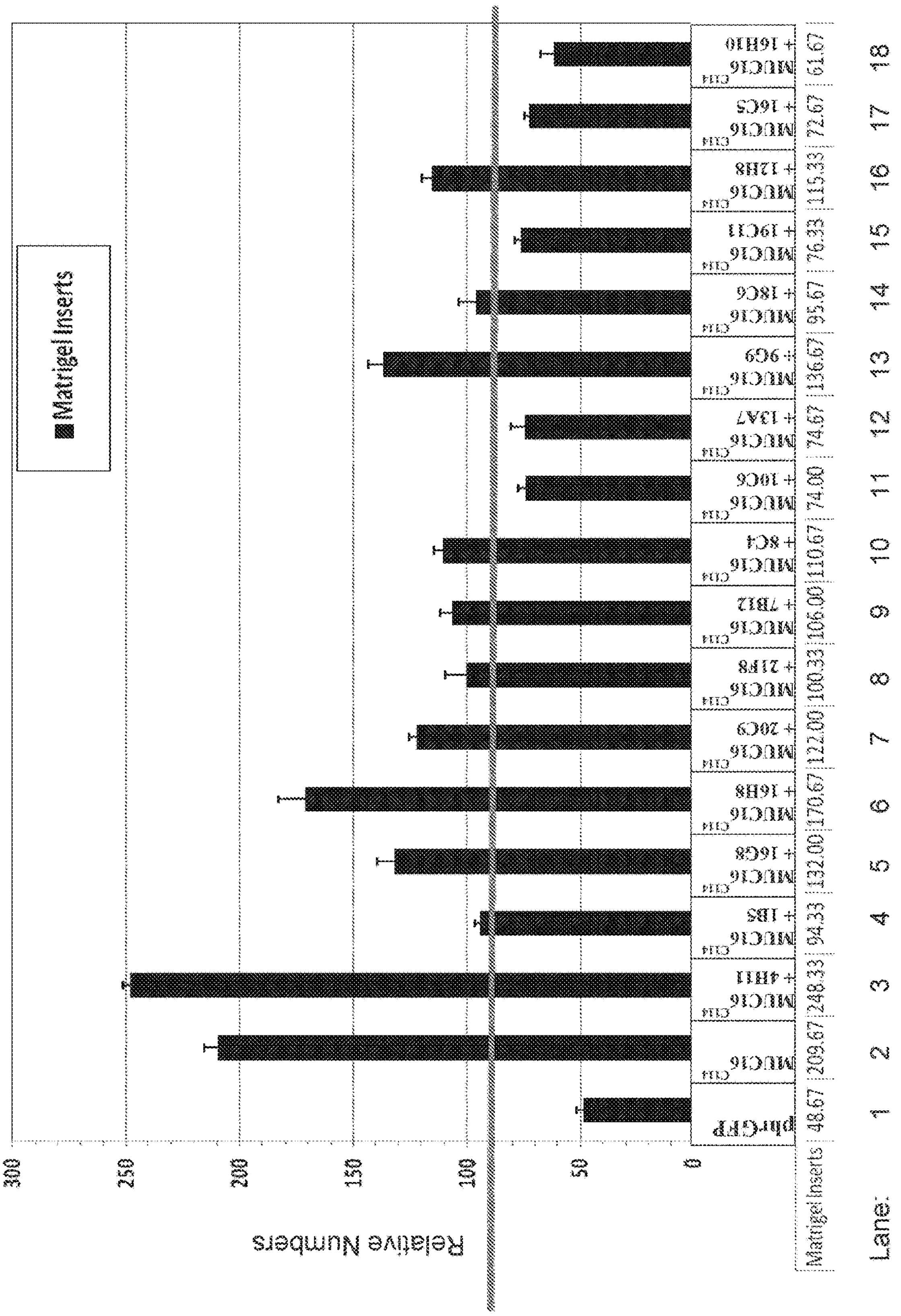
Figure 15B:
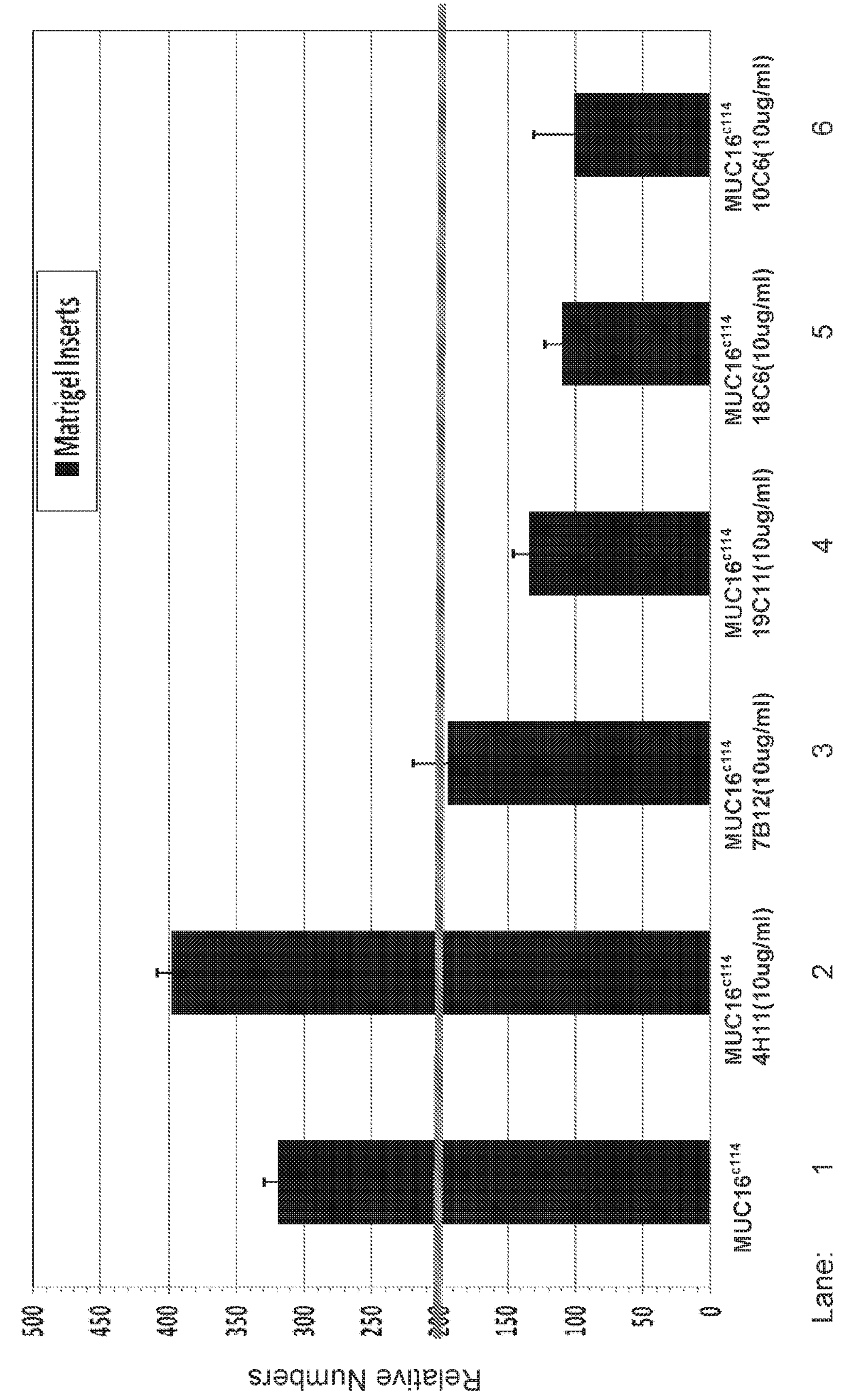

FIG. 15A-FIG. 15B. MUC16 Glycosylation Antibodies inhibit matrigel invasion. FIG. 15A depicts matrigel invasion of SKOV3 cells expressing phrGFP control vector or $MUC16^{c114}$ in the presence or absence of bioreactive supernatants from the generation of MUC16 Glycosylation Antibodies. The line is a reference line for the relative number of 200. FIG. 15B depicts matrigel invasion of SKOV3 cells expressing phrGFP control vector or $MUC16^{c114}$ in the presence or absence of purified MUC16 Glycosylation Antibodies. The line is a reference line for the relative number of 90.

Figure 16A:
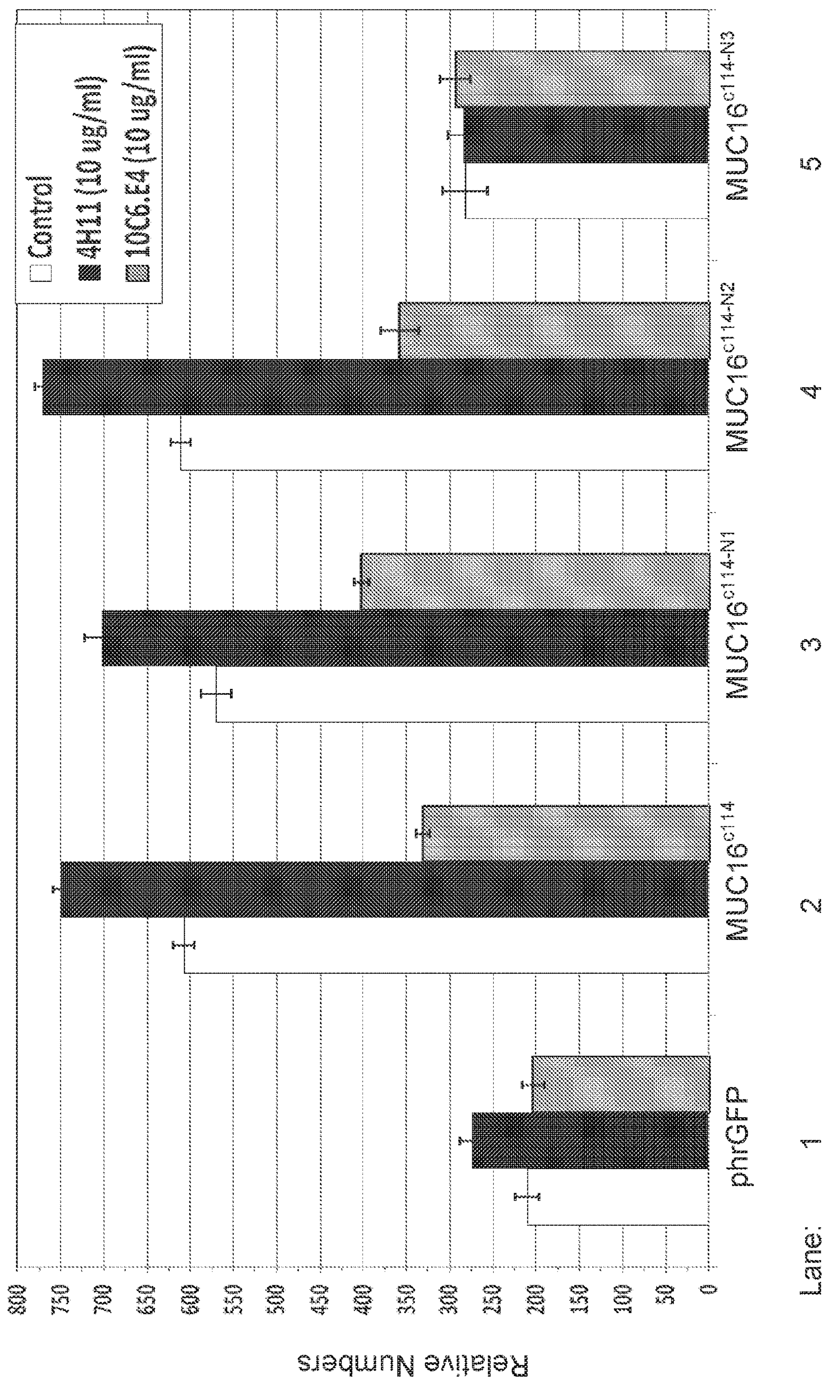
Figure 16B:
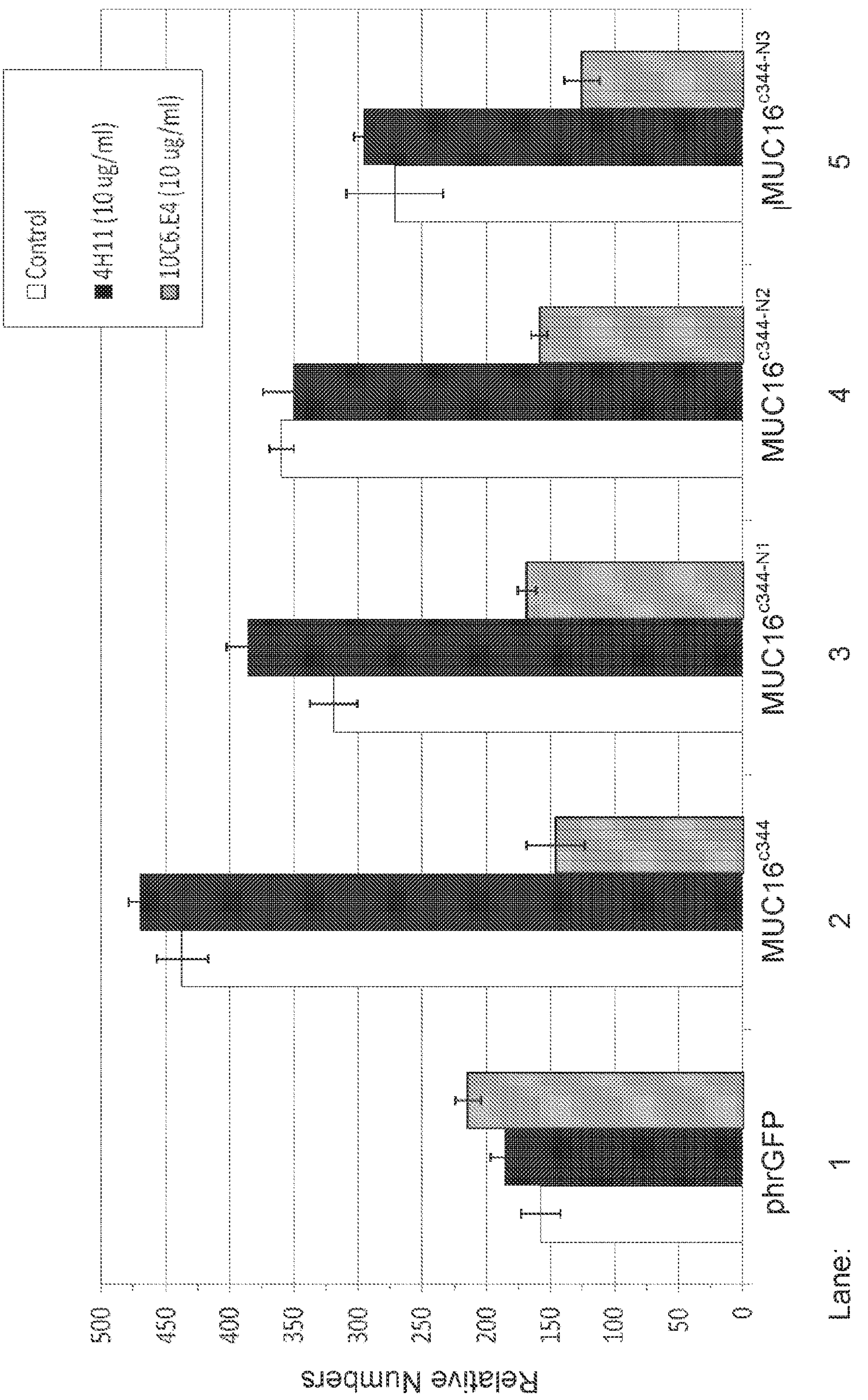
Figure 16C:
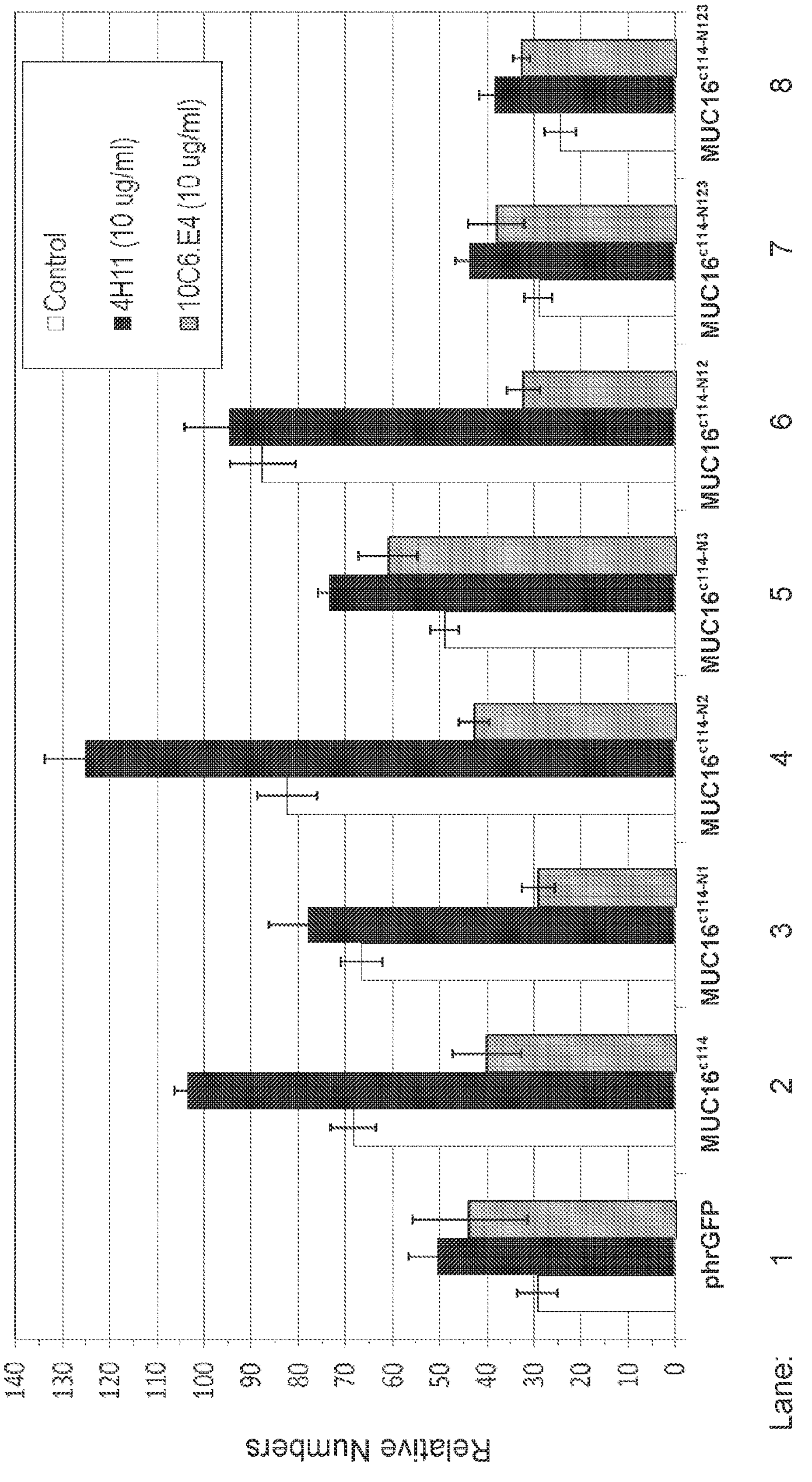
Figure 16D:
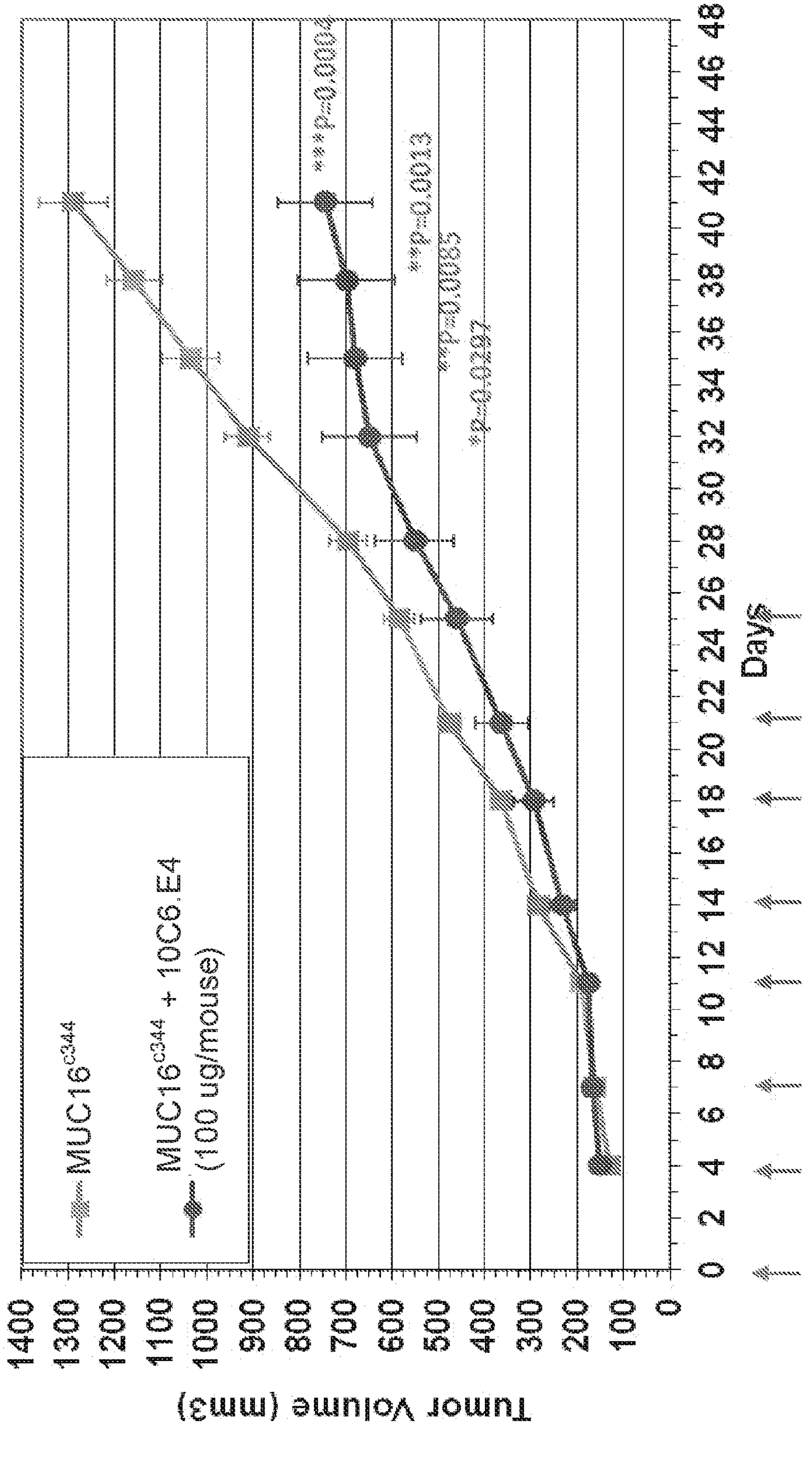
Figure 16E:
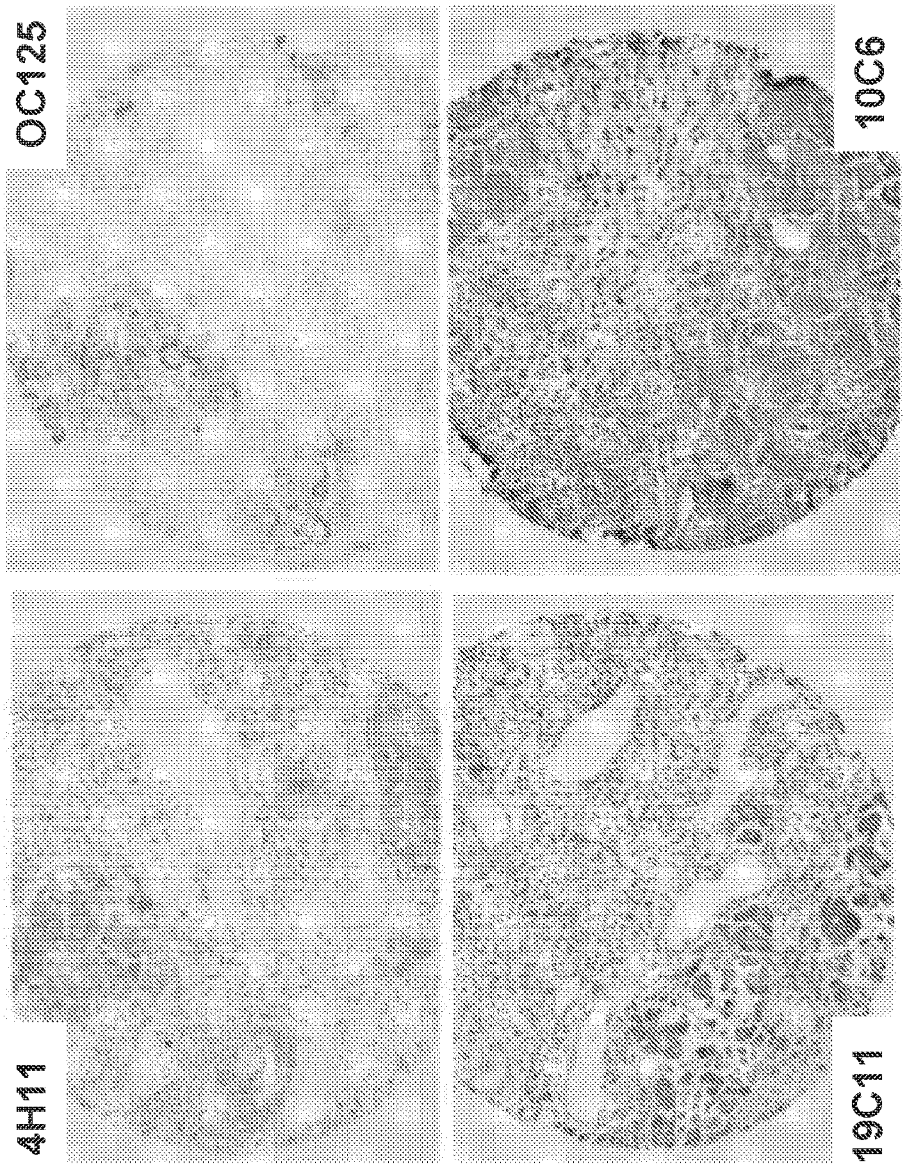

FIG. 16A-FIG. 16E. MUC16 Glycosylation Antibodies inhibit matrigel invasion. FIG. 16A depicts matrigel invasion of SKOV3 cells expressing phrGFP control vector or the indicated $MUC16^{c114}$ constructs in the presence of (i) control antibody; (ii) 4H11; or (iii) MUC16 Glycosylation Antibody clone 10C6.E4. FIG. 16B depicts matrigel invasion of SKOV3 cells stably expressing phrGFP control vector or the indicated $MUC16^{c344}$ constructs after a third FACs sort using 4H11, in the presence of (i) control antibody; (ii) 4H11; or (iii) MUC16 Glycosylation Antibody clone 10C6.E4. FIG. 16C depicts matrigel invasion of 3T3 cells expressing phrGFP control vector or the indicated $MUC16^{c114}$ constructs in the presence of (i) control antibody; (ii) 4H11; or (iii) MUC16 Glycosylation Antibody clone 10C6.E4. FIG. 16D depicts the tumor growth, as indicated by tumor volume, in athymic nude mice implanted with SKOV3 cells expressing $MUC16^{c344}$ and mock treated ($MUC16^{c344}$) or treated with the MUC16 Glycosylation Antibody 10C6.E4($MUC16^{c344}$+10C6.E4). Arrows indicate days on which 100 g of the MUC16 Glycosylation Antibody was administered. FIG. 16E depicts staining of human ovarian tumor samples with the indicated antibodies.

Figure 17:
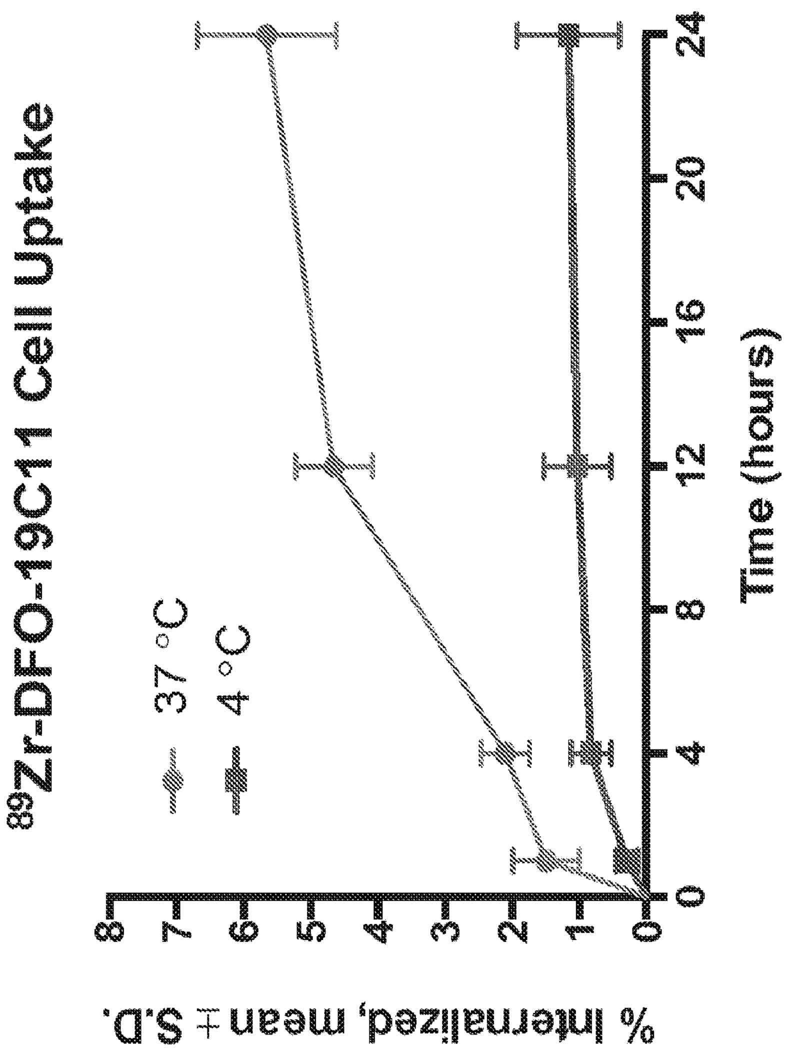

FIG. 17 depicts the percent of cells in which the labeled MUC16 Glycosylation Antibody is internalized at the indicated temperature and timepoints.

Figure 18A:
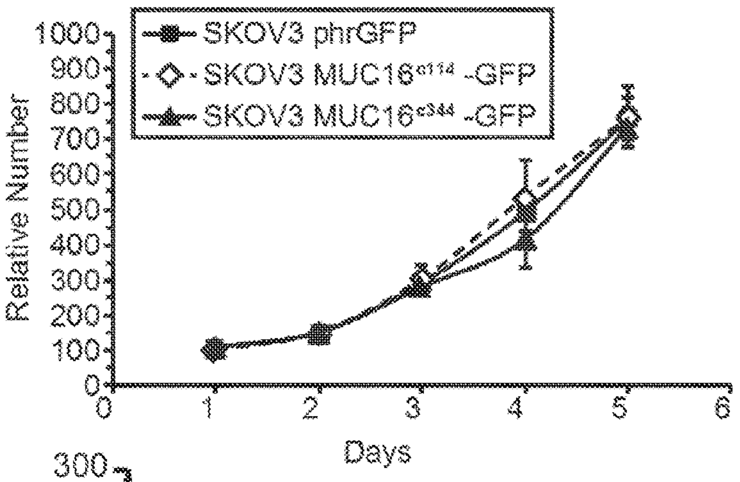
Figure 18B:
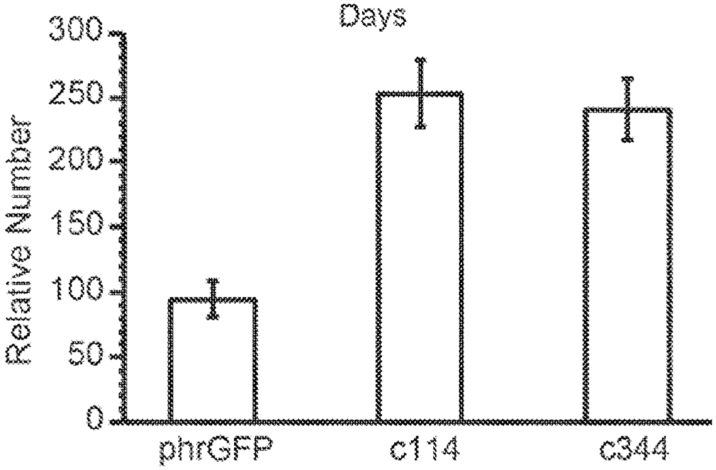
Figure 18C:
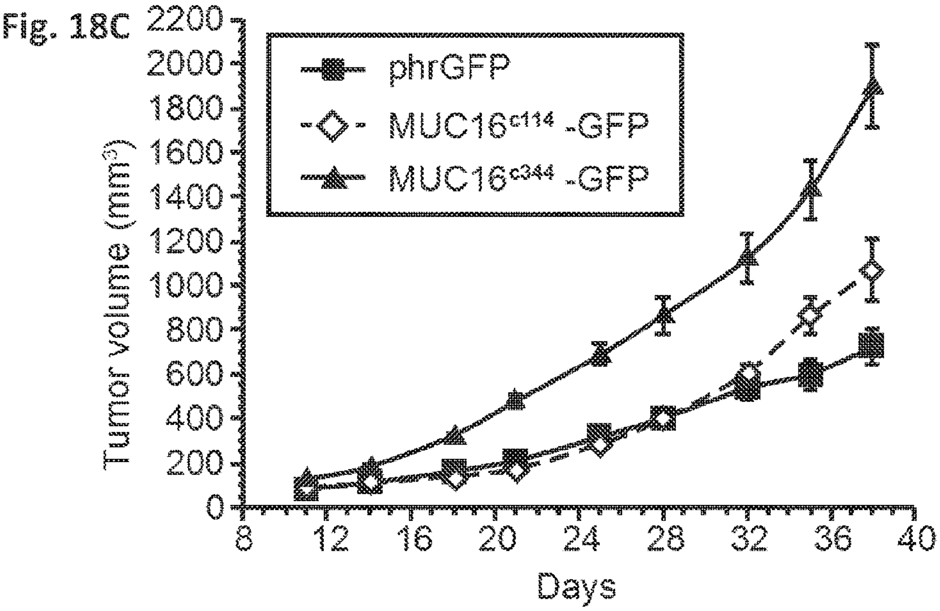

FIG. 18A depicts in vitro growth curves for MUC16 transfectants. 1000 SKOV3 cells/well in 96 well flat-bottomed plates were cultured with phrGFP vector control, phrGFP vector expressing $MUC16^{c114}$ (SEQ ID NO: 133), or phrGFP vector expressing $MUC16^{c344}$ (SEQ ID NO: 132) and incubated at 37° C. in 5% $CO_2$ for 5 days. Each day, a plate was stained with Alamar Blue and incubated at 37° C. in 5% $CO_2$ for 4 hours. Plates were read in a CytoFluor Fluorescent plate reader. No statistical differences were seen among the curves. FIG. 18B depicts matrigel invasion assay for SKOV3 phrGFP cells, SKOV3 $MUC16^{c114}$-GFP cells, or SKOV3-$MUC16^{c344}$-GFP cells. Each assay was performed two or more times in triplicate and counted by hand. Results are expressed as the relative number of invasive cells. c114 and c344 were statistically significant as compared with phrGFP. FIG. 18C depicts SKOV3 transfectant tumor growth in athymic female nude mice. Two million tumor cells were introduced into the flank of 10 nu/nu mice and the mice were observed for tumor formation. Tumors were measured by calipers twice weekly. The differences in mean tumor volume were statistically significantly greater for mice bearing $MUC16^{c344}$ tumors (p<0.0001) and $MUC16^{c114}$ tumors (p=0.002) when compared to phrGFP tumors. Abbreviations for FIG. 18A-FIG. 18C: "SKOV3 phrGFP" and "phrGFP" refer to SKOV3 cells expressing control phrGFP vector; "SKOV3 $MUC16^{c114}$-GFP" and "c114" refer to SKOV3 cells expressing $MUC16^{c114}$ (SEQ ID NO: 133); "SKOV3 $MUC16^{c344}$-GFP" and "c344" refer to SKOV3 cells expressing $MUC16^{c344}$ (SEQ ID NO: 132).

Figure 19A:
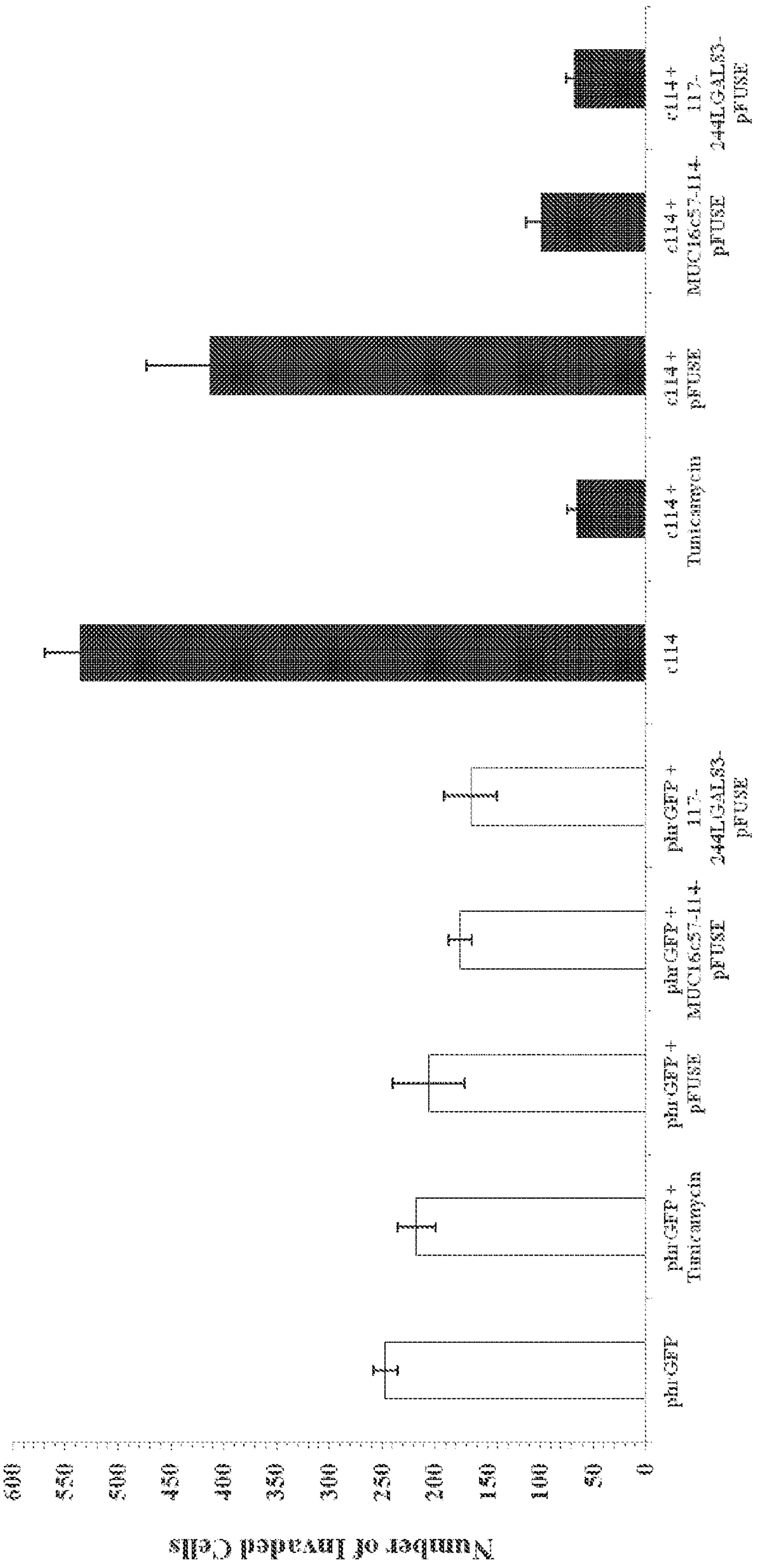
Figure 19B:
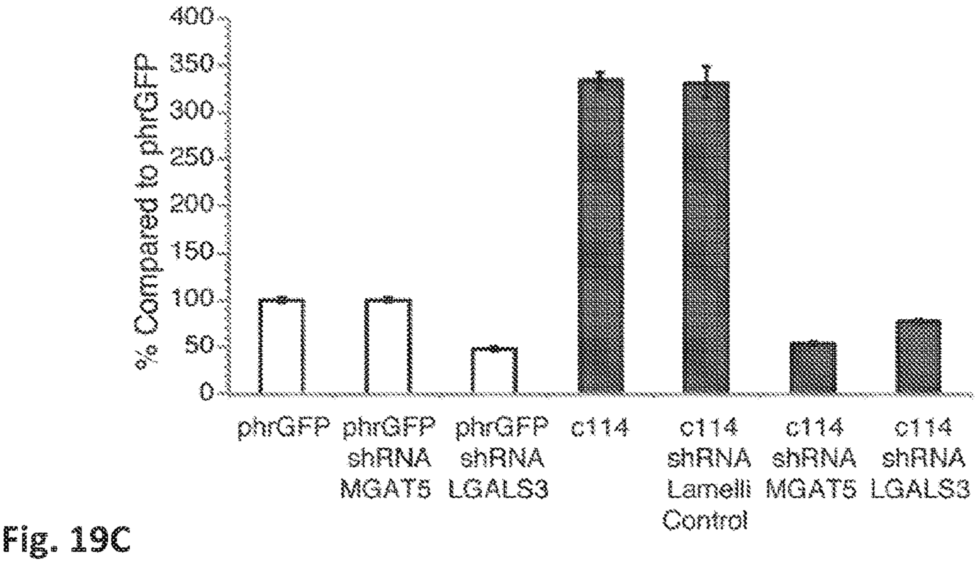
Figure 19C:
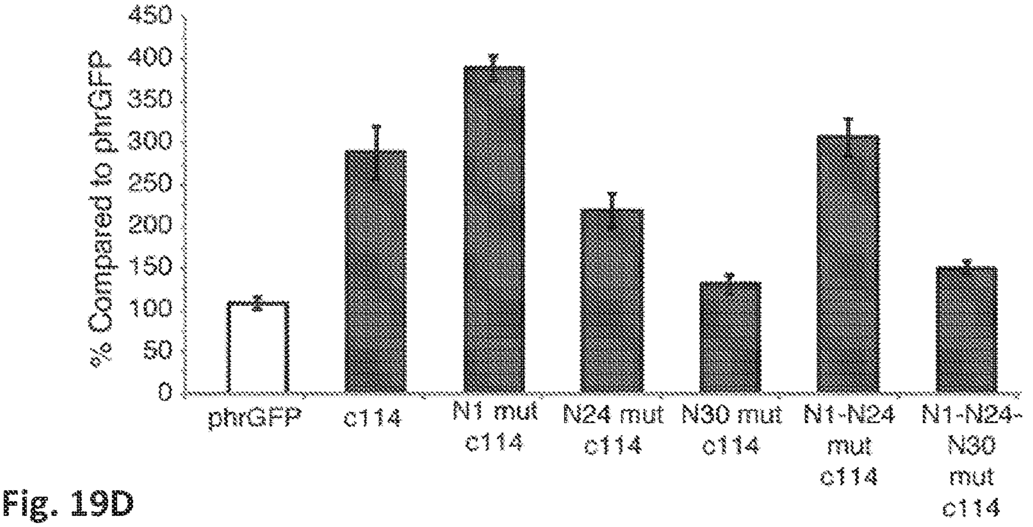
Figure 19D:
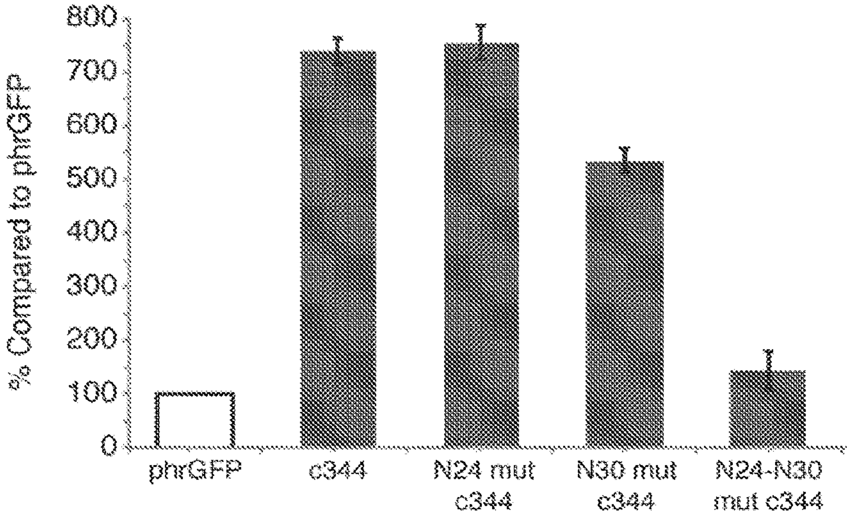
Figure 19E:
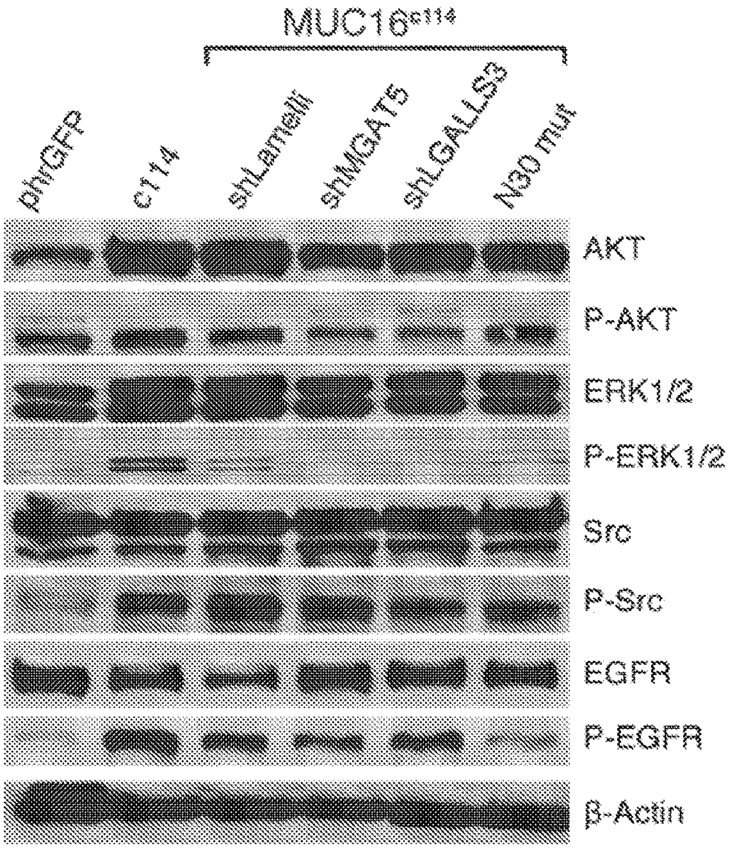
Figure 19F:
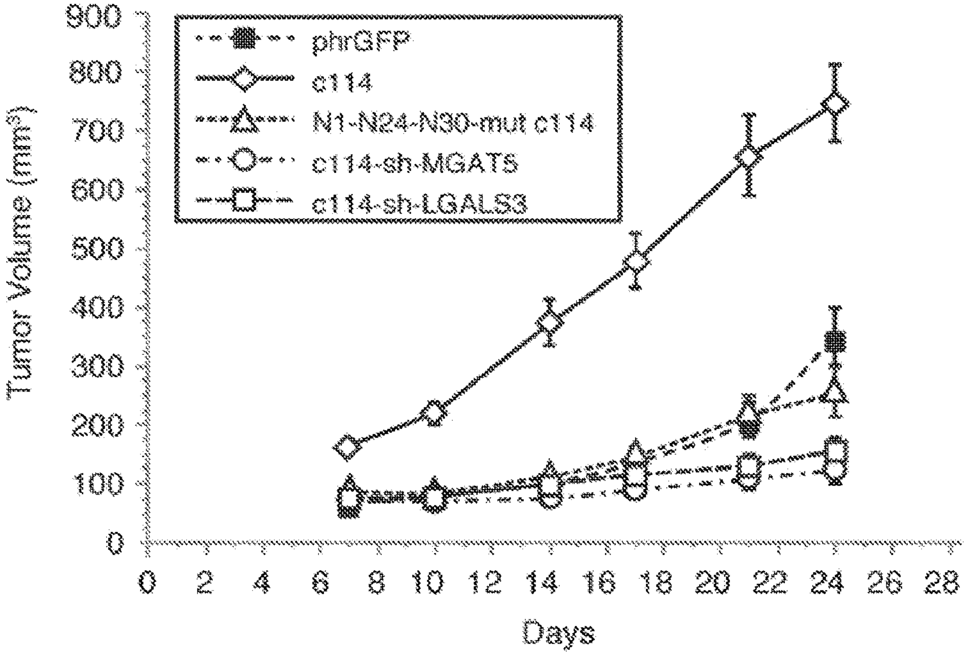

FIG. 19A-FIG. 19F depict the effect of MUC16 Expression on SKOV3 ovarian cancer cells. FIG. 19A depicts a matrigel invasion assay for SKOV3 cells expressing control phrGFP control vector ("phrGFP") or the phrGFP vector expressing $MUC16^{c114}$ (SEQ ID NO: 133; "c114") treated with or without the following: (1) 5 μg/mL tunicamycin; (2) 5 μg/mL of control pFUSE protein; (3) 5 μg/mL of $MUC16^{c57\text{-}114}$-pFUSE fusion protein; or (4) 5 μg/mL of $^{117\text{-}244}$LGALS3-pFUSE fusion protein. The results are expressed as number of invasive cells 48 hours-post-treatment. c114 cells were more invasive than phrGFP cells (p<0.0001). The invasive properties of the c114 cells were not affected by treatment with the pFUSE vector-only protein. Treatment with tunicamycin (an N-glycosylation inhibitor) decreased the invasive properties of the c114 cells. Treatment with MUC16$^{c57-114}$-pFUSE fusion protein or $^{117-244}$LGALS3-pFUSE decreased the invasive properties of the c114 cells (p<0.0001). FIG. 19B depicts a matrigel invasion assay for SKOV3 cells transfected with phrGFP vector control ("phrGFP") or phrGFP vector expressing MUC16$^{c114}$ (SEQ ID NO: 133) ("c114") in the presence or absence of lamelli control shRNA, MGAT5-specific shRNA, or LGALS3-specific shRNA. c114 cells treated with MGAT5-specific shRNA or LGALS3-specific shRNA had decreased invasion as compared to phrGFP cells treated with the shRNAs. The control shRNA has no impact on c114 cell invasion. Each assay was performed two or more times in triplicate and counted by hand. FIG. 19C depicts the glycosylation dependence of SKOV3-MUC16$^{c114}$ matrigel invasion. SKOV3 cells were transfected with phrGFP control vector or phrGFP vector expressing the following MUC16 mutants: c114 (SEQ ID NO: 133), N1 mut c114 (SEQ ID NO: 151), N24 muc c114 (SEQ ID NO: 152), N30 mut c114 (SEQ ID NO:139), N1-N24 mut c114 (SEQ ID NO: 153), N1-N24-N30 mut c114 (SEQ ID NO: 154). The c114-expressing cells displayed increased invasion when compared to the control phrGFP cells. The increased invasive property of the c114-expressing cells was dependent on N-glycosylation of the asparagines at amino acid positions 24 and 30 of MUC16$^{c114}$ (SEQ ID NO: 133). While both N24 and N30 sites were important, the N30 position appeared to be more crucial than the N24 site for this effect. Each assay was performed two or more times in triplicate and counted by hand. Results are expressed as % compared to phrGFP vector control. FIG. 19D depicts the glycosylation dependence of SKOV3-MUC16$^{c344}$ matrigel invasion. SKOV3 cells were transfected with phrGFP control vector or phrGFP vector expressing the following MUC16 mutants: c344 (SEQ ID NO: 132), N24 mut c344 (SEQ ID NO: 173), N30 mut c344 (SEQ ID NO: 174), or N24-N30 mut c344 (SEQ ID NO: 175). The c344-expressing cells displayed increased invasion when compared to the control phrGFP cells. The increased invasive property of the c344-expressing cells was dependent on N-glycosylation of the asparagines corresponding to amino acid positions 24 and 30 of MUC16$^{c114}$ (SEQ ID NO: 133). Each assay was performed two or more times in triplicate and counted by hand. FIG. 19E depicts the effect of MUC16-expression on selected signaling pathways. SKOV3 cells transfected with MUC16$^{c114}$ (SEQ ID NO: 133) were treated with or without control shRNA ("shLamelli") or shRNA against MGAT5 ("shMGAT5") or LGALS3 ("shLGALLS3") and compared to SKOV3 cells transfected phrGFP vector control ("phrGFP") or phrGFP vector expressing MUC16$^{c114\text{-}N30mut}$ (SEQ ID NO: 139) ("N30 mut") and the cells were examined for activation of the pAKT, pERK1/2, pSRC, and pEGF receptor (pEGFR) signaling pathways. Phosphorylation of AKT (S473) and ERK1/2 (pT202/Y204) were increased in the MUC16$^{c114}$ cells. Knockdown of MGAT5 (shMGAT5), knockdown of Galectin-3 (shLGALLS3), and the N30A mutation each reduced MUC16$^{c114}$-induced oncogene activation in the SKOV3 cell lines. FIG. 19F depicts SKOV3 transfectant tumor growth in athymic female nude mice. Two million tumor (described below) cells were introduced into the flank of 10 nu/nu mice for each condition, and mice were observed for tumor formation. Tumors were measured by calipers twice per week. In vivo growth of c114 tumor cells was much more aggressive (p<0.0001) as compared to phrGFP tumor cells. N1-N24-N30-mut c114, c114-sh-MGAT5, and c114-sh-LGALS3 tumor cells did not display growth enhancement when compared to phrGFP tumor cells. Description of tumor cells: "phrGFP" refers to SKOV3 cells transfected with phrGFP vector control; "c114" refers to SKOV3 cells transfected with phrGFP vector expressing MUC16$^{c114}$ (SEQ ID NO: 133); "N1-N24-N30-mut c114" refers to SKOV3 cells transfected with phrGFP vector expressing MUC16$^{c114\text{-}N1\text{-}N24\text{-}N30\text{-}mut}$ (SEQ ID NO: 154); "c114-sh-MGAT5" refers to SKOV3 cells transfected with phrGFP vector expressing MUC16$^{c114}$ (SEQ ID NO: 133) and treated with shRNA against MGAT5; and "c114-sh-LGALS3" refers to SKOV3 cells transfected with phrGFP vector expressing MUC16$^{c114}$ (SEQ ID NO: 133) and treated with shRNA against LGALS3.

Figure 20A:
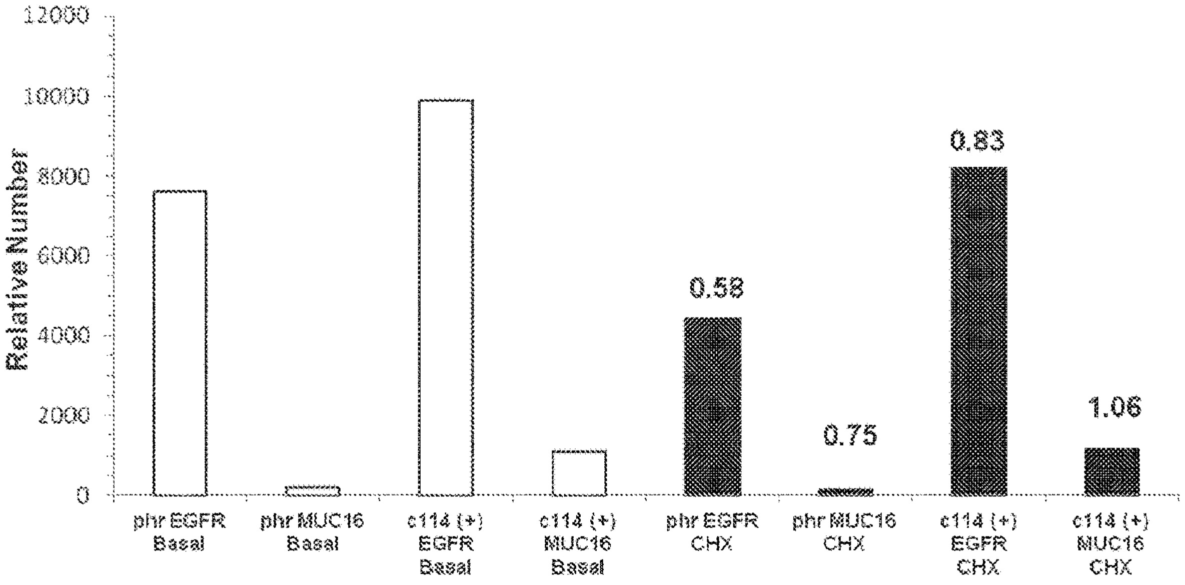
Figure 20B:
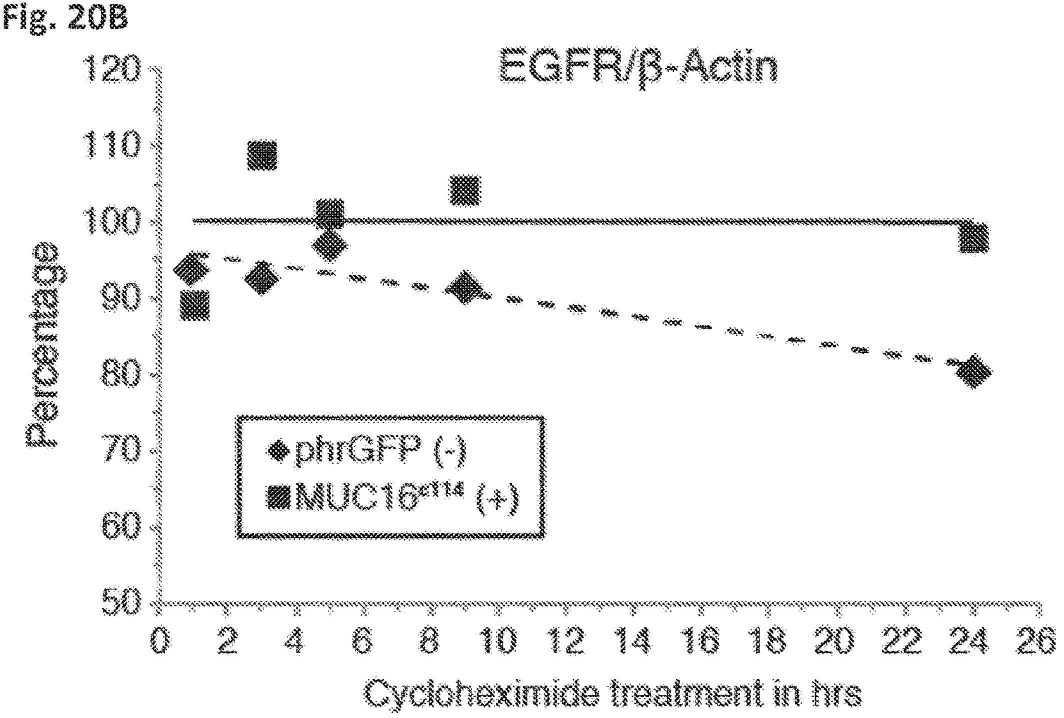
Figure 20C:
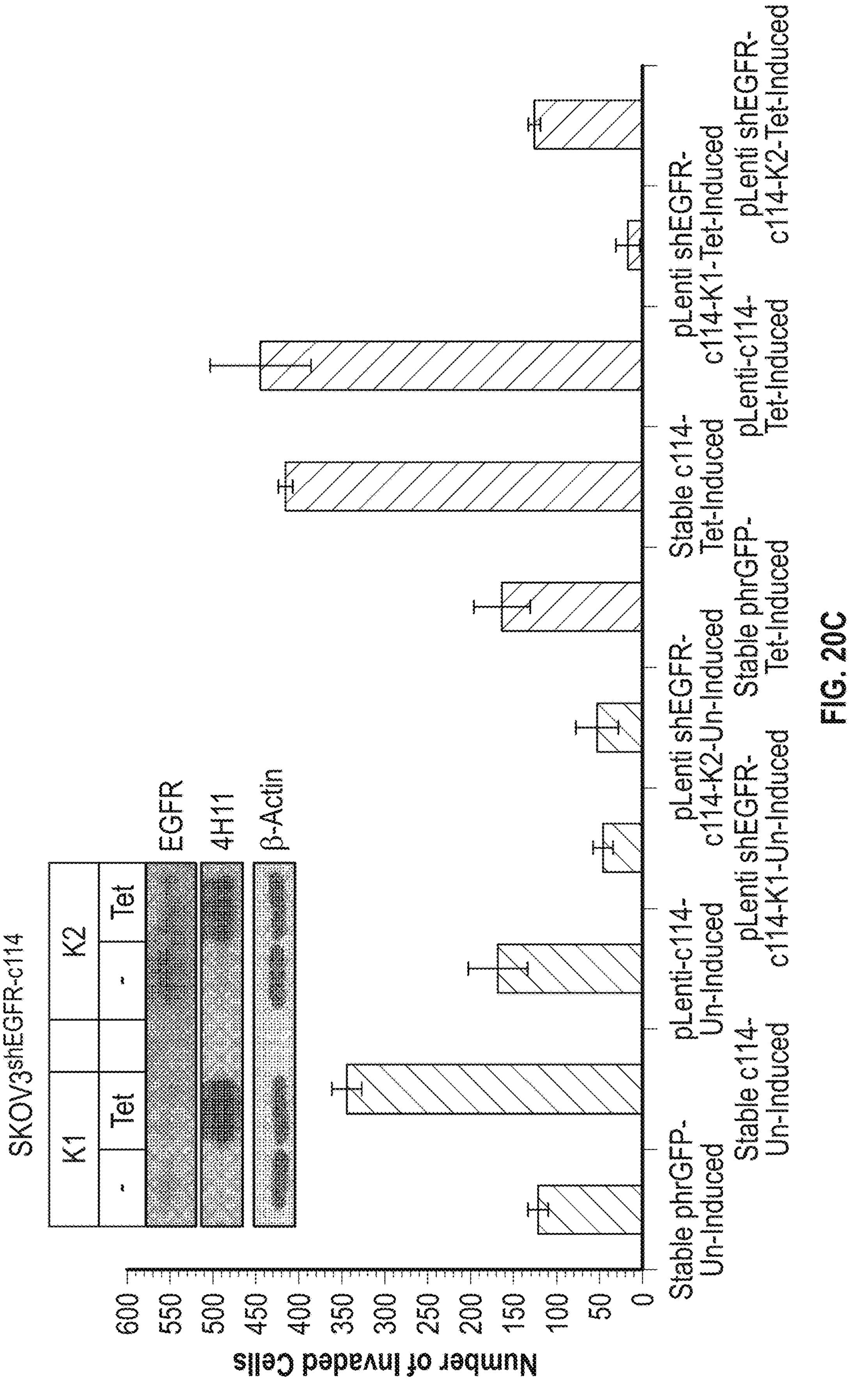
Figure 20D:
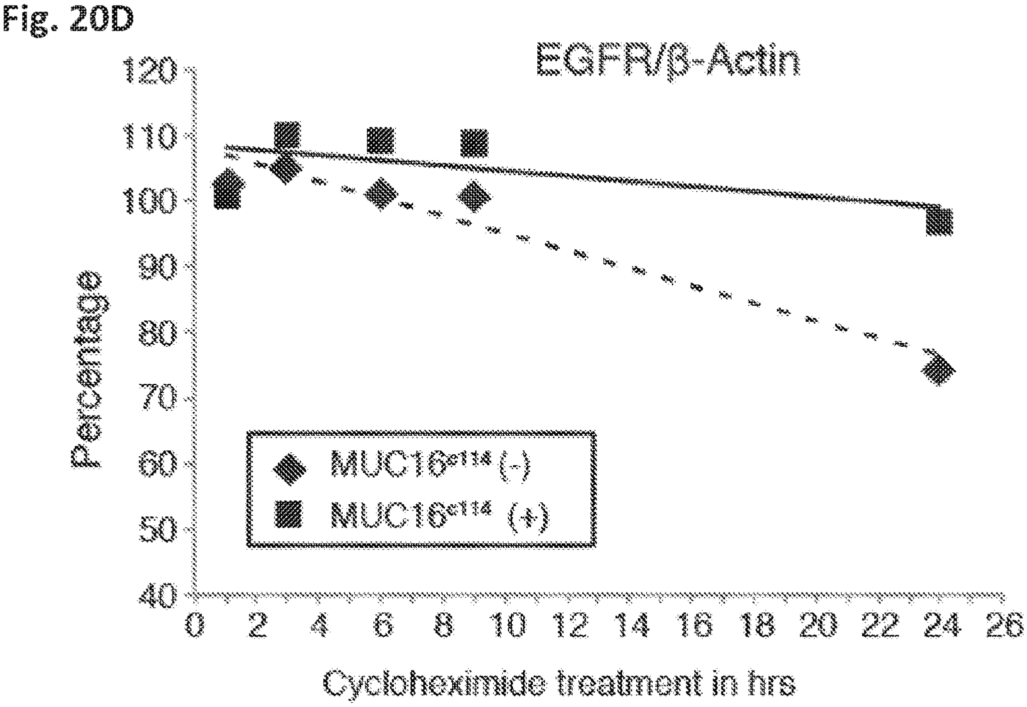

FIG. 20A depicts the effect of MUC16 expression on EGFR surface expression. SKOV3-phrGFP and SKOV3-MUC16$^{c114}$ transfectants were examined in the presence or absence of treatment with cycloheximide (CHX) for 24 hours. Geometric mean fluorescence of EGFR and MUC16 expression at basal and post-CHX treated levels is shown. EGFR in SKOV3-phrGFP samples was reduced to 58% of untreated levels after 24 hours of treatment with CHX. No significant MUC16 expression was present in these cells. In contrast, in the SKOV3-MUC16$^{c114}$ cells, there was roughly a 25% increase in EGFR geometric mean fluorescence, which decreased to 83% of that of the control after CHX exposure. MUC16$^{c114}$ mean fluorescence was not significantly reduced by CHX. FIG. 20B depicts densitometry of the EGFR/β-actin ratio from western blots of total cellular EGFR and illustrates that there was a steady loss of EGFR over time in SKOV3-phrGFP cells treated with CHX. In contrast, the total level of EGFR in SKOV3-MUC16$^{c114}$ cells was maintained, showing EGFR stabilization compared with the MUC16(−) control cell line ("phrGFP (−)"). FIG. 20C depicts a matrigel invasion assay for SKOV3 cells transfected with phrGFP control vector ("stable phrGFP"), SKOV3-MUC16$^{c114}$ and SKOV3-MUC16$^{c114(tet)}$ tetracycline-inducible cell lines, expressed as a fraction of control cell invasion. Tetracycline induction of SKOV3-MUC16$^{c114(tet)}$ cells resulted in an invasive phenotype similar to the stable SKOV3-MUC16$^{c114}$ (SKOV3$^{c114}$), while un-induced cells matched the MUC16-phrGFP control cells. This MUC16-induced increase in matrigel invasion was completely dependent on EGFR. When a hairpin RNA knockdown of EGFR (shEGFR) was introduced into SKOV3 cells, tetracycline induced expression of MUC16 (4H11 positive protein in western blot) but did not increase matrigel invasion. Each assay was performed in triplicate and counted by hand. FIG. 20D: EGFR stability in MUC16$^{c114}$(+) and MUC16$^{c114}$(−) cells. Cell extracts of un-induced or tetracycline-induced SKOV3-MUC16c114 (tet) cell lines treated with CHX for 24 hours and probed for total cellular EGFR are expressed as densitometry ratios, and normalized with β-Actin. The slope of the EGFR decline in tetracycline-induced SKOV3-MUC16$^{c114}$ cells replicates the EGFR stabilization effect of MUC16$^{c114}$ expression compared with the MUC16$^{c114}$(−) line. The result is similar to the effect of stable transfection shown above in FIG. 20B).

Figure 21:
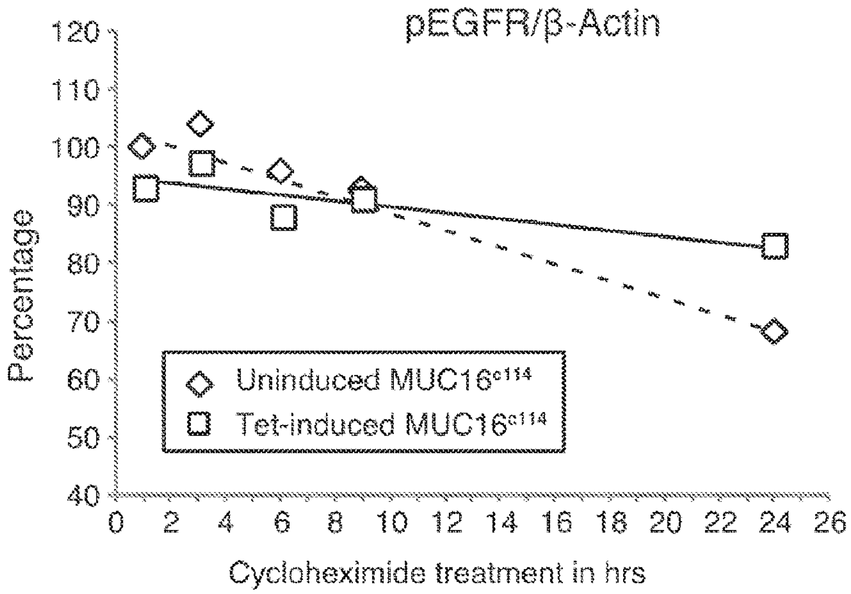

FIG. 21 depicts densitometry for western blot analysis of cell extracts of un-induced or tetracycline-induced SKOV3$^{c114}$ cell lines ("Uninduced MUC16$^{c114}$" and "Tet-induced MUC16$^{c114}$", respectively) treated with cycloheximide for 24 hours. The western blots were probed for pEGFR and protein levels were normalized to β-Actin levels. The slopes of the tetracycline-induced SKOV3$^{c114}$ pEGFR signal showed stabilized pEGFR compared with un-induced SKOV3$^{c114}$ cell line.

Figure 22B:
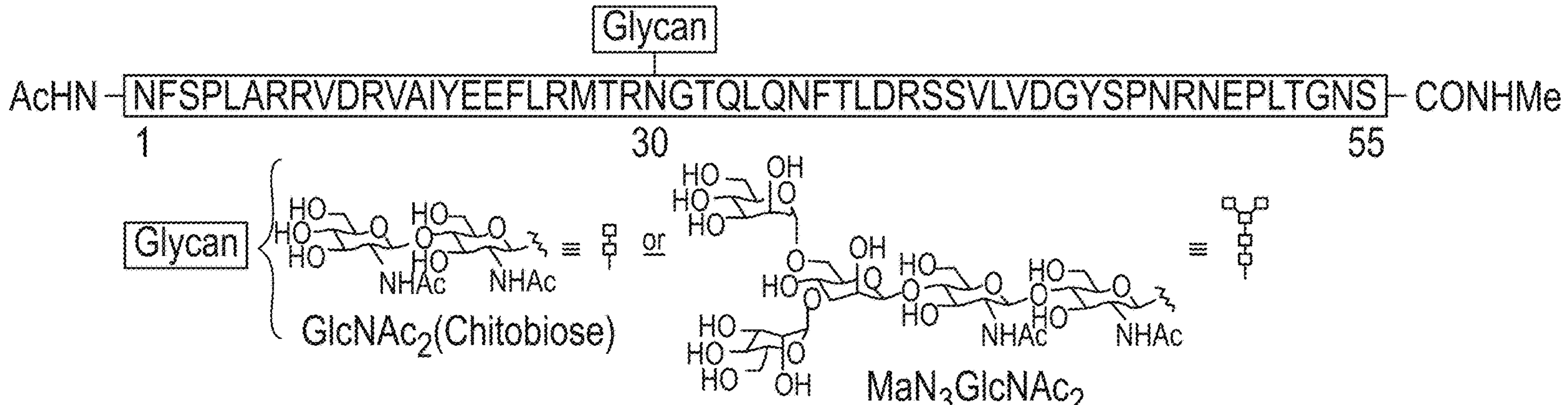
Figure 22C:
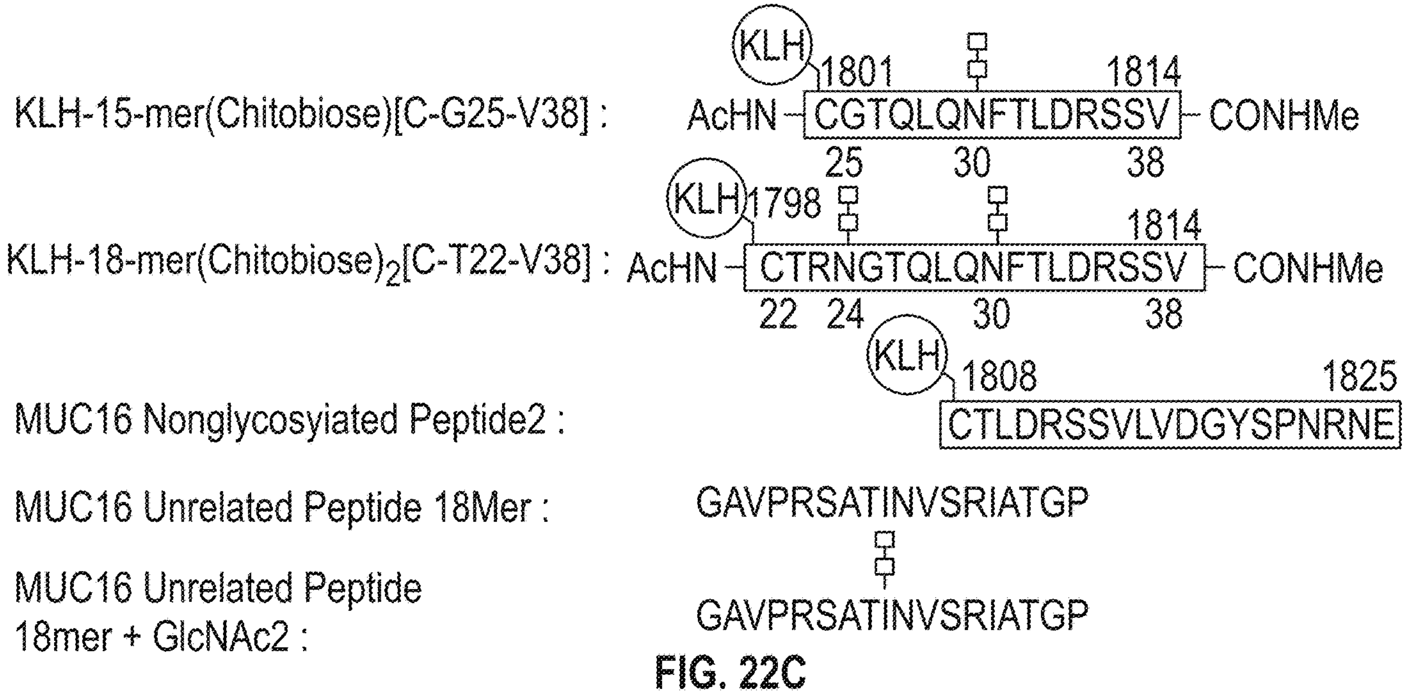

FIG. 22A-FIG. 22C depict the identification and chemical synthesis of MUC16 ectodomain N-glycosylated species. FIG. 22A: N-glycan profiling of SKOV3 cells transfected with phrGFP expressing N1-N24 mutated MUC16$^{c114}$ (SEQ ID NO: SEQ ID NO: 153). The glycans were detected and characterized by total ion mapping at the Complex Carbohydrate Research Center, University of Georgia. Triangles: fucose; squares: N-acetylglucosamin; circles, dark fill: mannose; circles, light fill: galactose; diamonds: N-acetylneuraminic acid. FIG. 22B depicts the schematic structure of a 55-mer MUC16 antigen with a single chitobiose ($GlcNAc_2$) glycan at the N30 position. This N-glycopeptide antigen was used to immunize mice to raise antibodies. The amino acid sequence is as set forth in SEQ ID NO: 129. Squares represent N-acetylglucosamin; circles represent mannose. FIG. 22C depicts the schematic structure of a KLH-conjugated, 15-mer MUC16 antigen mono-glycosylated with chitobiose at the N30 position, and KLH-conjugated, 18-mer MUC16 antigen bis-glycosylated with two chitobiose units at the N24 and N30 positions, respectively. These N-glycopeptide-KLH constructs were subsequently used to immunize mice to raise monoclonal antibodies against the $GlcNAc_2$-peptide epitope within the MUC16 ectodomain. Sequences of the MUC16-unrelated glycopeptides and the nonglycosylated MUC16 peptide 2 to elicit the 4H11 monoclonal antibody are included as well. The amino acid sequence for KLH-15-mer(chitobiose)[C-G25-V38] is as set forth in SEQ ID NO: 131. The amino acid sequence for KLH-18-mer$(chitobiose)_2$[C-T22-V38] is as set forth in SEQ ID NO: 130. The amino acid sequence for MUC16 Nonglycosylated Peptide2 is as set forth in SEQ ID NO: 168. The amino acid sequence for MUC16 unrelated peptide 18mer and MUC16 unrelated peptide 18mer+GlcNAc2 is as set forth in SEQ ID NO: 169. Squares represent N-acetylglucosamin.

Figure 23B:
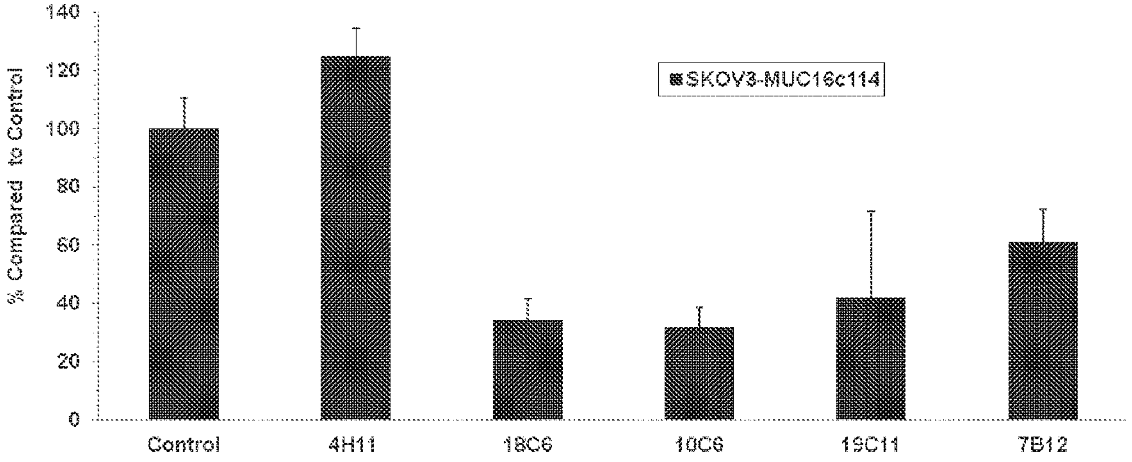
Figure 23C:
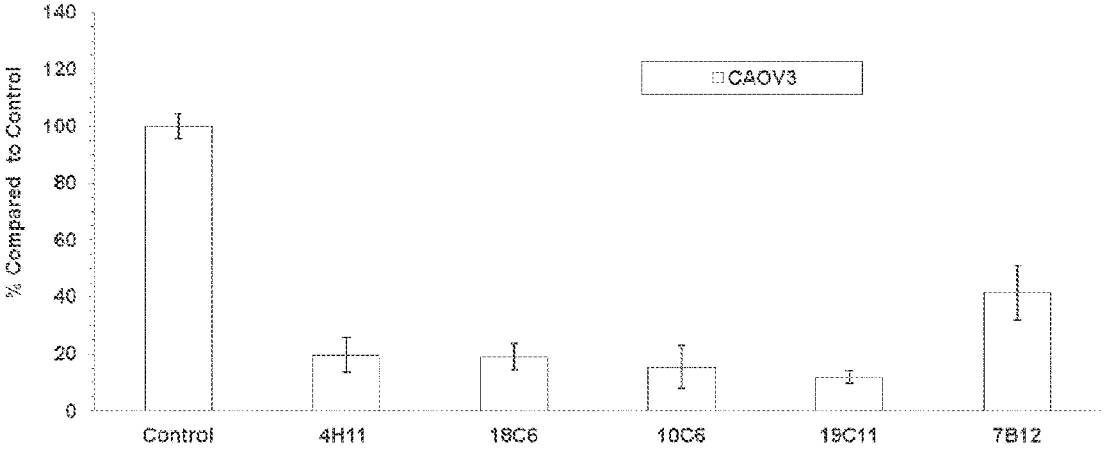
Figure 23D:
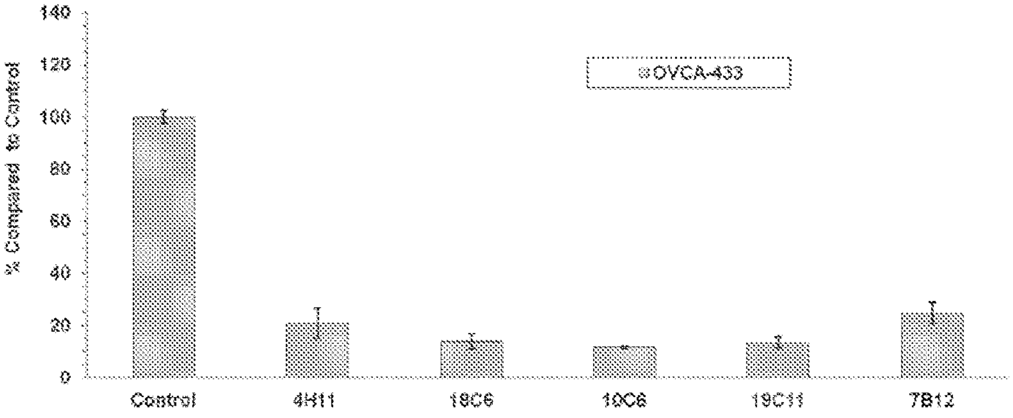
Figure 23E:
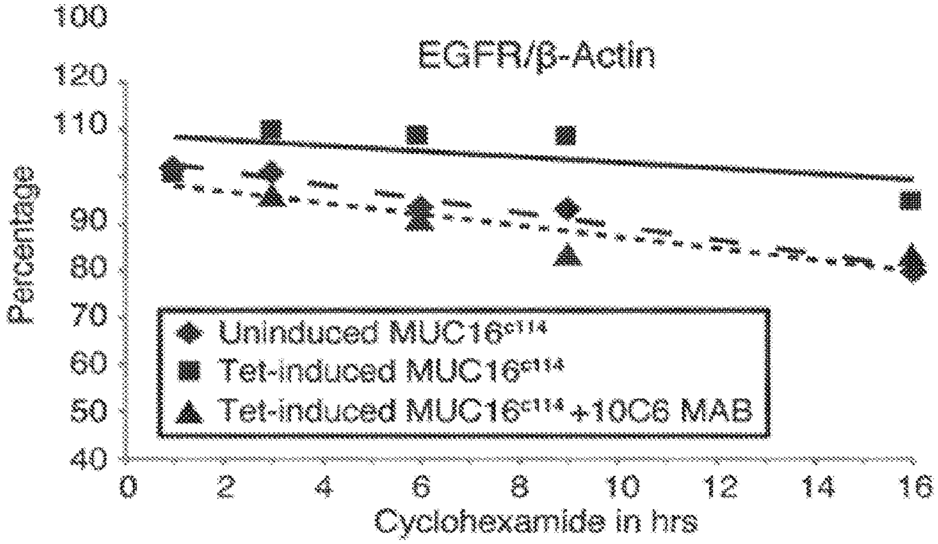
Figure 23F:
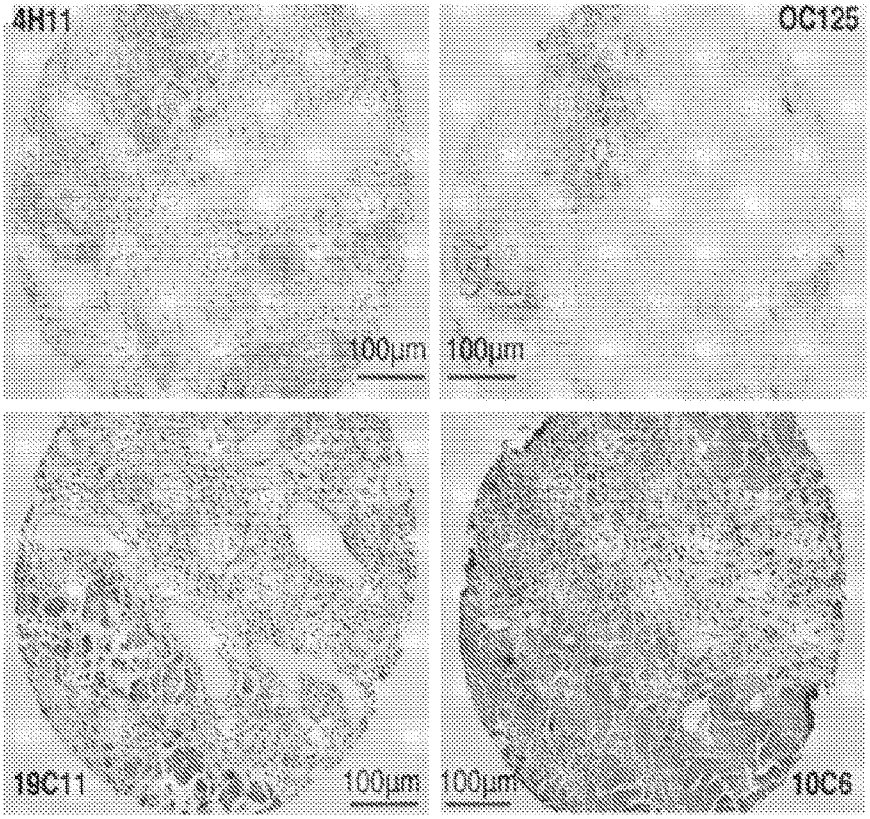
Figure 23G:
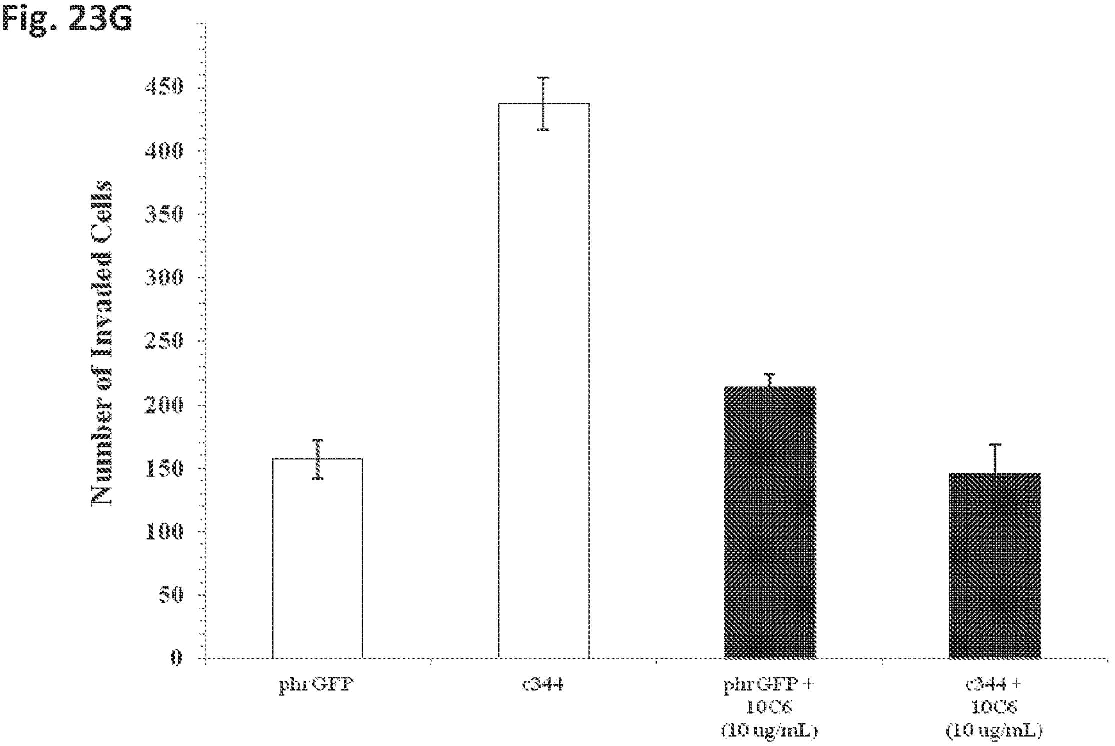
Figure 23H:
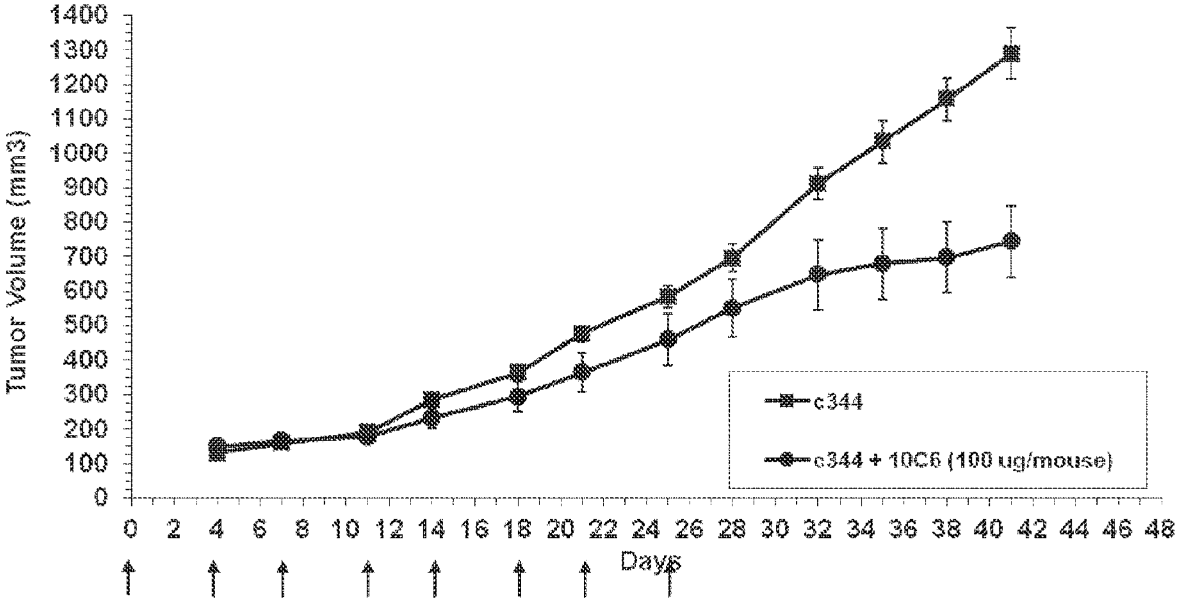

FIG. 23A-FIG. 23H depict MUC16 Glycosylation Antibody characterization. FIG. 23A depicts the reactivity of 4H11 and four lead $GlcNAc_2$-MUC16-ectodomain monoclonal antibodies (MUC16 Glycosylation Antibodies) to various MUC16 and $GlcNAc_2$-glycosylated peptides by sandwich ELISA. No glycan-MUC16 ectodomain cross reactivity was seen with the nonglycosylated MUC16 peptide 2 (SEQ ID NO: 168), or either of the unrelated peptides (SEQ ID NO: 169). Similarly, 4H11 had essentially no affinity for the $GlcNAc_2$-MUC16 15-mer (SEQ ID NO: 131) or $(GlcNAc_2)_2$-18-mer (SEQ ID NO: 130) N-glycopeptides. Squares represent N-acetylglusoamin; triangles represent fucose; circles represent mannose. FIG. 23B, FIG. 23C, and FIG. 23D depict the effect of MUC16 Glycosylation Antibodies on MUC16-enhanced matrigel invasion. Results are expressed as % compared to control. Matrigel assay of SKOV3 cells transfected with phrGFP expressing MUC16$^{c114}$ (SEQ ID NO: 133) (FIG. 23B), CAOV3 cells (FIG. 23C) and OVCA-433 cells (FIG. 23D) with or without (control) purified 4H11 or the four glycan-MUC16-ectodomain antibodies 18C6, 10C6, 19C22, or 7B12 at 5 μg/mL. Each of the four anti-glycan-MUC16-ectodomain antibodies (MUC16 Glycosylation Antibodies) inhibited the invasion of three different MUC16(+) ovarian cancer cell lines (CAOV3 and OVCA-433), while 4H11 had less effect on inhibiting invasion of the SKOV3-MUC16$^{c114}$ cells. FIG. 23E depicts the inhibition of EGFR stabilization by MUC16 Glycosylation Antibody monoclonal antibody ("MAB") 10C6. The densitometry of western blot analysis from cell extracts of un-induced SKOV3-MUC16$^{c114(tet)}$, tetracycline-induced SKOV3-MUC16$^{c114(tet)}$, or monoclonal MUC16 Glycosylation Antibody 10C6-treated, tetracycline-induced SKOV3-MUC16$^{c114(tet)}$ cell lines treated with CHX and then probed for total EGFR at the indicated hours (hrs) post-treatment with cyclohexamind. As seen in FIG. 20A, the slopes of the densitometry curves indicated that the presence of MUC16$^{c114}$ on the cell surface stabilized EGFR. The MUC16 Glycosylation Antibody 10C6 abrogated the MUC16$^{c114}$ stabilization of total EGFR protein, making it similar to the MUC16(−) un-induced control. FIG. 23F depicts human ovarian tissue microarrays stained with 4H11, OC125 (commercial), or monoclonal MUC16 Glycosylation Antibodies (10C6 and 19C11). The expression of MUC16 on the serous ovarian cancer was consistent and overlapped with OC125 and 4H11. FIG. 23G and FIG. 23H depict the effect of MUC16 Glycosylation Antibodies on tumor growth in athymic female nude mice. Two million tumor cells (SKOV3 cells transfected with phrGFP vector ("phrGFP") or phrGFP vector expressing MUC16$^{c344}$ (SEQ ID NO: 132; "c344")) were introduced into the flank of 20 nu/nu mice. Ten mice were treated intravenously from day 0 with purified monoclonal MUC16 Glycosylation Antibody 10C6 at 100 μg/mouse twice per week for 4 weeks. All mice were observed for tumor formation. Tumors were measured by calipers twice per week. FIG. 23G shows the matrigel invasion assay with the same cells performed in the presence and absence of purified monoclonal MUC16 Glycosylation Antibody 10C6 at 10 μg/mL. FIG. 23H demonstrates that differences in mean tumor volume were significantly decreased ($p=0.0004$) with monoclonal MUC16 Glycosylation Antibody 10C6-treated mice bearing MUC16$^{c344}$ tumors compared with untreated MUC16$^{c344}$ tumors, indicating protection against the effect of MUC16 on tumor growth.

Figure 24A:
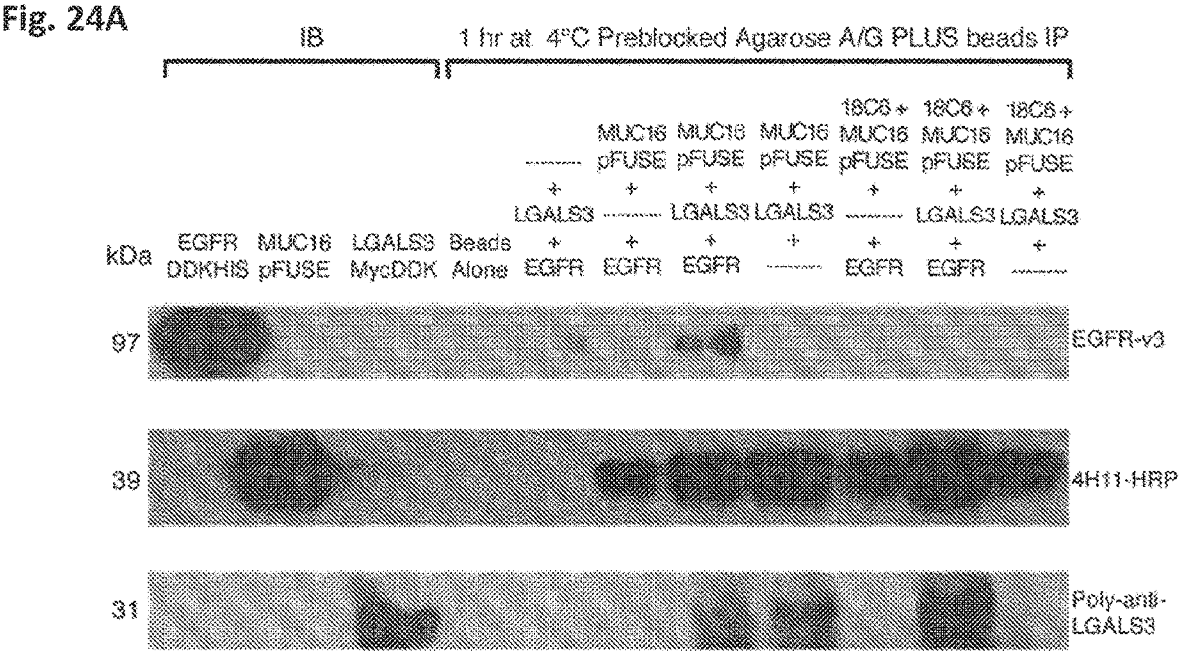
Figure 24B:
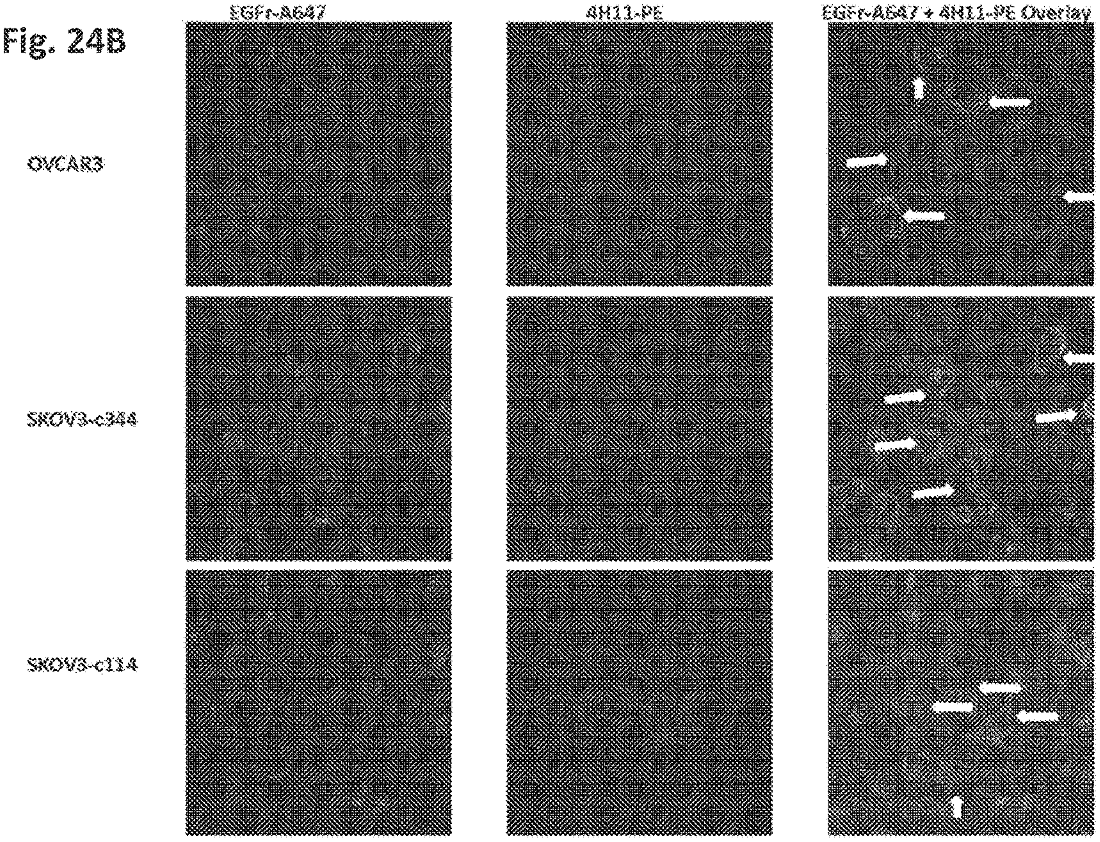
Figure 24C:
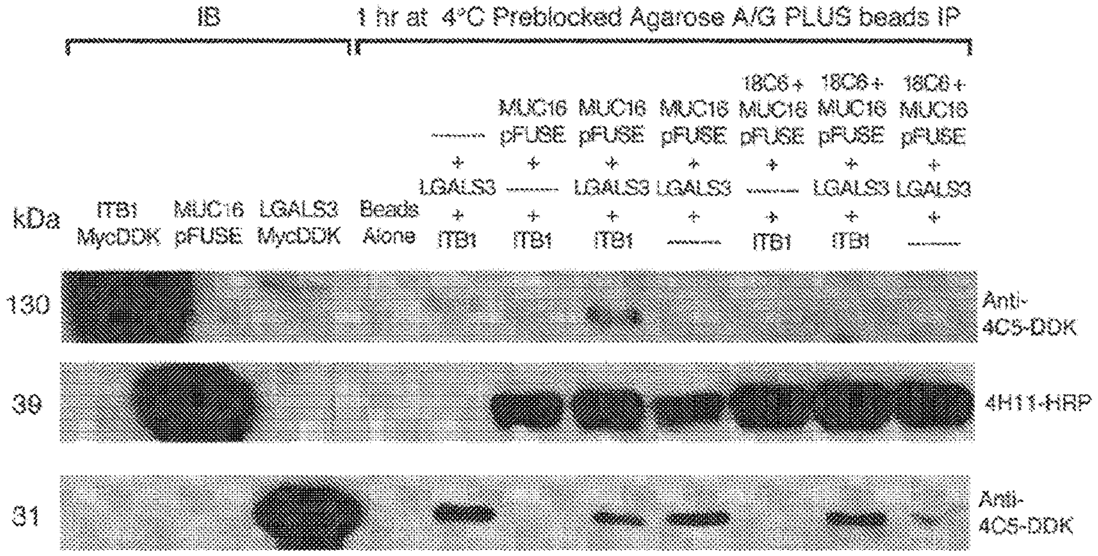
Figure 24D:
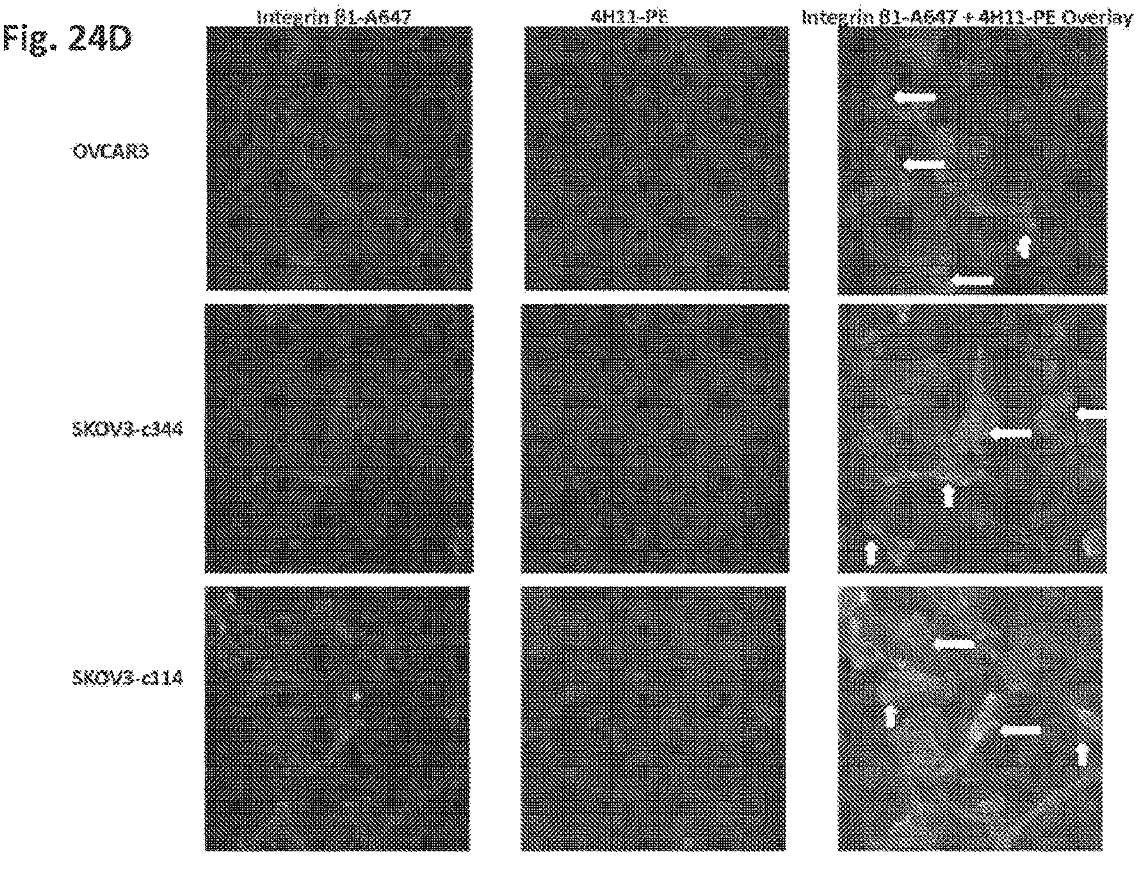

FIG. 24A-FIG. 24D depict galectin-mediated MUC16 protein-protein Interactions. FIG. 24A depicts immunoblot (IB) and immunoprecipitation (IP) of three glycosylated proteins (EGFR DDK-His; MUC16$^{c57-114}$-pFUSE; and LGALS3Myc-DDK). MUC16$^{c57-114}$-pFUSE glycosylated protein was combined with LGALS3 protein (0.13 μg) and EGFR (0.13 μg) and then rotated at 4° C. for 1 hour. Pre-blocked Protein A/G PLUS Agarose beads were added and were rotated at 4° C. overnight. IP pellets were washed extensively, boiled in loading buffer and separated by 10% SDS-PAGE gel electrophoresis, then transferred onto nitrocellulose membrane. The membrane was probed with anti-EGFR-v3, anti-4H11-HRP, or polyclonal anti-LGALS3 antibodies. As shown, the 4H11 binding showed that MUC16$^{c57-114}$-pFUSE was consistently present. LGALS3 bound in the lane positive for MUC16$^{c57-114}$-pFUSE, but EGFR was only detected when both LGALS3 and MUC16$^{c57-114}$-pFUSE were present. The presence of the monoclonal MUC16 Glycosylation Antibody 18C6 prevented the formation of these LGALS3, EGFR, and MUC16 protein complexes (right hand lanes). FIG. 24B depicts MUC16 and EGFR protein co-localization. Immunofluorescence staining of wild type OVCAR3 cells or SKOV3 cells transfected with phrGFP expressing MUC16$^{c344}$ (SEQ ID NO: 132; "SKOV3$^{c344}$") or with phrGFP expressing MUC16$^{c114}$ (SEQ ID NO: 133; "SKOV3$^{c114}$") with EGFR-A647 and 4H11-PE for MUC16, or a combination of both reagents EGFR-A647 and 4H11-PE for MUC16. Microscopic images (50 μm scale) indicated co-localization of EGFR and MUC16$^{c114}$ in all three cell lines (see arrows). FIG. 24C depicts immunoblot (IB) and immunoprecipitation (IP) of three glycosylated proteins (Integrin β1Myc-DDK; MUC16$^{c57-114}$-pFUSE and LGALS3Myc-DDK). Generally the same methods as in FIG. 24A were used. Western blot analysis of immunoblot and all immunoprecipitated samples were run on 10% SDS-PAGE gel, transferred onto nitrocellulose membrane, and probed either with anti-4C5-DDK for Integrin β1, or anti-4H11-HRP or anti-4C5-DDK for LGALS3 antibodies. As with EGFR, all three proteins were required to co-precipitate the Integrin β1 protein. The MUC16 Glycosylation Antibody 18C6 also blocked the combination of MUC16, LGALS3, and Integrin β1, as shown in the three right-hand lanes. FIG. 24D depicts MUC16 and Integrin β1 protein co-localization. Immunofluorescence staining of wild ty wild type OVCAR3 cells or SKOV3 cells transfected with phrGFP expressing MUC16$^{c344}$ (SEQ ID NO: 132; "SKOV3$^{c344}$") or with phrGFP expressing MUC16$^{c114}$ (SEQ ID NO: 133; "SKOV3$^{c114}$") with Integrin β1-A647 or 4H11-PE for MUC16 or a combination of both reagents Integrin β1-A647 or 4H11-PE for MUC16. Microscopic images (50 μm scale) indicated co-localization of the Integrin β1 and MUC16 in OVCAR3, SKOV3$^{c344}$, and SKOV3$^{c114}$ cells (see arrows).

Figure 25A:
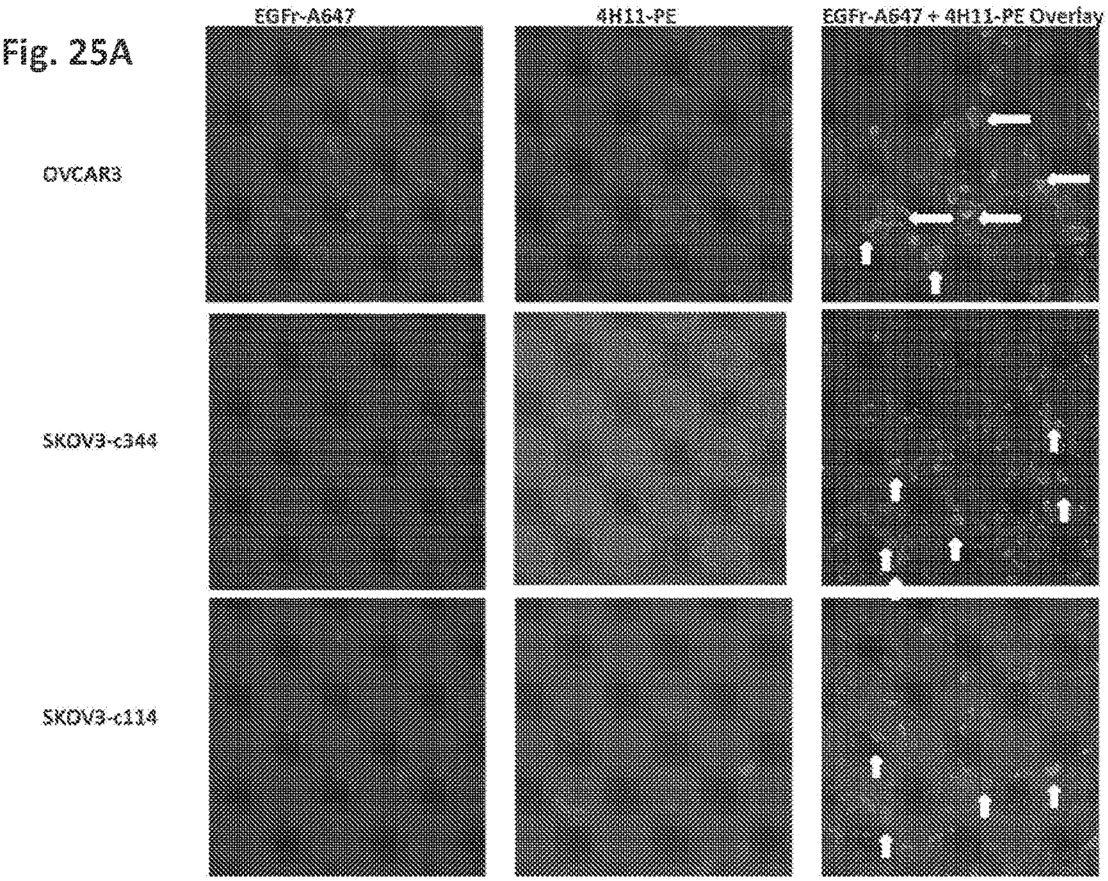
Figure 25B:
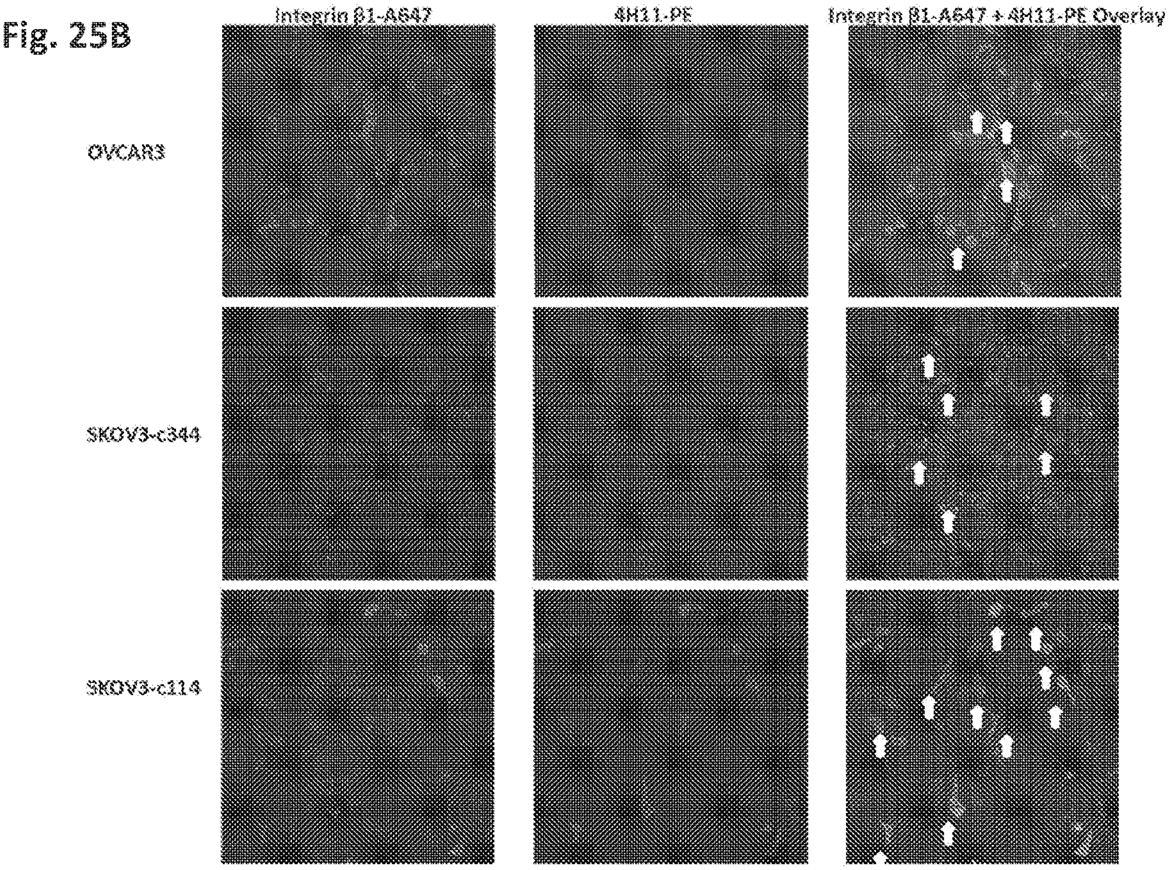

FIG. 25A depicts immunofluorescence staining of wild type OVCAR3 cells or SKOV3 cells transfected with phrGFP expressing MUC16$^{c344}$ (SEQ ID NO: 132; "SKOV3$^{c344}$") or with phrGFP expressing MUC16$^{c114}$ (SEQ ID NO: 133; "SKOV3$^{c114}$") or SKOV3$^{c344}$ or SKOV3$^{c114}$ cell lines with EGFR-A647 or 4H11-PE for MUC16 or a combination of both reagents. Microscopic images (scale 100 μm) clearly indicated co-localization of EGFR and MUC16 (see arrows). FIG. 25 B: Immunofluorescence staining of wild type OVCAR3 or SKOV3$^{c344}$ or cell lines with Integrin β1-A647 or 4H11-PE for MUC16 or a combination of both reagents. Microscopic images (scale 100 μm) clearly indicated co-localization of Integrin β1 and MUC16 (see arrows).

Figure 26A:
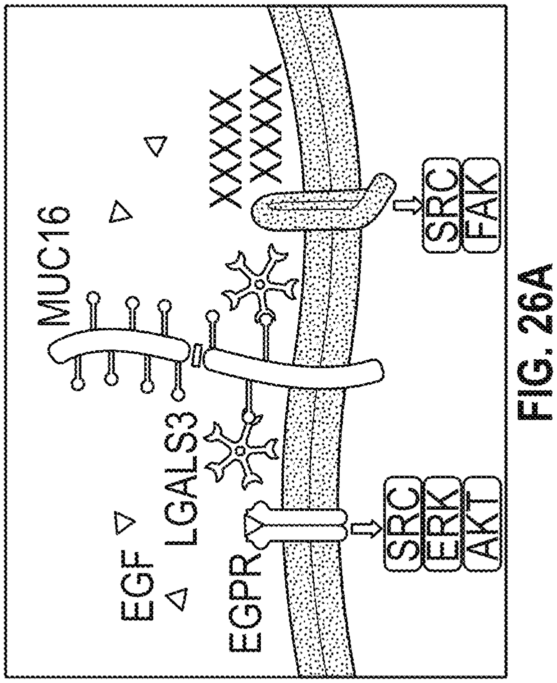
Figure 26B:
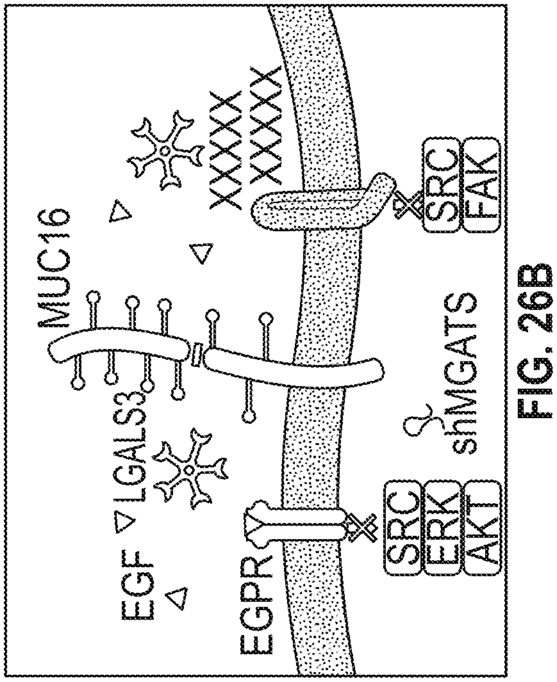
Figure 26C:
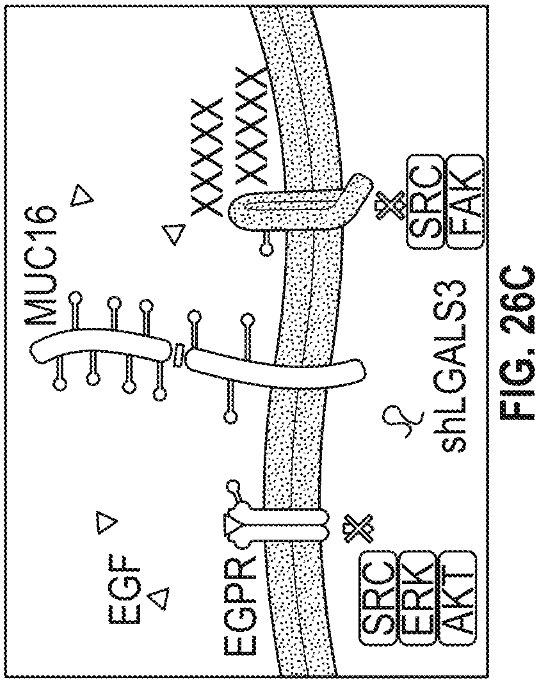
Figure 26D:
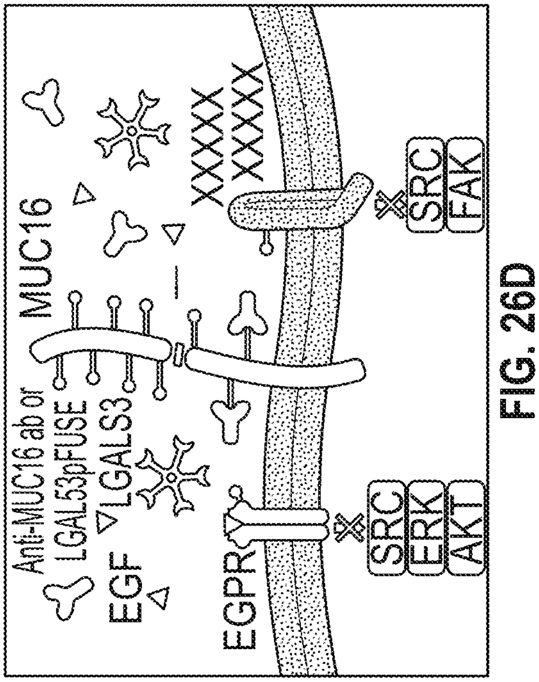

FIG. 26A-FIG. 26D depicts a model of MUC16 Tumor Promotion. FIG. 26A depicts an illustration of EGFR-LGALS3-MUC16 and LGALS3-Integrin β1-MUC16 relationships. Signal transduction of SRC/ERK/AKT by EGFR or of SRC/FAK by Integrin β1 depended on MUC16 and signaling-molecule interaction with LGALS3 pentamers. FIG. 26B depicts a model for glycosylation loss: in shMGAT5-transfected cell lines, the N-glycosylation at sites on MUC16, EGFR, and Integrin β1 was reduced by loss of the tetra-antennary structures, resulting in no binding to LGALS3. FIG. 26C depicts a model for galectin-3 loss: in shLGALS3 transfected cell lines, while the N-glycosylation sites on MUC16 were present, the absence of binding to LGALS3 resulted in a loss of MUC16/EGFR or MUC16/Integrin β1 association and reduction of inside-out signals. FIG. 26D depicts a model for potential inhibitors for MUC16/LGALS3 interactions. MUC16(+) cells exposed to MUC16 Glycosylation Antibody or "dummy" sham receptors (anti-MUC16$^{c57-114}$pFUSE or $^{117-244}$LGALS3-pFUSE) failed to bind to LGALS3 gels and subsequently also to either EGFR or Integrin β1.

Figure 27A:
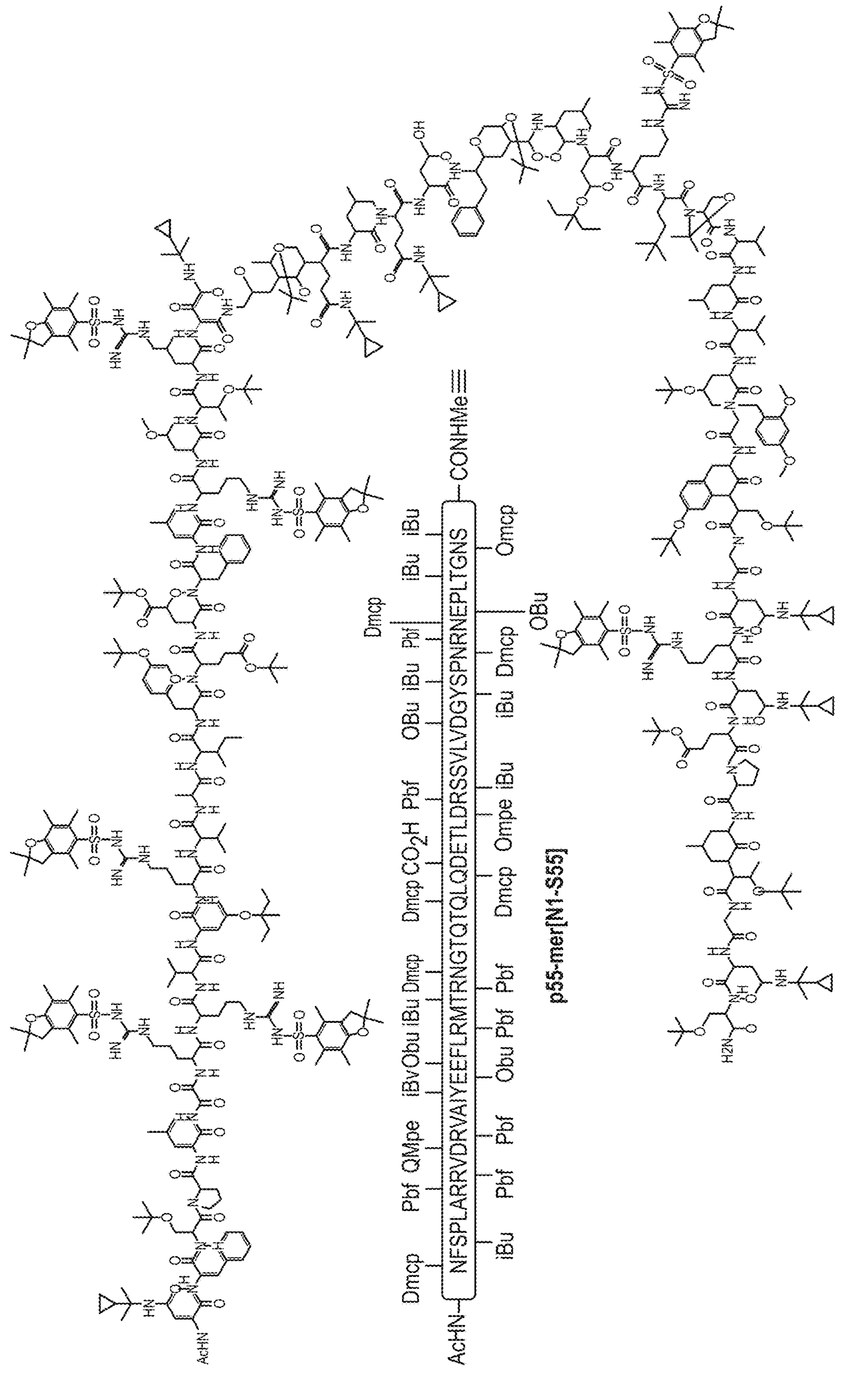
Figure 27B:
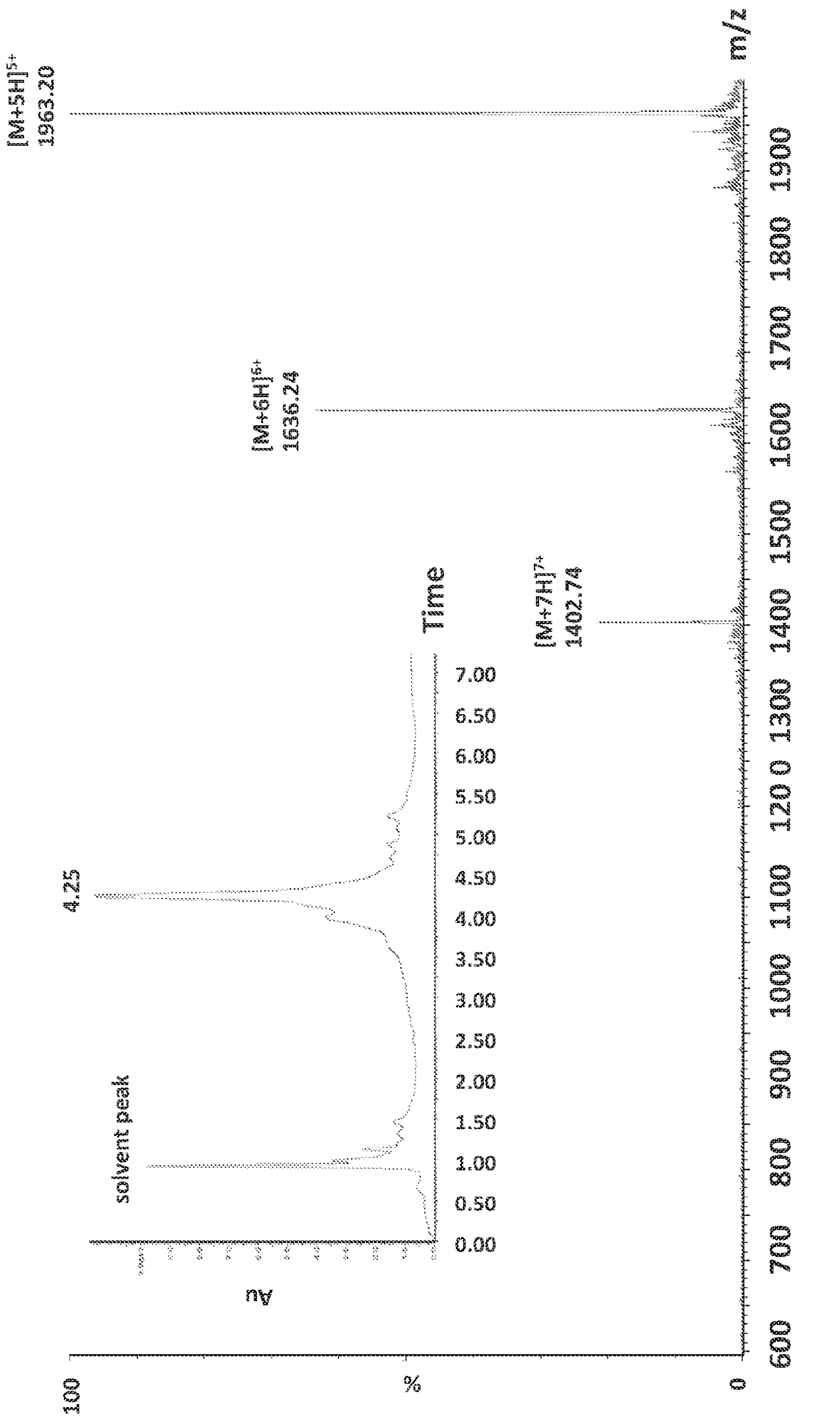

FIG. 27A depicts the side-chain protected N-acetylated 55-mer peptide amide (SEQ ID NO: 129). FIG. 27B depicts the ESI-MS and UV traces from UPLC analysis for glycopeptide p55-mer[N1-S55]. Calculated for $C_{486}H_{760}N_{84}O_{111}S_8$, 9812.25 (average isotopes) $[M+5H]^{5+}$ m/z 1963.45, found 1963.20; $[M+6H]^{6+}$ m/z 1636.38, found 1636.24; $[M+7H]^{7+}$ m/z 1402.75, found 1402.74. BEH C4 column, gradient: 80-99% acetonitrile/water over 6 minutes at a flow rate of 0.3 mL/min.

Figure 28A:
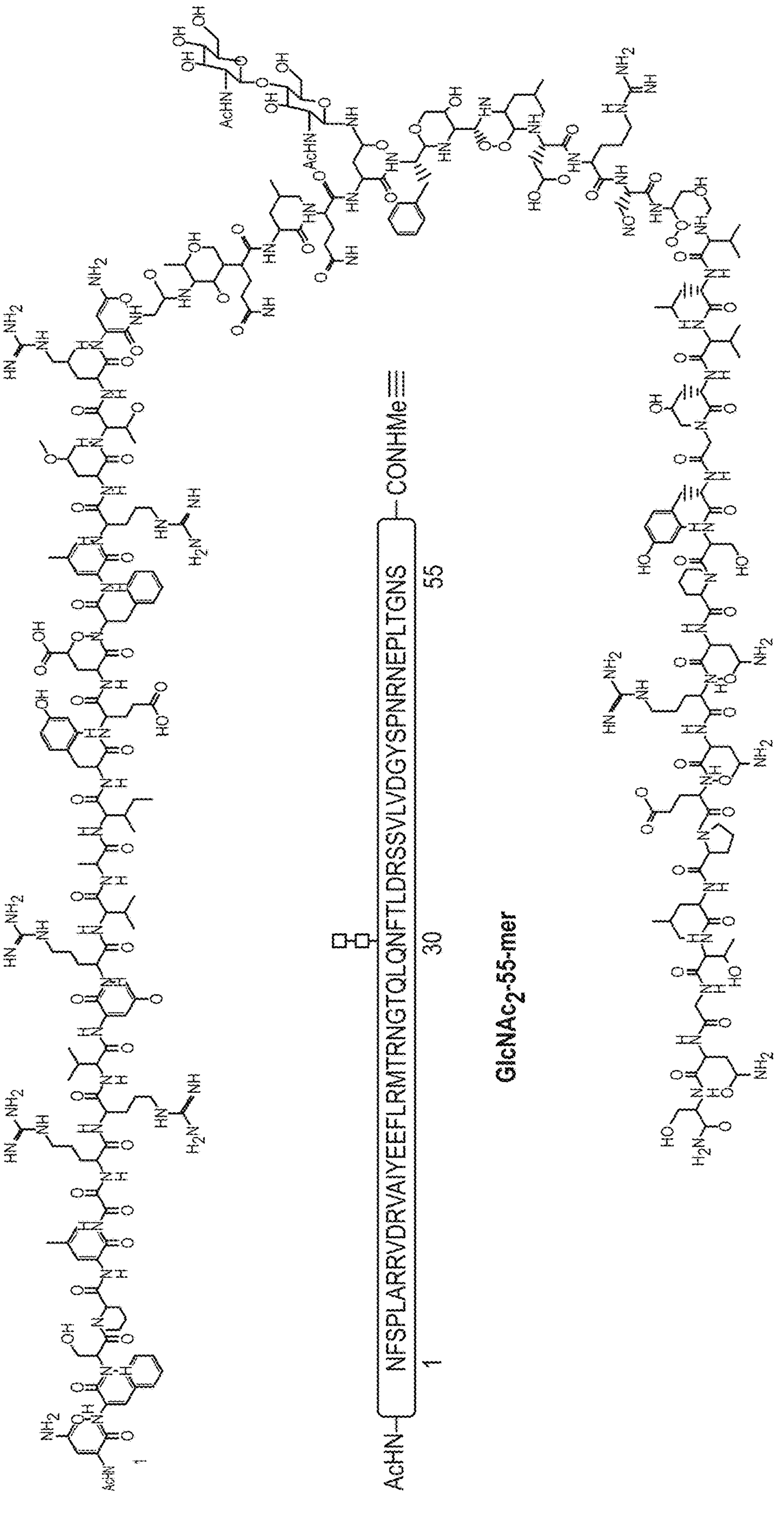
Figure 28B:
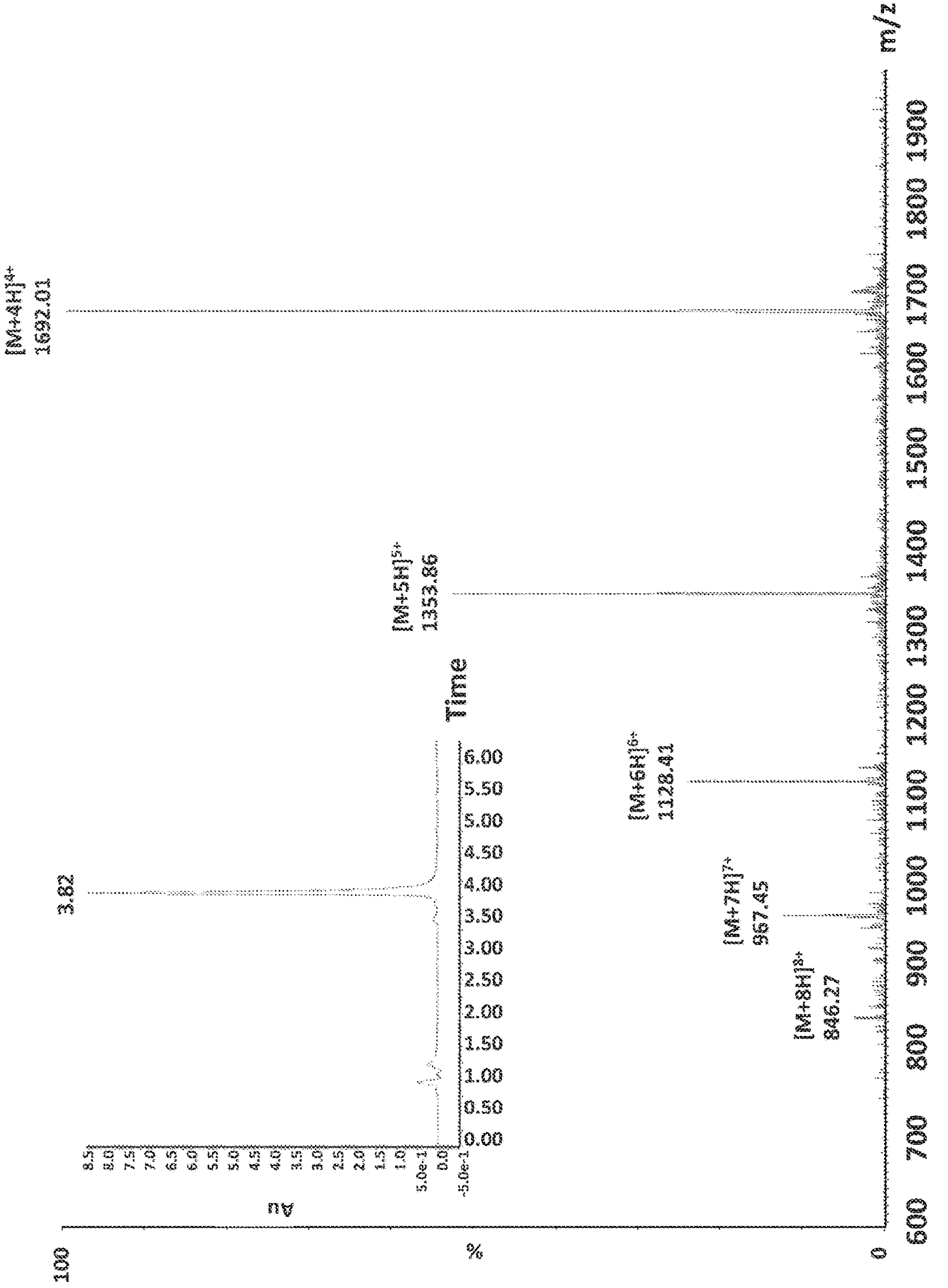

FIG. 28A depicts the chitobiose-bearing 55-mer glycopeptide: "55-mer(chitobiose)[N1-S55]" ($GlcNAc_2$-55-mer) (SEQ ID NO: 129). FIG. 28B depicts the ESI-MS and UV traces from UPLC analysis for glycopeptide "55 mer(chitobiose) [N1-S55]" ($GlcNAc_2$-55-mer). Calculated for $C_{291}H_{463}N_{87}O_{97}S$, 6764.38 (AVERAGE ISOTOPES) $[M+4H]^{4+}$ m/z 1692.10, found 1692.01; $[M+5H]^{5+}$ m/z 1353.88, found 1353.86; $[M+6H]^{6+}$ m/z 1128.40, found 1128.41; $[M+7H]^{7+}$ m/z 967.34, found 967.45; $[M+8H]^{8+}$ m/z 846.55, found 846.27. BEH C4 column, gradient: 20-40% acetonitrile/water over 6 minutes at a flow rate of 0.3 mL/min.

Figure 29A:
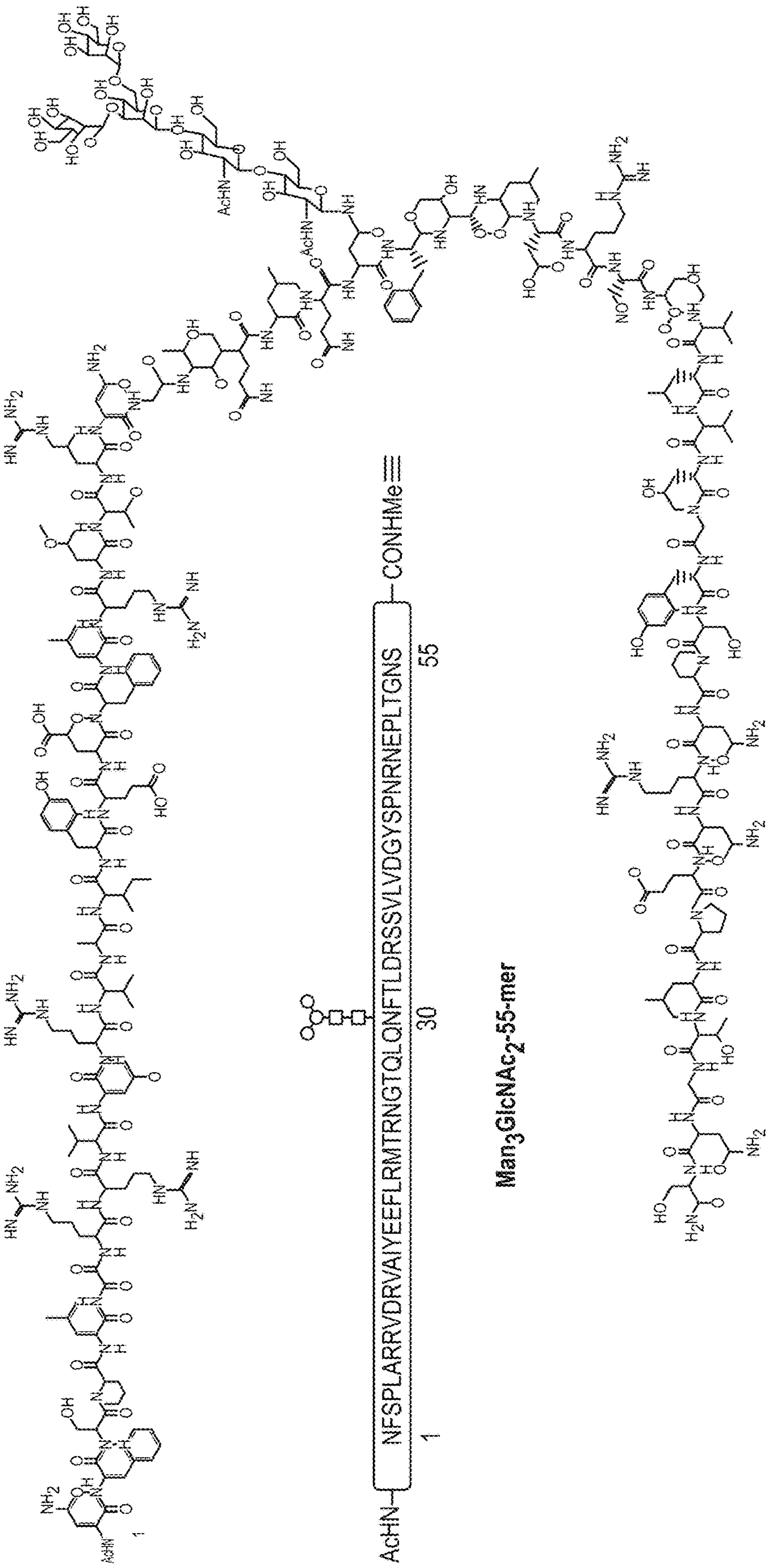
Figure 29B:
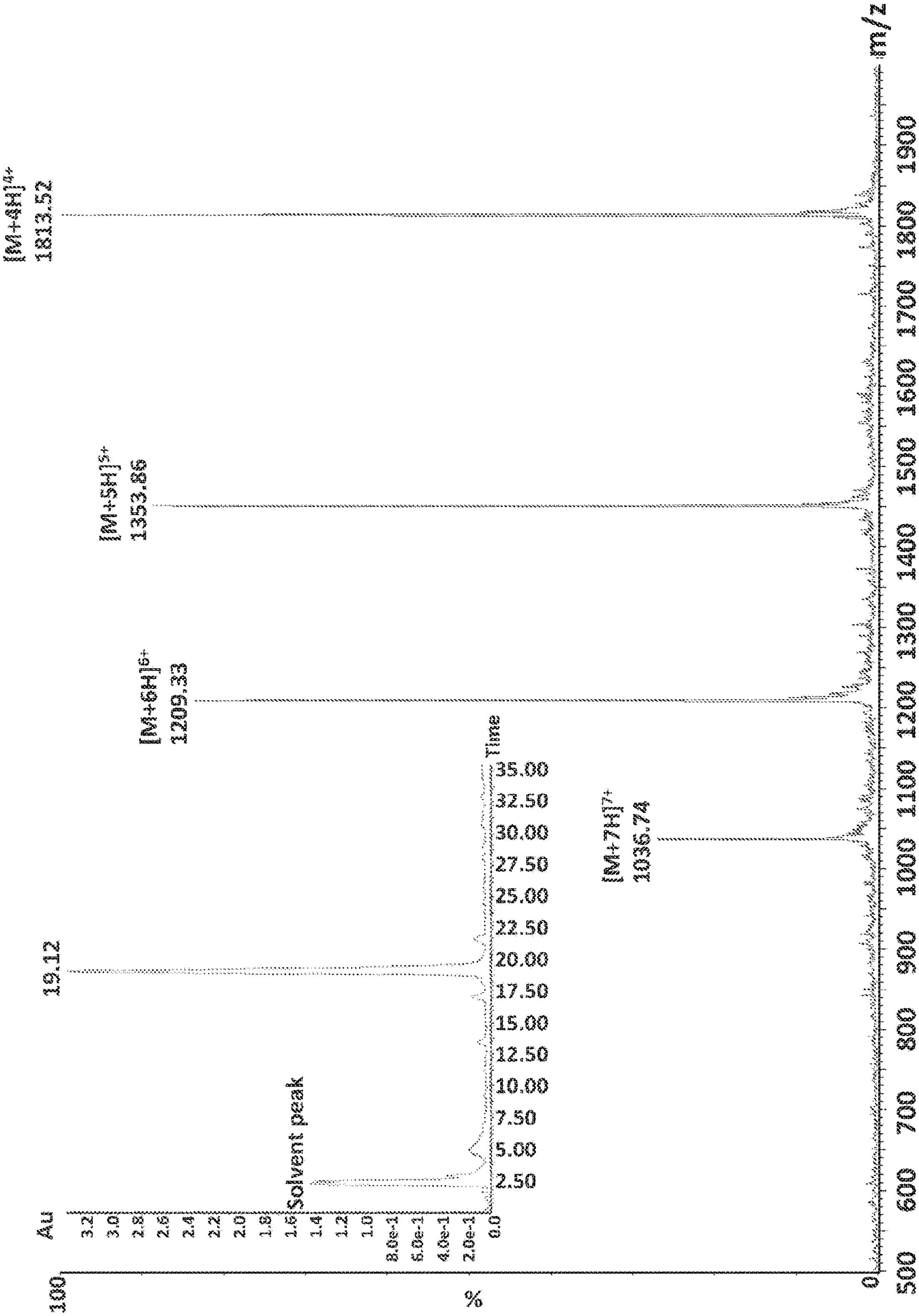

FIG. 29A depicts Man3GlcNAc2-bearing 55-mer glycopeptide: "55-mer($Man_3GlcNAc_2$)[N1-S55]" ($Man_3GlcNAc_2$-55-mer) (SEQ ID NO: 129). FIG. 29B depicts the ESI-MS and UV traces from analytical HPLC analysis for glycopeptide "55 mer($Man_3GlcNAc_2$)[N1-S55]" ($Man_3GlcNAc_2$-55-mer). Calculated for $C_{309}H_{493}N_{87}O_{112}S$, 7250.80 (average isotopes) $[M+4H]^{4+}$ m/z 1813.70, found 1813.52; $[M+5H]^{5+}$ m/z 1451.16, found 1451.02; $[M+6H]^{6+}$ m/z 1209.47, found 1209.33; $[M+7H]^{7+}$ m/z 1036.83, found 1036.74. Waters X-Bridge C18 column, gradient: 25-35% acetonitrile/water over 30 minutes at a flow rate of 0.2 mL/min.

Figure 30A:
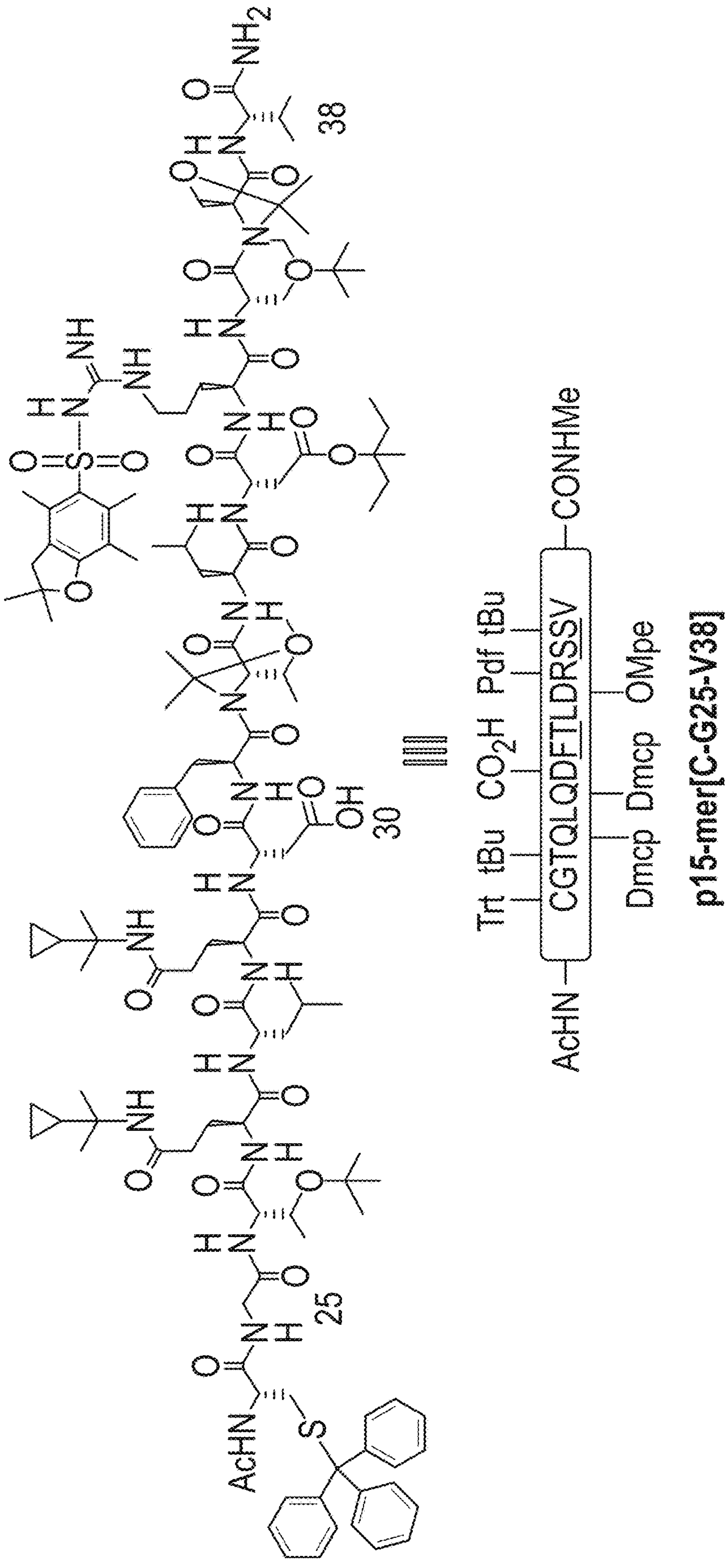
Figure 30B:
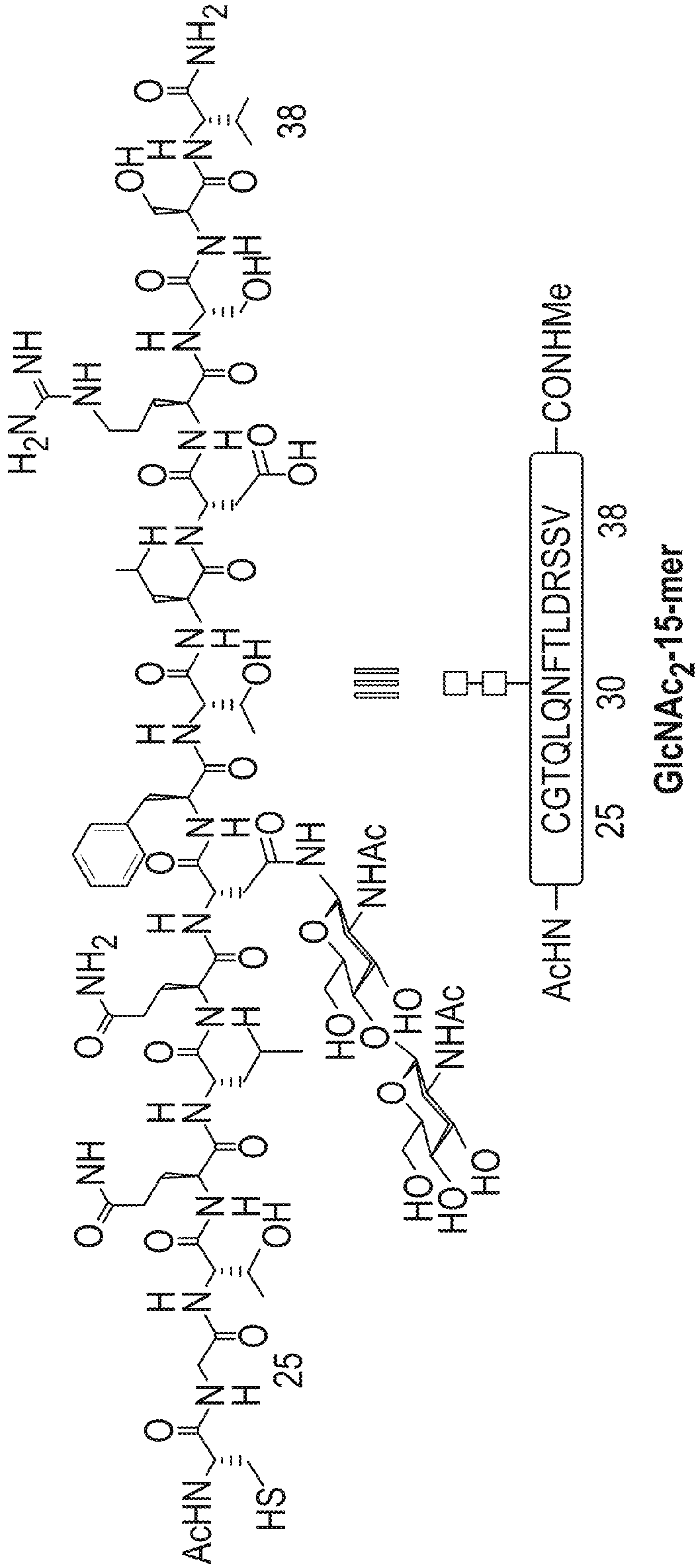
Figure 30C:
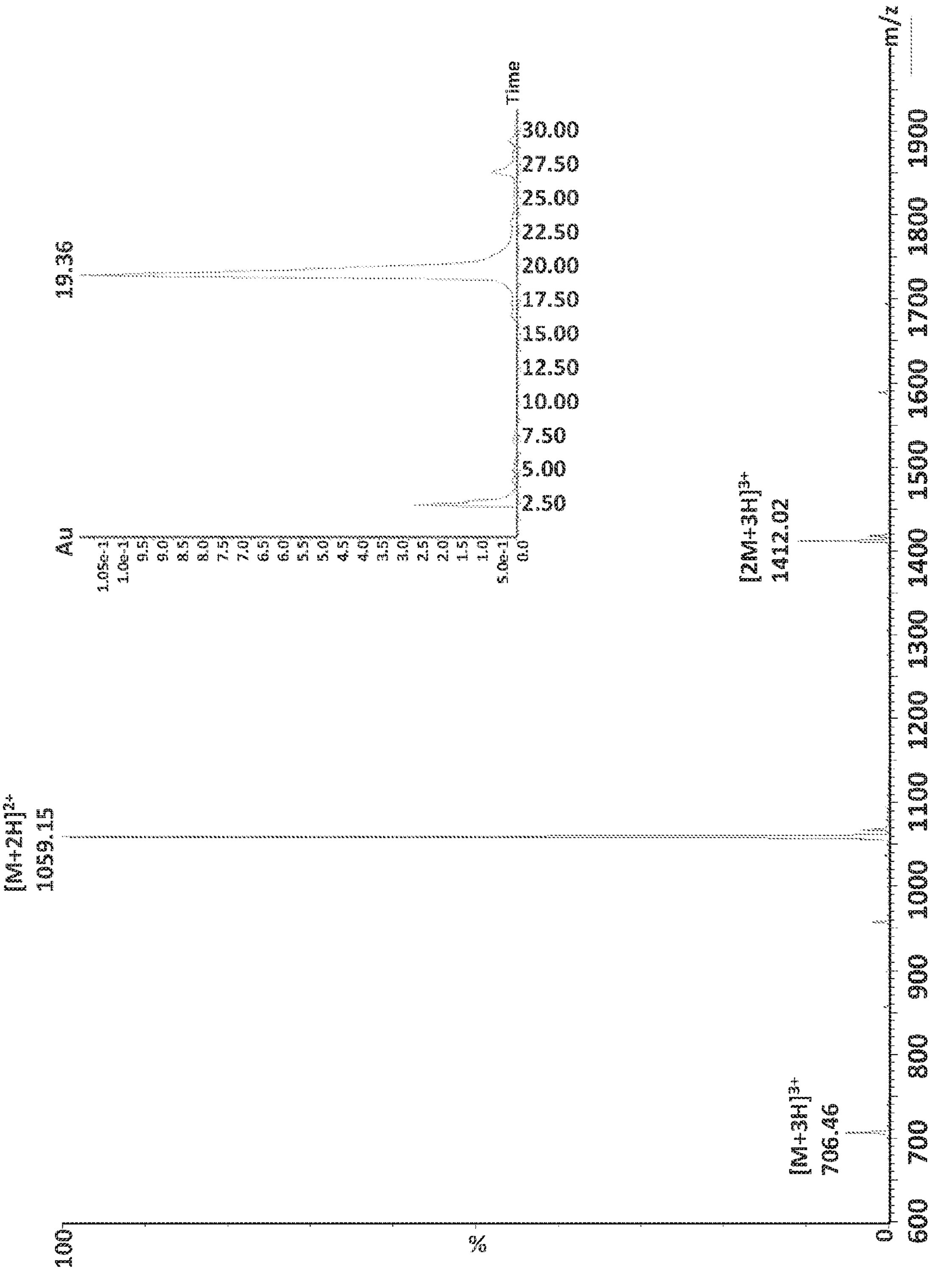

FIG. 30A depicts side-chain protected 15-mer peptide (p15-mer[C-G25-V38]) (SEQ ID NO: 131). FIG. 30B depicts chitobiose-monoglycosylated 15-mer glycopeptide: 15-mer(chitobiose)[C-G25-V38] ($GlcNAc_2$-15-mer) (SEQ ID NO: 132). FIG. 30C depicts ESI-MS and UV traces from analytical HPLC analysis for glycopeptide "15 mer(chitobiose)[C-G25-V38]" ($GlcNAc_2$-15-mer). Calculated for $C_{87}H_{142}N_{24}O_{35}S$, 2116.26 (average isotopes) $[2M+3H]^{3+}$ m/z 1411.84, found 1412.02; $[M+2H]^{2+}$ m/z 1059.13, found 1059.15; $[M+3H]^{3+}$ m/z 706.42, found 706.46. Varian Microsorb 300-5 C18 column, gradient: 15-30% acetonitrile/water over 30 minutes at a flow rate of 0.2 mL/min.

Figure 31A:
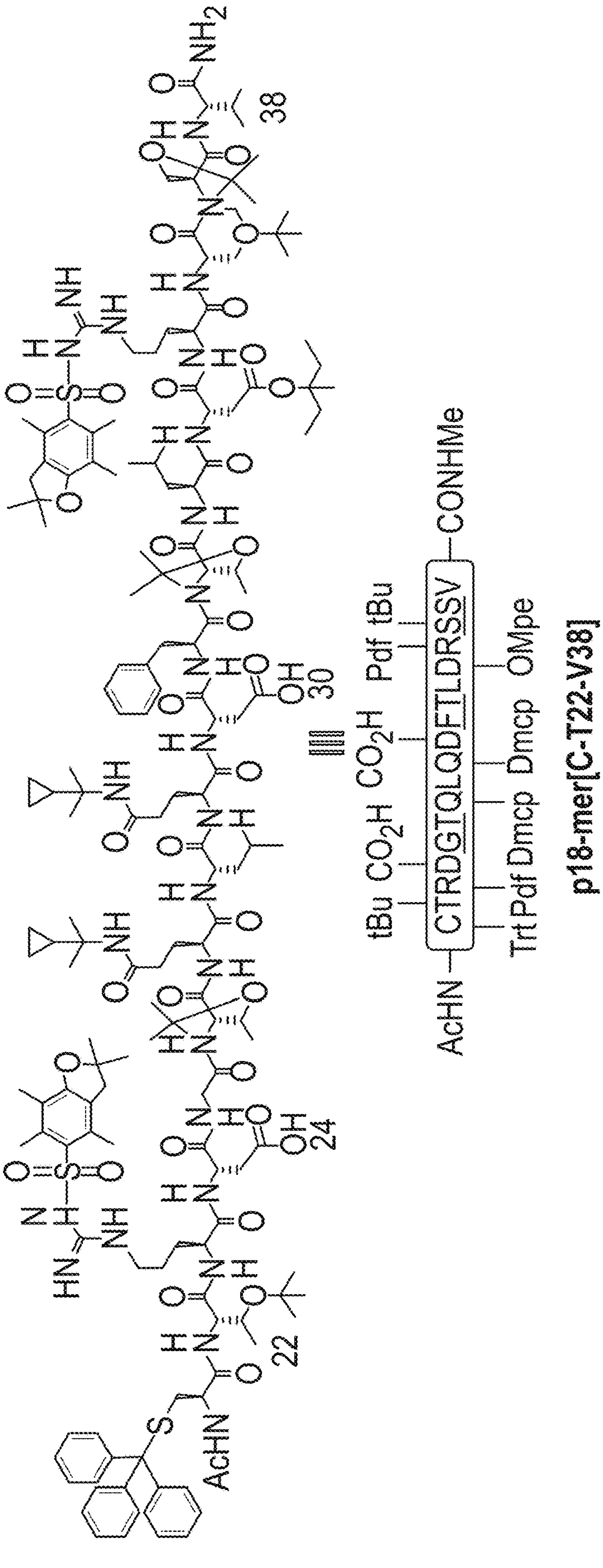
Figure 31B:
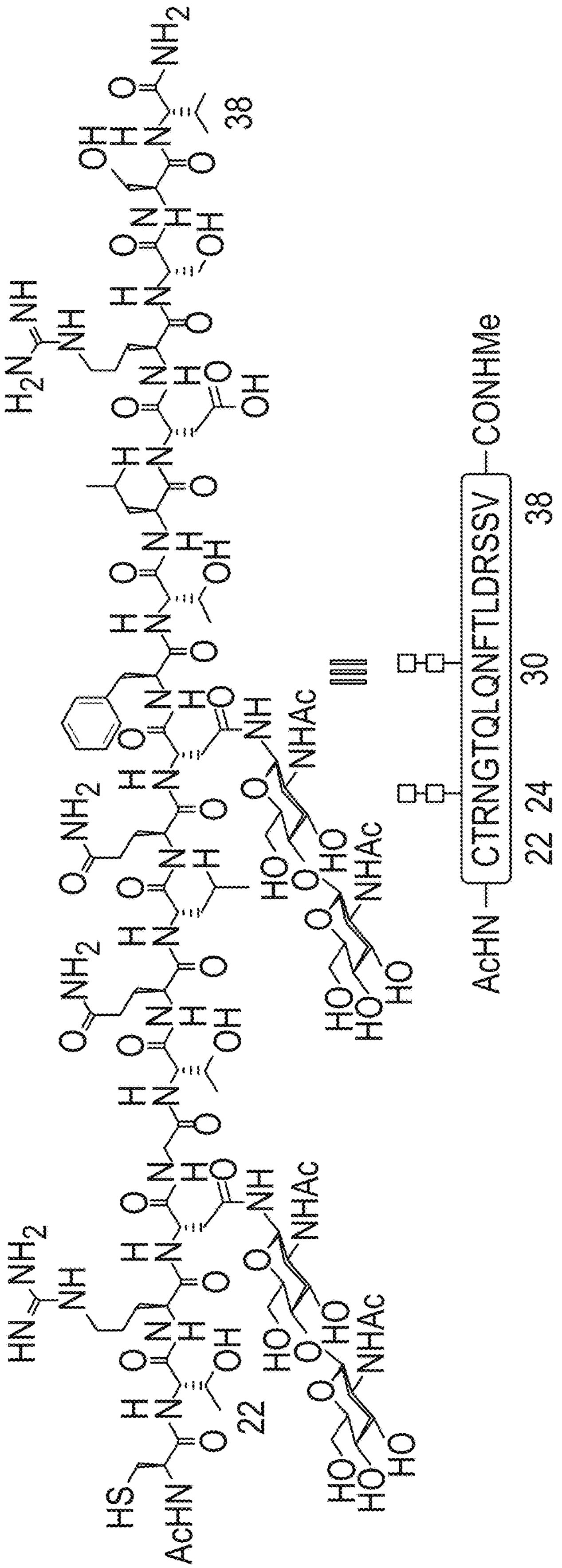
Figure 31C:
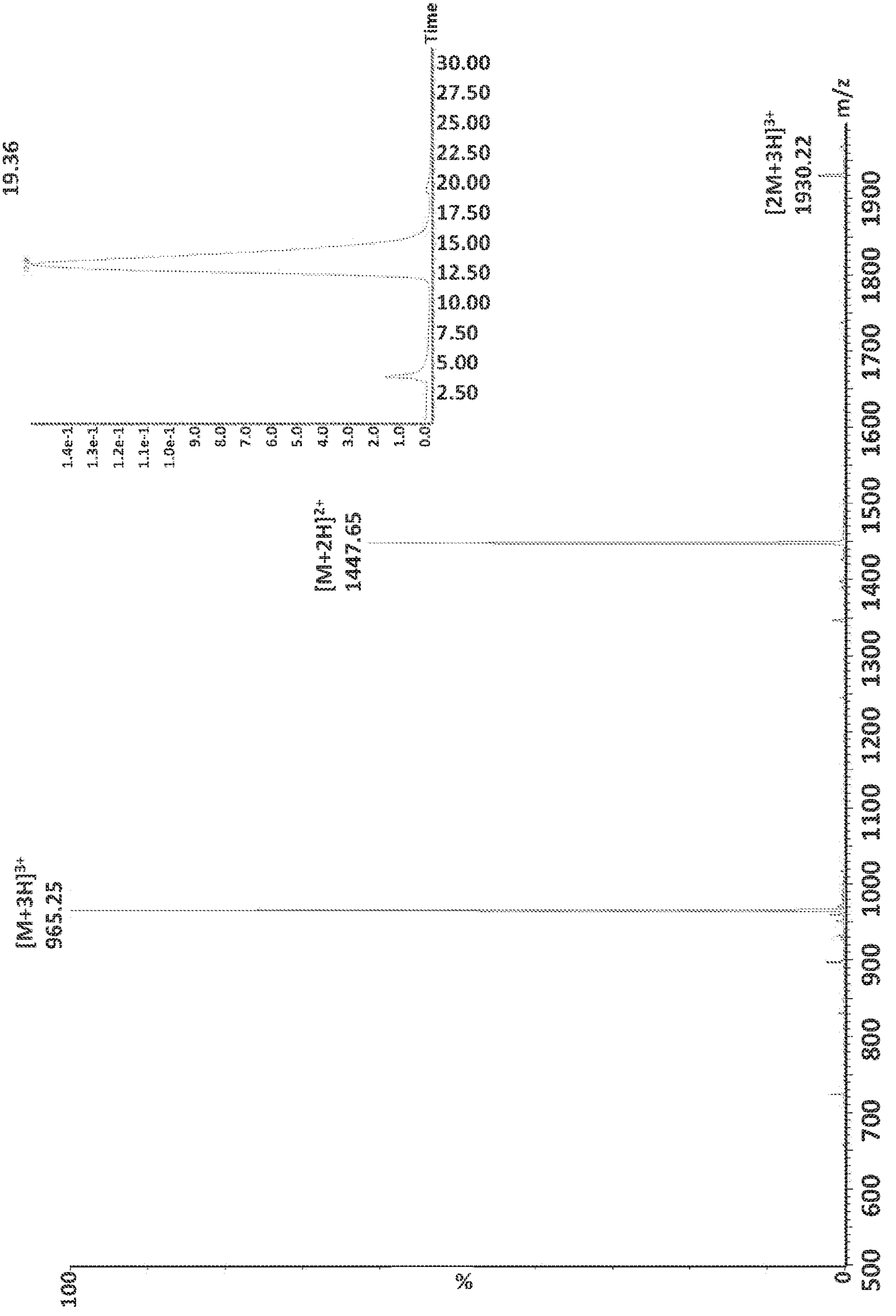

FIG. 31A depicts side-chain protected 18-mer peptide (p18-mer[C-G22-V38]) (AF-I-165) (SEQ ID NO: 130). FIG. 31B depicts chitobiose-bisglycosylated 18-mer glycopeptide: "18-mer(chitobiose)$_2$[C-T22-V38]" [$(GlcNAc_2)_2$-18-mer] (SEQ ID NO: 130). FIG. 31C depicts the ESI-MS and UV traces from analytical HPLC analysis for glycopeptide "18 mer(chitobiose)$_2$[C-T22-V38]" [$(GlcNAc_2)_2$-18-mer]. Calculated for $C_{117}H_{193}N_{33}O_{50}S$, 2894.04 (average isotopes) $[2M+3H]^{3+}$ m/z 1930.36, found 1930.22; $[M+2H]^{2+}$ m/z 1448.02, found 1447.65; $[M+3H]^{3+}$ m/z 965.68, found 965.25. Varian Microsorb 300-5 C8 column, gradient: 15-30% acetonitrile/water over 30 minute at a flow rate of 0.2 mL/min.

Figure 32A:
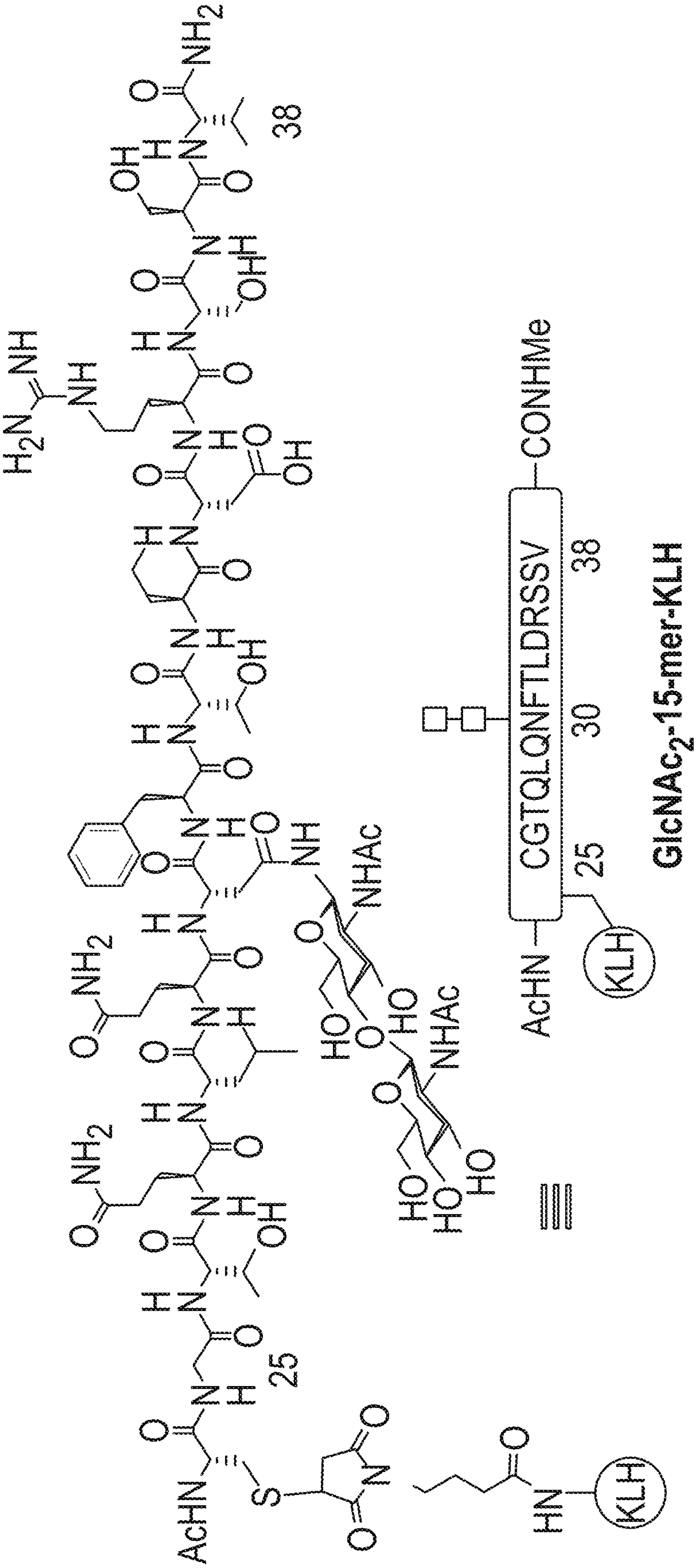
Figure 32B:
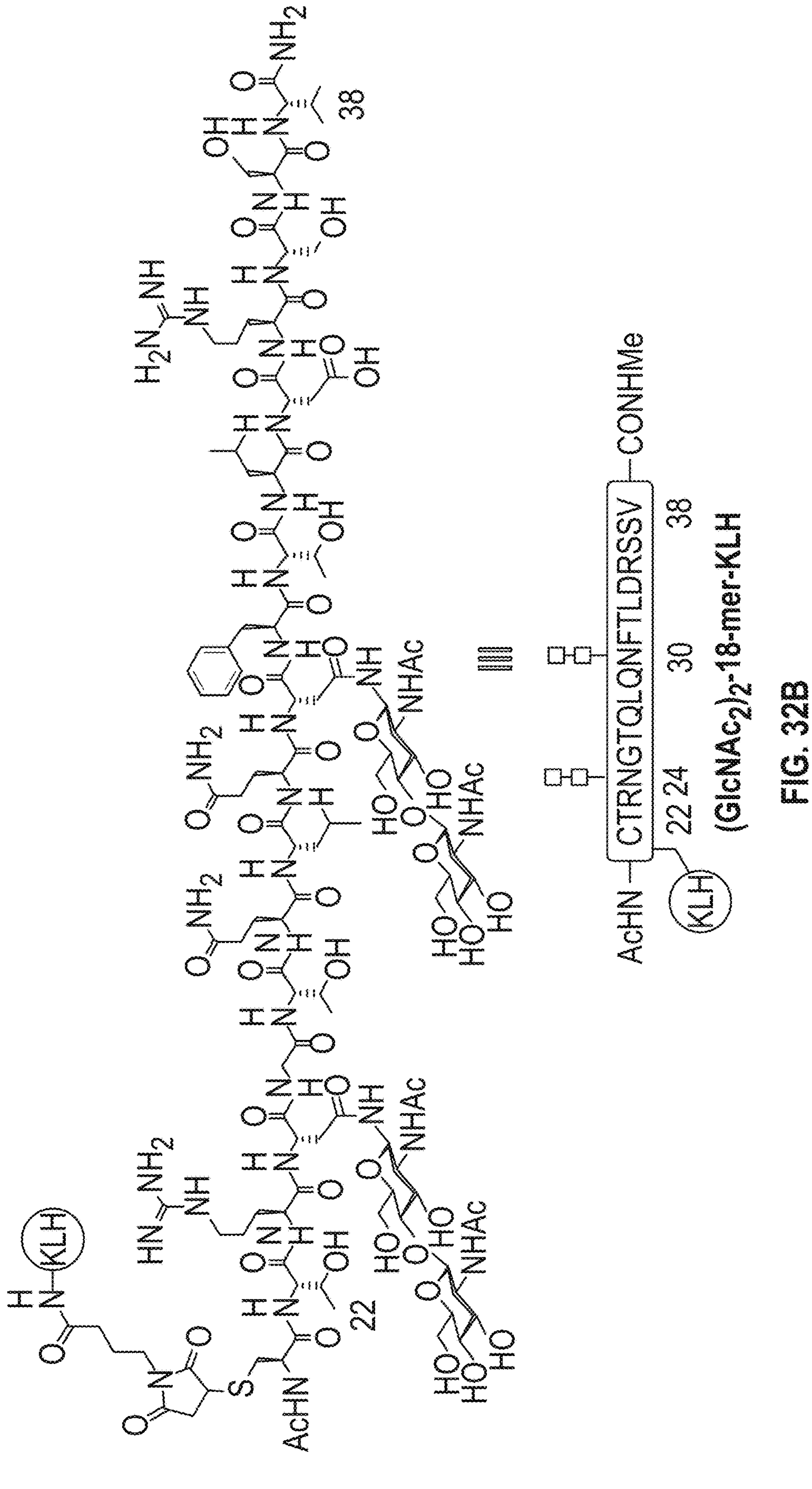

FIG. 32A depicts glycopeptide "15-mer(chitobiose)[C-G25-V38]", conjugated to KLH (SEQ ID NO: 131). FIG. 32B depicts glycopeptide "18-mer(chitobiose)$_2$[C-T22-V38]" conjugated to KLH (SEQ ID NO: 130).

5. DETAILED DESCRIPTION

Provided are antibodies and antigen-binding fragments thereof, and polypeptides including such antibodies or fragments, such as fusion proteins, conjugates, and/or chimeric antigen receptors, as well as cells expressing the same. Among the antibodies and fragments are those that specifically bind to epitopes of a MUC16 protein. Such antibodies are referred to herein as "MUC16 Glycosylation Antibodies". Such epitopes are typically epitopes within or substantially within an extracellular portion of a MUC16 molecule, generally a non-shed form of MUC16; in some embodiments, the epitope is not within, or the antibody or fragment does not bind to, a tandem repeat region of MUC16 and/or a secreted form of MUC16. In some embodiments, the epitope is within or includes residues within MUC16c114, and typically includes one or more glycosylated residues or glycosylation sites therein. In some embodiments, the epitope includes one or more glycosylation sites, such as sites for N-glycosylation. In some aspects, the epitope includes an asparagine residue corresponding to Asn1806 or Asn1800 of the MUC16 sequence set forth in SEQ ID NO: 150 (and/or a glycosylated form(s) thereof); in some aspects, the epitope includes an asparagine residue corresponding to Asn1806 of SEQ ID NO: 150, but does not include an asparagine residue corresponding to Asn1800 of SEQ ID NO: 150; in some aspects, the epitope includes an asparagine residue corresponding to Asn1800 of SEQ ID NO: 150, but does not include an asparagine residue corresponding to Asn1806 of of SEQ ID NO: 150. In some of any of such embodiments, such one or more asparagine is glycosylated, such as N-glycosylated. In some embodiments, the antibody or fragment binds to an epitope within or that includes residues within SEQ ID NO: 131; binds to an epitope within or that includes residues within SEQ ID NO: 130, or a combination thereof; in some embodiments, the antibody or fragment does not immunospecifically bind within a region of MUC16 corresponding to SEQ ID NO: 168, or within residues 2-19 of SEQ ID NO: 168.

In one aspect, provided herein are antibodies (e.g., monoclonal antibodies), and antigen-binding fragments thereof, that (i) immunospecifically bind to a cell recombinantly expressing a first form of MUC16, which first form is glycosylated, and wherein the amino acid sequence of the first form is SEQ ID NO:133; (ii) lack immunospecific binding to a cell recombinantly expressing a second form of MUC16, which second form is unglycosylated, and wherein the amino acid sequence of the second form is SEQ ID NO:139; and (iii) inhibit matrigel invasion in vitro of cells recombinantly expressing said first form of MUC16. In another aspect, provided herein are antibodies (e.g., monoclonal antibodies), and antigen-binding fragments thereof, that (i) immunospecifically bind to a cell recombinantly expressing a first form of MUC16, which first form is glycosylated, and wherein the amino acid sequence of the first form is SEQ ID NO:133; (ii) lack immunospecific binding to a cell recombinantly expressing a third form of MUC16, which third form is glycosylated, and wherein the amino acid sequence of the third form is SEQ ID NO:139; and (iii) inhibit matrigel invasion in vitro of cells recombinantly expressing said first form of MUC16. In a preferred embodiment, MUC16 Glycosylation Antibodies and antigen-binding fragments thereof described herein immunospecifically bind an epitope comprising amino acid residue 1806 (Asn1806) of SEQ ID NO:150, wherein Asn1806 is N-glycosylated (referred to herein as "Asn1806 Glycosylation"). As shown in the examples of Section 6 herein, Asn1806 Glycosylation is essential for MUC16-mediated invasion and growth of tumor cells. Thus, the MUC16 Glycosylation Antibodies and antigen-binding fragments thereof described herein are capable of binding blocking such invasion and growth of tumor cells.

In one embodiment, the MUC16 Glycosylation Antibody or antigen-binding fragment thereof requires an N-glycosylated Asn1800 in addition to an N-glycosylated Asn1806 for binding to MUC16 (i.e., both N-glycosylated sites are part of the epitope recognized by the MUC16 Glycosylation Antibody or antigen-binding fragment thereof). "Asn1800" refers to amino acid residue 1800 of SEQ ID NO:150. Such a MUC16 Glycosylation Antibody or antigen-binding fragment thereof can be identified by (i) its ability to immunospecifically bind to a cell recombinantly expressing a first form of MUC16, which first form is glycosylated, and wherein the amino acid sequence of the first form is SEQ ID NO:133; and (ii) its lack of immunospecific binding to a cell recombinantly expressing a fifth form of MUC16, which fifth form is glycosylated, and wherein the amino acid sequence of the fifth form is SEQ ID NO: 172, wherein the cell recombinantly expressing the first form of MUC16 is the same cell type as the cell recombinantly expressing the fifth form of MUC16.

In one embodiment, the MUC16 Glycosylation Antibody or antigen-binding fragment thereof requires an N-glycosylated Asn1806 but does not require an N-glycosylated Asn1800 for binding to MUC16 (i.e., N-glycosylated Asn1806 is part of the epitope recognized by the MUC16 Glycosylation Antibody or antigen-binding fragment thereof, but N-glycosylated Asn1800 is not part of the epitope recognized by the MUC16 Glycosylation Antibody or antigen-binding fragment thereof). Such a MUC16 Glycosylation Antibody or antigen-binding fragment thereof can be identified by (i) its ability to immunospecifically bind to a cell recombinantly expressing a first form of MUC16, which first form is glycosylated, and wherein the amino acid sequence of the first form is SEQ ID NO:133; (ii) its lack of immunospecific binding to a cell recombinantly expressing a third form of MUC16, which third form is glycosylated, and wherein the amino acid sequence of the third form is SEQ ID NO: 139; and (iii) its ability to immunospecifically bind to a cell recombinantly expressing a fourth form of MUC16, which fourth form is glycosylated, and wherein the amino acid sequence of the fourth form is SEQ ID NO: 152; and (iii) wherein the cell recombinantly expressing the first form of MUC16, the cell recombinantly expressing the third form of MUC16, and the cell recombinantly expressing the fourth form of MUC16 are of the same cell type.

The protein encoded by the amino acid sequence of SEQ ID NO:133 is also referred to herein as $MUC16^{c114}$ and consists of the C-terminal 114 amino acid residues of mature MUC16 (SEQ ID NO: 150 being the sequence of mature MUC16). $MUC16^{c114}$ is capable of being N-glycosylated at the asparagine amino acid residues at positions 1, 24, and 30 of SEQ ID NO: 133 (corresponding to amino acid positions Asn1777, Asn1800, and Asn1806 of SEQ ID NO: 150).

The protein encoded by the amino acid sequence of SEQ ID NO: 139 is also referred to herein as $MUC16^{c114\text{-}N3}$. $MUC16^{c114\text{-}N3}$ consists of the C-terminal 114 amino acid residues of mature MUC16 (SEQ ID NO: 150 being the sequence of mature MUC16), except that the asparagine at amino acid position 30 (corresponding to amino acid position 1806 of SEQ ID NO: 150) has been mutated to an alanine. Thus, $MUC16^{c114\text{-}N3}$ is not capable of being N-glycosylated at amino acid position 30 of SEQ ID NO: 139 (corresponding to amino acid position Asn1806 of SEQ ID NO: 150).

The protein encoded by the amino acid sequence of SEQ ID NO: 152 is also referred to herein as $MUC16^{c114\text{-}N2}$. $MUC16^{c114\text{-}N2}$ consists of the C-terminal 114 amino acid residues of mature MUC16 (SEQ ID NO: 150 being the sequence of mature MUC16), except that the asparagine at amino acid position 24 (corresponding to amino acid position Asn1800 of SEQ ID NO: 150) has been mutated to an alanine. Thus, $MUC16^{c114\text{-}N2}$ is not capable of being N-glycosylated at amino acid position 24 of SEQ ID NO: 152 (corresponding to amino acid position Asn1800 of SEQ ID NO: 150).

The protein encoded by the amino acid sequence of SEQ ID NO: 172 is also referred to herein as $MUC16^{c114\text{-}N23}$. $MUC16^{c114\text{-}N23}$ consists of the C-terminal 114 amino acid residues of mature MUC16 (SEQ ID NO:150 being the sequence of mature MUC16), except that the asparagines at amino acid positions 24 and 30 (corresponding to amino acid positions Asn1800 and Asn1806 of SEQ ID NO: 150) have been mutated to alanines. Thus, MUC16$^{c114\text{-}N23}$ is not capable of being N-glycosylated at amino acid positions 24 and 30 of SEQ ID NO: 157 (corresponding to amino acid positions Asn1800 and Asn1806 of SEQ ID NO: 150).

Also provided herein are heavy chains and light chains, wherein a MUC16 Glycosylation Antibody or antigen binding fragment thereof comprising said heavy and light chains (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16. Also provided herein are polynucleotides (e.g., isolated polynucleotides) comprising nucleic acid sequences (e.g., complementary DNA (cDNA)), encoding such antibodies, and antigen-binding fragments thereof, heavy chains, or light chains. Further provided are vectors (e.g., expression vectors) and cells (e.g., isolated cells or ex vivo cells) comprising polynucleotides (e.g., isolated polynucleotides) comprising nucleic acid sequences (e.g., complementary DNA (cDNA)), encoding such antibodies, and antigen-binding fragments thereof, heavy chains, or light chains. Also provided are methods of making such antibodies, antigen-binding fragments thereof, heavy chains, light chains, vectors, and cells. In other aspects, provided herein are methods and uses for MUC16 activity and/or MUC16-driven tumor growth, or treating or managing certain conditions or disorders described herein, such as treating or managing cancer. Related compositions (e.g., pharmaceutical compositions), kits, and diagnostic methods are also provided.

As used herein, the term "MUC16" or "MUC16 polypeptide" or "MUC16 peptide" refers to the MUC16 tethered mucin protein as described in Yin B W and Lloyd K O, 2001, J Biol Chem. 276(29):27371-5. GenBank™ accession number NM_024690.2 (SEQ ID NO:137) provides an exemplary human MUC16 nucleic acid sequence. GenBank™ accession number NP_078966.2 (SEQ ID NO: 136) provides an exemplary human MUC16 amino acid sequence. Native MUC16 comprises an intracellular domain, a transmembrane domain, an ectodomain proximal to the putative cleavage site, and a large, heavily glycosylated region of 12-20 repeats, each 156 amino acids long (FIG. 1A). "Immature" MUC16 refers to SEQ ID NO:136, which comprises the MUC16 signal sequence (amino acid residues 1-60 of SEQ ID NO:136). "Mature MUC16" refers to native MUC16 as expressed on the cell surface, i.e., where the signal sequence has been removed by cellular processing, for example, SEQ ID NO:150, where the first 60 amino acid residues of SEQ ID NO:136 have been removed (i.e., SEQ ID NO:136 is the "immature" form of MUC16).

With respect to antibody names, (i) 18C6 and 18C6.D12 are used interchangeably, (ii) 10C6 and 10C6.E4 are used interchangeably, (iii) 19C11 and 19C11.H6 are used interchangeably, and (iv) 7B12 and 7B12.B3 are used interchangeably. The antibody subclones (i.e., 18C6.D12, 10C6.E4, 19C11.H6, and 7B12.B3) were used in the experiments described in Section 6.

5.1 Antibodies

MUC16 Glycosylation Antibodies or antigen-binding fragments thereof can include, e.g., monoclonal antibodies, polyclonal antibodies, recombinantly produced antibodies, monospecific antibodies, multispecific antibodies (including bispecific antibodies), human antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, single domain antibodies, monovalent antibodies, single chain antibodies or single-chain variable fragments (scFv), camelized antibodies, affybodies, and disulfide-linked Fvs (dsFv), or fragments thereof. Such antibodies can be made by methods known in the art.

A multispecific antibody or fragment thereof refers to an antibody or fragment thereof that can bind simultaneously to at least two targets that are of different structure, e.g., two different antigens, two different epitopes on the same antigen, or a hapten and an antigen or epitope. One specificity could be for, for example, a B-cell, T-cell, myeloid-, plasma-, or mast-cell antigen or epitope, such as, for example CD3. Another specificity could be to a different antigen on the same or different cell type, such as for example, MUC16. Multispecific, multivalent antibodies are constructs that have more than one binding site, and the binding sites are of different specificity, for example, a bispecific diabody, where one binding site reacts with one antigen and the other with another antigen.

A bispecific antibody is an antibody that can bind simultaneously to two targets which are of different structure. Bispecific antibodies (bsAb) and bispecific antibody fragments (bsFab) have at least one arm that immunospecifically binds to a first target, for example, MUC16, and at least one other arm that immunospecifically binds to a second target, such as, for example, CD3. A variety of bispecific fusion proteins can be produced using molecular engineering. In one form, the bispecific fusion protein is divalent, consisting of, for example, (i) a scFv with a single binding site for one antigen and (ii) an antibody or a Fab fragment with a single binding site for a second antigen. In another form, the bispecific fusion protein is tetravalent, consisting of, for example, an IgG with two binding sites for one antigen and two identical scFv for a second antigen. See, for example, International Publication No. WO 2011/1160119, which is incorporated by reference in its entirety herein.

Recent methods for producing bispecific monoclonal antibodies include the use of engineered recombinant monoclonal antibodies which have additional cysteine residues so that they crosslink more strongly than the more common immunoglobulin isotypes. See, e.g., FitzGerald et al., Protein Eng. 10(10):1221-1225, 1997. Another approach is to engineer recombinant fusion proteins linking two or more different single-chain antibody or antibody fragment segments with the needed dual specificities. See, e.g., Coloma et al., Nature Biotech. 15:159-163, 1997. A variety of bispecific fusion proteins can be produced using molecular engineering.

Bispecific fusion proteins linking two or more different single-chain antibodies or antibody fragments can be produced in similar manner. Recombinant methods can be used to produce a variety of fusion proteins. In certain aspects, a flexible linker connects an scFv (e.g., an scFv targeting CD3) to the constant region of the light chain of a monoclonal antibody (e.g., a MUC16 Glycosylation Antibody described herein; see Section 5.1). Appropriate linker sequences necessary for the in-frame connection of the heavy chain Fc to the scFv are introduced into the VL and Vkappa domains through PCR reactions. The DNA fragment encoding the scFv is then ligated into a staging vector containing a DNA sequence encoding the CHI domain. The resulting construct is excised and ligated into a vector containing a DNA sequence encoding the VH region of the antibody (e.g., the MUC16 Glycosylation Antibody). The resulting vector can be used to transfect an appropriate host cell, such as a mammalian cell for the expression of the bispecific fusion protein.

The MUC16 Glycosylation Antibodies described herein (see Section 5.1) and fragments thereof in certain embodiments can also be used to prepare functional bispecific single-chain antibodies (bscAb), also called diabodies, and can be produced in mammalian cells using recombinant methods. See, e.g., Mack et al., Proc. Natl. Acad. Sci., 92: 7021-7025, 1995, incorporated herein by reference. For example, bscAb can be produced by joining two single-chain Fv fragments via a glycine-serine linker using recombinant methods. The VL and VH domains of two antibodies of interest are isolated using standard PCR methods known in the art. Bispecific single-chain antibodies and bispecific fusion proteins are included within the scope of the present invention.

In certain embodiments, MUC16 Glycosylation Antibodies or antigen-binding fragments thereof described herein refer to scFvs. A scFv is an art-recognized term. An scFv comprises a fusion protein of the variable regions of the heavy (VH) and light (VL) chains of an immunoglobulin, wherein the fusion protein retains the same antigen specificity as the whole immunoglobulin. The VH is fused to the VL via a peptide linker. In certain embodiments, the peptide linker is between 5 and 25, 5 and 15, 10 and 20, 10 and 15, or 15 and 25 amino acid residues in length. In certain embodiments, the scFv peptide linker displays one or more characteristics suitable for a peptide linker known to one of ordinary skill in the art. In certain embodiments, the scFv peptide linker comprises amino acids that allow for scFv peptide linker solubility, such as, for example, serine and threonine. In certain embodiments, the scFv peptide linker comprises amino acids that allow for scFv peptide linker flexibility, such as, for example, glycine. In certain embodiments, the scFv peptide linker connects the N-terminus of the VH to the C-terminus of the VL. In certain embodiments, the scFv peptide linker can connect the C-terminus of the VH to the N-terminus of the VL.

In certain embodiments, MUC16 Glycosylation Antibodies or antigen-binding fragments thereof described herein refer to chimeric antigen receptors (CARs). A CAR is an art-recognized term. A CAR can be targeted to a tumor associated antigen (e.g., MUC16). CARs as provided herein typically are composed of a scFv derived from a MUC16 Glycosylation Antibody, a transmembrane domain, which in some embodiments is a T cell co-stimulatory molecule-derived transmembrane domain (for example, a transmembrane domain derived from CD28, CD8, CD38, OX-40, or 4-1BB), and a primary signaling domain, such as the T cell receptor (TCR) zeta (ζ) chain cytoplasmic signaling domain. In some embodiments, the CAR further includes one or more additional regions or domains such as one or more spacer or linker, including an extracellular spacer, such as one derived from an antibody or other cell-surface molecule, such as a spacer containing gone or more of antibody CH2, CH3, and/or hinge regions, or a spacer derived from a CD28 molecule or a CD8 molecule, or other spacer. Also provided herein are cells, such as T cells engineered to express such CARs, such as those recombinantly expressing such a CAR. A CAR-expressing T cell, upon recognition of a MUC16 expressing tumor, preferably induces T cell activation, proliferation, and/or lysis of a cell of such a tumor.

MUC16 Glycosylation Antibodies can be of any type (e.g., IgG, IgE, IgM, IgD, IgA or IgY), any class (e.g., $IgG_1$, $IgG_2$, $IgG_3$, $IgG_4$, $IgA_1$ or $IgA_2$), or any subclass (e.g., $IgG_{2a}$ or $IgG_{2b}$) of immunoglobulin molecule. In certain embodiments, antibodies described herein are IgG antibodies, or a class or subclass thereof. In certain embodiments, antibodies described herein are $IgG_1$ antibodies. In certain embodiments, antibodies described herein are $IgG_2$ antibodies. In certain embodiments, antibodies described herein are $IgG_{2a}$ antibodies. In certain embodiments, antibodies described herein are $IgG_{2b}$ antibodies. In certain embodiments, antibodies described herein are a mixture of $IgG_{2a}$ and $IgG_{2b}$ antibodies. In a specific embodiment, the antibody is a humanized form of a rodent monoclonal antibody.

In a specific embodiment, the antigen to which the MUC16 Glycosylation Antibody or antigen-binding fragment thereof binds, is a form of MUC16 which is glycosylated, for example, wherein the amino acid sequence of the form of MUC16 is SEQ ID NO:133. The protein encoded by the amino acid sequence of SEQ ID NO: 133 is also referred to herein as $MUC16^{c114}$ and consists of the C-terminal 114 amino acid residues of mature MUC16. $MUC16^{c114}$ is capable of being N-glycosylated at the asparagine amino acids of positions 1, 24, and 30 of SEQ ID NO: 133 (corresponding to amino acid positions Asn1777, Asn1800, and Asn1806 of SEQ ID NO:150). Mature MUC16 (SEQ ID NO:150) refers to full length MUC16 wherein the signal sequence has been removed, and wherein the signal sequence consists of the first 60 amino acid residues of SEQ ID NO:136 (i.e., SEQ ID NO:136 is the "immature" form of MUC16).

Antigen binding fragments of MUC16 Glycosylation Antibodies can be Fab fragments, $F(ab')_2$ fragments, or a portion of MUC16 Glycosylation Antibody which comprises the amino acid residues that confer on the MUC16 Glycosylation Antibody its specificity for the antigen (e.g., the complementarity determining regions (CDR)). The MUC16 Glycosylation Antibody can be derived from any animal species, such as rodents (e.g., mouse, rat or hamster) and humans.

As used herein, the terms "variable region" or "variable domain" are used interchangeably and are common in the art. The variable region typically refers to a portion of an antibody, generally, a portion of a light or heavy chain, typically about the amino-terminal 110 to 120 amino acids in a mature heavy chain and about the amino-terminal 90 to 100 amino acids in a mature light chain, which differs extensively in sequence among antibodies and is used in the binding and specificity of a particular antibody for its particular antigen. The variability in sequence is concentrated in those regions called complementarity determining regions (CDRs) while the more highly conserved regions in the variable domain are called framework regions (FR). CDRs are flanked by FRs. Generally, the spatial orientation of CDRs and FRs are as follows, in an N-terminal to C-terminal direction: FR1-CDR1-FR2-CDR2-FR3-CDR3-FR4. Without wishing to be bound by any particular mechanism or theory, it is believed that the CDRs of the light and heavy chains are primarily responsible for the interaction and specificity of the antibody with antigen. In certain embodiments, the variable region is a rodent (e.g., mouse or rat) variable region. In certain embodiments, the variable region is a human variable region. In certain embodiments, the variable region comprises rodent (e.g., mouse or rat) CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs).

CDRs are defined in various ways in the art, including the Kabat, Chothia, and IMGT, and Exemplary definitions. The Kabat definition is based on sequence variability (Kabat, Elvin A. et al., Sequences of Proteins of Immunological Interest. Bethesda: National Institutes of Health, 1983). With respect to the Kabat numbering system, (i) the VH CDR1 is typically present at amino acid positions 31 to 35 of the heavy chain, which can optionally include one or two additional amino acids following amino acid position 35 (referred to in the Kabat numbering scheme as 35A and 35B); (ii) the VH CDR2 is typically present at amino acid positions 50 to 65 of the heavy chain; and (iii) the VH CDR2 is typically present at amino acid positions 95 to 102 of the heavy chain (Kabat, Elvin A. et al., Sequences of Proteins of Immunological Interest. Bethesda: National Institutes of Health, 1983). With respect to the Kabat numbering system, (i) the VL CDR1 is typically present at amino acid positions 24 to 34 of the light chain; (ii) the VL CDR2 is typically present at amino acid positions 50 to 56 of the light chain; and (iii) the VL CDR3 is typically present at amino acid positions 89 to 97 of the light chain (Kabat, Elvin A. et al., Sequences of Proteins of Immunological Interest. Bethesda: National Institutes of Health, 1983). As is well known to those of skill in the art, using the Kabat numbering system, the actual linear amino acid sequence of the antibody variable domain can contain fewer or additional amino acids due to a shortening or lengthening of a FR and/or CDR and, as such, an amino acid's Kabat number is not necessarily the same as its linear amino acid number.

The Chothia definition is based on the location of the structural loop regions (Chothia et al., (1987) J Mol Biol 196: 901-917; and U.S. Pat. No. 7,709,226). The term "Chothia CDRs," and like terms are recognized in the art and refer to antibody CDR sequences as determined according to the method of Chothia and Lesk, 1987, J. Mol. Biol., 196:901-917, which will be referred to herein as the "Chothia CDRs" (see also, e.g., U.S. Pat. No. 7,709,226 and Martin, A., "Protein Sequence and Structure Analysis of Antibody Variable Domains," in Antibody Engineering, Kontermann and Dibel, eds., Chapter 31, pp. 422-439, Springer-Verlag, Berlin (2001)). With respect to the Chothia numbering system, using the Kabat numbering system of numbering amino acid residues in the VH region, (i) the VH CDR1 is typically present at amino acid positions 26 to 32 of the heavy chain; (ii) the VH CDR2 is typically present at amino acid positions 53 to 55 of the heavy chain; and (iii) the VH CDR3 is typically present at amino acid positions 96 to 101 of the heavy chain. In a specific embodiment, with respect to the Chothia numbering system, using the Kabat numbering system of numbering amino acid residues in the VH region, (i) the VH CDR1 is typically present at amino acid positions 26 to 32 or 34 of the heavy chain; (ii) the VH CDR2 is typically present at amino acid positions 52 to 56 (in one embodiment, CDR2 is at positions 52A-56, wherein 52A follows position 52) of the heavy chain; and (iii) the VH CDR3 is typically present at amino acid positions 95 to 102 of the heavy chain (in one embodiment, there is no amino acid at positions numbered 96-100). With respect to the Chothia numbering system, using the Kabat numbering system of numbering amino acid residues in the VL region, (i) the VL CDR1 is typically present at amino acid positions 26 to 33 of the light chain; (ii) the VL CDR2 is typically present at amino acid positions 50 to 52 of the light chain; and (iii) the VL CDR3 is typically present at amino acid positions 91 to 96 of the light chain. In a specific embodiment, with respect to the Chothia numbering system, using the Kabat numbering system of numbering amino acid residues in the VL region, (i) the VL CDR1 is typically present at amino acid positions 24 to 34 of the light chain; (ii) the VL CDR2 is typically present at amino acid positions 50 to 56 of the light chain; and (iii) the VL CDR3 is typically present at amino acid positions 89 to 97 of the light chain (in one embodiment, there is no amino acid at positions numbered 96-100). These Chothia CDR positions may vary depending on the antibody, and may be determined according to methods known in the art.

The IMGT definition is from the IMGT ("IMGT®, the international ImMunoGeneTics information System® website imgt.org, founder and director: Marie-Paule Lefranc, Montpellier, France; see, e.g., Lefranc, M.-P., 1999, The Immunologist, 7:132-136 and Lefranc, M.-P. et al., 1999, Nucleic Acids Res., 27:209-212, both of which are incorporated herein by reference in their entirety). With respect to the IMGT numbering system, (i) the VH CDR1 is typically present at amino acid positions 25 to 35 of the heavy chain; (ii) the VH CDR2 is typically present at amino acid positions 51 to 57 of the heavy chain; and (iii) the VH CDR2 is typically present at amino acid positions 93 to 102 of the heavy chain. With respect to the IMGT numbering system, (i) the VL CDR1 is typically present at amino acid positions 27 to 32 of the light chain; (ii) the VL CDR2 is typically present at amino acid positions 50 to 52 of the light chain; and (iii) the VL CDR3 is typically present at amino acid positions 89 to 97 of the light chain.

5.1.1 Sequences and Structures

In certain embodiments, provided herein is a MUC16 Glycosylation Antibody or antigen-binding fragment thereof which comprises VH CDRs of any of the MUC16 Glycosylation Antibodies provided herein, e.g., as set forth in Tables 1, 3, and 5. In certain embodiments, a MUC16 Glycosylation Antibody or antigen-binding fragment thereof provided herein comprises the VH CDR1 of a MUC16 Glycosylation Antibody as set forth in Table 1, 3, or 5. In certain embodiments, a MUC16 Glycosylation Antibody or antigen-binding fragment thereof provided herein comprises the VH CDR2 of a MUC16 Glycosylation Antibody as set forth in Table 1, 3, or 5. In certain embodiments, a MUC16 Glycosylation Antibody or antigen-binding fragment thereof provided herein comprises the VH CDR3 of a MUC16 Glycosylation Antibody as set forth in Table 1, 3, or 5. In certain embodiments, a MUC16 Glycosylation Antibody or antigen-binding fragment thereof provided herein comprises one, two or all three of VH CDRs of a MUC16 Glycosylation Antibody as set forth in Table 1, 3, or 5 (e.g., the VL CDRs in row two of Table 1, e.g., all of the VH CDRs for antibody 10C6)

In certain embodiments, provided herein is a MUC16 Glycosylation Antibody or antigen-binding fragment thereof which comprises VL CDRs of any of the anti-MUC16 antibodies provided herein, e.g., as set forth in Tables 2, 4, and 6. In certain embodiments, a MUC16 Glycosylation Antibody or antigen-binding fragment thereof provided herein comprises the VH CDR1 of a MUC16 Glycosylation Antibody as set forth in Table 2, 4, or 6. In certain embodiments, a MUC16 Glycosylation Antibody or antigen-binding fragment thereof provided herein comprises the VH CDR2 of a MUC16 Glycosylation Antibody as set forth in Table 2, 4, or 6. In certain embodiments, an anti-MUC16 antibody or antigen-binding fragment thereof provided herein comprises the VH CDR3 of a MUC16 Glycosylation Antibody as set forth in Table 2, 4, or 6. In certain embodiments, a MUC16 Glycosylation Antibody or antigen-binding fragment thereof provided herein comprises one, two or all three of VL CDRs of a MUC16 Glycosylation Antibody in Table 2, 4, or 6 (e.g., the VL CDRs in row two of Table 2, e.g., all of the VH CDRs for antibody 10C6)

TABLE 1

VH CDR Amino Acid Sequences (Kabat).

| Antibody | VH CDR1 (SEQ ID NO) | VH CDR2 (SEQ ID NO) | VH CDR3 (SEQ ID NO) |
|---|---|---|---|
| 10C6 | TLGMGVG (SEQ ID NO:3) | HIWWDDDKYYNPALKS (SEQ ID NO: 4) | IGTAQATDALDY (SEQ ID NO: 5) |
| 7B12 | TVGMGVG (SEQ ID NO:23) | HIWWDDEDKYYNPALKS (SEQ ID NO: 24) | IGTAQATDALDY (SEQ ID NO: 25) |
| 19C11 | TLGMGVG (SEQ ID NO:43) | HIWWDDDKYYNPALKS (SEQ ID NO: 44) | IGTAQATDALDY (SEQ ID NO: 45) |
| 16C5 | TLGMGVG (SEQ ID NO:63) | HIWWDDDKYYYPALKS (SEQ ID NO: 64) | IGTAQATDALDY (SEQ ID NO: 65) |
| 18C6 | TVGMGVG (SEQ ID NO:83) | HIWWDDEDKYYNPALKS (SEQ ID NO: 84) | IGTAQATDALDY (SEQ ID NO: 85) |
| 10C6, 7B12, 19C11, 16C5, and 18C6 Consensus | $TX_1GMGVG$ (SEQ ID NO:103) wherein $X_1$ is L or V | $HIWWDDX_2DKYYX_3PALKS$ (SEQ ID NO: 104) wherein $X_2$ is E or absent and herein $X_3$ is Y or N | IGTAQATDALDY (SEQ ID NO: 105) |

TABLE 2

VL CDR Amino Acid Sequences (Kabat).

| Antibody | VL CDR1 (SEQ ID NO) | VL CDR2 (SEQ ID NO) | VL CDR3 (SEQ ID NO) |
|---|---|---|---|
| 10C6 | RASKSVSTSGYSYMH (SEQ ID NO: 6) | LVSNLES (SEQ ID NO: 7) | QHIRELTRS (SEQ ID NO: 8) |
| 7B12 | RSSKSLRKSNGNTYL (SEQ ID NO: 26) | YMSNLAS (SEQ ID NO: 27) | MQSLEYPLT (SEQ ID NO: 28) |
| 19C11 | RSSKSLLHSNGNTYLY (SEQ ID NO: 46) | YMSNLAS (SEQ ID NO: 47) | MQGLEHPLT (SEQ ID NO: 48) |
| 16C5 | LASEDIYSGIS (SEQ ID NO: 66) | GASNLES (SEQ ID NO: 67) | LGGYSYSSTLT (SEQ ID NO: 68) |
| 18C6 | RSSKSLLHSNGNTYLY (SEQ ID NO: 86) | YMSNLAS (SEQ ID NO: 87) | MQSLEYPLT (SEQ ID NO: 88) |
| 7B12, 19C11, and 18C6 Consensus | $RSSKSLX_4X_5SNGNTYLY$ (SEQ ID NO: 106) wherein $X_4$ is R or L, and wherein $X_5$ is K or H | YMSNLAS (SEQ ID NO: 107) | $MQX_6LEX_7PLT$ (SEQ ID NO: 108) wherein $X_6$ is G or S and wherein $X_7$ is H or Y |

TABLE 3

VH CDR Amino Acid Sequences (Chothia).

| Antibody | VH CDR1 (SEQ ID NO) | VH CDR2 (SEQ ID NO) | VH CDR3 (SEQ ID NO) |
|---|---|---|---|
| 10C6 | GFSLNTLGM (SEQ ID NO: 9) | WDD (SEQ ID NO: 10) | GTAQATDALD (SEQ ID NO: 11) |
| 7B12 | GFSLSTVGM (SEQ ID NO: 29) | WDDE (SEQ ID NO: 30) | GTAQATDALD (SEQ ID NO: 31) |

TABLE 3-continued

VH CDR Amino Acid Sequences (Chothia).

| Antibody | VH CDR1 (SEQ ID NO) | VH CDR2 (SEQ ID NO) | VH CDR3 (SEQ ID NO) |
|---|---|---|---|
| 19C11 | GFSLSTLGM (SEQ ID NO: 49) | WDD (SEQ ID NO: 50) | GTAQATDALD (SEQ ID NO: 51) |
| 16C5 | GFSLNTLGM (SEQ ID NO: 69) | WDD (SEQ ID NO: 70) | GTAQATDALD (SEQ ID NO: 71) |
| 18C6 | GFSLSTVGM (SEQ ID NO: 89) | WDDE (SEQ ID NO: 90) | GTAQATDALD (SEQ ID NO: 91) |
| 10C6, 7B12, 19C11, 16C5, and 18C6 Consensus | GFSL$X_8$T$X_9$GM (SEQ ID NO: 109) wherein $X_8$ is N or S, and wherein $X_9$ is L or V | WDD$X_{10}$ (SEQ ID NO: 110) wherein $X_{10}$ is E or absent | GTAQATDALD (SEQ ID NO: 111) |

TABLE 4

VL CDR Amino Acid Sequences (Chothia).

| Antibody | VL CDR1 (SEQ ID NO) | VL CDR2 (SEQ ID NO) | VL CDR3 (SEQ ID NO) |
|---|---|---|---|
| 10C6 | SKSVSTSGYSY (SEQ ID NO: 12) | LVS (SEQ ID NO: 13) | IRELTR (SEQ ID NO: 14) |
| 7B12 | SKSLRKSNGNTY (SEQ ID NO: 32) | YMS (SEQ ID NO: 33) | SLEYPL (SEQ ID NO: 34) |
| 19C11 | SKSLLHSNGNTY (SEQ ID NO: 52) | YMS (SEQ ID NO: 53) | GLEHPL (SEQ ID NO: 54) |
| 16C5 | SEDIYSG (SEQ ID NO: 72) | GAS (SEQ ID NO: 73) | GYSYSSTL (SEQ ID NO: 74) |
| 18C6 | SKSLLHSNGNTY (SEQ ID NO: 92) | YMS (SEQ ID NO: 93) | SLEYPL (SEQ ID NO: 94) |
| 7B12, 19C11, and 18C6 Consensus | SKSL$X_{11}$$X_{12}$SNGNTY (SEQ ID NO:112) wherein $X_{11}$ is L or R, and wherein $X_{12}$ is H or K | YMS (SEQ ID NO: 113) | $X_{13}$LE$X_{14}$PL (SEQ ID NO: 114) wherein $X_{13}$ is G or S, and wherein $X_{14}$ is H or Y |

TABLE 5

VH CDR Amino Acid Sequences (IMGT).

| Antibody | VH CDR1 (SEQ ID NO) | VH CDR2 (SEQ ID NO) | VH CDR3 (SEQ ID NO) |
|---|---|---|---|
| 10C6 | GFSLNTLGMG (SEQ ID NO: 15) | IWWDDDK (SEQ ID NO: 16) | SRIGTAQATDALDY (SEQ ID NO: 17) |
| 7B12 | GFSLSTVGMG (SEQ ID NO: 35) | IWWDDEDK (SEQ ID NO: 36) | TRIGTAQATDALDY (SEQ ID NO: 37) |
| 19C11 | GFSLSTLGMG (SEQ ID NO: 55) | IWWDDDK (SEQ ID NO: 56) | ARIGTAQATDALDY (SEQ ID NO: 57) |
| 16C5 | GFSLNTLGMG (SEQ ID NO: 75) | IWWDDDK (SEQ ID NO: 76) | ARIGTAQATDALDY (SEQ ID NO: 77) |
| 18C6 | GFSLSTVGMG (SEQ ID NO: 95) | IWWDDEDK (SEQ ID NO: 96) | TRIGTAQATDALDY (SEQ ID NO: 97) |

TABLE 5-continued

| VH CDR Amino Acid Sequences (IMGT). | | | |
|---|---|---|---|
| Antibody | VH CDR1 (SEQ ID NO) | VH CDR2 (SEQ ID NO) | VH CDR3 (SEQ ID NO) |
| 10C6, 7B12, 19C11, 16C5, and 18C6 Consensus | GFSLX$_{15}$TX$_{16}$GMG (SEQ ID NO: 115) wherein X$_{15}$ is N or S, and wherein X$_{16}$ is V or L | IWWDDX$_{17}$DK (SEQ ID NO: 116) wherein X$_{17}$ is E or absent | X$_{18}$RIGTAQATDALDY (SEQ ID NO: 117) wherein X$_{18}$ is T, A, or S |

TABLE 6

| VL CDR Amino Acid Sequences (IMGT). | | | |
|---|---|---|---|
| Antibody | VL CDR1 (SEQ ID NO) | VL CDR2 (SEQ ID NO) | VL CDR3 (SEQ ID NO) |
| 10C6 | KSVSTSGYSY (SEQ ID NO: 18) | LVS (SEQ ID NO: 19) | QHIRELTRS (SEQ ID NO: 20) |
| 7B12 | KSLRKSNGNTY (SEQ ID NO: 38) | YMS (SEQ ID NO: 39) | MQSLEYPLT (SEQ ID NO: 4) |
| 19C11 | KSLLHSNGNTY (SEQ ID NO: 58) | YMS (SEQ ID NO: 59) | MQGLEHPLT (SEQ ID NO: 60) |
| 16C5 | EDIYSG (SEQ ID NO: 78) | GAS (SEQ ID NO: 79) | LGGYSYSSTLT (SEQ ID NO: 80) |
| 18C6 | KSLLHSNGNTY (SEQ ID NO: 98) | YMS (SEQ ID NO: 99) | MQSLEYPLT (SEQ ID NO: 100) |
| 7B12, 19C11, and 18C6 Consensus | KSLX$_{19}$X$_{20}$SNGNTY (SEQ ID NO: 118) wherein X$_{19}$ is V or L, and wherein X$_{20}$ is H or K | YMS (SEQ ID NO: 119) | MQSLEYPLT (SEQ ID NO: 120) |

In a particular embodiment, a MUC16 Glycosylation Antibody or antigen-binding fragment thereof described herein, comprises a VH which comprises:

(a) a VH CDR1 comprising the amino acid sequence TX$_1$GMGVG (SEQ ID NO: 103), wherein X$_1$ is L or V;

(b) a VH CDR2 comprising the amino acid sequence HIWWDDX$_2$DKYYX$_3$PALKS (SEQ ID NO:104), wherein X$_2$ is E or absent, and X$_3$ is Y or N; and (c) a VH CDR3 comprising the amino acid sequence IGTAQATDALDY (SEQ ID NO:105).

In a particular embodiment, a MUC16 Glycosylation Antibody or antigen-binding fragment thereof described herein comprises a VH which comprises:

(a) a VH CDR1 comprising the amino acid sequence GFSLX$_8$TX$_9$GM (SEQ ID NO:109), wherein X$_8$ is N or S, and X$_9$ is L or V;

(b) a VH CDR2 comprising the amino acid sequence WDDX$_{10}$ (SEQ ID NO: 110), wherein X$_{10}$ is E or absent; and (c) a VH CDR3 comprising the amino acid sequence GTAQATDALD (SEQ ID NO:111).

In a particular embodiment, a MUC16 Glycosylation Antibody or antigen-binding fragment thereof described herein comprises a VH which comprises:

(a) a VH CDR1 comprising the amino acid sequence GFSLX$_{15}$TX$_{16}$GMG (SEQ ID NO: 115), wherein X$_{15}$ is N or S, and X$_{16}$ is V or L;

(b) a VH CDR2 comprising the amino acid sequence IWWDDX$_{17}$DK (SEQ ID NO: 116), wherein X$_{17}$ is E or absent; and (c) a VH CDR3 comprising the amino acid sequence X$_{18}$RIGTAQATDALDY (SEQ ID NO: 117), wherein X$_{18}$ is T, A, or S.

In a particular embodiment, a MUC16 Glycosylation Antibody or antigen-binding fragment thereof described herein comprises a VH which comprises a VH CDR1 comprising the amino acid sequence of SEQ ID NO:3, a VH CDR2 comprising the amino acid sequence of SEQ ID NO:4, and a VH CDR3 comprising the amino acid sequence of SEQ ID NO:5. In a particular embodiment, a MUC16 Glycosylation Antibody or antigen-binding fragment thereof described herein comprises a VH which comprises a VH CDR1 comprising the amino acid sequence of SEQ ID NO:9, a VH CDR2 comprising the amino acid sequence of SEQ ID NO:10, and a VH CDR3 comprising the amino acid sequence of SEQ ID NO:11. In a particular embodiment, a MUC16 Glycosylation Antibody or antigen-binding fragment thereof described herein comprises a VH which comprises a VH CDR1 comprising the amino acid sequence of SEQ ID NO:15, a VH CDR2 comprising the amino acid sequence of SEQ ID NO:16, and a VH CDR3 comprising the amino acid sequence of SEQ ID NO:17.

In a particular embodiment, a MUC16 Glycosylation Antibody or antigen-binding fragment thereof described herein comprises a VH which comprises a VH CDR1 comprising the amino acid sequence of SEQ ID NO:23, a VH CDR2 comprising the amino acid sequence of SEQ ID NO:24, and a VH CDR3 comprising the amino acid sequence of SEQ ID NO:25. In a particular embodiment, a MUC16 Glycosylation Antibody or antigen-binding fragment thereof a MUC16 Glycosylation Antibody or antigen-binding fragment thereof described herein comprises a VH which comprises a VH CDR1 comprising the amino acid sequence of SEQ ID NO:29, a VH CDR2 comprising the amino acid sequence of SEQ ID NO:30, and a VH CDR3 comprising the amino acid sequence of SEQ ID NO:31. In a particular embodiment, a MUC16 Glycosylation Antibody or antigen-binding fragment thereof a MUC16 Glycosylation Antibody or antigen-binding fragment thereof described herein comprises a VH which comprises a VH CDR1 comprising the amino acid sequence of SEQ ID NO:35, a VH CDR2 comprising the amino acid sequence of SEQ ID NO:36, and a VH CDR3 comprising the amino acid sequence of SEQ ID NO:37.

In a particular embodiment, a MUC16 Glycosylation Antibody or antigen-binding fragment thereof a MUC16 Glycosylation Antibody or antigen-binding fragment thereof described herein comprises a VH which comprises a VH CDR1 comprising the amino acid sequence of SEQ ID NO:43, a VH CDR2 comprising the amino acid sequence of SEQ ID NO:44, and a VH CDR3 comprising the amino acid sequence of SEQ ID NO:45. In a particular embodiment, a MUC16 Glycosylation Antibody or antigen-binding fragment thereof a MUC16 Glycosylation Antibody or antigen-binding fragment thereof described herein comprises a VH which comprises a VH CDR1 comprising the amino acid sequence of SEQ ID NO:49, a VH CDR2 comprising the amino acid sequence of SEQ ID NO:50, and a VH CDR3 comprising the amino acid sequence of SEQ ID NO:51. In a particular embodiment, a MUC16 Glycosylation Antibody or antigen-binding fragment thereof described herein comprises a VH which comprises a VH CDR1 comprising the amino acid sequence of SEQ ID NO:55, a VH CDR2 comprising the amino acid sequence of SEQ ID NO:56, and a VH CDR3 comprising the amino acid sequence of SEQ ID NO:57.

In a particular embodiment, a MUC16 Glycosylation Antibody or antigen-binding fragment thereof described herein comprises a VH which comprises a VH CDR1 comprising the amino acid sequence of SEQ ID NO:63, a VH CDR2 comprising the amino acid sequence of SEQ ID NO:64, and a VH CDR3 comprising the amino acid sequence of SEQ ID NO:65. In a particular embodiment, a MUC16 Glycosylation Antibody or antigen-binding fragment thereof comprises a VH which comprises a VH CDR1 comprising the amino acid sequence of SEQ ID NO:69, a VH CDR2 comprising the amino acid sequence of SEQ ID NO:70, and a VH CDR3 comprising the amino acid sequence of SEQ ID NO:71. In a particular embodiment, a MUC16 Glycosylation Antibody or antigen-binding fragment thereof described herein comprises a VH which comprises a VH CDR1 comprising the amino acid sequence of SEQ ID NO:75, a VH CDR2 comprising the amino acid sequence of SEQ ID NO:76, and a VH CDR3 comprising the amino acid sequence of SEQ ID NO:77.

In a particular embodiment, a MUC16 Glycosylation Antibody or antigen-binding fragment thereof a MUC16 Glycosylation Antibody or antigen-binding fragment thereof described herein comprises a VH which comprises a VH CDR1 comprising the amino acid sequence of SEQ ID NO:83, a VH CDR2 comprising the amino acid sequence of SEQ ID NO:84, and a VH CDR3 comprising the amino acid sequence of SEQ ID NO:85. In a particular embodiment, a MUC16 Glycosylation Antibody or antigen-binding fragment thereof described herein comprises a VH which comprises a VH CDR1 comprising the amino acid sequence of SEQ ID NO:89, a VH CDR2 comprising the amino acid sequence of SEQ ID NO:90, and a VH CDR3 comprising the amino acid sequence of SEQ ID NO:91. In a particular embodiment, a MUC16 Glycosylation Antibody or antigen-binding fragment thereof described herein comprises a VH which comprises a VH CDR1 comprising the amino acid sequence of SEQ ID NO:95, a VH CDR2 comprising the amino acid sequence of SEQ ID NO:96, and a VH CDR3 comprising the amino acid sequence of SEQ ID NO:97.

In a particular embodiment, a MUC16 Glycosylation Antibody or antigen-binding fragment thereof a MUC16 Glycosylation Antibody or antigen-binding fragment thereof described herein comprises a VL which comprises:

(a) a VL CDR1 comprising the amino acid sequence RSSKSL$X_4X_5$SNGNTYLY (SEQ ID NO:106), wherein $X_4$ is R or L, and $X_5$ is K or H;

(b) a VL CDR2 comprising the amino acid sequence YMSNLAS (SEQ ID NO:107); and (c) a VL CDR3 comprising the amino acid sequence MQ$X_6$LE$X_7$PLT (SEQ ID NO:108), wherein $X_6$ is G or S, and $X_7$ is H or Y.

In a particular embodiment, a MUC16 Glycosylation Antibody or antigen-binding fragment thereof described herein comprises a VL which comprises:

(a) a VL CDR1 comprising the amino acid sequence SKSL$X_{11}X_{12}$SNGNTY (SEQ ID NO: 112), wherein $X_{11}$ is L or R, and $X_{12}$ is H or K;

(b) a VL CDR2 comprising the amino acid sequence YMS (SEQ ID NO:113); and (c) a VL CDR3 comprising the amino acid sequence $X_{13}$LE$X_{14}$PL (SEQ ID NO:114), wherein $X_{13}$ is G or S, and $X_{14}$ is H or Y.

In a particular embodiment, a MUC16 Glycosylation Antibody or antigen-binding fragment thereof described herein comprises a VL which comprises:

(a) a VL complementarity determining region (CDR)1 comprising the amino acid sequence KSL$X_{19}X_{20}$SNGNTY (SEQ ID NO:118), wherein $X_{19}$ is V or L, and $X_{20}$ is H or K;

(b) a VL CDR2 comprising the amino acid sequence YMS (SEQ ID NO:119); and (c) a VL CDR3 comprising the amino acid sequence MQSLEYPLT (SEQ ID NO:120).

In a particular embodiment, a MUC16 Glycosylation Antibody or antigen-binding fragment thereof described herein comprises a VL which comprises a VL CDR1 comprising the amino acid sequence of SEQ ID NO:6, a VL CDR2 comprising the amino acid sequence of SEQ ID NO:7, and a VL CDR3 comprising the amino acid sequence of SEQ ID NO:8. In a particular embodiment, a MUC16 Glycosylation Antibody or antigen-binding fragment thereof described herein comprises a VL CDR1 comprising the amino acid sequence of SEQ ID NO:12, a VL CDR2 comprising the amino acid sequence of SEQ ID NO:13, and a VL CDR3 comprising the amino acid sequence of SEQ ID NO:14. In a particular embodiment, a MUC16 Glycosylation Antibody or antigen-binding fragment thereof described herein comprises a VL CDR1 comprising the amino acid sequence of SEQ ID NO:18, a VL CDR2 comprising the amino acid sequence of SEQ ID NO:19, and a VL CDR3 comprising the amino acid sequence of SEQ ID NO:20.

In a particular embodiment, a MUC16 Glycosylation Antibody or antigen-binding fragment thereof described herein comprises a VL which comprises a VL CDR1 comprising the amino acid sequence of SEQ ID NO:26, a VL CDR2 comprising the amino acid sequence of SEQ ID NO:27, and a VL CDR3 comprising the amino acid sequence of SEQ ID NO:28. In a particular embodiment, a MUC16 Glycosylation Antibody or antigen-binding fragment thereof described herein comprises a VL which comprises a VL CDR1 comprising the amino acid sequence of SEQ ID NO:32, a VL CDR2 comprising the amino acid sequence of SEQ ID NO:33, and a VL CDR3 comprising the amino acid sequence of SEQ ID NO:34. In a particular embodiment, a MUC16 Glycosylation Antibody or antigen-binding fragment thereof described herein comprises a VL CDR1 comprising the amino acid sequence of SEQ ID NO:38, a VL CDR2 comprising the amino acid sequence of SEQ ID NO:39, and a VL CDR3 comprising the amino acid sequence of SEQ ID NO:40.

In a particular embodiment, a MUC16 Glycosylation Antibody or antigen-binding fragment thereof described herein comprises a VL which comprises a VL CDR1 comprising the amino acid sequence of SEQ ID NO:46, a VL CDR2 comprising the amino acid sequence of SEQ ID NO:47, and a VL CDR3 comprising the amino acid sequence of SEQ ID NO:48. In a particular embodiment, a MUC16 Glycosylation Antibody or antigen-binding fragment thereof described herein comprises a VL which comprises a VL CDR1 comprising the amino acid sequence of SEQ ID NO:52, a VL CDR2 comprising the amino acid sequence of SEQ ID NO:53, and a VL CDR3 comprising the amino acid sequence of SEQ ID NO:54. In a particular embodiment, a MUC16 Glycosylation Antibody or antigen-binding fragment thereof described herein comprises a VL which comprises a VL CDR1 comprising the amino acid sequence of SEQ ID NO:58, a VL CDR2 comprising the amino acid sequence of SEQ ID NO:59, and a VL CDR3 comprising the amino acid sequence of SEQ ID NO:60.

In a particular embodiment, a MUC16 Glycosylation Antibody or antigen-binding fragment thereof described herein comprises a VL which comprises a VL CDR1 comprising the amino acid sequence of SEQ ID NO:66, a VL CDR2 comprising the amino acid sequence of SEQ ID NO:67, and a VL CDR3 comprising the amino acid sequence of SEQ ID NO:68. In a particular embodiment, a MUC16 Glycosylation Antibody or antigen-binding fragment thereof described herein comprises a VL which comprises a VL CDR1 comprising the amino acid sequence of SEQ ID NO:72, a VL CDR2 comprising the amino acid sequence of SEQ ID NO:73, and a VL CDR3 comprising the amino acid sequence of SEQ ID NO:74. In a particular embodiment, a MUC16 Glycosylation Antibody or antigen-binding fragment thereof described herein comprises a VL which comprises a VL CDR1 comprising the amino acid sequence of SEQ ID NO:78, a VL CDR2 comprising the amino acid sequence of SEQ ID NO:79, and a VL CDR3 comprising the amino acid sequence of SEQ ID NO:80.

In a particular embodiment, a MUC16 Glycosylation Antibody or antigen-binding fragment thereof described herein comprises a VL which comprises a VL CDR1 comprising the amino acid sequence of SEQ ID NO:86, a VL CDR2 comprising the amino acid sequence of SEQ ID NO:87, and a VL CDR3 comprising the amino acid sequence of SEQ ID NO:88. In a particular embodiment, a MUC16 Glycosylation Antibody or antigen-binding fragment thereof described herein comprises a VL which comprises a VL CDR1 comprising the amino acid sequence of SEQ ID NO:92, a VL CDR2 comprising the amino acid sequence of SEQ ID NO:93, and a VL CDR3 comprising the amino acid sequence of SEQ ID NO:94. In a particular embodiment, a MUC16 Glycosylation Antibody or antigen-binding fragment thereof described herein comprises a VL which comprises a VL CDR1 comprising the amino acid sequence of SEQ ID NO:98, a VL CDR2 comprising the amino acid sequence of SEQ ID NO:99, and a VL CDR3 comprising the amino acid sequence of SEQ ID NO:100.

In a particular embodiment, a MUC16 Glycosylation Antibody or antigen-binding fragment thereof described herein comprises:

(i) a VH which comprises:
  (a) a VH CDR1 comprising the amino acid sequence $TX_1GMGVG$ (SEQ ID NO: 103), wherein $X_1$ is L or V;
  (b) a VH CDR2 comprising the amino acid sequence $HIWWDDX_2DKYYX_3PALKS$ (SEQ ID NO:104), wherein $X_2$ is E or absent and wherein $X_3$ is Y or N; and
  (c) a VH CDR3 comprising the amino acid sequence IGTAQATDALDY (SEQ ID NO:105); and
(ii) a VL which comprises:
  (a) a VL CDR1 comprising the amino acid sequence $RSSKSLX_4X_5SNGNTYLY$ (SEQ ID NO:106), wherein $X_4$ is R or L, and wherein $X_5$ is K or H;
  (b) a VL CDR2 comprising the amino acid sequence YMSNLAS (SEQ ID NO:107); and
  (c) a VL CDR3 comprising the amino acid sequence $MQX_6LEX_7PLT$ (SEQ ID NO: 108), wherein $X_6$ is G or S and wherein $X_7$ is H or Y.

In a particular embodiment, a MUC16 Glycosylation Antibody or antigen-binding fragment thereof described herein comprises (i) a VH which comprises:
  (a) a VH CDR1 comprising the amino acid sequence $GFSLX_8TX_9GM$ (SEQ ID NO:109), wherein $X_8$ is N or S, and wherein $X_9$ is L or V;
  (b) a VH CDR2 comprising the amino acid sequence $WDDX_{10}$ (SEQ ID NO:110), wherein $X_{10}$ is E or absent; and
  (c) a VH CDR3 comprising the amino acid sequence GTAQATDALD (SEQ ID NO:111); and
(ii) a VL which comprises:
  (a) a VL CDR1 comprising the amino acid sequence $SKSLX_{11}X_{12}SNGNTY$ (SEQ ID NO:112), wherein $X_{11}$ is L or R, and wherein $X_{12}$ is H or K;
  (b) a VL CDR2 comprising the amino acid sequence YMS (SEQ ID NO:113); and
  (c) a VL CDR3 comprising the amino acid sequence $X_{13}LEX_{14}PL$ (SEQ ID NO:114), wherein $X_{13}$ is G or S, and wherein $X_{14}$ is H or Y.

In a particular embodiment, a MUC16 Glycosylation Antibody or antigen-binding fragment thereof described herein comprises (i) a VH which comprises:
  (a) a VH CDR1 comprising the amino acid sequence $GFSLX_{15}TX_{16}GMG$ (SEQ ID NO:115), wherein $X_{15}$ is N or S, and wherein $X_{16}$ is V or L;
  (b) a VH CDR2 comprising the amino acid sequence $IWWDDX_{17}DK$ (SEQ ID NO:116), wherein $X_{17}$ is E or absent; and
  (c) a VH CDR3 comprising the amino acid sequence $X_{18}RIGTAQATDALDY$ (SEQ ID NO:117), wherein $X_{18}$ is T, A, or S; and
(ii) a VL which comprises:
  (a) a VL CDR1 comprising the amino acid sequence $KSLX_{19}X_{20}SNGNTY$ (SEQ ID NO:118), wherein $X_{19}$ is V or L, and wherein $X_{20}$ is H or K;
  (b) a VL CDR2 comprising the amino acid sequence YMS (SEQ ID NO:119); and
  (c) a VL CDR3 comprising the amino acid sequence MQSLEYPLT (SEQ ID NO:120).

In a particular embodiment, a MUC16 Glycosylation Antibody or antigen-binding fragment thereof described herein comprises:

(i) a VH which comprises:
  (a) a VH CDR1 comprising the amino acid sequence $TX_1GMGVG$ (SEQ ID NO:103), wherein $X_1$ is L or V;
  (b) a VH CDR2 comprising the amino acid sequence $HIWWDDX_2DKYYX_3PALKS$ (SEQ ID NO:104), wherein $X_2$ is E or absent and wherein $X_3$ is Y or N; and
  (c) a VH CDR3 comprising the amino acid sequence IGTAQATDALDY (SEQ ID NO:105); and
(ii) a VL which comprises:
  (a) a VL CDR1 comprising the amino acid sequence SEQ ID NO:6;
  (b) a VL CDR2 comprising the amino acid sequence of SEQ ID NO:7; and
  (c) a VL CDR3 comprising the amino acid sequence of SEQ ID NO:8.

In a particular embodiment, a MUC16 Glycosylation Antibody or antigen-binding fragment thereof described herein comprises (i) a VH which comprises:
  (a) a VH CDR1 comprising the amino acid sequence $GFSLX_8TX_9GM$ (SEQ ID NO:109), wherein $X_8$ is N or S, and wherein $X_9$ is L or V;
  (b) a VH CDR2 comprising the amino acid sequence $WDDX_{10}$ (SEQ ID NO: 110), wherein $X_{10}$ is E or absent; and
  (c) a VH CDR3 comprising the amino acid sequence GTAQATDALD (SEQ ID NO:111); and
(ii) a VL which comprises:
  (a) a VL CDR1 comprising the amino acid sequence SEQ ID NO:12;
  (b) a VL CDR2 comprising the amino acid sequence of SEQ ID NO:13; and
  (c) a VL CDR3 comprising the amino acid sequence of SEQ ID NO:14.

In a particular embodiment, a MUC16 Glycosylation Antibody or antigen-binding fragment thereof described herein comprises a VH which comprises:
  (a) a VH CDR1 comprising the amino acid sequence $GFSLX_{15}TX_{16}GMG$ (SEQ ID NO:115), wherein $X_{15}$ is N or S, and wherein $X_{16}$ is V or L;
  (b) a VH CDR2 comprising the amino acid sequence $IWWDDX_{17}DK$ (SEQ ID NO:116), wherein $X_{17}$ is E or absent; and
  (c) a VH CDR3 comprising the amino acid sequence $X_{18}RIGTAQATDALDY$ (SEQ ID NO:117), wherein $X_{18}$ is T, A, or S; and
(ii) a VL which comprises:
  (a) a VL CDR1 comprising the amino acid sequence SEQ ID NO:18;
  (b) a VL CDR2 comprising the amino acid sequence of SEQ ID NO:19; and
  (c) a VL CDR3 comprising the amino acid sequence of SEQ ID NO:20.

In a particular embodiment, a MUC16 Glycosylation Antibody or antigen-binding fragment thereof described herein comprises (i) a VH which comprises:
  (a) a VH CDR1 comprising the amino acid sequence $TX_1GMGVG$ (SEQ ID NO:103), wherein $X_1$ is L or V;
  (b) a VH CDR2 comprising the amino acid sequence $HIWWDDX_2DKYYX_3PALKS$ (SEQ ID NO:104), wherein $X_2$ is E or absent and wherein $X_3$ is Y or N; and
  (c) a VH CDR3 comprising the amino acid sequence IGTAQATDALDY (SEQ ID NO:105); and
(ii) a VL which comprises:
  (a) a VL CDR1 comprising the amino acid sequence SEQ ID NO:26;
  (b) a VL CDR2 comprising the amino acid sequence of SEQ ID NO:27; and
  (c) a VL CDR3 comprising the amino acid sequence of SEQ ID NO:28.

In a particular embodiment, a MUC16 Glycosylation Antibody or antigen-binding fragment thereof described herein comprises:

(i) a VH which comprises:
  (a) a VH CDR1 comprising the amino acid sequence $GFSLX_8TX_9GM$ (SEQ ID NO:109), wherein $X_8$ is N or S, and wherein $X_9$ is L or V;
  (b) a VH CDR2 comprising the amino acid sequence $WDDX_{10}$ (SEQ ID NO:110), wherein $X_{10}$ is E or absent; and
  (c) a VH CDR3 comprising the amino acid sequence GTAQATDALD (SEQ ID NO:111); and
(ii) a VL which comprises:
  (a) a VL CDR1 comprising the amino acid sequence SEQ ID NO:32;
  (b) a VL CDR2 comprising the amino acid sequence of SEQ ID NO:33; and
  (c) a VL CDR3 comprising the amino acid sequence of SEQ ID NO:34.

In a particular embodiment, a MUC16 Glycosylation Antibody or antigen-binding fragment thereof described herein comprises:

(i) a VH which comprises:
  (a) a VH CDR1 comprising the amino acid sequence $GFSLX_{15}TX_{16}GMG$ (SEQ ID NO:115), wherein $X_{15}$ is N or S, and wherein $X_{16}$ is V or L;
  (b) a VH CDR2 comprising the amino acid sequence $IWWDDX_{17}DK$ (SEQ ID NO:116), wherein $X_{17}$ is E or absent; and
  (c) a VH CDR3 comprising the amino acid sequence $X_{18}RIGTAQATDALDY$ (SEQ ID NO:117), wherein $X_{18}$ is T, A, or S; and
(ii) a VL which comprises:
  (d) a VL CDR1 comprising the amino acid sequence SEQ ID NO:38;
  (e) a VL CDR2 comprising the amino acid sequence of SEQ ID NO:39; and
  (f) a VL CDR3 comprising the amino acid sequence of SEQ ID NO:40.

In a particular embodiment, a MUC16 Glycosylation Antibody or antigen-binding fragment thereof described herein comprises (a) a VH which comprises a VH CDR1 comprising the amino acid sequence of SEQ ID NO:3, a VH CDR2 comprising the amino acid sequence of SEQ ID NO:4, and a VH CDR3 comprising the amino acid sequence of SEQ ID NO:5; and (b) a VL which comprises a VL CDR1 comprising the amino acid sequence of SEQ ID NO:6, a VL CDR2 comprising the amino acid sequence of SEQ ID NO:7, and a VL CDR3 comprising the amino acid sequence of SEQ ID NO:8. In a particular embodiment, a MUC16 Glycosylation Antibody or antigen-binding fragment thereof described herein comprises (a) a VH which comprises a VH CDR1 comprising the amino acid sequence of SEQ ID NO:9, a VH CDR2 comprising the amino acid sequence of SEQ ID NO:10, and a VH CDR3 comprising the amino acid sequence of SEQ ID NO:11; and (b) a VL CDR1 comprising the amino acid sequence of SEQ ID NO:12, a VL CDR2 comprising the amino acid sequence of SEQ ID NO:13, and a VL CDR3 comprising the amino acid sequence of SEQ ID NO:14. In a particular embodiment, a MUC16 Glycosylation Antibody or antigen-binding fragment thereof described herein comprises (a) a VH which comprises a VH CDR1 comprising the amino acid sequence of SEQ ID NO:15, a VH CDR2 comprising the amino acid sequence of SEQ ID NO:16, and a VH CDR3 comprising the amino acid sequence of SEQ ID NO:17; and (b) a VL CDR1 comprising the amino acid sequence of SEQ ID NO:18, a VL CDR2 comprising the amino acid sequence of SEQ ID NO:19, and a VL CDR3 comprising the amino acid sequence of SEQ ID NO:20.

In a particular embodiment, a MUC16 Glycosylation Antibody or antigen-binding fragment thereof described herein comprises (a) a VH which comprises a VH CDR1 comprising the amino acid sequence of SEQ ID NO:23, a VH CDR2 comprising the amino acid sequence of SEQ ID NO:24, and a VH CDR3 comprising the amino acid sequence of SEQ ID NO:25; and (b) a VL which comprises a VL CDR1 comprising the amino acid sequence of SEQ ID NO:26, a VL CDR2 comprising the amino acid sequence of SEQ ID NO:27, and a VL CDR3 comprising the amino acid sequence of SEQ ID NO:28. In a particular embodiment, a MUC16 Glycosylation Antibody or antigen-binding fragment thereof described herein comprises (a) a VH which comprises a VH CDR1 comprising the amino acid sequence of SEQ ID NO:29, a VH CDR2 comprising the amino acid sequence of SEQ ID NO:30, and a VH CDR3 comprising the amino acid sequence of SEQ ID NO:31; and (b) a VL which comprises a VL CDR1 comprising the amino acid sequence of SEQ ID NO:32, a VL CDR2 comprising the amino acid sequence of SEQ ID NO:33, and a VL CDR3 comprising the amino acid sequence of SEQ ID NO:34. In a particular embodiment, a MUC16 Glycosylation Antibody or antigen-binding fragment thereof described herein comprises (a) a VH which comprises a VH CDR1 comprising the amino acid sequence of SEQ ID NO:35, a VH CDR2 comprising the amino acid sequence of SEQ ID NO:36, and a VH CDR3 comprising the amino acid sequence of SEQ ID NO:37; and (b) a VL CDR1 comprising the amino acid sequence of SEQ ID NO:38, a VL CDR2 comprising the amino acid sequence of SEQ ID NO:39, and a VL CDR3 comprising the amino acid sequence of SEQ ID NO:40.

In a particular embodiment, a MUC16 Glycosylation Antibody or antigen-binding fragment thereof described herein comprises (a) a VH which comprises a VH CDR1 comprising the amino acid sequence of SEQ ID NO:43, a VH CDR2 comprising the amino acid sequence of SEQ ID NO:44, and a VH CDR3 comprising the amino acid sequence of SEQ ID NO:45; and (b) a VL which comprises a VL CDR1 comprising the amino acid sequence of SEQ ID NO:46, a VL CDR2 comprising the amino acid sequence of SEQ ID NO:47, and a VL CDR3 comprising the amino acid sequence of SEQ ID NO:48. In a particular embodiment, a MUC16 Glycosylation Antibody or antigen-binding fragment thereof described herein comprises (a) a VH which comprises a VH CDR1 comprising the amino acid sequence of SEQ ID NO:49, a VH CDR2 comprising the amino acid sequence of SEQ ID NO:50, and a VH CDR3 comprising the amino acid sequence of SEQ ID NO:51; and (b) a VL which comprises a VL CDR1 comprising the amino acid sequence of SEQ ID NO:52, a VL CDR2 comprising the amino acid sequence of SEQ ID NO:53, and a VL CDR3 comprising the amino acid sequence of SEQ ID NO:54. In a particular embodiment, a MUC16 Glycosylation Antibody or antigen-binding fragment thereof described herein comprises (a) a VH which comprises a VH CDR1 comprising the amino acid sequence of SEQ ID NO:55, a VH CDR2 comprising the amino acid sequence of SEQ ID NO:56, and a VH CDR3 comprising the amino acid sequence of SEQ ID NO:57; and (b) a VL which comprises a VL CDR1 comprising the amino acid sequence of SEQ ID NO:58, a VL CDR2 comprising the amino acid sequence of SEQ ID NO:59, and a VL CDR3 comprising the amino acid sequence of SEQ ID NO:60.

In a particular embodiment, a MUC16 Glycosylation Antibody or antigen-binding fragment thereof described herein comprises (a) a VH which comprises a VH CDR1 comprising the amino acid sequence of SEQ ID NO:63, a VH CDR2 comprising the amino acid sequence of SEQ ID NO:64, and a VH CDR3 comprising the amino acid sequence of SEQ ID NO:65; and (b) a VL which comprises a VL CDR1 comprising the amino acid sequence of SEQ ID NO:66, a VL CDR2 comprising the amino acid sequence of SEQ ID NO:67, and a VL CDR3 comprising the amino acid sequence of SEQ ID NO:68. In a particular embodiment, a MUC16 Glycosylation Antibody or antigen-binding fragment thereof described herein comprises (a) a VH which comprises a VH CDR1 comprising the amino acid sequence of SEQ ID NO:69, a VH CDR2 comprising the amino acid sequence of SEQ ID NO:70, and a VH CDR3 comprising the amino acid sequence of SEQ ID NO:71; and (b) a VL which comprises a VL CDR1 comprising the amino acid sequence of SEQ ID NO:72, a VL CDR2 comprising the amino acid sequence of SEQ ID NO:73, and a VL CDR3 comprising the amino acid sequence of SEQ ID NO:74. In a particular embodiment, a MUC16 Glycosylation Antibody or antigen-binding fragment thereof described herein comprises (a) a VH which comprises a VH CDR1 comprising the amino acid sequence of SEQ ID NO:75, a VH CDR2 comprising the amino acid sequence of SEQ ID NO:76, and a VH CDR3 comprising the amino acid sequence of SEQ ID NO:77; and (b) a VL which comprises a VL CDR1 comprising the amino acid sequence of SEQ ID NO:78, a VL CDR2 comprising the amino acid sequence of SEQ ID NO:79, and a VL CDR3 comprising the amino acid sequence of SEQ ID NO:80.

In a particular embodiment, a MUC16 Glycosylation Antibody or antigen-binding fragment thereof described herein comprises (a) a VH which comprises a VH CDR1 comprising the amino acid sequence of SEQ ID NO:83, a VH CDR2 comprising the amino acid sequence of SEQ ID NO:84, and a VH CDR3 comprising the amino acid sequence of SEQ ID NO:85; and (b) a VL which comprises a VL CDR1 comprising the amino acid sequence of SEQ ID NO:86, a VL CDR2 comprising the amino acid sequence of SEQ ID NO:87, and a VL CDR3 comprising the amino acid sequence of SEQ ID NO:88. In a particular embodiment, a MUC16 Glycosylation Antibody or antigen-binding fragment thereof described herein comprises (a) a VH which comprises a VH CDR1 comprising the amino acid sequence of SEQ ID NO:89, a VH CDR2 comprising the amino acid sequence of SEQ ID NO:90, and a VH CDR3 comprising the amino acid sequence of SEQ ID NO:91; and (b) a VL which comprises a VL CDR1 comprising the amino acid sequence of SEQ ID NO:92, a VL CDR2 comprising the amino acid sequence of SEQ ID NO:93, and a VL CDR3 comprising the amino acid sequence of SEQ ID NO:94. In a particular embodiment, a MUC16 Glycosylation Antibody or antigen-binding fragment thereof described herein comprises (a) a VH which comprises a VH CDR1 comprising the amino acid sequence of SEQ ID NO:95, a VH CDR2 comprising the amino acid sequence of SEQ ID NO:96, and a VH CDR3 comprising the amino acid sequence of SEQ ID NO:97; and (b) a VL which comprises a VL CDR1 comprising the amino acid sequence of SEQ ID NO:98, a VL CDR2 comprising the amino acid sequence of SEQ ID NO:99, and a VL CDR3 comprising the amino acid sequence of SEQ ID NO:100.

TABLE 7

| VH Domain Amino Acid Sequences | |
|---|---|
| Antibody | VH (SEQ ID NO) |
| 10C6 | QVTLKESGPGILQPSQTLSLTCSFSGFSLNTLGMGVGWIRQPSGKGLEWLA<br>HIWWDDDKYYNPALKSRLTISKDSSKNQVFLKIANVDTADIATYYCSRIGT<br>AQATDALDYWGQGTSVTVSS (SEQ ID NO: 1) |
| 7B12 | QVTLKESGPGILQPSQTLSLTCSFSGFSLSTVGMGVGWSRQPSGKGLEWLA<br>HIWWDDEDKYYNPALKSRLTISKDTSKNQVFLKIANVDTADSATYYCTRI<br>GTAQATDALDYWGQGTSVTVSS (SEQ ID NO: 21) |
| 19C11 | QVNLKESGPGKLQPSQTLSLTCSFSGFSLSTLGMGVGWIRQSSGKGLEWL<br>AHIWWDDDKYYNPALKSRLTISRATSKNQVFLKIVNVGTADTATYYCARI<br>GTAQATDALDYWGQGTSVTVSS (SEQ ID NO: 41) |
| 16C5 | QVTLKESGPGILQPSQTLSLTCSFSGFSLNTLGMGVGWIRQPSGKGLEWLA<br>HIWWDDDKYYYPALKSRLTISRDTSKNQVFLKIANVDTADTATYYCARIG<br>TAQATDALDYWGQGTSVTVSS (SEQ ID NO: 61) |
| 18C6 | QVTLKESGPGILQPSQTLSLTCSFSGFSLSTVGMGVGWSRQPSGKGLEWLA<br>HIWWDDEDKYYNPALKSRLTISKDTSKNQVFLKIANVDTADTATYYCTRI<br>GTAQATDALDYWGQGTSVTVSS (SEQ ID NO: 81) |
| 10C6, 7B12, 19C11, 16C5, and 18C6 VH Consensus | QVX$_{21}$LKESGPGX$_{22}$LQPSQTLSLTCSFSGFSLX$_{23}$TX$_{24}$GMGVGWX$_{25}$RQX$_{26}$SG<br>KGLEWLAHIWWDDX$_{27}$DKYYX$_{28}$PALKSRLTISX$_{29}$X$_{30}$X$_{31}$SKNQVFLKIX$_{32}$N<br>VX$_{33}$TADX34ATYYCX35RIGTAQATDALDYWGQGTSVTVSS (SEQ ID<br>NO: 101)<br>wherein X$_{21}$ is T or N, X$_{22}$ is I or K, X$_{23}$ is N or<br>S, X$_{24}$ is V or L, X$_{25}$ is S or I, X$_{26}$ is P or S, X$_{27}$ is E or<br>absent, X$_{28}$ is N or Y, X$_{29}$ is K or R, X$_{30}$ is A or D, X$_{31}$ is<br>T or S, X$_{32}$ is V or A, X$_{33}$ is G or D, X$_{34}$ is T, I, or S,<br>and X$_{35}$ is T, S, or A |

TABLE 8

| VL Domain Amino Acid Sequences | |
|---|---|
| Antibody | VL (SEQ ID NO) |
| 10C6 | DIVLTQSPASLAVSLGQRATISYRASKSVSTSGYSYMHWNQQKPGQPPRLL<br>IYLVSNLESGVPARFSGSGSGTDFTLNIHPVEEEDAATYYCQHIRELTRSEG<br>GPSWKN (SEQ ID NO: 2) |
| 7B12 | DIVMTQAAPSVSVTPGESVSISCRSSKSLRKSNGNTYLYWFLQRPGQSPQR<br>LIYYMSNLASGVPDRFSGRGSGTDFTLRISRVEAEDVGVYYCMQSLEYPLT<br>FGGGTKLKIK (SEQ ID NO: 22) |
| 19C11 | DIVMTQAAPSIPVTPGESVSISCRSSKSLLHSNGNTYLYWFLQRPGQSPQRL<br>IYYMSNLASGVPDRFSGRGSGTDFTLKISRVEAGDVGVYYCMQGLEHPLT<br>FGGGTKLEIK (SEQ ID NO: 42) |
| 16C5 | ELDMTQTPPSLSASVGETVRIRCLASEDIYSGISWYQQKPGKPPTLLIYGAS<br>NLESGVPPRFSGSGSGTDYTLTIGGVQAEDAATYYCLGGYSYSSTLTFGAG<br>TNVEIK (SEQ ID NO: 62) |
| 18C6 | DIVMTQAAPSVPVTPGESVSISCRSSKSLLHSNGNTYLYWFLQRPGQSPQR<br>LIYYMSNLASGVPDRFSGRGSGTDFTLRISRVEAEDVGVYYCMQSLEYPLT<br>FGGGTKLEIK (SEQ ID NO: 82) |
| 7B12, 19C11, and 18C6 VH Consensus | DIVMTQAAPSX$_{36}$X$_{37}$VTPGESVSISCRSSKSLX$_{38}$X$_{39}$SNGNTYLYWFLQRPGQ<br>SPQRLIYYMSNLASGVPDRFSGRGSGTDFTLX$_{40}$ISRVEAX$_{41}$DVGVYYCMQ<br>X$_{42}$LEX$_{43}$PLTFGGGTKLEIK (SEQ ID NO: 102)<br>wherein X$_{36}$ is I or V, X$_{37}$ is P or S, X$_{38}$ is R or L, X$_{39}$ is<br>K or H, X$_{40}$ is R or K, X$_{41}$ is E or G, X$_{42}$ is S or G, and X$_{43}$<br>is Y or H |

In a particular embodiment, a MUC16 Glycosylation Antibody or antigen-binding fragment thereof described herein comprises a VH region comprising QVX$_{21}$LKESGPGX$_{22}$LQPSQTLSLTCSFSGFSLX$_{23}$TX$_{24}$GMGVGWX$_{25}$RQX$_{26}$SGKGLEWLAHIWWDDX$_{27}$DKYYX$_{28}$PALKSRLTISX$_{29}$X$_{30}$X$_{31}$SKNQVFLKIX$_{32}$NVX$_{33}$TADX$_{34}$ATYYCX$_{35}$RIGTAQATDALDYWGQGTSVTVSS (SEQ ID NO:101), wherein X$_{21}$ is T or N, X$_{22}$ is I or K, X$_{23}$ is N or S, X$_{24}$ is V or L, X$_{25}$ is S or I, X$_{26}$ is P or S, X$_{27}$ is E or absent, X$_{28}$ is N or Y, X$_{29}$ is K or R, X$_{30}$ is A or D, X$_{31}$ is T or S, X$_{32}$ is V or A, X$_{33}$ is G or D, X$_{34}$ is T, I, or S, and X$_{35}$ is T, S, or A.

In a particular embodiment, a MUC16 Glycosylation Antibody or antigen-binding fragment thereof described herein comprises a VL region comprising DIVMTQAAPS$X_{36}X_{37}$VTPGESVSISCRSSKSL$X_{38}X_{39}$S NGNTYLYWFLQRPGQSPQRLIYY MSNLASGVPD-RFSGRGSGTDFTL$X_{40}$ISRVEA$X_{41}$DVGVYYCMQ$X_{42}$-LE$X_{43}$PLTFGGGTKLEIK (SEQ ID NO:102), wherein $X_{36}$ is I or V, $X_{37}$ is P or S, $X_{38}$ is R or L, $X_{39}$ is K or H, $X_{40}$ is R or K, $X_{41}$ is E or G, $X_{42}$ is S or G, and $X_{43}$ is Y or H.

In a particular embodiment, a MUC16 Glycosylation Antibody or antigen-binding fragment thereof described herein comprises (a) VH region comprising QV$X_{21}$LKESGPG$X_{22}$ LQPSQTLSLTCSFSGFSL$X_{23}$T$X_{24}$GMGVGW$X_{25}$ RQ$X_{26}$SGKGLEWLAHIWWDD$X_{27}$DKYY$X_{28}$ PALKSRLTIS$X_{29}X_{30}X_{31}$SKNQVFLKI$X_{32}$NV$X_{33}$ TAD$X_{34}$ATYYC$X_{35}$RIGTAQATDALDYWGQGTS-VTVSS (SEQ ID NO:101), wherein $X_{21}$ is T or N, $X_{22}$ is I or K, $X_{23}$ is N or S, $X_{24}$ is V or L, $X_{25}$ is S or I, $X_{26}$ is P or S, $X_{27}$ is E or absent, $X_{28}$ is N or Y, $X_{29}$ is K or R, $X_{30}$ is A or D, $X_{31}$ is T or S, $X_{32}$ is V or A, $X_{33}$ is G or D, $X_{34}$ is T, I, or S, and $X_{35}$ is T, S, or A; and (b) a VL region comprising DIVMTQAAPS$X_{36}$ $X_{37}$VTPGESVSISCRSSKSL$X_{38}X_{39}$SNGNTYLYW-FLQRPGQSP QRLIYYMSNLASGVPDRFS-GRGSGT- DFTL$X_{40}$ISRVEA$X_{41}$DVGVYYCMQ$X_{42}$ LE$X_{43}$PLTFGGGTKLEIK (SEQ ID NO:102), wherein $X_{36}$ is I or V, $X_{37}$ is P or S, $X_{38}$ is R or L, $X_{39}$ is K or H, $X_{40}$ is R or K, $X_{41}$ is E or G, $X_{42}$ is S or G, and $X_{43}$ is Y or H.

In a particular embodiment, a MUC16 Glycosylation Antibody or antigen-binding fragment thereof described herein comprises (a) VH region comprising QV$X_{21}$LKESGPG$X_{22}$ LQPSQTLSLTCSFSGFSL$X_{23}$T$X_{24}$GMGVGW$X_{25}$ RQ$X_{26}$SGKGLEWLAHIWWDD$X_{27}$DKYY$X_{28}$PA-LKSRLTIS$X_{29}X_{30}X_{31}$SKNQVFLKI$X_{32}$NV$X_{33}$-TAD$X_{34}$ATYYC$X_{35}$RIGTAQATDALDYWGQGTS-VTVSS (SEQ ID NO:101), wherein $X_{21}$ is T or N, $X_{22}$ is I or K, $X_{23}$ is N or S, $X_{24}$ is V or L, $X_{25}$ is S or I, $X_{26}$ is P or S, $X_{27}$ is E or absent, $X_{28}$ is N or Y, $X_{29}$ is K or R, $X_{30}$ is A or D, $X_{31}$ is T or S, $X_{32}$ is V or A, $X_{33}$ is G or D, $X_{34}$ is T, I, or S, and $X_{35}$ is T, S, or A; and (b) a VL region comprising the amino acid sequence of SEQ ID NO:2.

In a particular embodiment, a MUC16 Glycosylation Antibody or antigen-binding fragment thereof described herein comprises (a) VH region comprising QV$X_{21}$LKESGPG$X_{22}$ LQPSQTLSLTCSFSGFSL$X_{23}$T$X_{24}$GMGVGW$X_{25}$ RQ$X_{26}$SGKGLEWLAHIWWDD$X_{27}$DKYY$X_{28}$ PALKSRLTIS$X_{29}X_{30}X_{31}$SKNQVFLKI$X_{32}$NV$X_{33}$ TAD$X_{34}$ATYYC$X_{35}$RIGTAQATDALDYWGQGTS-VTVSS (SEQ ID NO:101), wherein $X_{21}$ is T or N, $X_{22}$ is I or K, $X_{23}$ is N or S, $X_{24}$ is V or L, $X_{25}$ is S or I, $X_{26}$ is P or S, $X_{27}$ is E or absent, $X_{28}$ is N or Y, $X_{29}$ is K or R, $X_{30}$ is A or D, $X_{31}$ is T or S, $X_{32}$ is V or A, $X_{33}$ is G or D, $X_{34}$ is T, I, or S, and $X_{35}$ is T, S, or A; and (b) a VL region comprising the amino acid sequence of SEQ ID NO:62.

In a specific embodiment, a MUC16 Glycosylation Antibody or antigen-binding fragment thereof described herein comprises a VH comprising an amino acid sequence as set forth in Table 7. In a specific embodiment, a MUC16 Glycosylation Antibody or antigen-binding fragment thereof described herein comprises a heavy chain variable region sequence comprising the amino acid sequence of SEQ ID NO: 1 (Table 7) (e.g., the VH of antibody 10C6). In a specific embodiment, a MUC16 Glycosylation Antibody or antigen-binding fragment thereof described herein comprises a heavy chain variable region sequence comprising the amino acid sequence of SEQ ID NO:21 (Table 7) (e.g., the VH of antibody 7B12). In a specific embodiment, a MUC16 Glycosylation Antibody or antigen-binding fragment thereof described herein comprises a heavy chain variable region sequence comprising the amino acid sequence of SEQ ID NO:41 (Table 7) (e.g., the VH of antibody 19C11). In a specific embodiment, a MUC16 Glycosylation Antibody or antigen-binding fragment thereof described herein comprises a heavy chain variable region sequence comprising the amino acid sequence of SEQ ID NO:61 (Table 7) (e.g., the VH of antibody 16C5). In a specific embodiment, a MUC16 Glycosylation Antibody or antigen-binding fragment thereof described herein comprises a heavy chain variable region sequence comprising the amino acid sequence of SEQ ID NO:81 (Table 7) (e.g., the VH of antibody 18C6).

In a specific embodiment, a MUC16 Glycosylation Antibody or antigen-binding fragment thereof described herein comprises a VL comprising an amino acid sequence as set forth in Table 8. In a specific embodiment, a MUC16 Glycosylation Antibody or antigen-binding fragment thereof described herein comprises a light chain variable region sequence comprising the amino acid sequence of SEQ ID NO:2 (Table 8) (e.g., the VL of antibody 10C6). In a specific embodiment, a MUC16 Glycosylation Antibody or antigen-binding fragment thereof described herein comprises a light chain variable region sequence comprising the amino acid sequence of SEQ ID NO:22 (Table 8) (e.g., the VL of antibody 7B12). In a specific embodiment, a MUC16 Glycosylation Antibody or antigen-binding fragment thereof described herein comprises a light chain variable region sequence comprising the amino acid sequence of SEQ ID NO:42 (Table 8) (e.g., the VL of antibody 19C11). In a specific embodiment, a MUC16 Glycosylation Antibody or antigen-binding fragment thereof described herein comprises a light chain variable region sequence comprising the amino acid sequence of SEQ ID NO:62 (Table 8) (e.g., the VL of antibody 16C5). In a specific embodiment, a MUC16 Glycosylation Antibody or antigen-binding fragment thereof described herein comprises a light chain variable region sequence comprising the amino acid sequence of SEQ ID NO:82 (Table 8) (e.g., the VL of antibody 18C6).

In a specific embodiment, a MUC16 Glycosylation Antibody or antigen-binding fragment thereof described herein comprises (a) a VH comprising an amino acid sequence as set forth in Table 7; and (b) a VL comprising an amino acid sequence as set forth in Table 8. In a specific embodiment, a MUC16 Glycosylation Antibody or antigen-binding fragment thereof described herein comprises (a) a heavy chain variable region sequence comprising the amino acid sequence of SEQ ID NO:1 (Table 7) (e.g., the VH of antibody 10C6); and (b) a light chain variable region sequence comprising the amino acid sequence of SEQ ID NO:2 (Table 8) (e.g., the VL of antibody 10C6). In a specific embodiment, a MUC16 Glycosylation Antibody or antigen-binding fragment thereof described herein comprises (a) a heavy chain variable region sequence comprising the amino acid sequence of SEQ ID NO:21 (Table 7) (e.g., the VH of antibody 7B12); and (b) a light chain variable region sequence comprising the amino acid sequence of SEQ ID NO:22 (Table 8) (e.g., the VL of antibody 7B12). In a specific embodiment, a MUC16 Glycosylation Antibody or antigen-binding fragment thereof described herein comprises (a) a heavy chain variable region sequence comprising the amino acid sequence of SEQ ID NO:41 (Table 7) (e.g., the VH of antibody 19C11); and (b) a light chain variable region sequence comprising the amino acid sequence of SEQ ID NO:42 (Table 8) (e.g., the VL of antibody 19C11). In a specific embodiment, a MUC16 Glycosylation Antibody or antigen-binding fragment thereof described herein comprises (a) a heavy chain variable region sequence comprising the amino acid sequence of SEQ ID NO:61 (Table 7) (e.g., the VH of antibody 16C5); and (b) a light chain variable region sequence comprising the amino acid sequence of SEQ ID NO:62 (Table 8) (e.g., the VL of antibody 16C5). In a specific embodiment, a MUC16 Glycosylation Antibody or antigen-binding fragment thereof described herein comprises (a) a heavy chain variable region sequence comprising the amino acid sequence of SEQ ID NO:81 (Table 7) (e.g., the VH of antibody 18C6); and (b) a light chain variable region sequence comprising the amino acid sequence of SEQ ID NO:82 (Table 8) (e.g., the VL of antibody 18C6).

In certain embodiments, a MUC16 Glycosylation Antibody or antigen-binding fragment thereof described herein comprises VH CDRs (e.g., as set forth in Table 1, 3, or 5) of a VH comprising the amino acid sequence as set forth in Table 7 and VL CDRs (e.g., as set forth in Table 2, 4, or 6) of a VL comprising the amino acid sequence as set forth in Table 8.

In certain embodiments, a MUC16 Glycosylation Antibody or antigen binding fragment thereof described herein may be described by its VH domain alone, or its VL domain alone, or by its three VH CDRs alone, or by its three VL CDRs alone. See, e.g., Rader C et al., (1998) PNAS 95: 8910-8915, which is incorporated herein by reference in its entirety, which describes the humanization of the mouse anti-αvβ3 antibody by identifying a complementing light chain or heavy chain, respectively, from a human light chain or heavy chain library, resulting in humanized antibody variants having affinities as high or higher than the affinity of the original antibody. See also, Clackson T et al., (1991) Nature 352: 624-628, which is incorporated herein by reference in its entirety, describing methods of producing antibodies that bind a specific antigen by using a specific VH domain (or VL domain) and screening a library for the complementary variable domains. See also, Kim S J & Hong H J, (2007) J Microbiol 45: 572-577, which is incorporated herein by reference in its entirety, describing methods of producing antibodies that bind a specific antigen by using a specific VH domain and screening a library (e.g., human VL library) for complementary VL domains; the selected VL domains in turn could be used to guide selection of additional complementary (e.g., human) VH domains.

In certain embodiments, a MUC16 Glycosylation Antibody or antigen binding fragment thereof described herein may be a humanized antibody, for example, a humanized form of a rodent antibody. Humanized antibodies can be produced using a variety of techniques known in the art, including but not limited to, CDR-grafting (European Patent No. EP 239,400; International publication No. WO 91/09967; and U.S. Pat. Nos. 5,225,539, 5,530,101, and 5,585,089), chain shuffling (U.S. Pat. No. 5,565,332), veneering or resurfacing (European Patent Nos. EP 592,106 and EP 519,596; Padlan, 1991, Molecular Immunology 28(4/5):489-498; Studnicka et al., 1994, Protein Engineering 7(6):805-814; and Roguska et al., 1994, PNAS 91:969-973), and techniques disclosed in, e.g., U.S. Pat. Nos. 6,407,213, 5,766,886, WO 9317105, Sandhu J S, Gene 150(2):409-10 (1994), Pedersen et al., J. Mol. Biol. 235(3):959-73 (1994), Couto et al., Cancer Res. 55(8): 1717-22 (1995), Roguska et al., Protein Eng. 9(10):895 904 (1996), Baca et al., J. Biol. Chem. 272(16):10678-84 (1997), Couto et al., Cancer Res. 55 (23 Supp):5973s-5977s (1995), Caldas et al., Protein Eng. 13(5):353-60 (2000), Morea et al., Methods 20(3):267 79 (2000), and Tan et al., J. Immunol. 169:1119 25 (2002). See also U.S. Patent Pub. No. US 2005/0042664 A1 (Feb. 24, 2005), each of which is incorporated by reference herein in its entirety.

In certain embodiments, a MUC16 Glycosylation Antibody or antigen binding fragment thereof described herein may be a composite human antibody. A composite human antibody can be generated by, e.g., designing variable region sequences from fragments of multiple human antibody variable region sequences in a manner that avoids T cell epitopes, thereby minimizing the immunogenicity of the resulting antibody (see, e.g., Baker et al., 2010, Self Nonself., 1(4):314-322; Bryson et al., 2010, BioDrugs, 24(1):1-8; and Jones et al., 2009, Methods Mol Biol., 525:405-23). Such antibodies can comprise human constant region sequences, e.g., human light chain and/or heavy chain constant regions.

In certain embodiments, a MUC16 Glycosylation Antibody or antigen binding fragment thereof described herein may be a deimmunized antibody. A deimmunized antibody is an antibody in which T-cell epitopes have been removed. Methods for making deimmunized antibodies have been described. See, e.g., Jones et al., Methods Mol Biol. 2009; 525:405-23, xiv, and De Groot et al., Cell. Immunol. 244: 148-153 (2006)).

In specific embodiments, a MUC16 Glycosylation Antibody or antigen-binding fragment thereof described herein is a humanized immunoglobulin that comprises the 3 VH CDRs and the 3 VL CDRs (i.e., VH CDR1, VH CDR2, VH CDR3, VL CDR1, VL CDR2, and VL CDR3) of any of the antibodies in Table 1, Table 2, and Table 3, and Table 4, Table 5, and Table 6, respectively, human-derived framework regions, and human derived constant regions. Non-limiting examples of human framework regions are described in the art, e.g., see Kabat et al. (1991) *Sequences of Proteins of Immunological Interest*, Fifth Edition, U.S. Department of Health and Human Services, NIH Publication No. 91-3242). In certain embodiment, a MUC16 Glycosylation Antibody or antigen binding fragment thereof described herein comprises framework regions (e.g., framework regions of the VL domain and/or VH domain) that are human framework regions or derived from human framework regions. In certain embodiments, a MUC16 Glycosylation Antibody or antigen binding fragment thereof described herein comprises framework regions (e.g., framework regions of the VL domain and/or VH domain) that are primate (e.g., non-human primate) framework regions or derived from primate (e.g., non-human primate) framework regions. For example, CDRs from antigen-specific non-human antibodies, typically of rodent origin (e.g., mouse or rat), are grafted onto homologous human or non-human primate (e.g., Old World apes, e.g., *Pan troglodytes, Pan paniscus* or *Gorilla gorilla, Pan troglodytes*, Old World monkeys, e.g., from the genus *Macaca*, or the cynomolgus monkey *Macaca cynomolgus*). Non-human primate framework sequences are described in U.S. Patent Application Publication No. US 2005/0208625.

In a specific embodiment, the position of VH CDR1, VH CDR2, and/or VH CDR3 in the VH region and/or the position of VL CDR1, VL CDR2, and/or VL CDR2 in the VL region of a MUC16 Glycosylation Antibody or antigen binding fragment thereof described herein may vary by 1, 2, 3, 4, 5, 6, or more amino acid positions so long as (i) immunospecific binding to a cell recombinantly expressing a first form of MUC16, which first form is glycosylated, and wherein the amino acid sequence of the first form is SEQ ID NO:133 is maintained; (ii) lack of immunospecific binding to a cell recombinantly expressing a second form of MUC16, which second form is unglycosylated, and wherein the amino acid sequence of the second form is SEQ ID NO:139 is maintained; and (iii) inhibition of matrigel invasion in vitro of cells recombinantly expressing said first form of MUC16 is maintained (e.g., substantially maintained, e.g., at least 50%, at least 60%, at least 70%, at least 80%, at least 90%, at least 95%). In another embodiment, the length of VH CDR1, VH CDR2, and/or VH CDR3 in the VH region and/or the length of VL CDR1, VL CDR2, and/or VL CDR2 in the VL region of a MUC16 Glycosylation Antibody or antigen binding fragment thereof described herein may vary (e.g., be shorter or longer) by 1, 2, 3, 4, 5, 6, or more amino acids, so long as (i) immunospecific binding to a cell recombinantly expressing a first form of MUC16, which first form is glycosylated, and wherein the amino acid sequence of the first form is SEQ ID NO:133 is maintained; (ii) lack of immunospecific binding to a cell recombinantly expressing a second form of MUC16, which second form is unglycosylated, and wherein the amino acid sequence of the second form is SEQ ID NO:139 is maintained; and (iii) inhibition of matrigel invasion in vitro of cells recombinantly expressing said first form of MUC16 is maintained (e.g., substantially maintained, e.g., at least 50%, at least 60%, at least 70%, at least 80%, at least 90%, at least 95%). In another embodiment, the amino terminus and/or the carboxy terminus of a VH CDR1, VH CDR2, VH CDR3, VL CDR1, VL CDR2, and/or VL CDR3 described herein may be extended or shortened by 1, 2, 3, 4, 5, 6, or more amino acids compared to one or more of the CDRs described herein so long as (i) immunospecific binding to a cell recombinantly expressing a first form of MUC16, which first form is glycosylated, and wherein the amino acid sequence of the first form is SEQ ID NO:133 is maintained; (ii) lack of immunospecific binding to a cell recombinantly expressing a second form of MUC16, which second form is unglycosylated, and wherein the amino acid sequence of the second form is SEQ ID NO:139 is maintained; and (iii) inhibition of matrigel invasion in vitro of cells recombinantly expressing said first form of MUC16 is maintained (e.g., substantially maintained, e.g., at least 50%, at least 60%, at least 70%, at least 80%, at least 90%, at least 95%). As used herein, the terms "immunospecifically binds," "immunospecifically recognizes," "specifically binds," and "specifically recognizes" are analogous terms in the context of antibodies and refer to antibodies and antigen-binding fragments thereof that bind to an antigen (e.g., epitope or immune complex) via the antigen-binding sites as understood by one skilled in the art, and does not exclude cross-reactivity of the antibody or antigen-binding fragment with other antigens. Any method known in the art can be used to ascertain whether (i) immunospecific binding to a cell recombinantly expressing a first form of MUC16, which first form is glycosylated, and wherein the amino acid sequence of the first form is SEQ ID NO:133 is maintained; (ii) lack of immunospecific binding to a cell recombinantly expressing a second form of MUC16, which second form is unglycosylated, and wherein the amino acid sequence of the second form is SEQ ID NO:139 is maintained; and (iii) inhibition of matrigel invasion in vitro of cells recombinantly expressing said first form of MUC16 is maintained, e.g., ELISA binding assays or FACs analysis as described in Section 6, below.

In specific aspects, provided herein is a MUC16 Glycosylation Antibody or antigen-binding fragment thereof comprising an antibody heavy chain and/or light chain, e.g., a heavy chain alone, a light chain alone, or both a heavy chain and a light chain. With respect to the heavy chain, in a specific embodiment, the heavy chain of a MUC16 Glycosylation Antibody or an antigen-binding fragment thereof described herein can be an alpha (α), delta (δ), epsilon (ε), gamma (γ) or mu (μ) heavy chain. In another specific embodiment, the heavy chain of a MUC16 Glycosylation Antibody or antigen binding fragment thereof described can comprise a human alpha (α), delta (δ), epsilon (ε), gamma (γ) or mu (μ) heavy chain.

In a particular embodiment, a MUC16 Glycosylation Antibody or an antigen-binding fragment thereof described herein, which (i) immunospecifically binds to a cell recombinantly expressing a first form of MUC16, which first form is glycosylated, and wherein the amino acid sequence of the first form is SEQ ID NO:133; (ii) lacks immunospecific binding to a cell recombinantly expressing a second form of MUC16, which second form is unglycosylated, and wherein the amino acid sequence of the second form is SEQ ID NO:139; and (iii) inhibits matrigel invasion in vitro of cells recombinantly expressing said first form of MUC16, comprises a heavy chain wherein the amino acid sequence of the variable region of the heavy chain comprises a VH CDR1, VH CDR2, and VH CDR3 having the amino acid sequences of SEQ ID NO:103, SEQ ID NO:104, and SEQ ID NO:105, respectively, SEQ ID NO:109, SEQ ID NO:110, and SEQ ID NO:111, respectively, or SEQ ID NO:115, SEQ ID NO:116, and SEQ ID NO:117, respectively, and wherein the constant region of the heavy chain is a human alpha (α), delta (δ), epsilon (ε), gamma (γ) or mu (μ) heavy chain constant region. As used herein, the term "constant region" or "constant domain" is interchangeable and has its meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain. In a particular embodiment, a MUC16 Glycosylation Antibody or an antigen-binding fragment thereof described herein comprises a heavy chain wherein the amino acid sequence of the variable region of the heavy chain comprises a VH CDR1, VH CDR2, and VH CDR3 of antibody 10C6, 7B12, 19C11, 16C5, or 18C6 (i.e., those listed in Table 1, Table 3, or Table 5) and wherein the constant region of the heavy chain is a human alpha (α), delta (δ), epsilon (ε), gamma (γ) or mu (μ) heavy chain constant region.

In another particular embodiment, a MUC16 Glycosylated Antibody or an antigen-binding fragment thereof described herein comprises a heavy chain wherein the amino acid sequence of the variable region of the heavy chain comprises the amino acid sequence of SEQ ID NO:101, and wherein the constant region of the heavy chain is a human alpha (α), delta (δ), epsilon (ε), gamma (γ) or mu (μ) heavy chain constant region. In another particular embodiment, a MUC16 Glycosylated Antibody or an antigen-binding fragment thereof described herein comprises a heavy chain wherein the amino acid sequence of the variable region of the heavy chain comprises the amino acid sequence of SEQ ID NO:1, SEQ ID NO:21, SEQ ID NO:41, SEQ ID NO:61, or SEQ ID NO:81, and wherein the constant region of the heavy chain is a human alpha (α), delta (δ), epsilon (ε), gamma (γ) or mu (μ) heavy chain constant region.

In a specific embodiment, a MUC16 Glycosylated Antibody or an antigen-binding fragment thereof described herein comprises a heavy chain wherein the amino acid sequence of the variable region of the heavy chain comprises a VH CDR1, VH CDR2, and VH CDR3 having the amino acid sequences of SEQ ID NO:103, SEQ ID NO:104, and SEQ ID NO:105, respectively, or SEQ ID NO:109, SEQ ID NO:110; or SEQ ID NO:111, respectively, or SEQ ID NO:115, SEQ ID NO:116, or SEQ ID NO:117, respectively, and wherein the constant region of the heavy chain is a human heavy chain constant region. In a specific embodiment, a MUC16 Glycosylated Antibody or an antigen-binding fragment thereof described herein comprises a heavy chain wherein the amino acid sequence of the variable region of the heavy chain comprises a VH CDR1, VH CDR2, and VH CDR3 of any one of antibodies 10C6, 7B12, 19C11, 16C5, or 18C6 VH CDRs (i.e., those listed in Table 1, Table 3, and Table 5), and wherein the constant region of the heavy chain is a human heavy chain constant region. In a specific embodiment, a MUC16 Glycosylated Antibody or an antigen-binding fragment thereof described herein comprises a heavy chain wherein the amino acid sequence of the variable region of the heavy chain comprises the amino acid sequence of SEQ ID NO:101, and wherein the constant region of the heavy chain is a human heavy chain constant region. In a specific embodiment, a MUC16 Glycosylated Antibody or an antigen-binding fragment thereof described herein comprises a heavy chain wherein the amino acid sequence of the variable region of the heavy chain comprises the amino acid sequence of any one of antibodies 10C6, 7B12, 19C11, 16C5, or 18C6 VH CDRs (i.e., those listed in Table 7), and wherein the constant region of the heavy chain is a human heavy chain constant region. Non-limiting examples of human constant region sequences have been described in the art, e.g., see Kabat E A et al., (1991) supra.

With respect to the light chain, in a specific embodiment, the light chain of a MUC16 Glycosylation Antibody or an antigen-binding fragment thereof described herein is a kappa light chain. In another specific embodiment, the light chain of a MUC16 Glycosylation Antibody or an antigen-binding fragment thereof described herein is a lambda light chain. In yet another specific embodiment, the light chain of a MUC16 Glycosylation Antibody or an antigen-binding fragment thereof described herein is a human kappa light chain or a human lambda light chain.

In a particular embodiment, a MUC16 Glycosylation Antibody or an antigen-binding fragment thereof described herein comprises a light chain wherein the amino acid sequence of the variable region of the light chain comprises a VL CDR1, VL CDR2, and VL CDR3 having the amino acid sequences of antibody SEQ ID NO:106, SEQ ID NO:107, and SEQ ID NO:108, respectively, or SEQ ID NO:112, SEQ ID NO:113, and SEQ ID NO:114, respectively, or SEQ ID NO:118, SEQ ID NO:119, and SEQ ID NO:120, respectively, and wherein the constant region of the light chain is a kappa or lambda light chain constant region. In a particular embodiment, a MUC16 Glycosylation Antibody or an antigen-binding fragment thereof described herein comprises a light chain wherein the amino acid sequence of the variable region of the light chain comprises a VL CDR1, VL CDR2, and VL CDR3 of antibody 10C6, 7B12, 19C11, 16C5, or 18C6 (i.e., those listed in Table 2, Table 4, or Table 6) and wherein the constant region of the light chain is a kappa or lambda light chain constant region.

In another particular embodiment, a MUC16 Glycosylated Antibody or an antigen-binding fragment thereof described herein comprises a light chain wherein the amino acid sequence of the variable region of the light chain comprises the amino acid sequence of SEQ ID NO: 102, and wherein the constant region of the light chain is a kappa or lambda light chain constant region. In another particular embodiment, a MUC16 Glycosylated Antibody or an antigen-binding fragment thereof described herein comprises a light chain wherein the amino acid sequence of the variable region of the light chain comprises the amino acid sequence of SEQ ID NO:2, SEQ ID NO:22, SEQ ID NO:42, SEQ ID NO:62, or SEQ ID NO:82, and wherein the constant region of the light chain is a kappa or lambda light chain constant region.

In a specific embodiment, a MUC16 Glycosylated Antibody or an antigen-binding fragment thereof described herein comprises a light chain wherein the amino acid sequence of the variable region of the light chain comprises a VL CDR1, VL CDR2, and VL CDR3 having the amino acid sequences of SEQ ID NO:106, SEQ ID NO:107, and SEQ ID NO:108, respectively, or SEQ ID NO:112, SEQ ID NO:113, and SEQ ID NO:114, respectively, or SEQ ID NO:118, SEQ ID NO:119, and SEQ ID NO:120, respectively, and wherein the constant region of the light chain comprises the amino acid of a human light chain constant region. In a specific embodiment, a MUC16 Glycosylated Antibody or an antigen-binding fragment thereof described herein comprises a light chain wherein the amino acid sequence of the variable region of the light chain comprises a VL CDR1, VL CDR2, and VL CDR3 having the amino acid sequences of any one of antibodies 10C6, 7B12, 19C11, 16C5, or 18C6 VL CDRs (i.e., those listed in Table 2, Table 4, and Table 6), and wherein the constant region of the light chain is a human light chain constant region. In a specific embodiment, a MUC16 Glycosylated Antibody or an antigen-binding fragment thereof described herein comprises a light chain wherein the amino acid sequence of the variable region of the light chain comprises the amino acid sequence of SEQ ID NO:102, and wherein the constant region of the light chain is a human light chain constant region. In a specific embodiment, a MUC16 Glycosylated Antibody or an antigen-binding fragment thereof described herein comprises a light chain wherein the amino acid sequence of the variable region of the light chain comprises the amino acid sequence of any one of antibodies 10C6, 7B12, 19C11, 16C5, or 18C6 VL CDRs (i.e., those listed in Table 8), and wherein the constant region of the light chain is a human light chain constant region. Non-limiting examples of human constant region sequences have been described in the art, e.g., see Kabat E A et al., (1991) supra.

In a specific embodiment, a MUC16 Glycosylation Antibody or antigen-binding fragment thereof described herein comprises a heavy chain variable region (VH) and a light chain variable region (VL) as described herein, and wherein the constant regions are of the type found in an IgG, IgE, IgM, IgD, IgA or IgY immunoglobulin molecule, or a human IgG, IgE, IgM, IgD, IgA or IgY immunoglobulin molecule. In another specific embodiment, a MUC16 Glycosylation Antibody or antigen-binding fragment thereof described herein comprises a VH and a VL comprising any amino acid sequences described herein, and wherein the constant regions are of the type found in an IgG, IgE, IgM, IgD, IgA or IgY immunoglobulin molecule, any class (e.g., $IgG_1$, $IgG_2$, $IgG_3$, $IgG_4$, $IgA_1$ and $IgA_2$), or any subclass (e.g., $IgG_{2a}$ and $IgG_{2b}$) of immunoglobulin molecule. In a particular embodiment, the constant regions are of the type found in a human IgG, IgE, IgM, IgD, IgA or IgY immunoglobulin molecule, any class (e.g., $IgG_1$, $IgG_2$, $IgG_3$, $IgG_4$, $IgA_1$ and $IgA_2$), or any subclass (e.g., $IgG_2$a and $IgG_{2b}$) of immunoglobulin molecule.

In another particular embodiment, a MUC16 Glycosylation Antibody or an antigen-binding fragment thereof described herein comprises a heavy chain and/or a light chain, wherein (i) the heavy chain comprises (a) a variable region comprising a VH CDR1, VH CDR2, and VH CDR3 having the amino acid sequences of SEQ ID NO:103, SEQ ID NO:104, and SEQ ID NO:105, respectively, SEQ ID NO:109, SEQ ID NO:110, and SEQ ID NO:111, respectively, or SEQ ID NO:115, SEQ ID NO:116, and SEQ ID NO:117, respectively, and (b) comprises a constant heavy chain domain which is the constant domain of a human IgG heavy chain; and/or (ii) the light chain comprises (a) a variable region comprising a VL CDR1, VL CDR2, and VL CDR3 having the amino acid sequences of SEQ ID NO:106, SEQ ID NO:107, and SEQ ID NO:108, respectively, or SEQ ID NO:112, SEQ ID NO:113, and SEQ ID NO:114, respectively, or SEQ ID NO:118, SEQ ID NO:119, and SEQ ID NO:120, respectively, and (b) a constant light chain domain which is the constant domain of a human IgG. In another particular embodiment, a MUC16 Glycosylation Antibody or an antigen-binding fragment thereof described herein comprises a heavy chain and/or a light chain, wherein (i) the heavy chain comprises (a) a variable region comprising a VH CDR1, VH CDR2, and VH CDR3 having the amino acid sequences of any one of antibodies 10C6, 7B12, 19C11, 16C5, or 18C6 VH CDRs (i.e., those listed in Table 1, Table 3, and Table 5), and (b) comprises a constant heavy chain domain which is the constant domain of a human IgG heavy chain; and/or (ii) the light chain comprises (a) a variable region comprising a VL CDR1, VL CDR2, and VL CDR3 having the amino acid sequences of any one of antibodies 10C6, 7B12, 19C11, 16C5, or 18C6 VL CDRs (i.e., those listed in Table 2, Table 4, and Table 6), and (b) a constant light chain domain which is the constant domain of a human IgG.

In another particular embodiment, a MUC16 Glycosylation Antibody or an antigen-binding fragment thereof described herein comprises a heavy chain and/or a light chain, wherein (i) the heavy chain comprises (a) a variable region comprising the amino acid sequence of SEQ ID NO:101, and (b) a constant heavy chain domain which is the constant domain of a human IgG; and/or (ii) the light chain comprises (a) a variable region comprising the amino acid sequence of SEQ ID NO:102, and (b) a constant light chain domain is the constant domain of a human kappa light chain. In another particular embodiment, a MUC16 Glycosylation Antibody or an antigen-binding fragment thereof described herein comprises a heavy chain and/or a light chain, wherein (i) the heavy chain comprises (a) a variable region comprising the amino acid sequence of the VH of any one of antibodies 10C6, 7B12, 19C11, 16C5, or 18C6 (i.e., those listed in Table 7), and (b) a constant heavy chain domain which is the constant domain of a human IgG; and/or (ii) the light chain comprises (a) a variable region comprising the amino acid sequence of the VL of any one of antibodies 10C6, 7B12, 19C11, 16C5, or 18C6 (i.e., those listed in Table 8), and (b) a constant light chain domain is the constant domain of a human kappa light chain.

In certain embodiments, a MUC16 Glycosylation Antibody or antigen binding fragment thereof described herein or an antigen-binding fragment thereof comprises amino acid sequences with the percent identity described below relative to any one of SEQ ID NOs: 1-100. Mathematical algorithms can be utilized to determine percent identity between two sequences (e.g., amino acid sequences or nucleic acid sequences). A preferred, non-limiting example of a mathematical algorithm utilized for the comparison of two sequences is the algorithm of Karlin and Altschul, 1990, Proc. Natl. Acad. Sci. U.S.A. 87:2264 2268, modified as in Karlin and Altschul, 1993, Proc. Natl. Acad. Sci. U.S.A. 90:5873 5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules described herein. BLAST protein searches can be performed with the XBLAST program parameters set, e.g., to score 50, wordlength=3 to obtain amino acid sequences homologous to a protein molecule described herein. Gapped BLAST can be utilized as described in Altschul et al., 1997, Nucleic Acids Res. 25:3389 3402, to obtain gapped alignments for comparison purposes. Alternatively, an iterated search which detects distant relationships between molecules can be performed by PSI BLAST (Id.). The default parameters of the respective programs (e.g., of XBLAST and NBLAST) can be used (see, e.g., National Center for Biotechnology Information (NCBI) on the worldwide web, ncbi.nlm.nih.gov) when utilizing BLAST, Gapped BLAST, and PSI Blast programs. Another preferred, non limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Moreover, the percent identity between two sequences can be determined using techniques similar to those described above, with or without allowing gaps. Typically only exact matches are counted when calculating percent identity.

In certain embodiments, a MUC16 Glycosylation Antibody or antigen-binding fragment thereof comprises a VH having at least 80%, at least 85%, at least 90%, at least 95%, or at least 98% sequence identity to the amino acid sequence of SEQ ID NO: 101. In certain embodiments, a MUC16 Glycosylation Antibody or antigen-binding fragment thereof comprises a VH having at least 80%, at least 85%, at least 90%, at least 95%, or at least 98% sequence identity to the amino acid sequence of the VH of any one of antibodies 10C6, 7B12, 19C11, 16C5, or 1B5 (i.e., those listed in Table 7). In certain embodiments, a MUC16 Glycosylation Antibody or antigen-binding fragment thereof comprises a VH domain having at least 80%, at least 85%, at least 90%, at least 95%, or at least 98% sequence identity to the amino acid sequence of SEQ ID NO:101, wherein the antibody or antigen-binding fragment comprises CDRs (e.g., VH CDRs and/or VL CDRs) that are identical to the CDRs (e.g., VH CDRs and/or VL CDRs) set forth in Table 1, Table 2, Table 3, Table 4, Table 5, or Table 6. In certain embodiments, a MUC16 Glycosylation Antibody or antigen-binding fragment thereof comprises a VH domain having at least 80%, at least 85%, at least 90%, at least 95%, or at least 98% sequence identity to the amino acid sequence of the VH of any one of antibodies 10C6, 7B12, 19C11, 16C5, or 18C6 (i.e., those listed in Table 7), wherein the antibody or antigen-binding fragment comprises CDRs (e.g., VH CDRs and/or VL CDRs) that are identical to the CDRs (e.g., VH CDRs and/or VL CDRs) set forth in Table 1, Table 2, Table 3, Table 4, Table 5, or Table 6.

In certain embodiments, a MUC16 Glycosylation Antibody or antigen-binding fragment thereof comprises a VL having at least 80%, at least 85%, at least 90%, at least 95%, or at least 98% sequence identity to the amino acid sequence of SEQ ID NO:102. In certain embodiments, a MUC16 Glycosylation Antibody or antigen-binding fragment thereof comprises a VL having at least 80%, at least 85%, at least 90%, at least 95%, or at least 98% sequence identity to the amino acid sequence of the VL of any one of antibodies 10C6, 7B12, 19C11, 16C5, or 1B5 (i.e., those listed in Table 8). In certain embodiments, a MUC16 Glycosylation Antibody or antigen-binding fragment thereof comprises a VL domain having at least 80%, at least 85%, at least 90%, at least 95%, or at least 98% sequence identity to the amino acid sequence of SEQ ID NO:102, wherein the antibody or antigen-binding fragment comprises CDRs (e.g., VH CDRs and/or VL CDRs) that are identical to the CDRs (e.g., VH CDRs and/or VL CDRs) set forth in Table 1, Table 2, Table 3, Table 4, Table 5, or Table 6. In certain embodiments, a MUC16 Glycosylation Antibody or antigen-binding fragment thereof comprises a VL domain having at least 80%, at least 85%, at least 90%, at least 95%, or at least 98% sequence identity to the amino acid sequence of the VL of any one of antibodies 10C6, 7B12, 19C11, 16C5, or 18C6 (i.e., those listed in Table 7), wherein the antibody or antigen-binding fragment comprises CDRs (e.g., VH CDRs and/or VL CDRs) that are identical to the CDRs (e.g., VH CDRs and/or VL CDRs) set forth in Table 1, Table 2, Table 3, Table 4, Table 5, or Table 6.

In certain embodiments, a MUC16 Glycosylation Antibody or antigen-binding fragment thereof comprises: (i) a VH domain having at least 80%, at least 85%, at least 90%, at least 95%, or at least 98% sequence identity to the amino acid sequence of SEQ ID NO:101; and (ii) a VL domain having at least 80%, at least 85%, at least 90%, at least 95%, or at least 98% sequence identity to the amino acid sequence of SEQ ID NO: 102. In certain embodiments, a MUC16 Glycosylation Antibody or antigen-binding fragment thereof comprises: (i) a VH domain having at least 80%, at least 85%, at least 90%, at least 95%, or at least 98% sequence identity to the amino acid sequence of the VH of any one of antibodies 10C6, 7B12, 19C11, 16C5, or 18C6 (i.e., those listed in Table 8); and (ii) a VL domain having at least 80%, at least 85%, at least 90%, at least 95%, or at least 98% sequence identity to the amino acid sequence of the VL of any one of antibodies 10C6, 7B12, 19C11, 16C5, or 18C6 (i.e., those listed in Table 7), respectively. In certain embodiments, a MUC16 Glycosylation Antibody or antigen-binding fragment thereof comprises: (i) a VH domain having at least 80%, at least 85%, at least 90%, at least 95%, or at least 98% sequence identity to the amino acid sequence of SEQ ID NO:101; and (ii) a VL domain having at least 80%, at least 85%, at least 90%, at least 95%, or at least 98% sequence identity to the amino acid sequence of SEQ ID NO:102, wherein the antibody or antigen-binding fragment comprises CDRs (e.g., VH CDRs and/or VL CDRs) that are identical to the CDRs (e.g., VH CDRs and/or VL CDRs) set forth in Table 1, Table 2, Table 3, Table 4, Table 5, or Table 6. In certain embodiments, a MUC16 Glycosylation Antibody or antigen-binding fragment thereof comprises: (i) a VH domain having at least 80%, at least 85%, at least 90%, at least 95%, or at least 98% sequence identity to the amino acid sequence of the VH of any one of antibodies 10C6, 7B12, 19C11, 16C5, or 18C6 (i.e., those listed in Table 8); and (ii) a VL domain having at least 80%, at least 85%, at least 90%, at least 95%, or at least 98% sequence identity to the amino acid sequence of the VL of any one of antibodies 10C6, 7B12, 19C11, 16C5, or 18C6 (i.e., those listed in Table 7), respectively, wherein the antibody or antigen-binding fragment comprises CDRs (e.g., VH CDRs and/or VL CDRs) that are identical to the CDRs (e.g., VH CDRs and/or VL CDRs) set forth in Table 1, Table 2, Table 3, Table 4, Table 5, or Table 6.

In another aspect, provided herein are antibodies that bind the same or an overlapping epitope of a MUC16 Glycosylation Antibody or antigen-binding fragment thereof described herein (e.g., 10C6, 7B12, 19C11, 16C5, and/or 16C5). As used herein, an "epitope" is a term in the art and can refer to a localized region of an antigen to which an antibody can immunospecifically bind. An epitope can be, e.g., contiguous amino acids of a polypeptide (linear or contiguous epitope) or an epitope can, e.g., come together from two or more non-contiguous regions of a polypeptide or polypeptides (conformational, non-linear, discontinuous, or non-contiguous epitope). In certain embodiments, the epitope of an antibody can be determined by, e.g., NMR spectroscopy, X-ray diffraction crystallography studies, ELISA assays, hydrogen/deuterium exchange coupled with mass spectrometry (e.g., MALDI mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giege R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303). Antibody:antigen crystals may be studied using well known X-ray diffraction techniques and may be refined using computer software such as X-PLOR (Yale University, 1992, distributed by Molecular Simulations, Inc.; see e.g. Meth Enzymol (1985) volumes 114 & 115, eds Wyckoff H W et al.; U.S. Patent Application No. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323). Mutagenesis mapping studies may be accomplished using any method known to one of skill in the art. See, e.g., Champe M et al., (1995) and Cunningham B C & Wells J A (1989) for a description of mutagenesis techniques, including alanine scanning mutagenesis techniques. In addition, antibodies that recognize and bind to the same or overlapping epitopes can be identified using routine techniques such as an immunoassay, e.g., by showing the ability of one antibody to block the binding of another antibody to a target antigen, i.e., a competitive binding assay. Competition binding assays also can be used to determine whether two antibodies have similar binding specificity for an epitope. Competitive binding can be determined in an assay in which the immunoglobulin under test inhibits immunospecific binding of a reference antibody to a common antigen. Numerous types of competitive binding assays are known, e.g.: solid phase direct or indirect radioimmunoassay (RIA), solid phase direct or indirect enzyme immunoassay (EIA), sandwich competition assay (see Stahli C et al., (1983) Methods Enzymol 9: 242-253); solid phase direct biotin-avidin EIA (see Kirkland T N et al., (1986) J Immunol 137: 3614-9); solid phase direct labeled assay, solid phase direct labeled sandwich assay (see Harlow E & Lane D, (1988) Antibodies: A Laboratory Manual, Cold Spring Harbor Press); solid phase direct label RIA using I-125 label (see Morel G A et al., (1988) Mol Immunol 25(1): 7-15); solid phase direct biotin-avidin EIA (Cheung R C et al., (1990) Virology 176: 546-52); and direct labeled RIA. (Moldenhauer G et al., (1990) Scand J Immunol 32: 77-82). Typically, such an assay involves the use of purified antigen bound to a solid surface or cells bearing either of these, an unlabeled test immunoglobulin and a labeled reference immunoglobulin. Competitive inhibition can be measured by determining the amount of label bound to the solid surface or cells in the presence of the test immunoglobulin. Usually the test immunoglobulin is present in excess. Usually, when a competing antibody is present in excess, it will inhibit immunospecific binding of a reference antibody to a common antigen by at least 50-55%, 55-60%, 60-65%, 65-70% 70-75% or more. A competition binding assay can be configured in a large number of different formats using either labeled antigen or labeled antibody. In a common version of this assay, the antigen is immobilized on a 96-well plate. The ability of unlabeled antibodies to block the binding of labeled antibodies to the antigen is then measured using radioactive or enzyme labels. For further details see, e.g., Wagener C et al., (1983) J Immunol 130: 2308-2315; Wagener C et al., (1984) J Immunol Methods 68: 269-274; Kuroki M et al., (1990) Cancer Res 50: 4872-4879; Kuroki M et al., (1992) Immunol Invest 21: 523-538; Kuroki M et al., (1992) Hybridoma 11: 391-407 and Antibodies: A Laboratory Manual, Ed Harlow E & Lane D editors supra, pp. 386-389.

In certain aspects, competition binding assays can be used to determine whether an antibody is competitively blocked, e.g., in a dose dependent manner, by another antibody e.g., an antibody binds essentially the same epitope, or overlapping epitopes, as a reference antibody, when the two antibodies recognize identical or sterically overlapping epitopes in competition binding assays such as competition ELISA assays, which can be configured in all number of different formats, using either labeled antigen or labeled antibody. In a particular embodiment, an antibody can be tested in competition binding assays with a MUC16 Glycosylation Antibody or antigen binding fragment thereof described herein (e.g., a murine IgG antibody containing the variable region of 10C6, 7B12, 19C11, 16C5, or 16C5).

In another aspect, provided herein are antibodies that compete (e.g., in a dose dependent manner) for binding to MUC16 with a MUC16 Glycosylation Antibody or antigen binding fragment thereof described herein (e.g., a murine IgG antibody containing the variable region of 10C6, 7B12, 19C11, 16C5, or 16C5), as determined using assays known to one of skill in the art or described herein (e.g., ELISA). In another aspect, provided herein are antibodies that competitively inhibit (e.g., in a dose dependent manner) a MUC16 Glycosylation Antibody or antigen binding fragment thereof described herein (e.g., a murine IgG antibody containing the variable region of 10C6, 7B12, 19C11, 16C5, or 16C5) from binding to MUC16, as determined using assays known to one of skill in the art or described herein (e.g., ELISA).

In certain embodiments, provided herein is an antibody that competes with an antibody described herein for binding to the same extent that a MUC16 Glycosylation Antibody or antigen binding fragment thereof described herein self-competes for binding to MUC16. In certain embodiments, provided herein is a first antibody that competes with a MUC16 Glycosylation Antibody or antigen binding fragment thereof described herein for binding to MUC16, wherein the competition is exhibited as reduced binding of the first antibody to the epitope by more than 80% (e.g., 85%, 90%, 95%, or 98%, or between 80% to 85%, 80% to 90%, 85% to 90%, or 85% to 95%).

In specific aspects, provided herein is a MUC16 Glycosylation Antibody or antigen binding fragment thereof which competes (e.g., in a dose dependent manner) for immunospecific binding to MUC16, with a MUC16 Glycosylation Antibody or antigen binding fragment thereof comprising a VH comprising a VH CDR1, a VH CDR2, and/or a VH CDR3 comprising amino acid sequences as described in Table 1, Table 3, or Table 5. In a particular embodiment, provided herein is a MUC16 Glycosylation Antibody or antigen binding fragment thereof that competes (e.g., in a dose-dependent manner), for immunospecific binding to MUC16, with a MUC16 Glycosylation Antibody or antigen binding fragment thereof comprising the VH CDRS of 10C6 (see, Table 1, Table 3, and Table 5). In a particular embodiment, provided herein is a MUC16 Glycosylation Antibody or antigen binding fragment thereof that competes (e.g., in a dose-dependent manner), for immunospecific binding to MUC16, with a MUC16 Glycosylation Antibody or antigen binding fragment thereof comprising the VH CDRS of 7B12 (see, Table 1, Table 3, and Table 5). In a particular embodiment, provided herein is a MUC16 Glycosylation Antibody or antigen binding fragment thereof that competes (e.g., in a dose-dependent manner), for immunospecific binding to MUC16, with a MUC16 Glycosylation Antibody or antigen binding fragment thereof comprising the VH CDRS of 19C11 (see, Table 1, Table 3, and Table 5). In a particular embodiment, provided herein is a MUC16 Glycosylation Antibody or antigen binding fragment thereof that competes (e.g., in a dose-dependent manner), for immunospecific binding to MUC16, with a MUC16 Glycosylation Antibody or antigen binding fragment thereof comprising the VH CDRS of 16C5 (see, Table 1, Table 3, and Table 5). In a particular embodiment, provided herein is a MUC16 Glycosylation Antibody or antigen binding fragment thereof that competes (e.g., in a dose-dependent manner), for immunospecific binding to MUC16, with a MUC16 Glycosylation Antibody or antigen binding fragment thereof comprising the VH CDRS of 18C6 (see, Table 1, Table 3, and Table 5).

In specific aspects, provided herein is a MUC16 Glycosylation Antibody or antigen binding fragment thereof which competes (e.g., in a dose dependent manner) for immunospecific binding to MUC16, with a MUC16 Glycosylation Antibody or antigen binding fragment thereof comprising a VL comprising a VL CDR1, a VL CDR2, and/or a VL CDR3 comprising amino acid sequences as described in Table 2, Table 4, or Table 6. In a particular embodiment, provided herein is a MUC16 Glycosylation Antibody or antigen binding fragment thereof that competes (e.g., in a dose-dependent manner), for immunospecific binding to MUC16, with a MUC16 Glycosylation Antibody or antigen binding fragment thereof comprising the VL CDRS of 10C6 (see, Table 2, Table 4, and Table 6). In a particular embodiment, provided herein is a MUC16 Glycosylation Antibody or antigen binding fragment thereof that competes (e.g., in a dose-dependent manner), for immunospecific binding to MUC16, with a MUC16 Glycosylation Antibody or antigen binding fragment thereof comprising the VL CDRS of 7B12 (see, Table 2, Table 4, and Table 6). In a particular embodiment, provided herein is a MUC16 Glycosylation Antibody or antigen binding fragment thereof that competes (e.g., in a dose-dependent manner), for immunospecific binding to MUC16, with a MUC16 Glycosylation Antibody or antigen binding fragment thereof comprising the VL CDRS of 19C11 (see, Table 2, Table 4, and Table 6). In a particular embodiment, provided herein is a MUC16 Glycosylation Antibody or antigen binding fragment thereof that competes (e.g., in a dose-dependent manner), for immunospecific binding to MUC16, with a MUC16 Glycosylation Antibody or antigen binding fragment thereof comprising the VL CDRS of 16C5 (see, Table 2, Table 4, and Table 6). In a particular embodiment, provided herein is a MUC16 Glycosylation Antibody or antigen binding fragment thereof that competes (e.g., in a dose-dependent manner), for immunospecific binding to MUC16, with a MUC16 Glycosylation Antibody or antigen binding fragment thereof comprising the VL CDRS of 18C6 (see, Table 2, Table 4, and Table 6).

In specific aspects, provided herein is a MUC16 Glycosylation Antibody or antigen binding fragment thereof which competes (e.g., in a dose dependent manner) for immunospecific binding to MUC16, with a MUC16 Glycosylation Antibody or antigen binding fragment thereof comprising (a) a VH comprising a VH CDR1, a VH CDR2, and/or a VH CDR3 comprising amino acid sequences as described in Table 1, Table 3, or Table 5; and (b) a VL comprising a VL CDR1, a VL CDR2, and/or a VL CDR3 comprising amino acid sequences as described in Table 2, Table 4, or Table 6. In a particular embodiment, provided herein is a MUC16 Glycosylation Antibody or antigen binding fragment thereof that competes (e.g., in a dose-dependent manner), for immunospecific binding to MUC16, with a MUC16 Glycosylation Antibody or antigen binding fragment thereof comprising (a) the VH CDRS of 10C6 (see, Table 1, Table 3, and Table 5); and (b) the VL CDRS of 10C6 (see, Table 2, Table 4, and Table 6). In a particular embodiment, provided herein is a MUC16 Glycosylation Antibody or antigen binding fragment thereof that competes (e.g., in a dose-dependent manner), for immunospecific binding to MUC16, with a MUC16 Glycosylation Antibody or antigen binding fragment thereof comprising (a) the VH CDRS of 7B12 (see, Table 1, Table 3, and Table 5); and (b) the VL CDRS of 7B12 (see, Table 2, Table 4, and Table 6). In a particular embodiment, provided herein is a MUC16 Glycosylation Antibody or antigen binding fragment thereof that competes (e.g., in a dose-dependent manner), for immunospecific binding to MUC16, with a MUC16 Glycosylation Antibody or antigen binding fragment thereof comprising (a) the VH CDRS of 19C11 (see, Table 1, Table 3, and Table 5); and (b) the VL CDRS of 19C11 (see, Table 2, Table 4, and Table 6). In a particular embodiment, provided herein is a MUC16 Glycosylation Antibody or antigen binding fragment thereof that competes (e.g., in a dose-dependent manner), for immunospecific binding to MUC16, with a MUC16 Glycosylation Antibody or antigen binding fragment thereof comprising (a) the VH CDRS of 16C5 (see, Table 1, Table 3, and Table 5); and (b) the VL CDRS of 16C5 (see, Table 2, Table 4, and Table 6). In a particular embodiment, provided herein is a MUC16 Glycosylation Antibody or antigen binding fragment thereof that competes (e.g., in a dose-dependent manner), for immunospecific binding to MUC16, with a MUC16 Glycosylation Antibody or antigen binding fragment thereof comprising (a) the VH CDRS of 18C6 (see, Table 1, Table 3, and Table 5); and (b) the VL CDRS of 18C6 (see, Table 2, Table 4, and Table 6).

In specific aspects, provided herein is a MUC16 Glycosylation Antibody or antigen binding fragment thereof which competes (e.g., in a dose dependent manner) for immunospecific binding to MUC16, with a MUC16 Glycosylation Antibody or antigen binding fragment thereof comprising a VH domain having an amino acid sequence as described in Table 7. In specific aspects, provided herein is a MUC16 Glycosylation Antibody or antigen binding fragment thereof which competes (e.g., in a dose dependent manner) for immunospecific binding to MUC16, with a MUC16 Glycosylation Antibody or antigen binding fragment thereof comprising a VH domain having the amino acid sequence of SEQ ID NO:1. In specific aspects, provided herein is a MUC16 Glycosylation Antibody or antigen binding fragment thereof which competes (e.g., in a dose dependent manner) for immunospecific binding to MUC16, with a MUC16 Glycosylation Antibody or antigen binding fragment thereof comprising a VH domain having the amino acid sequence of SEQ ID NO:21. In specific aspects, provided herein is a MUC16 Glycosylation Antibody or antigen binding fragment thereof which competes (e.g., in a dose dependent manner) for immunospecific binding to MUC16, with a MUC16 Glycosylation Antibody or antigen binding fragment thereof comprising a VH domain having the amino acid sequence of SEQ ID NO:41. In specific aspects, provided herein is a MUC16 Glycosylation Antibody or antigen binding fragment thereof which competes (e.g., in a dose dependent manner) for immunospecific binding to MUC16, with a MUC16 Glycosylation Antibody or antigen binding fragment thereof comprising a VH domain having the amino acid sequence of SEQ ID NO:61. In specific aspects, provided herein is a MUC16 Glycosylation Antibody or antigen binding fragment thereof which competes (e.g., in a dose dependent manner) for immunospecific binding to MUC16, with a MUC16 Glycosylation Antibody or antigen binding fragment thereof comprising a VH domain having the amino acid sequence of SEQ ID NO:81.

In specific aspects, provided herein is a MUC16 Glycosylation Antibody or antigen binding fragment thereof which competes (e.g., in a dose dependent manner) for immunospecific binding to MUC16, with a MUC16 Glycosylation Antibody or antigen binding fragment thereof comprising a VL domain having an amino acid sequence as described in Table 8. In specific aspects, provided herein is a MUC16 Glycosylation Antibody or antigen binding fragment thereof which competes (e.g., in a dose dependent manner) for immunospecific binding to MUC16, with a MUC16 Glycosylation Antibody or antigen binding fragment thereof comprising a VL domain having the amino acid sequence of SEQ ID NO:2. In specific aspects, provided herein is a MUC16 Glycosylation Antibody or antigen binding fragment thereof which competes (e.g., in a dose dependent manner) for immunospecific binding to MUC16, with a MUC16 Glycosylation Antibody or antigen binding fragment thereof comprising a VL domain having the amino acid sequence of SEQ ID NO:22. In specific aspects, provided herein is a MUC16 Glycosylation Antibody or antigen binding fragment thereof which competes (e.g., in a dose dependent manner) for immunospecific binding to MUC16, with a MUC16 Glycosylation Antibody or antigen binding fragment thereof comprising a VL domain having the amino acid sequence of SEQ ID NO:42. In specific aspects, provided herein is a MUC16 Glycosylation Antibody or antigen binding fragment thereof which competes (e.g., in a dose dependent manner) for immunospecific binding to MUC16, with a MUC16 Glycosylation Antibody or antigen binding fragment thereof comprising a VL domain having the amino acid sequence of SEQ ID NO:62. In specific aspects, provided herein is a MUC16 Glycosylation Antibody or antigen binding fragment thereof which competes (e.g., in a dose dependent manner) for immunospecific binding to MUC16, with a MUC16 Glycosylation Antibody or antigen binding fragment thereof comprising a VL domain having the amino acid sequence of SEQ ID NO:82.

In specific aspects, provided herein is a MUC16 Glycosylation Antibody or antigen binding fragment thereof which competes (e.g., in a dose dependent manner) for immunospecific binding to MUC16, with a MUC16 Glycosylation Antibody or antigen binding fragment thereof comprising (a) a VH domain having an amino acid sequence as described in Table 7; and (b) a VL domain having an amino acid sequence as described in Table 8. In specific aspects, provided herein is a MUC16 Glycosylation Antibody or antigen binding fragment thereof which competes (e.g., in a dose dependent manner) for immunospecific binding to MUC16, with a MUC16 Glycosylation Antibody or antigen binding fragment thereof comprising (a) a VH domain having the amino acid sequence of SEQ ID NO: 1; and (b) a VL domain having the amino acid sequence of SEQ ID NO:2. In specific aspects, provided herein is a MUC16 Glycosylation Antibody or antigen binding fragment thereof which competes (e.g., in a dose dependent manner) for immunospecific binding to MUC16, with a MUC16 Glycosylation Antibody or antigen binding fragment thereof comprising (a) a VH domain having the amino acid sequence of SEQ ID NO:21; and (b) a VL domain having the amino acid sequence of SEQ ID NO:22. In specific aspects, provided herein is a MUC16 Glycosylation Antibody or antigen binding fragment thereof which competes (e.g., in a dose dependent manner) for immunospecific binding to MUC16, with a MUC16 Glycosylation Antibody or antigen binding fragment thereof comprising (a) a VH domain having the amino acid sequence of SEQ ID NO:41; and (b) a VL domain having the amino acid sequence of SEQ ID NO:42. In specific aspects, provided herein is a MUC16 Glycosylation Antibody or antigen binding fragment thereof which competes (e.g., in a dose dependent manner) for immunospecific binding to MUC16, with a MUC16 Glycosylation Antibody or antigen binding fragment thereof comprising (a) a VH domain having the amino acid sequence of SEQ ID NO:61; and (b) a VL domain having the amino acid sequence of SEQ ID NO:62. In specific aspects, provided herein is a MUC16 Glycosylation Antibody or antigen binding fragment thereof which competes (e.g., in a dose dependent manner) for immunospecific binding to MUC16, with a MUC16 Glycosylation Antibody or antigen binding fragment thereof comprising (a) a VH domain having the amino acid sequence of SEQ ID NO:81; and (b) a VL domain having the amino acid sequence of SEQ ID NO:82.

In specific aspects, provided herein is a MUC16 Glycosylation Antibody or antigen binding fragment thereof which binds to the same or an overlapping epitope of antibody comprising a VH comprising a VH CDR1, a VH CDR2, and/or a VH CDR3 comprising amino acid sequences as described in Table 1, Table 3, or Table 5. In a particular embodiment, provided herein is a MUC16 Glycosylation Antibody or antigen binding fragment thereof that binds to the same or an overlapping epitope of antibody comprising the VH CDRS of 10C6 (see, Table 1, Table 3, and Table 5). In a particular embodiment, provided herein is a MUC16 Glycosylation Antibody or antigen binding fragment thereof that binds to the same or an overlapping epitope of antibody comprising the VH CDRS of 7B12 (see, Table 1, Table 3, and Table 5). In a particular embodiment, provided herein is a MUC16 Glycosylation Antibody or antigen binding fragment thereof that competes (e.g., in a dose-dependent manner), for immunospecific binding to MUC16, with a MUC16 Glycosylation Antibody or antigen binding fragment thereof comprising the VH CDRS of 19C11 (see, Table 1, Table 3, and Table 5). In a particular embodiment, provided herein is a MUC16 Glycosylation Antibody or antigen binding fragment thereof that binds to the same or an overlapping epitope of antibody comprising the VH CDRS of 16C5 (see, Table 1, Table 3, and Table 5). In a particular embodiment, provided herein is a MUC16 Glycosylation Antibody or antigen binding fragment thereof that binds to the same or an overlapping epitope of antibody comprising the VH CDRS of 18C6 (see, Table 1, Table 3, and Table 5).

In specific aspects, provided herein is a MUC16 Glycosylation Antibody or antigen binding fragment thereof binds to the same or an overlapping epitope of antibody comprising a VL comprising a VL CDR1, a VL CDR2, and/or a VL CDR3 comprising amino acid sequences as described in Table 2, Table 4, or Table 6. In a particular embodiment, provided herein is a MUC16 Glycosylation Antibody or antigen binding fragment thereof that binds to the same or an overlapping epitope of antibody comprising the VL CDRS of 10C6 (see, Table 2, Table 4, and Table 6). In a particular embodiment, provided herein is a MUC16 Glycosylation Antibody or antigen binding fragment thereof that binds to the same or an overlapping epitope of antibody comprising the VL CDRS of 7B12 (see, Table 2, Table 4, and Table 6). In a particular embodiment, provided herein is a MUC16 Glycosylation Antibody or antigen binding fragment thereof that binds to the same or an overlapping epitope of antibody comprising the VL CDRS of 19C11 (see, Table 2, Table 4, and Table 6). In a particular embodiment, provided herein is a MUC16 Glycosylation Antibody or antigen binding fragment thereof that binds to the same or an overlapping epitope of antibody comprising the VL CDRS of 16C5 (see, Table 2, Table 4, and Table 6). In a particular embodiment, provided herein is a MUC16 Glycosylation Antibody or antigen binding fragment thereof that binds to the same or an overlapping epitope of antibody comprising the VL CDRS of 18C6 (see, Table 2, Table 4, and Table 6).

In specific aspects, provided herein is a MUC16 Glycosylation Antibody or antigen binding fragment thereof that binds to the same or an overlapping epitope of antibody comprising (a) a VH comprising a VH CDR1, a VH CDR2, and/or a VH CDR3 comprising amino acid sequences as described in Table 1, Table 3, or Table 5; and (b) a VL comprising a VL CDR1, a VL CDR2, and/or a VL CDR3 comprising amino acid sequences as described in Table 2, Table 4, or Table 6. In a particular embodiment, provided herein is a MUC16 Glycosylation Antibody or antigen binding fragment thereof that binds to the same or an overlapping epitope of antibody comprising (a) the VH CDRS of 10C6 (see, Table 1, Table 3, and Table 5); and (b) the VL CDRS of 10C6 (see, Table 2, Table 4, and Table 6). In a particular embodiment, provided herein is a MUC16 Glycosylation Antibody or antigen binding fragment thereof that binds to the same or an overlapping epitope of antibody comprising (a) the VH CDRS of 7B12 (see, Table 1, Table 3, and Table 5); and (b) the VL CDRS of 7B12 (see, Table 2, Table 4, and Table 6). In a particular embodiment, provided herein is a MUC16 Glycosylation Antibody or antigen binding fragment thereof that binds to the same or an overlapping epitope of antibody comprising (a) the VH CDRS of 19C11 (see, Table 1, Table 3, and Table 5); and (b) the VL CDRS of 19C11 (see, Table 2, Table 4, and Table 6). In a particular embodiment, provided herein is a MUC16 Glycosylation Antibody or antigen binding fragment thereof that binds to the same or an overlapping epitope of antibody comprising (a) the VH CDRS of 16C5 (see, Table 1, Table 3, and Table 5); and (b) the VL CDRS of 16C5 (see, Table 2, Table 4, and Table 6). In a particular embodiment, provided herein is a MUC16 Glycosylation Antibody or antigen binding fragment thereof that binds to the same or an overlapping epitope of antibody comprising (a) the VH CDRS of 18C6 (see, Table 1, Table 3, and Table 5); and (b) the VL CDRS of 18C6 (see, Table 2, Table 4, and Table 6).

In specific aspects, provided herein is a MUC16 Glycosylation Antibody or antigen binding fragment thereof that binds to the same or an overlapping epitope of antibody comprising a VH domain having an amino acid sequence as described in Table 7. In specific aspects, provided herein is a MUC16 Glycosylation Antibody or antigen binding fragment thereof that binds to the same or an overlapping epitope of antibody comprising a VH domain having the amino acid sequence of SEQ ID NO: 1. In specific aspects, provided herein is a MUC16 Glycosylation Antibody or antigen binding fragment thereof that binds to the same or an overlapping epitope of antibody comprising a VH domain having the amino acid sequence of SEQ ID NO:21. In specific aspects, provided herein is a MUC16 Glycosylation Antibody or antigen binding fragment thereof that binds to the same or an overlapping epitope of antibody comprising a VH domain having the amino acid sequence of SEQ ID NO:41. In specific aspects, provided herein is a MUC16 Glycosylation Antibody or antigen binding fragment thereof that binds to the same or an overlapping epitope of antibody comprising a VH domain having the amino acid sequence of SEQ ID NO:61. In specific aspects, provided herein is a MUC16 Glycosylation Antibody or antigen binding fragment thereof that binds to the same or an overlapping epitope of antibody comprising a VH domain having the amino acid sequence of SEQ ID NO:81.

In specific aspects, provided herein is a MUC16 Glycosylation Antibody or antigen binding fragment thereof that binds to the same or an overlapping epitope of antibody comprising a VL domain having an amino acid sequence as described in Table 8. In specific aspects, provided herein is a MUC16 Glycosylation Antibody or antigen binding fragment thereof that binds to the same or an overlapping epitope of antibody comprising a VL domain having the amino acid sequence of SEQ ID NO:2. In specific aspects, provided herein is a MUC16 Glycosylation Antibody or antigen binding fragment thereof that binds to the same or an overlapping epitope of antibody comprising a VL domain having the amino acid sequence of SEQ ID NO:22. In specific aspects, provided herein is a MUC16 Glycosylation Antibody or antigen binding fragment thereof that binds to the same or an overlapping epitope of antibody comprising a VL domain having the amino acid sequence of SEQ ID NO:42. In specific aspects, provided herein is a MUC16 Glycosylation Antibody or antigen binding fragment thereof that binds to the same or an overlapping epitope of antibody comprising a VL domain having the amino acid sequence of SEQ ID NO:62. In specific aspects, provided herein is a MUC16 Glycosylation Antibody or antigen binding fragment thereof that binds to the same or an overlapping epitope of antibody comprising a VL domain having the amino acid sequence of SEQ ID NO:82.

In specific aspects, provided herein is a MUC16 Glycosylation Antibody or antigen binding fragment thereof that binds to the same or an overlapping epitope of antibody comprising (a) a VH domain having an amino acid sequence as described in Table 7; and (b) a VL domain having an amino acid sequence as described in Table 8. In specific aspects, provided herein is a MUC16 Glycosylation Antibody or antigen binding fragment thereof that binds to the same or an overlapping epitope of antibody comprising (a) a VH domain having the amino acid sequence of SEQ ID NO:1; and (b) a VL domain having the amino acid sequence of SEQ ID NO:2. In specific aspects, provided herein is a MUC16 Glycosylation Antibody or antigen binding fragment thereof that binds to the same or an overlapping epitope of antibody comprising (a) a VH domain having the amino acid sequence of SEQ ID NO:21; and (b) a VL domain having the amino acid sequence of SEQ ID NO:22. In specific aspects, provided herein is a MUC16 Glycosylation Antibody or antigen binding fragment thereof that binds to the same or an overlapping epitope of antibody comprising (a) a VH domain having the amino acid sequence of SEQ ID NO:41; and (b) a VL domain having the amino acid sequence of SEQ ID NO:42. In specific aspects, provided herein is a MUC16 Glycosylation Antibody or antigen binding fragment thereof that binds to the same or an overlapping epitope of antibody comprising (a) a VH domain having the amino acid sequence of SEQ ID NO:61; and (b) a VL domain having the amino acid sequence of SEQ ID NO:62. In specific aspects, provided herein is a MUC16 Glycosylation Antibody or antigen binding fragment thereof that binds to the same or an overlapping epitope of antibody comprising (a) a VH domain having the amino acid sequence of SEQ ID NO:81; and (b) a VL domain having the amino acid sequence of SEQ ID NO:82.

Assays known to one of skill in the art or described herein (e.g., X-ray crystallography, ELISA assays, etc.) can be used to determine if two antibodies bind to the same epitope. Affinity can be measured and/or expressed in a number of ways known in the art, including, but not limited to, equilibrium dissociation constant ($K_D$), and equilibrium association constant ($K_A$). The $K_D$ can be determined by techniques known to one of ordinary skill in the art, such as biolayer interferometry.

In certain embodiments, the epitope of a MUC16 Glycosylation Antibody or antigen binding fragment thereof described herein is used as an immunogen to produce antibodies. See, e.g., Section 5.3 and Section 6.2 for methods for producing antibodies.

5.1.2 Functional Characteristics

In certain embodiments, a MUC16 Glycosylation Antibody or an antigen-binding fragment thereof described herein binds to MUC16 with a $k_d$ of less than $0.5\times10^{-3}$/s, $1\times10^{-3}$/s, $1.5\times10^{-3}$/s, $2\times10^{-3}$/s, $2.5\times10^{-3}$/s, $3\times10^{-3}$/s, $4\times10^{-3}$/s, $5\times10^{-3}$/s, $6\times10^{-3}$/s, $7\times10^{-3}$/s, $8\times10^{-3}$/s, $9\times10^{-3}$/s, $1\times10^{-4}$/s, $2\times10^{-4}$/s, $3\times10^{-4}$/s, $4\times10^{-4}$/s, $5\times10^{-4}$/s, $6\times10^{-4}$/s, $7\times10^{-4}$/s, or $8\times10^{-4}$/s. In some embodiments, a MUC16 Glycosylation Antibody or an antigen-binding fragment thereof described herein binds to MUC16 with a $k_d$ of about $0.5\times10^{-3}$/s, $1\times10^{-3}$/s, $1.5\times10^{-3}$/s, $2\times10^{-3}$/s, $2.5\times10^{-3}$/s, $3\times10^{-3}$/s, $4\times10^{-3}$/s, $5\times10^{-3}$/s, $6\times10^{-3}$/s, $7\times10^{-3}$/s, $8\times10^{-3}$/s, $9\times10^{-3}$/s, $1\times10^{-4}$/s, $2\times10^{-4}$/s, $3\times10^{-4}$/s, $4\times10^{-4}$/s, $5\times10^{-4}$/s, $6\times10^{-4}$/s, $7\times10^{-4}$/s, or $8\times10^{-4}$/s. In some embodiments, a MUC16 Glycosylation Antibody or an antigen-binding fragment thereof described herein binds to MUC16 with a $k_d$ of about $0.5\times10^{-3}$/s to $8\times10^{-4}$/s. In a specific embodiment, a MUC16 Glycosylation Antibody or an antigen-binding fragment thereof described herein binds to MUC16 with a $k_d$ of about $1\times10^{-3}$/s. In a specific embodiment, a MUC16 Glycosylation Antibody or an antigen-binding fragment thereof described herein binds to MUC16 with a $k_d$ of about $1.5\times10^{-3}$/s. In a specific embodiment, a MUC16 Glycosylation Antibody or an antigen-binding fragment thereof described herein binds to MUC16 with a $k_d$ of about $2\times10^{-3}$/s. In a specific embodiment, a MUC16 Glycosylation Antibody or an antigen-binding fragment thereof described herein binds to MUC16 with a $k_d$ of about $2\times10^{-4}$/s. In a specific embodiment, a MUC16 Glycosylation Antibody or an antigen-binding fragment thereof described herein binds to MUC16 with a $k_d$ of about $7\times10^{-4}$/s.

In certain embodiments, a MUC16 Glycosylation Antibody or an antigen-binding fragment thereof described herein binds to MUC16 with a $k_a$ of at least $2.5\times10^4$/s, $3\times10^4$/s, $3.5\times10^4$/s, $4\times10^4$/s, $4.5\times10^4$/s, $5\times10^4$/s, $5.5\times10^4$/s, $6\times10^4$/s, $6.5\times10^4$/s, $7\times10^4$/s, $7.5\times10^4$/s, $8\times10^4$/s, $9\times10^4$/s, or $9\times10^5$/s. In some embodiments, a MUC16 Glycosylation Antibody or an antigen-binding fragment thereof described herein binds to MUC16 with a $k_a$ of about $2.5\times10^4$/s, $3\times10^4$/s, $3.5\times10^4$/s, $4\times10^4$/s, $4.5\times10^4$/s, $5\times10^4$/s, $5.5\times10^4$/s, $6\times10^4$/s, $6.5\times10^4$/s, $7\times10^4$/s, $7.5\times10^4$/s, $8\times10^4$/s, $9\times10^4$/s, or $9\times10^5$/s. In some embodiments, a MUC16 Glycosylation Antibody or an antigen-binding fragment thereof described herein, binds to MUC16 with a $k_a$ of about $4\times10^4$/s. In a specific embodiment, a MUC16 Glycosylation Antibody or an antigen-binding fragment thereof described herein binds to MUC16 with a $k_a$ of about $6\times10^4$/s. In a specific embodiment, a MUC16 Glycosylation Antibody or an antigen-binding fragment thereof described herein binds to MUC16 with a $k_a$ of about $7.5\times10^4$/s.

In certain embodiments, a MUC16 Glycosylation Antibody or an antigen-binding fragment thereof described herein binds to MUC16 with a $K_D$ of less than 1000 nM, 500 nM, 100 nM, 50 nM, 25 nM, 20 nM, 15 nM, 10 nM, 5 nM, 4 nM, 3 nM, 2 nM, 1 nM, 0.5 nM, 0.1 nM, or 0.05 nM. In some embodiments, a MUC16 Glycosylation Antibody or an antigen-binding fragment thereof described herein binds to MUC16 with a $K_D$ of about 1000 nM, 500 nM, 100 nM, 50 nM, 25 nM, 20 nM, 15 nM, 10 nM, 5 nM, 4 nM, 3 nM, 2 nM, 1 nM, 0.5 nM, 0.1 nM, or 0.05 nM. In some embodiments, a MUC16 Glycosylation Antibody or an antigen-binding fragment thereof described herein binds to MUC16 with a $K_D$ of about 500 nM to 1000 nM. In some embodiments, a MUC16 Glycosylation Antibody or an antigen-binding fragment thereof described herein binds to MUC16 with a $K_D$ of about 5 nM to 75 nM. In a specific embodiment, a MUC16 Glycosylation Antibody or an antigen-binding fragment thereof described herein binds to MUC16 with a $K_D$ of about 7 nM. In another specific embodiment, a MUC16 Glycosylation Antibody or an antigen-binding fragment thereof described herein binds to MUC16 with a $K_D$ of about 10 pM. In another specific embodiment, a MUC16 Glycosylation Antibody or an antigen-binding fragment thereof described herein binds to MUC16 with a $K_D$ of about 15 pM. In another specific embodiment, a MUC16 Glycosylation Antibody or an antigen-binding fragment thereof described herein binds to MUC16 with a $K_D$ of about 20 pM. In another specific embodiment, a MUC16 Glycosylation Antibody or an antigen-binding fragment thereof described herein binds to MUC16 with a $K_D$ of about 25 pM. In another specific embodiment, a MUC16 Glycosylation Antibody or an antigen-binding fragment thereof described herein binds to MUC16 with a $K_D$ of about 65 pM. As used herein, the terms "about" when used to modify a numeric value or numeric range, indicate that deviations of 5% to 10% above and 5% to 10% below the value or range remain within the intended meaning of the recited value or range.

In certain embodiments, a MUC16 Glycosylation Antibody or an antigen-binding fragment thereof described herein binds to a cell recombinantly expressing a first form of MUC16, which first form is glycosylated, and wherein the amino acid sequence of the first form is SEQ ID NO:133. In certain embodiments, the cell is a cancer cell (e.g., an ovarian cancer cell, a lung cancer cell, a pancreatic cancer cell, a breast cancer cell, a fallopian tube cancer cell, a uterine (e.g., endometrial) cancer cell, or a primary peritoneum cancer cell). In certain embodiments, the cell is an ovarian cancer cell. In certain embodiments, the cell is a lung cancer cell. In certain embodiments, the cell is a pancreatic cancer cell. In certain embodiments, the cell is a breast cancer cell. In certain embodiments, the cell is a uterine (e.g., endometrial) cancer cell. In certain embodiments, the cell is a fallopian tube cancer cell. In certain embodiments, the cell is a primary peritoneum cancer cell. In certain embodiments, the cell is a SKOV3 cell. In certain embodiments, the MUC16 Glycosylation Antibody or antigen-binding fragment thereof provided herein binds to a cell recombinantly expressing a first form of MUC16, which first form is glycosylated, and wherein the amino acid sequence of the first form is SEQ ID NO: 133 at least 10, 20, 30, 40, 50, 60, 70, 80, 90, 100, 250, 500, or 1000 fold more than an isotype control antibody binds to the cells. An isotype control antibody is an art-recognized term. In certain embodiments, the MUC16 Glycosylation Antibody or antigen-binding fragment thereof provided herein binds to a cell recombinantly expressing a first form of MUC16, which first form is glycosylated, and wherein the amino acid sequence of the first form is SEQ ID NO: 133 about 10, 20, 30, 40, 50, 60, 70, 80, 90, 100, 250, 500, or 1000 fold more than an isotype control antibody binds to the cell. In certain embodiments, the MUC16 Glycosylation Antibody or antigen-binding fragment thereof provided herein binds to a cell recombinantly expressing a first form of MUC16, which first form is glycosylated, and wherein the amino acid sequence of the first form is SEQ ID NO:133 between 10 and 50, 50 and 100, 100 and 250, 250 and 500, or 500 and 1000 fold more than an isotype control antibody binds to the cell.

The protein encoded by the amino acid sequence of SEQ ID NO: 133 is also referred to herein as $MUC16^{c114}$ and consists of the C-terminal 114 amino acid residues of mature MUC16 (SEQ ID NO: 150 being the sequence of mature MUC16). $MUC16^{c114}$ is capable of being N-glycosylated at the asparagine amino acids of positions 1, 24, and 30 of SEQ ID NO: 133 (corresponding to amino acid positions Asn1777, Asn1800, and Asn1806 of SEQ ID NO: 150).

In certain embodiments, a MUC16 Glycosylation Antibody or an antigen-binding fragment thereof described herein lacks immunospecific binding to a cell recombinantly expressing a second form of MUC16, which second form is unglycosylated, and wherein the amino acid sequence of the second form is SEQ ID NO:139. In certain embodiments, the cells are ovarian cancer cells. In certain embodiments, the cells are lung cancer cells. In certain embodiments, the cells are pancreatic cancer cells. In certain embodiments, the cells are breast cancer cells. In certain embodiments, the cells are uterine (e.g., endometrial) cancer cells. In certain embodiments, the cells are fallopian tube cancer cells. In certain embodiments, the cells are primary peritoneum cancer cells. In certain embodiments, the cells are SKOV3 cells. In certain embodiments, the second form of MUC16 is fused to a detectable protein, such as, for example, green fluorescent protein or red fluorescent protein. In certain embodiments, the MUC16 Glycosylation Antibody or antigen-binding fragment thereof provided herein binds to a cell recombinantly expressing a second form of MUC16, which second form is unglycosylated, and wherein the amino acid sequence of the second form is SEQ ID NO:139, at most 1.1, 1.2, 1.3, 1.4, 1.5, 2, 3, 4, or 5 fold more than an isotype control antibody binds to the cells. In certain embodiments, the MUC16 Glycosylation Antibody or antigen-binding fragment thereof provided herein binds to a cell recombinantly expressing a second form of MUC16, which second form is unglycosylated, and wherein the amino acid sequence of the second form is SEQ ID NO: 139, about 1.1, 1.2, 1.3, 1.4, 1.5, 2, 3, 4, or 5 fold more than an isotype control antibody binds to the cells. In certain embodiments, the MUC16 Glycosylation Antibody or antigen-binding fragment thereof provided herein binds to a cell recombinantly expressing a second form of MUC16, which second form is unglycosylated, and wherein the amino acid sequence of the second form is SEQ ID NO:139, between 0 and 1.1, 1.1 and 1.5, 1.5 and 3, or 3 and 5 fold more than an isotype control antibody binds to the cells.

The protein encoded by the amino acid sequence of SEQ ID NO: 139 is also referred to herein as MUC16$^{c114\text{-}N3}$. MUC16$^{c114\text{-}N3}$ consists of the C-terminal 114 amino acid residues of mature MUC16 (SEQ ID NO: 150 being the sequence of mature MUC16), except that the asparagine at amino acid position 30 (corresponding to amino acid position 1806 of SEQ ID NO: 150) has been mutated to an alanine. Thus, MUC16$^{c114\text{-}N3}$ is not capable of being N-glycosylated at amino acid position 30 of SEQ ID NO: 139 (corresponding to amino acid position Asn1806 of SEQ ID NO: 150).

In certain embodiments, the MUC16 Glycosylation Antibody or antigen-binding fragment thereof provided herein binds to a cell recombinantly expressing a second form of MUC16, which second form is unglycosylated, and wherein the amino acid sequence of the second form is SEQ ID NO:139, at least 3, 4, 5, 6, 7, 8, 9, 10, 11, 12, 13, 14, 15, 20, 30, or 40 fold less than 4H11 binds to the cells. In certain embodiments, the MUC16 Glycosylation Antibody or antigen-binding fragment thereof provided herein binds to a cell recombinantly expressing a second form of MUC16, which second form is unglycosylated, and wherein the amino acid sequence of the second form is SEQ ID NO:139, about 3, 4, 5, 6, 7, 8, 9, 10, 11, 12, 13, 14, 15, 20, 30, or 40 fold less than 4H11 binds to the cells. In certain embodiments, the MUC16 Glycosylation Antibody or antigen-binding fragment thereof provided herein binds to a cell recombinantly expressing a second form of MUC16, which second form is unglycosylated, and wherein the amino acid sequence of the second form is SEQ ID NO:139, between 3 and 5, 5 and 10, 10 and 20, or 20 and 40 fold less than 4H11 binds to the cell.

Assays to determine binding of a MUC16 Glycosylation Antibody or antigen-binding fragment thereof described herein to a cell, such as, for example, FACs, are known to a person skilled in the art. See, for example, the methods described in Section 6.2.

As used herein, “4H11” refers to the monoclonal anti-MUC16 antibody designated as 4H11 in Rao et al. Appl. Immunohistochem Mol Morphol, 2010, 18(5):462-72 and in International Patent Application Publication No. WO 2011/119979.

In certain embodiments, a MUC16 Glycosylation Antibody or an antigen-binding fragment thereof described herein, binds to a peptide comprising the amino acid sequence CTRNGTQLQNFTLDRSSV (SEQ ID NO:130), wherein amino acid residue number 4 (N4) and amino acid residue number 10 (N10) of CTRNGTQLQNFTLDRSSV (SEQ ID NO:130) are glycosylated. In certain embodiments, the peptide consists of the amino acid sequence CTRNGTQLQNFTLDRSSV (SEQ ID NO:130), wherein amino acid residue number 4 (N4) and amino acid residue number 10 (N10) of CTRNGTQLQNFTLDRSSV (SEQ ID NO:130) are glycosylated. In certain embodiments, the glycosylation consists of an N-linked chitobiose. In certain embodiments, a MUC16 Glycosylation Antibody or an antigen-binding fragment thereof binds to a peptide comprising the amino acid sequence CGTQLQNFTLDRSSV (SEQ ID NO:131), wherein amino acid residue number 7 (N7) of CGTQLQNFTLDRSSV (SEQ ID NO:131) is glycosylated. In certain embodiments, the peptide consists of the amino acid sequence CGTQLQNFTLDRSSV (SEQ ID NO:131), wherein amino acid residue number 7 (N7) of CGTQLQNFTLDRSSV (SEQ ID NO:131) is glycosylated. In certain embodiments, the glycosylation consists of an N-linked chitobiose. In certain embodiments, a MUC16 Glycosylation Antibody or an antigen-binding fragment thereof binds to a mixture of peptides, wherein the mixture of peptides comprises (a) a first peptide comprising the amino acid sequence CTRNGTQLQNFTLDRSSV (SEQ ID NO:130), wherein amino acid residue number 4 (N4) and amino acid residue number 10 (N10) of CTRNGTQLQNFTLDRSSV (SEQ ID NO:130) are glycosylated, and (b) a second peptide comprising of the amino acid sequence CGTQLQNFTLDRSSV (SEQ ID NO:131), wherein amino acid residue number 7 (N7) of CGTQLQNFTLDRSSV (SEQ ID NO:131) is glycosylated. In certain embodiments, the first peptide consists of the amino acid sequence CTRNGTQLQNFTLDRSSV (SEQ ID NO:130), wherein amino acid residue number 4 (N4) and amino acid residue number 10 (N10) of CTRNGTQLQNFTLDRSSV (SEQ ID NO:130) are glycosylated. In certain embodiments, the second peptide consists of amino acid sequence CGTQLQNFTLDRSSV (SEQ ID NO:131), wherein amino acid residue number 7 (N7) of CGTQLQNFTLDRSSV (SEQ ID NO:131) is glycosylated. In certain embodiments, the glycosylation consists of an N-linked chitobiose.

Assays to determine binding of a MUC16 Glycosylation Antibody or antigen-binding fragment thereof described herein to a cell, such as, for example, ELISA, are known to a person skilled in the art. See, for example, the methods described in Section 6.2. In certain embodiments, the MUC16 Glycosylation Antibody or antigen-binding fragment thereof provided herein binds to the peptide(s) at least 2, 3, 4, 5, 6, 7, 8, 9, 10, 11, 12, 13, 14, 15, 16, 17, 18, 19, 20, or 30 fold more than binding of anti-MUC16 monoclonal antibody 4H11 to the peptide. In certain embodiments, the MUC16 Glycosylation Antibody or antigen-binding fragment thereof provided herein binds to the peptide(s) at about 2, 3, 4, 5, 6, 7, 8, 9, 10, 11, 12, 13, 14, 15, 16, 17, 18, 19, 20, or 30 fold more than binding of anti-MUC16 monoclonal antibody 4H11 to the peptide.

In certain embodiments, the MUC16 Glycosylation Antibody or antigen-binding fragment thereof provided herein binds to the peptide(s) with a $k_d$ of less than $0.5\times10^{-3}$/s, $1\times10^{-3}$/s, $1.5\times10^{-3}$/s, $2\times10^{-3}$/s, $2.5\times10^{-3}$/s, $3\times10^{-3}$/s, $4\times10^{-3}$/s, $5\times10^{-3}$/s, $6\times10^{-3}$/s, $7\times10^{-3}$/s, $8\times10^{-3}$/s, $9\times10^{-3}$/s, $1\times10^{-4}$/s, $2\times10^{-4}$/s, $3\times10^{-4}$/s, $4\times10^{-4}$/s, $5\times10^{-4}$/s, $6\times10^{-4}$/s, $7\times10^{-4}$/s, or $8\times10^{-4}$/s. In some embodiments, the MUC16 Glycosylation Antibody or antigen-binding fragment thereof provided herein binds to the peptide(s) with a $k_d$ of about $0.5\times10^{-3}$/s, $1\times10^{-3}$/s, $1.5\times10^{-3}$/s, $2\times10^{-3}$/s, $2.5\times10^{-3}$/s, $3\times10^{-3}$/s, $4\times10^{-3}$/s, $5\times10^{-3}$/s, $6\times10^{-3}$/s, $7\times10^{-3}$/s, $8\times10^{-3}$/s, $9\times10^{-3}$/s, $1\times10^{-4}$/s, $2\times10^{-4}$/s, $3\times10^{-4}$/s, $4\times10^{-4}$/s, $5\times10^{-4}$/s, $6\times10^{-4}$/s, $7\times10^{-4}$/s, or $8\times10^{-4}$/s. In some embodiments, the MUC16 Glycosylation Antibody or antigen-binding fragment thereof provided herein binds to the peptide(s) with a $k_d$ of about $0.5\times10^{-3}$/s to $8\times10^{-4}$/s.

In certain embodiments, the MUC16 Glycosylation Antibody or antigen-binding fragment thereof provided herein binds to the peptide(s) with a $k_a$ of at least $2.5\times10^{4}$/s, $3\times10^{4}$/s, $3.5\times10^{4}$/s, $4\times10^{4}$/s, $4.5\times10^{4}$/s, $5\times10^{4}$/s, $5.5\times10^{4}$/s, $6\times10^{4}$/s, $6.5\times10^{4}$/s, $7\times10^{4}$/s, $7.5\times10^{4}$/s, $8\times10^{4}$/s, $9\times10^{4}$/s, or $9\times10^{5}$/s. In some embodiments, the MUC16 Glycosylation Antibody or antigen-binding fragment thereof provided herein binds to the peptide(s) with a $k_a$ of about $2.5\times10^{4}$/s, $3\times10^4$/s, $3.5\times10^4$/s, $4\times10^4$/s, $4.5\times10^4$/s, $5\times10^4$/s, $5.5\times10^4$/s, $6\times10^4$/s, $6.5\times10^4$/s, $7\times10^4$/s, $7.5\times10^4$/s, $8\times10^4$/s, $9\times10^4$/s, or $9\times10^5$/s. In some embodiments, the MUC16 Glycosylation Antibody or antigen-binding fragment thereof provided herein binds to the peptide(s) with a $k_a$ of about $2.5\times10^{-4}$/s to $9\times10^{-5}$/s.

In certain embodiments, the MUC16 Glycosylation Antibody or antigen-binding fragment thereof provided herein binds to the peptide(s) with a $K_D$ of less than 1000 nM, 500 nM, 100 nM, 50 nM, 25 nM, 20 nM, 15 nM, 10 nM, 5 nM, 4 nM, 3 nM, 2 nM, 1 nM, 0.5 nM, 0.1 nM, or 0.05 nM. In some embodiments, the MUC16 Glycosylation Antibody or antigen-binding fragment thereof provided herein binds to the peptide(s) with a $K_D$ of about 1000 nM, 500 nM, 100 nM, 50 nM, 25 nM, 20 nM, 15 nM, 10 nM, 5 nM, 4 nM, 3 nM, 2 nM, 1 nM, 0.5 nM, 0.1 nM, or 0.05 nM. In some embodiments, the MUC16 Glycosylation Antibody or antigen-binding fragment thereof provided herein binds to the peptide(s) with a $K_D$ of about 500 nM to 1000 nM.

In certain embodiments, a MUC16 Glycosylation Antibody or an antigen-binding fragment lacks immunospecific binding to the amino acid sequence CTRNGTQLQNFTLDRSSV (SEQ ID NO: 130), wherein amino acid residue number 4 (N4) and amino acid residue number 10 (N10) of CTRNGTQLQNFTLDRSSV (SEQ ID NO:130) are not glycosylated. In certain embodiments, a MUC16 Glycosylation Antibody or an antigen-binding fragment thereof lacks immunospecific binding to the amino acid sequence CGTQLQNFTLDRSSV (SEQ ID NO: 131), wherein amino acid residue number 7 (N7) of CGTQLQNFTLDRSSV (SEQ ID NO:131) is glycosylated. In certain embodiments, a MUC16 Glycosylation Antibody or an antigen-binding fragment thereof described herein, lacks immunospecific binding to a mixture of peptides, wherein the mixture of peptides comprises (a) a first peptide consisting of the amino acid sequence CTRNGTQLQNFTLDRSSV (SEQ ID NO: 130), wherein amino acid residue number 4 (N4) and amino acid residue number 10 (N10) of CTRNGTQLQNFTLDRSSV (SEQ ID NO:130) are glycosylated and (b) a second peptide consisting of the amino acid sequence CGTQLQNFTLDRSSV (SEQ ID NO:131), wherein amino acid residue number 7 (N7) of CGTQLQNFTLDRSSV (SEQ ID NO:131) is glycosylated.

In certain embodiments, a MUC16 Glycosylation Antibody or an antigen-binding fragment thereof described herein inhibits matrigel invasion in vitro of cells recombinantly expressing a form of MUC16 which is glycosylated and wherein the amino acid sequence of the form of MUC16 is SEQ ID NO:133 ($MUC16^{c114}$). In certain embodiments, the cells recombinantly expressing glycosylated $MUC16^{c114}$ are SKOV3 cells. In certain embodiments, the glycosylated form of $MUC16^{c114}$ is N-glycosylated. In certain embodiments, the glycosylated form of $MUC16^{c114}$ is N-glycosylated at amino acid residue Asn30 (corresponding to Asn1806 of mature MUC16 (SEQ ID NO:150)). In certain embodiments, the glycosylated form of $MUC16^{c114}$ is N-glycosylated at amino acid residues Asn 24 and Asn30 (corresponding to Asn1800 and Asn1806, respectively, of mature MUC16 (SEQ ID NO:150)). In certain embodiments, the glycosylated form of $MUC16^{c114}$ is N-glycosylated at amino acid residues Asn1, Asn24, and Asn30 (corresponding to Asn1777, Asn1800, and Asn1806, respectively, of mature MUC16 (SEQ ID NO:150)). In certain embodiments, the glycosylation comprises N-linked chitobiose. In certain embodiments, the glycosylation consists of an N-linked chitobiose. In certain embodiments, matrigel invasion is inhibited by at least 1.25, 1.5, 1.75, 2, 3, 4, 5, 6, 7, 8, 9, or 10 fold as compared to matrigel invasion in vitro of the cells wherein the cells are treated with a control antibody (e.g., an antibody that does not target MUC16) or with 4H11. In certain embodiments, matrigel invasion is inhibited by about 1.25, 1.5, 1.75, 2, 3, 4, 5, 6, 7, 8, 9, or 10 fold as compared to matrigel invasion in vitro of the cells wherein the cells are treated with a control antibody (e.g., an antibody that does not target MUC16) or with 4H11.

Assays to determine the MUC16 Glycosylation Antibody- or antigen-binding fragment-mediated inhibition of matrigel invasion are known to a person skilled in the art. See, for example, the methods described in Section 6.2. For example, BD BioCoat™ Matrigel™ Invasion Inserts or Chambers (catalog #354480 in 24 well plate) and Control Inserts (catalog #354578 in 24 well plate) can be purchased from BD Biosciences, MA. Matrigel Invasion assay can be performed as per manufacturer's protocol. Briefly, the matrigel chambers in 24 well plates (stored at −20° C.) and control inserts (stored at 4° C.) are allowed to come to room temperature. Both inserts are rehydrated with 0.5 mL of serum free medium in the insert as well as in the outside well of the 24 well plate, for 2 hrs at 37° C. 5% $CO_2$ humidified incubator. Cultured SKOV3 cells are trypsinized and washed with culture medium. A million cells are separated into another centrifuge tube and washed 3 times with serum free medium. These cells are later adjusted to give 5,000 cells in 0.5 mL serum free medium. The medium in the rehydrated inserts are removed and the insert was transferred into a new 24 well plate containing 0.75 mL of 10% Foetal Bovine Serum (FBS) containing culture medium in the well which serves as a chemo attractant. Immediately, 0.5 mL of the cells (5,000 cells) in serum free medium is added to the insert. Proper care is taken to see that there is no air bubble is trapped in the insert and the outside well. The 24 well plate is incubated at 37° C. 5% $CO_2$ humidified incubator for 48 hrs. After incubation, the non-invading cells are removed from the upper surface of the membrane by "scrubbing" by inserting a cotton tipped swab into matrigel or control insert and gently applied pressure while moving the tip of the swab over the membrane surface. The scrubbing is repeated with a second swab moistened with medium. Then the inserts are stained in a new 24 well plate containing 0.5 mL of 0.5% crystal violet stain in distilled water for 30 minutes. Following staining the inserts are rinsed in 3 beakers of distilled water to remove excess stain. The inserts are air dried for in a new 24 well plate. The invaded cells are hand counted under an inverted microscope at 200× magnification. Several fields of triplicate membranes were counted and recorded in the figure.

In certain embodiments, a MUC16 Glycosylation Antibody or an antigen-binding fragment thereof described herein is capable of inhibiting or reducing metastasis, inhibiting tumor growth or inducing tumor regression in mouse model studies. For example, tumor cell lines can be introduced into athymic nude mice, and the athymic mice can be administered MUC16 Glycosylation Antibodies described herein one or more times, and tumor progression of the injected tumor cells can be monitored over a period of weeks and/or months. In some cases, administration of the MUC16 Glycosylation Antibodies or antigen-binding fragments thereof to the athymic nude mice can occur prior to introduction of the tumor cell lines. In a certain embodiment, SKOV3 cells expressing $MUC16^{c114}$ are utilized for the mouse xenograft models described herein. See, e.g., Section 6.2 and Section 6.3.

In specific embodiments, MUC16 Glycosylation Antibodies or antigen-binding fragments thereof described herein inhibit tumor growth or induce tumor regression in a mouse model by at least about 5%, 10%, 15%, 20%, 25%, 30%, 35%, 40%, 45%, 50%, 55%, 60%, 65%, 70%, 75%, 80%, 85%, 90%, 95%, 98%, 99%, or 100% as assessed by methods described herein or known to one of skill in the art, as compared to mock treated mice. In specific embodiments, MUC16 Glycosylation Antibodies or antigen-binding fragments thereof described herein inhibit tumor growth or induce tumor regression in a mouse model by at least about 25% or 35%, optionally to about 75%, as assessed by methods described herein or known to one of skill in the art, as compared to mock-treated mice. In specific embodiments, MUC16 Glycosylation Antibodies or antigen-binding fragments thereof described herein inhibit tumor growth or induce tumor regression in a mouse model by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art, as compared to mock-treated mice. Mock-treated mice can, for example, be treated with phosphate buffered saline or a control (e.g., anti-IgG antibody).

Determining tumor growth inhibition or tumor regression can be assessed, for example, by monitoring tumor size over a period of time, such as by physical measurement of palpable tumors, or other visual detection methods. For example, tumor cell lines can be generated to recombinantly express a visualization agent, such as green fluorescent protein (GFP) or luciferase, then in vivo visualization of GFP can be carried out by microscopy, and in vivo visualization of luciferase can be carried out by administering luciferase substrate to the xenograft mice and detecting luminescent due to the luciferase enzyme processing the luciferase substrate. The degree or level of detection of GFP or luciferase correlates to the size of the tumor in the xenograft mice.

In certain embodiments, MUC16 Glycosylation Antibodies or antigen-binding fragments thereof described herein can increase survival of animals in tumor xenograft models as compared to mock-treated mice. In specific embodiments, MUC16 Glycosylation Antibodies or antigen-binding fragments thereof described herein increase survival of mice in tumor xenograft models by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, as compared to mock-treated mice. In specific embodiments, MUC16 Glycosylation Antibodies or antigen-binding fragments thereof described herein increase survival of mice in tumor xenograft models by at least about 25% or 35%, optionally to about 75%, as assessed by methods described herein or known to one of skill in the art, as compared to mock-treated mice in tumor xenograft models. In specific embodiments, MUC16 Glycosylation Antibodies or antigen-binding fragments thereof described herein increase survival of mice in tumor xenograft models by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art, as compared to mock-treated mice in tumor xenograft models. Survival can, for example, be determined by plotting a survival curve of number of surviving mice against time (e.g., days or weeks) after tumor cell line injection. Mock-treated mice can, for example, be treated with phosphate buffered saline or a control (e.g., anti-IgG antibody).

In certain embodiments, a MUC16 Glycosylation Antibody or an antigen-binding fragment thereof described herein is internalized into a cell expressing a form of MUC16, which is glycosylated, and wherein the amino acid sequence of the form of MUC16 is SEQ ID NO: 133 ($MUC16^{c114}$) upon contacting the cell with the MUC16 Glycosylation Antibody or antigen-binding fragment thereof. "Internalized" or "internalization," when in reference to a molecule that is internalized by a cell, refers to passage of the molecule that is in contact with the extracellular surface of a cell membrane across the cell membrane to the intracellular surface of the cell membrane and/or into the cell cytoplasm. In certain embodiments, the cells recombinantly expressing glycosylated $MUC16^{c114}$ are SKOV3 cells. In certain embodiments, the glycosylated form of $MUC16^{c114}$ is N-glycosylated. In certain embodiments, the glycosylated form of $MUC16^{c114}$ is N-glycosylated at amino acid residue Asn30 (corresponding to Asn1806 of mature MUC16 (SEQ ID NO:150)). In certain embodiments, the glycosylated form of $MUC16^{c114}$ is N-glycosylated at amino acid residues Asn 24 and Asn30 (corresponding to Asn1800 and Asn1806, respectively, of mature MUC16 (SEQ ID NO:150)). In certain embodiments, the glycosylated form of $MUC16^{c114}$ is N-glycosylated at amino acid residues Asn1, Asn24, and Asn30 (corresponding to Asn1777, Asn1800, and Asn1806, respectively, of mature MUC16 (SEQ ID NO:150)). In certain embodiments, the glycosylation comprises N-linked chitobiose. In certain embodiments, the glycosylation consists of an N-linked chitobiose.

Assays to determine internalization of a MUC16 Glycosylation Antibody or antigen-binding fragment thereof described herein to a cell, such as, for example, using radiolabeled antibodies, are known to a person skilled in the art. See, for example, the methods described in Section 6.2. For example, internalization of $^{89}$Zr-labeled antibody can be investigated on SKOV3 cells expressing $MUC16^{c114}$. Briefly, approximately $1\times10^5$ cells are seeded in a 12-well plate and incubated overnight at 37° C. 5% $CO_2$ incubator. A volume of radiolabeled protein is added to each well and the plates are incubated at 37° C. and 4° C. for 1, 5, 12, and 24 hours. Following each incubation period, the medium is collected and the cells are rinsed with 1 mL of phosphate buffered saline (PBS). Surface-bound activity is collected by washing the cells in 1 mL of 100 mM acetic acid with 100 mM glycine (1:1, pH 3.5) at 4° C. The adherent cells are then lysed with 1 mL of 1 M NaOH. Each wash is collected and counted for activity. The ratio of activity of the final wash to the total activity of all the washes is used to determine the % internalized. In certain embodiments, the assay is performed at 37° C. In certain embodiments, the MUC16 Glycosylation Antibody or antigen-binding fragment thereof is internalized in at least 1, 2, 3, 5, 6, 7, 8, 9, or 10 percent of cells incubated with the MUC16 Glycosylation Antibody or antigen-binding fragment thereof. In certain embodiments, the MUC16 Glycosylation Antibody or antigen-binding fragment thereof is internalized in about 1, 2, 3, 5, 6, 7, 8, 9, or 10 percent of cells incubated with the MUC16 Glycosylation Antibody or antigen-binding fragment thereof. In certain embodiments, the MUC16 Glycosylation Antibody or antigen-binding fragment thereof is internalized within 1, 2, 3, 4, 8, 12, 16, 20, or 24 hours of contacting the cells with the MUC16 Glycosylation Antibody or antigen-binding fragment thereof.

5.2 Antibody Conjugates

In preferred embodiments, a MUC16 Glycosylation Antibody or antigen-binding fragment thereof (see, Section 5.1) provided herein is not conjugated to any other molecule, such as an organic moiety, a detectable label, or an isotope. In alternative embodiments, MUC16 Glycosylation Antibody or antigen-binding fragment thereof (see, Section 5.1) provided herein is conjugated to one or more organic moieties. In alternative embodiments, MUC16 Glycosylation Antibody or antigen-binding fragment thereof provided herein is conjugated to one or more detectable labels. In alternative embodiments, MUC16 Glycosylation Antibody or antigen-binding fragment thereof provided herein is conjugated to one or more isotopes.

5.2.1 Detectable Labels and Isotopes

In certain embodiments, provided herein are MUC16 Glycosylation Antibody or antigen-binding fragment thereof (see, Section 5.1) conjugates, wherein said MUC16 Glycosylation Antibody or antigen-binding fragment thereof is conjugated to one or more agent, e.g., an imaging agent or a cytotoxic agent. Also provided herein are bispecific antibody conjugates, wherein said bispecific antibody is conjugated to one or more agent, e.g., an imaging agent or a cytotoxic agent. Also provided herein are antibody heavy chain conjugates, wherein said antibody heavy chain is conjugated to one or more agent, e.g., an imaging agent or a cytotoxic agent. Also provided herein are antibody light chain conjugates, wherein said antibody light chain is conjugated to one or more agent, e.g., an imaging agent or a cytotoxic agent. Also provided herein are fusion protein conjugates, wherein said fusion protein is conjugated to an agent, e.g., an imaging agent or a cytotoxic agent. In certain embodiments, the agent is conjugated covalently or non-covalently.

In certain embodiments, the imaging agent is a detectable label, such as, a chromogenic, enzymatic, radioisotopic, isotopic, fluorescent, toxic, chemiluminescent, nuclear magnetic resonance contrast agent or other label.

Non-limiting examples of suitable chromogenic labels include diaminobenzidine and 4-hydroxyazo-benzene-2-carboxylic acid.

Non-limiting examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Non-limiting examples of suitable radioisotopic labels include $^{3}H$, $^{111}In$, $^{125}I$, $^{131}I$, $^{32}P$, $^{35}S$, $^{14}C$, $^{51}Cr$, $^{57}To$, $^{58}Co$, $^{59}Fe$, $^{75}Se$, $^{152}Eu$, $^{90}Y$, $^{67}Cu$, $^{217}Ci$, $^{211}At$, $^{212}Pb$, $^{47}Sc$, $^{223}Ra$, $^{223}Ra$, $^{89}Zr$, $^{177}Lu$, and $^{109}Pd$. In certain embodiments, $^{111}In$ is a preferred isotope for in vivo imaging as it avoids the problem of dehalogenation of $^{125}I$ or $^{131}I$-labeled MUC16 Glycosylation Antibodies or antigen-binding fragments thereof in the liver. In addition, $^{111}In$ has a more favorable gamma emission energy for imaging (Perkins et al, Eur. J. Nucl. Med. 70:296-301 (1985); Carasquillo et ah, J. Nucl. Med. 25:281-287 (1987)). For example, $^{111}In$ coupled to monoclonal antibodies with 1-(P-isothiocyanatobenzyl)-DPTA has shown little uptake in non-tumorous tissues, particularly the liver, and therefore enhances specificity of tumor localization (Esteban et al., J. Nucl. Med. 28:861-870 (1987)).

Non-limiting examples of suitable non-radioactive isotopic labels include $^{157}Gd$, $^{55}Mn$, $^{162}Dy$, $^{52}Tr$, and $^{56}Fe$.

Non-limiting examples of suitable fluorescent labels include a $^{152}Eu$ label, a fluorescein label, an isothiocyanate label, a rhodamine label, a phycoerythrin label, a phycocyanin label, an allophycocyanin label, a Green Fluorescent Protein (GFP) label, an o-phthaldehyde label, and a fluorescamine label.

Non-limiting examples of chemiluminescent labels include a luminol label, an isoluminol label, an aromatic acridinium ester label, an imidazole label, an acridinium salt label, an oxalate ester label, a luciferin label, a luciferase label, and an aequorin label.

Non-limiting examples of nuclear magnetic resonance contrasting agents include heavy metal nuclei such as Gd, Mn, and iron.

Techniques known to one of ordinary skill in the art for conjugating the above-described labels to said MUC16 Glycosylation Antibodies or antigen-binding fragments thereof, bispecific antibodies, antibody heavy chains, antibody light chains, and fusion proteins are described in, for example, Kennedy et al., Clin. CMm. Acta 70:1-31 (1976), and Schurs et al, Clin. CMm. Acta 81:1-40 (1977). Coupling techniques mentioned in the latter are the glutaraldehyde method, the periodate method, the dimaleimide method, the m-maleimidobenzyl-N-hydroxy-succinimide ester method, all of which methods are incorporated by reference herein.

Nonlimiting examples of cytotoxic agents include a cytostatic or cytocidal agent, a radioactive metal ion, e.g., alpha-emitters, and toxins, e.g., *pseudomonas* exotoxin, abrin, cholera toxin, ricin A, and diphtheria toxin.

In certain embodiments, the agent is a diagnostic agent. A diagnostic agent is an agent useful in diagnosing or detecting a disease by locating the cells containing the antigen. Useful diagnostic agents include, but are not limited to, radioisotopes, dyes (such as with the biotin-streptavidin complex), contrast agents, fluorescent compounds or molecules and enhancing agents (e.g., paramagnetic ions) for magnetic resonance imaging (MRI). U.S. Pat. No. 6,331,175 describes MRI technique and the preparation of antibodies conjugated to a MRI enhancing agent and is incorporated in its entirety by reference. Preferably, the diagnostic agents are selected from the group consisting of radioisotopes, enhancing agents for use in magnetic resonance imaging, and fluorescent compounds. In order to load a MUC16 Glycosylation Antibody or antigen-binding fragment thereof with radioactive metals or paramagnetic ions, it may be necessary to react it with a reagent having a long tail to which are attached a multiplicity of chelating groups for binding the ions. Such a tail can be a polymer such as a polylysine, polysaccharide, or other derivatized or derivatizable chain having pendant groups to which can be bound chelating groups such as, for example, ethylenediaminetetraacetic acid (EDTA), diethylenetriaminepentaacetic acid (DTPA), porphyrins, polyamines, crown ethers, bis-thiosemicarbazones, polyoximes, and like groups known to be useful for this purpose. Chelates are coupled to the antibodies using standard chemistries. The chelate is normally linked to the antibody by a group which enables formation of a bond to the molecule with minimal loss of immunoreactivity and minimal aggregation and/or internal cross-linking other, more unusual, methods and reagents for conjugating chelates to antibodies are disclosed in U.S. Pat. No. 4,824,659 to Hawthorne, entitled "Antibody Conjugates," issued Apr. 25, 1989, the disclosure of which is incorporated herein in its entirety by reference. Particularly useful metal-chelate combinations include 2-benzyl-DTPA and its monomethyl and cyclohexyl analogs, used with diagnostic isotopes for radio-imaging. The same chelates, when complexed with non-radioactive metals, such as manganese, iron and gadolinium are useful for MRI, when used along with a MUC16 Glycosylation Antibody or antigen-binding fragment thereof provided herein. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates such as macrocyclic polyethers, which are of interest for stably binding nuclides, such as $^{223}Ra$ for RAIT are encompassed herein.

In certain embodiments, the agent is an organic agent. Such organic agents can produce a conjugate with improved pharmacokinetic properties (e.g., increased in vivo serum half-life). The organic moiety can be a hydrophilic polymeric group, fatty acid group, or fatty acid ester group. As used herein, the term "fatty acid" encompasses mono-carboxylic acids and di-carboxylic acids. As used herein, a "hydrophilic polymeric group" refers to an organic polymer that is more soluble in water than in octane, e.g., polylysine. Hydrophilic polymers suitable for modifying a MUC16 Glycosylation Antibody or antigen-binding fragment thereof provided herein can be linear or branched and include, for example, polyalkane glycols (e.g., polyethylene glycol, (PEG), monomethoxy-polyethylene glycol, and polypropylene glycol), carbohydrates (e.g., dextran, cellulose, oligosaccharides, and polysaccharides), polymers of hydrophilic amino acids (e.g., polylysine, polyarginine, and polyaspartate), polyalkane oxides (e.g., polyethylene oxide and polypropylene oxide) and polyvinyl pyrolidone. In certain embodiments, the hydrophilic polymer that modifies a MUC16 Glycosylation Antibody or antigen-binding fragment thereof, a bispecific antibody, an antibody heavy chain, an antibody light chain, or a fusion protein provided herein has a molecular weight of about 800 to about 150,000 Daltons as a separate molecular entity. For example $PEG_{5000}$ and $PEG_{20,000}$, wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N,N-carbonyl diimidazole) on a fatty acid or fatty acid ester can be coupled to a hydroxyl group on a polymer.

Fatty acids and fatty acid esters suitable for modifying a MUC16 Glycosylation Antibody or antigen-binding fragment thereof, a bispecific antibody, an antibody heavy chain, an antibody light chain, or a fusion protein provided herein can be saturated or can contain one or more units of unsaturation. Fatty acids that are suitable for modifying a MUC16 Glycosylation Antibody or antigen-binding fragment thereof, a bispecific antibody, an antibody heavy chain, an antibody light chain, or a fusion protein provided herein include, for example, n-dodecanoate, n-tetradecanoate, n-octadecanoate, n-eicosanoate, n-docosanoate, n-triacontanoate, n-tetracontanoate, cis-delta-9-octadecanoate, all cis-delta-5,8,11,14-eicosatetraenoate, octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably one to about six, carbon atoms.

The conjugates provided herein can be prepared using suitable methods, such as by reaction with one or more modifying agents. As used herein, an "activating group" is a chemical moiety or functional group that can, under appropriate conditions, react with a second chemical group thereby forming a covalent bond between the modifying agent and the second chemical group. For example, amine-reactive activating groups include electrophilic groups such as, for example, tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see, for example, Hernanson, G. T., Bioconjugate Techniques, Academic Press: San Diego, Calif. (1996)). An activating group can be bonded directly to the organic group (e.g., hydrophilic polymer, fatty acid, fatty acid ester), or through a linker moiety, for example a divalent $C_1$-$C_{12}$ group, wherein one or more carbon atoms can be replaced by a heteroatom such as oxygen, nitrogen or sulfur. Suitable linker moieties include, for example, tetraethylene glycol, $(CH_2)_3$, and NH. Modifying agents that comprise a linker moiety can be produced, for example, by reacting a mono-Boc-alkyldiamine (e.g., mono-Boc-ethylenediamine or mono-Boc-diaminohexane) with a fatty acid in the presence of 1-ethyl-3-(3-dimethylaminopropyl)carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate as described, or can be reacted with maleic anhydride and the resulting product cyclized to produce an activated maleimido derivative of the fatty acid. (See, for example, Thompson, et al., WO 92/16221 the entire teachings of which are incorporated herein by reference.)

A "modifying agent" can refer to a suitable organic group (e.g., hydrophilic polymer, a fatty acid, and a fatty acid ester) that comprises an activating group. For example, the organic moieties can be bonded to the MUC16 Glycosylation Antibody or antigen-binding fragment thereof in a non-site specific manner by employing an amine-reactive modifying agent, for example, an N-hydroxysuccinimide ester of PEG. Modified MUC16 Glycosylation Antibody or antigen-binding fragment thereof can also be prepared by reducing disulfide bonds (e.g., intrachain disulfide bonds) of the MUC16 Glycosylation Antibody or antigen-binding fragment thereof, bispecific antibody, antibody heavy chain, antibody light chain, or fusion protein. The reduced MUC16 Glycosylation Antibody or antigen-binding fragment thereof, bispecific antibody, antibody heavy chain, antibody light chain, or fusion protein can then be reacted with a thiol-reactive modifying agent to produce the conjugates provided herein. Conjugates comprising an organic moiety that is bonded to specific sites of a MUC16 Glycosylation Antibody or antigen-binding fragment thereof provided herein can be prepared using suitable methods, such as reverse proteolysis (Fisch et al., Bioconjugate Chem., 3:147-153 (1992); Werlen et al., Bioconjugate Chem., 5:411-417 (1994); Kumaran et al., Protein Sci. 6(10):2233-2241 (1997); Itoh et al., Bioorg. Chem., 24(1): 59-68 (1996); Capellas et al., Biotechnol. Bioeng., 56(4):456-463 (1997)), and the methods described in Hermanson, G. T., Bioconjugate Techniques, Academic Press: San Diego, Calif. (1996).

5.3 Antibody Production 5.3.1 Producing and Screening Antibodies

In another aspect, provided herein are methods of producing MUC16 Glycosylation Antibodies or antigen-binding fragments thereof (see, Section 5.1 and Section 5.2).

The antibodies or antigen-binding fragments thereof described herein can be produced by any method known in the art for the synthesis of antibodies, e.g., by chemical synthesis or by recombinant expression techniques. The methods described herein employs, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, e.g., in the references cited herein and are fully explained in the literature. See, e.g., Maniatis T et al., (1982) Molecular Cloning: A Laboratory Manual, Cold Spring Harbor Laboratory Press; Sambrook J et al., (1989), Molecular Cloning: A Laboratory Manual, Second Edition, Cold Spring Harbor Laboratory Press; Sambrook J et al., (2001) Molecular Cloning: A Laboratory Manual, Cold Spring Harbor Laboratory Press, Cold Spring Harbor, N.Y.; Ausubel F M et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren B et al., (eds.) (1999) Genome Analysis: A Laboratory Manual, Cold Spring Harbor Laboratory Press.

In a specific embodiment, a MUC16 Glycosylation Antibody or antigen binding fragment thereof described herein is an antibody (e.g., recombinant antibody) prepared, expressed, created or isolated by any means that involves creation, e.g., via synthesis, genetic engineering of DNA sequences. In certain embodiments, such antibody comprises sequences that are encoded by DNA sequences that do not naturally exist within the antibody germline repertoire of an animal or mammal (e.g., human) in vivo. In a specific embodiment, a MUC16 Glycosylation Antibody or antigen binding fragment thereof described herein is made by a method comprising using a glycosylated form of SEQ ID NO:129, SEQ ID NO:130, and/or SEQ ID NO:131. In a specific embodiment, the glycosylated form of SEQ ID NO:129, SEQ ID NO:130, and/or SEQ ID NO:131 is glycosylated with one or more chitobiose. See, e.g., Section 6.2, Section 6.3, and Section 6.4 for a detailed description of how to produce antibodies described herein.

In a certain aspect, provided herein is an immunogenic glycopeptide comprising one or more glycosylation sites, wherein (i) the immunogenic glycopeptide is 10 to 60 amino acid residues, 10 to 30 amino acid residues, 15 to 25 amino acid residues, 15 to 20 amino acid residues, or 15 to 18 amino acid residues in length, and (ii) at least one of the one or more glycosylation sites is linked with a carbohydrate.

In some embodiments, the immunogenic glycopeptide comprises one, two, or three glycosylation sites. In a specific embodiment, the immunogenic glycopeptide comprises one glycosylation site. In another specific embodiment, the immunogenic glycopeptide comprises two glycosylation sites.

In specific embodiments, the immunogenic glycopeptide comprises one glycosylation site that is linked with a carbohydrate. In specific embodiments, the immunogenic glycopeptide comprises two glycosylation sites that are each linked with a carbohydrate.

Carbohydrate linked to the one or more glycosylation sites of the immunogenic glycopeptide can be an N-linked carbohydrate, an O-linked carbohydrate, or a C-linked carbohydrate. N-linked carbohydrate is attached to an asparagine residue, and is the most common form found in nature. The majority of N-linked carbohydrates are linked to peptides in the form of GlcNAc-β-Asn. O-linked carbohydrate is attached to an amino acid hydroxyl side chain (usually from serine or threonine). The majority of O-linked carbohydrates are linked to peptides in the form of GlcNAc-β-Ser/Thr or GlcNAc-α-Ser/Thr. C-linked carbohydrate refers to a mannose attached to a tryptophan residue, and is the least common form found in nature. In one embodiment, the carbohydrate in the immunogenic glycopeptide is an N- or O-linked carbohydrate. In a specific embodiment, the carbohydrate in the immunogenic glycopeptide is an N-linked carbohydrate.

Carbohydrate linked to the one or more glycosylation sites of the immunogenic glycopeptide can be a monosaccharide, a disaccharide, an oligosaccharide (e.g., a trisaccharide, a tetrasaccharide, or a pentasaccharide), or a polysaccharide. In certain embodiments, the carbohydrate is a monosaccharide, a disaccharide, a trisaccharide, a tetrasaccharide, or a pentasaccharide. In a specific embodiment, the carbohydrate is a disaccharide. In a particular embodiment, the disaccharide is a chitobiose. In another specific embodiment, the carbohydrate is $Man_3GlcNAc_2$. In specific embodiments, the N-terminus of the immunogenic glycopeptide is acetylated. In specific embodiments, the C-terminus of the immunogenic glycopeptide is in the form of an N-methylcarboxamide derivative.

In certain embodiments, the immunogenic glycopeptide is conjugated to an immunogenic carrier protein. In most cases, small antigens (e.g., short peptides or small haptens) are not sufficiently complex to elicit the production of antibodies. The immunogenic carrier proteins, because of their large size and complex structure, may confer immunogenicity to conjugated small antigens, resulting in antibodies being produced against epitopes on the small antigens and the immunogenic carrier proteins. Therefore, small antigens are always chemically conjugated with immunogenic carrier proteins to intensify the immune response for successful production of antibodies. Commonly used immunogenic carrier proteins include, but are not limited to, keyhole limpet hemocyanin (KLH), concholepas concholepas hemocyanin (CCH), bovine serum albumin (BSA), and ovalbumin (OVA). In a specific embodiment, the immunogenic glycopeptide is conjugated to KLH. KLH is a copper-containing polypeptide that belongs to a group of non-heme proteins called hemocyanins, which are found in arthropods and mollusks. KLH is isolated from keyhole limpets (*Megathura crenulata*). Because of its evolutionary distance from mammals, high molecular weight, complex structure, and a large surface containing several hundred lysine groups that provide primary amines as targets for conjugation, KLH is an extremely immunogenic and effective carrier protein in mammals.

In certain embodiments, the immunogenic glycopeptide is 10 to 60 amino acid residues in length. In some embodiments, the immunogenic glycopeptide is 10 to 30 amino acid residues in length. In some embodiments, the immunogenic glycopeptide is 15 to 25 amino acid residues in length. In some embodiments, the immunogenic glycopeptide is 15 to 20 amino acid residues in length. In specific embodiments, the immunogenic glycopeptide is 15 to 18 amino acid residues in length. In a particular aspect of such specific embodiments wherein the immunogenic glycopeptide is 15 to 18 amino acid residues in length, the immunogenic glycopeptide comprises a glycosylation site that is linked with a chitobiose. In another particular aspect of such specific embodiments wherein the immunogenic glycopeptide is 15 to 18 amino acid residues in length, the immunogenic glycopeptide comprises two glycosylation sites that are each linked with a chitobiose. In a specific embodiment, the immunogenic glycopeptide is 55 amino acid residues in length. In a particular aspect of such specific embodiment wherein the immunogenic glycopeptide is 55 amino acid residues in length, the immunogenic glycopeptide comprises a glycosylation site that is linked with a chitobiose. In a specific embodiment, the immunogenic glycopeptide is 18 amino acid residues in length. In a particular aspect of such specific embodiment wherein the immunogenic glycopeptide is 18 amino acid residues in length, the immunogenic glycopeptide comprises two glycosylation sites that are each linked with a chitobiose. In another specific embodiment, the immunogenic glycopeptide is 15 amino acid residues in length. In a particular aspect of such specific embodiment wherein the immunogenic glycopeptide is 15 amino acid residues in length, the immunogenic glycopeptide comprises a glycosylation site that is linked with a chitobiose.

In certain embodiments, the immunogenic glycopeptide comprises an at least 10 amino acid portion of the amino acid sequence of SEQ ID NO:150, and at least one of the one or more glycosylation sites of the immunogenic glycopeptide is in said portion of the amino sequence. In certain other embodiments, the immunogenic glycopeptide comprises an at least 15, 20, 25, or 30 amino acid portion of the amino acid sequence of SEQ ID NO:150, and at least one of the one or more glycosylation sites of the immunogenic glycopeptide is in said portion of the amino sequence. In specific embodiments, the immunogenic glycopeptide is 15 to 18 amino acid residues in length. In specific embodiments, the immunogenic glycopeptide is 55 amino acid residues in length. In specific embodiments, the immunogenic glycopeptide comprises the amino acid sequence of SEQ ID NO:129. In a specific embodiment, the immunogenic glycopeptide is 55 amino acid residues in length and comprises the amino acid sequence of SEQ ID NO:129. In a particular embodiment, the immunogenic glycopeptide comprising the amino acid sequence of SEQ ID NO:129 comprises a glycosylation site at the $30^{th}$ residue (Asn) that is linked with a chitobiose. In another particular embodiment, the immunogenic glycopeptide comprising the amino acid sequence of SEQ ID NO:129 comprises a glycosylation site at the $30^{th}$ residue (Asn) of SEQ ID NO: 129 that is linked with a $Man_3GlcNAc_2$ moiety. In specific embodiments, the immunogenic glycopeptide is 18 amino acid residues in length. In specific embodiments, the immunogenic glycopeptide comprises the amino acid sequence of SEQ ID NO:130. In a specific embodiment, the immunogenic glycopeptide is 18 amino acid residues in length and comprises the amino acid sequence of SEQ ID NO:130. In a particular embodiment, the immunogenic glycopeptide comprising the amino acid sequence of SEQ ID NO:130 comprises the two glycosylation sites at the $4^{th}$ residue (Asn) and the $10^{th}$ residue (Asn) that are each linked with a chitobiose. In specific embodiments, the immunogenic glycopeptide is 15 amino acid residues in length. In specific embodiments, the immunogenic glycopeptide comprises the amino acid sequence of SEQ ID NO:131. In a specific embodiment, the immunogenic glycopeptide is 15 amino acid residues in length and comprises the amino acid sequence of SEQ ID NO: 131. In a particular embodiment, the immunogenic glycopeptide comprising the amino acid sequence of SEQ ID NO:131 comprises a glycosylation site at the $7^{th}$ residue (Asn) that is linked with a chitobiose.

In another aspect, provided herein is a method of generating an antibody or an antigen-binding fragment thereof that specifically binds to a glycoprotein, comprising immunizing a subject with an immunogenic glycopeptide comprising one or more glycosylation sites as described above. In certain embodiments, the immunogenic glycopeptide comprises an at least 10 amino acid portion of the amino acid sequence of the glycoprotein, and at least one of the one or more glycosylation sites of the immunogenic glycopeptide is in said portion of the amino acid sequence. In other certain embodiments, the immunogenic glycopeptide comprises an at least 15, 20, 25 or 30 amino acid portion of the amino acid sequence of the glycoprotein, and at least one of the one or more glycosylation sites of the immunogenic glycopeptide is in said portion of the amino acid sequence. In a particular embodiment, the glycoprotein comprises the amino acid sequence of SEQ ID NO: 150. In a specific embodiment, the antibody or antigen-binding fragment thereof lacks specific binding to a non-glycosylated form of the glycoprotein. The subject immunized in accordance with the methods described herein can be, but is not limited to, a goat, a sheep, a donkey, a chicken, a guinea pig, a rat, a rabbit, or a mouse. In some embodiments, the subject immunized in accordance with the methods described herein is a rat, a rabbit, or a mouse. In a specific embodiment, the subject immunized in accordance with the methods described herein is a mouse. Immunization of the subject can be performed by any method known in the art, for example, by administering the immunogenic glycopeptide and an adjuvant to the subject as described in Example 2 and Example 3 (see, Section 6.2 and Section 6.3).

In another aspect, also provided herein is a method of preparing an immunogenic glycopeptide described herein. In certain embodiments, the method of preparing the immunogenic glycopeptide comprises linking one or more glycosylation sites of the immunogenic glycopeptide described herein with a carbohydrate (e.g., a chitobiose). In certain embodiments, the method of preparing the immunogenic glycopeptide also comprises synthesizing the peptide moiety. The peptide moiety of the immunogenic glycopeptide can be synthesized by any method known in the art, for example, by Fmoc solid-phase peptide synthesis as described in Example 2 (see, Section 6.2). In certain embodiments, the amino acid (e.g., asparagine) at the one or more glycosylation sites is protected by a protecting group during the synthesis of the immunogenic glycopeptide. In a specific embodiment, only one asparagine residue of the peptide moiety is linked with a carbohydrate (e.g., a chitobiose), and the protecting group on the asparagine is an allyl group. In another specific embodiment, more than one (e.g., two) asparagine residues of the peptide moiety are each linked with a carbohydrate (e.g., a chitobiose), and the protecting group on the asparagine residues is O-2-phenylisopropyl ester (O-2-Phi Pr, OPp). The linking step can be performed by any method known in the art. In a preferred embodiment, the carbohydrate moiety is linked with the peptide moiety using a one-flask aspartylation/deprotection procedure as described in Example 2 (see Section 6.2.2.1).

Methods to produce MUC16 Glycosylation Antibodies or antigen-binding fragments thereof described herein are known to one of ordinary skill in the art, for example, by chemical synthesis, by purification from biological sources, or by recombinant expression techniques, including, for example, from mammalian cell or transgenic preparations. The methods described herein employs, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, for example, Maniatis et al. (1982) Molecular Cloning: A Laboratory Manual, Cold Spring Harbor Laboratory Press; Sambrook et al. (1989), Molecular Cloning: A Laboratory Manual, Second Edition, Cold Spring Harbor Laboratory Press; Sambrook et al. (2001) Molecular Cloning: A Laboratory Manual, Cold Spring Harbor Laboratory Press, Cold Spring Harbor, N.Y.; Ausubel et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren et al. (eds.) (1999) Genome Analysis: A Laboratory Manual, Cold Spring Harbor Laboratory Press.

A variety of methods exist in the art for the production of MUC16 Glycosylation Antibodies or antigen-binding fragments thereof described herein (see, Section 5.1 and Section 5.2). For example, the MUC16 Glycosylation Antibody or antigen-binding fragment thereof may be made by recombinant DNA methods, such as those described in U.S. Pat. No. 4,816,567. The one or more DNAs encoding a MUC16 Glycosylation Antibody or antigen-binding fragment thereof provided herein can be readily isolated and sequenced using conventional procedures (e.g., by using oligonucleotide probes that are capable of binding specifically to genes encoding the heavy and light chains of murine antibodies, or such chains from human, humanized, or other sources). Once isolated, the DNA may be placed into expression vectors, which are then transformed into host cells such as NS0 cells, Simian COS cells, Chinese hamster ovary (CHO) cells, yeast cells, algae cells, eggs, or myeloma cells that do not otherwise produce immunoglobulin protein, to obtain the synthesis of the MUC16 Glycosylation Antibody or antigen-binding fragment thereof in the recombinant host cells. The DNA also may be modified, for example, by substituting the coding sequence for human heavy and light chain constant domains of a desired species in place of the homologous human sequences (U.S. Pat. No. 4,816,567; Morrison et al, supra) or by covalently joining to the immunoglobulin coding sequence all or part of the coding sequence for a non-immunoglobulin polypeptide. Such a non-immunoglobulin polypeptide can be substituted for the constant domains of a MUC16 Glycosylation Antibody or antigen-binding fragment thereof provided herein. In certain embodiments, the DNA is as described in Section 5.3.2.

MUC16 Glycosylation Antibodies or antigen-binding fragments thereof provided herein can also be prepared using at least one MUC16 Glycosylation Antibody- or antigen-binding fragment thereof-encoding polynucleotide to provide transgenic animals or mammals, such as goats, cows, horses, sheep, and the like, that produce such antibodies in their milk. Such animals can be provided using known methods. See, for example, but not limited to, U.S. Pat. Nos. 5,827,690; 5,849,992; 4,873,316; 5,849,992; 5,994,616, 5,565,362; 5,304,489, and the like, each of which is entirely incorporated herein by reference.

In certain embodiments, MUC16 Glycosylation Antibodies or antigen-binding fragments thereof provided herein can additionally be prepared using at least one MUC16 Glycosylation Antibody- or antigen-binding fragment thereof-encoding polynucleotide provided herein to provide transgenic plants and cultured plant cells (for example, but not limited to tobacco and maize) that produce such antibodies, specified portions or variants in the plant parts or in cells cultured there from. As a non-limiting example, transgenic tobacco leaves expressing recombinant proteins have been successfully used to provide large amounts of recombinant proteins, for example, using an inducible promoter. See, for example, Cramer et al., Curr. Top. Microbol. Immunol. 240:95-118 (1999) and references cited therein. Also, transgenic maize have been used to express mammalian proteins at commercial production levels, with biological activities equivalent to those produced in other recombinant systems or purified from natural sources. See, for example, Hood et al., Adv. Exp. Med. Biol. 464:127-147 (1999) and references cited therein. Antibodies have also been produced in large amounts from transgenic plant seeds including antibody fragments, such as scFvs, including tobacco seeds and potato tubers. See, for example, Conrad et al., Plant Mol. Biol. 38:101-109 (1998) and references cited therein. Thus, MUC16 Glycosylation Antibodies or antigen-binding fragments thereof can also be produced using transgenic plants, according to known methods. See also, for example, Fischer et al., Biotechnol. Appl. Biochem. 30:99-108 (October, 1999), Ma et al., Trends Biotechnol. 13:522-7 (1995); Ma et al., Plant Physiol. 109:341-6 (1995); Whitelam et al., Biochem Soc. Trans. 22:940-944 (1994); and references cited therein. Each of the above references is entirely incorporated herein by reference.

In certain embodiments, MUC16 Glycosylation Antibodies or antigen-binding fragments thereof provided herein can be prepared using at least one MUC16 Glycosylation Antibody- or antigen-binding fragment thereof-encoding polynucleotide provided herein to provide bacteria that produce such MUC16 Glycosylation Antibodies or antigen-binding fragments. As a non-limiting example, *E. coli* expressing recombinant proteins has been successfully used to provide large amounts of recombinant proteins. See, for example, Verma et al., 1998, 216(1-2): 165-181 and references cited therein.

Methods for making multispecific (e.g., bispecific antibodies) have been described, see, e.g., U.S. Pat. Nos. 7,951,917; 7,183,076; 8,227,577; 5,837,242; 5,989,830; 5,869,620; 6,132,992 and 8,586,713.

In certain embodiments, MUC16 Glycosylation Antibodies or antigen-binding fragments thereof provided herein (see, Section 5.1 and Section 5.2) are utilized in the generation of bispecific antibodies. Bispecific antibodies can be made by fusing two hybridomas to create hybrid immunoglobulin molecules with two binding sites. Bispecific antibodies not only handcuff tumors to T-cells; they cross-link CD3 on T-cells and initiate the activation cascade. This way, T cell receptor-based cytotoxicity is redirected to desired tumor targets bypassing MHC restrictions. Arming of polyclonally activated T cells (ATC) with an anti-CD3-anti-MUC16 bispecific binding molecule combines the targeting specificity of the MUC16 Glycosylation Antibody with the non-MHC-restricted perforin/granzyme mediated cytotoxicity of T cells. Bispecific binding molecules BsAb or BiTE can arm ex vivo expanded activated T cells before infusion into a patient. This strategy converts every ATC into a specific CTL (Thakur and Lum, 2010, Curr Opin Mol Ther 12, 340-349; Grabert et al., 2006, Clin Cancer Res 12, 569-576).

Bispecific binding molecules may be comprised of a MUC16 Glycosylation Antibody, wherein the MUC16 Glycosylation Antibody is an immunoglobulin, wherein each light chain of the immunoglobulin is a fusion protein, wherein the fusion protein is the immunoglobulin light chain linked via a peptide linker to a scFv targeting CD3. A N297A mutation in the CH2 domain results in aglycosylation leading to no FcR or Clq binding.

A MUC16 Glycosylation Antibody or antigen-binding fragment thereof may be utilized to generate a CAR. CARs are most commonly composed of a single chain variable fragment length antibody (scFv), such as one derived from a monoclonal antibody targeting a given tumor associated antigen and/or variant thereof, a transmembrane domain (for example, a transmembrane domain derived from a T Cell surface molecule such as a costimulatory molecule such as CD8, CD28, OX-40, and 4-1BB), a signaling portion of a TCR complex, such as an intracellular domain and/or additional portion(s) of a TCR zeta (ζ) chain, such as a cytoplasmic signaling domain thereof. In a specific embodiment, the heavy and light chain variable regions of a monoclonal MUC16 Glycosylation Antibody described herein are isolated from a hybridoma cell line which generates a monoclonal MUC16 Glycosylation Antibody. For example, RNA is extracted from the hybridoma cell line and cDNA is generated from the RNA by reverse transcription PCR. The VH and VL chain variable regions are cloned by standard PCR utilizing primers specific for such variable regions. The resulting VH and VL fragments are subcloned into a shuttle vector, such as, for example TopoTA PCR 2.1 cloning vector (Invitrogen), and sequenced. The VH and VL fragments are subsequently ligated to a $(Gly_4Ser)_3$ spacer domain, generating a MUC16 Glycosylation Antibody scFv and fused to the human CD8 leader peptide (CD8L) (CD8L-MUC16 Glycosylation Antibody scFv) by overlapping PCR (see, e.g., Maher J, et al. Nat Biotechnol 2002; 20(1):70-5.; and Gong M C et al., Neoplasia 1999; 1(2):123-7). The coding region of the CD8L-MUC16 Glycosylation Antibody scFv is fused to the human CD8 hinge and transmembrane domains, or alternatively to the CD28 transmembrane and cytoplasmic signaling domains, fused to the T cell receptor CD3-ζ signaling domain (see, e.g., Maher J, et al. Nat Biotechnol 2002; 20(1):70-5.; Brentjens R J, et al. Nat Med 2003; 9(3):279-86; and Brentjens R J, et al., Clin Cancer Res 2007; 13(18 Pt 1):5426-35).

Also provided herein is a T cell expressing a CAR described herein. Methods for the generation of a T cell expressing a CAR are known in the art. For example, a CAR construct can be sub-cloned into a modified MMLV retroviral vector SFG (see, e.g., Riviere I, et al., Proc Natl Acad Sci USA 1995; 92(15):6733-7) or other suitable retroviral vectors. In some embodiments, the retroviral vector is a lentiviral vector, for example, an HIV-based vector. VSV-G pseudotyped retroviral supernatants derived from transduced gpg29 fibroblasts can be used to construct stable PG13 gibbon ape leukemia virus (GaLV) envelope-pseudotyped retroviral producing cell lines (see, e.g., Gong M C, et al. Neoplasia 1999; 1(2):123-7). Isolated healthy donor peripheral blood mononuclear cells (PBMCs) can be activated with phytohemagglutinin (PHA) at 2 μg/ml (Sigma. St. Louis, Mo.) and retrovirally transduced on retronectin coated non-tissue culture plates (Quintas-Cardama A, et al., Hum Gene Ther 2007; 18(12):1253-60) to generate the T cell recombinantly expressing the CAR. Gene transfer of the CAR into the T cell can be assessed by FACS.

Single domain antibodies, e.g., antibodies lacking the light chains, can be produced by methods well known in the art. See Riechmann L & Muyldermans S (1999) J Immunol 231: 25-38; Nuttall S D et al., (2000) Curr Pharm Biotechnol 1(3): 253-263; Muyldermans S, (2001) J Biotechnol 74(4): 277-302; U.S. Pat. No. 6,005,079; and International Publication Nos. WO 94/04678, WO 94/25591 and WO 01/44301.

In particular embodiments, a MUC16 Glycosylation Antibody or antigen binding fragment thereof described herein, which binds to the same or an overlapping epitope as a MUC16 Glycosylation Antibody described herein, is a human MUC16 Glycosylation Antibody or antigen-binding fragment thereof. In particular embodiments, a MUC16 Glycosylation Antibody or antigen binding fragment thereof described herein, which competitively blocks (e.g., in a dose-dependent manner) any one of the antibodies described herein, from binding to MUC16, is a human MUC16 Glycosylation Antibody or antigen-binding fragment thereof. Human antibodies can be produced using any method known in the art. For example, transgenic mice which are incapable of expressing functional endogenous immunoglobulins, but which can express human immunoglobulin genes, can be used. In particular, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered nonfunctional separately or simultaneously with the introduction of human immunoglobulin loci by homologous recombination. In particular, homozygous deletion of the $J_H$ region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of an antigen. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see, e.g., Lonberg N & Huszar D (1995) Int Rev Immunol 13:65-93. For a detailed discussion of this technology for producing human antibodies and human monoclonal antibodies and protocols for producing such antibodies, see, e.g., International Publication Nos. WO 98/24893, WO 96/34096 and WO 96/33735; and U.S. Pat. Nos. 5,413,923, 5,625,126, 5,633,425, 5,569,825, 5,661,016, 5,545,806, 5,814,318 and 5,939,598. Examples of mice capable of producing human antibodies include the Xenomouse™ (Abgenix, Inc.; U.S. Pat. Nos. 6,075,181 and 6,150,184), the HuAb-Mouse™ (Mederex, Inc./Gen Pharm; U.S. Pat. Nos. 5,545,806 and 5,569,825), the Trans Chromo Mouse™ (Kirin) and the KM Mouse™ (Medarex/Kirin).

Human antibodies which immunospecifically bind to MUC16 can be made by a variety of methods known in the art including phage display methods described above using antibody libraries derived from human immunoglobulin sequences. See also U.S. Pat. Nos. 4,444,887, 4,716,111, and 5,885,793; and International Publication Nos. WO 98/46645, WO 98/50433, WO 98/24893, WO 98/16654, WO 96/34096, WO 96/33735, and WO 91/10741.

In some embodiments, human antibodies can be produced using mouse-human hybridomas. For example, human peripheral blood lymphocytes transformed with Epstein-Barr virus (EBV) can be fused with mouse myeloma cells to produce mouse-human hybridomas secreting human monoclonal antibodies, and these mouse-human hybridomas can be screened to determine ones which secrete human monoclonal antibodies that immunospecifically bind to a target antigen. Such methods are known and are described in the art, see, e.g., Shinmoto H et al., (2004) Cytotechnology 46: 19-23; Naganawa Y et al., (2005) Human Antibodies 14: 27-31.

In specific embodiments, the methods of producing antibodies or antigen-binding fragments thereof that immunospecifically bind to MUC16 are as described in Section 6.2, infra.

In specific embodiments, the methods of screening and selecting antibodies or antigen-binding fragments thereof that immunospecifically bind to MUC16 are as described in Section 6.2, infra.

Once a MUC16 Glycosylation Antibody or an antigen-binding fragment thereof described herein has been produced, it can be purified by any method known in the art for purification of an immunoglobulin molecule, e.g., by chromatography (e.g., ion exchange, affinity, particularly by affinity for the specific antigen after Protein A, and sizing column chromatography), centrifugation, differential solubility, or by any other standard technique for the purification of proteins. Further, the antibodies described herein can be fused to heterologous polypeptide sequences described herein or otherwise known in the art to facilitate purification.

In specific embodiments, a MUC16 Glycosylation Antibody or an antigen-binding fragment thereof described herein is isolated or purified. Generally, an isolated antibody is one that is substantially free of other antibodies with different antigenic specificities than the isolated antibody. For example, in a particular embodiment, a preparation of a MUC16 Glycosylation Antibody or antigen binding fragment thereof described herein is substantially free of cellular material and/or chemical precursors. The language "substantially free of cellular material" includes preparations of a MUC16 Glycosylation Antibody or antigen binding fragment thereof in which the antibody is separated from cellular components of the cells from which it is isolated or recombinantly produced. Thus, a MUC16 Glycosylation Antibody or antigen binding fragment thereof that is substantially free of cellular material includes preparations of antibody having less than about 30%, 20%, 10%, 5%, 2%, 1%, 0.5%, or 0.1% (by dry weight) of heterologous protein (also referred to herein as a "contaminating protein") and/or variants of a MUC16 Glycosylation Antibody or antigen binding fragment thereof, e.g., different post-translational modified forms of a MUC16 Glycosylation Antibody or antigen binding fragment thereof or other different versions of a MUC16 Glycosylation Antibody or antigen binding fragment thereof (e.g., antibody fragments). When the antibody is recombinantly produced, it is also generally substantially free of culture medium, i.e., culture medium represents less than about 20%, 10%, 2%, 1%, 0.5%, or 0.1% of the volume of the protein preparation. When the antibody is produced by chemical synthesis, it is generally substantially free of chemical precursors or other chemicals, i.e., it is separated from chemical precursors or other chemicals which are involved in the synthesis of the protein. Accordingly, such preparations of the antibody have less than about 30%, 20%, 10%, or 5% (by dry weight) of chemical precursors or compounds other than the antibody of interest. In a specific embodiment, antibodies described herein are isolated or purified.

5.3.2 Polynucleotides

In certain embodiments, provided herein are polynucleotides comprising a nucleotide sequence encoding a MUC16 Glycosylation Antibody or antigen-binding fragment thereof (see, Section 5.1 and Section 5.2). Also provided herein are vectors comprising such polynucleotides (see, Section 5.3.3). Also provided herein are polynucleotides encoding antigens of the MUC16 Glycosylation Antibody or antigen-binding fragment thereof described herein (see, Section 5.1 and Section 5.2). Also provided herein are polynucleotides that hybridize under stringent or lower stringency hybridization conditions to polynucleotides that encode a MUC16 Glycosylation Antibody or antigen-binding fragment thereof described herein.

The language "purified" includes preparations of polynucleotide or nucleic acid molecule having less than about 15%, 10%, 5%, 2%, 1%, 0.5%, or 0.1% (in particular less than about 10%) of other material, e.g., cellular material, culture medium, other nucleic acid molecules, chemical precursors and/or other chemicals. In a specific embodiment, a nucleic acid molecule(s) encoding a MUC16 Glycosylation Antibody or antigen-binding fragment thereof described herein (see, Section 5.1 and Section 5.2) is isolated or purified.

Nucleic acid molecules provided herein can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

In certain embodiments, provided herein is a polynucleotide comprising nucleotide sequences encoding MUC16 Glycosylation Antibody or antigen-binding fragment thereof described herein (see, Section 5.1 and Section 5.2).

In particular aspects, also provided herein are polynucleotides comprising nucleotide sequences encoding MUC16 Glycosylation Antibodies or antigen-binding fragments thereof (see, Section 5.1 and Section 5.2), which immunospecifically bind to MUC16, and comprise an amino acid sequence as described herein, as well as antibodies which compete with such MUC16 Glycosylation Antibody or antigen-binding fragment thereof for binding to MUC16, or which binds to the same epitope as that of such antibodies.

The polynucleotides provided herein can be obtained by any method known in the art. For example, if the nucleotide sequence encoding a MUC16 Glycosylation Antibody or antigen-binding fragment thereof (see, Section 5.1 and Section 5.2) described herein is known, a polynucleotide encoding the MUC16 Glycosylation Antibody or antigen-binding fragment thereof can be may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding a MUC16 Glycosylation Antibody or antigen-binding fragment thereof (see, Section 5.1 and Section 5.2) may be generated from nucleic acid from a suitable source. If a clone containing a nucleic acid encoding a particular MUC16 Glycosylation Antibody or antigen-binding fragment thereof is not available, but the sequence of the MUC16 Glycosylation Antibody or antigen-binding fragment thereof is known, a nucleic acid encoding the MUC16 Glycosylation Antibody or antigen-binding fragment thereof may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express a MUC16 Glycosylation Antibody or antigen binding fragment thereof provided herein) by PCR amplification using synthetic primers that hybridize to the 3' and 5' ends of the sequence or by cloning using an oligonucleotide probe specific for the particular gene sequence to identify, for example, a cDNA clone from a cDNA library that encodes the antibody. Amplified nucleic acids generated by PCR may then be cloned into replicable cloning vectors using any method well known in the art (see, for example, Section 5.3.3).

In such embodiments, a polynucleotide encoding such a MUC16 Glycosylation Antibody or antigen-binding fragment thereof may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, N.Y., which are both incorporated by reference herein in their entireties), to generate MUC16 Glycosylation Antibodies or antigen-binding fragments thereof having a different amino acid sequence, for example, to create amino acid substitutions, deletions, and/or insertions. For example, such manipulations can be performed to render the encoded amino acid aglycosylated, or to destroy the antibody's ability to bind to Clq, Fc receptor, or to activate the complement system.

Isolated nucleic acid molecules provided herein can include nucleic acid molecules comprising an open reading frame (ORF), optionally with one or more introns, for example, but not limited to, at least one specified portion of at least one complementarity determining region (CDR), as CDR1, CDR2 and/or CDR3 of at least one heavy chain or light chain; nucleic acid molecules comprising the coding sequence for a MUC16 Glycosylation Antibody or variable region; and nucleic acid molecules which comprise a nucleotide sequence substantially different from those described above but which, due to the degeneracy of the genetic code, still encode at least one MUC16 Glycosylation Antibody or antigen-binding fragment thereof as described herein.

Also provided herein are isolated nucleic acids that hybridize under selective hybridization conditions to a polynucleotide disclosed herein. Thus, the polynucleotides of this embodiment can be used for isolating, detecting, and/or quantifying nucleic acids comprising such polynucleotides. For example, polynucleotides provided herein can be used to identify, isolate, or amplify partial or full-length clones in a deposited library. In some embodiments, the polynucleotides are genomic or cDNA sequences isolated, or otherwise complementary to, a cDNA from a human or mammalian nucleic acid library.

The nucleic acids can conveniently comprise sequences in addition to a polynucleotide provided herein. For example, a multi-cloning site comprising one or more endonuclease restriction sites can be inserted into the nucleic acid to aid in isolation of the polynucleotide. In addition, translatable sequences can be inserted to aid in the isolation of the translated polynucleotide provided herein. For example, a hexa-histidine marker sequence provides a convenient means to purify the polypeptides provided herein. The nucleic acid provided herein—excluding the coding sequence—is optionally a vector, adapter, or linker for cloning and/or expression of a polynucleotide provided herein.

Additional sequences can also be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra).

In a specific embodiment, using routine recombinant DNA techniques, one or more of the CDRs of a MUC16 Glycosylation Antibody or antigen binding fragment thereof described herein may be inserted within known framework regions. The framework regions may be naturally occurring or consensus framework regions, and preferably human framework regions (see, e.g., Chothia et al., J. Mol. Biol. 278: 457-479 (1998) for a listing of human framework regions). Preferably, the polynucleotide generated by the combination of the framework regions and CDRs encodes a MUC16 Glycosylation Antibody or antigen binding fragment thereof that immunospecifically binds MUC16. One or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are provided herein and within the skill of the art.

In certain embodiments, the isolated or purified nucleic acid molecule, or fragment thereof, upon linkage with another nucleic acid molecule, can encode a fusion protein. The generation of fusion proteins is within the ordinary skill in the art and can involve the use of restriction enzyme or recombinational cloning techniques (see, for example, Gateway™. (Invitrogen)). See, also, U.S. Pat. No. 5,314,995.

In certain embodiments, a polynucleotide provided herein is in the form of a vector (e.g., expression vector) as described in Section 5.3.3.

In certain aspects, provided herein are polynucleotides comprising a nucleotide sequence encoding a MUC16 Glycosylation Antibody or antigen binding fragment thereof described herein or an antigen-binding fragment thereof (e.g., a variable light chain region and/or variable heavy chain region) that immunospecifically binds to MUC16, and vectors, e.g., vectors comprising such polynucleotides for their efficient expression in host cells (e.g., *E. coli* and mammalian cells). In some embodiments, a polynucleotide is isolated or purified.

As used herein, an "isolated" polynucleotide or nucleic acid molecule is one which is separated from other nucleic acid molecules which are present in the natural source (e.g., in a mouse or a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecule having less than about 15%, 10%, 5%, 2%, 1%, 0.5%, or 0.1% of other material, e.g., cellular material, culture medium, other nucleic acid molecules, chemical precursors and/or other chemicals.

In particular aspects, provided herein are polynucleotides comprising nucleotide sequences encoding MUC16 Glycosylation Antibodies or antigen binding fragments thereof and comprise an amino acid sequence as described herein, as well as antibodies which compete with such antibodies for binding to MUC16 (e.g., in a dose-dependent manner), or which binds to the same or an overlapping epitope as that of such antibodies.

In certain aspects, provided herein are polynucleotides comprising a nucleic acid sequence encoding the light chain or heavy chain of a MUC16 Glycosylation Antibody or antigen binding fragment thereof described herein. The polynucleotides can comprise nucleotide sequences encoding a heavy chain comprising the VH CDRs described herein (see, e.g., Table 1, Table 3, and Table 5). The polynucleotides can comprise nucleotide sequences encoding a light chain comprising the VL CDRs described herein (see, e.g., Table 2, Table 4, and Table 6).

In particular embodiments, provided herein are polynucleotides comprising a nucleotide sequence encoding a MUC16 Glycosylation Antibody comprising three VH CDRs, e.g., containing VH CDR1, VH CDR2, and VH CDR3 as described in Table 1, Table 3, or Table 5. In specific embodiments, a polynucleotide described herein encodes a VH CDR1, a VH CDR2, and a VH CDR3 of the 10C6, 7B12, 19C11, 16C5, and 18C6 consensus VH CDRs (i.e., SEQ ID NO:103, SEQ ID NO:104, and SEQ ID NO:105, respectively, or SEQ ID NO:109, SEQ ID NO:110, and SEQ ID NO:111, respectively, or SEQ ID NO:115, SEQ ID NO:116, and SEQ ID NO:117). In specific embodiments, a polynucleotide described herein encodes a VH CDR1, a VH CDR2, and a VH CDR3 of 10C6 (i.e., SEQ ID NO:3, SEQ ID NO:4, and SEQ ID NO:5, respectively, or SEQ ID NO:9, SEQ ID NO:10, and SEQ ID NO:11, respectively, or SEQ ID NO:15, SEQ ID NO:16, and SEQ ID NO:17, respectively). In specific embodiments, a polynucleotide described herein encodes a VH CDR1, a VH CDR2, and a VH CDR3 of 7B12 (i.e., SEQ ID NO:23, SEQ ID NO:24, and SEQ ID NO:25, respectively, or SEQ ID NO:29, SEQ ID NO:30, and SEQ ID NO:31, respectively, or SEQ ID NO:35, SEQ ID NO:36, and SEQ ID NO:37, respectively). In specific embodiments, a polynucleotide described herein encodes a VH CDR1, a VH CDR2, and a VH CDR3 of 19C11 (i.e., SEQ ID NO:43, SEQ ID NO:44, and SEQ ID NO:45, respectively, or SEQ ID NO:49, SEQ ID NO:50, and SEQ ID NO:51, respectively, or SEQ ID NO:55, SEQ ID NO:56, and SEQ ID NO:57, respectively). In specific embodiments, a polynucleotide described herein encodes a VH CDR1, a VH CDR2, and a VH CDR3 of 16C5 (i.e., SEQ ID NO:63, SEQ ID NO:64, and SEQ ID NO:65, respectively, or SEQ ID NO:69, SEQ ID NO:70, and SEQ ID NO:71, respectively, or SEQ ID NO:75, SEQ ID NO:76, and SEQ ID NO:77, respectively). In specific embodiments, a polynucleotide described herein encodes a VH CDR1, a VH CDR2, and a VH CDR3 of 18C6 (i.e., SEQ ID NO:83, SEQ ID NO:84, and SEQ ID NO:85, respectively, or SEQ ID NO:89, SEQ ID NO:90, and SEQ ID NO:91, respectively, or SEQ ID NO:95, SEQ ID NO:96, and SEQ ID NO:97, respectively).

In specific embodiments, provided herein are polynucleotides comprising a nucleotide sequence encoding MUC16 Glycosylation Antibody comprising (a) three VH CDRs, e.g., containing VH CDR1, VH CDR2, and VH CDR3 as described in Table 1, Table 3, or Table 5, and (b) three VL chain CDRs, e.g., containing VL CDR1, VL CDR2, and VL CDR3 as described in Table 2, Table 4, or Table 6. In specific embodiments, a polynucleotide described herein encodes (a) a VH CDR1, a VH CDR2, and a VH CDR3 of the 10C6, 7B12, 19C11, 16C5, and 18C6 consensus VH CDRs (i.e., SEQ ID NO:103, SEQ ID NO:104, and SEQ ID NO:105, respectively, or SEQ ID NO:109, SEQ ID NO:110, and SEQ ID NO:111, respectively, or SEQ ID NO:115, SEQ ID NO:116, and SEQ ID NO:117), and (b) a VL CDR1, a VL CDR2, and a VL CDR3 of the 10C6, 7B12, 19C11, 16C5, and 18C6 consensus VL CDRs (i.e., SEQ ID NO:106, SEQ ID NO:107, and SEQ ID NO:108, respectively, or SEQ ID NO:112, SEQ ID NO:113, and SEQ ID NO:114, respectively, or SEQ ID NO:118, SEQ ID NO:119, and SEQ ID NO:120). In specific embodiments, a polynucleotide described herein encodes (a) a VH CDR1, a VH CDR2, and a VH CDR3 of 10C6 (i.e., SEQ ID NO:3, SEQ ID NO:4, and SEQ ID NO:5, respectively, or SEQ ID NO:9, SEQ ID NO:10, and SEQ ID NO:11, respectively, or SEQ ID NO:15, SEQ ID NO:16, and SEQ ID NO:17, respectively), and (b) a VL CDR1, a VL CDR2, and a VL CDR3 of 10C6 (i.e., SEQ ID NO:6, SEQ ID NO:7, and SEQ ID NO:8, respectively, or SEQ ID NO:12, SEQ ID NO:13, and SEQ ID NO:14, respectively, or SEQ ID NO:18, SEQ ID NO:19, and SEQ ID NO:20, respectively). In specific embodiments, a polynucleotide described herein encodes (a) a VH CDR1, a VH CDR2, and a VH CDR3 of 7B12 (i.e., SEQ ID NO:23, SEQ ID NO:24, and SEQ ID NO:25, respectively, or SEQ ID NO:29, SEQ ID NO:30, and SEQ ID NO:31, respectively, or SEQ ID NO:35, SEQ ID NO:36, and SEQ ID NO:37, respectively), and (b) a VL CDR1, a VL CDR2, and a VL CDR3 of 7B12 (i.e., SEQ ID NO:26, SEQ ID NO:27, and SEQ ID NO:28, respectively, or SEQ ID NO:32, SEQ ID NO:33, and SEQ ID NO:34, respectively, or SEQ ID NO:38, SEQ ID NO:39, and SEQ ID NO:40, respectively). In specific embodiments, a polynucleotide described herein encodes (a) a VH CDR1, a VH CDR2, and a VH CDR3 of 19C11 (i.e., SEQ ID NO:43, SEQ ID NO:44, and SEQ ID NO:45, respectively, or SEQ ID NO:49, SEQ ID NO:50, and SEQ ID NO:51, respectively, or SEQ ID NO:55, SEQ ID NO:56, and SEQ ID NO:57, respectively), and (b) a VL CDR1, a VL CDR2, and a VL CDR3 of 19C11 (i.e., SEQ ID NO:46, SEQ ID NO:47, and SEQ ID NO:48, respectively, or SEQ ID NO:52, SEQ ID NO:53, and SEQ ID NO:54, respectively, or SEQ ID NO:58, SEQ ID NO:59, and SEQ ID NO:60, respectively). In specific embodiments, a polynucleotide described herein encodes (a) a VH CDR1, a VH CDR2, and a VH CDR3 of 16C5 (i.e., SEQ ID NO:63, SEQ ID NO:64, and SEQ ID NO:65, respectively, or SEQ ID NO:69, SEQ ID NO:70, and SEQ ID NO:71, respectively, or SEQ ID NO:75, SEQ ID NO:76, and SEQ ID NO:77, respectively), and (b) a VL CDR1, a VL CDR2, and a VL CDR3 of 16C5 (i.e., SEQ ID NO:66, SEQ ID NO:67, and SEQ ID NO:68, respectively, or SEQ ID NO:72, SEQ ID NO:73, and SEQ ID NO:74, respectively, or SEQ ID NO:78, SEQ ID NO:79, and SEQ ID NO:80, respectively). In specific embodiments, a polynucleotide described herein encodes (a) a VH CDR1, a VH CDR2, and a VH CDR3 of 18C6 (i.e., SEQ ID NO:83, SEQ ID NO:84, and SEQ ID NO:85, respectively, or SEQ ID NO:89, SEQ ID NO:90, and SEQ ID NO:91, respectively, or SEQ ID NO:95, SEQ ID NO:96, and SEQ ID NO:97, respectively), and (b) a VL CDR1, a VL CDR2, and a VL CDR3 of 18C6 (i.e., SEQ ID NO:86, SEQ ID NO:87, and SEQ ID NO:88, respectively, or SEQ ID NO:92, SEQ ID NO:93, and SEQ ID NO:94, respectively, or SEQ ID NO:98, SEQ ID NO:99, and SEQ ID NO:100, respectively).

In certain embodiments, a polynucleotide described herein comprises a nucleotide sequence encoding a MUC16 Glycosylation Antibody described herein comprising a heavy chain variable region that comprises an amino acid sequence described herein (e.g., SEQ ID NO:1, SEQ ID NO:21, SEQ ID NO:41, SEQ ID NO:61, SEQ ID NO:81, or SEQ ID NO:101), wherein the antibody immunospecifically binds to MUC16.

In certain embodiments, a polynucleotide described herein comprises a nucleotide sequence encoding a MUC16 Glycosylation Antibody described herein comprising a light chain variable region that comprises an amino acid sequence described herein (e.g., SEQ ID NO:2, SEQ ID NO:22, SEQ ID NO:42, SEQ ID NO:62, SEQ ID NO:82, or SEQ ID NO:102), wherein the antibody immunospecifically binds to MUC16.

In certain embodiments, a polynucleotide described herein comprises a nucleotide sequence encoding a MUC16 Glycosylation Antibody described herein comprising a heavy chain variable region that comprises the amino acid sequence of SEQ ID NO:101, and a light chain variable region that comprises the amino acid sequence of SEQ ID NO:102. In certain embodiments, a polynucleotide described herein comprises a nucleotide sequence encoding a MUC16 Glycosylation Antibody described herein comprising a heavy chain variable region that comprises the amino acid sequence of SEQ ID NO:101, and a light chain variable region that comprises the amino acid sequence of SEQ ID NO:2. In certain embodiments, a polynucleotide described herein comprises a nucleotide sequence encoding a MUC16 Glycosylation Antibody described herein comprising a heavy chain variable region that comprises the amino acid sequence of SEQ ID NO:101, and a light chain variable region that comprises the amino acid sequence of SEQ ID NO:42. In certain embodiments, a polynucleotide described herein comprises a nucleotide sequence encoding a MUC16 Glycosylation Antibody described herein comprising a heavy chain variable region that comprises the amino acid sequence of SEQ ID NO:1, and a light chain variable region that comprises the amino acid sequence of SEQ ID NO:2. In certain embodiments, a polynucleotide described herein comprises a nucleotide sequence encoding a MUC16 Glycosylation Antibody described herein comprising a heavy chain variable region that comprises the amino acid sequence of SEQ ID NO:21, and a light chain variable region that comprises the amino acid sequence of SEQ ID NO:22. In certain embodiments, a polynucleotide described herein comprises a nucleotide sequence encoding a MUC16 Glycosylation Antibody described herein comprising a heavy chain variable region that comprises the amino acid sequence of SEQ ID NO:41, and a light chain variable region that comprises the amino acid sequence of SEQ ID NO:42. In certain embodiments, a polynucleotide described herein comprises a nucleotide sequence encoding a MUC16 Glycosylation Antibody described herein comprising a heavy chain variable region that comprises the amino acid sequence of SEQ ID NO:61, and a light chain variable region that comprises the amino acid sequence of SEQ ID NO:62. In certain embodiments, a polynucleotide described herein comprises a nucleotide sequence encoding a MUC16 Glycosylation Antibody described herein comprising a heavy chain variable region that comprises the amino acid sequence of SEQ ID NO:81, and a light chain variable region that comprises the amino acid sequence of SEQ ID NO:82.

In certain embodiments, a polynucleotide described herein encodes a VH comprising a nucleic acid sequence of SEQ ID NO:140, SEQ ID NO:142, SEQ ID NO:144, SEQ ID NO:146, or SEQ ID NO:148. In certain embodiments, a polynucleotide described herein encodes a VL comprising a nucleic acid sequence of SEQ ID NO:141, SEQ ID NO:143, SEQ ID NO:145, SEQ ID NO:147, or SEQ ID NO:149. In a specific embodiment, a polynucleotide described herein encodes a VH comprising a nucleic acid sequence of SEQ ID NO:140, and a VL comprising the nucleic acid sequence of SEQ ID NO:141 (e.g., 10C6). In a specific embodiment, a polynucleotide described herein encodes a VH comprising a nucleic acid sequence of SEQ ID NO:142, and a VL comprising the nucleic acid sequence of SEQ ID NO:143 (e.g., 7B12). In a specific embodiment, a polynucleotide described herein encodes a VH comprising a nucleic acid sequence of SEQ ID NO:144, and a VL comprising the nucleic acid sequence of SEQ ID NO:145 (e.g., 19C11). In a specific embodiment, a polynucleotide described herein encodes a VH comprising a nucleic acid sequence of SEQ ID NO:146, and a VL comprising the nucleic acid sequence of SEQ ID NO:147 (e.g., 16C5). In a specific embodiment, a polynucleotide described herein encodes a VH comprising a nucleic acid sequence of SEQ ID NO:148, and a VL comprising the nucleic acid sequence of SEQ ID NO:149 (e.g., 18C6).

In specific aspects, provided herein is a polynucleotide comprising a nucleotide sequence encoding a MUC16 Glycosylation Antibody or antigen binding fragment thereof comprising a light chain and a heavy chain, e.g., a separate light chain and heavy chain. With respect to the heavy chain, in a specific embodiment, a polynucleotide provided herein comprises a nucleotide sequence encoding a gamma (e.g., gamma1, gamma2, gamma3, or gamma4) heavy chain. In a particular embodiment, a polynucleotide provided herein comprises a nucleotide sequence encoding a MUC16 Glycosylation Antibody or antigen binding fragment thereof described herein wherein the antibody comprises a heavy chain, and wherein the amino acid sequence of the variable region of the heavy chain can comprise any amino acid sequence of SEQ ID NO:1, SEQ ID NO:21, SEQ ID NO:41, SEQ ID NO:61, SEQ ID NO:81, or SEQ ID NO:101, and wherein the constant region of the heavy chain is a human gamma heavy chain constant region.

With respect to the light chain, in a specific embodiment, a polynucleotide provided herein comprises a nucleotide sequence encoding a kappa light chain. In another specific embodiment, a polynucleotide provided herein comprises a nucleotide sequence encoding a lambda light chain. In yet another specific embodiment, a polynucleotide provided herein comprises a nucleotide sequence encoding a MUC16 Glycosylation Antibody or antigen binding fragment thereof described herein comprising a human kappa light chain or a human lambda light chain. In a particular embodiment, a polynucleotide provided herein comprises a nucleotide sequence encoding a MUC16 Glycosylation Antibody or antigen binding fragment thereof described herein wherein the antibody comprises a light chain, and wherein the amino acid sequence of the variable region of the light chain can comprise any amino acid sequence of SEQ ID NO:2, SEQ ID NO:22, SEQ ID NO:42, SEQ ID NO:62, SEQ ID NO:82, or SEQ ID NO:102, and wherein the constant region of the light chain is a human kappa light chain constant region. In another particular embodiment, a polynucleotide provided herein comprises a nucleotide sequence encoding a MUC16 Glycosylation Antibody or antigen binding fragment thereof described herein comprise a light chain, wherein the amino acid sequence of the variable region of the light chain can comprise any amino acid sequence of SEQ ID NO:2, SEQ ID NO:22, SEQ ID NO:42, SEQ ID NO:62, SEQ ID NO:82, or SEQ ID NO:102, and wherein the constant region of the light chain is a human lambda light chain constant region.

For a detailed example for the generation of MUC16 Glycosylation Antibodies described herein, see, Section 6.2 and Section 6.3.

5.3.3 Cells and Vectors

In certain embodiments, provided herein are cells (e.g., ex vivo cells) expressing (e.g., recombinantly) one or more MUC16 Glycosylation Antibodies or antigen-binding fragments thereof (see, Section 5.1 and Section 5.2). Also provided herein are vectors (e.g., expression vectors) comprising nucleotide sequences (see, for example, Section 5.3.2) encoding a MUC16 Glycosylation Antibody or antigen-binding fragment thereof described herein for recombinant expression in host cells, preferably in mammalian cells. Also provided herein are cells (e.g., ex vivo cells) comprising such vectors or nucleotide sequences for recombinantly expressing a MUC16 Glycosylation Antibody or antigen-binding fragment thereof described here. Also provided herein are methods for producing a MUC16 Glycosylation Antibody or antigen-binding fragment thereof described herein, comprising expressing such MUC16 Glycosylation Antibody or antigen-binding fragment thereof from a cell (e.g., ex vivo cell). In a preferred embodiment, the cell is an ex vivo cell.

A vector (e.g., expression vector) is a DNA molecule comprising a gene that is expressed in a cell (e.g., ex vivo cell). Typically, gene expression is placed under the control of certain regulatory elements, including constitutive or inducible promoters, tissue-specific regulatory elements and enhancers. Such a gene is said to be "operably linked to" the regulatory elements, e.g., a promoter. A recombinant host may be any prokaryotic or eukaryotic cell that contains either a cloning vector or expression vector. This term also includes those prokaryotic or eukaryotic cells, as well as a transgenic animal, that have been genetically engineered to contain the cloned gene(s) in the chromosome or genome of the host cell or cells of the host cells (e.g., ex vivo cells). In one embodiment, the promoter is the CMV promoter.

In certain embodiments, provided herein is a vector comprising one or more polynucleotide as described in Section 5.3.2. In certain embodiments, a polynucleotide as described in Section 5.3.2 can be cloned into a suitable vector and can be used to transform or transfect any suitable host. Vectors and methods to construct such vectors are known to one of ordinary skill in the art and are described in general technical references (see, in general, "Recombinant DNA Part D," Methods in Enzymology, Vol. 153, Wu and Grossman, eds., Academic Press (1987)). In certain embodiments, the vector comprises regulatory sequences, such as transcription and translation initiation and termination codons, which are specific to the type of host (e.g., bacterium, fungus, plant, insect, or mammal) into which the vector is to be introduced, as appropriate and taking into consideration whether the vector is DNA or RNA. In certain embodiments, the vector comprises regulatory sequences that are specific to the genus of the host. In certain embodiments, the vector comprises regulatory sequences that are specific to the species of the host.

In certain embodiments, the vector comprises one or more marker genes, which allow for selection of transformed or transfected hosts. Non-limiting examples of marker genes include biocide resistance, e.g., resistance to antibiotics, heavy metals, etc., complementation in an auxotrophic host to provide prototrophy, and the like. In a preferred embodiment, the vector comprises ampicillin and hygromycin selectable markers.

In certain embodiments, an expression vector can comprise a native or normative promoter operably linked to a polynucleotide as described in Section 5.3.2. The selection of promoters, for example, strong, weak, inducible, tissue-specific and developmental-specific, is within the skill in the art. Similarly, the combining of a nucleic acid molecule, or fragment thereof, as described above with a promoter is also within the skill in the art.

Non-limiting examples of suitable vectors include those designed for propagation and expansion or for expression or both. For example, a cloning vector can be selected from the group consisting of the pUC series, the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as lamda-GT10, lamda-GT11, lamda-ZapII (Stratagene), lamda-EMBL4, and lamda-NM1149, can also be used. Non-limiting examples of plant expression vectors include pBI110, pBI101.2, pBI101.3, pBI121 and pBIN19 (Clontech). Non-limiting examples of animal expression vectors include pEUK-C1, pMAM and pMAMneo (Clontech). The TOPO cloning system (Invitrogen, Carlsbad, Calif.) can also be used in accordance with the manufacturer's recommendations.

In certain embodiments, the vector is a mammalian vector. In certain embodiments, the mammalian vector contains at least one promoter element, which mediates the initiation of transcription of mRNA, the MUC16 Glycosylation Antibody or antigen-binding fragment thereof coding sequence, and signals required for the termination of transcription and polyadenylation of the transcript. In certain embodiments, the mammalian vector contains additional elements, such as, for example, enhancers, Kozak sequences and intervening sequences flanked by donor and acceptor sites for RNA splicing. In certain embodiments, highly efficient transcription can be achieved with, for example, the early and late promoters from SV40, the long terminal repeats (LTRS) from retroviruses, for example, RSV, HTLVI, HIVI and the early promoter of the cytomegalovirus (CMV). However, cellular elements can also be used (e.g., the human actin promoter). Non-limiting examples of mammalian expression vectors include, vectors such as pIRESlneo, pRetro-Off, pRetro-On, PLXSN, or pLNCX (Clonetech Labs, Palo Alto, Calif.), pcDNA3.1 (+/−), pcDNA/Zeo (+/−) or pcDNA3.1/Hygro (+/−) (Invitrogen), PSVL and PMSG (Pharmacia, Uppsala, Sweden), pRSVcat (ATCC 37152), pSV2dhfr (ATCC 37146) and pBC12MI (ATCC 67109). Non-limiting example of mammalian host cells that can be used in combination with such mammalian vectors include human Hela 293, H9 and Jurkat cells, mouse NIH3T3 and C127 cells, Cos 1, Cos 7 and CV 1, quail QC1-3 cells, mouse L cells and Chinese hamster ovary (CHO) cells.

In certain embodiments, the vector is a viral vector, for example, retroviral vectors, parvovirus-based vectors, e.g., adeno-associated virus (AAV)-based vectors, AAV-adenoviral chimeric vectors, and adenovirus-based vectors, and lentiviral vectors, such as Herpes simplex (HSV)-based vectors. In certain embodiments, the viral vector is manipulated to render the virus replication deficient. In certain embodiments, the viral vector is manipulated to eliminate toxicity to the host. These viral vectors can be prepared using standard recombinant DNA techniques described in, for example, Sambrook et al., Molecular Cloning, a Laboratory Manual, 2d edition, Cold Spring Harbor Press, Cold Spring Harbor, N.Y. (1989); and Ausubel et al., Current Protocols in Molecular Biology, Greene Publishing Associates and John Wiley & Sons, New York, N.Y. (1994).

In certain embodiments, a vector or polynucleotide described herein can be transferred to a cell (e.g., an ex vivo cell) by conventional techniques and the resulting cell can be cultured by conventional techniques to produce a MUC16 Glycosylation Antibody or antigen-binding fragment thereof described herein. Accordingly, provided herein are cells comprising a polynucleotide encoding a MUC16 Glycosylation Antibody or antigen-binding fragment thereof, a heavy or light chain thereof, or a light chain fusion polypeptide thereof, operably linked to a promoter for expression of such sequences in the host cell. In certain embodiments, a vector encoding the heavy chain operably linked to a promoter and a vector encoding the light chain operably linked to a promoter can be co-expressed in the cell for expression of the entire MUC16 Glycosylation Antibody. In certain embodiments, a vector encoding a heavy chain operably linked to a promoter and a vector encoding a light chain fusion polypeptide operably linked to a promoter can be co-expressed in the cell for expression of an entire bispecific binding molecule. In certain embodiments, a cell comprises a vector comprising a polynucleotide encoding both the heavy chain and the light chain polypeptide of a MUC16 Glycosylation Antibody described herein operably linked to a promoter. In certain embodiments, a cell comprises a vector comprising a polynucleotide encoding both the heavy chain and the light chain fusion polypeptide of a bispecific binding molecule described herein operably linked to a promoter. In certain embodiments, a cell comprises two different vectors, a first vector comprising a polynucleotide encoding a heavy chain operably linked to a promoter, and a second vector comprising a polynucleotide encoding a light chain polypeptide operably linked to a promoter. In certain embodiments, a cell comprises two different vectors, a first vector comprising a polynucleotide encoding a heavy chain operably linked to a promoter, and a second vector comprising a polynucleotide encoding a light chain fusion polypeptide operably linked to a promoter. In certain embodiments, a first cell comprises a first vector comprising a polynucleotide encoding a heavy chain of a MUC16 Glycosylation Antibody described herein, and a second cell comprises a second vector comprising a polynucleotide encoding a light chain polypeptide of a MUC16 Glycosylation Antibody described herein. In certain embodiments, provided herein is a mixture of cells comprising such first cell and such second cell. In certain embodiments, a first cell comprises a first vector comprising a polynucleotide encoding a heavy chain of a bispecific binding molecule described herein, and a second cell comprises a second vector comprising a polynucleotide encoding a light chain fusion polypeptide of a bispecific binding molecule described herein. In certain embodiments, provided herein is a mixture of cells comprising such first cell and such second cell. In a preferred embodiment, the cell expresses the vector or vectors such that the oligonucleotide is both transcribed and translated efficiently by the cell.

In embodiment, the cell expresses the vector, such that the oligonucleotide, or fragment thereof, is both transcribed and translated efficiently by the cell.

In certain embodiments, the cell is present in a host, which can be an animal, such as a mammal. Examples of cells include, but are not limited to, a human cell, a human cell line, *E. coli* (e.g., *E. coli* TB-1, TG-2, DH5a, XL-Blue MRF' (Stratagene), SA2821 and Y1090), *B. subtilis, P. aeruginosa, S. cerevisiae, N. crassa*, insect cells (e.g., Sf9, Ea4) and others set forth herein below. In a preferred embodiment, the cell is a CHO cell. In an especially preferred embodiment, the cell is a CHO-S cell.

In certain embodiments, a polynucleotide described herein can be expressed in a stable cell line that comprises the polynucleotide integrated into a chromosome by introducing the polynucleotide into the cell. In certain embodiments, the polynucleotide is introduced into the cell by, for example, electroporation. In certain embodiments, the polynucleotide is introduced into the cell by, for example, transfection of a vector comprising the polynucleotide into the cell. In certain embodiments, the vector is co-transfected with a selectable marker such as DHFR, GPT, neomycin, or hygromycin to allow for the identification and isolation of the transfected cells. In certain embodiments, the transfected polynucleotide can also be amplified to express large amounts of the encoded MUC16 Glycosylation Antibody or antigen-binding fragment thereof. For example, the DHFR (dihydrofolate reductase) marker can be utilized to develop cell lines that carry several hundred or even several thousand copies of the polynucleotide of interest. Another example of a selection marker is the enzyme glutamine synthase (GS) (Murphy, et al., Biochem. J. 227:277-279 (1991); Bebbington, et al., Bio/Technology 10:169-175 (1992)). Using these markers, the cells are grown in selective medium and the cells with the highest resistance are selected. These cell lines contain the amplified gene(s) integrated into a chromosome. Chinese hamster ovary (CHO) and NSO cells are often used for the production of antibodies.

In one embodiment, the vector comprises (i) a first polynucleotide sequence encoding an immunoglobulin light chain that binds to MUC16, operably linked to a first promoter and (ii) a second polynucleotide encoding an immunoglobulin heavy chain that binds to MUC16, operably linked to a second promoter. In certain embodiments, the vector is a viral vector.

In one embodiment, the vector comprises (i) a first polynucleotide sequence encoding a light chain fusion polypeptide comprising an immunoglobulin light chain fused to a scFv, via a peptide linker, wherein the light chain binds to MUC16 and wherein the scFv binds to CD3, operably linked to a first promoter and (ii) a second polynucleotide encoding an immunoglobulin heavy chain that binds to MUC16 operably linked to a second promoter. In certain embodiments, the vector is a viral vector.

5.4 Pharmaceutical Compositions

In certain embodiments, provided herein are compositions (e.g., pharmaceutical compositions) and kits comprising a pharmaceutically effective amount of one or more MUC16 Glycosylation Antibodies or antigen-binding fragments thereof (see, Section 5.1 and Section 5.2). In certain embodiments, the pharmaceutical compositions comprise immune cells, for example T cells, recombinantly expressing an antibody, antigen-binding fragment thereof, and/or CAR described herein. Compositions may be used in the preparation of individual, single unit dosage forms. Compositions provided herein can be formulated for parenteral, subcutaneous, intramuscular, intravenous, intrarticular, intrabronchial, intraabdominal, intracapsular, intracartilaginous, intracavitary, intracelial, intracerebellar, intracerebroventricular, intra-Ommaya, intraocular, intravitreous, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, intrathecal, intraventricular in the brain, intraparenchymal in the brain, or transdermal administration. In a preferred embodiment, the composition is formulated for parenteral administration. In an especially preferred embodiment, the composition is formulated for intravenous administration. In a preferred embodiment, the composition is formulated for intraperitoneal administration. In a specific embodiment, the composition is formulated for intraperitoneal administration to treat peritoneal metastases. In a preferred embodiment, the composition is formulated for intrathecal administration. In a specific embodiment, the composition is formulated for intrathecal administration to treat brain metastases. See, for example, Kramer et al, 2010, 97: 409-418. In a preferred embodiment, the composition is formulated for intraventricular administration in the brain. In a specific embodiment, the composition is formulated for intraventricular administration to treat brain metastases. See, for example, Kramer et al, 2010, 97: 409-418. In a preferred embodiment, the composition is formulated for intraparenchymal administration in the brain. In a specific embodiment, the composition is formulated for intraparenchymal administration to treat a brain tumor or brain tumor metastases. See, for example, Luther et al., 2014, Neuro Oncol, 16: 800-806, and Clinical Trial ID NO NCT01502917.

In a specific embodiment, the composition is formulated for intraperitoneal administration for peritoneal metastases.

In certain embodiments, provided herein is a composition comprising one or more polynucleotide comprising nucleotide sequences encoding a MUC16 Glycosylation Antibody or an antigen-binding fragment thereof described herein. In certain embodiments, provided herein is a composition comprising a cell, wherein the cell comprises one or more polynucleotide comprising nucleotide sequences encoding a MUC16 Glycosylation Antibody or an antigen-binding fragment thereof described herein. In certain embodiments, provided herein is a composition comprising a vector, wherein the vector comprises one or more polynucleotide comprising nucleotide sequences encoding a MUC16 Glycosylation Antibody or an antigen-binding fragment thereof described herein. In certain embodiments, provided herein is a composition comprising a cell, wherein the cell comprises a vector, wherein the vector comprises one or more polynucleotide comprising nucleotide sequences encoding a MUC16 Glycosylation Antibody or an antigen-binding fragment thereof described herein.

In certain embodiments, a composition described herein is a stable or preserved formulation. In certain embodiments, the stable formulation comprises a phosphate buffer with saline or a chosen salt. In certain embodiments, a composition described is a multi-use preserved formulation, suitable for pharmaceutical or veterinary use. In certain embodiments, a composition described herein comprises a preservative. Preservatives are known to one of ordinary skill in the art. Non-limiting examples of preservatives include phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, and sodium dehydroacetate and thimerosal, or mixtures thereof in an aqueous diluent. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3, 0.4, 0.5, 0.9, 1.0%), 0.1-3% benzyl alcohol (e.g., 0.5, 0.9, 1.1, 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

It can be sometimes desirable to deliver the compositions provided herein to a subject over prolonged periods of time, for example, for periods of one week to one year or more from a single administration. Various slow release, depot or implant dosage forms can be utilized. For example, a dosage form can contain a pharmaceutically acceptable non-toxic salt of the compounds that has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzyl-ethylenediamine or ethylenediamine; or (c) combinations of (a) and (b) e.g., a zinc tannate salt. Additionally, a composition provided herein, preferably, a relatively insoluble salt such as those just described, can be formulated in a gel, for example, an aluminum monostearate gel with, e.g., sesame oil, suitable for injection. Particularly preferred salts are zinc salts, zinc tannate salts, pamoate salts, and the like. Another type of slow release depot formulation for injection would contain the compound or salt dispersed for encapsulated in a slow degrading, non-toxic, non-antigenic polymer such as a polylactic acid/polyglycolic acid polymer, for example, as described in U.S. Pat. No. 3,773,919. The compounds or, preferably, relatively insoluble salts such as those described above can also be formulated in cholesterol matrix silastic pellets, particularly for use in animals. Additional slow release, depot or implant compositions, e.g., gas or liquid liposomes are known in the literature (U.S. Pat. No. 5,770,222 and "Sustained and Controlled Release Drug Delivery Systems", J. R. Robinson ed., Marcel Dekker, Inc., N.Y., 1978).

The range of at least one MUC16 Glycosylation Antibody or antigen-binding fragment thereof composition provided herein (see, Section 5.1 and Section 5.2) includes amounts yielding upon reconstitution, if in a wet/dry system, concentrations from about 1.0 microgram/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

In certain embodiments, compositions provided herein comprise at least one of any suitable auxiliary, such as, but not limited to, diluent, binder, stabilizer, buffers, salts, lipophilic solvents, preservative, adjuvant or the like. In certain embodiments, pharmaceutically acceptable auxiliaries are preferred. Non-limiting examples of, and methods of preparing such sterile solutions are well known in the art, such as, but not limited to, Gennaro, Ed., Remington's Pharmaceutical Sciences, $18^{th}$ Edition, Mack Publishing Co. (Easton, Pa.) 1990. Pharmaceutically acceptable carriers can be routinely selected that are suitable for the mode of administration, solubility and/or stability of the MUC16 Glycosylation Antibody or antigen-binding fragment thereof described herein.

In certain embodiments, compositions provided herein contain one or more pharmaceutical excipient and/or additive. Non-limiting examples of pharmaceutical excipients and additives are proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Non-limiting examples of protein excipients include serum albumin such as human serum albumin (HSA), recombinant human albumin (rHA), gelatin, casein, and the like. Non-limiting examples of amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. In certain embodiments, the amino acid is glycine. Non-limiting examples of carbohydrate excipients include monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. In certain embodiments, the carbohydrate excipient is mannitol, trehalose, or raffinose.

In certain embodiments, a composition provided herein includes one or more buffer or a pH adjusting agent; typically, the buffer is a salt prepared from an organic acid or base. Non-limiting examples of buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. In certain embodiments, the buffer is an organic acid salts such as citrate. Other excipients, e.g., isotonicity agents, buffers, antioxidants, preservative enhancers, can be optionally and preferably added to the diluent. An isotonicity agent, such as glycerin, is commonly used at known concentrations. A physiologically tolerated buffer is preferably added to provide improved pH control. The compositions can cover a wide range of pHs, such as from about pH 4 to about pH 10, and preferred ranges from about pH 5 to about pH 9, and a most preferred range of about 6.0 to about 8.0. Preferably, the compositions provided herein have pH between about 6.8 and about 7.8. Preferred buffers include phosphate buffers, most preferably sodium phosphate, particularly phosphate buffered saline (PBS).

In certain embodiments, a composition provided herein includes one or more polymeric excipient/additive such as, for example, polyvinylpyrrolidones, ficolls (a polymeric sugar), dextrates (e.g., cyclodextrins, such as 2-hydroxypropyl-.beta.-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and/or chelating agents (e.g., EDTA).

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) or nonionic surfactants such as polysorbate 20 or 80 or poloxamer 184 or 188, Pluronic® polyls, other block copolymers, and chelators such as EDTA and EGTA can optionally be added to the compositions to reduce aggregation. These additives are particularly useful if a pump or plastic container is used to administer the composition. The presence of pharmaceutically acceptable surfactant mitigates the propensity for the protein to aggregate.

Additional pharmaceutical excipients and/or additives suitable for use in a composition provided herein are known to one of skill in the art and are referenced in, for example, "Remington: The Science & Practice of Pharmacy", 19.sup.th ed., Williams & Williams, (1995), and in the "Physician's Desk Reference", $52^{nd}$ ed., Medical Economics, Montvale, N.J. (1998), which are entirely incorporated herein by reference. In certain preferred embodiments, the carrier or excipient materials are carbohydrates (e.g., saccharides and alditols) and buffers (e.g., citrate) or polymeric agents.

Preferably, the aqueous diluent optionally further comprises a pharmaceutically acceptable preservative. Preferred preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the composition is a concentration sufficient to yield an anti-microbial effect. Such concentrations are dependent on the preservative selected and are readily determined by the skilled artisan.

The compositions provided herein can be prepared by a process which comprises mixing at least one MUC16 Glycosylation Antibody or antigen-binding fragment thereof described herein (see, Section 5.1 and Section 5.2) and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing the at least one MUC16 Glycosylation Antibody or antigen-binding fragment thereof described herein and preservative in an aqueous diluent is carried out using conventional dissolution and mixing procedures. To prepare a suitable composition, for example, a measured amount of at least one MUC16 Glycosylation Antibody or antigen-binding fragment thereof described herein in buffered solution is combined with the desired preservative in a buffered solution in quantities sufficient to provide the MUC16 Glycosylation Antibody or antigen-binding fragment thereof described herein and preservative at the desired concentrations. The compositions provided herein can be prepared by a process that comprises mixing at least one MUC16 Glycosylation Antibody or antigen-binding fragment thereof described herein and a selected buffer, preferably a phosphate buffer containing saline or a chosen salt. Mixing the at least one MUC16 Glycosylation Antibody or antigen-binding fragment thereof described herein and buffer in an aqueous diluent is carried out using conventional dissolution and mixing procedures. To prepare a suitable composition, for example, a measured amount of at least one MUC16 Glycosylation Antibody or antigen-binding fragment thereof described herein in water or buffer is combined with the desired buffering agent in water in quantities sufficient to provide the protein and buffer at the desired concentrations. Variations of these processes would be recognized by one of ordinary skill in the art. For example, the order the components are added, whether additional additives are used, the temperature and pH at which the composition is prepared, are all factors that can be optimized for the concentration and means of administration used.

5.4.1 Parenteral Formulations

In certain embodiments, a composition provided herein is formulated for parenteral injectable administration. As used herein, the term "parenteral" includes intravenous, intravascular, intramuscular, intradermal, subcutaneous, and intraocular. For parenteral administration, the composition can be formulated as a solution, suspension, emulsion or lyophilized powder in association, or separately provided, with a pharmaceutically acceptable parenteral vehicle. Non-limiting examples of such vehicles are water, saline, Ringer's solution, dextrose solution, glycerol, ethanol, and 1-10% human serum albumin. Liposomes and nonaqueous vehicles such as fixed oils can also be used. The vehicle or lyophilized powder can contain additives that maintain isotonicity (e.g., sodium chloride, mannitol) and chemical stability (e.g., buffers and preservatives). The formulation is sterilized by known or suitable techniques.

Suitable pharmaceutical carriers are described in the most recent edition of Remington's Pharmaceutical Sciences, A. Osol, a standard reference text in this field.

Formulations for parenteral administration can contain as common excipients sterile water or saline, polyalkylene glycols such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent such as aqueous solution or a sterile injectable solution or suspension in a solvent. As the usable vehicle or solvent, water, Ringer's solution, isotonic saline, etc. are allowed; as an ordinary solvent, or suspending solvent, sterile involatile oil can be used. For these purposes, any kind of involatile oil and fatty acid can be used, including natural or synthetic or semisynthetic fatty oils or fatty acids; natural or synthetic or semisynthetic mono- or di- or tri-glycerides. Parental administration is known in the art and includes, but is not limited to, conventional means of injections, a gas pressured needle-less injection device as described in U.S. Pat. No. 5,851,198, and a laser perforator device as described in U.S. Pat. No. 5,839,446 entirely incorporated herein by reference.

5.4.2 Pulmonary Formulations

In certain embodiments, a composition comprising a MUC16 Glycosylation Antibody or an antigen-binding fragment thereof described herein (see, Section 5.1 and Section 5.2) is formulated for pulmonary administration. For pulmonary administration, the composition is delivered in a particle size effective for reaching the lower airways of the lung or sinuses. Compositions for pulmonary administration can be delivered by any of a variety of inhalation or nasal devices known in the art for administration of a therapeutic agent by inhalation. These devices capable of depositing aerosolized formulations in the sinus cavity or alveoli of a patient include metered dose inhalers, nebulizers, dry powder generators, sprayers, and the like. Other devices suitable for directing the pulmonary or nasal administration of a MUC16 Glycosylation Antibody or an antigen-binding fragment thereof described herein are also known in the art. All such devices use formulations suitable for the administration for the dispensing of a MUC16 Glycosylation Antibody or an antigen-binding fragment thereof described herein in an aerosol. Such aerosols can be comprised of either solutions (both aqueous and non aqueous) or solid particles. Metered dose inhalers like the Ventolin® metered dose inhaler, typically use a propellent gas and require actuation during inspiration (See, e.g., WO 94/16970, WO 98/35888). Dry powder inhalers like Turbuhaler™ (Astra), Rotahaler®. (Glaxo), Diskus® (Glaxo), devices marketed by Inhale Therapeutics, to name a few, use breath-actuation of a mixed powder (U.S. Pat. No. 4,668,218 Astra, EP 237507 Astra, WO 97/25086 Glaxo, WO 94/08552 Dura, U.S. Pat. No. 5,458,135 Inhale, WO 94/06498 Fisons, entirely incorporated herein by reference). Nebulizers like the Ultravent® nebulizer (Mallinckrodt), and the Acorn II® nebulizer (Marquest Medical Products) (U.S. Pat. No. 5,404,871 Aradigm, WO 97/22376), the above references entirely incorporated herein by reference, produce aerosols from solutions, while metered dose inhalers, dry powder inhalers, etc. generate small particle aerosols. Such examples of commercially available inhalation devices are non-limiting examples are not intended to be limiting in scope.

In certain embodiments, a spray comprising a MUC16 Glycosylation Antibody or an antigen-binding fragment thereof described herein (see, Section 5.1 and Section 5.2) can be produced by forcing a suspension or solution of at least one MUC16 Glycosylation Antibody or antigen-binding fragment thereof described herein through a nozzle under pressure. The nozzle size and configuration, the applied pressure, and the liquid feed rate can be chosen to achieve the desired output and particle size. An electrospray can be produced, for example, by an electric field in connection with a capillary or nozzle feed. Advantageously, particles of a composition comprising at least one MUC16 Glycosylation Antibody or antigen-binding fragment thereof described herein delivered by a sprayer have a particle size less than about 10 um, preferably in the range of about 1 um to about 5 um, and most preferably about 2 um to about 3 um.

Formulations of a composition comprising at least one MUC16 Glycosylation Antibody or antigen-binding fragment thereof described herein (see, Section 5.1 and Section 5.2) suitable for use with a sprayer typically include the at least one MUC16 Glycosylation Antibody or antigen-binding fragment thereof described herein in an aqueous solution at a concentration of about 0.1 mg to about 100 mg per ml of solution or mg/gm, or any range or value therein, e.g., but not limited to, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/ml or mg/gm. The formulation can include agents such as an excipient, a buffer, an isotonicity agent, a preservative, a surfactant, and, preferably, zinc. The formulation can also include an excipient or agent for stabilization of the MUC16 Glycosylation Antibody or antigen-binding fragment thereof composition, such as a buffer, a reducing agent, a bulk protein, or a carbohydrate. Bulk proteins useful in formulating such a composition include albumin, protamine, or the like. Typical carbohydrates useful in formulating antibody composition proteins include sucrose, mannitol, lactose, trehalose, glucose, or the like. The composition can also include a surfactant, which can reduce or prevent surface-induced aggregation of the composition caused by atomization of the solution in forming an aerosol. Various conventional surfactants can be employed, such as polyoxyethylene fatty acid esters and alcohols, and polyoxy ethylene sorbitol fatty acid esters. Amounts will generally range between 0.001 and 14% by weight of the formulation. Preferred surfactants are polyoxyethylene sorbitan monooleate, polysorbate 80, polysorbate 20, or the like.

In certain embodiments, the composition is administered via a nebulizer, such as jet nebulizer or an ultrasonic nebulizer. Typically, in a jet nebulizer, a compressed air source is used to create a high-velocity air jet through an orifice. As the gas expands beyond the nozzle, a low-pressure region is created, which draws a solution of antibody composition protein through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer. In an ultrasonic nebulizer, high-frequency electrical energy is used to create vibrational, mechanical energy, typically employing a piezoelectric transducer. This energy is transmitted to the formulation of antibody composition protein either directly or through a coupling fluid, creating an aerosol including the antibody composition protein. Advantageously, particles of antibody composition protein delivered by a nebulizer have a particle size less than about 10 um, preferably in the range of about 1 um to about 5 um, and most preferably about 2 um to about 3 um.

In certain embodiments, the composition is administered via a metered dose inhaler (MDI), wherein a propellant, at least one MUC16 Glycosylation Antibody or antigen-binding fragment thereof described herein (see, Section 5.1 and Section 5.2), and any excipients or other additives are contained in a canister as a mixture including a liquefied compressed gas. Actuation of the metering valve releases die mixture as an aerosol, preferably containing particles in the size range of less than about 10 um, preferably about 1 um to about 5 um, and most preferably about 2 um to about 3 um. The desired aerosol particle size can be obtained by employing a formulation of antibody composition protein produced by various methods known to those of skill in the art, including jet-milling, spray drying, critical point condensation, or the like. Preferred metered dose inhalers include those manufactured by 3M or Glaxo and employing a hydrofluorocarbon propellant.

Formulations of a MUC16 Glycosylation Antibody or an antigen-binding fragment thereof described herein (see, Section 5.1 and Section 5.2) for use with a metered-dose inhaler device will generally include a finely divided powder containing at least one Anti-IL-6 antibody as a suspension in a non-aqueous medium, for example, suspended in a propellant with the aid of a surfactant. The propellant can be any conventional material employed for this purpose, such as chlorofluorocarbon, a hydrochlorofluorocarbon, a hydrofluorocarbon, or a hydrocarbon, including trichlorofluoromethane, dichlorodifluoromethane, dichlorotetrafluoroethanol and 1,1,1,2-tetrafluoroethane, HFA-134a (hydrofluoroalkane-134a), HFA-227 (hydrofluoroalkane-227), or the like. Preferably the propellant is a hydrofluorocarbon. The surfactant can be chosen to stabilize the at least one MUC16 Glycosylation Antibody or antigen-binding fragment thereof described herein as a suspension in the propellant, to protect the active agent against chemical degradation, and the like. Suitable surfactants include sorbitan trioleate, soya lecithin, oleic acid, or the like. In some cases solution aerosols are preferred using solvents such as ethanol. Additional agents known in the art for formulation of a protein can also be included in the formulation.

5.4.3 Oral Formulations

In certain embodiments, a composition provided herein is formulated for oral administration. In certain embodiments, for oral administration, compositions and methods of administering at least one MUC16 Glycosylation Antibody or antigen-binding fragment thereof described herein rely on the co-administration of adjuvants such as, for example, resorcinols and nonionic surfactants such as polyoxyethylene oleyl ether and n-hexadecylpolyethylene ether, to artificially increase the permeability of the intestinal walls, as well as the co-administration of enzymatic inhibitors such as, for example, pancreatic trypsin inhibitors, diisopropylfluorophosphate (DFF) and trasylol, to inhibit enzymatic degradation. The active constituent compound of the solid-type dosage form for oral administration can be mixed with at least one additive, including sucrose, lactose, cellulose, mannitol, trehalose, raffinose, maltitol, dextran, starches, agar, arginates, chitins, chitosans, pectins, gum tragacanth, gum arabic, gelatin, collagen, casein, albumin, synthetic or semisynthetic polymer, and glyceride. These dosage forms can also contain other type(s) of additives, such as, for example, inactive diluting agent, lubricant such as magnesium stearate, paraben, preserving agent such as sorbic acid, ascorbic acid, alpha.-tocopherol, antioxidant such as cysteine, disintegrator, binder, thickener, buffering agent, sweetening agent, flavoring agent, perfuming agent, etc.

In certain embodiments, tablets and pills for oral administration can be further processed into enteric-coated preparations. In certain embodiments, liquid preparations for oral administration include, for example, emulsion, syrup, elixir, suspension and solution preparations allowable for medical use. These preparations can contain inactive diluting agents ordinarily used in said field, for example, water. Liposome preparations can be utilized for oral administration preparations, for example, as described for insulin and heparin (U.S. Pat. No. 4,239,754). Additionally, microspheres of artificial polymers of mixed amino acids (proteinoids) can be utilized to in oral administration of pharmaceuticals, for example, as described in U.S. Pat. No. 4,925,673. Furthermore, carrier compounds, such as those described in U.S. Pat. Nos. 5,879,681 and 5,871,753, are used in oral administration of biologically active agents.

5.4.4 Mucosal Formulations

In certain embodiments, a composition provided herein is formulated for absorption through mucosal surfaces. In certain embodiments, for absorption through mucosal surfaces, compositions and methods of administering at least one MUC16 Glycosylation Antibody or antigen-binding fragment thereof described herein (see, Section 5.1 and Section 5.2) include an emulsion comprising a plurality of submicron particles, a mucoadhesive macromolecule, a bioactive peptide, and an aqueous continuous phase, which promotes absorption through mucosal surfaces by achieving mucoadhesion of the emulsion particles (U.S. Pat. No. 5,514,670). Mucous surfaces suitable for application of the emulsions provided herein can include, for example, corneal, conjunctival, buccal, sublingual, nasal, vaginal, pulmonary, stomachic, intestinal, and rectal routes of administration. Formulations for vaginal or rectal administration, for example, suppositories, can contain as excipients, for example, polyalkyleneglycols, vaseline, cocoa butter, and the like. Formulations for intranasal administration can be solid and contain as excipients, for example, lactose or can be aqueous or oily solutions of nasal drops. For buccal administration excipients include, for example, sugars, calcium stearate, magnesium stearate, pregelinatined starch, and the like (U.S. Pat. No. 5,849,695).

5.4.5 Transdermal Formulations

In certain embodiments, a composition provided herein is formulated for transdermal administration. In certain embodiments, for transdermal administration, the composition comprises at least one MUC16 Glycosylation Antibody or antigen-binding fragment thereof described herein (see, Section 5.1 and Section 5.2) encapsulated in a delivery device such as, for example, a liposome or polymeric nanoparticles, microparticle, microcapsule, or microspheres (referred to collectively as microparticles unless otherwise stated). A number of suitable devices are known for transdermal administration, including microparticles made of synthetic polymers such as polyhydroxy acids such as polylactic acid, polyglycolic acid and copolymers thereof, polyorthoesters, polyanhydrides, and polyphosphazenes, and natural polymers such as collagen, polyamino acids, albumin and other proteins, alginate and other polysaccharides, and combinations thereof (U.S. Pat. No. 5,814,599).

5.4.6 Kits

Also provided herein are kits comprising one or more antibodies described herein, or antigen-binding fragments thereof, or conjugates thereof. In a specific embodiment, provided herein is a pharmaceutical pack or kit comprising one or more containers filled with one or more of the ingredients of the pharmaceutical compositions described herein, such as one or more antibodies or an antigen-binding fragment thereof described herein. In some embodiments, the kits contain a pharmaceutical composition described herein and a prophylactic or therapeutic agent.

Optionally associated with such container(s) can be a notice in the form prescribed by a governmental agency regulating the manufacture, use or sale of pharmaceuticals or biological products, a dosage form, and/or instructions for use thereof. In certain embodiments, the instructions included with the kit provide guidance with respect to the dosage amounts and/or dosing regimens for administration of the pharmaceutical composition(s).

Examples of pharmaceutical packaging materials include, but are not limited to, blister packs, bottles, packets, sachets, tubes, inhalers, pumps, bags, vials, containers, syringes and any packaging material suitable for a selected pharmaceutical composition and intended mode of administration and treatment.

Kits provided herein can further include devices that are used to administer the active ingredients. Examples of such devices include, but are not limited to, syringes, needle-less injectors, drip bags, patches and inhalers.

Kits provided herein can further include pharmaceutically acceptable vehicles that can be used to administer the ingredients. For example, if an ingredient is provided in a solid form that must be reconstituted for parenteral administration, the kit can comprise a sealed container of a suitable vehicle in which the ingredient can be dissolved to form a particulate-free sterile solution that is suitable for parenteral administration or can be reconstituted as a suspension for oral administration. Examples of pharmaceutically acceptable vehicles include, but are not limited to: aqueous vehicles including, but not limited to, Water for Injection USP, Sodium Chloride Injection, Ringer's Injection, Dextrose Injection, Dextrose and Sodium Chloride Injection, and Lactated Ringer's Injection; water-miscible vehicles including, but not limited to, ethyl alcohol, polyethylene glycol, and polypropylene glycol; and non-aqueous vehicles including, but not limited to, corn oil, cottonseed oil, peanut oil, sesame oil, ethyl oleate, isopropyl myristate, and benzyl benzoate.

5.5 Uses and Methods 5.5.1 Therapeutic Uses and Methods

In certain embodiments, provided herein are methods for treating a cancer in a subject, in particular, a MUC16-positive cancer in a subject, comprising administering to the subject in need thereof a therapeutically effective amount of a MUC16 Glycosylation Antibody or antigen-binding fragment thereof (see, Section 5.1 and Section 5.2). In a specific embodiment, the subject is a subject as described in Section 5.5.5. In a specific embodiment, the MUC16 Glycosylation Antibody or antigen-binding fragment thereof is administered at a dose as described in Section 5.5.3. In a specific embodiment, the MUC16 Glycosylation Antibody or antigen-binding fragment thereof is administered according to a method as described in Section 5.5. In a specific embodiment, the MUC16 Glycosylation Antibody or antigen-binding fragment thereof is administered in combination with one or more additional pharmaceutically active agents as described in Section 5.5.4.

For use of a MUC16 Glycosylation Antibody or fragment thereof in a subject of a particular species, a MUC16 Glycosylation Antibody or fragment thereof is used that binds to MUC16 of that particular species. For example, to treat a human, a MUC16 Glycosylation Antibody or antigen-binding fragment thereof is used that binds to human MUC16. In a specific embodiment, the MUC16 Glycosylation Antibody or antigen-binding fragment thereof is an immunoglobulin.

In addition, for use of a MUC16 Glycosylation Antibody or fragment thereof in a subject of a particular species, the MUC16 Glycosylation Antibody, preferably, the constant region of a MUC16 Glycosylation Antibody or antigen binding fragment thereof, is derived from that particular species. For example, to treat a human, the MUC16 Glycosylation Antibody or fragment thereof can comprise a MUC16 Glycosylation Antibody or antigen binding fragment thereof that is an immunoglobulin, wherein the immunoglobulin comprises a human constant region. In a specific embodiment, the subject is a human.

In a specific embodiment, the MUC16-positive cancer is ovarian cancer, lung cancer, pancreatic cancer, breast cancer, fallopian tube cancer, uterine (e.g., endometrial) cancer, primary peritoneum cancer or cancer of any other tissue that expresses the MUC16 receptor.

In specific embodiments, treatment can be to achieve beneficial or desired clinical results including, but not limited to, alleviation of a symptom, diminishment of extent of a disease, stabilizing (i.e., not worsening) of state of a disease, delay or slowing of disease progression, amelioration or palliation of the disease state, and remission (whether partial or total), whether detectable or undetectable. In a specific embodiment, "treatment" can also be to prolong survival as compared to expected survival if not receiving treatment. In specific embodiments, the administration of a MUC16 Glycosylation Antibody or antigen binding fragment thereof described herein, or a pharmaceutical composition described herein to a subject with cancer (e.g., ovarian cancer, lung cancer, pancreatic cancer, breast cancer, fallopian tube cancer, uterine (e.g., endometrial) cancer, or primary peritoneum cancer, or cancer of any other tissue that expresses the MUC16 receptor) achieves at least one, two, three, four or more of the following effects: (i) the reduction or amelioration of the severity of one or more symptoms of cancer; (ii) the reduction in the duration of one or more symptoms associated with cancer; (iii) the prevention in the recurrence of a symptom associated with cancer; (iv) the reduction in hospitalization of a subject; (v) a reduction in hospitalization length; (vi) the increase in the survival of a subject; (vii) the enhancement or improvement of the therapeutic effect of another therapy; (viii) the inhibition of the development or onset of one or more symptoms associated with cancer; (ix) the reduction in the number of symptoms associated with cancer; (x) improvement in quality of life as assessed by methods well known in the art; (x) inhibition of the recurrence of a tumor; (xi) the regression of tumors and/or one or more symptoms associated therewith; (xii) the inhibition of the progression of tumors and/or one or more symptoms associated therewith; (xiii) a reduction in the growth of a tumor; (xiv) a decrease in tumor size (e.g., volume or diameter); (xv) a reduction in the formation of a newly formed tumor; (xvi) prevention, eradication, removal, or control of primary, regional and/or metastatic tumors; (xvii) a decrease in the number or size of metastases; (xviii) a reduction in mortality; (xix) an increase in relapse free survival; (xx) the size of the tumor is maintained and does not increase or increases by less than the increase of a tumor after administration of a standard therapy as measured by conventional methods available to one of skill in the art, such as magnetic resonance imaging (MRI), dynamic contrast-enhanced MRI (DCE-MRI), X-ray, and computed tomography (CT) scan, or a positron emission tomography (PET) scan; and/or (xxi) an increase in the length of remission in patients. Treatment can be to achieve one or more of the foregoing.

5.5.2 Diagnostic Uses

In certain embodiments, MUC16 Glycosylation Antibodies or antigen-binding fragments thereof (see, Section 5.1 and Section 5.2) described herein can be used for diagnostic purposes to detect, diagnose, or monitor a condition described herein (e.g., a condition involving MUC16-positive cancer cells). In certain embodiments, MUC16 Glycosylation Antibodies or antigen-binding fragments thereof for use in diagnostic purposes are labeled as described in Section 5.2.

In certain embodiments, provided herein are methods for the detection of a condition described herein comprising (a) assaying the expression of MUC16 or a fragment thereof in cells or a tissue sample of a subject using one or more MUC16 Glycosylation Antibodies or antigen-binding fragments thereof described herein; and (b) comparing the level of MUC16 or the fragment thereof expression with a control level, for example, levels in normal tissue samples (e.g., from a subject not having a condition described herein, or from the same patient before onset of the condition), whereby an increase or decrease in the assayed level of MUC16 or the fragment thereof expression compared to the control level of MUC16 or the fragment thereof expression is indicative of a condition described herein.

Antibodies described herein can be used to assay the levels of MUC16 or a fragment thereof in a biological sample using classical immunohistological methods as described herein or as known to those of skill in the art (e.g., see Jalkanen et al., 1985, J. Cell. Biol. 101:976-985; and Jalkanen et al., 1987, J. Cell. Biol. 105:3087-3096). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{125}I$, $^{121}I$), carbon ($^{14}C$), sulfur ($^{35}S$), tritium ($^{3}H$), indium ($^{121}In$), and technetium ($^{99}Tc$); luminescent labels, such as luminol; and fluorescent labels, such as fluorescein and rhodamine, and biotin.

In certain embodiments, monitoring of a condition described herein (e.g., a MUC16-positive cancer), is carried out by repeating the method for diagnosing for a period of time after initial diagnosis.

Presence of the labeled molecule can be detected in the subject using methods known in the art for in vivo scanning. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

5.5.3 Doses and Regimens

A MUC16 Glycosylation Antibody or antigen-binding fragment thereof (see, Section 5.1 and Section 5.2), or composition (see, Section 5.4), or cells expressing the antibodies, or antigen-binding fragments thereof, described herein may be delivered to a subject by a variety of routes. These include, but are not limited to, parenteral, intranasal, intratracheal, oral, intradermal, topical, intramuscular, intraperitoneal, transdermal, intravenous, intratumoral, conjunctival and subcutaneous routes. Pulmonary administration can also be employed, e.g., by use of an inhaler or nebulizer, and formulation with an aerosolizing agent for use as a spray. In one embodiment, a MUC16 Glycosylation Antibody or antigen-binding fragment thereof, or a composition described herein is administered parenterally to a subject (e.g., a subject as described in Section 5.5.5). In a specific embodiment, said parenteral administration is intravenous, intramuscular, or subcutaneous.

The amount of a MUC16 Glycosylation Antibody or antigen-binding fragment thereof, or composition which will be effective in the treatment and/or prevention of a condition will depend on the nature of the disease, and can be determined by standard clinical techniques.

The precise dose to be employed in a composition will also depend on the route of administration, and the type of cancer, and should be decided according to the judgment of the practitioner and each subject's circumstances. For example, effective doses may also vary depending upon means of administration, target site, physiological state of the patient (including age, body weight and health), whether the patient is human or animal, other medications administered, or whether treatment is prophylactic or therapeutic. Treatment dosages are optimally titrated to optimize safety and efficacy.

In certain embodiments, an in vitro assay is employed to help identify optimal dosage ranges. Effective doses may be extrapolated from dose response curves derived from in vitro or animal model test systems.

For a MUC16 Glycosylation Antibody or antigen binding fragment thereof, the dosage may range from about 0.0001 to 100 mg/kg, and more usually 0.01 to 15 mg/kg, of the patient body weight. For example, dosages can be 1 mg/kg body weight, 10 mg/kg body weight, or within the range of 1-10 mg/kg or in other words, 70 mg or 700 mg or within the range of 70-700 mg, respectively, for a 70 kg patient. Generally, human antibodies have a longer half-life within the human body than antibodies from other species due to the immune response to the foreign polypeptides. Thus, lower dosages of human antibodies and less frequent administration is often possible.

In certain embodiments, such as in the administration of engineered cells expressing the antibodies or antigen-binding fragments thereof, or CARs, a subject is administered to the subject at a range of about one million to about 100 billion cells, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges. In some embodiments, the dose of total cells and/or dose of individual sub-populations of cells is within a range of between at or about 104 and at or about 109 cells/kilograms (kg) body weight, such as between 105 and 106 cells/kg body weight, for example, at or about $1\times10^5$ cells/kg, $1.5\times10^5$ cells/kg, $2\times10^5$ cells/kg, or $1\times10^6$ cells/kg, $2\times10^6$ cells/kg, $5\times10^6$ cells/kg, or $10\times10^6$ cells/kg body weight. For example, in some embodiments, the cells are administered at, or within a certain range of error of, between at or about $10^4$ and at or about $10^9$ T cells/kilograms (kg) body weight, such as between $10^5$ and $10^7$ T cells/kg body weight.

A MUC16 Glycosylation Antibody or antigen-binding fragment thereof can be administered on multiple occasions. Intervals between single dosages can be 1 week, 2 weeks, 3 weeks, 4 weeks, 1 month, 2 months, 3 months, 6 months, 1 year, or 2 years.

5.5.4 Combination Therapies

In a specific embodiment, the methods provided herein for treating cancer (e.g., ovarian cancer, pancreatic cancer, lung cancer, breast cancer, fallopian tube cancer, uterine (e.g., endometrial) cancer, or primary peritoneum cancer) in a subject, comprising administering to a subject in need thereof a pharmaceutical composition comprising a MUC16 Glycosylation Antibody or an antigen-binding fragment thereof described herein (see, Section 5.1 and Section 5.2), further comprise administering to the subject one or more additional therapeutic agents. In a specific embodiment, the additional therapeutic agent is for treating the cancer in the subject (e.g., ovarian cancer, pancreatic cancer, lung cancer, breast cancer, fallopian tube cancer, uterine (e.g., endometrial) cancer, and primary peritoneum cancer). In a specific embodiment, the additional therapeutic agent is for treating any side effects of treatment with a MUC16 Glycosylation Antibody or an antigen-binding fragment described herein described herein (see, Section 5.1 and Section 5.2).

In one embodiment, a first MUC16 Glycosylation Antibody or antigen-binding fragment thereof is administered that recognizes an epitope in MUC16 that comprises N-glycosylated Asn1806 but does not comprise N-glycosylated Asn1800 (i.e., it requires N-glycosylated Asn1806, but not N-glycosylated Asn1800, for binding to MUC16) in combination with a second MUC16 Glycosylation Antibody or antigen-binding fragment thereof that recognizes an epitope in MUC16 that comprises N-glycosylated Asn1806 and also comprises N-glycosylated Asn1800 (i.e., both N-glycosylated sites are part of the epitope recognized by the MUC16 Glycosylation Antibody or antigen-binding fragment thereof). Such a first MUC16 Glycosylation Antibody or antigen binding fragment thereof can be identified by (i) its ability to immunospecifically bind a cell recombinantly expressing a first form of MUC16, which first form of MUC16 is glycosylated, and wherein the amino acid sequence of the first form is SEQ ID NO: 133; (ii) its lack of immunospecific binding to a cell recombinantly expressing a third form of MUC16, which third form is glycosylated, and wherein the amino acid sequence of the third form is SEQ ID NO: 139; and (iii) its ability to immunospecifically bind a cell recombinantly expressing a fourth form of MUC16, which fourth form is glycosylated, and wherein the amino acid sequence of the fourth form is SEQ ID NO: 152, wherein the cell recombinantly expressing the first form of MUC16, the cell recombinantly expressing the third form of MUC16, and the cell recombinantly expressing the fourth form of MUC16 are of the same cell type. Such a second MUC16 Glycosylation Antibody or antigen-binding fragment thereof can be identified by (i) its ability to immunospecifically bind to a cell recombinantly expressing a first form of MUC16, which first form is glycosylated, and wherein the amino acid sequence of the first form is SEQ ID NO:133; and (ii) its lack of immunospecific binding to a cell recombinantly expressing a fifth form of MUC16, which fifth form is glycosylated, and wherein the amino acid sequence of the fifth form is SEQ ID NO:172, wherein the cell recombinantly expressing the first form of MUC16 is the same type of cell as the cell recombinantly expressing the fifth form of MUC16. The protein encoded by the amino acid sequence of SEQ ID NO: 172 is also referred to herein as $MUC16^{c114\text{-}N23}$. $MUC16^{c114\text{-}N23}$ consists of the C-terminal 114 amino acid residues of mature MUC16 (SEQ ID NO: 150 being the sequence of mature MUC16), except that the asparagines at amino acid positions 24 and 30 (corresponding to amino acid positions Asn1800 and Asn1806 of SEQ ID NO: 150) have been mutated to alanines. Thus, $MUC16^{c114\text{-}N23}$ is not capable of being N-glycosylated at amino acids positions 24 and 30 of SEQ ID NO: 172 (corresponding to amino acid positions Asn1800 and Asn1806 of SEQ ID NO: 150).

In one embodiment, a first MUC16 Glycosylation Antibody or antigen-binding fragment thereof is administered that recognizes an epitope in MUC16 that comprises N-glycosylated Asn1806 but does not comprise N-glycosylated Asn1800 (i.e., it requires N-glycosylated Asn1806, but not N-glycosylated Asn1800, for binding to MUC16) in combination with a second antibody or antigen-binding fragment thereof that recognizes an epitope in MUC16 that comprises N-glycosylated Asn1800 but does not comprise N-glycosylated Asn1806 (i.e., it requires N-glycosylated Asn1800, but not N-glycosylated Asn1806, for binding to MUC16). Such a first MUC16 Glycosylation Antibody or antigen binding fragment thereof can be identified by (i) its ability to immunospecifically bind a cell recombinantly expressing a first form of MUC16, which first form of MUC16 is glycosylated, and wherein the amino acid sequence of the first form is SEQ ID NO: 133; (ii) its lack of immunospecific binding to a cell recombinantly expressing a third form of MUC16, which third form is glycosylated, and wherein the amino acid sequence of the third form is SEQ ID NO: 139; and (iii) its ability to immunospecifically bind a cell recombinantly expressing a fourth form of MUC16, which fourth form is glycosylated, and wherein the amino acid sequence of the fourth form is SEQ ID NO: 152, wherein the cell recombinantly expressing the first form of MUC16, the cell recombinantly expressing the third form of MUC16, and the cell recombinantly expressing the fourth form of MUC16 are of the same cell type. Such a second antibody or antigen-binding fragment thereof can be identified by (i) its ability to immunospecifically bind to a cell recombinantly expressing a first form of MUC16, which first form is glycosylated, and wherein the amino acid sequence of the first form is SEQ ID NO:133; (ii) its ability to immunospecifically bind to a cell recombinantly expressing a third form of MUC16, which third form is glycosylated, and wherein the amino acid sequence of the third form is SEQ ID NO: 139; and (iii) its lack of immunospecific binding to a cell recombinantly expressing a fourth form of MUC16, which fourth form is glycosylated, wherein the amino acid sequence of the fourth form is SEQ ID NO:152, wherein the cell recombinantly expressing the first form of MUC16, the cell recombinantly expressing the third form of MUC16, and the cell recombinantly expressing the fourth form of MUC16 are of the same type of cell.

In specific embodiments, the additional agent is an agent used to treat ovarian cancer. In specific embodiments, the additional agent is an agent used to treat pancreatic cancer. In specific embodiments, the additional agent is an agent used to treat lung cancer. In specific embodiments, the additional agent is an agent used to treat breast cancer. In specific embodiments, the additional agent is an agent used to treat fallopian tube cancer. In specific embodiments, the additional agent is an agent used to treat uterine (e.g., endometrial) cancer. In specific embodiments, the additional agent is an agent used to treat primary peritoneum cancer.

A MUC16 Glycosylation Antibody or an antigen-binding fragment thereof described herein (see, Section 5.1 and Section 5.2) described herein can be administered with an additional therapeutic agent concurrently or sequentially (before and/or after). The antibody or antigen binding fragment thereof and the additional therapeutic agent can be administered in the same or different compositions, and by the same or different routes of administration. A first therapy (which is a MUC16 Glycosylation Antibody or an antigen-binding fragment thereof described herein (see, Section 5.1 and Section 5.2), or the additional therapeutic agent) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the second therapy (the MUC16 Glycosylation Antibody or antigen-binding fragment thereof described herein (see, Section 5.1 and Section 5.2) described herein, or the additional therapeutic agent) to a subject with cancer (e.g., ovarian cancer, pancreatic cancer, lung cancer, breast cancer, fallopian tube cancer, uterine (e.g., endometrial) cancer, and primary peritoneum cancer). In certain embodiments, an additional therapeutic agent administered to a subject in combination with MUC16 Glycosylation Antibody or antigen-binding fragment thereof described herein (see, Section 5.1 and Section 5.2) is administered in the same composition (pharmaceutical composition). In other embodiments, an additional therapeutic agent administered in combination with MUC16 Glycosylation Antibody or an antigen-binding fragment thereof described herein (see, Section 5.1 and Section 5.2) is administered to a subject in a different composition than the MUC16 Glycosylation Antibody or antigen-binding fragment thereof described herein (see, Section 5.1 and Section 5.2) (e.g., two or more pharmaceutical compositions are used).

5.5.5 Patient Population

A subject treated in accordance with the methods provided herein can be any mammal, such as a rodent, a cat, a canine, a horse, a cow, a pig, a monkey, a primate, or a human, etc. In a preferred embodiment, the subject is a human. In another preferred embodiment, the subject is a canine. As used herein, the terms "subject" and "patient" are used interchangeably.

In certain embodiments, a subject treated in accordance with the methods provided herein has been diagnosed with a MUC16-positive cancer, including but not limited to, ovary, lung, pancreas, breast, uterine, fallopian tube, or primary peritoneum cancer, or cancer of any other tissue that expresses the MUC16.

The following examples are offered by way of illustration and not by way of limitation.

6. EXAMPLES

6.1 Example 1: Expression of the Carboxy-Terminal Portion of MUC16/CA125 Induces Transformation and Tumor Invasion

6.1.1 Introduction

The serum CA125 antigen, an antigenic fragment of MUC16, has been a mainstay of ovarian cancer assessment and management since the early 1980s, but its biology and contribution to ovarian cancer manifestations have been poorly understood (see, References 1-3 as recited in Section 6.1.5, below). The cloning of CA125, achieved in 2001, first identified MUC16 as a tethered mucin with a small intracellular domain, a transmembrane domain, an ectodomain proximal to the putative cleavage site, and a large, heavily glycosylated region of 12-20 tandem repeats, each 156 amino acids long (FIG. 1A) (see, References 4-6 as recited in Section 6.1.5, below). Serous cancers of the ovary, fallopian tube, and uterus often express large amounts of MUC16, and aberrant MUC16 expression can be found in several other malignancies, including cancers of the lung, pancreas, and breast. Expression of other tethered mucins is a common feature of epithelial organs, and they are often over-expressed in malignancy. Two prominent examples are MUC1, which is over-expressed in many breast and ovarian cancers, and MUC4, which is characteristically abundant in pancreatic and gastrointestinal cancers (see, Reference 7 as recited in Section 6.1.5, below). Both of these mucins have been identified as having transforming properties (see, References 8 and 9 as recited in Section 6.1.5, below). The transforming mechanisms are different and incompletely understood. MUC1 has a beta-catenin homology region that has been shown to translocate to the nucleus and act as a transcription factor (see, References 10 and 11 as recited in Section 6.1.5, below). In contrast, MUC4 has HER-binding domains within its transmembrane region and acts, at least in part, through the HER family kinases (see, References 12 and 13 as recited in Section 6.1.5, below). MUC16 lacks homologous regions to either of these domains and appears to have evolved independently (see, Reference 12 as recited in Section 6.1.5, below). Compared to both MUC1 and MUC4, the expression of MUC16 is more restricted and is normally expressed, almost exclusively, to the Müllerian tract and the ocular epithelium (see, References 14-16 as recited in Section 6.1.5, below). The tandem repeat regions of the MUC16 molecule appear to function as key interacting proteins with mesothelin and other stromal proteins (see, Reference 17 as recited in Section 6.1.5, below). These interactions are probably responsible for the classic patterns of serosal spread by ovarian cancers. In clinical settings, high levels of the circulating elements from MUC16, which encode the CA125 antigen, are associated with an adverse clinical outcome, independent of stage, grade and other traditional clinical factors (see, Reference 18 as recited in Section 6.1.5, below). Others have identified the C-terminal of MUC16 as important in invasion and growth, but the specific regions of the proximal MUC16 sequence responsible for transformation have not been delineated (see, e.g., Therialt et al. Gynecol Oncol 2011, 121(3):434-443 and Giannakouros et al. Int. J. Oncol. 2015, 41(1):91-98). Amplification of genomic regions encoding MUC16 in ovarian cancer DNA and over-expression of MUC16 mRNA have been observed in The Cancer Genome Atlas (TCGA) ovarian cancer project and is associated with worse outcome (see, Reference 19 as recited in Section 6.1.5, below). Loss of MUC16 in the mouse is not associated with a distinct phenotype, but the effect of persistent or aberrant MUC16 expression is not known (see, Reference 20 as recited in Section 6.1.5, below). The data in this example show that the expression of the 114 C-terminal amino acid residues of MUC16 (MUC16$^{c114}$, SEQ ID NO:133), and in particular, glycosylation of residue Asn30 of MUC16$^{c114}$ (corresponding to Asn1806 of mature MUC16 (SEQ ID NO: 150)) is associated with specific alterations of signal transduction, gene expression, and aggressive biological behavior.

6.1.2 Materials and Methods 6.1.2.1 Synthesis of MUC16 Carboxy-Terminus (MUC16c114) and MUC16-CA125 Domain (MUC16c344) DNA Constructs and Glycosylated Fusion Protein DNA constructs encoding truncated forms of MUC16 (designated MUC16$^{c344}$, MUC16$^{c114}$, MUC16$^{c80}$, and MUC16$^{C86}$; FIG. 1B and FIG. 1C) were generated. EcoRV and NotI multiple cloning sites of the phrGFP II-C vector (phrGFP) (Stratagene, LaJolla, Calif.) were used to incorporate MUC16$^{c114}$, MUC16$^{c80}$, MUC16$^{c86}$ and MUC16$^{c344}$ DNAs to generate GFP fusion constructs were obtained with the GFP protein present on the carboxy-terminus of the truncated MUC16 fusion protein. PCR products for the MUC16 fragments (MUC16$^{c344}$, MUC16$^{c114}$, MUC16$^{c80}$, and MUC16$^{c86}$) were created using pBK-CMV-MUC16-B53 DNA as a template (Yin B W T, et al., International Journal of Cancer, 2002, 98(5):737-740), and PCR products were purified in a 1% agarose gel, sequenced, and inserted into the EcoRV and NotI multiple cloning sites of the phrGFP II-C vector (phrGFP). The pFUSE-hIgG1-Fc2 vector was purchased from InvivoGen (San Diego, Calif.). Polymerase chain reaction (PCR) primers were designed for the ectodomain MUC16$^{c57-114}$ (from position 1777 to 1834 of SEQ ID NO:150) or the sugar-binding domain of $^{117-244}$LGALS3 DNA sequences were synthesized (Sigma-Genosys, The Woodlands, Tex.) with the restriction enzyme site EcoRV as the forward primer and the restriction enzyme site NcoI as the reverse primer. PCR products for the MUC16$^{c57-114}$ fragment were created using pBK-CMV-MUC16-B53 DNA as a template and LGALS3 cDNA clone (MGC:2058 IMAGE:3050135 GenBank: AAH01120.1; DBSource accession BC001120.2), which was obtained from ATCC (Manassas, Va.) was used as a DNA template to synthesize the sugar-binding domain of the LGALS3 PCR product. PCR products were purified in a 1% agarose gel, sequenced, and inserted into the pFUSE-hIgG1-Fc2 vector.

6.1.2.2 Primers and PCR

Forward and Reverse primers for MUC16-cytoplasmic domain (MUC16$^{c114}$, carboxy-terminus 114 aa) (5'-CCATGCGATATCGCCACCATGGTGAACTTCTCGC-CACTGGCT-3' and 5'-TACGGCGGCCGCTTGCA-GATCCTCCAGGTCTAGG-3', SEQ ID NO:121 and SEQ ID NO:122, respectively). MUC16$^{c344}$ (one tandem repeat which has only one cysteine loop, 344 aa) (5'-CCATGC-GATATCGCCACCATGGTGACAGGCCCTGGGCT-GGACAGA-3' and 5'-TACGGCGGCCGCTTGCA-GATCCTCCAGGTCTAGG-3', SEQ ID NO:123 and SEQ ID NO: 124, respectively) with EcoRV and KOZAK in the forward primer and NotI in the reverse primer. MUC16$^{c114}$-GFP DNA construct was used to create MUC16$^{c80}$ and MUC16$^{c86}$ constructs by quick change primers. Forward and Reverse primers for MUC16$^{c57-114}$ pFUSE-hIgG1-Fc2 vector (5'-CCATGCGATATCAAACTTCTCGCCACTGGCT-3' and 5'-AGATCTAACCATGGGAAGGTCAGAAT-TCCCAGT-3', SEQ ID NO:125 and SEQ ID NO:126, respectively) and Forward and Reverse primers for the sugar binding domain of $^{117-244}$LGALS3 for pFUSE-hIgG1-Fc2 vector (5'-CATGCGATATCACCTTATAACCTGCCTTTG-3' and 5'-AGATCTAACCATGGTATATGAAGCACTGGT-3', SEQ ID NO:127 and SEQ ID NO:128, respectively) with EcoRV in the forward primer and NcoI in the reverse primer. All the above primers were synthesized by Sigma Genosys, The Woodlands, Tex.

PCR conditions were achieved by the following processes: DNA was melted at 95° C. for 5 minutes in order to achieve denaturation. Thirty repeat cycles of heating at 97° C. for 30 seconds, annealing at 60° C. for 1 minute, and extending at 72° C. for 1 minute were conducted. This was followed by an extension of the generated PCR product strand at 72° C. for 5 minute and then cooled at 4° C. overnight.

phrGFP II-C vector DNA, MUC16$^{c114}$, MUC16$^{c80}$, MUC16$^{c86}$, MUC16$^{c344}$, and MUC16$^{c678}$ gel purified DNAs individually digested overnight at 37° C. water bath with EcoRV and NotI (New England Biolabs, Beverly, Mass.) restriction enzymes. pFUSE-hIgG1-Fc2 vector DNA, MUC16$^{c57-114}$ and $^{117-244}$LGALS3 gel purified DNAs individually digested overnight at 37° C. water bath with EcoRV and NcoI (New England Biolabs, Beverly, Mass.) restriction enzymes. MUC16$^{c114}$ and phrGFP; MUC16$^{c344}$ and phrGFP; or MUC16$^{c678}$ and phrGFP restriction digested DNA's were gel purified and ligated overnight using T4 Ligase (Roche Diagnostics Corporation, Indianapolis, Ind.). Similarly, MUC16$^{c57-114}$ and pFUSE-hIgG1-Fc2; $^{117-244}$LGALS3 and pFUSE-hIgG1-Fc2 restrict digested DNA's were gel purified and ligated overnight using T4 Ligase (Roche Diagnostics Corporation, Indianapolis, Ind.). Ligated DNA were transformed into XL-1 Blue super competent cells (Stratagene, La Jolla, Calif.) following manufacturer's protocol and plated them on agar plates with LB medium containing Kanamycin (50 μg/mL, Sigma Chemical Co., St. Louis, Mo.) for phrGFP vectors or on agar plates with LB medium containing 25 μg/ml of Zeocin (Invitrogen, CA). Clones were selected the following day and Miniprep DNA was extracted using Wizard Plus Miniprep DNA purification system (Promega Corporation, Madison, Wis.). Selected clones DNA was sequence at MSKCC DNA sequencing core facility using forward and reverse primers of MUC16 and phrGFP to confirm MUC16 and phrGFP presence in the sequences as a fused constructs or MUC16$^{c57-114}$ and pFUSE-hIgG1-Fc2 or $^{117-244}$LGALS3 and pFUSE-hIgG1-Fc2. Megaprep DNA from such clones were made by using Wizard Plus Megaprep DNA purification system (Promega Corporation, Madison, Wis.) which were also confirmed for the presence of MUC16 and phrGFP or MUC16$^{c57-114}$ and pFUSE-hIgG1-Fc2 or $^{117-244}$LGALS3 and pFUSE-hIgG1-Fc2 in their sequences as a fused constructs.

6.1.2.3 Fluorescent Activated Cell Sorting (FACS)

Transfected cells were trypsinized, washed and counted by haemocytometer. Cells were distributed into multiple eppendorf tubes with at least 0.5-1×10$^6$/tube. Cells were washed with PBS containing 1% FCS and 0.025% Sodium Azide (FACS buffer). For surface FACS staining, cells were incubated either without (for second antibody control) or with 1 μg/tube of bioreactive supernatants of MUC16-carboxy-terminus monoclonals (4H11.2.5), Mouse anti-human OC125 (M3519) (DakoCytomation, Dako North America Inc., Carpinteria, Calif.) for 30 minutes on ice. Cells in eppendorf tubes were also for surface stained with 1 μg/tube of non-specific isotype matched control mouse antibodies (13C4 for IgG1 and 4E11 for IgG2b monoclonals obtained from MSKCC Monoclonal core facility) (data not shown) and incubated on ice for 30 minutes. All cells were washed 3 times with FACS buffer. Cells were incubated with 1 μg/tube of second antibody Goat anti-mouse IgG1-PE or IgG2b-PE for 30 minutes on ice and then washed 3 times with FACS buffer. The cells were analyzed by FACS Calibur.

6.1.2.4 Cell Cultures

NIH/3T3 (3T3) cells (fibroblasts) were obtained through the American Type Culture Collection (ATCC, Manassas, Va.), and A2780 cells are a human ovarian carcinoma cell line (see, Reference 28 as recited in Section 6.1.5, below). Both cell lines were maintained according to published conditions. Stable MUC16-positive cell lines were created by transfection of MUC16 expression vectors (phrGFP-MUC16$^{c344}$, phrGFP-MUC16$^{c114}$, phrGFP-MUC16$^{c80}$, and phrGFP-MUC16$^{c86}$) and selected using geneticin (G418, Invitrogen, Grand Island, N.Y.) in their respective culture medium and isolated based on expression of green fluorescence protein (GFP). The MUC16$^{c114}$ transfectants have cell surface expression of MUC16 protein from the putative cleavage site to the carboxy-terminus (amino acids 1777 to 1890 of SEQ ID NO:150) (see, Reference 5 as recited in Section 6.1.5, below). Cell lines with longer MUC16 fragments were prepared in a similar manner, including lines with expression of MUC16$^{c344}$-GFP vector that have cell surface expression of MUC16 protein as a 344 amino acid fragment extending to the carboxy-terminus of MUC16 (amino acids 1547 to 1890) (see, Reference 5 as recited in Section 6.1.5, below).

6.1.2.5 Transfection

All of the constructs were introduced into NIH/3T3 (3T3) and A2780 cells using DOTAP (Roche Diagnostics, Indianapolis Corporation, IN) following the manufacturer's protocol. Stable transfectants were selected with 400 μg/mL of G418 for 3T3 and A2780 cells in their respective culture media. They were cell sorted twice for GFP expression at the MSKCC Flow Cytometry Core Facility (FCCF), and selected cells were grown as lines for up to 15 passages. Routine monitoring by FACS analysis was done to confirm the GFP-positivity of these lines. Protein extracts of these lines were analyzed by western blot using anti-hrGFP (Stratagene, La Jolla, Calif.) and anti-MUC16-carboxy-terminus monoclonal antibodies (see, References 5 and 14 as recited in Section 6.1.5, below).

6.1.2.6 Growth Curves

One thousand stable transfected cells/well were seeded in 200 L of culture media/well in multiple 96 well flat bottomed plates and incubated at 37° C. and 5% $CO_2$ for 5 days. Every day, triplicate cultured plates were developed with 25 μL/well of Alamar Blue (ABD Serotec Co. UK) and incubated at 37° C. and 5% $CO_2$ for 4 hours. Plates were read on PerSeptive Biosystems CytoFluor Multiwell Fluorescent Plate Reader Model #4000 with excitation at 530 nM and emission at 620 nM. Growth curves over 4 days were recorded, and the mean values from triplicate plates were plotted accordingly.

6.1.2.7 Soft Agar Assay

Stable transfected cells were placed in an agarose suspension and plated over a thin agarose layer and analyzed for their ability to form anchorage independent colonies. One to five million cells in 10 mL of media-agarose suspension were plated per dish and incubated at 37° C. and 5% $CO_2$. The plates were monitored for colony formation. Additional culture media was overlaid every 4-5 days. After 11-14 days of culture, colonies were enumerated, and pictures of the colonies were taken.

6.1.2.8 Transfection into Eukaryotic Expression Vectors

The MUC16$^{c57-114}$-pFUSE-hIgG1-Fc2 and $^{117-244}$LGALS3-pFUSE-hIgG1-Fc2 constructs were separately transfected into human embryonic kidney (HEK) FreeStyle 293F cells (Invitrogen, CA) that express and secrete fusion proteins into serum free media. Three 10% SDS-PAGE gels were run with 5 μg/lane of fusion protein supernatants from transient transfected HEK 293F cells with pFUSE-hIgG1-Fc2 control empty vector, MUC16$^{c57-114}$-pFUSE-hIgG1-Fc2 vector, and LGALS3-pFUSE-hIgG1-Fc2 vector. One gel was directly stained with Gelcode reagent, as per the manufacturer's protocol. Proteins from two gels were transferred onto two nitrocellulose membranes that were blocked with 5% non-fat milk-Phosphate Buffered Saline containing 0.1% Tween-20 (PBST) for 1 hour at room temperature on a shaker. The membranes were probed with anti-human IgG1-Fc-HRP (γ1 chain specific) (Southern Biotech Inc., CA) at 1:5,000 dilution in 5% non-fat milk PBST; 4H11-HRP mAb at 1:2000 dilution (see, Reference 14 as recited in Section 6.1.5, below) in 5% non-fat milk PBST and anti-human GAL3 mAb (Santa Cruz Biotechnology, CA) at 1:200 dilution in 5% non-fat milk PBST overnight at 4° C. on a shaker. The GAL3-membrane was washed thrice with PBST and labeled with anti-mouse IgG-HRP second antibody at 1:3,000 dilution in 5% non-fat milk PBST for 1 hour at room temperature on a shaker. Membranes were washed thrice with PBST, and then they were treated with ECL reagent (Perkin Elmer, N.Y.) chemiluminiscence substrate for 5 minutes, and the illuminated signals were captured on X-ray films.

6.1.2.9 Invasion

Basement membrane invasion was determined in matrigel invasion chambers (BD Biosciences, Bedford, Mass.). Matrigel migration was measured at 48 hours in triplicate wells and compared with phrGFP vector controls and expressed as % phrGFP Control matrigel invasion. 0.1 μg/mL of Tunicamycin (Sigma-Aldrich, St. Louis Mo. cat # T7765) or 5 μg/mL of MUC16$^{57-c114}$-pFUSE-hIgG1-Fc2 or 5 μg/mL of $^{117-244}$LGALS3 pFUSE-hIgG1-Fc2 fusion protein treated stable cell line matrigel migration after 48 hours was measured and expressed as % phrGFP Control matrigel invasion.

BD BioCoat™ Matrigel™ Invasion Inserts or Chambers (catalog #354480 in 24 well plate) and Control Inserts (catalog #354578 in 24 well plate) were purchased from BD Biosciences, MA. Matrigel Invasion assay was performed as per manufacturer's protocol. Briefly, the matrigel chambers in 24 well plates (stored at −20° C.) and control inserts (stored at 4° C.) were allowed to come to room temperature. Both inserts were rehydrated with 0.5 mL of serum free medium in the insert as well as in the outside well of the 24 well plate, for 2 hrs at 37° C. 5% $CO_2$ humidified incubator. Cultured 3T3 or A2780 cells were trypsinized and washed with culture medium. A million cells were separated into another centrifuge tube and washed 3 times with serum free medium. These cells were later adjusted to give 10,000 cells in 0.5 mL serum free medium. The medium in the rehydrated inserts were removed and the insert was transferred into a new 24 well plate containing 0.75 mL of 10% Foetal Bovine Serum (FBS) containing culture medium in the well which serves as a chemo attractant. Immediately, 0.5 mL of the cells (10,000 cells) in serum free medium was added to the insert. Proper care was taken to see that there was no air bubble trapped in the insert and the outside well. The 24 well plate was incubated at 37° C. 5% $CO_2$ humidified incubator for 48 hrs. After incubation, the non-invading cells were removed from the upper surface of the membrane by "scrubbing" by inserting a cotton tipped swab into matrigel or control insert and gently applied pressure while moving the tip of the swab over the membrane surface. The scrubbing was repeated with a second swab moistened with medium. Then the inserts were stained in a new 24 well plate containing 0.5 mL of 0.5% crystal violet stain in distilled water for 30 minutes. Following staining, the inserts were rinsed in 3 beakers of distilled water to remove excess stain. The inserts were air dried in a new 24 well plate. The invaded cells were hand counted under an inverted microscope at 200× magnification. Several fields of triplicate membranes were counted and recorded in the figure.

6.1.2.10 Real-Time Polymerase Chain Reaction

RNA isolation was prepared by following the RiboPure Kit (Ambion, Austin, Tex.) protocol. RT PCR for a panel of metastasis and extracellular matrix protein genes was performed utilizing the RT2 Profiler PCR Array system (Super Array, Frederick, Md.), as previously described (see, Reference 29 as recited in Section 6.1.5, below).

6.1.2.11 Tumor Growth in Athymic Nude Mice

Transfected cell lines and appropriate control cell lines were introduced into the flank or peritoneal cavity of athymic nude mice, and routine animal care was provided by the MSKCC Antitumor Assessment Core Facility. For tumor growth assessment experiments, 2 million cells from each tumor line were implanted into each of 5-15 athymic nude mice. Tumor measurements were taken twice a week, and tumor growth was recorded to a maximum size of 1500 $mm^3$ per MSKCC RARC guidelines.

6.1.2.12 Western Blot Analysis

Stable cell lines were cultured in 10 cm dishes in their respective culture media and incubated at 37° C. and 5% $CO_2$ for 3 days. They were then washed twice with ice cold PBS and scraped with 1-2 mL of ice cold PBS and centrifuged. The pelleted cells were lysed with 0.2 mL of modified Ripa lysis buffer (20 mM Tris-HCL, pH 7.4; 150 mM NaCl; 1% NP-40; 1 mM Na3VO4; 1 mM PMSF; 1 mM DTT; with protease and phosphatase inhibitors cocktails (cat #11836170001 from Roche Diagnostics, IN)) for 30 min on ice and centrifuged at 4° C. for 10 min. Protein concentration of the supernatant was measured using Bio-Rad Protein Assay (BioRaD Laboratories, Hercules, Calif.). Equal amounts of protein were separated by SDS-Poly Acrylamide Gel Electrophoresis (SDS-PAGE) and transferred to PVDF membrane using BioRad transfer apparatus at 4° C. The membranes were blocked with 3% Bovine Serum Albumin (BSA) or 5% non-fat milk in PBS with 0.1% Tween-20 (PBST) at 4° C. overnight. Membranes were developed with a variety of primary antibodies (Cell Signaling, MA: Akt cat #9272; Phospho-Akt (Ser473)(193H12) cat #4058; p44/43 MAPK (Erk1/2) cat #9102; Phospho-p44/43 MAPK (Erk1/2)(Thr202/Tyr204) cat #9101); (Sigma-Aldrich, Inc., St. Louis, Mo.: β-Actin cat #A5441); (Southern BioTech, Birmingham, Ala.: Anti-human-Fc-IgG1-HRP cat #9054-05 and Abgent, San Diego, Calif.: Polyclonal LGALS3 antibody cat # AP11938b) at 4° C. overnight. The membranes were washed three times with PBST, and developed with HRP conjugated anti-mouse or anti-rabbit antibody (GE Healthcare, UK) (1:5000 dilution) for 1 hour at room temperature. Membranes were then washed three times with PBS-T and developed with a Western Lightning Chemiluminescence reagent (ECL, Perkin Elmer) for 1-5 minutes at room temperature, and the signals were developed on HyBlot CL film (Denville Scientific Inc. Metuchen, N.J.).

6.1.2.13 TCGA Expression Analysis of MUC16

Comprehensive genomic data were available for 316 serous ovarian cancer samples as part of the TCGA project (tcga.cancer.gov). Gene-level DNA copy-number calls were derived from CBS-segmented Agilent 1M microarray data using GISTIC. MUC16 mRNA expression was measured using three different platforms (Agilent 244K Whole Genome Expression Array, Affymetrix HT-HG-U133A, and Affymetrix Exon 1.0 arrays), and gene expression values were derived as described previously (see, Reference 30 as recited in Section 6.1.5, below). Somatic mutations in MUC16 were identified whole exome capture followed by next-generation sequencing (SOLiD or Illumina). All TCGA data were downloaded from the cBio Cancer Genomics Portal (www.cbioportal.org). mRNA expression values were then correlated with the corresponding DNA copy-number categories (homozygous deletion, hemizygous deletion, diploid, gain, high-level amplification) and somatic mutations were overlaid across all samples and plotted as a boxplot using the statistical framework R (www.R-project.org) as previously described (see, Reference 31 as recited in Section 6.1.5, below). Clinical data were obtained from the TCGA data portal (tcga-data.nci.nih.gov/tcga/).

6.1.2.14 $MUC16^{c354}$ Transgenic Mice

The conditional carboxy-terminus 354 amino acids ($MUC16^{c354}$) transgenic construct was made using vector phrGFP II-C(Stratagene, La Jolla, Calif.), and CMV promoter was replaced with CAG promoter from vector pCAG-CreERT2 (Addgene, Cambridge, Mass.). $MUC16^{c354}$ fragment was amplified by PCR from the construct B53 that was made by Yin B W et al (see, References 5 and 6 as recited in Section 6.1.5, below). The $MUC16^{c354}$ conditional construct contains the following units: pCAG, 5' loxP, hrGFP, BGHpA, 3' loxP, $MUC16^{c354}$, HA, and SV40pA.

Using the above $MUC16^{c354}$ conditional transgenic construct, the MSKCC Mouse Genetics Core Facility performed the microinjection procedure on B6CBAF1/J mice. Twelve $MUC16^{c354}$ conditional transgenic mice were identified from 99 mice by Southern Blot. All 12 pro-founders were mated with B6.FVB-Tg(EIIa-cre)C5379Lmgd/J mice (The Jackson Laboratory, Bar Harbor, Mich.) to remove hrGFP, which was located between two loxPs. $MUC16^{c354}$ PCR positive female mice for each pro-founder were dissected. The organs (brain, colon, heart, kidney, liver, lung, ovary, and spleen) from these dissected mice were minced and homogenized. The protein samples were analyzed by western blot to identify the founders which highly express $MUC16^{c354}$. The resulting transgenic mice were maintained on a mixed background.

Two founders of transgenic $MUC16^{c354}$ mice were crossed with p53 heterozygous mice (B6.129S2-Trp53tm1Tyj/J) (The Jackson Laboratory, Bar Harbor, Mich.) to create double transgenic MUC16c354:p53+/−.

The resulting transgenic mice were maintained on a mixed background. All mice were genotyped by PCR using extracted toe or tail DNA. All experimental animals were maintained in accordance with the guidelines approved by the MSKCC Institutional Animal Care and Use Committee and Research Animal Resource Center and the NIH Guide for the Care and Use of Laboratory Animals.

6.1.2.15 Histological Analysis

Mice at 12 months of age were sacrificed and necropsied. Following macroscopic examination, dissected tissue samples were fixed for 24 hours in 10% neutral buffered formalin, then processed in alcohol and xylene, embedded in paraffin, sectioned at 5 m thickness, and stained with hematoxylin and eosin (H&E). Tissues were examined by a veterinary pathologist (SM), and neoplastic and non-neoplastic lesions were diagnosed according to published guidelines on rodent pathology nomenclature.

6.1.2.16 Statistical Analysis

Student's two sided paired t test was used to compare groups for studies of in vitro growth, invasion, and soft agar growth potential. The chi square test was used to analyze RT-PCR data for significance, according to provided software (SuperArray). The comparisons of the tumor volumes were made using area under the curve assessments for total tumor volume over time in each animal. The assessment of tumor volume was made based on the last day that all animals were alive in both groups. A non-parametric test for ranks (Wilcoxon two sample test) was used to test for a difference in distributions among the groups. In the animal survival studies, a time to event analysis was performed, with the event defined as time to tumor volume exceeding 1,500 $mm^3$ or ulceration. Animals with tumor volume less than 1,500 $mm^3$ were followed for up to 60 days and then censored. The Kaplan-Meier method was used to estimate survival distribution (see, Reference 32 as recited in Section 6.1.5, below).

6.1.3 Results

Following apparent cleavage and release of the tandem repeat region of the MUC16 protein, approximately 114 amino acids of the carboxy-terminus (c114) of the protein are thought to remain on the cell surface, and the potential functions of this part of the molecule are not known. The role of this most proximal part of the MUC16 protein in malignant transformation and behavior in 3T3 fibroblasts and ovarian cancer cell lines was analyzed. To test the effect of the residual c114 amino acid element proximal to the cleavage site, two vectors were designed: (1) MUC16$^{c114}$-GFP vector, and (2) the truncated MUC16$^{c344}$-GFP vector (FIG. 1) and these vectors and the phrGFP control vector, were independently transfected into 3T3 fibroblast cells. MUC16$^{c114}$- and MUC16$^{c344}$-expressing cell lines were selected and maintained with G418, and MUC16$^{c114}$ and MUC16$^{c344}$ stable expression was confirmed by FACS analysis using monoclonal antibodies that recognize unique amino acid sequences of the MUC16 carboxy-terminus (see, Reference 14 as recited in Section 6.1.5, below). The cell lines that express 344 amino acids from the MUC16 (SEQ ID NO:132) protein (MUC16$^{c344}$-GFP lines) bear the classic CA125 epitope, which is recognized by the OC125 antibody on the cell surface by FACS analysis, and the CA125 is released into the cell culture supernatant. OC125 does not recognize MUC16$^{c114}$-GFP cells. However, all of the transfected lines were cell surface positive for the MUC16$^{c114}$ extracellular sequences (SEQ ID NO:133), proximal to the putative cleavage site and recognized by the MUC16 ectodomain-specific 4H11 antibody (see, Reference 14 as recited in Section 6.1.5, below; FIG. 1).

6.1.3.1 3T3 Cells

To investigate the transforming properties conferred by the residual, post-cleavage elements of MUC16, the characteristics of the 3T3 MUC16$^{c114}$-GFP and 3T3 MUC16$^{c344}$-GFP cell lines were analyzed and the effects of these two minimal MUC16 elements were compared to the vector controls. Expression of either the most proximal 114 amino acids (MUC16$^{c114}$) or the proximal 344 amino acids (MUC16$^{c344}$) of the MUC16 sequence had no significant effect on the in vitro growth rates for any of the transfected cell lines when compared with that of the parental line FIG. 2A. However, expression of the same elements of the MUC16 protein substantially altered 3T3 anchorage dependent growth in soft agar cloning. Both the minimal c114 fragment and the c344 fragment significantly increased the number of soft agar colonies compared to the vector only controls (FIG. 3A). The proximal portions of MUC16 protein expression also enhanced the migration ($p<0.0001$) of MUC16+3T3 cells in classic matrigel invasion assays compared to the 3T3 cells transfected with phrGFP vector controls (FIG. 3B). When the 3T3 cells expressing various MUC16 protein fragments were examined for expression of selected metastasis and invasion gene transcripts, there were multiple invasion genes upregulated, including chemokine ligand 12 (CXCL12), Cadherin 11 (CDH11), and the matrix metalloproteinases MMP2 and MMP9 (FIG. 3C). Other transcripts including Fibronectin (FN1) and Neurofibromin (NF2) are consistently decreased. MUC16 might act through canonical signaling pathways in ways similar to the effects of MUC1 and MUC4, since MUC16 alters in vivo tumor growth and increases invasive properties of cells bearing the MUC16 protein. The interacting ERK and AKT pathways have previously been identified as important signaling mechanisms in ovarian cancer and regulators of tumor cell invasion (see, References 21 and 22 as recited in Section 6.1.5, below). As shown in FIG. 3D, there was activation of both pathways as evidenced by increases in pAKT(S473) and pERK (T202/Y204).

The most unambiguous hallmark of oncogenic transformation is the ability to promote growth in immunodeficient mice. In order to measure the effects of MUC16 on tumor growth rate, a flank tumor model was utilized to facilitate regular tumor measurements. As shown in FIG. 3E, when the MUC16 expressing 3T3 cell lines (vector phrGFP, MUC16$^{c114}$-GFP and MUC16$^{c344}$-GFP) were implanted into the flanks of athymic nude mice, both the MUC16$^{c114}$-GFP and MUC16$^{c344}$-GFP formed larger tumors compared to the vector only controls at 4 weeks. There was not a statistical difference between the cell line expressing the MUC16$^{c114}$-GFP and MUC16$^{c344}$-GFP proteins (FIG. 3E), suggesting the oncogenic effects of MUC16 expression are linked to the most proximal parts of the molecule. This increase in tumor growth rate was seen throughout the period of tumor growth and is consistent with the clinical linkage between high levels of MUC16 expression (as serum CA125) and poor survival (see, Reference 18 as recited in Section 6.1.5, below).

6.1.3.2 A2780 Human Ovarian Cancer Cells

While the expression of MUC16 protein in 3T3 cells was clearly linked to hallmarks of transformation, some fully transformed ovarian cancer cell lines lack MUC16 expression when cultured. In order to explore the contribution of MUC16 to the behavior of human ovarian cancer cells, A2780 cells (a human ovarian carcinoma cell line that does not express MUC16) were transfected with MUC16$^{c114}$-GFP or MUC16$^{c344}$-GFP. The MUC16-expressing cells were selected by G418 and subjected to FACS for MUC16 and GFP expression. Since these cells grow well in soft agar in the absence of MUC16 expression, the effect of MUC16$^{c344}$ and MUC16$^{c114}$ on matrigel invasion was analyzed. As shown in FIG. 4A, MUC16$^{c114}$ and MUC16$^{c344}$ expression clearly promoted matrigel invasion in A2780 cells. Likewise, the effect of MUC16$^{c114}$ and MUC16$^{c344}$ on the activation of the ERK and AKT pathways is similar to that seen in the 3T3 cells, increasing the basal levels of both pAKT(S473) and pERK (T202/Y204) (FIG. 4B). Thus, even in the malignant ovarian cell lines, increased expression of MUC16 carboxy-terminus elements is linked to increased invasion and oncogene activation. In addition, the in vivo tumor growth of MUC16$^{c114}$- and MUC16$^{c344}$-transfected A2780 lines was analyzed (FIG. 4C). In both settings, the MUC16$^{c114}$ cell line and the MUC16$^{c344}$ cell line grew more rapidly than the vector only controls. In this human cancer model, the vector controls did grow at a sufficient rate to eventually kill the animals.

6.1.3.3 Glycosylation Studies

To determine the specific part of MUC16$^{c114}$ responsible for transformation, two additional MUC16 fragments were constructed: (1) MUC16$^{c80}$, wherein a 34 amino acid sequence from the ectodomain of MUC16$^{c114}$ (from position 1798 to 1831, as numbered in the original publication) was deleted (FIG. 1D; SEQ ID NO: 135) (see, Reference 5 as recited in Section 6.1.5, below); and (2) MUC16$^{c86}$, wherein the MUC16$^{c114}$ construct retained the entire ectodomain of MUC16 but removed a 28 amino acid sequence from the cytoplasmic domain's putative Ezrin domain, the potential tyrosine phosphorylation sites and SH2 domain (from position 1857 to 1884) (FIG. 1D; SEQ ID NO:134). These constructs were introduced into 3T3 cells and selected by FACS for cell surface expression of the remaining MUC16$^{c80}$ and MUC$^{c86}$ sequences. These two additional cell populations were then examined for MUC16$^{c80}$- and MUC$^{c86}$-dependent changes. The MUC16$^{c86}$ construct (construct with the intact ectodomain) retained a much greater capacity for soft agar colony formation than the MUC16$^{c80}$ construct (construct with the intact cytoplasmic) domain (FIG. 5A). This was also true of the capacity for matrigel invasion (FIG. 5B). The MUC16$^{c80}$ expressing 3T3 cells had a rate of invasion that was not statistically different than that of the phrGFP vector control. In contrast, the MUC16$^{c86}$ expressing 3T3 cells retained a more invasive phenotype, similar to the intact MUC16$^{c114}$ and MUC16$^{c344}$ cells. When the activation of AKT and ERK pathways was examined, the results were consistent with the soft agar colony and matrigel invasion studies (FIG. 5C). Expression of the MUC16$^{c80}$ fragment (without the complete intact ectodomain) did not activate ERK and AKT and was similar to the phrGFP vector control, in contrast, the MUC16$^{c86}$ (with the intact ectodomain) expressing 3T3 cells were similar to the full MUC16$^{c114}$ expressing 3T3 cells in the activation of ERK and AKT. Finally, the importance of the intact ectodomain was confirmed in the xenograft tumor models.

Loss of the intact MUC16 ectodomain (3T3 MUC16$^{c80}$) resulted in a loss of MUC16$^{c114}$-dependent 3T3 growth enhancement compared to the MUC16$^{c114}$ control, while the MUC16$^{c86}$-expressing 3T3 cells had a modest growth delay but had a similar overall effect to the MUC16$^{c114}$ expressing 3T3 cells (FIG. 5D). Thus, the extracellular part of the MUC16$^{c114}$ fragment was responsible for the transformative effects of MUC16 in 3T3 cells. To further investigate the role of the extracellular fragment of MUC16$^{c114}$, co-precipitation studies were performed with the MUC16$^{c114}$-expressing 3T3 cell, using a panel of MUC16-targeting antibodies (see, Reference 14 as recited in Section 6.1.5, below). No co-precipitating single bands were identified by silver staining, and specific western blots for EGFR, integrins and HER3 were negative. However, analysis of the MUC16$^{c114}$ sequence suggested that the three potential N-glycosylation sites (Asn1777, Asn1800, and Asn1806 (FIG. 6, SEQ ID NO:132 and SEQ ID NO:133)) in the ectodomain might play a role. The role of these N-glycosylation sites was analyzed. Using site-specific point mutation, all three of the asparagines were changed to alanines. This modified MUC16$^{c114}$ construct, designated MUC16$^{c114\text{-}N123}$, was introduced into 3T3 cells, and MUC16$^{c114\text{-}N123}$-expressing cells were isolated by FACS and 4H11 ectodomain antibodies. As shown in FIG. 7A, these asparagine to alanine mutations completely abrogated the MUC16$^{c114}$-induced enhancement of matrigel invasion seen with the parent MUC16$^{c114}$ expression vector in 3T3 cells. To confirm the role of N-glycosylation, the 3T3 cells were treated with the glycosylation inhibitor Tunicamycin (0.1 μg/mL), and a significant decreasement in matrigel invasion was noted. Two synthetic protein inhibitors were also tested to further explore the role of the MUC16$^{c114}$ extracellular sequence. The MUC16 external sequence (from position 1777 to 1834 as numbered in Reference 5 as recited in Section 6.1.5, below) was attached to a human Fc backbone pFUSE (MUC16$^{c57\text{-}c114}$ pFUSE) to provide a "dummy" receptor. This construct was compared to both the MUC16$^{c114}$ invasion and a pFUSE vector control. As shown in FIG. 7B, the "dummy" receptor construct diminished the overall effect of the MUC16$^{c114}$ expression vector on matrigel invasion (FIG. 7). Presuming that lectins were linked to the effect of the glycosylated MUC16$^{c114}$ protein, a second inhibitor was constructed from the sugar-binding domain of LGALS3 (amino acids 117 to 244; FIG. 7 and FIG. 8) (see, Reference 23 as recited in Section 6.1.5, below) attached to the same pFUSE backbone ($^{117\text{-}244}$LGALS3pFUSE). Like Tunicamycin, both of these protein inhibitors interfered with the interaction of MUC16$^{c114}$ with other cell surface proteins while the pFUSE vector alone had no effect (FIG. 7B). As with other interventions, the effect on pAKT expression and pERK was diminished in parallel with the loss of matrigel invasion when the N-glycosylation sites were removed, as shown in FIG. 7C. However, the MUC16$^{c114\text{-}N123}$ construct had high levels of expression of the MUC16$^{c114\text{-}N123}$ protein, as demonstrated by 4H11 (MUC16 ectodomain-specific) binding. The impact of N-glycosylation loss was likewise confirmed in the reduction of growth in the transfected 3T3 cells in nu/nu mice, as shown in FIG. 7D.

6.1.3.4 Transgenic Mouse

The effect of expression of the carboxy-terminal MUC16 elements in transgenic mice and the rate of spontaneous tumor formation was examined. Conditional transgenic mice expressing MUC16$^{c354}$ (the full c114 sequence and the most proximal CA125 bearing tandem repeat) were generated. The CMV early enhancer plus chicken 3 actin promoter (CAG) was utilized to force substantial MUC16$^{c354}$ expression in all murine tissues. This strategy was chosen because the physiology of the human ovary is very different from the murine reproductive system, and tissue-specific ovarian promoters have been weak and relatively difficult to use in transgenic systems. The strategy for these mice is shown in FIG. 9A.

Conditional transgenic animals were selected by southern blot, as shown in FIG. 9B, and crossed with EIIa-Cre mice to produce MUC16$^{c354}$ transgenic founders. As shown in FIG. 9C, two founders were chosen and a colony of MUC16$^{c354}$ transgenic mice was created. The two founders highly express MUC16$^{c354}$ in many organs, e.g., brain, colon, heart, kidney, liver, lung, ovary, and spleen. These mice have no effect from the widespread ectopic expression of MUC16$^{c354}$, with normal ratios of male:female progeny, normal rates of fertility, and apparently normal life span, exceeding 2 years. Necropsy of two apparently healthy animals (one male and one female) from the control population and the MUC16$^{c354}$ transgenic mice at 3-month intervals up to 1 year was only remarkable for mild/moderate uterine endometrial hyperplasia in older female mice, but the incidence and severity was not significantly different than the wild type controls. Selected tissues are shown in FIG. 10. Only one spontaneous soft tissue tumor (sarcoma) was observed in the colony of more than 100 animals observed for 2 years or more.

Based on this result, it was hypothesized that a "second hit" would potentially be required. It is noteworthy than murine models of BRCA1 mutation also require a second hit, and loss of p53 significantly increased the frequency of tumors. MUC16$^{c354}$ mice were crossed with p53+/− mice from The Jackson Laboratory. There was limited early effect. However, after approximately 6 months, MUC16$^{c354}$ mice with p53+/− began to develop spontaneous sarcomatous tumors of the soft tissue and lymphoma at a rate higher than that of normal control animals. Selected tumors are shown in the panel insets of FIG. 9D. The Kaplan-Meier survival for these mice is shown in FIG. 9E. The MUC16$^{c354}$:p53+/− mice showed a significantly worse overall survival due to spontaneous tumor development ($p<0.014$). The total number of tumors seen in each group were: p53+/− mice, 20/107 mice; MUC16$^{c354}$ and p53+/− mice, 34/91 mice; MUC16$^{c354}$ mice, 1/72 mice; wildtype mice, 0/91 mice. When 8 collected tumors were examined for p53 genomic sequencing, all of the spontaneous tumors had loss of the normal allele of p53, indicating that MUC16 dependent tumor development also requires loss of normal p53 function.

6.1.3.5 Ovarian TCGA

Based on the of the MUC16 fragments on transformation and tumor aggressiveness in the experimental models, the link between genetic alterations in MUC16 and the outcomes in ovarian cancer was examined. The TCGA ovarian cancer project is a well-studied collection containing 316 serous ovarian cancers with complete data, including clinical outcome data. Since expression of MUC16 protein is an important driver of cancer behavior, the impact of MUC16 copy number on MUC16 mRNA expression was analyzed. The MUC16 transcript expression was generally related to the MUC16 gene copy number, although there was a broad variation in MUC16 transcript expression in all of the groups examined (except, of course, the rare homozygous deletion of MUC16). In most cases, the MUC16 mRNA expression was clustered at higher transcript numbers than the normal fallopian tube samples included as controls. Gene copy number is one of several variables that will potentially alter the expression of MUC16 protein, but it is clear that MUC16 mRNA expression (and MUC16 protein, of course) is often increased in serous ovarian cancer. The combined impact of MUC16 over-expression or mutation on clinical outcomes in the TCGA data set was also examined. When the TCGA data set is divided into MUC16 expression quintiles, the 20% of patients with the highest MUC16 expression had a significantly worse survival than the patients with lower MUC16 expression ($p=0.02969$). This relationship was further strengthened when the 18 patients with MUC16 mutations were included in the high MUC16 expression group ($p=0.02117$), as shown in FIG. 11A. Taken together, this analysis demonstrates that MUC16 expression has an adverse impact on the survival of patients with ovarian cancer and confirms the negative biologic effects of MUC16 expression identified in our preclinical models.

Ovarian cancers often demonstrate activation of the PI3K pathway. These activations occur primarily through amplification and overexpression rather than point mutation events as ovarian cancer is generally characterized by alterations in copy number. Based on the activation of the PI3K/AKT pathway in our cell line models, the relationship between MUC16 and other activating genetic alterations in the PI3K pathway was examined. As shown in FIG. 11B, overexpression and mutation events associated with MUC16 are generally complementary with other pathway events like PTEN loss, amplification of AKT1, AKT2, or PI3KCA. The mechanism of this MUC16-driven AKT activation remains unknown. Further, the role of ERK activation was examined but no link between MUC16 expression and ERK pathway mutations was identified.

6.1.4 Discussion

MUC16, encoding the CA125 antigen, circulates in the plasma of many patients with ovarian cancer (see, Reference 1 as recited in Section 6.1.5, below). MUC16 is unique among the tethered mucins for its limited expression outside mullerian tissues (see, References 2 and 14 as recited in Section 6.1.5, below). While increasingly viewed as an adverse prognostic factor independent of tumor bulk, the biological mechanism for its negative impact has not been well understood (see, Reference 18 as recited in Section 6.1.5, below). The $NH_2$-portion of the molecule contains multiple tandem repeats that encode the CA125 antigen and appear to serve as important adhesion partners to mesothelin and some galectins (FIG. 1A) (see, References 5, 17, and 24-26 as recited in Section 6.1.5, below). While these adhesion functions have been suggested to be critical in MUC16-related adverse outcome, these studies do not explain all of the observed changes in ovarian cancer cell behavior. The cloning of the MUC16 glycoprotein has provided basic structural information about the MUC16 gene product (see, References 4 and 5 as recited in Section 6.1.5, below). The data presented in this example are the first data to indicate that MUC16 may mediate signaling from the environment into the cancer cell, in particular, the data presented in this example identify the glycosylated MUC16 ectodomain as critical to MUC16 alterations in cancer cell behavior.

This example demonstrates that 114 amino acids from the carboxy-terminus of MUC16 are sufficient to transform NIH/3T3 (3T3) cells, supporting both increased soft agar growth and increased matrigel invasiveness. While others have identified the most membrane proximal C-terminal portion of MUC16 as the critical elements in MUC16-induced behaviors, we link these behaviors to the N-glycosylation sites in the retained MUC16 ectodomain. These changes are associated with an altered gene-expression profile and increased expression of critical invasion genes such as MMP2, MMP9, CXCL12, and CDH11. While longer elements can induce a more virulent behavior, even the residual 114 amino acids proximal to the putative cleavage site are sufficient in 3T3 cells to induce the same changes in invasion gene expression. Moreover, glycosylation of Asn30 of MUC16$^{c114}$ (corresponding to Asn1806 of mature MUC16 (SEQ ID NO:150) was essential for MUC16$^{c114}$ oncogenic properties. Without being bound by any particular theory, these findings are most consistent with an "outside in" signal transduction by the most proximal portions of the protein, including a residual extracellular domain along with the transmembrane domain and cytoplasmic tail. In contrast to the results of Theriault (Therialt et al. Gynecol Oncol 2011, 121(3):434-443) and Giannakouros (Giannakouros et al. Int. J. Oncol. 2015, 41(1):91-98), loss of the intracellular cytoplasmic domain had less impact than loss of the glycosylated ectodomain. These differences may reflect the specific mutations chosen and the methodology to reduce expression. The "inside-out" signal appears to activate a transcription of a gene program that facilitates the implantation and growth of MUC16 expressing cells in soft agar and nude mice. When the transfected cells are examined for activation of common oncogenic pathways, both AKT and ERK pathways appear to be activated by constitutive expression of MUC16. The mechanism by which MUC16 increases AKT/ERK phosphorylation is unclear and will require further studies. The absence of co-precipitating receptors suggests that other mechanisms may also be involved. Although MUC16 sequences are very different, other tethered mucins, including both MUC1 and MUC4, have been shown to act as signal-generating oncogenes in 3T3 cells and rat fibroblasts (see, References 8 and 9 as recited in Section 6.1.5, below). It is likely that the role of mucins on the cancer cell surface play important roles through mechanisms that are still being defined.

Based on the findings in 3T3 cells, the results of the MUC16 transgenic mouse experiment is highly supportive. By itself, the same MUC16 proximal 354 sequence could be readily expressed in nearly all murine tissues with no adverse effect in the transgenic mouse. The rate of spontaneous tumor formation was very low in those mice, and reproductive function seemed unaffected. However, like other murine ovarian cancer models, loss of p53 function appears to play a strong permissive role in MUC16-dependent tumor formation (see, Reference 27 as recited in Section 6.1.5, below). These results certainly are consistent with uniform p53 inactivation, which characterizes ovarian cancer in the TCGA data set.

These findings describe MUC16-linked changes in cellular behavior and gene transcription. The in vitro and in vivo models are consistent with the adverse effects of MUC16 expression levels in serous ovarian cancer and promote the understanding of MUC16 as a pathogenic contributor to the behaviors of ovarian cancer. The adverse impact of increasing CA125 expression is consistent with increased in vivo tumor growth and lethality of MUC16 (+) 3T3 transfectants (see, Reference 18 as recited in Section 6.1.5, below).

6.1.5 References Cited in Example 1

1. Bast R C Jr, Klug T L, St John E, Jenison E, Niloff J M, et al. (1983) A radioimmunoassay using a monoclonal antibody to monitor the course of epithelial ovarian cancer. N Engl J Med 309: 883-887.
2. Kabawat S E, Bast R C Jr, Bhan A K, Welch W R, Knapp R C, et al. (1983) Tissue distribution of a coelomic-epithelium-related antigen recognized by the monoclonal antibody OC125. Int J Gynecol Pathol 2: 275-285.
3. Bast R C Jr, Badgwell D, Lu Z, Marquez R, Rosen D, et al. (2005) New tumor markers: CA125 and beyond. Int J Gynecol Cancer 15 Suppl 3: 274-281.
4. O'Brien T J, Beard J B, Underwood L J, Dennis R A, Santin A D, et al. (2001) The CA 125 gene: an extracellular superstructure dominated by repeat sequences. Tumour Biol 22: 348-366.
5. Yin B W, Lloyd K O (2001) Molecular cloning of the CA125 ovarian cancer antigen: identification as a new mucin, MUC16. J Biol Chem 276: 27371-27375.
6. Yin B W, Dnistrian A, Lloyd K O (2002) Ovarian cancer antigen CA125 is encoded by the MUC16 mucin gene. Int J Cancer 98: 737-740.
7. Hollingsworth M A, Swanson B J (2004) Mucins in cancer: protection and control of the cell surface. Nat Rev Cancer 4: 45-60.
8. Li Y, Liu D, Chen D, Kharbanda S, Kufe D (2003) Human DF3/MUC1 carcinoma-associated protein functions as an oncogene. Oncogene 22: 6107-6110.
9. Bafna S, Singh A P, Moniaux N, Eudy J D, Meza J L, et al. (2008) MUC4, a multifunctional transmembrane glycoprotein, induces oncogenic transformation of NIH3T3 mouse fibroblast cells. Cancer Res 68: 9231-9238.
10. Huang L, Chen D, Liu D, Yin L, Kharbanda S, et al. (2005) MUC1 oncoprotein blocks glycogen synthase kinase 3beta-mediated phosphorylation and degradation of beta-catenin. Cancer Res 65: 10413-10422.
11. Li Q, Ren J, Kufe D (2004) Interaction of human MUC1 and beta-catenin is regulated by Lck and ZAP-70 in activated Jurkat T cells. Biochem Biophys Res Commun 315: 471-476.
12. Duraisamy S, Ramasamy S, Kharbanda S, Kufe D (2006) Distinct evolution of the human carcinoma-associated transmembrane mucins, MUC1, MUC4 AND MUC16. Gene 373: 28-34.
13. Ramsauer V P, Carraway C A, Salas P J, Carraway K L (2003) Muc4/sialomucin complex, the intramembrane ErbB2 ligand, translocates ErbB2 to the apical surface in polarized epithelial cells. J Biol Chem 278: 30142-30147.
14. Dharma Rao T, Park K J, Smith-Jones P, Iasonos A, Linkov I, et al. (2010) Novel Monoclonal Antibodies Against the Proximal (Carboxy-Terminal) Portions of MUC16. Appl Immunohistochem Mol Morphol 18: 462-72.
15. Corrales R M, Galarreta D, Herreras J M, Saez V, Arranz I, et al. (2009) Conjunctival mucin mRNA expression in contact lens wear. Optom Vis Sci 86: 1051-1058.
16. Govindarajan B, Gipson I K (2010) Membrane-tethered mucins have multiple functions on the ocular surface. Exp Eye Res 90: 655-663.
17. Kaneko O, Gong L, Zhang J, Hansen J K, Hassan R, et al. (2009) A binding domain on mesothelin for CA125/MUC16. J Biol Chem 284: 3739-3749.
18. Zorn K K, Tian C, McGuire W P, Hoskins W J, Markman M, et al. (2009) The prognostic value of pretreatment CA 125 in patients with advanced ovarian carcinoma: a Gynecologic Oncology Group study. Cancer 115: 1028-1035.
19. The Cancer Genome Atlas. Available from: http://cancergenome.nih.gov/.
20. Cheon D J, Wang Y, Deng J M, Lu Z, Xiao L, et al. (2009) CA125/MUC16 is dispensable for mouse development and reproduction. PLoS One 4: e4675.
21. Mazzoletti M, Broggini M (2010) PI3K/AKT/mTOR Inhibitors In Ovarian Cancer. Curr Med Chem 17: 4433-4447.
22. Ventura A P, Radhakrishnan S, Green A, Rajaram S K, Allen A N, et al. (2010) Activation of the MEK-S6 pathway in high-grade ovarian cancers. Appl Immunohistochem Mol Morphol 18: 499-508.
23. Strausberg R L, Feingold E A, Grouse L H, Derge J G, Klausner R D, et al. (2002) Generation and initial analysis of more than 15,000 full-length human and mouse cDNA sequences. Proc Natl Acad Sci USA 99: 16899-16903.

24. Seelenmeyer C, Wegehingel S, Lechner J, Nickel W (2003) The cancer antigen CA125 represents a novel counter receptor for galectin-1. J Cell Sci. 116(Pt 7): 1305-1318.
25. Lloyd K O, Yin B W (2001) Synthesis and secretion of the ovarian cancer antigen CA 125 by the human cancer cell line NIH:OVCAR-3. Tumour Biol 22: 77-82.
26. Liu J, Yang G, Thompson-Lanza J A, Glassman A, Hayes K, et al. (2004) A genetically defined model for human ovarian cancer. Cancer Res 64: 1655-1663.
27. Xing D, Orsulic S (2006) A mouse model for the molecular characterization of brca1-associated ovarian carcinoma. Cancer Res 66: 8949-8953.
28. Rao T D, Rosales N, Spriggs D R (2011) Dual-fluorescence isogenic high-content screening for MUC16/CA125 selective agents. Mol Cancer Ther 10: 1939-1948.
29. Shinoda Y, Ogata N, Higashikawa A, Manabe I, Shindo T, et al. (2008) Kruppel-like factor 5 causes cartilage degradation through transactivation of matrix metalloproteinase 9. J Biol Chem 283: 24682-24689.
30. TCGA (2008) Comprehensive genomic characterization defines human glioblastoma genes and core pathways. Nature 455: 1061-1068.
31. Taylor B S, Schultz N, Hieronymus H, Gopalan A, Xiao Y, et al. (2010) Integrative genomic profiling of human prostate cancer. Cancer Cell 18: 11-22.
32. Heller G, Vendatraman E (1996) Resampling procedures to compare two survival distributions in the presence of right censored data. Biometrics 52: 1204-1213.

6.2 Example 2: MUC16 Glycosylation Antibodies

6.2.1 Introduction

The CA125 antigen, recognized by the OC125 antibody (see, Reference 1 as recited in Section 6.2.5, below) is a heavily glycosylated antigen expressed in the tandem repeat domains from the extracellular portion of the MUC16 glycoprotein (see, References 2 and 3 as recited in Section 6.2.5, below). This circulating antigen is predominantly derived from benign or malignant Mullerian tissues and is FDA approved as a tumor marker for human ovarian cancer but its function and role in carcinogenesis is not known (see, References 4-6 as recited in Section 6.2.5, below). MUC16 belongs to a family of complex tethered mucins and it consists of a large, heavily glycosylated extracellular domain, a small ectodomain between the membrane and the putative cleavage site, a hydrophobic transmembrane region, and a short intracellular tail (FIG. 1) (see, References 7 and 8 as recited in Section 6.2.5, below). Most MUC16 protein is released into the surrounding space following cleavage and the ectodomain remains on the cell surface. OC125 and most of other MUC16-reactive monoclonal antibodies (mAb) react with antigens in the tandem repeat region present exclusively in the cleaved portion of the molecule. Since these epitopes are likely to be found in circulation, the existing mAbs cannot be used to track the fate of the remaining MUC16 protein fragment, and may not accurately reflect the true distribution of MUC16 expression (see, Reference 9 as recited in Section 6.2.5, below). Others have shown that glycosylation surface proteins can regulate cell proliferation and differentiation through galectin 3 based interactions with the N-glycosylation sites of tyrosine kinase receptors like EGFR, PDGFR and others (K S Lau Cell 129:123, 2007). As demonstrated in Example 1 (see, Section 6.1), proximal parts of MUC16 (as little as 114 amino acids) can transform immortalized 3T3 cells and this effect appears to be abrogated by Tunicamycin.

This example demonstrates the precise glycosylation sites which mediate these effects and the mandatory role of Galectin 3 in MUC16 dependent transformation. Thus, antibodies able to bind to the proximal peptide sequence (e.g., $MUC16^{c114}$) in a glycosylation-specific manner were developed to inhibit key MUC16-mediated cancer functions such as adhesion and invasion. Monoclonal antibodies directed at the crucial N-glycosylation site within MUC16 ectodomain were generated by using defined synthetic N-glycopeptide antigens as key epitope mimics. These antibodies inhibited the oncogenic biology of MUC16 by decreasing MUC16-driven matrigel invasion, oncogene activation and tumor growth in contrast to other non-glycosylated protein directed mAbs which had no effect. These antibodies demonstrated a mechanism for mucin transformation and provide a useful tool for diagnostic and therapeutic use in MUC16 positive tumors.

6.2.2 Materials and Methods

6.2.2.1 Synthesis of Glycopeptides

Antibodies specific for the third glycosylation site (Asn30, analogous to Asn1806 of MUC16) of a 55-amino acid sequence of MUC16 ($MUC16^{55}$: NFSPLARRVDR-VAIYEEFLRMTRNGTQLQNFTLDRSSVLVDGYSPNR-NEPLTGNS (SEQ ID NO: 129) were generated using synthetic glycopeptides as key epitope mimics incorporating a well-defined chitobiose ($GlcNAc_2$) on Asn30 of $MUC16^{55}$ (SEQ ID NO:129, FIG. 13). The synthesis of the homogeneous N-glycopeptide was highly convergent and involved a coupling between the partially protected full-length peptide ($MUC16^{55}$; SEQ ID NO: 129) and the chitobiose amine under Lansbury aspartylation conditions (see, Reference 11 as recited in Section 6.2.5, below). $MUC16^{55}$ (SEQ ID NO: 129) was obtained by microwave-assisted, Fmoc solid-phase peptide synthesis (SPPS), followed by on-resin N-acetylation (Ac2O, DIEA), deallyation of $Asp^{30}$ ($Pd(PPh_3)_4$, $PhSiH_3$) and subsequent cleavage off resin (1-2% TFA/CH2Cl2). Using a one-flask aspartylation/deprotection procedure (as described in Reference 12 as recited in Section 6.2.5, below), the free carboxylic acid side chain at position Asn30 was coupled with chitobiose amine (see, Reference 13 as recited in Section 6.2.5, below), followed by TFA-treatment (Cocktail R: 90% TFA, 5% thioanisol, 3% ethanedithiol, 2% anisol) to provide glycopeptide $GlcNAc_2$-55-mer. The presence of pseudoproline motifs served to mitigate undesired aspartimide formation during the aspartylation.

In addition, the $Man_3GlcNAc_2$-containing peptide was prepared in a similar one-flask sequence.

Shorter glycopeptides encompassing Asn30 and Asn24 (analogous to Asn1800 and Asn1806, respectively, of MUC16) of $MUC16^{55}$ (SEQ ID NO:129) were prepared (1) 18-mer: CTRNGTQLQNFTLDRSSV (SEQ ID NO:130), and (2) 15-mer: CGTQLQNFTLDRSSV (SEQ ID NO:131). The 18-mer and 15-mer glycopeptides were conjugated to heyhole limpet Hemocyanin (KLH). The 15-mer (SEQ ID NO:131) incorporated chitobiose at Asn7 (analogous to Asn1806 of MUC16). The 15-mer glycopeptides was synthesized in a manner analogous to the synthesis of the 55mer glycopeptides.

The 18-mer (SEQ ID NO:130) incorporated chitobiose at Asn4 and Asn10 (analogous to Asn1800 and Asn1806, respectively, of MUC16). Allyl-protection of Asn4 and Asn10 of the 18-mer (analogous to Asn1800 and Asn1806, respectively, of MUC16) resulted in significant aspartimide formation. Thus, the more hindered O-2-phenylisopropyl ester (O-2-PhiPr, OPp) was used in the SPPS to provide after N-acetylation, and simultaneous resin cleavage/OPp removal (1-2% TFA/CH2Cl2) the partially protected peptide with free Asn4 and Asn10 side chains of the 18-mer (analogous to Asn1800 and Asn1806, respectively, of MUC16). Highly convergent installation of two chitobiose units through a double Lansbury aspartylation followed by global acid deprotection was performed to generate the bis-glycosylated 18-mer peptide (27% after HPLC purification).

Final coupling of the N-terminal cysteine residues of the 18-mer and 15-mer glycopeptides with the maleimide-derivatized carrier protein provided the KLH-conjugated constructs for mouse vaccination.

6.2.2.2 Mouse Immunization Protocol.

Five BALB/c and five Swiss Webster mice were immunized with the 55-mer glycopeptide (see, Section 6.2.2.1) three times every three weeks in the presence of 25 μL of Titermax adjuvant to immunize mice. Three weeks later, the mice were immunized with a mixture of mono-glycosylated 15-mer (SEQ ID NO:131) and bis-glycosylated 18-mer (SEQ ID NO:130) KLH-conjugated constructs. Sera were analyzed for reactivity against the 55-mer $GlcNAc_2$-glycosylated and the shorter glycopeptides unconjugated to KLH. Unglycosylated 55-mer, 15-mer and 18-mer peptides, together with two MUC16-unrelated chitobiose-containing peptides were used as negative controls for screening. Mice were further immunized with the 15-mer and 18-mer KLH-conjugates two more times every three weeks and the responses were analyzed by ELISA after each immunization.

6.2.2.3 Invasion

See, Section 6.1.2.9. For shRNA experiments, BD BioCoat™ Matrigel™ Invasion Inserts or Chambers (catalog #354480 in 24 well plate) and Control Inserts (catalog #354578 in 24 well plate) were purchased from BD Biosciences, MA. Matrigel Invasion assay was performed as per manufacturer's protocol. Briefly, the matrigel chambers in 24 well plates (stored at −20° C.) and control inserts (stored at 4° C.) were allowed to come to room temperature. Both inserts were rehydrated with 0.5 mL of serum free medium in the insert as well as in the outside well of the 24 well plate, for 2 hrs at 37° C. 5% $CO_2$ humidified incubator. Cultured SKOV3 cells were trypsinized and washed with culture medium. A million cells were separated into another centrifuge tube and washed 3 times with serum free medium. These cells were later adjusted to give 5,000 cells in 0.5 mL serum free medium. The medium in the rehydrated inserts were removed and the insert was transferred into a new 24 well plate containing 0.75 mL of 10% Foetal Bovine Serum (FBS) containing culture medium in the well which serves as a chemo attractant. Immediately, 0.5 mL of the cells (5,000 cells) in serum free medium was added to the insert. Proper care was taken to see that there was no air bubble trapped in the insert and the outside well. The 24 well plate was incubated at 37° C. 5% $CO_2$ humidified incubator for 48 hrs. After incubation, the non-invading cells are removed from the upper surface of the membrane by "scrubbing" by inserting a cotton tipped swab into matrigel or control insert and gently applied pressure while moving the tip of the swab over the membrane surface. Scrubbing was repeated with a second swab moistened with medium. Then the inserts were stained in a new 24 well plate containing 0.5 mL of 0.5% crystal violet stain in distilled water for 30 minutes. Following staining the inserts were rinsed in 3 beakers of distilled water to remove excess stain. The inserts were air dried in a new 24 well plate. The invaded cells were hand counted under an inverted microscope at 200× magnification. Several fields of triplicate membranes were counted and recorded in the figure.

6.2.2.4 Tumor Growth in Athymic Nude Mice

See, Section 6.1.2.11.

6.2.2.5 Binding Assay of Biotinylated Glycopeptides

Binding affinity was determined using ForeBio Octet QK. 5 μg/mL of biotinylated chitobiose-conjugated 18-mer glycopeptide was loaded onto a streptavidin biosensor. After washing off excess antigen, mouse antibodies were tested at 10 μg/mL for association and dissociation steps, respectively. Binding parameters were calculated using 1:1 binding site model, partial fit.

6.2.2.6 Immunohistochemistry of Tissue Microarray

Core-needle biopsies of pre-existing paraffin-embedded tissue were obtained from the so-called donor blocks and then relocated into a recipient paraffin-arrayed "master" block by using the techniques by Kononen et al. (see, Kononen J, et al. Nat Med 1998; 4(7):8447) and subsequently modified by Hedvat et al (see, Hedvat C V et al. Hum Pathol 2002; 33(10):968-74). A manually operated Tissue Arrayer MTA-1 from Beecher Instruments Inc. (Sun Prairie, Wis.) was used to produce sample circular spots (cores) that measured 0.6 to 1.0 mm in diameter. The cores were arrayed 0.3 to 0.4 mm apart from each other. A layer of control tissues was strategically laid around the actual tissue microarrays in order to avoid edging effects. The specific composition of each tissue microarray is delineated below. Slides of tissue microarrays for ovarian cancer or control tissue were prepared by cutting 4 um sections from formalin-fixed paraffin-embedded tissue.

Immunohistochemistry was performed on the tissue microarrays standard OC125 (Ventana, Tucson, Ariz.), 4H11 (see, Rao et al. Appl. Immunohistochem Mol Morphol, 2010, 18(5):462-72) and the 19C11 monoclonal antibody. Sections of the tissue microarrays were cut at 4 microns, placed on Superfrost/Plus microscope slides (Fisher brand) and baked in a 60° oven for at least 60 minutes. The slides were then deparaffinized and hydrated to distilled water, soaked in citrate buffer at pH 6.00 for 30 minutes at 97° C., washed in running water for 2-5 minutes, incubated for 5 minutes in 3% hydrogen peroxide diluted in distilled water. Slides were washed in distilled water for 1 minute, transferred to a bath of phosphate buffered saline (PBS), pH 7.2, for two changes of 5 minutes each and placed in 0.05% BSA diluted in PBS for a minimum of 1 minute. After drying around tissue sections, normal serum was applied at a 1:20 dilution in 2% BSA/PBS and incubated for a minimum of 10 minutes at room temperature in a humidity chamber. The serum was then suctioned off without allowing the sections to dry, and approximately 150 lambda of new antibody at a dilution of 1:1000 was placed on the tissue. The slide was incubated overnight (approximately 15-18 hours) at 4° C. in a humidity chamber. Primary antibody was washed off using three changes of PBS for 10 minutes each. Secondary antibody, biotinylated α-mouse from Vector laboratories (Burlingame, Ca), was applied at 1:500 dilution in 1% BSA/PBS and incubated for 45-60 minutes at room temperature in humidity chamber. The antibody was washed off again using three changes of PBS as above. Slides were then transferred to a bath of diaminobenzidine (DAB), diluted in PBS for 5-15 minutes. The slides were then washed in tap water for 1 minute, counterstained using Harris modified hematoxylin (Fisher), decolorized with 1% acid alcohol and blue in ammonia water, dehydrated with 3 changes each of 95% ethanol, 100% ethanol and xylene for 2 minutes each and coverslipped with permanent mounting medium.

6.2.2.7 Internalization Assay

Internalization of $^{89}$Zr-19C11 was investigated on SKOV3 cells expressing $MUC16^{c114}$. Approximately $1\times10^5$ cells were seeded in a 12-well plate and incubated overnight at 37° C. 5% $CO_2$ incubator. A volume of radiolabeled protein was added to each well and the plates were incubated at 37° C. and 4° C. for 1, 5, 12, and 24 hours. Following each incubation period, the medium was collected and the cells were rinsed with 1 mL of phosphate buffered saline (PBS). Surface-bound activity was collected by washing the cells in 1 mL of 100 mM acetic acid with 100 mM glycine (1:1, pH 3.5) at 4° C. The adherent cells were then lysed with 1 mL of 1 M NaOH. Each wash was collected and counted for activity. The ratio of activity of the final wash to the total activity of all the washes was used to determine the % internalized.

6.2.3 Results 6.2.3.1 MUC16 Patho-Biology is Dependent on N-Glycosylation of C-Terminal MUC16 Ectodomain.

Example 1 (see, Section 6.1) demonstrated that expression of MUC16$^{c114}$ resulted in a more aggressive in vitro/in vivo behavior of 3T3 mouse fibroblasts, resulting in significant increase in MUC16$^{c114}$-driven matrigel invasion and a more rapid tumor growth in vivo. Thus, the SKOV-3 cell line (a human ovarian cell line lacking expression of MUC16), was examined for the effect of MUC16$^{c114}$ dependent properties. MUC16$^{c114}$ expression led to cell surface expression and a nearly 3 fold increase in matrigel invasion (compare lanes 1 and 2 of FIG. 12A). This increase in invasion was dependent upon the N-glycosylation of asparagine at amino acid position 1 (Asn1), 24 (Asn24), and 30 (Asn 30) of MUC16$^{c114}$ (corresponding to Asn1777, Asn1800, and Asn1806 of mature MUC16 (SEQ ID NO:150), respectively; MUC16$^{c114\text{-}N123}$), as mutation of Asn30 to alanine (MUC16$^{c114\text{-}N3}$, FIG. 12A, lane 3), mutation of Asn1 and Asn24 to alanine (MUC16$^{c114\text{-}N12}$, FIG. 12A, lane 4), and mutation of Asn1, Asn24, and Asn30 to alanine (MUC16$^{c114\text{-}N123}$, FIG. 12A, lane 4), abrogated matrigel invasion. See, also, FIG. 12B. Moreover, MUC16$^{c114}$-induced increased matrigel invasion was dependent upon MGAT5 (the first enzyme involved in the N-glycosylation reaction) and/or LGALS3 (an enzyme amplified in many high grade serous cancers), as knockdown shRNA experiments which reduced MGAT5 or LGALS3 expression had a similar effect as MUC16$^{c114}$ mutation at the N-glycosylation sites and reduced invasion to near basal levels (FIG. 12A, lanes 6-10).

The most unambiguous hallmark of oncogenic transformation is the ability to promote growth in immunodeficient mice. In order to measure the effects of MUC16 N-glycosylation, MGAT5, and LGALS2 on tumor growth rate, a flank tumor model was utilized to facilitate regular tumor measurements. As shown in FIG. 12C, when 3T3 cell lines expressing vector (phrGFP), MUC16$^{c114}$, MUC16$^{c114\text{-}N123}$, MUC16$^{c114}$ and an anti-MGAT5 shRNA (MUC16$^{c114}$-shMGAT5), or MUC16$^{c114}$ and an anti-LGALS3 shRNA (MUC16$^{c114}$-shLGALS3) were implanted into the flanks of athymic nude mice, only the MUC16$^{c114}$ 3T3 cells formed larger tumors compared to the vector only controls at 24 days. These data corroborate the in vitro analyses indicating that MUC16 N-glycosylation, MGAT5, and LGALS3 are required for tumor growth.

6.2.3.2 Synthesis of Homogeneous N-Glycopeptides as Key Epitope Mimics for mAb Development Since N-glycosylation at the Asn30 site of MUC16$^{c114}$ (corresponding to Asn 1806 of mature MUC16 (SEQ ID NO:150); MUC16$^{c114\text{-}N3}$) was determined to be a central requirement for MUC16 oncogenic action, glycan profiling of MUC16$^{c114\text{-}N12}$ expressed in SKOV3 cells was performed, as MUC16$^{c114\text{-}N12}$ retains the capacity to be N-glycosylated at Asn30 (corresponding to Asn 1806 of mature MUC16 (SEQ ID NO:150)). The glycome analysis showed a highly diverse N-glycosylation pattern for this C-terminal MUC16 fragment, with the critical chitobiose ($GlcNAc_2$) stem as the minimal repeating unit to which various mannose moieties are attached (FIG. 13A).

Thus, glycosylation-directed mAbs were generated in an effort to inhibit the glycosylation-dependent effects of MUC16 on metastasis and invasion. These antibodies were designed to target N-glycopeptide epitopes containing the crucial third glycosylation site (Asn30 of MUC16$^{c114}$) on a shorter 55-amino acid sequence within the MUC16 ectodomain (MUC16$^{C55}$; SEQ ID NO:129). See, Section 6.2.2.1 and FIG. 13B, FIG. 13C, and FIG. 13D for a description of the synthesis of the glycopeptides utilized as immunogens. See, Section 6.2.2.2 for a description of the immunization process.

Antibodies were generated via immunization with short (55-mer, 18-mer, and 15-mer) MUC16 glycopeptides comprising chitobiose at the amino acid residues corresponding to Asn24 and/or Asn30 of MUC16$^{c114}$ (corresponding to Asn1800 and Asn1806, respectively, of mature MUC16 (SEQ ID NO:150)). In addition to being the smallest motif common to larger N glycans, chitobiose would also enable a better exposure of the underlying MUC16-derived peptide for inducing antibodies that not only show dependence on the glycan but also peptide specificity. This hypoglycosylation is a frequent, distinctive feature in mucin glycoproteins on the surface of tumor cells in comparison with normal cells.

6.2.3.3 Mouse Vaccination with Synthetic Glycopeptides/Glycoconjugates and Serologic Assays Mouse vaccination and sera collection was performed according to the protocol described in the Section 6.2.2.2. After three immunizations with $GlcNAc_2$-55-mer (FIG. 13B), mice were further immunized with a mixture of KLH-conjugated constructs (mono-glycosylated 15-mer (SEQ ID NO:131; FIG. 13C) and bis-glycosylated 18-mer (SEQ ID NO:130; FIG. 13D)), two out of ten mice showed positive ELISA signals for both 55-mers (with and without GlcNAc2) but the response was generally weak, suggesting that mice did not fully sensitize with the 55-mer immunizations. Two more immunizations with KLH conjugates ($GlcNAc_2$-15-mer (FIG. 13C) and $(GlcNAc_2)_2$-18-mer (FIG. 13D)), resulted in enhanced IgG immune responses against the shorter 15-mer and 18-mer glycopeptides, particularly in two mice (Mouse 7 and Mouse 8). However, these antibodies did not show any detectable reactivity by ELISA with the 55-mer-glyco-peptides, which suggests that, in this particular assay, the epitope in this large fragment is either inaccessible or conformationally different. Mouse 5, which responded to both of the 55-mers (chitobiose-containing and/or non-glycosylated peptide) was negative to $Man_3GlcNAc_2$-derivatized 55-mer. Not surprisingly, the 4H11 mAb (Rao et al. Appl. Immunohistochem Mol Morphol, 2010, 18(5):462-72), which is directed to the non-glycosylated peptide backbone, showed no binding to the unconjugated 15/18-mer glycopeptides, indicating that there may be some differences in available epitopes. See, FIG. 14.

6.2.3.4 Glycosylation-Dependent Monoclonal Antibody Development and In Vitro Biological Assays—MUC16-Driven Matrigel Invasion One of ten mice (Mouse 7) were selected whose serum showed the highest reactivity ratio to the short glycopeptides versus the non-glycosylated ones, and therefore showed some preference for the presence of the sugar. The spleen of mouse 7 was harvested and standard hybridoma culture technology provided IgG-producing hybridoma cell lines. The splenocytes were fused with hybridoma fusion partner giving an extraordinarily high fusion efficiency (>5.5 colonies/well on average, with >30,000 hybridomas). Supernatants were selected and screened for reactivity by ELISA against the individual glycopeptides. Preliminary ELISA analysis for the fusion test plate against 15mer-chitobiose peptide and 18mer-chitobiose peptide (combined in the same well) showed some positive signals, which points to the presence of anti-peptide antibodies, albeit their glycosylation dependence could not be fully assessed at this point. See, FIG. 14. Nonetheless, a higher ratio of antibodies with favored positivity, and therefore more specific, to the chitobiose-glycosylated antigens was observed in comparison to the non-glycosylated ones. Upon culture dilution, a single clone growing in each well (1:1 ratio above) was obtained and primary screening revealed that antibodies produced by these hybridomas do not recognize the 4H11 epitope, which lies close to the non-glycosylated 15-/18-mer. See, FIG. 14. After completing the monoclonal antibody screening at higher dilution, antibodies showing preference for the glycopeptide epitope were obtained. Thus, this process afforded 36 chitobiose-dependent primary mAbs that were tested for reactivity against MUC16. Out of those, 15 mAbs were evaluated (in parallel to 4H11) for their effect on invasion by matrigel assay with SKOV3-MUC16$^{c114}$ transfectant (FIG. 15A). MUC16 Glycosylation Antibodies 1B5, 10C6, 13A7, 18C6, 19C11, 16C5, 6H10, 21F8, 7B12 showed inhibition of matrigel invasion, whereas 4H11 had no effect on this property, indicating that antibodies directed to Asn30 of MUC16$^{c114}$ (corresponding to Asn1806 of mature MUC16 (SEQ ID NO: 150)) inhibit the biology of MUC16. MUC16 Glycosylation Antibodies were subsequently subcloned and purified. Binding parameters for certain MUC16 Glycosylated Antibodies were determined (see, Table 9).

TABLE 9

Binding parameters of MUC16 Glycosylated Antibodies

| Antibody | $k_d$ (1/s) | Error in $k_d$ (1/s) | $k_a$ (1/s) | $K_D$ (nM) |
|---|---|---|---|---|
| 10C6.E4 | * | — | ** | >1000 |
| 19C11.H6 | $2.42 \times 10^{-3}$ | $2.35 \times 10^{-4}$ | $3.80 \times 10^{4}$ | 63.7 |
| 13A7.C8 | * | — | ** | >1000 |
| 16C5.C1 | $1.72 \times 10^{-3}$ | $1.20 \times 10^{-4}$ | $6.68 \times 10^{4}$ | 25.7 |
| 7B12.B3 | $1.04 \times 10^{-3}$ | $1.09 \times 10^{-4}$ | $7.50 \times 10^{4}$ | 13.8 |
| 18C6.D12 | $6.78 \times 10^{-4}$ | $1.83 \times 10^{-4}$ | $6.14 \times 10^{4}$ | 11.1 |
| 1B5.A7 | $1.49 \times 10^{-3}$ | $1.12 \times 10^{-4}$ | $7.35 \times 10^{4}$ | 20.2 |
| 4H11 | — | — | — | — |

* = Low calculation confidence; no fit for off-rate
 = $k_a$ is too low for association rate determination Finally, immunohistochemistry of human ovarian tissue samples performed with the MUC16 Glycosylation Antibody 10C6 displayed improved detection of MUC16 as compared to immunohistochemistry performed 4H11 or OC125 (FIG. 16**E).

6.2.3.5 MUC16 Glycosylation Antibodies are Specific for MUC16 Glycosylation.

To investigate the specificity of the MUC16 Glycosylation Antibodies, FACs analyses were performed on (i) cells expressing native (mature) MUC16 (OVCA-433 cells), (ii) SKOV3 cells, which lack MUC16 expression, expressing a control vector (SKOV3 phrGFP cells), (iii) SKOV3 cells expressing MUC16$^{c114}$ (SKOV3 MUC16$^{c114}$), (iv) SKOV3 cells expressing MUC16$^{c114\text{-}N1}$ (SKOV3 MUC16$^{c114\text{-}N1}$), (v) SKOV3 cells expressing MUC16$^{c114\text{-}N3}$ SKOV3 MUC16$^{c114\text{-}N3}$), or (vi) SKOV3 cells expressing SKOV3 MUC16$^{c114\text{-}N123}$ (SKOV3 MUC16$^{c114\text{-}N123}$), in the presence or absence of MUC16 Glycosylated Antibody (18C6, 19C11, 10C6, 1B5, or 13A7) or the monoclonal anti-MUC16 antibody, 4H11 (Table 10). Antibodies 4H11, 18C6, 19C11, 10C6, 1B5, and 13A7 demonstrated binding to OVCA-433 cells (Table 10; compare ID NOs: 3-8 to negative controls, ID NOs: 1 and 2). In contrast, as expected based upon the design of the studies and generation of the antibodies, none of antibodies 4H11, 18C6, 19C11, 10C6, 1B5, and 13A7 bound SKOV3 phrGFP cells (Table 10, ID NOs: 11-16 as compared to the negative controls, ID NOs: 9 and 10). Antibodies 4H11, 18C6, 19C11, 10C6, 1B5, and 13A7 bound SKOV3 MUC16$^{c114}$ (Table 10, ID NOs: 19-24 as compared to the negative controls, ID NOs: 17 and 18). Mutation of Asn1 of MUC16$^{c114}$ (corresponding to Asn1777 of mature MUC16 (SEQ ID NO:150)) did not inhibit antibody binding to SKOV3 MUC16$^{c114\text{-}N1}$ cells (Table 10, ID NOs: 27-32 as compared to negative controls, ID NOs: 25 and 26). However, mutation of Asn30 of MUC16$^{c114}$ (corresponding to Asn1806 of mature MUC16 (SEQ ID NO:150)) abrogated binding of MUC16 Glycosylated Antibodies 18C6, 19C11, 10C6, 1B5, and 13A7 (Table 10, ID NOs: 36-40, as compared to negative controls, ID NOs: 33 and 34). Moreover, mutation of Asn30 of MUC16$^{c114}$ (corresponding to Asn1806 of mature MUC16 (SEQ ID NO:150)) did not abrogate binding of antibody 4H11, which is not a MUC16 Glycosylated Antibody (Table 10, ID NO: 35, as compared to negative controls, ID NOs: 33 and 34). In addition, asparagine to alanine mutations at Asn1, Asn24, and Asn30 (corresponding to Asn1777, Asn1800, and Asn1806, respectively, of mature MUC16 (SEQ ID NO:150)), abrogated binding of MUC16 Glycosylated Antibodies 18C6, 19C11, 10C6, and 1B5 (Table 10, ID NOs: 44-47, as compared to negative controls, ID NOs: 41 and 42), while binding of 4H11 was not abrogated. It is noted that 13A7 maintained binding to the SKOV3 MUC16$^{c114\text{-}N123}$ cells. These data demonstrate that MUC16 Glycosylation Antibodies bind to MUC16$^{c114}$ in a glycosylation-dependent fashion.

TABLE 10

FACs analysis of MUC16 Glycosylation Antibodies with OVCA-433 or SKOV3-transfectant cells.

| ID NO | Muc16 Glycosylation Antibodies | Mean % PE |
|---|---|---|
| 1 | OVCA-433 cells | 0.12* |
| 2 | OVCA-433 + G anti M IgG PE | 5.01* |
| 3 | OVCA-433 + 4H11 + G anti M IgG PE | 82.4 |
| 4 | OVCA-433 + 18C6 + G anti M IgG PE | 91.4 |
| 5 | OVCA-433 + 19C11 + G anti M IgG PE | 93.7 |
| 6 | OVCA-433 + 10C6 + G anti M IgG PE | 84.5 |
| 7 | OVCA-433 + 1B5 + G anti M IgG PE | 94.6 |
| 8 | OVCA-433 + 13A7 + G anti M IgG PE | 92.8 |
| 9 | SKOV3 phrGFP cells | 1.01* |
| 10 | SKOV3 phrGFP + G anti M IgG PE | 1.2* |
| 11 | SKOV3 phrGFP + 4H11 + G anti M IgG PE | 3.39* |
| 12 | SKOV3 phrGFP + 18C6 + G anti M IgG PE | 2.09* |
| 13 | SKOV3 phrGFP + 19C11 + G anti M IgG PE | 1.69* |
| 14 | SKOV3 phrGFP + 10C6 + G anti M IgG PE | 1.84* |
| 15 | SKOV3 phrGFP + 1B5 + G anti M IgG PE | 1.5* |
| 16 | SKOV3 phrGFP + 13A7 + G anti M IgG PE | 2.66* |
| 17 | SKOV3 MUC16$^{c114}$ cells | 0.218* |
| 18 | SKOV3 MUC16$^{c114}$ + G anti M IgG PE | 2.42* |
| 19 | SKOV3 MUC16$^{c114}$ + 4H11 + G anti M IgG PE | 85.7 |
| 20 | SKOV3 MUC16$^{c114}$ + 18C6 + G anti M IgG PE | 73.1 |
| 21 | SKOV3 MUC16$^{c114}$ + 19C11 + G anti M IgG PE | 69.3 |
| 22 | SKOV3 MUC16$^{c114}$ + 10C6 + G anti M IgG PE | 72.9 |
| 23 | SKOV3 MUC16$^{c114}$ + 1B5 + G anti M IgG PE | 73.2 |
| 24 | SKOV3 MUC16$^{c114}$ + 13A7 + G anti M IgG PE | 68.4 |

TABLE 10-continued

FACs analysis of MUC16 Glycosylation Antibodies with OVCA-433 or SKOV3-transfectant cells.

| ID NO | Muc16 Glycosylation Antibodies | Mean % PE |
|---|---|---|
| 25 | SKOV3 MUC16$^{c114-N1}$ cells | 0.139* |
| 26 | SKOV3 MUC16$^{c114-N1}$ + G anti M IgG PE | 2.84* |
| 27 | SKOV3 MUC16$^{c114-N1}$ + 4H11 + G anti M IgG PE | 91.5 |
| 28 | SKOV3 MUC16$^{c114-N1}$ + 18C6 + G anti M IgG PE | 83 |
| 29 | SKOV3 MUC16$^{c114-N1}$ + 19C11 + G anti M IgG PE | 81.7 |
| 30 | SKOV3 MUC16$^{c114-N1}$ + 10C6 + G anti M IgG PE | 83 |
| 31 | SKOV3 MUC16$^{c114-N1}$ + 1B5 + G anti M IgG PE | 85.4 |
| 32 | SKOV3 MUC16$^{c114-N1}$ + 13A7 + G anti M IgG PE | 84.5 |
| 33 | SKOV3 MUC16$^{c114-N3}$ cells | 0.0202* |
| 34 | SKOV3 MUC16$^{c114-N3}$ + G anti M IgG PE | 0.856* |
| 35 | SKOV3 MUC16$^{c114-N3}$ + 4H11 + G anti M IgG PE | 15.6 |
| 36 | SKOV3 MUC16$^{c114-N3}$ + 18C6 + G anti M IgG PE | 1.48* |
| 37 | SKOV3 MUC16$^{c114-N3}$ + 19C11 + G anti M IgG PE | 1.25* |
| 38 | SKOV3 MUC16$^{c114-N3}$ + 10C6 + G anti M IgG PE | 1.4* |
| 39 | SKOV3 MUC16$^{c114-N3}$ + 1B5 + G anti M IgG PE | 1.06* |
| 40 | SKOV3 MUC16$^{c114-N3}$ + 13A7 + G anti M IgG PE | 2.39* |
| 41 | SKOV3 MUC16$^{c114-N123}$ cells | 0.274* |
| 42 | SKOV3 MUC16$^{c114-N123}$ + G anti M IgG PE | 7.02* |
| 43 | SKOV3 MUC16$^{c114-N123}$ + 4H11 + G anti M IgG PE | 32.3 |
| 44 | SKOV3 MUC16$^{c114-N123}$ + 18C6 + G anti M IgG PE | 11.6* |
| 45 | SKOV3 MUC16$^{c114-N123}$ + 19C11 + G anti M IgG PE | 5.25* |
| 46 | SKOV3 MUC16$^{c114-N123}$ + 10C6 + G anti M IgG PE | 5.84* |
| 47 | SKOV3 MUC16$^{c114-N123}$ + 1B5 + G anti M IgG PE | 7.39* |
| 48 | SKOV3 MUC16$^{c114-N123}$ + 13A7 + G anti M IgG PE | 28.7 |

*Indicates no binding is considered to be observed.

6.2.3.6 MUC16 Glycosylation Antibodies Inhibit Matrigel Invasion.

Given the glycosylation specificity of MUC16 Glycosylation Antibodies (Table 9), the ability of the MUC16 Glycosylation Antibody bioreactive supernatants to inhibit matrigel invasion in a glycosylation-specific manner was evaluated. Thus, matrigel invasion assays were performed with SKOV3 ovarian cancer stable cell lines expressing phrGFP (FIG. 15A, lane 1) or phr-GFP-MUC16$^{c114}$ (MUC16$^{c114}$; FIG. 15A, lanes 2-18) in the presence (FIG. 15A, lanes 3-18) or absence (FIG. 15A, lanes 1 and 2) of MUC16 Glycosylation Antibody bioreactive supernatants. The MUC16 monoclonal antibody 4H11 (FIG. 15A, lane 3) was used as a control for the MUC16 Glycosylation Antibody bioreactive supernatants (FIG. 15A, lanes 4-18) to evaluate glycosylation dependency in matrigel invasion. Expression of MUC16$^{c114}$, either alone in the presence of 4H11 (FIG. 15A, lanes 2 and 3, respectively), resulted in an increase in matrigel invasion activity. In contrast, incubation with MUC16 Glycosylation Antibodies (FIG. 15A, lanes 4-18) decreased matrigel invasion of the MUC16$^{c114}$-expressing ovarian cancer cells.

Next, the ability of purified MUC16 Glycosylated Antibodies to inhibit matrigel invasion was evaluated. To this end, SKOV3 cells expressing MUC16$^{c114}$ were incubated in the presence and absence the MUC16 antibody 4H11 or purified MUC16 Glycosylated Antibodies (FIG. 15B). MUC16 Glycosylated Antibodies 7B12, 19C11, 18C6, and 10C6 inhibited MUC16$^{c114}$-induced matrigel invasion (FIG. 15B, compare lanes 3-6 to the negative control, lane 2). In contrast, the monoclonal anti-MUC16 antibody 4H11 did not inhibit MUC16$^{c114}$-induced matrigel invasion (FIG. 15B, compare lanes 2 to the negative control, lane 1). These data demonstrate that, in contrast to the monoclonal antibody 4H11, MUC16 Glycosylation Antibodies (e.g., 7B12, 19C11, 18C6, and 10C6) block matrigel invasion.

The ability of the MUC16 Glycosylation Antibodies to inhibit matrigel invasion was assayed in the context of MUC16$^{c114}$ N-glycosylation mutants (FIG. 16A). To this end, matrigel invasion assays were performed on SKOV3 phrGFP cells, SKOV3 MUC16$^{c114}$ cells, SKOV3 MUC16$^{c114-N1}$ cells, SKOV3 MUC16$^{c114-N2}$ cells, or SKOV3 MUC16$^{c114-N3}$ cells (FIG. 16A, lanes 1-5, respectively), in the presence of (i) a control antibody; (ii) 4H11 antibody; or (iii) the MUC16 Glycosylation Antibody 10C6. MUC16$^{c114}$-induced matrigel invasion was inhibited in SKOV3 MUC16$^{c114-N3}$ cells, as Asn30 of MUC16$^{c114}$ is necessary for MUC16$^{c114}$ matrigel invasion. Moreover, matrigel invasion was induced in SKOV3 MUC16$^{c114}$ cells, SKOV3 MUC16$^{c114-N1}$ cells, and SKOV3 MUC16$^{c114-N2}$ cells in the presence and absence of the MUC16 monoclonal antibody 4H11. In contrast, incubation of these cells with the MUC16 Glycosylation Antibody 10C6 abrogated matrigel invasion (FIG. 16A). These data were also corroborated in FIG. 16B and in 3T3 cells expressing MUC16$^{c344}$ mutants (FIG. 16C).

Taken together, these data indicate that MUC16 Glycosylation Antibodies, in contrast to the monoclonal anti-MUC16 antibody 4H11, are able to inhibit matrigel invasion in a glycosylation-dependent manner.

6.2.3.7 the MUC16 Glycosylation Antibody 19C11 is Internalized.

Finally, the ability of a MUC16 Glycosylation Antibody targeting Asn30 of MUC16$^{c114}$ to be internalized was assessed. SKOV3 cells expressing MUC16$^{c114}$ were incubated with $^{89}$Zr-DFO-labeled 19C11 antibody and internalization was determined via Radiotracer (FIG. 17). These data demonstrate that the labeled 19C11 antibody was internalized when incubated with MUC16$^{c114}$-expressing SKOV3 cells incubated at 37° C. as early as 1 hour post-treatment with the antibody. Cellular uptake of the labeled antibody was decreased at 4° C.

6.2.4 Discussion

The MUC16/CA125 antigen, a member of the mucin family with substantial homology to MUC1, has long been associated with gynecological malignancies (see, Reference 4 as recited in Section 6.2.5, below). Despite not being sufficiently sensitive or specific as a general screening tool, CA125 measurement is regularly used to monitor patients with ovarian cancer through antibody-based detection methods. The vast majority of MUC16-reactive antibodies, such as OC125, are directed against glycosylation-dependent epitopes found in the cleaved fraction of the molecule, and are not useful as screening tools to detect the proximal portion of MUC16 after cleavage. As a consequence, biological studies of the remaining MUC16 protein fragment are lacking. The data in Example 1 (Section 6.1) demonstrated that a 114 amino acid sequence of the proximal MUC16 region (MUC16$^{c114}$) is sufficient to increase invasion and tumor growth on several ovarian cancer cell lines. The striking discovery herein that N-glycosylation of this C-terminal ectodomain, in particular at the third Asn site (Asn30, corresponding to Asn1806 of mature MUC16 (SEQ ID NO:150)), is crucial for MUC16 oncogenic effects suggests new roles for MUC16, which could then be considered not only a passive marker of disease but also a pathogenic molecule. Based on this premise, the development of monoclonal antibodies against these retained portions of MUC16 appears as a powerful tool to explore the patho-biology of this mucin and create MUC16 targeted therapeutics.

Previous studies identified mAbs against the non-cleaved C-terminal region of MUC16, although in contrast to prior antibodies, they were directed at the non-glycosylated peptide backbone instead of at complex glycoprotein epitopes. In particular, 4H11 showed high-affinity binding to the MUC16 ectodomain, and internalized by ovarian cancer cells more efficiently than OC125 because of the proximate location of the epitope. This finding suggested that the proximal region of the glycoprotein has an independent biology from the shed portion of MUC16 distal to the putative cleavage site. However, since 4H11 does not recognize the crucial glycosylation sites within the ectodomain that are required for MUC16 pathogenic action, its potential for future studies in targeted therapy is limited.

A panel of glycosylation-dependent monoclonal antibodies directed to the key glycopeptide epitopes in the MUC16 ectodomain were developed by using KLH-conjugated, synthetic glycopeptide mimics in combination with hybridoma technology. This methodology is preferred over polyclonal antibody generation, as at the polyclonal stage, the glycopeptide specificity was not complete and some binding was also detected to non-glycosylated MUC16 peptide fragments. To obtain the MUC16 Glycosylation Antibodies, a primary selection for monoclonal antibody generation was based on a higher ratio of glycosylation dependence in the multiclonal culture associated to some degree of preference for the presence of the sugar. The power of the new monoclonal antibodies and their higher specificity for the glycopeptide epitope has been demonstrated by studying their effect on MUC16-driven matrigel invasion. These MUC16 Glycosylation Antibodies were able to inhibit invasion in a matrigel assay whereas the non-glycosylation directed 4H11 was not. Based on the finding that N-glycosylation at Asn30 is essential for MUC16 action, these results confirm that the newly generated antibodies specifically target the key glycopeptide epitope of MUC16 ectodomain, which results in inhibition of the MUC16 pathobiology. Importantly, the MUC16 Glycosylation Antibody 10C6 significantly delayed MUC16-positive tumor growth in an athymic nude mouse model implanted with $MUC16^{c114}$-expressing ovarian cancer cells, demonstrating the potential of these monoclonal antibodies to emerge as a promising tool for their therapeutic use in optimized clinical applications.

6.2.5 References Cited

1. Bast, R. C. Jr. et al. Reactivity of a monoclonal antibody with human ovarian carcinoma. J. Clin. Invest. 68, 1331-1337 (1981).
2. Yin, B. W. & Lloyd, K. O. Molecular cloning of the CA125 ovarian cancer antigen: identification as a new mucin, MUC16. J. Biol. Chem. 276, 27371-27375 (2001).
3. O'Brien, T. J. et al. The CA 125 gene: an extracellular superstructure dominated by repeat sequences. Tumor Biol. 22, 348-366 (2001).
4. Bast, R. C. Jr., et al. CA125: the past and the future. Int. J. Biol. Markers 13, 179□187 (1998).
5. Rustin, G. J. S. Use of CA-125 in clinical trial evaluation of new therapeutic drugs for ovarian cancer. Clin. Cancer Res. 10, 3919-3926 (2004).
6. Scholler, N. & Urban, N. CA125 in ovarian cancer. Biomark. Med. 1, 513-523 (2007).
7. Yin, B. W., Dnistrian, A. & Lloyd, K. O. Ovarian cancer antigen CA125 is encoded by the MUC16 mucin gene. Int. J. Cancer 2002, 98, 737-740.
8. O'Brien, T. J., Beard, J. B., Underwood, L. J. & Shigemasa, K. The CA 125 gene: a newly discovered extension of the glycosylated N-terminal domain doubles the size of this extracellular superstructure. Tumor Biol. 23, 154-169 (2002).
9. Nap, M. et al. Immunohistochemical characterization of 22 monoclonal antibodies against the CA125 antigen: 2nd report from the ISOBM TD-1 workshop. Tumor Biol. 17, 325-331 (1996).
10. Rao, T. D. et al. Novel monoclonal antibodies against the proximal (carboxy-terminal) portions of MUC16. Appl. Immunohistochem. Mol. Morphol. 18, 462-472 (2010).
11. Cohen-Anisfeld, S. T., Lansbury, P. T. A practical, convergent method for glycopeptide synthesis. J. Am. Chem. Soc. 115, 10531-10537 (1993).
12. Wang, P., Aussedat, B., Vohra, Y. & Danishefsky, S. J. An advance in the chemical synthesis of homogeneous N-linked glycopolypeptides by convergent aspartylation. Angew. Chem. Int. Ed. 51, 11571-11575 (2012).
13. Likhosherstov, L. M., Novikova, O. S., Derevitskaja, V. & Kochetkov, N. K. A new simple synthesis of amino sugar 3-d-glycosylamines. Carbohydr. Res. 146, C1-C5 (1986).
14. Nakada, H. et al. Epitopic structure of Tn glycophorin A for an anti-Tn antibody (MLS 128). Proc. Natl. Acad. Sci. USA 90, 2495-2499 (1993).
15. Osinaga, E. et al. Analysis of the fine specificity of Tn-binding proteins using synthetic glycopeptide epitopes and a biosensor based on surface plasmon resonance spectroscopy. FEBS Lett. 469, 24-28 (2000).
16. Mazal, D. et al. Monoclonal antibodies toward different Tn-amino acid backbones display distinct recognition patterns on human cancer cells. Implications for effective immuno-targeting of cancer. Cancer Immunol. Immunother. 62, 1107-1122 (2013).
17. Rosen, D. G. et al. Potential markers that complement expression of CA125 in epithelial ovarian cancer. Gynecol Oncol. 99, 267-277 (2005).
18. Moore, R. G., Maclaughlan, S. & Bast, R. C. Jr. Current state of biomarker development for clinical application in epithelial ovarian cancer. Gynecol Oncol. 116, 240-245 (2010).

6.3 Example 3: Tumor Promoting Effects of MUC16 Require Interaction with Galectin-3 and Cell Surface Receptors This example provides (a) a more detailed description of certain of the experiments described in Example 2 (Section 6.2); and (b) additional experiments as compared to Example 2 (Section 6.2).

6.3.1 Introduction

Overexpression of MUC16/CA125 is common in serous ovarian cancer and elevated serum CA125 levels are associated with decreased survival. The CA125 antigen, recognized by the OC125 antibody, is a heavily glycosylated antigen expressed within the tandem repeat domains from the extracellular portion of the MUC16 glycoprotein (see References 3 and 22 in Section 6.3.13, below). This antigen is predominantly expressed by benign or malignant Mullerian tissues, but its function and role in carcinogenesis are not currently fully understood (see Reference 4 in Section 6.3.13, below). MUC16 is a highly complex tethered mucin consisting of a large, heterogeneously glycosylated extracellular domain, a 58 amino acid ectodomain between the cell membrane and the putative cleavage site, a hydrophobic transmembrane region, and a short intracellular tail (see Reference 21 in Section 6.3.13, below). OC125 and most other MUC16-reactive monoclonal antibodies (mAbs) recognize the immunogenic 156 amino acid tandem repeat region present in the cleaved portion of the molecule. Newer ectodomain-specific antibodies (e.g., 4H11 and 4A5) recognize a peptide epitope in the post-cleavage, retained portion of MUC16 (see Reference 6 in Section 6.3.13, below). The C-terminal part of MUC16 ($MUC16^{c114}$) has been demonstrated to transform immortalized 3T3 cells, as measured by increased anchorage independent growth, activation of the AKT and ERK pathways, increased matrigel invasion, and enhanced growth in nude mouse xenografts (see Section 6.1 and Reference 19 in Section 6.3.13, below). These effects were dependent on the ectodomain of MUC16, while the loss of the 31 amino acid cytoplasmic tail had little effect on those properties. The mechanisms by which the ectodomain promotes oncogenic behaviors are not fully understood (see Reference 19 in Section 6.3.13, below). While there are no consensus protein-binding domains present, the 58 amino acid sequence of the MUC16 ectodomain includes three N-glycosylation sites that represent potential interaction/regulatory sites for MUC16 with other cell surface molecules.

The N-glycosylation sites of tyrosine kinase receptors such as epidermal growth factor receptor (EGFR), platelet-derived growth factor receptor (PDGFR), and others appear to interact with cellular lectins such as Galectin-3 to regulate surface residency, intensity of signaling, and cellular behavior (see Reference 12 in Section 6.3.13, below). The effects of N-glycosylation depend on the number of N-glycosylation sites on growth-enhancing receptors and on the affinity of Galectin-3 for complex N-glycosylated species. There are fewer N-glycosylation sites on the countervailing inhibitory signals from cell surface molecules such as transforming growth factor-beta (TGF-β) receptors. These receptors are sensitive to growth factor-related high nutrient fluxes and provide a dampening function in normal circumstances. However, mechanisms of cancer-associated glycoprotein interactions with classic receptor tyrosine kinases are not known. MUC1, MUC4, and MUC16 are all heavily glycosylated tethered glycoproteins characterized by the presence of transmembrane domains and overexpressed in epithelial cancers (see Reference 10 in Section 6.3.13, below).

This Example (Section 6.3) demonstrates that glycosylation of MUC16 plays a key role in mucin-related transformation by mediating complex cell surface interactions.

The C-terminal portion of MUC16 promoted oncogene activation, matrigel invasion and tumor growth. These effects were dependent on MGAT5 dependent glycosylation of two proximal N glycosylation sites in the 58 amino acid retained MUC16 ectodomain. Neither N-nor O-glycosylation sites in the more distal MUC16 tandem repeat region could functionally substitute for those two sites. Patterns of MUC16 glycosylation were diverse, but a chitobiose stem characterized the base of all N-glycosylation species. Antibodies against proximal, chitobiose containing MUC16 glycopeptides blocked Galectin 3-mediated binding to cell surface signaling receptors and inhibited the tumor promoting effects of MUC16.

Systematic alterations in MUC16 glycopeptides were employed to directly interrogate the relationship between glycan structure and the tumor-promoting effects exerted by MUC16 expression. These effects, including colocalization, oncogene activation, matrigel invasion, and tumor xenograph growth, were exerted by Galectin-3-mediated binding between a N-glycosylated sequence on the retained, noncirculating portion of MUC16 and cell surface molecules such as epidermal growth factor receptor (EGFR) and Integrin β1. Extracellular, mucin-driven tumor promotion is a mechanism supported by findings and data presented herein that can be successfully targeted by N-glycosylation site directed antibodies.

As shown in this Example: (1) the extracellular glycosylation state of MUC16 drove ovarian serous cancer behavior; (2) invasion and MUC16+ xenograft growth depended on specific MUC16 N-glycosylation sites; (3) MUC16 formed heterotrimeric complexes with Galectin-3 and either EGFR or Integrin β1; and (4) anti-glycosylation site antibodies blocked extracellular MUC16 tumor promotion.

6.3.2 Materials and Methods 6.3.2.1 Synthesis of MUC16 Carboxy-Terminus ($MUC16^{c114}$), MUC16-CA125 Domain ($MUC16^{c344}$), and Glycosylated Fusion Protein DNA Constructs See Sections 6.1.2 and 6.2.2, and Reference 19 in Section 6.3.13, below, for a description of MUC16 C-terminal constructs. The pFUSE-human IgG1-Fc2 vector (pFUSE) was purchased from InvivoGen (San Diego, Calif.), and the construction of the chimeric proteins $MUC16^{c57-114}$-pFUSE and $^{117-244}$LGALS3-pFUSE are also described in Sections 6.1.2 and 6.2.2, and Reference 19 in Section 6.3.13 below.

6.3.2.2 Cell Culture, Transfection, and Cell Line Characterization

The SKOV3, CAOV3, and OVCAR3 cell lines were obtained and maintained as described in Sections 6.1.2 and 6.2.2, and Reference 19 in Section 6.3.13 below. See Section 6.3.6 for details.

6.3.2.3 Synthesis of Glycopeptides

See Section 6.4 for a description of the detailed synthesis of the MUC16 glycopeptides.

6.3.2.4 Matrigel Invasion

Basement membrane invasion was determined in matrigel invasion chambers (BD Biosciences, Bedford, Mass.). Stable cell lines were treated with 5 μg/mL of tunicamycin (Sigma-Aldrich, St. Louis Mo. cat # T7765), or 5 μg/mL of $MUC16^{57-c114}$-pFUSE, or with 5 μg/mL of $^{117-244}$LGALS3-pFUSE fusion protein; matrigel migration was then measured after 48 hours in triplicate wells and compared with phrGFP vector control and $MUC16^{c114}$ transfectants. See, also, Sections 6.1.2 and 6.2.2, and Reference 19 in Section 6.3.13 below.

6.3.2.5 Tumor Growth in Athymic Nude Mice

Transfected cell lines and appropriate control cell lines were introduced into the flank of athymic female nude mice, and routine animal care was provided by the Memorial Sloan Kettering Cancer Center Antitumor Assessment Core Facility. Tumor measurements were taken twice per week, and tumor growth was recorded to a maximum size of 1,500 $mm^3$ per Memorial Sloan Kettering Cancer Center Research Animal Resource Center guidelines. See, also, Sections 6.1.2 and 6.2.2, and Reference 19 in Section 6.3.13 below.

6.3.2.6 Monoclonal Antibody Preparation; Mouse Immunization Protocol

The immunization protocol started with chitobiose-containing 55-mer MUC16 glycopeptide ($GlcNAc_2$-55-mer; SEQ ID NO: 129), which was administered to five BALB/c and five Swiss Webster mice three times every 3 weeks in the presence of an adjuvant. The fourth immunization was carried out with a mixture of KLH-conjugated, monoglycosylated 15-mer ($GlcNAc_2$-15-mer-KLH; SEQ ID NO: 131) and bis-glycosylated 18-mer ([$GlcNAc_2$]2-18-mer-KLH; SEQ ID NO: 130) MUC16 constructs. Sera were analyzed for reactivity against the $GlcNAc_2$-55-mer (SEQ ID NO: 129) and the unconjugated, chitobiose-bearing 15/18-mer glycopeptides (SEQ ID NO: 131 and SEQ ID NO: 130, respectively). In addition, non-glycosylated 55-mer (SEQ ID NO: 129), 15-mer (SEQ ID NO: 131) and 18-mer peptides (SEQ ID NO: 130), together with two MUC16-unrelated, chitobiose-containing peptides were used as negative controls for screening (SEQ ID NOs: 168 and 169). Mice were further immunized with the shorter KLH-conjugates (SEQ ID NO: 130 and SEQ ID NO: 131) two more times every 3 weeks and the responses were analyzed by ELISA after each immunization. See also Section 6.2.2.

6.3.2.7 ELISA

Sandwich ELISA was performed to assess the positivity of the antibodies to individual (glycol)peptides following routine core facility protocol for ELISA assay. See also Section 6.2.2.

6.3.2.8 Western Blot Analysis

Equal amounts of protein were separated by SDS-Poly Acrylamide Gel Electrophoresis (SDS-PAGE) and transferred to polyvinylidene difluoride (PVDF) or nitrocellulose membranes using BioRad transfer apparatus at 4° C. The membranes were blocked with 3% Bovine Serum Albumin (BSA) or 5% non-fat milk in PBS with 0.1% Tween-20 (PBST) for 1 hour at room temperature. Membranes were developed with a variety of primary antibodies [Cell Signaling, MA: Akt cat #9272; Phospho-Akt (Ser473)(193H12) cat #4058; p44/43 MAPK (Erk1/2) cat #9102; Phospho-p44/43 MAPK (Erk1/2)(Thr202/Tyr204) cat #9101; Src cat #2109S; Phospho-Src cat #2101L; EGFR cat #2237L; Phospho-EGFR (Y1068)(D7A5) XP(R) cat #3777S]; (Sigma-Aldrich, Inc., St. Louis, Mo.: beta-actin cat # A5441); (Southern BioTech, Birmingham, Ala.: anti-human-Fc-IgG1-HRP cat #9054-05); (Abgent, San Diego, Calif.: polyclonal LGALS3 antibody cat # AP11938b); and (Origene, Rockville, Md.: mouse monoclonal anti-EGFR v3 clone OTI3H2 cat # TA506224; mouse monoclonal anti-DDK clone 4C5 cat # TA50011-100) at 4° C. overnight. The membranes were washed three times with PBS-T and developed with HRP-conjugated anti-mouse or anti-rabbit antibody (GE Healthcare, UK) (1:5000 dilution) for 1 hour at room temperature. Membranes were then washed three times with PBS-T and developed with a Western Lightning Chemiluminescence reagent (ECL, Perkin Elmer) for 1-5 minutes at room temperature, and the signals were developed on HyBlot CL film (Denville Scientific Inc. Metuchen, N.J.).

See also Sections 6.1.2 and 6.2.2, and Reference 6 in Section 6.3.13 below, for descriptions of western blot analysis protocols.

6.3.3 Immunohistochemistry of Tissue Microarray (TMA)

Immunohistochemistry of human TMA screening was performed as previously described (see Reference 6 in Section 6.3.13, below).

6.3.4 Immunofluorescence Staining of OVCAR3, SKOV3-MUC16$^{C344}$, and SKOV3-MUC16$^{C114}$ 50,000 cells were seeded in Delta TPG 0.17 mm dishes separately and cultured in their respective media at 37° C. in 5% $CO_2$ overnight. The adhered cells were washed twice with PBS containing 1% fetal calf serum (FCS) and 0.025% Sodium Azide (FACS buffer). Cells were stained at 1:50 dilution with either EGFR(R-1)-Alexa Fluor 647 nm (Santa Cruz Biotechnology, CA, cat # sc-101 AF647) and 4H11 or Integrin β1(4B7R)-Alexa Fluor 647 nm (Santa Cruz Biotechnology, CA, cat # sc-9970 AF647) and 4H11 for 30 minutes at 4° C. Cells were washed with FACS buffer three times and then labeled with goat anti-mouse IgG2b-PE (Santa Cruz Biotechnology, CA, cat # sc-3766-PE) for 30 minutes at 4° C. Cells were washed with FACS buffer three times, and images were taken on a Zeiss Axio Observer Z1 with 20×/0.8NA air and 63×/1.4NA oil objectives using the ZEN2 acquisition software.

6.3.5 Statistical Analysis

To compare groups evaluated in the in vitro and in vivo studies of growth and invasion, data were analyzed for statistical significance using two-tailed Student's t-test with the GraphPad Prism software (San Diego, Calif.).

6.3.6 Cell Culture, Transfection, and Cell Line Characterization

See Reference 3 in Section 6.3.13 regarding the OVCA-433 cell line. The pLenti tetracycline-inducible system was purchased from Invitrogen, CA (cat # K4925-00) and was used to create pLenti-SKOV3$^{c114}$. shRNA hairpin knockout for EGFR-expressing viral plasmids were obtained by the Memorial Sloan Kettering Cancer Center High Throughput Screening (HTS) Core Facility; transfected HEK293 cells and viral supernatants were collected from HEK293 cells to infect pLenti-SKOV3$^{c114}$-shEGFR cell lines. The MUC16$^{c114}$ transfectants had cell surface expression of MUC16 protein from the putative cleavage site to the carboxy-terminus (amino acids 1777 to 1890 of SEQ ID NO: 150) (see Reference 21 in Section 6.3.13, below). Cell lines with longer MUC16 fragments were prepared in a similar manner, including lines with expression of MUC16$^{c344}$-GFP vector that have cell surface expression of MUC16 protein as a 344 amino acid fragment extending to the carboxy-terminus of MUC16 (amino acids 1547 to 1890 of SEQ ID NO: 150) (see References 19 and 22 in Section 6.3.13, below).

6.3.7 Transfection

DNA constructs were introduced into SKOV3 cells using DOTAP (Roche Diagnostics, Indianapolis Corporation, IN) following the manufacturer's protocol. Stable transfectants were selected with 800 μg/mL of G418 for SKOV3 cells in their culture media. They were cell sorted twice for GFP expression, and selected cells were grown as lines of up to 15 passages. Routine monitoring of FACS analysis was done to confirm the GFP positivity of these lines. Protein extracts of these lines were analyzed by Western blot using anti-hrGFP (Stratagene, La Jolla, Calif.) and anti-MUC16-carboxy-terminus monoclonal antibodies (see Reference 19 in Section 6.3.13, below). As described in Section 6.1, the MUC16$^{c57-114}$-pFUSE-hIgG1-Fc2 and $^{117-244}$LGALS3-pFUSE-hIgG1-Fc2 constructs were separately transfected into human embryonic kidney (HEK) FreeStyle 293F cells (Invitrogen, CA) that express and secrete fusion proteins into serum free media, as per the manufacturer's protocol (see Section 6.1 and Reference 19 in Section 6.3.13, below). Secreted fusion proteins were purified and characterized by Western blot analysis using anti-human IgG1-Fc-HRP (γ1 chain specific) (Southern Biotech Inc., Birmingham, Ala.) or 4H11-HRP or polyclonal anti-human LGALS3 antibody (Abgent, San Diego, Calif.). EGFRDDK-HIS (cat # TP700043), LGALS3Myc-DDK (cat # TP308785), and Integrin-β1Myc-DDK (cat # TP303818) purified proteins expressed in HEK293 cells were purchased from Origene, Rockville, Md.

6.3.8 Immunofluorescence Staining by FACS Analysis

MUC16 expression FACS analysis was performed as described in Section 6.1 and Reference 6 in Section 6.3.13 below.

6.3.9 Growth Curves

Growth Curves were performed as described in Sections 6.1 and 6.2 and References 18 and 19 in Section 6.3.13 below.

6.3.10 Nomenclature

As used in Example 3 (Section 6.3), "N1" refers to the asparagine at position 1777 of SEQ ID NO: 150, also referred to as "Asn1777". As used in Example 3 (Section 6.3), "N24" refers to the asparagine at position 1800 of SEQ ID NO: 150, also referred to as "Asn1800". As used in Example 3 (Section 6.3), "N30" refers to the asparagine at position 1806 of SEQ ID NO: 150, also referred to as "Asn1806".

6.3.11 Results 6.3.11.1 MUC16 Pathobiology is Dependent on N-Glycosylation of C-Terminal MUC16 Ectodomain Expression of the most proximal 114 amino acids of the C-terminal MUC16 ectodomain (MUC16c114) led to more aggressive in vitro/in vivo behavior of 3T3 mouse fibroblasts, including a significant increase in MUC16-driven matrigel invasion and more rapid tumor growth in vivo (see Section 6.1 and Reference 19 in Section 6.3.13 below). To examine the role of MUC16 and its glycosylation effects in human ovarian cells, the MUC16-negative SKOV3 human ovarian cell line was examined for the impact of MUC16 expression (FIGS. 18A-18C). The transfection of SKOV3 cells with a MUC16$^{c114}$ stable expression vector led to high levels of cell surface MUC16 expression and greater than a two-fold increase in matrigel invasion, as shown in FIG. 19A. Twenty-four hour exposure of the cells to the N-glycosylation inhibitor tunicamycin profoundly decreased the invasive properties of SKOV3-MUC16$^{c114}$ cells but had little effect on the matrigel invasion of SKOV3-phrGFP vector-only transfected cells (FIG. 19A).

Lectins have previously been implicated in the mediation of glycosylation effects (see Reference 17 in Section 6.3.13, below), and because Galectin-3 is often overexpressed in human ovarian cancers, a lectin-blocking construct was created by combining the sugar-binding domain of Galectin-3 ($^{117-244}$LGALS3) with a truncated pFUSE-human IgG1-Fc2 sequence (pFUSE) lacking a variable binding domain ("$^{117-244}$LGALS3-pFUSE") (see Reference 1 in Section 6.3.13, below). This chimeric molecule binds Galectin-3 ligands but lacks the ability to form Galectin-3 pentamers. As shown in FIG. 19A, when this galectin-blocking construct was introduced into cells, it had little effect on matrigel invasion by control SKOV3-phrGFP cells but significantly reduced SKOV3-MUC16$^{c114}$ invasion. The control pFUSE vector lacking the Galectin-3 sugar-binding domain had no effect. A soluble MUC16 ectodomain, constructed by linking the same pFUSE vector to the 58 amino acids from the MUC16 ectodomain was also generated ("MUC16$^{c57-114}$-pFUSE"). As with the Galectin-3-pFUSE ($^{117-244}$LGALS3-pFUSE)-blocking construct, the MUC16$^{c57-114}$-pFUSE construct also significantly decreased invasion for the SKOV3-MUC16$^{c114}$ cells, but not for the SKOV3-phrGFP cells. MGAT5 is the glycosylation enzyme that catalyzes the formation of the tetra-antennary N-glycans with the highest affinity for Galectin-3 binding (see Reference 9 in Section 6.3.13, below). MGAT5 knockout mice are resistant to tumor growth (see Reference 8 in Section 6.3.13, below). Without being bound by any particular theory, it was hypothesized that MUC16 effects would be dependent on both Galectin-3 and MGAT5 expression. As shown in FIG. 19B, shRNAs that reduce either MGAT5 or Galectin-3 (LGALS3) markedly decreased SKOV3-MUC16$^{c114}$ invasion, while a negative control shRNA knocking down Lamelli had no effect.

Introduction of mutations to MUC16 ectodomain N-glycosylation sites (asparagine residues at positions N1, N24, and N30 of the MUC16$^{c114}$ ectodomain) reduced observed MUC16-glycosylation dependent alterations. As shown in FIG. 19C, the asparagine to alanine mutation of the most distal asparagine (N1), adjacent to the cleavage site, had no negative effect on invasion. In contrast, the asparagine to alanine mutations of either of the more proximal asparagines (N24 or N30) negatively affected the invasion. In particular, preservation of the asparagine closest to the membrane surface (N30) was the most critical for enhancement of invasion, and that effect was not materially increased by additional asparagine to alanine mutations of the other asparagine residues. A larger MUC16 construct with 344 amino acids from the MUC16 C-terminus (MUC16$^{c344}$) was also examined. When expression vectors bearing MUC16 mutations at N30 of MUC16$^{c344}$ or N24 and N30 of MUC16$^{c344}$ were transfected into the SKOV3 cell line, matrigel invasion was significantly reduced (FIG. 19D). Although this larger construct has seven additional N-glycosylation sites distal to the cleavage site, mutating the crucial proximal N24 and N30 sites still decreased the matrigel invasion, as shown in FIG. 19D, just as those mutations altered invasion with SKOV3-MUC16$^{c114}$.

Downstream activation of both the ERK and PI3K/AKT pathways in MUC16$^{c114}$ transformation of 3T3 cells has been demonstrated (see Section 6.1 and Reference 19 in Section 6.3.13 below). In FIG. 19E, it can be seen that transfection of SKOV3 cells with MUC16$^{c114}$ activated a variety of oncogenes, including pERK1/2, pSRC, and phosphorylation of EGFR. FIG. 19E demonstrates that each of the following conditions impairs MUC16$^{c114}$-induced oncogene activation: knockdown of MGAT5 (shMGAT5), knockdown of Galectin-3 (shLGALS3), and the asparagine to alanine mutation of N30. These data are consistent with the decreases observed in matrigel invasion related to MUC16$^{c114}$ expression.

The effects of knocking down MGAT5 or LGALS3 or mutation of the MUC16$^{c114}$ ectodomain N-glycosylation sites were examined in xenograft tumor growth in nude mice. As shown in FIG. 19F, there was a complete abrogation of the MUC16$^{c114}$-induced tumor growth with any of these N-glycosylation directed interventions. The effect of MUC16$^{c114}$ on receptor stability was also examined. The presence of both N-glycosylation and linkage to the galectin lattice has been associated with stabilization of EGFR on the cell surface (see Reference 11 in Section 6.3.13 below). Without being bound by any particular theory, it was reasoned that increased presence of MUC16 stabilizes a cell surface galectin lattice, thereby stabilizing EGFR on the cell surface. As shown in FIG. 20A, the presence of EGFR on the cell surface of SKOV3 cells was increased when stable SKOV3-MUC16$^{c114}$ transfectants were compared to the vector-only controls using FACS analysis. Moreover, MUC16$^{c114}$ expression nearly doubled EGFR on the cell surface following cycloheximide (CHX) treatment to inhibit new EGFR synthesis, compared to phrGFP vector controls. The stability of the MUC16$^{c114}$ ectodomain (4H11 positive) was unchanged by CHX. Total EGFR over time was compared in stable SKOV3-MUC16$^{c114}$ and SKOV3-phrGFP cells treated with CHX for 24 hours by Western blotting, and EGFR was compared to β-Actin. Densitometry curves (FIG. 20B) indicated that the presence of MUC16$^{c114}$ on the cell surface stabilized EGFR in comparison to phrGFP-vector control. To exclude the possibility that this effect was related to selection of SKOV3-stable MUC16$^{c114}$ clones, a tetracycline-inducible MUC16$^{c114}$ system was utilized. As shown in FIG. 20C, tetracycline exposure for 24 hours had no effect on matrigel invasion for either control SKOV3 cells transfected with the empty phrGFP vector or the stable CMV-driven MUC16$^{c114}$ expression vector. In the MUC16$^{c114}$ tetracycline-inducible system, tetracycline exposure induced MUC16$^{c114}$ dependent matrigel invasion similar to the stable transfectants, both control and MUC16$^{c114}$. The requirement for EGFR was examined via stable expression of an shRNA construct (shEGFR) introduced into SKOV3 cells that reduced EGFR expression. Both of the single cell clones for the shEGFR-transfected cells showed markedly decreased matrigel invasion. Tetracycline-induced expression of MUC16$^{c114}$ in these two shEGFR cell lines had minimal effect on matrigel invasion compared to SKOV3-MUC16$^{c114}$ cell lines, confirming that SKOV3-MUC16$^{c114}$-induced matrigel invasion was codependent on expression of EGFR. The stability of EGFR in tetracycline-induced SKOV3-MUC16$^{c114}$ treated with CHX was studied by western blotting, and compared to β-actin. As shown in FIG. 20D, CHX exposure over 24 hours resulted in the steady decline of total EGFR protein in the un-induced MUC16(−) SKOV3 cells. When the same experiment was performed following tetracycline induction of SKOV3-MUC16$^{c114(tet)}$ cells, the CHX-induced rate of EGFR loss was reduced. Not only did MUC16 stabilize the EGFR content of the cells, it also stabilized the pEGFR expression levels in the tetracycline-induced SKOV3-MUC16$^{c114(tet)}$ cells compared to the uninduced SKOV3-MUC16$^{c114(tet)}$ cells (FIG. 21).

6.3.11.2 Synthesis of Homogeneous N-Glycopeptides as Epitope Mimics for Monoclonal Antibody (mAb) Development Having identified N-glycosylation at the N24 and N30 sites of MUC16$^{c114}$ as a central requirement for MUC16 action, the glycan profile of a MUC16$^{c114}$ mutated glycopeptide containing alanine to asparagine mutations at N1 and N24, purified from the SKOV3-MUC16$^{c114}$ cell line, was analyzed (FIG. 22). This purified glycopeptide thus contained a single asparagine residue (N30) for N-glycosylation. The glycome analysis of the purified glycopeptide is shown in FIG. 22A. It was characterized by a diverse N-glycosylation pattern consisting largely of truncated glycosylated species that shared the common, proximal chitobiose ($GlcNAc_2$) disaccharide as the minimal repeating unit to which fucose and various mannose residues are attached (FIG. 22A).

It was hypothesized that antibodies targeted against a MUC-16-ectodomain epitope encompassing the crucial N30 glycosylation site might inhibit MUC16 interaction with the galectin lattice, decreasing the adverse effects of MUC16 expression, including tumor growth and invasion. Thus, synthetic peptide antigens of various lengths (i.e., 55, 18 and 15 amino acids in length; SEQ ID NOs: 129, 131, and 130, respectively) within the MUC16 ectodomain, glycosylated with chitobiose at this N30 site, were designed. Besides being the minimal motif common to larger, more complex N-glycans, the chitobiose disaccharide should also enable a better exposure of the underlying peptide to elicit glycan-directed antibodies that retain peptide specificity.

The synthesis of the 55-mer MUC16-ectodomain N-glycopeptide ($GlcNAc_2$-55-mer; SEQ ID NO: 129) was highly convergent and involved a coupling between conveniently protected full-length peptide (55-mer) and chitobiose amine, followed by acidic global deprotection using our one-flask aspartylation/deprotection procedure (see Sections 6.2 and 6.4 and references 7 and 20 in Section 6.3.13 below). Following a similar approach, the more elaborate $Man_3GlcNAc_2$-55-mer glycopeptide bearing a terminal trimannose glycan was also prepared by convergent aspartylation.

In order to focus the immune response against a smaller-sized epitope around the relevant glycosylation site, the shorter 15- and 18-mer glycopeptides bearing one (N30) and two chitobiose glycans (N24 and N30) respectively, were also synthesized (FIG. 22C; SEQ ID NOs: 131 and 130, respectively), the latter by analogy to the cluster presentation of the Tn antigen (GalNAc-α-O-Ser/Thr), which has been shown to be required for binding to some mAbs (see Sections 6.2 and 6.4 and references 14-16 in Section 6.3.13 below). These glycopeptides were then conjugated to the KLH carrier protein via an N-terminal cysteine to generate the corresponding immunogens for mouse vaccination.

6.3.11.3 Mouse Vaccination with Synthetic Glycopeptides/Glycoconjugates and Serologic Assays Mouse vaccination and sera collection were performed according to the protocol described in Sections 6.2 and 6.4. After 3 immunizations with the $GlcNAc_2$-55-mer glycopeptide (SEQ ID NO: 129, FIG. 22B) followed by an immunization with an equal mixture of the chitobiose-bearing, KLH-conjugated constructs (mono-glycosylated 15-mer (SEQ ID NO: 131) and bis-glycosylated 18-mer(SEQ ID NO: 130)), only 2 of 10 mice showed weakly positive ELISA signals for both 55-mers (with and without $GlcNAc_2$ (SEQ ID NO: 129)), suggesting that the mice had limited immune response to the 55-mer immunizations. Two more booster immunizations with both KLH conjugates ($GlcNAc_2$-15-mer (SEQ ID NO: 131) and $(GlcNAc_2)_2$-18-mer (SEQ ID NO: 130)) resulted in enhanced immune responses (IgG type) against the shorter glycopeptides, particularly in two mice (mouse 7 & mouse 8). The 4H11 mAb, directed at a different, non-glycosylated portion of the MUC16 peptide backbone, showed no binding to the 15-mer/18-mer glycopeptides, indicating a distinct recognized epitope separate from the mouse sera positivity.

The polyclonal serum from mouse 7 was further characterized by ELISA and screened by FACS on several cell lines with and without MUC16$^{c114}$ expression. These cell-sorting studies confirmed positive signals to both SKOV3-MUC16$^{c114}$ cells and OVCAR3 cells, similar to the anti-MUC16 4H11 antibody control (see Reference 6 in Section 6.3.13, below). SKOV3-phrGFP control cells lacking MUC16 were negative for binding with mouse 7 serum.

6.3.11.4 Glycosylation-Directed mAb Selection

The spleen of mouse 7 was harvested and the splenocytes were fused with hybridoma fusion partner with high fusion efficiency. Supernatants were selected and screened for reactivity by ELISA against the individual glycopeptides (FIG. 22C). Although multiple supernatants were reactive with the $GlcNAc_2$-15-mer and $(GlcNAc_2)_2$-18-mer glycopeptides, none of the hybridoma supernatants screened demonstrated a high degree of selectivity for the glycosylated over the non-glycosylated peptides in ELISA screening. MUC16 specificity was maintained and none of the positive supernatants were reactive with irrelevant peptides glycosylated with chitobiose. No overlap was seen with the peptide sequence recognized by the 4H11 mAb.

After serial subcloning, the process afforded multiple chitobiose-directed primary mAbs that were reactive with MUC16-glycosylated epitopes and the homologous non-glycosylated sequences but not with chitobiose-bearing irrelevant peptides serving as negative control. Of this pool, four high-affinity antibodies were selected and further purified for characterization.

6.3.11.5 Characterization of Anti-MUC16 N30 Glycosylation-Targeted/Directed mAbs The results of the confirmatory characterization studies for four representative antibodies are shown by ELISA in FIG. 23A. The binding of the candidate antibodies to the various synthetic peptides was evaluated and compared to the binding of the 4H11 antibody, which recognizes the MUC16-ectodomain peptide backbone. The unrelated chitobiose-linked peptides exhibited no significant binding by any of the anti-glycan-MUC16 antibodies selected. All of the candidate antibodies showed similar binding affinities for both MUC16-derived 15-mers (i.e., the non-glycosylated peptide and the corresponding chitobiose glycopeptide). Additional synthetic glycopeptides bearing alternative sugar moieties, including a single GlcNAc, a terminal trimannose-chitobiose ($Man_3GlcNAc_2$), and a fucosylated chitobiose ($GlcNAc_2Fuc$), did not substantially alter the antibody reactivity to the chitobiose-linked MUC16 peptides used for immunization.

Each antibody was also tested for glycan-MUC16$^{c114}$ and glycan-MUC16$^{c344}$ specificities on an extended panel of cell lines expressing differentially glycosylated MUC16 peptides (Table 11). In these studies, SKOV3-phrGFP transfectants were compared with the SKOV3-MUC16$^{c114}$ (full N-glycosylation), SKOV3-MUC16$^{N24c114}$ mutants (no N24 glycosylation site), SKOV3-MUC16$^{N30c114}$ (no N30 glycosylation site), and SKOV3-MUC16$^{N1\text{-}N24\text{-}N30c114}$ (no N1, N24, or N30 glycosylation sites). SKOV3-MUC16$^{c114}$ refers to SKOV3 cells expressing a truncated form of MUC16 which is capable of being N-glycosylated at N1, N24, and N30. SKOV3-MUC16$^{N24c114}$ refers to SKOV3 cells expressing a truncated mutant form of MUC16, wherein the amino acid position corresponding to Asn1800 of SEQ ID NO: 150 comprises an asparagine to alanine mutation, and, thus, is not capable of being N-glycosylated at this position. SKOV3-MUC16$^{N30c114}$ refers to SKOV3 cells expressing a truncated mutant form of MUC16, wherein the amino acid position corresponding to Asn1806 of SEQ ID NO: 150 comprises an asparagine to alanine mutation, and, thus, is not capable of being N-glycosylated at this position. SKOV3-MUC16$^{N1\text{-}N24\text{-}N30c114}$ refers to SKOV3 cells expressing a truncated mutant form of MUC16, wherein the amino acid positions corresponding to Asn1777, Asn1800, and Asn1806 of SEQ ID NO: 150 comprise asparagine to alanine mutations, and, thus, are not capable of being N-glycosylated at these positions. As with the ELISA data, the results indicated that MUC16-specific targeting was present.

However, in contrast to the ELISA data, the loss of both N24 and N30 glycosylation sites in the MUC16 ectodomain reduced the glycosylation-targeted antibody reactivity, whereas reactivity to the 4H11 antibody was retained, thereby confirming the presence of cell-surface SKOV3-MUC16$^{c114}$. Cells bearing a MUC16 C-terminal chain extended to 344 amino acids (e.g. SKOV3-MUC16$^{c344}$) had also a similar requirement for N24 or N30 glycosylation (Table 11). Further, the reactivity with the antibodies against the glycan-MUC16 ectodomain was not diminished by downregulation of MGAT5 (Table 11), confirming that a chitobiose at the N24/N30 sites contributes to antibody binding with whole cells, regardless of more complex branching.

TABLE 11

Table 11 provides the geometric mean phycoerythrin (PE) fluorescence of 4H11 and four $GlcNAc_2$-MUC16 ectodomain monoclonal antibodies on SKOV3-MUC16 transfections with N-glycosylation site modifications. 4H11 retains binding to all of the cell lines (except the SKOV3-phrGFP line, which does not express MUC16) regardless of glycosylation modification, thus confirming MUC16 protein on the cell surface. When both the N24 and N30 sites of glycosylation were lost, there was a reduction of glycan-MUC16 antibody binding for both the MUC16$^{c114}$ and the MUC16$^{c344}$ transfectants. Limited loss of reactivity for the MGAT5 knockdown cell line confirmed that chitobiose is essential for each $GlcNAc_2$-MUC16 ectodomain antibody, while more extensive branching had limited effect.

| | | | | | Anti-glycosylated-MUC16 ectodomain antibodies | | | |
|---|---|---|---|---|---|---|---|---|
| | Cells alone | G anti M IgG2a-PE | G anti M IgG2b-PE | 4H11 + G anti M IgG2b-PE | 18C6 + G anti M IgG2b-PE | 10C6 + G anti M IgG2a-PE | 19C11 + G anti M IgG2a-PE | 7B12 + G anti M IgG2a-PE |
| SKOV3-phrGFP | 46 | 50 | 57 | 77 | 56 | 70 | 77 | 80 |
| SKOV3-c114 | 56 | 74 | 104 | 1124 | 2054 | 571 | 617 | 492 |
| SKOV3-N24 mutc114 | 43 | 62 | 78 | 2654 | 1830 | 435 | 486 | 471 |
| SKOV3-N30 mutc114 | 49 | 65 | 90 | 696 | 1696 | 645 | 536 | 444 |
| SKOV3-N24N30 mutc114 | 125 | 142 | 155 | 655 | 461 | 264 | 236 | 185 |
| SKOV3-N1-N24-N30mutc114 | 37 | 50 | 71 | 514 | 34 | 74 | 61 | 82 |
| SKOV3-shMGAT5-c114 | 108 | 133 | 145 | 2384 | 855 | 645 | 525 | 289 |
| SKOV3-c344 | 53 | 66 | 68 | 559 | 1652 | 792 | 578 | 422 |
| SKOV3-N24mutc344 | 89 | 102 | 64 | 574 | 1569 | 991 | 661 | 512 |
| SKOV3-N30mutc344 | 93 | 104 | 47 | 661 | 1064 | 687 | 454 | 440 |
| SKOV3-N24-N30mutc344 | 80 | 161 | 140 | 765 | 277 | 231 | 195 | 220 |

"G anti M" refers to goat anti-mouse.
"PE" refers to phycoerythrin.

The four representative MUC16 Glycosylation Antibodies (18C6, 10C6, 19C11, 7B12) characterized were evaluated together with 4H11 for binding affinity (Table 12) and their effect on invasion by matrigel assay with the SKOV3-MUC16$^{c114}$ transfectants. As shown in FIGS. 23B-23D, the newly developed antibodies showed broad inhibition of matrigel invasion, whereas 4H11 was distinguished by its inability to block SKOV3-MUC16$^{c114}$ mediated invasion, indicating that these antibodies targeting glycosylated peptide epitopes in the MUC16 ectodomain inhibited some of the crucial biological properties of MUC16 better than antibodies targeting closely adjacent epitopes. All of the MUC16 Glycosylation Antibodies were inhibitory in ovarian cancer cells expressing native, full length MUC16, such as CAOV3 and OVCA-433 cells. This suggests that the N24/N30 glycosylation sites were critical for the enhanced invasive properties of MUC16, while the presence of other MUC16 N- and O-glycosylation sites were insufficient to overcome MUC16 Glycosylation Antibody blocking of this critical epitope. Without being bound by any particular theory, antibody inhibition of the N24/30 binding of Galectin-3 to MUC16 would be predicted to impair EGFR cell surface stabilization as well. FIGS. 23B-23D demonstrate that when one of these antibodies (10C6) was introduced into the cell culture, the EGFR stabilizing effect of tetracycline-induced SKOV3-MUC16$^{c114(tet)}$ was overcome, and the rate of EGFR loss in CHX-exposed cells was similar to that of the un-induced SKOV3-MUC16$^{c114(tet)}$ cell lines without MUC16$^{c114}$ expression. Immunohistochemistry staining with the antibodies was also examined in ovarian cancer tissue microarrays. As shown in FIG. 23E, each of the glycan directed-MUC16 ectodomain antibodies bound to serous ovarian cancer cells in paraffin-fixed tissue with limited interaction with other stromal tissue, similar to the 4H11 behavior. Finally, the effect of 10C6 antibody on the growth of SKOV3-MUC16$^{c344}$ in immunocompromised mice was tested. The SKOV3-MUC16$^{c344}$ cells were utilized instead of the SKOV3-MUC16$^{c114}$ cells as a more stringent test of antibody effect in MUC16-positive tumor cells with multiple N- and O-glycosylation sites. The 10C6 antibody decreased matrigel invasion by MUC16$^{c344}$ cells (FIG. 23F), and significantly reduced the growth of SKOV3-MUC16$^{c344}$ tumor cells in the mouse flank when administered to tumor-bearing mice twice per week (FIG. 23G).

TABLE 12

| Antibody | kd [1/s] | Error in kd [1/s] | ka [1/s] | kD [nM] |
|---|---|---|---|---|
| 10C6.E4 | * | — | ** | >1000 |
| 19C11.H6 | $2.42 \times 10^{-3}$ | $2.35 \times 10^{-3}$ | $3.80 \times 10^{-4}$ | 63.7 |
| 7B12.B3 | $1.04 \times 10^{-3}$ | $1.09 \times 10^{-4}$ | $7.50 \times 10^{-4}$ | 13.8 |
| 18C6.D12 | $6.78 \times 10^{-4}$ | $1.83 \times 10^{-4}$ | $6.14 \times 10^{-4}$ | 11.1 |
| 4H11 | — | — | — | — |

* low calculation confidence, no fit for off-rate ka is too low for association rate determination 6.3.11.6 Galectin-Dependent Co-Localization of MUC16 and Other Cell Surface Proteins MUC16-stabilized EGFR appears to be an important driver of ovarian cancer cell invasion, and this interaction depends on EGFR, appropriately N-glycosylated MUC16 protein ectodomain, and the presence of Galectin-3. This interaction was evaluated with purified proteins to establish the necessary/sufficient three-way interaction among these three proteins. For this purpose, purified MUC16$^{c57-114}$-pFUSE (produced in human embryonic kidney [HEK] FreeStyle 293F cells) (as the MUC16 part of the interaction), purified EGFR (produced by HEK293 cells), and purified Galectin-3 (LGALS3; produced by HEK293 cells) proteins were utilized. Because these proteins were produced in human cells, they were expected to bear typical, native glycosylated species. Without being bound by any particular theory, it was hypothesized that the three proteins would form heteromers that could be identified by immuno-coprecipitation. FIG. 24A illustrates the results of this immunocoprecipitation, wherein each of the three proteins detected are shown in the direct immunoblot in the left three lanes. Using Agarose Protein A/G PLUS beads, one can see that the MUC16$^{c57-114}$-pFUSE protein bound to the Protein A/G PLUS-conjugated beads and was present in the eluate when separated on the SDS-PAGE gel. EGFR was only present in the combined eluate with MUC16$^{c57-114}$-pFUSE when Galectin-3 (LGALS3) was also present. Antibody 18C6 eliminated the EGFR-MUC16 interaction by blocking the N-glycosylation binding site of Galectin-3 (see FIG. 24A). Direct molecular dual immunofluorescence imaging also was used to confirm colocalization of the EGFR and MUC16 in living cells. As shown in FIG. 24B and FIG. 25A, EGFR and MUC16 were tightly co-localized in OVCAR3, SKOV3-MUC16c344, and SKOV3-MUC16$^{c114}$ cells (see arrows in FIGS. 24B and 25A). These studies strongly confirmed that MUC16 combined with Galectin-3 to associate with EGFR on the surface of MUC16-positive ovarian cancer cells. Without being bound by any particular theory, since many growth-enhancing receptors are glycosylated, it was reasoned that lectin-dependent MUC16 cell-surface effects might include other N-glycosylated proteins and not be restricted to EGFR. The integrin proteins are often altered in cancer and participate in the "outside-in" signaling initiated by stromal-epithelial interactions triggering SRC phosphorylation and other downstream effects. FIG. 24C depicts the MUC16 interactions with Integrin β1, an integrin component frequently associated with cancer development and progression. As in the case of EGFR, purified MUC16$^{c57-114}$-pFUSE bound to Integrin β1 in a Galectin-3-dependent manner, and this heterotrimeric interaction required all 3 proteins. As with EGFR, the interaction was completely blocked by an anti-MUC16c114 glycosylation site-blocking antibody, 18C6. Colocalization of MUC16 and Integrin β1 was also confirmed by dual immunofluorescence in several ovarian cancer cell lines (FIG. 24D and FIG. 25**B). Thus, N-glycosylation at key sites on MUC16-ectodomain peptide epitopes mediated the interaction with cell-surface protein receptors in a lectin-specific manner to generate the characteristics of malignant behavior, including matrigel invasion, activation of the PI3K/ERK and SRC pathways, as well as enhanced MUC16-positive tumor growth in immunocompromised mice.

Without being bound by any particular mechanism, the mechanistic model for the cancer-related mucin, MUC16, and its effect on ovarian cancer cell behavior is shown in FIG. 26. In FIG. 26A, MUC16 binds to EGFR and Integrin β1 through Galectin-3 to enhance the stability and "inside-out" signals that promote growth and invasion. When the MUC16 ectodomain N-glycosylation sites are mutated or MGAT5 activity is suppressed (FIG. 26B), the binding is prevented and EGFR/Integrin signals are reduced. Similarly, if Galectin-3 protein expression is suppressed (FIG. 26C), the molecular association is lost, and the signals and invasion are reduced. Finally, when MUC16-ectodomain chimeric antibodies or chimeric "TRAP" LGALS3 molecules prevent molecular interaction, the cancer cell lacks any of the observed MUC16 tumor-promoting properties (FIG. 26D).

6.3.12 Discussion

MUC16 and other tethered mucins, such as MUC1 and MUC4 can transform 3T3 cells and are associated with adverse outcomes. The mechanisms of aberrantly expressed mucins in cancer are complex and diverse. It is well described that N-glycosylation patterns play important roles in cellular growth in response to the local environment. The diversity of glycoprotein patterns is influenced by environmentally dependent hexosamine flux through Golgi-based glycosylation. Common growth factor receptors such as EGFR, insulin-like growth factor receptor (IGF1R), and PDGFR are preferentially glycosylated first in a nutrient-dependent manner, and those heavily glycosylated receptors are preferentially delivered to the cell surface. In contrast, inhibitory receptors such as TGF-β have fewer N-glycosylation sites and are presented on the cell surface later, with consequent inhibition of the growth program (see Reference 12 in Section 6.3.13 below). In ovarian cancer, EGFR expression has been linked to invasive behaviors and EGFR signaling is dependent on the glycosylation state of the receptors and the affinity of the N-glycosylated species for lectins (see Reference 2 in Section 6.3.13 below). The enzyme MGAT5 appears to be crucial for the synthesis of tetraantenary, branched N-glycans that have the highest affinity for Galectin-3, an important lectin overexpressed in cancer cells (see Reference 17 in Section 6.3.13 below).

This Example provided evidence that the behaviors associated with MUC16 expression are mediated through these processes on specific N-glycosylation sites on the most proximal ectodomain region of MUC16 relative to the cell surface. MGAT5-dependent patterns of N-glycosylation were required for high affinity interaction with Galectin-3 and cell-surface proteins to promote invasion, oncogene activation, and increased tumor growth in immunocompromised mice. In particular, N-glycosylation at the most proximal sites on the retained ectodomain of MUC16 after cleavage was critically important for this interaction. Interventions that removed these N-glycosylation sites, blocked the sites with dummy receptors, or interfered with their full N-glycosylation all impaired the transforming effects of MUC16. These transforming effects appeared to depend, not only on MUC16 alone, but also on the interaction of N-glycosylated MUC16 with Galectin-3 and other cell surface proteins at the proximal N-glycosylation sites. MUC16 ectodomain expression was shown to stabilize EGFR, a mediator of growth and invasion, and prolonged its residence on the SKOV3-MUC16$^{c114}$ cell surface, compared to the parent SKOV3phrGFP cells. Even in a simplified MUC16 glycopeptide model retaining only one N-glycosylation site, the stochastic nature of glycosylation resulted in the presence of a variety of N-glycans that were all linked to the MUC16 protein backbone through a shared chitobiose stem. Thus, antibodies were prepared against the chitobiose-linked (at the N24/N30 sites) MUC16$^{c114}$ glycan-peptide epitope of the MUC16 ectodomain. These new antibodies (MUC16 Glycosylation Antibodies) blocked MUC16 enhanced invasion, oncogene activation and in vivo tumor growth. Importantly, these MUC16 Glycosylation Antibodies inhibited the MUC16-related properties in cells with full-length MUC16 expression as well as test, truncated constructs with shorter MUC16 C-terminal expression. The MUC16 Glycosylation Antibodies interfered with EGFR stabilization of the ovarian cancer cell surface in the presence of CHX and impaired transplanted growth in nude mice. In addition, the effect of the MUC16 Glycosylation Antibodies also prevented the interaction of purified MUC16 with either purified EGFR or Integrin β1 in the presence of recombinant Galectin-3.

This Example reveals insights into the role of mucin overexpression in cancer. Through the formation of lectin-mediated, low affinity multi-molecular complexes, MUC16 was able to enhance the "outside-in" signal transduction in a glycosylation-dependent manner. The specific N-glycosylation sites responsible for maximal effect were unique and close to the cell surface, while other, more distal N-glycosylation sites may have been less important. There are Galectin-3 inhibitors in clinical development but a dummy receptor "Galectin-3-TRAP" construct or truncated "MUC16-TRAP" molecules had a similar effect in the in vitro models of this Example. The MUC16 Glycosylation Antibodies identified in this Example inhibited the transforming effects of MUC16.

6.3.13 References

1. Ahmad, N., Gabius, H. J., Andre, S., Kaltner, H., Sabesan, S., Roy, R., Liu, B., Macaluso, F., and Brewer, C. F. (2004). Galectin-3 precipitates as a pentamer with synthetic multivalent carbohydrates and forms heterogeneous cross-linked complexes. J Biol Chem 279, 10841-10847.
2. Alper, O., Bergmann-Leitner, E. S., Bennett, T. A., Hacker, N. F., Stromberg, K., and Stetler-Stevenson, W. G. (2001). Epidermal growth factor receptor signaling and the invasive phenotype of ovarian carcinoma cells. J Natl Cancer Inst 93, 1375-1384.
3. Bast, R. C., Jr., Feeney, M., Lazarus, H., Nadler, L. M., Colvin, R. B., and Knapp, R. C. (1981). Reactivity of a monoclonal antibody with human ovarian carcinoma. The Journal of clinical investigation 68, 1331-1337.
4. Burton, D. R., and Mascola, J. R. (2015). Antibody responses to envelope glycoproteins in HIV-1 infection. Nat Immunol 16, 571-576.
5. Dharma Rao, T., Park, K. J., Smith-Jones, P., Iasonos, A., Linkov, I., Soslow, R. A., and Spriggs, D. R. (2010). Novel monoclonal antibodies against the proximal (carboxy-terminal) portions of MUC16. Appl Immunohistochem Mol Morphol 18, 462-472.
6. Fernandez-Tejada, A., Vadola, P. A., and Danishefsky, S. J. (2014). Chemical synthesis of the β-subunit of human luteinizing (hLH) and chorionic gonadotropin (hCG) glycoprotein hormones. J Am Chem Soc 136, 8450-8458.
7. Granovsky, M., Fata, J., Pawling, J., Muller, W. J., Khokha, R., and Dennis, J. W. (2000). Suppression of tumor growth and metastasis in Mgat5-deficient mice. Nat Med 6, 306-312.
8. Hirabayashi, J., Hashidate, T., Arata, Y., Nishi, N., Nakamura, T., Hirashima, M., Urashima, T., Oka, T., Futai, M., Muller, W. E., et al. (2002). Oligosaccharide specificity of galectins: a search by frontal affinity chromatography. Biochim Biophys Acta 1572, 232-254.
9. Hollingsworth, M. A., and Swanson, B. J. (2004). Mucins in cancer: protection and control of the cell surface. Nat Rev Cancer 4, 45-60.
10. Lajoie, P., Partridge, E. A., Guay, G., Goetz, J. G., Pawling, J., Lagana, A., Joshi, B., Dennis, J. W., and Nabi, I. R. (2007). Plasma membrane domain organization regulates EGFR signaling in tumor cells. J Cell Biol 179, 341-356.
11. Lau, K. S., Partridge, E. A., Grigorian, A., Silvescu, C. I., Reinhold, V. N., Demetriou, M., and Dennis, J. W. (2007). Complex N-glycan number and degree of branching cooperate to regulate cell proliferation and differentiation. Cell 129, 123-134.

12. Mascola, J. R., and Haynes, B. F. (2013). HIV-1 neutralizing antibodies: understanding nature's pathways. Immunol Rev 254, 225-244.

13. Mazal, D., Lo-Man, R., Bay, S., Pritsch, O., Deriaud, E., Ganneau, C., Medeiros, A., Ubillos, L., Obal, G., Berois, N., et al. (2013). Monoclonal antibodies toward different Tn-amino acid backbones display distinct recognition patterns on human cancer cells. Implications for effective immuno-targeting of cancer. Cancer Immunol Immunother 62, 1107-1122.

14. Nakada, H., Inoue, M., Numata, Y., Tanaka, N., Funakoshi, I., Fukui, S., Mellors, A., and Yamashina, I. (1993). Epitopic structure of Tn glycophorin-a for an anti-Tn antibody (Mls-128). Proc Natl Acad Sci USA 90, 2495-2499.

15. Osinaga, E., Bay, S., Tello, D., Babino, A., Pritsch, O., Assemat, K., Cantacuzene, D., Nakada, H., and Alzari, P. (2000). Analysis of the fine specificity of Tn-binding proteins using synthetic glycopeptide epitopes and a biosensor based on surface plasmon resonance spectroscopy. FEBS Lett 469, 24-28.

16. Partridge, E. A., Le Roy, C., Di Guglielmo, G. M., Pawling, J., Cheung, P., Granovsky, M., Nabi, I. R., Wrana, J. L., and Dennis, J. W. (2004). Regulation of cytokine receptors by Golgi N-glycan processing and endocytosis. Science 306, 120-124.

17. Rao, T. D., Rosales, N., and Spriggs, D. R. (2011). Dual-fluorescence isogenic high-content screening for MUC16/CA125 selective agents. Mol Cancer Ther 10, 1939-1948.

18. Rao, T. D., Tian, H., Ma, X., Yan, X., Thapi, S., Schultz, N., Rosales, N., Monette, S., Wang, A., Hyman, D. M., et al. (2015). Expression of the carboxy-terminal portion of MUC16/CA125 induces transformation and tumor invasion. PLoS One 10, e0126633.

19. Strausberg, R. L., Feingold, E. A., Grouse, L. H., Derge, J. G., Klausner, R. D., Collins, F. S., Wagner, L., Shenmen, C. M., Schuler, G. D., Altschul, S. F., et al. (2002). Generation and initial analysis of more than 15,000 full-length human and mouse cDNA sequences. Proc Natl Acad Sci USA 99, 16899-16903.

20. Wang, P., Aussedat, B., Vohra, Y., and Danishefsky, S. J. (2012). An advance in the chemical synthesis of homogeneous N-linked glycopolypeptides by convergent aspartylation. Angew Chem Int Edit 51, 11571-11575.

21. Yin, B. W., Dnistrian, A., and Lloyd, K. O. (2002). Ovarian cancer antigen CA125 is encoded by the MUC16 mucin gene. Int J Cancer 98, 737-740.

22. Yin, B. W., and Lloyd, K. O. (2001). Molecular cloning of the CA125 ovarian cancer antigen: identification as a new mucin, MUC16. J Biol Chem 276, 27371-27375.

6.4 Example 4: Supplemental Chemistry Information

This example provides (a) a more detailed description of certain of the methods used and experiments described in Examples 2 and 3 (Sections 6.2 and 6.3); and (b) additional information as compared to Examples 2 and 3 (Sections 6.2 and 6.3).

6.4.1 General Materials and Methods

All commercially available materials (Aldrich, Fluka, Novabiochem) were used without further purification. N-α-Fmoc protected amino acids, pseudoproline dipeptides, Oxyma Pure and NovaSyn TG Sieber resin were purchased from Novabiochem. 1-[Bis(dimethylamino)methylene]-1H-1,2,3-triazolo[4,5-b]pyridinium 3-oxid hexafluorophosphate (HATU) was purchased from Genscript. (7-Azabenzotriazol-1-yloxy)tripyrrolidinophosphonium hexafluorophosphate (PyAOP) was purchased from Oakwood Products, Inc. Chitobiose octaacetate was purchased from Carbosynth Limited. TCEP solution (0.5 M, neutral pH) and heterobifunctional linker sulfo-GMBS was purchased from Pierce, ThermoScientific. All other reagents, including Keyhole Limpet Hemocyanin (KLH) were purchased from Aldrich. All solvents were reagent grade or HPLC grade (Fisher Scientific). Anhydrous tetrahydrofuran, diethyl ether, dichloromethane, toluene, and benzene were obtained from a dry solvent system (passed through column of neutral alumina under an argon atmosphere) and used without further drying.

Reactions were performed under an atmosphere of pre-purified dry argon. Air- and moisture-sensitive liquids and solutions were transferred via syringe. The appropriate carbohydrate reagents were dried via azeotropic removal of water with toluene. Molecular sieves were activated at 350° C. and were crushed immediately prior to use, then flame-dried under vacuum. Organic solutions were concentrated under reduced pressure by rotary evaporation below 30° C. NMR spectra ($^1H$ and $^{13}C$) were recorded on a Bruker Advance DRX-600 MHz spectrometer, and referenced to TMS or residual solvent. Low-resolution mass spectral analyses were performed with a JOEL JMS-DX-303-HF mass spectrometer or Waters Micromass ZQ mass spectrometer. Analytical TLC was performed on E. Merck silica gel 60 F254 plates and visualized under UV light (254 nm) or by staining with cerium ammonium molybdenate (CAM) or 5% sulfuric acid in methanol. Silica flash column chromatography was performed on E. Merck 230-400 mesh silica gel 60.

6.4.1.1 UPLC/LC-MS Analyses and RP-HPLC Purification.

All reverse-phase chromatographic separations involved a mobile phase consisting of 0.05% trifluoroacetic acid (TFA) (v/v) in water and 0.04% TFA in acetonitrile. Reaction progress was monitored by UPLC-MS analysis on a Waters Acquity™ Ultra Preformance Liquid Chromatography system with a photodiode detector and single quadrupole mass detector, equipped with Acquity UPLC BEH C18/C8/C4 columns (1.7 μm, 2.1×100 mm), at a flow rate of 0.3 mL/min. Analytical LC-MS analyses were performed on a Waters 2695 Separations Module equipped with a Waters 2996 Photodiode Array Detector, using a Varian Microsorb C18 column (150×2.0 mm), a Varian Microsorb C8/C4 column (250×2.0 mm) or a Waters X-Bridge C18 column (150×2.1 mm), at a flow rate of 0.2 mL/min. Preparative scale HPLC purification was carried out on a Ranin HPLC solvent delivery system equipped with a Rainin UV-1 detector, using an Agilent Dynamax reverse phase HPLC Microsorb C18/C8/C4 column (250×21.4 mm), or a Waters X-Bridge C18 column (150×19.0 mm), at a flow rate of 16.0 mL/min.

6.4.2 Experimental Procedures

6.4.2.1 Fmoc-Based Solid Phase Peptide Synthesis (SPPS)

Automated peptide synthesis was performed on a CEM Liberty Microwave Peptide Synthesizer. Peptides were synthesized under standard Fmoc protocols on NovaSyn TG Sieber resin. The deblock mixture consisted of a solution of Oxyma Pure (0.1 M) in 20% piperidine/DMF. The following Fmoc amino acids from Novabiochem were used: Fmoc-Ala-OH, Fmoc-Arg(Pbf)-OH, Fmoc-Asn(Dmcp)-OH, Fmoc-Asp(OMpe)-OH, Fmoc-Asp(OPp)-OH, Fmoc-Asp(OAllyl)-OH, Fmoc-Cys(Trt)-OH, Fmoc-Gln(Dmcp)-OH, Fmoc-Glu(OtBu)-OH, Fmoc-Gly-OH, Fmoc-Ile-OH, Fmoc-Leu-OH, Fmoc-Met-OH, Fmoc-Phe-OH, Fmoc-Pro-OH, Fmoc-Ser(OtBu)-OH, Fmoc-Thr(OtBu)-OH, Fmoc-Tyr (OtBu)-OH, Fmoc-Val-OH. The following Dmb (2,4-dimethoxybenzyl) and pseudoproline dipeptides (Novabiochem) were used: Fmoc-Asp(OtBu)-(Dmb)Gly-OH, Fmoc-Gly-Thr($\psi^{Me,Me}$Pro)-OH, Fmoc-Phe-Thr($\psi^{Me,Me}$Pro)-OH, Fmoc-Ser(tBu)-Ser($\psi^{Me,Me}$Pro)-OH.

6.4.2.2 N-Terminal Acetylation of the Peptide-Resin

Upon completion of automated synthesis on a 0.1 mmol scale, the peptide-resin was washed with DMF (2 mL) into a peptide synthesis vessel, and treated with acetic anhydride (188 μL, 2 mmol) and DIEA (384 μL, 2.2 mmol) in DMF (2 mL). The mixture was shaken by mild nitrogen bubbling for 1 hour, and then washed with DMF and $CH_2Cl_2$, before being subjected to deallylation.

6.4.2.3 On-Resin Deallylation of Aspartic Acid Side Chain, Asp(OAllyl)

The N-acetylated resin-bound peptide (0.1 mol) was treated with $Pd(PPh_3)_4$ (7.5 mg, 6.5 μmol) and phenylsilane (75 μL, 0.6 mmol) in $DMF/CH_2Cl_2$ (4 mL, 1:1). After 20 minutes of mild nitrogen bubbling, the $Pd(PPh_3)_4$/phenylsilane treatment was repeated twice. The peptide-resin was then washed with DMF, $CH_2Cl_2$ and methanol, and dried under vacuum.

6.4.2.4 Cleavage from Resin [and Simultaneous Asp(O-2-Ph$^i$Pr) Side-Chain Deprotection, where Applicable]

After drying, the peptide-resin was subjected to a cleavage cocktail (1% TFA/CH$_2$Cl2, 4 mL) 5 cycles×5 min, and this process was repeated four times. Additional cleavage sequences included treatment with 1.5% TFA/CH$_2$Cl2 (4 mL 5 cycles×5 min), and 2% $TFA/CH_2Cl_2$ (4 mL 5 cycles×5 min). The respective portions of cleavage solution were individually pooled into ice-cold $Et_2O$ and concentrated. The corresponding oily residues were resuspended in a minimum amount of trifluoroethanol and precipitated with water. The resulting mixtures were immediately lyophilized to give the crude protected peptides bearing a C-terminal amide.

6.4.2.5 Coupling of Partially Protected Full-Length Peptide (55-Mer) with Glycan Amine Via Lansbury Aspartylation Followed by Removal of Acid-Labile Protecting Groups with Cocktail R Partially protected full-length peptide (1.0 equiv) and glycan amine (chitobiose: 4.0 equiv; Man$_3$GlcNAc2 1.6 equiv) were combined and dissolved in anhydrous DMSO. To this mixture, a freshly prepared solution of PyAOP (4.0 equiv) in DMSO was added, followed by DIEA (6.0 equiv). The reaction mixture was stirred for 3 hours, and quenched by addition of 1 mL of ice-cold water (0.05% TFA). The precipitate formed was isolated by centrifugation, resuspended in water/$CH_3CN$ (1:1, 0.05% TFA) and immediately lyophilized.

The protected glycopeptide was then subjected to global acid deprotection by treatment with cocktail R (90% TFA, 5% thioanisol, 3% ethanedithiol, 2% anisol) (1 mL) for 2 hours. The residue was precipitated with ice-cold $Et_2O$ (12 mL), and the resulting suspension was centrifuged to give a white pellet. The supernant was decanted and the pellet was triturated with ice-cold diethyl ether (12 mL). This process was repeated three times in total, and the resulting precipitate was solubilized in water/$CH_3CN$ (1:1, 0.05% TFA) and lyophilized. The corresponding crude glycopeptide was purified by RP-HPLC.

6.4.2.6 Coupling of Partially Protected Small-Sized Peptides (15- and 18-Mers) with Chitobiose Amine Via Lansbury/Double Lansbury Aspartylation Followed by Removal of Acid-Labile Protecting Groups Partially protected peptide (1.0 equiv) and chitobiose amine (3.0 equiv/7.0 equiv for the double Lansbury aspartylation) were combined and dissolved in anhydrous DMSO. To this mixture, a freshly prepared solution of PyAOP (4 equiv/6 equiv in the latter case) in DMSO was added, followed by DIEA (6 equiv/8 equiv, respectively). The reaction mixture was stirred for 2.5 hours, and quenched by addition of 1 mL of ice-cold water (0.05% TFA). The precipitate formed was isolated by centrifugation, resuspended in water/$CH_3CN$ (1:1, 0.05% TFA) and immediately lyophilized.

The protected glycopeptide was then subjected to global acid deprotection by treatment with a TFA cocktail (94% TFA, 2.5% $H_2O$, 2.5% EDT, 1% TIPSH) (1 mL) for 2 hours. The residue was precipitated with ice-cold $Et_2O$ (12 mL), and the suspension was centrifuged to give a white pellet. The supernant was decanted and the pellet was triturated with ice-cold diethyl ether (12 mL). This process was repeated three times in total, and the resulting precipitate was dissolved in water/$CH_3CN$ (1:1, 0.05% TFA) and lyophilized. The corresponding crude glycopeptide was purified by RP-HPLC.

6.4.2.7 KLH-Conjugation of 15/18-mer Glycopeptides

KLH was first incubated with the heterobifunctional crosslinker sulfo-GMBS) in pH 7 phosphate buffer saline (PBS) for 2 hours. The unconjugated crosslinker was removed by size exclusion chromatography (passage over Bio-Gel P-10 fine column, respectively) and maleimide-activated KLH was then obtained. The freshly deprotected (glyco)peptides bearing a terminal thiol functionality were mixed with maleimide-containing KLH in pH 7 PBS and incubated at room temperature for 6 hours. After this time, unreacted (glyco)peptide was removed using an Amicon Ultra-4 centrifugal filter (50 000 molecular weight cut off). Finally, the corresponding KLH conjugates were obtained as a PBS solution.

6.4.3 Synthesis of Full-Length MUC16 Glycopeptides (55-Mers)

6.4.3.1 Synthesis of Chitobiose-Bearing, Full-Length Glycopeptide

Upon completion of the automated synthesis according to the methods of Section 6.4.2.1, the peptide-resin was subjected to N-acetylation and deallylation (see Section 6.4.2.2 and Section 6.4.2.3, respectively) to provide after cleavage from the resin (see Section 6.4.2.4) the partially protected peptide p55-mer[N1-S55] bearing the free carboxylic acid at Asp30 side chain. A fraction of this crude peptide was purified by silica gel column chromatography eluting with 5→12% $MeOH/CH_2Cl_2$ to give peptide p55-mer[N1-S55] (70 mg) as a white solid upon lyophilization. FIG. 27A depicts the side-chain protected N-acetylated 55-mer peptide amide. FIG. 27B depicts the ESI-MS and UV traces from UPLC analysis for glycopeptide p55-mer[N1-S55].

According to Section 6.4.2.6, peptide p55-mer[N1-S55] (20 mg, 2.0 μmol) and chitobiose (GlcNAc$_2$) anomeric amine (3.5 mg, 8.1 μmol) were combined and dissolved in anhydrous DMSO (100 μL). A solution of PyAOP (4.3 mg, 8.1 μmol) in DMSO (30 μL) was then added, followed by DIEA (2.0 μL, 12.2 μmol). The golden-yellow mixture was stirred for 3 hours, quenched by addition of 1 mL of ice-cold water (0.05% TFA), frozen and lyophilized.

The protected glycopeptide was then subjected to cocktail R (1.0 mL) for 2 hours, precipitated with ice-cold $Et_2O$, centrifuged, resuspended, and lyophilized as described in Section 6.4.2.6. The crude peptide was dissolved in 25% acetonitrile/water (0.05% TFA) (2 mL) and purified by HPLC on a X-Bridge C18 column, using a linear gradient of 25-35% acetonitrile in water (0.05% TFA) over 30 minutes. The fractions containing the desired product, which eluted at 20 minutes, were collected and lyophilized to provide glycopeptide “55-mer(chitobiose)[N1-S55]” ($GlcNAc_2$-55-mer) (3.0 mg, 22% yield) as a white solid (FIG. 28A). FIG. 28B provides the ESI-MS and UV traces from UPLC analysis for glycopeptide “55 mer(chitobiose) [N1-S55]” ($GlcNAc_2$-55-mer).

6.4.3.2 Synthesis of Pentasaccharide-Bearing, Full-Length Glycopeptide

According to Section 6.4.2.6, peptide p55-mer[N1-S55] (10 mg, 1.0 μmol) and pentasaccharide $Man_3GlcNAc_2$ anomeric amine (1.5 mg, 1.6 μmol) were combined and dissolved in anhydrous DMSO (30 μL). A solution of PyAOP (2.1 mg, 4.1 μmol) in DMSO (5 μL) was then added, followed by DIEA (1.0 μL, 6.1 μmol). The golden-yellow mixture was stirred for 3 hours, quenched by addition of 1 mL of ice-cold water (0.05% TFA), frozen and lyophilized.

The protected glycopeptide was then subjected to cocktail R (1.0 mL) for 2 hours, precipitated with ice-cold $Et_2O$, centrifuged, resuspended, and lyophilized as described in Section 6.4.2.6. The crude peptide was dissolved in 25% acetonitrile/water (0.05% TFA) (2 mL) and purified by HPLC on a X-Bridge C18 column, using a linear gradient of 25-35% acetonitrile in water (0.05% TFA) over 30 minutes. The fractions containing the desired product, which eluted at 18 minutes, were collected and lyophilized to provide glycopeptide “55-mer($Man_3GlcNAc_2$)[N1-S55]” ($Man_3GlcNAc_2$-55-mer) (1.5 mg, 20% yield) as a white solid. FIG. 29A depicts Man3GlcNAc2-bearing 55-mer glycopeptide: “55-mer($Man_3GlcNAc_2$)[N1-S55]” ($Man_3GlcNAc_2$-55-mer). FIG. 29B depicts the ESI-MS and UV traces from analytical HPLC analysis for glycopeptide “55 mer($Man_3GlcNAc_2$)[N1-S55]” ($Man_3GlcNAc_2$-55-mer).

6.4.4 Synthesis of Smaller-Sized Glycopeptides (15-mer and 18-mer)

6.4.4.1 Synthesis of Chitobiose-Monoglycosylated 15-Mer

Upon completion of the automated synthesis according to Section 6.4.2.1, the peptide-resin was subjected to N-acetylation and deallylation (see Section 6.4.2.2 and Section 6.4.2.3, respectively) to provide after cleavage from the resin (see Section 6.4.2.4) the partially protected peptide p15-mer[C-G25-V38] bearing the free carboxylic acid at Asp30 (corresponding to Asn1806 of SEQ ID NO: 150) side chain. FIG. 30A. This peptide was used in the next step without further purification.

Peptide p15-mer[C-G25-V38] (10 mg, 3.8 μmol) and chitobiose ($GlcNAc_2$) anomeric amine (4.8 mg, 11.3 μmol) were combined and dissolved in anhydrous DMSO (80 μL). A solution of PyAOP (5.9 mg, 11.3 μmol) in DMSO (20 μL) was added, followed by DIEA (2.6 μL, 15 μmol), and the golden-yellow mixture was stirred for 2.5 hours, frozen and lyophilized. The protected glycopeptide was then subjected to a TFA cocktail (1 mL) for 2 hours, precipitated with ice-cold diethyl ether, centrifuged, resuspended, and lyophilized according to Section 6.4.2.6. The crude peptide was dissolved in 15% acetonitrile/water (0.05% TFA) (2 mL) and purified by HPLC on a C18 column, using a linear gradient of 15-35% acetonitrile in water (0.05% TFA) over 30 minutes. The fractions containing the desired product, which eluted at 17 minutes, were collected and lyophilized to provide glycopeptide “15-mer(chitobiose)[C-G25-V38]” (GlcNAc2-15-mer) (2.0 mg, 25% yield) as a white solid. See FIG. 30B for chitobiose-monoglycosylated 15-mer glycopeptide: 15-mer(chitobiose)[C-G25-V38] ($GlcNAc_2$-15-mer). FIG. 30C depicts the ESI-MS and UV traces from analytical HPLC analysis for glycopeptide “15 mer(chitobiose)[C-G25-V38]” ($GlcNAc_2$-15-mer).

6.4.4.2 Synthesis of Chitobiose-Bisglycosylated 18-mer

Upon completion of the automated synthesis according to Section 6.4.2.1, the peptide-resin was subjected to N-acetylation (see 6.4.2.2). Then, cleavage from the resin and concomitant removal of the OPp protecting groups was effected following the methods set forth in Section 6.4.2.4 to afford the partially protected peptide p18-mer[C-T22-V38] bearing the free carboxylic acid at both Asp24 and Asp30 side chains (corresponding to Asn1800 and Asn1806, respectively, of SEQ ID NO: 150). This peptide was used in the next step without further purification. See FIG. 32A.

Peptide p18-mer[C-T22-V38] (30 mg, 9.1 μmol) and chitobiose (GlcNAc2) anomeric amine (27 mg, 63.4 μmol) were combined and dissolved in anhydrous DMSO (150 μL). PyAOP (28.5 mg, 54.6 μmol) was then added in DMSO (50 μL) followed by DIEA (2.6 μL, 15 μmol), and the golden-yellow mixture was stirred for 2.5 hours, frozen and lyophilized. The protected glycopeptide was then subjected to a TFA cocktail (1 mL) for 2 hours, precipitated with ice-cold diethyl ether, centrifuged, resuspended, and lyophilized according to Section 6.4.2.6. The crude peptide was dissolved in 15% acetonitrile/water (0.05% TFA) (6 mL) and purified by HPLC on a C8 column, using a linear gradient of 15-27% acetonitrile in water (0.05% TFA) over 30 minutes. The fractions containing the desired product, which eluted at 15 minutes, were collected and lyophilized to provide glycopeptide “18-mer$(chitobiose)_2$[C-T22-V38]” [$(GlcNAc_2)_2$-18-mer] (6.5 mg, 25% yield) as a white solid. See FIG. 32B. FIG. 32C depicts ESI-MS and UV traces from analytical HPLC analysis for glycopeptide “18 mer$(chitobiose)_2$[C-T22-V38]” [$(GlcNAc_2)_2$-18-mer].

6.5 KLH-Conjugation of 15-mer and 18-mer MUC16 Glycopeptides

Glycopeptides “15-mer(chitobiose)[C-G25-V38]” and “18-mer$(chitobiose)_2$[C-T22-V38]” were conjugated to KLH following the procedure set forth in Section 6.4.2.7 to afford the corresponding KLH conjugates, $GlcNAc_2$-15-mer-KLH and $(GlcNAc_2)_2$-18-mer-KLH, respectively. See FIG. 33A and FIG. 33B.

7. TABLE OF SEQUENCES

TABLE 13

Table of Sequences.

| SEQ ID NO | NAME | SEQ |
|---|---|---|
| 1 | 10C6 VH | QVTLKESGPGILQPSQTLSLTCSFSGFSLNTLGMGVGWIRQPSG KGLEWLAHIWWDDDKYYNPALKSRLTISKDSSKNQVFLKIAN VDTADIATYYCSRIGTAQATDALDYWGQGTSVTVSS |

TABLE 13-continued

Table of Sequences.

| SEQ ID NO | NAME | SEQ |
|---|---|---|
| 2 | 10C6 VL | DIVLTQSPASLAVSLGQRATISYRASKSVSTSGYSYMEIWNQQK PGQPPRLLIYLVSNLESGVPARFSGSGSGTDFTLNIHPVEEEDA ATYYCQHIRELTRSEGGPSWKN |
| 3 | 10C6 HCDR1 (KABAT) | TLGMGVG |
| 4 | 10C6 HCDR2 (KABAT) | HIWWDDDKYYNPALKS |
| 5 | 10C6 HCDR3 (KABAT) | IGTAQATDALDY |
| 6 | 10C6 LCDR1 (KABAT) | RASKSVSTSGYSYMEI |
| 7 | 10C6 LCDR2 (KABAT) | LVSNLES |
| 8 | 10C6 LCDR3 (KABAT) | QHIRELTRS |
| 9 | 10C6 HCDR1 (CHOTHIA) | GFSLNTLGM |
| 10 | 10C6 HCDR2 (CHOTHIA) | WDD |
| 11 | 10C6 HCDR3 (CHOTHIA) | GTAQATDALD |
| 12 | 10C6 LCDR1 (CHOTHIA) | SKSVSTSGYSY |
| 13 | 10C6 LCDR2 (CHOTHIA) | LVS |
| 14 | 10C6 LCDR3 (CHOTHIA) | IRELTR |
| 15 | 10C6 HCDR1 (IMGT) | GFSLNTLGMG |
| 16 | 10C6 HCDR2 (IMGT) | IWWDDDK |
| 17 | 10C6 HCDR3 (IMGT) | SRIGTAQATDALDY |
| 18 | 10C6 LCDR1 (IMGT) | KSVSTSGYSY |
| 19 | 10C6 LCDR2 (IMGT) | LVS |
| 20 | 10C6 LCDR3 (IMGT) | QHIRELTRS |
| 21 | 7B12 VH | QVTLKESGPGILQPSQTLSLTCSFSGFSLSTVGMGVGWSRQPSG KGLEWLAHIWWDDEDKYYNPALKSRLTISKDTSKNQVFLKIA NVDTADSATYYCTRIGTAQATDALDYWGQGTSVTVSS |
| 22 | 7B12 VL | DIVMTQAAPSVSVTPGESVSISCRSSKSLRKSNGNTYLYWFLQ RPGQSPQRLIYYMSNLASGVPDRFSGRGSGTDFTLRISRVEAED VGVYYCMQSLEYPLTFGGGTKLKIK |
| 23 | 7B12 HCDR1 (KABAT) | TVGMGVG |
| 24 | 7B12 HCDR2 (KABAT) | HIWWDDEDKYYNPALKS |

TABLE 13-continued

Table of Sequences.

| SEQ ID NO | NAME | SEQ |
|---|---|---|
| 25 | 7B12 HCDR3 (KABAT) | IGTAQATDALDY |
| 26 | 7B12 LCDR1 (KABAT) | RSSKSLRKSNGNTYLY |
| 27 | 7B12 LCDR2 (KABAT) | YMSNLAS |
| 28 | 7B12 LCDR3 (KABAT) | MQSLEYPLT |
| 29 | 7B12 HCDR1 (CHOTHIA) | GFSLSTVGM |
| 30 | 7B12 HCDR2 (CHOTHIA) | WDDE |
| 31 | 7B12 HCDR3 (CHOTHIA) | GTAQATDALD |
| 32 | 7B12 LCDR1 (CHOTHIA) | SKSLRKSNGNTY |
| 33 | 7B12 LCDR2 (CHOTHIA) | YMS |
| 34 | 7B12 LCDR3 (CHOTHIA) | SLEYPL |
| 35 | 7B12 HCDR1 (IMGT) | GFSLSTVGMG |
| 36 | 7B12 HCDR2 (IMGT) | IWWDDEDK |
| 37 | 7B12 HCDR3 (IMGT) | TRIGTAQATDALDY |
| 38 | 7B12 LCDR1 (IMGT) | KSLRKSNGNTY |
| 39 | 7B12 LCDR2 (IMGT) | YMS |
| 40 | 7B12 LCDR3 (IMGT) | MQSLEYPLT |
| 41 | 19C11 VH | QVNLKESGPGKLQPSQTLSLTCSFSGFSLSTLGMGVGWIRQSS GKGLEWLAHIWWDDDKYYNPALKSRLTISRATSKNQVFLKIV NVGTADTATYYCARIGTAQATDALDYWGQGTSVTVSS |
| 42 | 19C11 VL | DIVMTQAAPSIPVTPGESVSISCRSSKSLLHSNGNTYLYWFLQR PGQSPQRLIYYMSNLASGVPDRFSGRGSGTDFTLKISRVEAGD VGVYYCMQGLEHPLTFGGGTKLEIK |
| 43 | 19C11 HCDR1 (KABAT) | TLGMGVG |
| 44 | 19C11 HCDR2 (KABAT) | HIWWDDDKYYNPALKS |
| 45 | 19C11 HCDR3 (KABAT) | IGTAQATDALDY |
| 46 | 19C11 LCDR1 (KABAT) | RSSKSLLHSNGNTYLY |
| 47 | 19C11 LCDR2 (KABAT) | YMSNLAS |
| 48 | 19C11 LCDR3 (KABAT) | MQGLEHPLT |

TABLE 13-continued

Table of Sequences.

| SEQ ID NO | NAME | SEQ |
|---|---|---|
| 49 | 19C11 HCDR1 (CHOTHIA) | GFSLSTLGM |
| 50 | 19C11 HCDR2 (CHOTHIA) | WDD |
| 51 | 19C 11 HCDR3 (CHOTHIA) | GTAQATDALD |
| 52 | 19C11 LCDR1 (CHOTHIA) | SKSLLHSNGNTY |
| 53 | 19C11 LCDR2 (CHOTHIA) | YMS |
| 54 | 19C11 LCDR3 (CHOTHIA) | GLEHPL |
| 55 | 19C11 HCDR1 (IMGT) | GFSLSTLGMG |
| 56 | 19C11 HCDR2 (IMGT) | IWWDDDK |
| 57 | 19C11 HCDR3 (IMGT) | ARIGTAQATDALDY |
| 58 | 19C11 LCDR1 (IMGT) | KSLLHSNGNTY |
| 59 | 19C11 LCDR2 (IMGT) | YMS |
| 60 | 19C11 LCDR3 (IMGT) | MQGLEHPLT |
| 61 | 16C5 VH | QVTLKESGPGILQPSQTLSLTCSFSGFSLNTLGMGVGWIRQPSG KGLEWLAHIWWDDDKYYYPALKSRLTISRDTSKNQVFLKIAN VDTADTATYYCARIGTAQATDALDYWGQGTSVTVSS |
| 62 | 16C5 VL | ELDMTQTPPSLSASVGETVRIRCLASEDIYSGISWYQQKPGKPP TLLIYGASNLESGVPPRFSGSGSGTDYTLTIGGVQAEDAATYYC LGGYSYSSTLTFGAGTNVEIK |
| 63 | 16C5 HCDR1 (KABAT) | TLGMGVG |
| 64 | 16C5 HCDR2 (KABAT) | HIWWDDDKYYYPALKS |
| 65 | 16C5 HCDR3 (KABAT) | IGTAQATDALDY |
| 66 | 16C5 LCDR1 (KABAT) | LASEDIYSGIS |
| 67 | 16C5 LCDR2 (KABAT) | GASNLES |
| 68 | 16C5 LCDR3 (KABAT) | LGGYSYSSTLT |
| 69 | 16C5 HCDR1 (CHOTHIA) | GFSLNTLGM |
| 70 | 16C5 HCDR2 (CHOTHIA) | WDD |
| 71 | 16C5 HCDR3 (CHOTHIA) | GTAQATDALD |
| 72 | 16C5 LCDR1 (CHOTHIA) | SEDIYSG |

TABLE 13-continued

Table of Sequences.

| SEQ ID NO | NAME | SEQ |
|---|---|---|
| 73 | 16C5 LCDR2 (CHOTHIA) | GAS |
| 74 | 16C5 LCDR3 (CHOTHIA) | GYSYSSTL |
| 75 | 16C5 HCDR1 (IMGT) | GFSLNTLGMG |
| 76 | 16C5 HCDR2 (IMGT) | IWWDDDK |
| 77 | 16C5 HCDR3 (IMGT) | ARIGTAQATDALDY |
| 78 | 16C5 LCDR1 (IMGT) | EDIYSG |
| 79 | 16C5 LCDR2 (IMGT) | GAS |
| 80 | 16C5 LCDR3 (IMGT) | LGGYSYSSTLT |
| 81 | 18C6 VH | QVTLKESGPGILQPSQTLSLTCSFSGFSLSTVGMGVGWSRQPSG KGLEWLAHIWWDDEDKYYNPALKSRLTISKDTSKNQVFLKIA NVDTADTATYYCTRIGTAQATDALDYWGQGTSVTVSS |
| 82 | 18C6 VL | DIVMTQAAPSVPVTPGESVSISCRSSKSLLHSNGNTYLYWFLQR PGQSPQRLIYYMSNLASGVPDRFSGRGSGTDFTLRISRVEAEDV GVYYCMQSLEYPLTFGGGTKLEIK |
| 83 | 18C6 HCDR1 (KABAT) | TVGMGVG |
| 84 | 18C6 HCDR2 (KABAT) | HIWWDDEDKYYNPALKS |
| 85 | 18C6 HCDR3 (KABAT) | IGTAQATDALDY |
| 86 | 18C6 LCDR1 (KABAT) | RSSKSLLHSNGNTYLY |
| 87 | 18C6 LCDR2 (KABAT) | YMSNLAS |
| 88 | 18C6 LCDR3 (KABAT) | MQSLEYPLT |
| 89 | 18C6 HCDR1 (CHOTHIA) | GFSLSTVGM |
| 90 | 18C6 HCDR2 (CHOTHIA) | WDDE |
| 91 | 18C6 HCDR3 (CHOTHIA) | GTAQATDALD |
| 92 | 18C6 LCDR1 (CHOTHIA) | SKSLLHSNGNTY |
| 93 | 18C6 LCDR2 (CHOTHIA) | YMS |
| 94 | 18C6 LCDR3 (CHOTHIA) | SLEYPL |
| 95 | 18C6 HCDR1 (IMGT) | GFSLSTVGMG |
| 96 | 18C6 HCDR2 (IMGT) | IWWDDEDK |

TABLE 13-continued

Table of Sequences.

| SEQ ID NO | NAME | SEQ |
|---|---|---|
| 97 | 18C6 HCDR3 (IMGT) | TRIGTAQATDALDY |
| 98 | 18C6 LCDR1 (IMGT) | KSLLHSNGNTY |
| 99 | 18C6 LCDR2 (IMGT) | YMS |
| 100 | 18C6 LCDR3 (IMGT) | MQSLEYPLT |
| 101 | 1006-18C6 VH consensus | QVX$_{21}$LKESGPGX$_{22}$LQPSQTLSLTCSFSGFSLX$_{23}$TX$_{24}$GMGVGW X$_{25}$RQX$_{26}$SGKGLEWLAHIWWDDX$_{27}$DKYYX$_{28}$PALKSRLTISX$_{29}$ X$_{30}$X$_{31}$SKNQVFLKIX$_{32}$NVX$_{33}$TADX$_{34}$ATYYCX$_{35}$RIGTAQATDAL DYWGQGTSVTVSS<br>Wherein X$_{21}$ is T or N, X$_{22}$ is I or K, X$_{23}$ is N or S, X$_{24}$ is V or L, X$_{25}$ is S or I, X$_{26}$ is P or S, X$_{27}$ is E or absent, X$_{28}$ is N or Y, X$_{29}$ is K or R, X$_{30}$ is A or D, X$_{31}$ is T or S, X$_{32}$ is V or A, X$_{33}$ is G or D, X$_{34}$ is T, I, or S, and X$_{35}$ is T, S, or A |
| 102 | 7B12, 19C11, 18C6 VL consensus | DIVMTQAAPSX$_{36}$X$_{37}$VTPGESVSISCRSSKSLX$_{38}$X$_{39}$SNGNTYLY WFLQRPGQSPQRLIYYMSNLASGVPDRFSGRGSGTDFTLX$_{40}$IS RVEAX$_{41}$DVGVYYCMQX$_{42}$LEX$_{43}$PLTFGGGTKLEIK<br>Wherein X$_{36}$ is I or V, X$_{37}$ is P or S, X$_{38}$ is R or L, X$_{39}$ is K or H, X$_{40}$ is R or K, X$_{41}$ is E or G, X$_{42}$ 1S S or G, and X$_{43}$ is Y or H |
| 103 | HCDR1 KABAT CONSENSUS | TX$_1$GMGVG<br>Wherein X$_1$ is L or V |
| 104 | HCDR2 KABAT CONSENSUS | HIWWDDX$_2$DKYYX$_3$PALKS<br>Wherein X$_2$ is E or absent and X$_3$ is Y or N |
| 105 | HCDR3 KABAT CONSENSUS | IGTAQATDALDY |
| 106 | 7B12, 19C11, 18C6 LCDR1 KABAT CONSENSUS | RSSKSLX$_4$X$_5$SNGNTYLY<br>Wherein X$_4$ is R or L, and X$_5$ is K or H |
| 107 | 7B12, 19C11, 18C6 LCDR2 KABAT CONSENSUS | YMSNLAS |
| 108 | 7B12, 19C11, 18C6 LCDR3 KABAT CONSENSUS | MQX$_6$LEX$_7$PLT<br>Wherein X$_6$ is G or S and X$_7$ is H or Y |
| 109 | 10C6-18C6 HCDR1 CHOTHIA CONSENSUS | GFSLX$_8$TX$_9$GM<br>Wherein X$_8$ is N or S, and X$_9$ is L or V |
| 110 | 10C6-18C6 HCDR2 CHOTHIA CONSENSUS | WDDX$_{10}$<br>Wherein X$_{10}$ is E or absent |
| 111 | 10C6-18C6 HCDR3 CHOTHIA CONSENSUS | GTAQATDALD |

TABLE 13-continued

| Table of Sequences. | | |
|---|---|---|
| SEQ ID NO | NAME | SEQ |
| 112 | 7B12, 19C11, 18C6 LCDR1 CHOTHIA CONSENSUS | SKSL$X_{11}X_{12}$SNGNTY<br>Wherein $X_{11}$ is L or R, and $X_{12}$ is H or K |
| 113 | 7B12, 19C11, 18C6 LCDR2 CHOTHIA CONSENSUS | YMS |
| 114 | 7B12, 19C11, 18C6 LCDR3 CHOTHIA CONSENSUS | $X_{13}$LE$X_{14}$PL<br>Wherein $X_{13}$ is G or S, and $X_{14}$ is H or Y |
| 115 | 10C6-18C6 HCDR1 IMGT CONSENSUS | GFSL$X_{15}$T$X_{16}$GMG<br>Wherein $X_{15}$ is N or S, and $X_{16}$ is V or L |
| 116 | 10C6-18C6 HCDR2 IMGT CONSENSUS | IWWDD$X_{17}$DK<br>Wherein $X_{17}$ is E or absent |
| 117 | 10C6-18C6 HCDR3 IMGT CONSENSUS | $X_{18}$RIGTAQATDALDY<br>Wherein $X_{18}$ is T, A, or S |
| 118 | 7B12, 19C11, 18C6 LCDR1 IMGT CONSENSUS | KSL$X_{19}X_{20}$SNGNTY<br>Wherein $X_{19}$ is V or L, and $X_{20}$ is H or K |
| 119 | 7B12, 19C11, 18C6 LCDR2 IMGT CONSENSUS | YMS |
| 120 | 7B12, 19C11, 18C6 LCDR3 IMGT CONSENSUS | MQSLEYPLT |
| 121 | MUC16c114 F primer | CCATGCGATATCGCCACCATGGTGAACTTCTCGCCACTGGC<br>T |
| 122 | MUC16c114 R primer | TACGGCGGCCGCTTGCAGATCCTCCAGGTCTAGG |
| 123 | MUC16c344 F primer | CCATGCGATATCGCCACCATGGTGACAGGCCCTGGGCTGGA<br>CAGA |
| 124 | MUC16c344 R primer | TACGGCGGCCGCTTGCAGATCCTCCAGGTCTAGG |
| 125 | MUC16c57-114F primer | CCATGCGATATCAAACTTCTCGCCACTGGCT |
| 126 | MUC16c57-114 R primer | AGATCTAACCATGGGAAGGTCAGAATTCCCAGT |
| 127 | 117-244LGALS3 F primer | CCATGCGATATCACCTTATAACCTGCCTTTG |
| 128 | 117-244LGALS3 R primer | AGATCTAACCATGGTATATGAAGCACTGGT |
| 129 | 55mer immunizing peptide | NFSPLARRVDRVAIYEEFLRMTRNGTQLQNFTLDRSSVLVDGY<br>SPNRNEPLTGNS |

TABLE 13-continued

| Table of Sequences. | | |
|---|---|---|
| SEQ ID NO | NAME | SEQ |
| 130 | 18mer immunizing peptide | CTRNGTQLQNFTLDRSSV |
| 131 | 15mer immunizing peptide | CGTQLQNFTLDRSSV |
| 132 | MUC16c344 | WELSQLTHGVTQLGFYVLDRDSLFINGYAPQNLSIRGEYQINF<br>HIVNQNLSNPDPTSSEYITLLRDIQDKVTTLYKGSQLHDTFRFC<br>LVTNLTMDSVLVTVKALFSSNLDPSLVEQVFLDKTLNASFHQL<br>GSTYQLVDIHVTEMESSVYQPTSSSSTQHFYLNFTITNLPYSQD<br>KAQPGTTNYQRNKRNIEDALNQLFRNSSIKSYFSDCQVSTFRS<br>VPNRHHTGVDSLCNFSPLARRVDRVAIYEEFLRMTRNGTQLQ<br>NFTLDRSSVLVDGYSPNRNEPLTGNSDLPFWAVILIGLAGLLGL<br>ITCLICGVLVTTRRRKKEGEYNVQQQCPGYYQSHLDLEDLQ |
| 133 | MUC16c114 | NFSPLARRVDRVAIYEEFLRMTRNGTQLQNFTLDRSSVLVDGY<br>SPNRNEPLTGNSDLPFWAVILIGLAGLLGLITCLICGVLVTTRRR<br>KKEGEYNVQQQCPGYYQSHLDLEDLQ |
| 134 | MUC16c86 | NFSPLARRVDRVAIYEEFLRMDLPFWAVILIGLAGLLGLITCLIC<br>GVLVTTRRRKKEGEYNVQQQCPGYYQSHLDLEDLQ |
| 135 | MUC16c80 | NFSPLARRVDRVAIYEEFLRMTRNGTQLQNFTLDRSSVLVDGY<br>SPNRNEPLTGNSDLPFWAVILIGLAGLLGLITCLICGDLEDLQ |
| 136 | Immature Human MUC16 amino acid sequence (NP_078966.2) | MLKPSGLPGSSSPTRSLMTGSRSTKATPEMDSGLTGATLSPKTS<br>TGAIVVTEHTLPFTSPDKTLASPTSSVVGRTTQSLGVMSSALPE<br>STSRGMTHSEQRTSPSLSPQVNGTPSRNYPATSMVSGLSSPRTR<br>TSSTEGNFTKEASTYTLTVETTSGPVTEKYTVPTETSTTEGDST<br>ETPWDTRYIPVKITSPMKTFADSTASKENAPVSMTPAETTVTDS<br>HTPGRTNPSFGTLYSSFLDLSPKGTPNSRGETSLELILSTTGYPF<br>SSPEPGSAGHSRISTSAPLSSSASVLDNKISETSIFSGQSLTSPLSP<br>GVPEARASTMPNSAIPFSMTLSNAETSAERVRSTISSLGTPSIST<br>KQTAETILTFHAFAETMDIPSTHIAKTLASEWLGSPGTLGGTST<br>SALTTTSPSTTLVSEETNTHHSTSGKETEGTLNTSMTPLETSAP<br>GEESEMTATLVPTLGFTTLDSKIRSPSQVSSSHPTRELRTTGSTS<br>GRQSSSTAAHGSSDILRATTSSTSKASSWTSESTAQQFSEPQHT<br>QWVETSPSMKTERPPASTSVAAPITTSVPSVVSGFTTLKTSSTK<br>GIWLEETSADTLIGESTAGPTTHQFAVPTGISMTGGSSTRGSQG<br>TTHLLTRATASSETSADLTLATNGVPVSVSPAVSKTAAGSSPPG<br>GTKPSYTMVSSVIPETSSLQSSAFREGTSLGLTPLNTRHPFSSPE<br>PDSAGHTKISTSIPLLSSASVLEDKVSATSTFSHHKATSSITTGTP<br>EISTKTKPSSAVLSSMTLSNAATSPERVRNATSPLTHPSPSGEET<br>AGSVLTLSTSAETTDSPNIHPTGTLTSESSESPSTLSLPSVSGVKT<br>TFSSSTPSTHLFTSGEETEETSNPSVSQPETSVSRVRTTLASTSVP<br>TPVFPTMDTWPTRSAQFSSSHLVSELRATSSTSVTNSTGSALPK<br>ISHLTGTATMSQTNRDTENDSAAPQSTTWPETSPREKTGLPSAT<br>TTVSTSATSLSATVMVSKFTSPATSSMEATSIREPSTTILTTETT<br>NGPGSMAVASTNIPIGKGYITEGRLDTSHLPIGTTASSETSMDFT<br>MAKESVSMSVSPSQSMDAAGSSTPGRTSQFVDTFSDDVYHLTS<br>REITIPRDGTSSALTPQMTATHPPSPDPGSARSTWLGILSSSPSSP<br>TPKVTMSSTFSTQRVTTSMIMDTVETSRWNMPNLPSTTSLTPS<br>NIPTSGAIGKSTLVPLDTPSPATSLEASEGGLPTLSTYPESTNTPS<br>IHLGAHASSESPSTIKLTMASVVKPGSYTPLTFPSIETHIHVSTA<br>RMAYSSGSSPEMTAPGETNTGSTWDPTTYITTTDPKDTSSAQV<br>STPHSVRTLRTTENHPKTESATPAAYSGSPKISSSPNLTSPATKA<br>WTITDTTEHSTQLHYTKLAEKSSGFETQSAPGPVSVVIPTSPTIG<br>SSTLELTSDVPGEPLVLAPSEQTTITLPMATWLSTSLTEEMAST<br>DLDISSPSSPMSTFAIFPPMSTPSHELSKSEADTSAIRNTDSTTLD<br>QHLGIRSLGRTGDLTTVPITPLTTTWTSVIEHSTQAQDTLSATM<br>SPTHVTQSLKDQTSIPASASPSHLTEVYPELGTQGRSSSEATTF<br>WKPSTDTLSREIETGPTNIQSTPPMDNTTTGSSSSGVTLGIAHLP<br>IGTSSPAETSTNMALERRSSTATVSMAGTMGLLVTSAPGRSISQ<br>SLGRVSSVLSESTTEGVTDSSKGSSPRLNTQGNTALSSSLEPSY<br>AEGSQMSTSIPLTSSPTTPDVEFIGGSTFWTKEVTTVMTSDISKS<br>SARTESSSATLMSTALGSTENTGKEKLRTASMDLPSPTPSMEV<br>TPWISLTLSNAPNTTDSLDLSHGVHTSSAGTLATDRSLNTGVTR<br>ASRLENGSDTSSKSLSMGNSTHTSMTYTEKSEVSSSIHPRPETS<br>APGAETTLTSTPGNRAISLTLPFSSIPVEEVISTGITSGPDINSAPM<br>THSPITPPTIVWTSTGTIEQSTQPLHAVSSEKVSVQTQSTPYVNS<br>VAVSASPTHENSVSSGSSTSSPYSSASLESLDSTISRRNAITSWL |

TABLE 13-continued

Table of Sequences.

| SEQ ID NO | NAME | SEQ |
|---|---|---|
| | | WDLTTSLPTTTWPSTSLSEALSSGHSGVSNPSSTTTEFPLFSAAS<br>TSAAKQRNPETETHGPQNTAASTLNTDASSVTGLSETPVGASIS<br>SEVPLPMAITSRSDVSGLTSESTANPSLGTASSAGTKLTRTISLP<br>TSESLVSFRMNKDPWTVSIPLGSHPTTNTETSIPVNSAGPPGLST<br>VASDVIDTPSDGAESIPTVSFSPSPDTEVTTISHFPEKTTHSFRTIS<br>SLTHELTSRVTPIPGDWMSSAMSTKPTGASPSITLGERRTITSAA<br>PTTSPIVLTASFTETSTVSLDNETTVKTSDILDARKTNELPSDSSS<br>SSDLINTSIASSTMDVTKTASISPTSISGMTASSSPSLFSSDRPQV<br>PTSTTETNTATSPSVSSNTYSLDGGSNVGGTPSTLPPFTITHPVE<br>TSSALLAWSRPVRTFSTMVSTDTASGENPTSSNSVVTSVPAPGT<br>WTSVGSTTDLPAMGFLKTSPAGEAHSLLASTIEPATAFTPHLSA<br>AVVTGSSATSEASLLTTSESKAIHSSPQTPTTPTSGANWETSATP<br>ESLLVVTETSDTTLTSKILVTDTILFSTVSTPPSKFPSTGTLSGAS<br>FPTLLPDTPAIPLTATEPTSSLATSFDSTPLVTIASDSLGTVPETT<br>LTMSETSNGDALVLKTVSNPDRSIPGITIQGVTESPLHPSSTSPS<br>KIVAPRNTTYEGSITVALSTLPAGTTGSLVFSQSSENSETTALVD<br>SSAGLERASVMPLTTGSQGMASSGGIRSGSTHSTGTKTFSSLPL<br>TMNPGEVTAMSEITTNRLTATQSTAPKGIPVKPTSAESGLLTPV<br>SASSSPSKAFASLTTAPPTWGIPQSTLTFEFSEVPSLDTKSASLPT<br>PGQSLNTIPDSDASTASSSLSKSPEKNPRARMMTSTKAISASSFQ<br>STGFTETPEGSASPSMAGHEPRVPTSGTGDPRYASESMSYPDPS<br>KASSAMTSTSLASKLTTLFSTGQAARSGSSSSPISLSTEKETSFL<br>SPTASTSRKTSLFLGPSMARQPNILVHLQTSALTLSPTSTLNMS<br>QEEPPELTSSQTIAEEEGTTAETQTLTFTPSETPTSLLPVSSPTEP<br>TARRKSSPETWASSISVPAKTSLVETTDGTLVTTIKMSSQAAQG<br>NSTWPAPAEETGSSPAGTSPGSPEMSTTLKIMSSKEPSISPEIRST<br>VRNSPWKTPETTVPMETTVEPVTLQSTALGSGSTSISHLPTGTT<br>SPTKSPTENMLATERVSLSPSPPEAWTNLYSGTPGGTRQSLAT<br>MSSVSLESPTARSITGTGQQSSPELVSKTTGMEFSMWHGSTGG<br>TTGDTHVSLSTSSNILEDPVTSPNSVSSLTDKSKHKTETWVSTT<br>AIPSTVLNNKIMAAEQQTSRSVDEAYSSTSSWSDQTSGSDITLG<br>ASPDVTNTLYITSTAQTTSLVSLPSGDQGITSLTNPSGGKTSSAS<br>SVTSPSIGLETLRANVSAVKSDIAPTAGHLSQTSSPAEVSILDVT<br>TAPTPGISTTITTMGTNSISTTTPNPEVGMSTMDSTPATERRTTS<br>TEHPSTWSSTAASDSWTVTDMTSNLKVARSPGTISTMHTTSFL<br>ASSTELDSMSTPHGRITVIGTSLVTPSSDASAVKTETSTSERTLS<br>PSDTTASTPISTFSRVQRMSISVPDILSTSWTPSSTEAEDVPVSM<br>VSTDHASTKTDPNTPLSTFLFDSLSTLDWDTGRSLSSATATTSA<br>PQGATTPQELTLETMISPATSQLPFSIGHITSAVTPAAMARS SGV<br>TFSRPDPTSKKAEQTSTQLPTTTSAHPGQVPRSAATTLDVIPHT<br>AKTPDATFQRQGQTALTTEARATSDSWNEKEKSTPSAPWITE<br>MMNSVSEDTIKEVTSSSSVLRTLNTLDINLESGTTSSPSWKSSP<br>YERIAPSESTTDKEAIHPSTNTVETTGWVTSSEHASHSTIPAHSA<br>SSKLTSPVVTTSTREQAIVSMSTTTWPESTRARTEPNSFLTIELR<br>DVSPYMDTSSTTQTSIISSPGSTAITKGPRTEITSSKRISSSFLAQS<br>MRSSDSPSEAITRLSNFPAMTESGGMILAMQTSPPGATSLSAPT<br>LDTSATASWTGTPLATTQRFTYSEKTTLFSKGPEDTSQPSPPSV<br>EETSSSSSLVPIHATTSPSNILLTSQGHSPSSTPPVTSVFLSETSGL<br>GKTTDMSRISLEPGTSLPPNLSSTAGEALSTYEASRDTKAIHHS<br>ADTAVTNMEATSSEYSPIPGHTKPSKATSPLVTSHEVIGDITSSTS<br>VFGSSETTEIETVSSVNQGLQERSTSQVASSATETSTVITHVSSG<br>DATTHVTKTQATFSSGTSISSPHQFITSTNTFTDVSTNPSTSLEVIT<br>ESSGVTITTQTGPTGAATQGPYLLDTSTMPYLTETPLAVTPDFM<br>QSEKTTLISKGPKDVSWTSPPSVAETSYPSSLTPFLVTTIPPATST<br>LQGQHTSSPVSATSVLTSGLVKTTDMLNTSMEPVTNSPQNLNN<br>PSNEILATLAATTDIETIHPSINKAVTNMGTASSAHVLHSTLPVS<br>SEPSTATSPMVPASSMGDALASISIPGSETTDIEGEPTSSLTAGR<br>KENSTLQEMNSTTESNIILSNVSVGAITEATKMEVPSFDATFIPT<br>PAQSTKFPDIFSVASSRLSNSPPMTISTHMTTTQTGSSGATSKIP<br>LALDTSTLETSAGTPSVVTEGFAHSKITTAMNNDVKDVSQTNP<br>PFQDEASSPSSQAPVLVTTLPSSVAFTPQWHSTSSPVSMSSVLT<br>SSLVKTAGKVDTSLETVTSSPQSMSNTLDDISVTSAATTDIETT<br>HPSINTVVTNVGTTGSAFESHSTVSAYPEPSKVTSPNVTTSTME<br>DTTISRSIPKSSKTTRTETETTSSLTPKLRETSISQEITSSTETSTVP<br>YKELTGATTEVSRTDVTSSSSTSFPGPDQSTVSLDISTETNTRLS<br>TSPIMTESAEITITTQTGPHGATSQDTFTMDPSNTTPQAGIHSAM<br>THGFSQLDVTTLMSRIPQDVSWTSPPSVDKTSSPSSFLSSPAMT<br>TPSLISSTLPEDKLSSPMTSLLTSGLVKITDILRTRLEPVTSSLPNF<br>SSTSDKILATSKDSKDTKEIFPSINTEETNVKANNSGHESHSPAL<br>ADSETPKATTQMVITTTVGDPAPSTSMPVHGSSETTNIKREPTY<br>FLTPRLRETSTSQESSEPTDTSELLSKVPTGTITEVSSTGVNSSSK<br>ISTPDHDKSTVPPDTFTGEIPRVFTSSIKTKSAEMTITTQASPPES<br>ASHSTLPLDTSTTLSQGGTHSTVTQGFPYSEVTTLMGMGPGNV<br>SWMTTPPVEETSSVSSLMSSPAMTSPSPVSSTSPQSIPSSPLPVT |

TABLE 13-continued

Table of Sequences.

| SEQ ID NO | NAME | SEQ |
|---|---|---|
| | | ALPTSVLVTTTDVLGTTSPESVTSSPPNLSSITHERPATYKDTAH |
| | | TEAAMHHSTNTAVTNVGTSGSGHKSQSSVLADSETSKATPLM |
| | | STTSTLGDTSVSTSTPNISQTNQIQTEPTASLSPRLRESSTSEKTS |
| | | STTETNTAFSYVPTGAITQASRTEISSSRTSISDLDRPTIAPDISTG |
| | | MITRLFTSPIMTKSAEMTVTTQTTTPGATSQGILPWDTSTTLFQ |
| | | GGTHSTVSQGFPHSEITTLRSRTPGDVSWMTTPPVEETSSGFSL |
| | | MSPSMTSPSPVSSTSPESIPSSPLPVTALLTSVLVTTTNVLGTTSP |
| | | EPVTSSPPNLSSPTQERLTTYKDTAHTEAMHASMHTNTAVAN |
| | | VGTSISGHESQSSVPADSHTSKATSPMGITFAMGDTSVSTSTPA |
| | | FFETRIQTESTSSLIPGLRDTRTSEEINTVTETSTVLSEVPTTTTTE |
| | | VSRTEVITSSRTTISGPDHSKMSPYISTETITRLSTFPFVTGSTEM |
| | | AITNQTGPIGTISQATLTLDTSSTASWEGTHSPVTQRFPHSEETT |
| | | TMSRSTKGVSWQSPPSVEETSSPSSPVPLPAITSHSSLYSAVSGS |
| | | SPTSALPVTSLLTSGRRKTIDMLDTHSELVTSSLPSASSFSGEILT |
| | | SEASTNTETIHFSENTAETNMGTTNSMEIKLHSSVSIHSQPSGHT |
| | | PPKVTGSMMEDAIVSTSTPGSPETKNVDRDSTSPLTPELKEDST |
| | | ALVMNSTTESNTVFSSVSLDAATEVSRAEVTYYDPTFMPASAQ |
| | | STKSPDISPEASSSHSNSPPLTISTHKTIATQTGPSGVTSLGQLTL |
| | | DTSTIATSAGTPSARTQDFVDSETTSVMNNDLNDVLKTSPF SAE |
| | | EANSLSSQAPLLVTTSPSPVTSTLQEHSTSSLVSVTSVPTPTLAK |
| | | ITDMDTNLEPVTRSPQNLRNTLATSEATTDTHTMHPSINTAVA |
| | | NVGTTSSPNEFYFTVSPDSDPYKATSAVVITSTSGDSIVSTSMPR |
| | | SSAMKKIESETTFSLIFRLRETSTSQKIGSSSDTSTVFDKAFTAAT |
| | | TEVSRTELTSSSRTSIQGTEKPTMSPDTSTRSVTMLSTFAGLTKS |
| | | EERTIATQTGPHRATSQGTLTWDTSITTSQAGTHSAMTHGFSQ |
| | | LDLSTLTSRVPEYISGTSPPSVEKTSSSSSLLSLPAITSPSPVPTTL |
| | | PESRPSSPVHLTSLPTSGLVKTTDMLASVASLPPNLGSTSHKIPT |
| | | TSEDIKDTEKMYPSTNIAVTNVGTTTSEKESYSSVPAYSEPPKV |
| | | TSPMVTSFNIRDTIVSTSMPGSSEITRIEMESTFSLAHGLKGTSTS |
| | | QDPIVSTEKSAVLHKLTTGATETSRTEVASSRRTSIPGPDHSTES |
| | | PDISTEVIPSLPISLGITESSNMTIITRTGPPLGSTSQGTFTLDTPTT |
| | | SSRAGTHSMATQEFPHSEMTTVMNKDPEILSWTIPPSIEKTSFSS |
| | | SLMPSPAMTSPPVSSTLPKTIHTTPSPMTSLLTPSLVMTTDTLGT |
| | | SPEPTTSSPPNLSSTSHEILTTDEDTTAIEAMHPSTSTAATNVETT |
| | | SSGHGSQSSVLADSEKTKATAPMDTTSTMGHTTVSTSMSVSSE |
| | | TTKIKRESTYSLTPGLRETSISQNASFSTDTSIVLSEVPTGTTAEV |
| | | SRTEVTSSGRTSIPGPSQSTVLPEISTRTMTRLFASPTMTESAEM |
| | | TIPTQTGPSGSTSQDTLTLDTSTTKSQAKTHSTLTQRFPHSEMT |
| | | TLMSRGPGDMSWQSSPSLENPSSLPSLLSLPATTSPPPISSTLPV |
| | | TISSSPLPVTSLLTSSPVTTTDMLHTSPELVTSSPPKLSHTSDERL |
| | | TTGKDTTNTEAVHPSTNTAASNVEIPSSGHESPSSALADSETSK |
| | | ATSPMFITSTQEDTTVAISTPHFLETSRIQKESISSLSPKLRETGSS |
| | | VETSSAIETSAVLSEVSIGATTEISRTEVTSSSRTSISGSAESTMLP |
| | | EISTTRKIIKFPTSPILAESSEMTIKTQTSPPGSTSESTFTLDTSTTP |
| | | SLVITHSTMTQRLPHSEITTLVSRGAGDVPRPSSLPVEETSPPSS |
| | | QLSLSAMISPSPVSSTLPASSHSSSASVTSLLTPGQVKTTEVLDA |
| | | SAEPETSSPPSLSSTSVEILATSEVTTDTEKIHPFSNTAVTKVGTS |
| | | SSGHESPSSVLPDSETTKATSAMGTISIMGDTSVSTLTPALSNTR |
| | | KIQSEPASSLTTRLRETSTSEETSLATEANTVLSKVSTGATTEVS |
| | | RTEAISFSRTSMSGPEQSTMSQDISIGTIPRISASSVLTESAKMTI |
| | | TTQTGPSESTLESTLNLNTATTPSWVETHSIVIQGFPHPEMTTS |
| | | MGRGPGGVSWPSPPFVKETSPPSSPLSLPAVTSPHPVSTTFLAHI |
| | | PPSPLPVTSLLTSGPATTTDILGTSTEPGTSSSSSLSTTSHERLTT |
| | | YKDTAHTEAVHPSTNTGGTNVATTSSGYKSQSSVLADSSPMC |
| | | TTSTMGDTSVLTSTPAFLETRRIQTELASSLTPGLRESSGSEGTS |
| | | SGTKMSTVLSKVPTGATTEISKEDVTSIPGPAQSTISPDISTRTVS |
| | | WFSTSPVMTESAEITMNTHTSPLGATTQGTSTLDTSSTTSLTMT |
| | | HSTISQGFSHSQMSTLMRRGPEDVSWMSPPLLEKTRPSFSLMSS |
| | | PATTSPSPVSSTLPESISSSPLPVTSLLTSGLAKTTDMLHKSSEPV |
| | | TNSPANLSSTSVEILATSEVTTDTEKTHPSSNRTVTDVGTSSSG |
| | | HESTSFVLADSQTSKVTSPMVITSTMEDTSVSTSTPGFFETSRIQ |
| | | TEPTSSLTLGLRKTSSSEGTSLATEMSTVLSGVPTGATAEVSRT |
| | | EVTSSSRTSISGFAQLTVSPETSTETITRLPTSSIMTESAEMMIKT |
| | | QTDPPGSTPESTHTVDISTTPNWVETHSTVTQRFSHSEMTTLVS |
| | | RSPGDMLWPSQSSVEETSSASSLLSLPATTSPSPVSSTLVEDFPS |
| | | ASLPVTSLLNPGLVITTDRMGISREPGTSSTSNLSSTSHERLTTL |
| | | EDTVDTEDMQPSTHTAVTNVRTSISGHESQSSVLSDSETPKATS |
| | | PMGTTYTMGETSVSISTSDFFETSRIQIEPTSSLTSGLRETSSSERI |
| | | SSATEGSTVLSEVPSGATTEVSRTEVISSRGTSMSGPDQFTISPDI |
| | | STEAITRLSTSPIMTESAESAITIETGSPGATSEGTLTLDTSTTTF |
| | | WSGTHSTASPGFSHSEMTTLMSRTPGDVPWPSLPSVEEASSVS |
| | | SSLSSPAMTSTSFFSTLPESISSSPHPVTALLTLGPVKTTDMLRTS |
| | | SEPETSSPPNLSSTSAEILATSEVTKDREKIHPSSNTPVVNVGTVI |
| | | YKHLSPSSVLADLVTTKPTSPMATTSTLGNTSVSTSTPAFPETM |

TABLE 13-continued

Table of Sequences.

| SEQ ID NO | NAME | SEQ |
|---|---|---|
| | | MTQPTSSLTSGLREISTSQETSSATERSASLSGMPTGATTKVSRT |
| | | EALSLGRTSTPGPAQSTISPEISTETITRISTPLTTTGSAEMTITPK |
| | | TGHSGASSQGTFTLDTSSRASWPGTHSAATHRSPHSGMTTPMS |
| | | RGPEDVSWPSRPSVEKTSPPSSLVSLSAVTSPSPLYSTPSESSHSS |
| | | PLRVTSLFTPVMMKTTDMLDTSLEPVTTSPPSMNITSDESLATS |
| | | KATMETEAIQLSENTAVTQMGTISARQEFYSSYPGLPEPSKVTS |
| | | PVVTSSTIKDIVSTTIPASSEITRIEMESTSTLTPTPRETSTSQEIHS |
| | | ATKPSTVPYKALTSATIEDSMTQVMSSSRGPSPDQSTMSQDIST |
| | | EVITRLSTSPIKTESTEMTITTQTGSPGATSRGTLTLDTSTTFMS |
| | | GTHSTASQGFSHSQMTALMSRTPGDVPWLSHPSVEEASSASFS |
| | | LSSPVMTSSSPVSSTLPDSIHSSSLPVTSLLTSGLVKTTELLGTSS |
| | | EPETSSPPNLSSTSAEILAITEVTTDTEKLEMTNVVTSGYTHESP |
| | | SSVLADSVTTKATSSMGITYPTGDTNVLTSTPAFSDTSRIQTKS |
| | | KLSLTPGLMETSISEETSSATEKSTVLSSVPTGATTEVSRTEAISS |
| | | SRTSIPGPAQSTMSSDTSMETITRISTPLTRKESTDMAITPKTGPS |
| | | GATSQGTFTLDSSSTASWPGTHSATTQRFPQSVVTTPMSRGPE |
| | | DVSWPSPLSVEKNSPPSSLVSSSSVTSPSPLYSTPSGSSHSSPVPV |
| | | TSLFTSIMMKATDMLDASLEPETTSAPNMNITSDESLAASKATT |
| | | ETEAIHVFENTAASHVETTSATEELYSSSPGFSEPTKVISPVVTS |
| | | SSIRDNMVSTTMPGSSGITRIEIESMSSLTPGLRETRTSQDITSST |
| | | ETSTVLYKMPSGATPEVSRTEVMPSSRTSIPGPAQSTMSLDISD |
| | | EVVTRLSTSPIMTESAEITITTQTGYSLATSQVTLPLGTSMTFLS |
| | | GTHSTMSQGLSHSEMTNLMSRGPESLSWTSPRFVETTRSSSSLT |
| | | SLPLTTSLSPVSSTLLDSSPSSPLPVTSLILPGLVKTTEVLDTSSEP |
| | | KTSSSPNLSSTSVEIPATSEIMTDTEKIHPSSNTAVAKVRTSSSV |
| | | HESHSSVLADSETTITIPSMGITSAVDDTTVFTSNPAFSETRRIPT |
| | | EPTFSLTPGFRETSTSEETTSITETSAVLYGVPTSATTEVSMTEI |
| | | MSSNRIHIPDSDQSTMSPDIITEVITRLSSSSMMSESTQMTITTQK |
| | | SSPGATAQSTLTLATTTAPLARTHSTVPPRFLHSEMTTLMSRSP |
| | | ENPSWKSSLFVEKTSSSSSLLSLPVTTSPSVSSTLPQSIPSSSFSVT |
| | | SLLTPGMVKTTDTSTEPGTSLSPNLSGTSVEILAASEVTTDTEKI |
| | | HPSSSMAVTNVGTTSSGHELYSSVSIHSEPSKATYPVGTPSSMA |
| | | ETSISTSMPANFETTGFEAEPFSHLTSGFRKTNMSLDTSSVTPTN |
| | | TPSSPGSTHLLQSSKTDFTSSAKTSSPDWPPASQYTEIPVDIITPF |
| | | NASPSITESTGITSFPESRFTMSVTESTHHLSTDLLPSAETISTGT |
| | | VMPSLSEAMTSFATTGVPRAISGSGSPFSRTESGPGDATLSTIAE |
| | | SLPSSTPVPFSSSTFTTTDSSTIPALHEITSSSATPYRVDTSLGTES |
| | | STTEGRLVMVSTLDTSSQPGRTSSSPILDTRMTESVELGTVTSA |
| | | YQVPSLSTRLTRTDGIMEHITKIPNEAAHRGTIRPVKGPQTSTSP |
| | | ASPKGLHTGGTKRMETTTTALKTTTTALKTTSRATLTTSVYTP |
| | | TLGTLTPLNASMQMASTIPTEMMITTPYVFPDVPETTSSLATSL |
| | | GAETSTALPRTTPSVFNRESETTASLVSRSGAERSPVIQTLDVSS |
| | | SEPDTTASWVIHPAETIPTVSKTTPNFFHSELDTVSSTATSHGAD |
| | | VSSAIPTNISPSELDALTPLVTISGTDTSTTFPTLTKSPHETETRTT |
| | | WLTHPAETSSTIPRTIPNFSHHESDATPSIATSPGAETSSAIPIMT |
| | | VSPGAEDLVTSQVTSSGTDRNMTIPTLTLSPGEPKTIASLVTHPE |
| | | AQTSSAIPTSTISPAVSRLVTSMVTSLAAKTSTTNRALTNSPGEP |
| | | ATTVSLVTHPAQTSPTVPWTTSIFFHSKSDTTPSMTTSHGAESS |
| | | SAVPTPTVSTEVPGVVTPLVTSSRAVISTTIPILTLSPGEPETTPS |
| | | MATSHGEEASSAIPTPTVSPGVPGVVTSLVTSSRAVTSTTIPILT |
| | | FSLGEPETTPSMATSHGTEAGSAVPTVLPEVPGMVTSLVASSR |
| | | AVTSTTLPTLTLSPGEPETTPSMATSHGAEASSTVPTVSPEVPG |
| | | VVTSLVTSSSGVNSTSIPTLILSPGELETTPSMATSHGAEASSAV |
| | | PTPTVSPGVSGVVTPLVTSSRAVTSTTIPILTLSSSEPETTPSMAT |
| | | SHGVEASSAVLTVSPEVPGMVTSLVTSSRAVTSTTIPTLTISSDE |
| | | PETTTSLVTHSEAKMISAIPTLAVSPTVQGLVTSLVTSSGSETSA |
| | | FSNLTVASSQPETIDSWVAHPGTEASSVVPTLTVSTGEPFTNISL |
| | | VTHPAESSSTLPRTTSRFSHSELDTMPSTVTSPEAESSSAISTTIS |
| | | PGIPGVLTSLVTSSGRDISATEPTVPESPHESEATASWVTHPAVT |
| | | STTVPRTTPNYSHSEPDTTPSIATSPGAEATSDFPTITVSPDVPD |
| | | MVTSQVTSSGTDTSITIPTLTLSSGEPETTTSFITYSETHTSSAIPT |
| | | LPVSPGASKMLTSLVISSGTDSTTTFPTLTETPYEPETTAIQLIHP |
| | | AETNTMVPRTTPKFSHSKSDTTLPVAITSPGPEASSAVSTTTISP |
| | | DMSDLVTSLVPSSGTDTSTTFPTLSETPYEPETTATWLTHPAET |
| | | STTVSGTIPNFSHRGSDTAPSMVTSPGVDTRSGVPTTTIPPSIPG |
| | | VVTSQVTSSATDTSTAIPTLTPSPGEPETTASSATHPGTQTGFTV |
| | | PIRTVPSSEPDTMASWVTHPPQTSTPVSRTTSSFSHSSPDATPV |
| | | MATSPRTEASSAVLTTISPGAPEMVTSQITSSGAATSTTVPTLTH |
| | | SPGMPETTALLSTHPRTETSKTFPASTVFPQVSETTASLTIRPGA |
| | | ETSTALPTQTTSSLFTLLVTGTSRVDLSPTASPGVSAKTAPLSTH |
| | | PGTETSTMIPTSTLSLGLLETTGLLATSSSAETSTSTLTLTVSPAV |
| | | SGLSSASITTDKPQTVTSWNTETSPSVTSVGPPEFSRTVTGTTM |
| | | TLIPSEMPTPPKTSHGEGVSPTTILRTTMVEATNLATTGSSPTVA |
| | | KTTTTENTLAGSLFTPLTTPGMSTLASESVTSRTSYNHRSWIST |

TABLE 13-continued

Table of Sequences.

| SEQ ID NO | NAME | SEQ |
|---|---|---|
| | | TSSYNRRYWTPATSTPVTSTFSPGISTSSIPSSTAATVPFMVPFTL<br>NFTITNLQYEEDMRHPGSRKFNATERELQGLLKPLFRNSSLEYL<br>YSGCRLASLRPEKDSSATAVDAICTHRPDPEDLGLDRERLYWE<br>LSNLTNGIQELGPYTLDRNSLYVNGFTHRSSMPTTSTPGTSTVD<br>VGTSGTPSSSPSPTTAGPLLMPFTLNFTITNLQYEEDMRRTGSR<br>KENTMESVLQGLLKPLEKNTSVGPLYSGCRLTLLRPEKDGAAT<br>GVDAICTHRLDPKSPGLNREQLYWELSKLTNDIEELGPYTLDR<br>NSLYVNGFTHQSSVSTTSTPGTSTVDLRTSGTPSSLSSPTIMAA<br>GPLLVPFTLNETITNLQYGEDMGHPGSRKENTTERVLQGLLGPI<br>FKNTSVGPLYSGCRLTSLRSEKDGAATGVDAICIHHLDPKSPGL<br>NRERLYWELSQLTNGIKELGPYTLDRNSLYVNGFTHRTSVPTS<br>STPGTSTVDLGTSGTPFSLPSPATAGPLLVLFTLNFTITNLKYEE<br>DMHRPGSRKENTTERVLQTLLGPMEKNTSVGLLYSGCRLTLLR<br>SEKDGAATGVDAICTHRLDPKSPGVDREQLYWELSQLTNGIKE<br>LGPYTLDRNSLYVNGFTHWIPVPTSSTPGTSTVDLGSGTPSSLP<br>SPTTAGPLLVPFTLNFTITNLKYEEDMHCPGSRKFNTTERVLQS<br>LLGPMFKNTSVGPLYSGCRLTLLRSEKDGAATGVDAICTHRLD<br>PKSPGVDREQLYWELSQLTNGIKELGPYTLDRNSLYVNGFTHQ<br>TSAPNTSTPGTSTVDLGTSGTPSSLPSPTSAGPLLVPFTLNFTITN<br>LQYEEDMHHPGSRKFNTTERVLQGLLGPMFKNTSVGLLYSGC<br>RLTLLRPEKNGAATGMDAICSHRLDPKSPGLNREQLYWELSQL<br>THGIKELGPYTLDRNSLYVNGFTHRSSVAPTSTPGTSTVDLGTS<br>GTPSSLPSPTTAVPLLVPFTLNFTITNLQYGEDMRHPGSRKFNT<br>TERVLQGLLGPLFKNSSVGPLYSGCRLISLRSEKDGAATGVDAI<br>CTHHLNPQSPGLDREQLYWQLSQMTNGIKELGPYTLDRNSLY<br>VNGFTHRSSGLTTSTPWTSTVDLGTSGTPSPVPSPTTTGPLLVPF<br>TLNFTITNLQYEENIVIGHPGSRKFNITESVLQGLLKPLFKSTSVG<br>PLYSGCRLTLLRPEKDGVATRVDAICTHRPDPKIPGLDRQQLY<br>WELSQLTHSITELGPYTLDRDSLYVNGFTQRSSVPTTSTPGTFT<br>VQPETSETPSSLPGPTATGPVLLPFTLNFTITNLQYEEDMRRPGS<br>RKFNTTERVLQGLLMPLFKNTSVSSLYSGCRLTLLRPEKDGAA<br>TRVDAVCTHRPDPKSPGLDRERLYWKLSQLTHGITELGPYTLD<br>RHSLYVNGFTHQSSMTTTRTPDTSTMEILATSRTPASLSGPMTA<br>SPLLVLFTINFTITNLRYEENMHHPGSRKFNTTERVLQGLLRPV<br>FKNTSVGPLYSGCRLTLLRPKKDGAATKVDAICTYRPDPKSPG<br>LDREQLYWELSQLTHSITELGPYTLDRDSLYVNGFTQRSSVPTT<br>SIPGTPTVDLGTSGTPVSKPGPSAASPLLVLFTLNFTITNLRYEE<br>NMQHPGSRKFNTTERVLQGLLRSLFKSTSVGPLYSGCRLTLLR<br>PEKDGTATGVDAICTHHPDPKSPRLDREQLYWELSQLTHNITE<br>LGPYALDNDSLFVNGFTHRSSVSTTSTPGTPTVYLGASKTPASI<br>FGPSAASHLLILFTLNFTITNLRYEENMWPGSRKFNTTERVLQG<br>LLRPLFKNTSVGPLYSGCRLTLLRPEKDGEATGVDAICTHRPDP<br>TGPGLDREQLYLELSQLTHSITELGPYTLDRDSLYVNGFTHRSS<br>VPTTSTGVVSEEPFTLNFTINNLRYMADMGQPGSLKFNITDNV<br>MQHLSPLFQRSSLGARYTGCRVIALRSVKNGAETRVDLLCTY<br>LQPLSGPGLPIKQVFHELSQQTHGITRLGPYSLDKDSLYLNGYN<br>EPGPDEPPTTPKPATTFLPPLSEATTAMGYHLKTLTLNFTISNLQ<br>YSPDMGKGSATFNSTEGVLQHLLRPLFQKSSMGPFYLGCQLIS<br>LRPEKDGAATGVDTTCTYHPDPVGPGLDIQQLYWELSQLTHG<br>VTQLGFYVLDRDSLFINGYAPQNLSIRGEYQINFHIVNWNLSNP<br>DPTSSEYITLLRDIQDKVTTLYKGSQLHDTFRFCLVTNLTMDSV<br>LVTVKALFSSNLDPSLVEQVFLDKTLNASFHWLGSTYQLVDIH<br>VTEMESSVYQPTSSSSTQHFYLNFTITNLPYSQDKAQPGTTNYQ<br>RNKRNIEDALNQLFRNSSIKSYFSDCQVSTFRSVPNRHHTGVDS<br>LCNFSPLARRVDRVAIYEEFLRMTRNGTQLQNFTLDRSSVLVD<br>GYSPNRNEPLTGNSDLPFWAVILIGLAGLLGVITCLICGVLVTT<br>RRRKKEGEYNVQQQCPGYYQSHLDLEDLQ |
| 137 | Immature Human MUC 16 nucleic acid sequence (NM_024690.2) | AGCGTTGCACAATTCCCCCAACCTCCATACATACGGCAGCT<br>CTTCTAGACACAGGTTTTCCCAGGTCAAATGCGGGGACCCC<br>AGCCATATCTCCCACCCTGAGAAATTTGGAGTTTCAGGGA<br>GCTCAGAAGCTCTGCAGAGGCCACCCTCTCTGAGGGGATTC<br>TTCTTAGACCTCCATCCAGAGGCAAATGTTGACCTGTCCATG<br>CTGAAACCCTCAGGCCTTCCTGGGTCATCTTCTCCCACCCGC<br>TCCTTGATGACAGGGAGCAGGAGCACTAAAGCCACACCAG<br>AAATGGATTCAGGACTGACAGGAGCCACCTTGTCACCTAAG<br>ACATCTACAGGTGCAATCGTGGTGACAGAACATACTCTGCC<br>CTTTACTTCCCCAGATAAGACCTTGGCCAGTCCTACATCTTC<br>GGTTGTGGGAAGAACCACCCAGTCTTTGGGGGTGATGTCCT<br>CTGCTCTCCCTGAGTCAACCTCTAGAGGAATGACACACTCC<br>GAGCAAAGAACCAGCCCATCGCTGAGTCCCCAGGTCAATGG<br>AACTCCCTCTAGGAACTACCCTGCTACAAGCATGGTTTCAG<br>GATTGAGTTCCCCAAGGACCAGGACCAGTTCCACAGAAGGA<br>AATTTTACCAAAGAAGCATCTACATACACACTCACTGTAGA |

TABLE 13-continued

Table of Sequences.

| SEQ ID NO | NAME | SEQ |
|---|---|---|
| | | GACCACAAGTGGCCCAGTCACTGAGAAGTACACAGTCCCCA<br>CTGAGACCTCAACAACTGAAGGTGACAGCACAGAGACCCC<br>CTGGGACACAAGATATATTCCTGTAAAAATCACATCTCCAA<br>TGAAAACATTTGCAGATTCAACTGCATCCAAGGAAAATGCC<br>CCAGTGTCTATGACTCCAGCTGAGACCACAGTTACTGACTC<br>ACATACTCCAGGAAGGACAAACCCATCATTTGGGACACTTT<br>ATTCTTCCTTCCTTGACCTATCACCTAAAGGGACCCCAAATT<br>CCAGAGGTGAAACAAGCCTGGAACTGATTCTATCAACCACT<br>GGATATCCCTTCTCCTCTCCTGAACCTGGCTCTGCAGGACAC<br>AGCAGAATAAGTACCAGTGCGCCTTTGTCATCATCTGCTTC<br>AGTTCTCGATAATAAAATATCAGAGACCAGCATATTCTCAG<br>GCCAGAGTCTCACCTCCCCTCTGTCTCCTGGGGTGCCCGAG<br>GCCAGAGCCAGCACAATGCCCAACTCAGCTATCCCTTTTTC<br>CATGACACTAAGCAATGCAGAAACAAGTGCCGAAAGGGTC<br>AGAAGCACAATTTCCTCTCTGGGGACTCCATCAATATCCAC<br>AAAGCAGACAGCAGAGACTATCCTTACCTTCCATGCCTTCG<br>CTGAGACCATGGATATACCCAGCACCCACATAGCCAAGACT<br>TTGGCTTCAGAATGGTTGGGAAGTCCAGGTACCCTTGGTGG<br>CACCAGCACTTCAGCGCTGACAACCACATCTCCATCTACCA<br>CTTTAGTCTCAGAGGAGACCAACACCCATCACTCCACGAGT<br>GGAAAGGAAACAGAAGGAACTTTGAATACATCTATGACTCC<br>ACTTGAGACCTCTGCTCCTGGAGAAGAGTCCGAAATGACTG<br>CCACCTTGGTCCCCACTCTAGGTTTTACAACTCTTGACAGCA<br>AGATCAGAAGTCCATCTCAGGTCTCTTCATCCCACCCAACA<br>AGAGAGCTCAGAACCACAGGCAGCACCTCTGGGAGGCAGA<br>GTTCCAGCACAGCTGCCCACGGGAGCTCTGACATCCTGAGG<br>GCAACCACTTCCAGCACCTCAAAAGCATCATCATGGACCAG<br>TGAAAGCACAGCTCAGCAATTTAGTGAACCCCAGCACACAC<br>AGTGGGTGGAGACAAGTCCTAGCATGAAAACAGAGAGACC<br>CCCAGCATCAACCAGTGTGGCAGCCCCTATCACCACTTCTG<br>TTCCCTCAGTGGTCTCTGGCTTCACCACCCTGAAGACCAGCT<br>CCACAAAAGGGATTTGGCTTGAAGAAACATCTGCAGACACA<br>CTCATCGGAGAATCCACAGCTGGCCCAACCACCCATCAGTT<br>TGCTGTTCCCACTGGGATTTCAATGACAGGAGGCAGCAGCA<br>CCAGGGGAAGCCAGGGCACAACCCACCTACTCACCAGAGC<br>CACAGCATCATCTGAGACATCCGCAGATTTGACTCTGGCCA<br>CGAACGGTGTCCCAGTCTCCGTGTCTCCAGCAGTGAGCAAG<br>ACGGCTGCTGGCTCAAGTCCTCCAGGAGGGACAAAGCCATC<br>ATATACAATGGTTTCTTCTGTCATCCCTGAGACATCATCTCT<br>ACAGTCCTCAGCTTTCAGGGAAGGAACCAGCCTGGGACTGA<br>CTCCATTAAACACTAGACATCCCTTCTCTTCCCCTGAACCAG<br>ACTCTGCAGGACACACCAAGATAAGCACCAGCATTCCTCTG<br>TTGTCATCTGCTTCAGTTCTTGAGGATAAAGTGTCAGCGACC<br>AGCACATTCTCACACCACAAAGCCACCTCATCTATTACCAC<br>AGGGACTCCTGAAATCTCAACAAAGACAAAGCCCAGCTCA<br>GCCGTTCTTTCCTCCATGACCCTAAGCAATGCAGCAACAAG<br>TCCTGAAAGAGTCAGAAATGCAACTTCCCCTCTGACTCATC<br>CATCTCCATCAGGGGAAGAGACAGCAGGGAGTGTCCTCACT<br>CTCAGCACCTCTGCTGAGACTACAGACTCACCTAACATCCA<br>CCCAACTGGGACACTGACTTCAGAATCGTCAGAGAGTCCTA<br>GCACTCTCAGCCTCCCAAGTGTCTCTGGAGTCAAAACCACA<br>TTTTCTTCATCTACTCCTTCCACTCATCTATTTACTAGTGGAG<br>AAGAAACAGAGGAAACTTCGAATCCATCTGTGTCTCAACCT<br>GAGACTTCTGTTTCCAGAGTAAGGACCACCTTGGCCAGCAC<br>CTCTGTCCCTACCCCAGTATTCCCCACCATGGACACCTGGCC<br>TACACGTTCAGCTCAGTTCTCTTCATCCCACCTAGTGAGTGA<br>GCTCAGAGCTACGAGCAGTACCTCAGTTACAAACTCAACTG<br>GTTCAGCTCTTCCTAAAATATCTCACCTCACTGGGACGGCA<br>ACAATGTCACAGACCAATAGAGACACGTTTAATGACTCTGC<br>TGCACCCCAAAGCACAACTTGGCCAGAGACTAGTCCCAGAT<br>TCAAGACAGGGTTACCTTCAGCAACAACCACTGTTTCAACC<br>TCTGCCACTTCTCTCTCTGCTACTGTAATGGTCTCTAAATTC<br>ACTTCTCCAGCAACTAGTTCCATGGAAGCAACTTCTATCAG<br>GGAACCATCAACAACCATCCTCACAACAGAGACCACGAAT<br>GGCCCAGGCTCTATGGCTGTGGCTTCTACCAACATCCCAATT<br>GGAAAGGGCTACATTACTGAAGGAAGATTGGACACAAGCC<br>ATCTGCCCATTGGAACCACAGCTTCCTCTGAGACATCTATG<br>GATTTTACCATGGCCAAAGAAAGTGTCTCAATGTCAGTATC<br>TCCATCTCAGTCCATGGATGCTGCTGGCTCAAGCACTCCAG<br>GAAGGACAAGCCAATTCGTTGACACATTTTCTGATGATGTC<br>TATCATTTAACATCCAGAGAAATTACAATACCTAGAGATGG<br>AACAAGCTCAGCTCTGACTCCACAAATGACTGCAACTCACC<br>CTCCATCTCCTGATCCTGGCTCTGCTAGAAGCACCTGGCTTG<br>GCATCTTGTCCTCATCTCCTTCTTCTCCTACTCCCAAAGTCA |

TABLE 13-continued

| Table of Sequences. | | |
|---|---|---|
| SEQ ID NO | NAME | SEQ |
| | | CAATGAGCTCCACATTTTCAACTCAGAGAGTCACCACAAGC ATGATAATGGACACAGTTGAAACTAGTCGGTGGAACATGCC CAACTTACCTTCCACGACTTCCTTGACACCAAGTAATATTCC AACAAGTGGTGCCATAGGAAAAAGCACCCTGGTTCCCTTGG ACACTCCATCTCCAGCCACATCATTGGAGGCATCAGAAGGG GGACTTCCAACCCTCAGCACCTACCCTGAATCAACAAACAC ACCCAGCATCCACCTCGGAGCACACGCTAGTTCAGAAAGTC CAAGCACCATCAAACTTACCATGGCTTCAGTAGTAAAACCT GGCTCTTACACACCTCTCACCTTCCCCTCAATAGAGACCCAC ATTCATGTATCAACAGCCAGAATGGCTTACTCTTCTGGGTCT TCACCTGAGATGACAGCTCCTGGAGAGACTAACACTGGTAG TACCTGGGACCCCACCACCTACATCACCACTACGGATCCTA AGGATACAAGTTCAGCTCAGGTCTCTACACCCCACTCAGTG AGGACACTCAGAACCACAGAAAACCATCCAAAGACAGAGT CCGCCACCCCAGCTGCTTACTCTGGAAGTCCTAAAATCTCA AGTTCACCCAATCTCACCAGTCCGGCCACAAAAGCATGGAC CATCACAGACACAACTGAACACTCCACTCAATTACATTACA CAAAATTGGCAGAAAAATCATCTGGATTTGAGACACAGTCA GCTCCAGGACCTGTCTCTGTAGTAATCCCTACCTCCCCTACC ATTGGAAGCAGCACATTGGAACTAACTTCTGATGTCCCAGG GGAACCCCTGGTCCTTGCTCCCAGTGAGCAGACCACAATCA CTCTCCCCATGGCAACATGGCTGAGTACCAGTTTGACAGAG GAAATGGCTTCAACAGACCTTGATATTTCAAGTCCAAGTTC ACCCATGAGTACATTTGCTATTTTTCCACCTATGTCCACACC TTCTCATGAACTTTCAAAGTCAGAGGCAGATACCAGTGCCA TTAGAAATACAGATTCAACAACGTTGGATCAGCACCTAGGA ATCAGGAGTTTGGGCAGAACTGGGGACTTAACAACTGTTCC TATCACCCCACTGACAACCACGTGGACCAGTGTGATTGAAC ACTCAACACAAGCACAGGACACCCTTTCTGCAACGATGAGT CCTACTCACGTGACACAGTCACTCAAAGATCAAACATCTAT ACCAGCCTCAGCATCCCCTTCCCATCTTACTGAAGTCTACCC TGAGCTCGGGACACAAGGGAGAAGCTCCTCTGAGGCAACC ACTTTTTGGAAACCATCTACAGACACACTGTCCAGAGAGAT TGAGACTGGCCCAACAAACATTCAATCCACTCCACCCATGG ACAACACAACAACAGGGAGCAGTAGTAGTGGAGTCACCCT GGGCATAGCCCACCTTCCCATAGGAACATCCTCCCCAGCTG AGACATCCACAAACATGGCACTGGAAAGAAGAAGTTCTAC AGCCACTGTCTCTATGGCTGGGACAATGGGACTCCTTGTTA CTAGTGCTCCAGGAAGAAGCATCAGCCAGTCATTAGGAAGA GTTTCCTCTGTCCTTTCTGAGTCAACTACTGAAGGAGTCACA GATTCTAGTAAGGGAAGCAGCCCAAGGCTGAACACACAGG GAAATACAGCTCTCTCCTCCTCTCTTGAACCCAGCTATGCTG AAGGAAGCCAGATGAGCACAAGCATCCCTCTAACCTCATCT CCTACAACTCCTGATGTGGAATTCATAGGGGGCAGCACATT TTGGACCAAGGAGGTCACCACAGTTATGACCTCAGACATCT CCAAGTCTTCAGCAAGGACAGAGTCCAGCTCAGCTACCCTT ATGTCCACAGCTTTGGGAAGCACTGAAAATACAGGAAAAG AAAAACTCAGAACTGCCTCTATGGATCTTCCATCTCCAACTC CATCAATGGAGGTGACACCATGGATTTCTCTCACTCTCAGT AATGCCCCCAATACCACAGATTCACTTGACCTCAGCCATGG GGTGCACACCAGCTCTGCAGGGACTTTGGCCACTGACAGGT CATTGAATACTGGTGTCACTAGAGCCTCCAGATTGGAAAAC GGCTCTGATACCTCTTCTAAGTCCCTGTCTATGGGAAACAGC ACTCACACTTCCATGACTTACACAGAGAAGAGTGAAGTGTC TTCTTCAATCCATCCCCGACCTGAGACCTCAGCTCCTGGAGC AGAGACCACTTTGACTTCCACTCCTGGAAACAGGGCCATAA GCTTAACATTGCCTTTTTCATCCATTCCAGTGGAAGAAGTCA TTTCTACAGGCATAACCTCAGGACCAGACATCAACTCAGCA CCCATGACACATTCTCCCATCACCCCACCAACAATTGTATG GACCAGTACAGGCACAATTGAACAGTCCACTCAACCACTAC ATGCAGTTTCTTCAGAAAAAGTTTCTGTGCAGACACAGTCA ACTCCATATGTCAACTCTGTGGCAGTGTCTGCTTCCCCTACC CATGAGAATTCAGTCTCTTCTGGAAGCAGCACATCCTCTCC ATATTCCTCAGCCTCACTTGAATCCTTGGATTCCACAATCAG TAGGAGGAATGCAATCACTTCCTGGCTATGGGACCTCACTA CATCTCTCCCCACTACAACTTGGCCAAGTACTAGTTTATCTG AGGCACTGTCCTCAGGCCATTCTGGGGTTTCAAACCCAAGT TCAACTACGACTGAATTTCCACTCTTTTCAGCTGCATCCACA TCTGCTGCTAAGCAAAGAAATCCAGAAACAGAGACCCATG GTCCCCAGAATACAGCCGCGAGTACTTTGAACACTGATGCA TCCTCGGTCACAGGTCTTTCTGAGACTCCTGTGGGGGCAAG TATCAGCTCTGAAGTCCCTCTTCCAATGGCCATAACTTCTAG ATCAGATGTTTCTGGCCTTACATCTGAGAGTACTGCTAACCC GAGTTTAGGCACAGCCTCTTCAGCAGGGACCAAATTAACTA |

TABLE 13-continued

| Table of Sequences. | | |
|---|---|---|
| SEQ ID NO | NAME | SEQ |
| | | GGACAATATCCCTGCCCACTTCAGAGTCTTTGGTTTCCTTTA<br>GAATGAACAAGGATCCATGGACAGTGTCAATCCCTTTGGGG<br>TCCCATCCAACTACTAATACAGAAACAAGCATCCCAGTAAA<br>CAGCGCAGGTCCACCTGGCTTGTCCACAGTAGCATCAGATG<br>TAATTGACACACCTTCAGATGGGGCTGAGAGTATTCCCACT<br>GTCTCCTTTTCCCCCTCCCCTGATACTGAAGTGACAACTATC<br>TCACATTTCCCAGAAAAGACAACTCATTCATTTAGAACCAT<br>TTCATCTCTCACTCATGAGTTGACTTCAAGAGTGACACCTAT<br>TCCTGGGGATTGGATGAGTTCAGCTATGTCTACAAAGCCCA<br>CAGGAGCCAGTCCCTCCATTACACTGGGAGAGAGAAGGAC<br>AATCACCTCTGCTGCTCCAACCACTTCCCCCATAGTTCTCAC<br>TGCTAGTTTCACAGAGACCAGCACAGTTTCACTGGATAATG<br>AAACTACAGTAAAAACCTCAGATATCCTTGACGCACGGAAA<br>ACAAATGAGCTCCCCTCAGATAGCAGTTCTTCTTCTGATCTG<br>ATCAACACCTCCATAGCTTCTTCAACTATGGATGTCACTAAA<br>ACAGCCTCCATCAGTCCCACTAGCATCTCAGGAATGACAGC<br>AAGTTCCTCCCCATCTCTCTTCTCTTCAGATAGACCCCAGGT<br>TCCCACATCTACAACAGAGACAAATACAGCCACCTCTCCAT<br>CTGTTTCCAGTAACACCTATTCTCTTGATGGGGGCTCCAATG<br>TGGGTGGCACTCCATCCACTTTACCACCCTTTACAATCACCC<br>ACCCTGTCGAGACAAGCTCGGCCCTATTAGCCTGGTCTAGA<br>CCAGTAAGAACTTTCAGCACCATGGTCAGCACTGACACTGC<br>CTCCGGAGAAAATCCTACCTCTAGCAATTCTGTGGTGACTTC<br>TGTTCCAGCACCAGGTACATGGACCAGTGTAGGCAGTACTA<br>CTGACTTACCTGCCATGGGCTTTCTCAAGACAAGTCCTGCA<br>GGAGAGGCACACTCACTTCTAGCATCAACTATTGAACCAGC<br>CACTGCCTTCACTCCCCATCTCTCAGCAGCAGTGGTCACTGG<br>ATCCAGTGCTACATCAGAAGCCAGTCTTCTCACTACGAGTG<br>AAAGCAAAGCCATTCATTCTTCACCACAGACCCCAACTACA<br>CCCACCTCTGGAGCAAACTGGGAAACTTCAGCTACTCCTGA<br>GAGCCTTTTGGTAGTCACTGAGACTTCAGACACAACACTTA<br>CCTCAAAGATTTTGGTCACAGATACCATCTTGTTTTCAACTG<br>TGTCCACGCCACCTTCTAAATTTCCAAGTACGGGGACTCTGT<br>CTGGAGCTTCCTTCCCTACTTTACTCCCGGACACTCCAGCCA<br>TCCCTCTCACTGCCACTGAGCCAACAAGTTCATTAGCTACAT<br>CCTTTGATTCCACCCCACTGGTGACTATAGCTTCGGATAGTC<br>TTGGCACAGTCCCAGAGACTACCCTGACCATGTCAGAGACC<br>TCAAATGGTGATGCACTGGTTCTTAAGACAGTAAGTAACCC<br>AGATAGGAGCATCCCTGGAATCACTATCCAAGGAGTAACAG<br>AAAGTCCACTCCATCCTTCTTCCACTTCCCCCTCTAAGATTG<br>TTGCTCCACGGAATACAACCTATGAAGGTTCGATCACAGTG<br>GCACTTTCTACTTTGCCTGCGGGAACTACTGGTTCCCTTGTA<br>TTCAGTCAGAGTTCTGAAAACTCAGAGACAACGGCTTTGGT<br>AGACTCATCAGCTGGGCTTGAGAGGGCATCTGTGATGCCAC<br>TAACCACAGGAAGCCAGGGTATGGCTAGCTCTGGAGGAATC<br>AGAAGTGGGTCCACTCACTCAACTGGAACCAAAACATTTTC<br>TTCTCTCCCTCTGACCATGAACCCAGGTGAGGTTACAGCCAT<br>GTCTGAAATCACCACGAACAGACTGACAGCTACTCAATCAA<br>CAGCACCCAAAGGGATACCTGTGAAGCCCACCAGTGCTGAG<br>TCAGGCCTCCTAACACCTGTCTCTGCCTCCTCAAGCCCATCA<br>AAGGCCTTTGCCTCACTGACTACAGCTCCCCCAACTTGGGG<br>GATCCCACAGTCTACCTTGACATTTGAGTTTTCTGAGGTCCC<br>AAGTTTGGATACTAAGTCCGCTTCTTTACCAACTCCTGGACA<br>GTCCCTGAACACCATTCCAGACTCAGATGCAAGCACAGCAT<br>CTTCCTCACTGTCCAAGTCTCCAGAAAAAAACCCAAGGGCA<br>AGGATGATGACTTCCACAAAGGCCATAAGTGCAAGCTCATT<br>TCAATCAACAGGTTTTACTGAAACCCCTGAGGGATCTGCCT<br>CCCCTTCTATGGCAGGGCATGAACCCAGAGTCCCCACTTCA<br>GGAACAGGGGACCCTAGATATGCCTCAGAGAGCATGTCTTA<br>TCCAGACCCAAGCAAGGCATCATCAGCTATGACATCGACCT<br>CTCTTGCATCAAAACTCACAACTCTCTTCAGCACAGGTCAA<br>GCAGCAAGGTCTGGTTCTAGTTCCTCTCCCATAAGCCTATCC<br>ACTGAGAAAGAAACAAGCTTCCTTTCCCCCACTGCATCCAC<br>CTCCAGAAAGACTTCACTATTTCTTGGGCCTTCCATGGCAAG<br>GCAGCCCAACATATTGGTGCATCTTCAGACTTCAGCTCTGA<br>CACTTTCTCCAACATCCACTCTAAATATGTCCCAGGAGGAG<br>CCTCCTGAGTTAACCTCAAGCCAGACCATTGCAGAAGAAGA<br>GGGAACAACAGCTGAAACACAGACGTTAACCTTCACACCAT<br>CTGAGACCCCAACATCCTTGTTACCTGTCTCTTCTCCCACAG<br>AACCCACAGCCAGAAGAAAGAGTTCTCCAGAAACATGGGC<br>AAGCTCTATTTCAGTTCCTGCCAAGACCTCCTTGGTTGAAAC<br>AACTGATGGAACGCTAGTGACCACCATAAAGATGTCAAGCC<br>AGGCAGCACAAGGAAATTCCACGTGGCCTGCCCCAGCAGA<br>GGAGACGGGGAGCAGTCCAGCAGGCACATCCCCAGGAAGC |

TABLE 13-continued

Table of Sequences.

| SEQ ID NO | NAME | SEQ |
|---|---|---|
| | | CCAGAAATGTCTACCACTCTCAAAATCATGAGCTCCAAGGA |
| | | ACCCAGCATCAGCCCAGAGATCAGGTCCACTGTGAGAAATT |
| | | CTCCTTGGAAGACTCCAGAAACAACTGTTCCCATGGAGACC |
| | | ACAGTGGAACCAGTCACCCTTCAGTCCACAGCCCTAGGAAG |
| | | TGGCAGCACCAGCATCTCTCACCTGCCCACAGGAACCACAT |
| | | CACCAACCAAGTCACCAACAGAAAATATGTTGGCTACAGAA |
| | | AGGGTCTCCCTCTCCCCATCCCCACCTGAGGCTTGGACCAA |
| | | CCTTTATTCTGGAACTCCAGGAGGGACCAGGCAGTCACTGG |
| | | CCACAATGTCCTCTGTCTCCCTAGAGTCACCAACTGCTAGA |
| | | AGCATCACAGGGACTGGTCAGCAAAGCAGTCCAGAACTGG |
| | | TTTCAAAGACAACTGGAATGGAATTCTCTATGTGGCATGGC |
| | | TCTACTGGAGGGACCACAGGGGACACACATGTCTCTCTGAG |
| | | CACATCTTCCAATATCCTTGAAGACCCTGTAACCAGCCCAA |
| | | ACTCTGTGAGCTCATTGACAGATAAATCCAAACATAAAACC |
| | | GAGACATGGGTAAGCACCACAGCCATTCCCTCCACTGTCCT |
| | | GAATAATAAGATAATGGCAGCTGAACAACAGACAAGTCGA |
| | | TCTGTGGATGAGGCTTATTCATCAACTAGTTCTTGGTCAGAT |
| | | CAGACATCTGGGAGTGACATCACCCTTGGTGCATCTCCTGA |
| | | TGTCACAAACACATTATACATCACCTCCACAGCACAAACCA |
| | | CCTCACTAGTGTCTCTGCCCTCTGGAGACCAAGGCATTACA |
| | | AGCCTCACCAATCCCTCAGGAGGAAAAACAAGCTCTGCGTC |
| | | ATCTGTCACATCTCCTTCAATAGGGCTTGAGACTCTGAGGG |
| | | CCAATGTAAGTGCAGTGAAAAGTGACATTGCCCCTACTGCT |
| | | GGGCATCTATCTCAGACTTCATCTCCTGCGGAAGTGAGCAT |
| | | CCTGGACGTAACCACAGCTCCTACTCCAGGTATCTCCACCA |
| | | CCATCACCACCATGGGAACCAACTCAATCTCAACTACCACA |
| | | CCCAACCCAGAAGTGGGTATGAGTACCATGGACAGCACCCC |
| | | GGCCACAGAGAGGCGCACAACTTCTACAGAACACCCTTCCA |
| | | CCTGGTCTTCCACAGCTGCATCAGATTCCTGGACTGTCACAG |
| | | ACATGACTTCAAACTTGAAAGTTGCAAGATCTCCTGGAACA |
| | | ATTTCCACAATGCATACAACTTCATTCTTAGCCTCAAGCACT |
| | | GAATTAGACTCCATGTCTACTCCCCATGGCCGTATAACTGTC |
| | | ATTGGAACCAGCCTGGTCACTCCATCCTCTGATGCTTCAGCT |
| | | GTAAAGACAGAGACCAGTACAAGTGAAAGAACATTGAGTC |
| | | CTTCAGACACAACTGCATCTACTCCCATCTCAACTTTTTCTC |
| | | GTGTCCAGAGGATGAGCATCTCAGTTCCTGACATTTTAAGT |
| | | ACAAGTTGGACTCCCAGTAGTACAGAAGCAGAAGATGTGCC |
| | | TGTTTCAATGGTTTCTACAGATCATGCTAGTACAAAGACTG |
| | | ACCCAAATACGCCCCTGTCCACTTTTCTGTTTGATTCTCTGT |
| | | CCACTCTTGACTGGGACACTGGGAGATCTCTGTCATCAGCC |
| | | ACAGCCACTACCTCAGCTCCTCAGGGGGCCACAACTCCCCA |
| | | GGAACTCACTTTGGAAACCATGATCAGCCCAGCTACCTCAC |
| | | AGTTGCCCTTCTCTATAGGGCACATTACAAGTGCAGTCACA |
| | | CCAGCTGCAATGGCAAGGAGCTCTGGAGTTACTTTTTCAAG |
| | | ACCAGATCCCACAAGCAAAAAGGCAGAGCAGACTTCCACT |
| | | CAGCTTCCCACCACCACTTCTGCACATCCAGGGCAGGTGCC |
| | | CAGATCAGCAGCAACAACTCTGGATGTGATCCCACACACAG |
| | | CAAAAACTCCAGATGCAACTTTTCAGAGACAAGGGCAGAC |
| | | AGCTCTTACAACAGAGGCAAGAGCTACATCTGACTCCTGGA |
| | | ATGAGAAAGAAAAATCAACCCCAAGTGCACCTTGGATCACT |
| | | GAGATGATGAATTCTGTCTCAGAAGATACCATCAAGGAGGT |
| | | TACCAGCTCCTCCAGTGTATTAAGGACCCTGAATACGCTGG |
| | | ACATAAACTTGGAATCTGGGACGACTTCATCCCCAAGTTGG |
| | | AAAAGCAGCCCATATGAGAGAATTGCCCCTTCTGAGTCCAC |
| | | CACAGACAAAGAGGCAATTCACCCTTCTACAAACACAGTAG |
| | | AGACCACAGGCTGGGTCACAAGTTCCGAACATGCTTCTCAT |
| | | TCCACTATCCCAGCCCACTCAGCGTCATCCAAACTCACATCT |
| | | CCAGTGGTTACAACCTCCACCAGGGAACAAGCAATAGTTTC |
| | | TATGTCAACAACCACATGGCCAGAGTCTACAAGGGCTAGAA |
| | | CAGAGCCTAATTCCTTCTTGACTATTGAACTGAGGGACGTC |
| | | AGCCCTTACATGGACACCAGCTCAACCACACAAACAAGTAT |
| | | TATCTCTTCCCCAGGTTCCACTGCGATCACCAAGGGGCCTA |
| | | GAACAGAAATTACCTCCTCTAAGAGAATATCCAGCTCATTC |
| | | CTTGCCCAGTCTATGAGGTCGTCAGACAGCCCCTCAGAAGC |
| | | CATCACCAGGCTGTCTAACTTTCCTGCCATGACAGAATCTG |
| | | GAGGAATGATCCTTGCTATGCAAACAAGTCCACCTGGCGCT |
| | | ACATCACTAAGTGCACCTACTTTGGATACATCAGCCACAGC |
| | | CTCCTGGACAGGGACTCCACTGGCTACGACTCAGAGATTTA |
| | | CATACTCAGAGAAGACCACTCTCTTTAGCAAAGGTCCTGAG |
| | | GATACATCACAGCCAAGCCCTCCCTCTGTGGAAGAAACCAG |
| | | CTCTTCCTCTTCCCTGGTACCTATCCATGCTACAACCTCGCC |
| | | TTCCAATATTTTGTTGACATCACAAGGGCACAGTCCCTCCTC |
| | | TACTCCACCTGTGACCTCAGTTTTCTTGTCTGAGACCTCTGG |
| | | CCTGGGGAAGACCACAGACATGTCGAGGATAAGCTTGGAA |

TABLE 13-continued

Table of Sequences.

| SEQ ID NO | NAME | SEQ |
|---|---|---|
| | | CCTGGCACAAGTTTACCTCCCAATTTGAGCAGTACAGCAGG |
| | | TGAGGCGTTATCCACTTATGAAGCCTCCAGAGATACAAAGG |
| | | CAATTCATCATTCTGCAGACACAGCAGTGACGAATATGGAG |
| | | GCAACCAGTTCTGAATATTCTCCTATCCCAGGCCATACAAA |
| | | GCCATCCAAAGCCACATCTCCATTGGTTACCTCCCACATCAT |
| | | GGGGGACATCACTTCTTCCACATCAGTATTTGGCTCCTCCGA |
| | | GACCACAGAGATTGAGACAGTGTCCTCTGTGAACCAGGGAC |
| | | TTCAGGAGAGAAGCACATCCCAGGTGGCCAGCTCTGCTACA |
| | | GAGACAAGCACTGTCATTACCCATGTGTCTAGTGGTGATGC |
| | | TACTACTCATGTCACCAAGACACAAGCCACTTTCTCTAGCG |
| | | GAACATCCATCTCAAGCCCTCATCAGTTTATAACTTCTACCA |
| | | ACACATTTACAGATGTGAGCACCAACCCCTCCACCTCTCTG |
| | | ATAATGACAGAATCTTCAGGAGTGACCATCACCACCCAAAC |
| | | AGGTCCTACTGGAGCTGCAACACAGGGTCCATATCTCTTGG |
| | | ACACATCAACCATGCCTTACTTGACAGAGACTCCATTAGCT |
| | | GTGACTCCAGATTTTATGCAATCAGAGAAGACCACTCTCAT |
| | | AAGCAAAGGTCCCAAGGATGTGTCCTGGACAAGCCCTCCCT |
| | | CTGTGGCAGAAACCAGCTATCCCTCTTCCCTGACACCTTTCT |
| | | TGGTCACAACCATACCTCCTGCCACTTCCACGTTACAAGGG |
| | | CAACATACATCCTCTCCTGTTTCTGCGACTTCAGTTCTTACC |
| | | TCTGGACTGGTGAAGACCACAGATATGTTGAACACAAGCAT |
| | | GGAACCTGTGACCAATTCACCTCAAAATTTGAACAATCCAT |
| | | CAAATGAGATACTGGCCACTTTGGCAGCCACCACAGATATA |
| | | GAGACTATTCATCCTTCCATAAACAAAGCAGTGACCAATAT |
| | | GGGGACTGCCAGTTCAGCACATGTACTGCATTCCACTCTCC |
| | | CAGTCAGCTCAGAACCATCTACAGCCACATCTCCAATGGTT |
| | | CCTGCCTCCAGCATGGGGGACGCTCTTGCTTCTATATCAATA |
| | | CCTGGTTCTGAGACCACAGACATTGAGGGAGAGCCAACATC |
| | | CTCCCTGACTGCTGGACGAAAAGAGAACAGCACCCTCCAGG |
| | | AGATGAACTCAACTACAGAGTCAAACATCATCCTCTCCAAT |
| | | GTGTCTGTGGGGGCTATTACTGAAGCCACAAAAATGGAAGT |
| | | CCCCTCTTTTGATGCAACATTCATACCAACTCCTGCTCAGTC |
| | | AACAAAGTTCCCAGATATTTTCTCAGTAGCCAGCAGTAGAC |
| | | TTTCAAACTCTCCTCCCATGACAATATCTACCCACATGACCA |
| | | CCACCCAGACAGGGTCTTCTGGAGCTACATCAAAGATTCCA |
| | | CTTGCCTTAGACACATCAACCTTGGAAACCTCAGCAGGGAC |
| | | TCCATCAGTGGTGACTGAGGGGTTTGCCCACTCAAAAATAA |
| | | CCACTGCAATGAACAATGATGTCAAGGACGTGTCACAGACA |
| | | AACCCTCCCTTTCAGGATGAAGCCAGCTCTCCCTCTTCTCAA |
| | | GCACCTGTCCTTGTCACAACCTTACCTTCTTCTGTTGCTTTCA |
| | | CACCGCAATGGCACAGTACCTCCTCTCCTGTTTCTATGTCCT |
| | | CAGTTCTTACTTCTTCACTGGTAAAGACCGCAGGCAAGGTG |
| | | GATACAAGCTTAGAAACAGTGACCAGTTCACCTCAAAGTAT |
| | | GAGCAACACTTTGGATGACATATCGGTCACTTCAGCAGCCA |
| | | CCACAGATATAGAGACAACGCATCCTTCCATAAACACAGTA |
| | | GTTACCAATGTGGGGACCACCGGTTCAGCATTTGAATCACA |
| | | TTCTACTGTCTCAGCTTACCCAGAGCCATCTAAAGTCACATC |
| | | TCCAAATGTTACCACCTCCACCATGGAAGACACCACAATTT |
| | | CCAGATCAATACCTAAATCCTCTAAGACTACAAGAACTGAG |
| | | ACTGAGACAACTTCCTCCCTGACTCCTAAACTGAGGGAGAC |
| | | CAGCATCTCCCAGGAGATCACCTCGTCCACAGAGACAAGCA |
| | | CTGTTCCTTACAAAGAGCTCACTGGTGCCACTACCGAGGTA |
| | | TCCAGGACAGATGTCACTTCCTCTAGCAGTACATCCTTCCCT |
| | | GGCCCTGATCAGTCCACAGTGTCACTAGACATCTCCACAGA |
| | | AACCAACACCAGGCTGTCTACCTCCCCAATAATGACAGAAT |
| | | CTGCAGAAATAACCATCACCACCCAAACAGGTCCTCATGGG |
| | | GCTACATCACAGGATACTTTTACCATGGACCCATCAAATAC |
| | | AACCCCCCAGGCAGGGATCCACTCAGCTATGACTCATGGAT |
| | | TTTCACAATTGGATGTGACCACTCTTATGAGCAGAATTCCAC |
| | | AGGATGTATCATGGACAAGTCCTCCCTCTGTGGATAAAACC |
| | | AGCTCCCCCTCTTCCTTTCTGTCCTCACCTGCAATGACCACA |
| | | CCTTCCCTGATTTCTTCTACCTTACCAGAGGATAAGCTCTCC |
| | | TCTCCTATGACTTCACTTCTCACCTCTGGCCTAGTGAAGATT |
| | | ACAGACATATTACGTACACGCTTGGAACCTGTGACCAGCTC |
| | | ACTTCCAAATTTCAGCAGCACCTCAGATAAGATACTGGCCA |
| | | CTTCTAAAGACAGTAAAGACACAAAGGAAATTTTTCCTTCT |
| | | ATAAACACAGAAGAGACCAATGTGAAAGCCAACAACTCTG |
| | | GACATGAATCCCATTCCCCTGCACTGGCTGACTCAGAGACA |
| | | CCCAAAGCCACAACTCAAATGGTTATCACCACCACTGTGGG |
| | | AGATCCAGCTCCTTCCACATCAATGCCAGTGCATGGTTCCTC |
| | | TGAGACTACAAACATTAAGAGAGAGCCAACATATTTCTTGA |
| | | CTCCTAGACTGAGAGAGACCAGTACCTCTCAGGAGTCCAGC |
| | | TTTCCCACGGACACAAGTTTTCTACTTTCCAAAGTCCCCACT |
| | | GGTACTATTACTGAGGTCTCCAGTACAGGGGTCAACTCTTCT |

TABLE 13-continued

Table of Sequences.

| SEQ ID NO | NAME | SEQ |
|---|---|---|
| | | AGCAAAATTTCCACCCCAGACCATGATAAGTCCACAGTGCC |
| | | ACCTGACACCTTCACAGGAGAGATCCCCAGGGTCTTCACCT |
| | | CCTCTATTAAGACAAAATCTGCAGAAATGACGATCACCACC |
| | | CAAGCAAGTCCTCCTGAGTCTGCATCGCACAGTACCCTTCC |
| | | CTTGGACACATCAACCACACTTTCCCAGGGAGGGACTCATT |
| | | CAACTGTGACTCAGGGATTCCCATACTCAGAGGTGACCACT |
| | | CTCATGGGCATGGGTCCTGGGAATGTGTCATGGATGACAAC |
| | | TCCCCCTGTGGAAGAAACCAGCTCTGTGTCTTCCCTGATGTC |
| | | TTCACCTGCCATGACATCCCCTTCTCCTGTTTCCTCCACATC |
| | | ACCACAGAGCATCCCCTCCTCTCCTCTTCCTGTGACTGCACT |
| | | TCCTACTTCTGTTCTGGTGACAACCACAGATGTGTTGGGCAC |
| | | AACAAGCCCAGAGTCTGTAACCAGTTCACCTCCAAATTTGA |
| | | GCAGCATCACTCATGAGAGACCGGCCACTTACAAAGACACT |
| | | GCACACACAGAAGCCGCCATGCATCATTCCACAAACACCGC |
| | | AGTGACCAATGTAGGGACTTCCGGGTCTGGACATAAATCAC |
| | | AATCCTCTGTCCTAGCTGACTCAGAGACATCGAAAGCCACA |
| | | CCTCTGATGAGTACCACCTCCACCCTGGGGGACACAAGTGT |
| | | TTCCACATCAACTCCTAATATCTCTCAGACTAACCAAATTCA |
| | | AACAGAGCCAACAGCATCCCTGAGCCCTAGACTGAGGGAG |
| | | AGCAGCACGTCTGAGAAGACCAGCTCAACAACAGAGACAA |
| | | ATACTGCCTTTTCTTATGTGCCCACAGGTGCTATTACTCAGG |
| | | CCTCCAGAACAGAAATCTCCTCTAGCAGAACATCCATCTCA |
| | | GACCTTGATCGGCCCACAATAGCACCCGACATCTCCACAGG |
| | | AATGATCACCAGGCTCTTCACCTCCCCCATCATGACAAAAT |
| | | CTGCAGAAATGACCGTCACCACTCAAACAACTACTCCTGGG |
| | | GCTACATCACAGGGTATCCTTCCCTGGGACACATCAACCAC |
| | | ACTTTTCCAGGGAGGGACTCATTCAACCGTGTCTCAGGGAT |
| | | TCCCACACTCAGAGATAACCACTCTTCGGAGCAGAACCCCT |
| | | GGAGATGTGTCATGGATGACAACTCCCCCTGTGGAAGAAAC |
| | | CAGCTCTGGGTTTTCCCTGATGTCACCTTCCATGACATCCCC |
| | | TTCTCCTGTTTCCTCCACATCACCAGAGAGCATCCCCTCCTC |
| | | TCCTCTCCCTGTGACTGCACTTCTTACTTCTGTTCTGGTGAC |
| | | ACCACAAATGTATTGGGCACAACAAGCCCAGAGCCCGTA |
| | | ACGAGTTCACCTCCAAATTTAAGCAGCCCCACACAGGAGAG |
| | | ACTGACCACTTACAAAGACACTGCGCACACAGAAGCCATGC |
| | | ATGCTTCCATGCATACAAACACTGCAGTGGCCAACGTGGGG |
| | | ACCTCCATTTCTGGACATGAATCACAATCTTCTGTCCCAGCT |
| | | GATTCACACACATCCAAAGCCACATCTCCAATGGGTATCAC |
| | | CTTCGCCATGGGGGATACAAGTGTTTCTACATCAACTCCTGC |
| | | CTTCTTTGAGACTAGAATTCAGACTGAATCAACATCCTCTTT |
| | | GATTCCTGGATTAAGGGACACCAGGACGTCTGAGGAGATCA |
| | | ACACTGTGACAGAGACCAGCACTGTCCTTTCAGAAGTGCCC |
| | | ACTACTACTACTACTGAGGTCTCCAGGACAGAAGTTATCAC |
| | | TTCCAGCAGAACAACCATCTCAGGGCCTGATCATTCCAAAA |
| | | TGTCACCCTACATCTCCACAGAAACCATCACCAGGCTCTCC |
| | | ACTTTTCCTTTTGTAACAGGATCCACAGAAATGGCCATCACC |
| | | AACCAAACAGGTCCTATAGGGACTATCTCACAGGCTACCCT |
| | | TACCCTGGACACATCAAGCACAGCTTCCTGGGAAGGGACTC |
| | | ACTCACCTGTGACTCAGAGATTTCCACACTCAGAGGAGACC |
| | | ACTACTATGAGCAGAAGTACTAAGGGCGTGTCATGGCAAAG |
| | | CCCTCCCTCTGTGGAAGAAACCAGTTCTCCTTCTTCCCCAGT |
| | | GCCTTTACCTGCAATAACCTCACATTCATCTCTTTATTCCGC |
| | | AGTATCAGGAAGTAGCCCCACTTCTGCTCTCCCTGTGACTTC |
| | | CCTTCTCACCTCTGGCAGGAGGAAGACCATAGACATGTTGG |
| | | ACACACACTCAGAACTTGTGACCAGCTCCTTACCAAGTGCA |
| | | AGTAGCTTCTCAGGTGAGATACTCACTTCTGAAGCCTCCAC |
| | | AAATACAGAGACAATTCACTTTTCAGAGAACACAGCAGAA |
| | | ACCAATATGGGGACCACCAATTCTATGCATAAACTACATTC |
| | | CTCTGTCTCAATCCACTCCCAGCCATCCGGACACACACCTCC |
| | | AAAGGTTACTGGATCTATGATGGAGGACGCTATTGTTTCCA |
| | | CATCAACACCTGGTTCTCCTGAGACTAAAAATGTTGACAGA |
| | | GACTCAACATCCCCTCTGACTCCTGAACTGAAAGAGGACAG |
| | | CACCGCCCTGGTGATGAACTCAACTACAGAGTCAAACACTG |
| | | TTTTCTCCAGTGTGTCCCTGGATGCTGCTACTGAGGTCTCCA |
| | | GGGCAGAAGTCACCTACTATGATCCTACATTCATGCCAGCT |
| | | TCTGCTCAGTCAACAAAGTCCCCAGACATTTCACCTGAAGC |
| | | CAGCAGCAGTCATTCTAACTCTCCTCCCTTGACAATATCTAC |
| | | ACACAAGACCATCGCCACACAAACAGGTCCTTCTGGGGTGA |
| | | CATCTCTTGGCCAACTGACCCTGGACACATCAACCATAGCC |
| | | ACCTCAGCAGGAACTCCATCAGCCAGAACTCAGGATTTTGT |
| | | AGATTCAGAAACAACCAGTGTCATGAACAATGATCTCAATG |
| | | ATGTGTTGAAGACAAGCCCTTTCTCTGCAGAAGAAGCCAAC |
| | | TCTCTCTCTTCTCAGGCACCTCTCCTTGTGACAACCTCACCT |
| | | TCTCCTGTAACTTCCACATTGCAAGAGCACAGTACCTCCTCT |

TABLE 13-continued

Table of Sequences.

| SEQ ID NO | NAME | SEQ |
|---|---|---|
| | | CTTGTTTCTGTGACCTCAGTACCCACCCCTACACTGGCGAAG |
| | | ATCACAGACATGGACACAAACTTAGAACCTGTGACTCGTTC |
| | | ACCTCAAAATTTAAGGAACACCTTGGCCACTTCAGAAGCCA |
| | | CCACAGATACACACACAATGCATCCTTCTATAAACACAGCA |
| | | GTGGCCAATGTGGGGACCACCAGTTCACCAAATGAATTCTA |
| | | TTTTACTGTCTCACCTGACTCAGACCCATATAAAGCCACATC |
| | | CGCAGTAGTTATCACTTCCACCTCGGGGGACTCAATAGTTTC |
| | | CACATCAATGCCTAGATCCTCTGCGATGAAAAAGATTGAGT |
| | | CTGAGACAACTTTCTCCCTGATATTTAGACTGAGGGAGACT |
| | | AGCACCTCCCAGAAAATTGGCTCATCCTCAGACACAAGCAC |
| | | GGTCTTTGACAAAGCATTCACTGCTGCTACTACTGAGGTCTC |
| | | CAGAACAGAACTCACCTCCTCTAGCAGAACATCCATCCAAG |
| | | GCACTGAAAAGCCCACAATGTCACCGGACACCTCCACAAGA |
| | | TCTGTCACCATGCTTTCTACTTTTGCTGGCCTGACAAAATCC |
| | | GAAGAAAGGACCATTGCCACCCAAACAGGTCCTCATAGGG |
| | | CGACATCACAGGGTACCCTTACCTGGGACACATCAATCACA |
| | | ACCTCACAGGCAGGGACCCACTCAGCTATGACTCATGGATT |
| | | TTCACAATTAGATTTGTCCACTCTTACGAGTAGAGTTCCTGA |
| | | GTACATATCAGGGACAAGCCCACCCTCTGTGGAAAAAACCA |
| | | GCTCTTCCTCTTCCCTTCTGTCTTTACCAGCAATAACCTCAC |
| | | CGTCCCCTGTACCTACTACATTACCAGAAAGTAGGCCGTCTT |
| | | CTCCTGTTCATCTGACTTCACTCCCCACCTCTGGCCTAGTGA |
| | | AGACCACAGATATGCTGGCATCTGTGGCCAGTTTACCTCCA |
| | | AACTTGGGCAGCACCTCACATAAGATACCGACTACTTCAGA |
| | | AGACATTAAAGATACAGAGAAAATGTATCCTTCCACAAACA |
| | | TAGCAGTAACCAATGTGGGGACCACCACTTCTGAAAAGGAA |
| | | TCTTATTCGTCTGTCCCAGCCTACTCAGAACCACCCAAAGTC |
| | | ACCTCTCCAATGGTTACCTCTTTCAACATAAGGGACACCATT |
| | | GTTTCCACATCCATGCCTGGCTCCTCTGAGATTACAAGGATT |
| | | GAGATGGAGTCAACATTCTCCCTGGCTCATGGGCTGAAGGG |
| | | AACCAGCACCTCCCAGGACCCCATCGTATCCACAGAGAAAA |
| | | GTGCTGTCCTTCACAAGTTGACCACTGGTGCTACTGAGACCT |
| | | CTAGGACAGAAGTTGCCTCTTCTAGAAGAACATCCATTCCA |
| | | GGCCCTGATCATTCCACAGAGTCACCAGACATCTCCACTGA |
| | | AGTGATCCCCAGCCTGCCTATCTCCCTTGGCATTACAGAATC |
| | | TTCAAATATGACCATCATCACTCGAACAGGTCCTCCTCTTGG |
| | | CTCTACATCACAGGGCACATTTACCTTGGACACACCAACTA |
| | | CATCCTCCAGGGCAGGAACACACTCGATGGCGACTCAGGAA |
| | | TTTCCACACTCAGAAATGACCACTGTCATGAACAAGGACCC |
| | | TGAGATTCTATCATGGACAATCCCTCCTTCTATAGAGAAAA |
| | | CCAGCTTCTCCTCTTCCCTGATGCCTTCACCAGCCATGACTT |
| | | CACCTCCTGTTTCCTCAACATTACCAAAGACCATTCACACCA |
| | | CTCCTTCTCCTATGACCTCACTGCTCACCCCTAGCCTAGTGA |
| | | TGACCACAGACACATTGGGCACAAGCCCAGAACCTACAACC |
| | | AGTTCACCTCCAAATTTGAGCAGTACCTCACATGAGATACT |
| | | GACAACAGATGAAGACACCACAGCTATAGAAGCCATGCAT |
| | | CCTTCCACAAGCACAGCAGCGACTAATGTGGAAACCACCAG |
| | | TTCTGGACATGGGTCACAATCCTCTGTCCTAGCTGACTCAGA |
| | | AAAAACCAAGGCCACAGCTCCAATGGATACCACCTCCACCA |
| | | TGGGGCATACAACTGTTTCCACATCAATGTCTGTTTCCTCTG |
| | | AGACTACAAAAATTAAGAGAGAGTCAACATATTCCTTGACT |
| | | CCTGGACTGAGAGAGACCAGCATTTCCCAAAATGCCAGCTT |
| | | TTCCACTGACACAAGTATTGTTCTTTCAGAAGTCCCCACTGG |
| | | TACTACTGCTGAGGTCTCCAGGACAGAAGTCACCTCCTCTG |
| | | GTAGAACATCCATCCCTGGCCCTTCTCAGTCCACAGTTTTGC |
| | | CAGAAATATCCACAAGAACAATGACAAGGCTCTTTGCCTCG |
| | | CCCACCATGACAGAATCAGCAGAAATGACCATCCCCACTCA |
| | | AACAGGTCCTTCTGGGTCTACCTCACAGGATACCCTTACCTT |
| | | GGACACATCCACCACAAAGTCCCAGGCAAAGACTCATTCAA |
| | | CTTTGACTCAGAGATTTCCACACTCAGAGATGACCACTCTC |
| | | ATGAGCAGAGGTCCTGGAGATATGTCATGGCAAAGCTCTCC |
| | | CTCTCTGGAAAATCCCAGCTCTCTCCCTTCCCTGCTGTCTTT |
| | | ACCTGCCACAACCTCACCTCCTCCCATTTCCTCCACATTACC |
| | | AGTGACTATCTCCTCCTCTCCTCTTCCTGTGACTTCACTTCTC |
| | | ACCTCTAGCCCGGTAACGACCACAGACATGTTACACACAAG |
| | | CCCAGAACTTGTAACCAGTTCACCTCCAAAGCTGAGCCACA |
| | | CTTCAGATGAGAGACTGACCACTGGCAAGGACACCACAAAT |
| | | ACAGAAGCTGTGCATCCTTCCACAAACACAGCAGCGTCCAA |
| | | TGTGGAGATTCCCAGCTCTGGACATGAATCCCCTTCCTCTGC |
| | | CTTAGCTGACTCAGAGACATCCAAAGCCACATCACCAATGT |
| | | TTATTACCTCCACCCAGGAGGATACAACTGTTGCCATATCA |
| | | ACCCCTCACTTCTTGGAGACTAGCAGAATTCAGAAAGAGTC |
| | | AATTTCCTCCCTGAGCCCTAAATTGAGGGAGACAGGCAGTT |
| | | CTGTGGAGACAAGCTCAGCCATAGAGACAAGTGCTGTCCTT |

TABLE 13-continued

| SEQ ID NO | NAME | SEQ |
|---|---|---|
| | | TCTGAAGTGTCCATTGGTGCTACTACTGAGATCTCCAGGAC AGAAGTCACCTCCTCTAGCAGAACATCCATCTCTGGTTCTGC TGAGTCCACAATGTTGCCAGAAATATCCACCACAAGAAAAA TCATTAAGTTCCCTACTTCCCCCATCCTGGCAGAATCATCAG AAATGACCATCAAGACCCAAACAAGTCCTCCTGGGTCTACA TCAGAGAGTACCTTTACATTAGACACATCAACCCACTCCCTC CTTGGTAATAACCCATTCGACTATGACTCAGAGATTGCCAC ACTCAGAGATAACCACTCTTGTGAGTAGAGGTGCTGGGGAT GTGCCACGGCCCAGCTCTCTCCCTGTGGAAGAAACAAGCCC TCCATCTTCCCAGCTGTCTTTATCTGCCATGATCTCACCTTCT CCTGTTTCTTCCACATTACCAGCAAGTAGCCACTCCTCTTCT GCTTCTGTGACTTCACTTCTCACACCAGGCCAAGTGAAGAC TACTGAGGTGTTGGACGCAAGTGCAGAACCTGAAACCAGTT CACCTCCAAGTTTGAGCAGCACCTCAGTTGAAATACTGGCC ACCTCTGAAGTCACCACAGATACGGAGAAAATTCATCCTTT CTCAAACACGGCAGTAACCAAAGTTGGAACTTCCAGTTCTG GACATGAATCCCCTTCCTCTGTCCTACCTGACTCAGAGACA ACCAAAGCCACATCGGCAATGGGTACCATCTCCATTATGGG GGATACAAGTGTTTCTACATTAACTCCTGCCTTATCTAACAC TAGGAAAATTCAGTCAGAGCCAGCTTCCTCACTGACCACCA GATTGAGGGAGACCAGCACCTCTGAAGAGACCAGCTTAGCC ACAGAAGCAAACACTGTTCTTTCTAAAGTGTCCACTGGTGC TACTACTGAGGTCTCCAGGACAGAAGCCATCTCCTTTAGCA GAACATCCATGTCAGGCCCTGAGCAGTCCACAATGTCACAA GACATCTCCATAGGAACCATCCCCAGGATTTCTGCCTCCTCT GTCCTGACAGAATCTGCAAAAATGACCATCACAACCCAAAC AGGTCCTTCGGAGTCTACACTAGAAAGTACCCTTAATTTGA ACACAGCAACCACACCCTCTTGGGTGGAAACCCACTCTATA GTAATTCAGGGATTTCCACACCCAGAGATGACCACTTCCAT GGGCAGAGGTCCTGGAGGTGTGTCATGGCCTAGCCCTCCCT TTGTGAAAGAAACCAGCCCTCCATCCTCCCCGCTGTCTTTAC CTGCCGTGACCTCACCTCATCCTGTTTCCACCACATTCCTAG CACATATCCCCCCCTCTCCCCTTCCTGTGACTTCACTTCTCA CCTCTGGCCCGGCGACAACCACAGATATCTTGGGTACAAGC ACAGAACCTGGAACCAGTTCATCTTCAAGTTTGAGCACCAC CTCCCATGAGAGACTGACCACTTACAAAGACACTGCACATA CAGAAGCCGTGCATCCTTCCACAAACACAGGAGGGACCAAT GTGGCAACCACCAGCTCTGGATATAAATCACAGTCCTCTGT CCTAGCTGACTCATCTCCAATGTGTACCACCTCCACCATGGG GGATACAAGTGTTCTCACATCAACTCCTGCCTTCCTTGAGAC TAGGAGGATTCAGACAGAGCTAGCTTCCTCCCTGACCCCTG GATTGAGGGAGTCCAGCGGCTCTGAAGGGACCAGCTCAGG CACCAAGATGAGCACTGTCCTCTCTAAAGTGCCCACTGGTG CTACTACTGAGATCTCCAAGGAAGACGTCACCTCCATCCCA GGTCCCGCTCAATCCACAATATCACCAGACATCTCCACAAG AACCGTCAGCTGGTTCTCTACATCCCCTGTCATGACAGAATC AGCAGAAATAACCATGAACACCCATACAAGTCCTTTAGGGG CCACAACACAAGGCACCAGTACTTTGGACACGTCAAGCACA ACCTCTTTGACAATGACACACTCAACTATATCTCAAGGATTT TCACACTCACAGATGAGCACTCTTATGAGGAGGGGTCCTGA GGATGTATCATGGATGAGCCCTCCCCTTCTGGAAAAAACTA GACCTTCCTTTTCTCTGATGTCTTCACCAGCCACAACTTCAC CTTCTCCTGTTTCCTCCACATTACCAGAGAGCATCTCTTCCT CTCCTCTTCCTGTGACTTCACTCCTCACGTCTGGCTTGGCAA AAACTACAGATATGTTGCACAAAAGCTCAGAACCTGTAACC AACTCACCTGCAAATTTGAGCAGCACCTCAGTTGAAATACT GGCCACCTCTGAAGTCACCACAGATACAGAGAAAACTCATC CTTCTTCAAACAGAACAGTGACCGATGTGGGGACCTCCAGT TCTGGACATGAATCCACTTCCTTTGTCCTAGCTGACTCACAG ACATCCAAAGTCACATCTCCAATGGTTATTACCTCCACCATG GAGGATACGAGTGTCTCCACATCAACTCCTGGCTTTTTTGAG ACTAGCAGAATTCAGACAGAACCAACATCCTCCCTGACCCT TGGACTGAGAAAGACCAGCAGCTCTGAGGGGACCAGCTTA GCCACAGAGATGAGCACTGTCCTTTCTGGAGTGCCCACTGG TGCCACTGCTGAAGTCTCCAGGACAGAAGTCACCTCCTCTA GCAGAACATCCATCTCAGGCTTTGCTCAGCTCACAGTGTCA CCAGAGACTTCCACAGAAACCATCACCAGACTCCCTACCTC CAGCATAATGACAGAATCAGCAGAAATGATGATCAAGACA CAAACAGATCCTCCTGGGTCTACACCAGAGAGTACTCATAC TGTGGACATATCAACAACACCCAACTGGGTAGAAACCCACT CGACTGTGACTCAGAGATTTTCACACTCAGAGATGACCACT CTTGTGAGCAGAAGCCCTGGTGATATGTTATGGCCTAGTCA ATCCTCTGTGGAAGAAACCAGCTCTGCCTCTTCCCTGCTGTC TCTGCCTGCCACGACCTCACCTTCTCCTGTTTCCTCTACATT |

TABLE 13-continued

Table of Sequences.

| SEQ ID NO | NAME | SEQ |
|---|---|---|
| | | AGTAGAGGATTTCCCTTCCGCTTCTCTTCCTGTGACTTCTCTT |
| | | CTCAACCCTGGCCTGGTGATAACCACAGACAGGATGGGCAT |
| | | AAGCAGAGAACCTGGAACCAGTTCCACTTCAAATTTGAGCA |
| | | GCACCTCCCATGAGAGACTGACCACTTTGGAAGACACTGTA |
| | | GATACAGAAGACATGCAGCCTTCCACACACACAGCAGTGAC |
| | | CAACGTGAGGACCTCCATTTCTGGACATGAATCACAATCTT |
| | | CTGTCCTATCTGACTCAGAGACACCCAAAGCCACATCTCCA |
| | | ATGGGTACCACCTACACCATGGGGGAAACGAGTGTTTCCAT |
| | | ATCCACTTCTGACTTCTTTGAGACCAGCAGAATTCAGATAG |
| | | AACCAACATCCTCCCTGACTTCTGGATTGAGGGAGACCAGC |
| | | AGCTCTGAGAGGATCAGCTCAGCCACAGAGGGAAGCACTG |
| | | TCCTTTCTGAAGTGCCCAGTGGTGCTACCACTGAGGTCTCCA |
| | | GGACAGAAGTGATATCCTCTAGGGGAACATCCATGTCAGGG |
| | | CCTGATCAGTTCACCATATCACCAGACATCTCTACTGAAGC |
| | | GATCACCAGGCTTTCTACTTCCCCCATTATGACAGAATCAGC |
| | | AGAAAGTGCCATCACTATTGAGACAGGTTCTCCTGGGGCTA |
| | | CATCAGAGGGTACCCTCACCTTGGACACCTCAACAACAACC |
| | | TTTTGGTCAGGGACCCACTCAACTGCATCTCCAGGATTTTCA |
| | | CACTCAGAGATGACCACTCTTATGAGTAGAACTCCTGGAGA |
| | | TGTGCCATGGCCGAGCCTTCCCTCTGTGGAAGAAGCCAGCT |
| | | CTGTCTCTTCCTCACTGTCTTCACCTGCCATGACCTCAACTT |
| | | CTTTTTTCTCCACATTACCAGAGAGCATCTCCTCCTCTCCTC |
| | | ATCCTGTGACTGCACTTCTCACCCTTGGCCCAGTGAAGACC |
| | | ACAGACATGTTGCGCACAAGCTCAGAACCTGAAACCAGTTC |
| | | ACCTCCAAATTTGAGCAGCACCTCAGCTGAAATATTAGCCA |
| | | CGTCTGAAGTCACCAAAGATAGAGAGAAAATTCATCCCTCC |
| | | TCAAACACACCTGTAGTCAATGTAGGGACTGTGATTTATAA |
| | | ACATCTATCCCCTTCCTCTGTTTTGGCTGACTTAGTGACAAC |
| | | AAAACCCACATCTCCAATGGCTACCACCTCCACTCTGGGGA |
| | | ATACAAGTGTTTCCACATCAACTCCTGCCTTCCCAGAAACTA |
| | | TGATGACACAGCCAACTTCCTCCCTGACTTCTGGATTAAGG |
| | | GAGATCAGTACCTCTCAAGAGACCAGCTCAGCAACAGAGA |
| | | GAAGTGCTTCTCTTTCTGGAATGCCCACTGGTGCTACTACTA |
| | | AGGTCTCCAGAACAGAAGCCCTCTCCTTAGGCAGAACATCC |
| | | ACCCCAGGTCCTGCTCAATCCACAATATCACCAGAAATCTC |
| | | CACGGAAACCATCACTAGAATTTCTACTCCCCTCACCACGA |
| | | CAGGATCAGCAGAAATGACCATCACCCCCAAAACAGGTCAT |
| | | TCTGGGGCATCCTCACAAGGTACCTTTACCTTGGACACATC |
| | | AAGCAGAGCCTCCTGGCCAGGAACTCACTCAGCTGCAACTC |
| | | ACAGATCTCCACACTCAGGGATGACCACTCCTATGAGCAGA |
| | | GGTCCTGAGGATGTGTCATGGCCAAGCCGCCCATCAGTGGA |
| | | AAAAACTAGCCCTCCATCTTCCCTGGTGTCTTTATCTGCAGT |
| | | AACCTCACCTTCGCCACTTTATTCCACACCATCTGAGAGTAG |
| | | CCACTCATCTCCTCTCCGGGTGACTTCTCTTTTCACCCCTGTC |
| | | ATGATGAAGACCACAGACATGTTGGACACAAGCTTGGAACC |
| | | TGTGACCACTTCACCTCCCAGTATGAATATCACCTCAGATG |
| | | AGAGTCTGGCCACTTCTAAAGCCACCATGGAGACAGAGGCA |
| | | ATTCAGCTTTCAGAAAACACAGCTGTGACTCAGATGGGCAC |
| | | CATCAGCGCTAGACAAGAATTCTATTCCTCTTATCCAGGCCT |
| | | CCCAGAGCCATCCAAAGTGACATCTCCAGTGGTCACCTCTT |
| | | CCACCATAAAAGACATTGTTTCTACAACCATACCTGCTTCCT |
| | | CTGAGATAACAAGAATTGAGATGGAGTCAACATCCACCCTG |
| | | ACCCCCACACCAAGGGAGACCAGCACCTCCCAGGAGATCC |
| | | ACTCAGCCACAAAGCCAAGCACTGTTCCTTACAAGGCACTC |
| | | ACTAGTGCCACGATTGAGGACTCCATGACACAAGTCATGTC |
| | | CTCTAGCAGAGGACCTAGCCCTGATCAGTCCACAATGTCAC |
| | | AAGACATATCCACTGAAGTGATCACCAGGCTCTCTACCTCC |
| | | CCCATCAAGACAGAATCTACAGAAATGACCATTACCACCCA |
| | | AACAGGTTCTCCTGGGGCTACATCAAGGGGTACCCTTACCT |
| | | TGGACACTTCAACAACTTTTATGTCAGGGACCCACTCAACT |
| | | GCATCTCAAGGATTTTCACACTCACAGATGACCGCTCTTATG |
| | | AGTAGAACTCCTGGAGATGTGCCATGGCTAAGCCATCCCTC |
| | | TGTGGAAGAAGCCAGCTCTGCCTCTTTCTCACTGTCTTCACC |
| | | TGTCATGACCTCATCTTCTCCCGTTTCTTCCACATTACCAGA |
| | | CAGCATCCACTCTTCTTCGCTTCCTGTGACATCACTTCTCAC |
| | | CTCAGGGCTGGTGAAGACCACAGAGCTGTTGGGCACAAGCT |
| | | CAGAACCTGAAACCAGTTCACCCCCAAATTTGAGCAGCACC |
| | | TCAGCTGAAATACTGGCCATCACTGAAGTCACTACAGATAC |
| | | AGAGAAACTGGAGATGACCAATGTGGTAACCTCAGGTTATA |
| | | CACATGAATCTCCTTCCTCTGTCCTAGCTGACTCAGTGACAA |
| | | CAAAGGCCACATCTTCAATGGGTATCACCTACCCCACAGGA |
| | | GATACAAATGTTCTCACATCAACCCCTGCCTTCTCTGACACC |
| | | AGTAGGATTCAAACAAAGTCAAAGCTCTCACTGACTCCTGG |
| | | GTTGATGGAGACCAGCATCTCTGAAGAGACCAGCTCTGCCA |

TABLE 13-continued

| Table of Sequences. | | |
|---|---|---|
| SEQ ID NO | NAME | SEQ |
| | | CAGAAAAAAGCACTGTCCTTTCTAGTGTGCCCACTGGTGCT<br>ACTACTGAGGTCTCCAGGACAGAAGCCATCTCTTCTAGCAG<br>AACATCCATCCCAGGCCCTGCTCAATCCACAATGTCATCAG<br>ACACCTCCATGGAAACCATCACTAGAATTTCTACCCCCCTC<br>ACAAGGAAAGAATCAACAGACATGGCCATCACCCCCAAAA<br>CAGGTCCTTCTGGGGCTACCTCGCAGGGTACCTTTACCTTGG<br>ACTCATCAAGCACAGCCTCCTGGCCAGGAACTCACTCAGCT<br>ACAACTCAGAGATTTCCACAGTCAGTGGTGACAACTCCTAT<br>GAGCAGAGGTCCTGAGGATGTGTCATGGCCAAGCCCGCTGT<br>CTGTGGAAAAAAACAGCCCTCCATCTTCCCTGGTATCTTCAT<br>CTTCAGTAACCTCACCTTCGCCACTTTATTCCACACCATCTG<br>GGAGTAGCCACTCCTCTCCTGTCCCTGTCACTTCTCTTTTCA<br>CCTCTATCATGATGAAGGCCACAGACATGTTGGATGCAAGT<br>TTGGAACCTGAGACCACTTCAGCTCCCAATATGAATATCAC<br>CTCAGATGAGAGTCTGGCCGCTTCTAAAGCCACCACGGAGA<br>CAGAGGCAATTCACGTTTTTGAAAATACAGCAGCGTCCCAT<br>GTGGAAACCACCAGTGCTACAGAGGAACTCTATTCCTCTTC<br>CCCAGGCTTCTCAGAGCCAACAAAAGTGATATCTCCAGTGG<br>TCACCTCTTCCTCTATAAGAGACAACATGGTTTCCACAACA<br>ATGCCTGGCTCCTCTGGCATTACAAGGATTGAGATAGAGTC<br>AATGTCATCTCTGACCCCTGGACTGAGGGAGACCAGAACCT<br>CCCAGGACATCACCTCATCCACAGAGACAAGCACTGTCCTT<br>TACAAGATGCCCTCTGGTGCCACTCCTGAGGTCTCCAGGAC<br>AGAAGTTATGCCCTCTAGCAGAACATCCATTCCTGGCCCTG<br>CTCAGTCCACAATGTCACTAGACATCTCCGATGAAGTTGTC<br>ACCAGGCTGTCTACCTCTCCCATCATGACAGAATCTGCAGA<br>AATAACCATCACCACCCAAACAGGTTATTCTCTGGCTACAT<br>CCCAGGTTACCCTTCCCTTGGGCACCTCAATGACCTTTTTGT<br>CAGGGACCCACTCAACTATGTCTCAAGGACTTTCACACTCA<br>GAGATGACCAATCTTATGAGCAGGGGTCCTGAAAGTCTGTC<br>ATGGACGAGCCCTCGCTTTGTGGAAACAACTAGATCTTCCT<br>CTTCTCTGACATCATTACCTCTCACGACCTCACTTTCTCCTGT<br>GTCCTCCACATTACTAGACAGTAGCCCCTCCTCTCCTCTTCC<br>TGTGACTTCACTTATCCTCCCAGGCCTGGTGAAGACTACAG<br>AAGTGTTGGATACAAGCTCAGAGCCTAAAACCAGTTCATCT<br>CCAAATTTGAGCAGCACCTCAGTTGAAATACCGGCCACCTC<br>TGAAATCATGACAGATACAGAGAAAATTCATCCTTCCTCAA<br>ACACAGCGGTGGCCAAAGTGAGGACCTCCAGTTCTGTTCAT<br>GAATCTCATTCCTCTGTCCTAGCTGACTCAGAAACAACCAT<br>AACCATACCTTCAATGGGTATCACCTCCGCTGTGGACGATA<br>CCACTGTTTTCACATCAAATCCTGCCTTCTCTGAGACTAGGA<br>GGATTCCGACAGAGCCAACATTCTCATTGACTCCTGGATTC<br>AGGGAGACTAGCACCTCTGAAGAGACCACCTCAATCACAG<br>AAACAAGTGCAGTCCTTTATGGAGTGCCCACTAGTGCTACT<br>ACTGAAGTCTCCATGACAGAAATCATGTCCTCTAATAGAAT<br>ACACATCCCTGACTCTGATCAGTCCACGATGTCTCCAGACA<br>TCATCACTGAAGTGATCACCAGGCTCTCTTCCTCATCCATGA<br>TGTCAGAATCAACACAAATGACCATCACCACCCAAAAAAGT<br>TCTCCTGGGGCTACAGCACAGAGTACTCTTACCTTGGCCAC<br>AACAACAGCCCCCTTGGCAAGGACCCACTCAACTGTTCCTC<br>CTAGATTTTTACACTCAGAGATGACAACTCTTATGAGTAGG<br>AGTCCTGAAAATCCATCATGGAAGAGCTCTCTCTTTGTGGA<br>AAAAACTAGCTCTTCATCTTCTCTGTTGTCCTTACCTGTCAC<br>GACCTCACCTTCTGTTTCTTCCACATTACCGCAGAGTATCCC<br>TTCCTCCTCTTTTTCTGTGACTTCACTCCTCACCCCAGGCATG<br>GTGAAGACTACAGACACAAGCACAGAACCTGGAACCAGTT<br>TATCTCCAAATCTGAGTGGCACCTCAGTTGAAATACTGGCT<br>GCCTCTGAAGTCACCACAGATACAGAGAAAATTCATCCTTC<br>TTCAAGCATGGCAGTGACCAATGTGGGAACCACCAGTTCTG<br>GACATGAACTATATTCCTCTGTTTCAATCCACTCGGAGCCAT<br>CCAAGGCTACATACCCAGTGGGTACTCCCTCTTCCATGGCT<br>GAAACCTCTATTTCCACATCAATGCCTGCTAATTTTGAGACC<br>ACAGGATTTGAGGCTGAGCCATTTTCTCATTTGACTTCTGGA<br>TTTAGGAAGACAAACATGTCCCTGGACACCAGCTCAGTCAC<br>ACCAACAAATACACCTTCTTCTCCTGGGTCCACTCACCTTTT<br>ACAGAGTTCCAAGACTGATTTCACCTCTTCTGCAAAAACAT<br>CATCCCCAGACTGGCCTCCAGCCTCACAGTATACTGAAATT<br>CCAGTGGACATAATCACCCCCTTTAATGCTTCTCCATCTATT<br>ACGGAGTCCACTGGGATAACCTCCTTCCCAGAATCCAGGTT<br>TACTATGTCTGTAACAGAAAGTACTCATCATCTGAGTACAG<br>ATTTGCTGCCTTCAGCTGAGACTATTTCCACTGGCACAGTGA<br>TGCCTTCTCTATCAGAGGCCATGACTTCATTTGCCACCACTG<br>GAGTTCCACGAGCCATCTCAGGTTCAGGTAGTCCATTCTCTA<br>GGACAGAGTCAGGCCCTGGGGATGCTACTCTGTCCACCATT |

TABLE 13-continued

Table of Sequences.

| SEQ ID NO | NAME | SEQ |
| --- | --- | --- |
| | | GCAGAGAGCCTGCCTTCATCCACTCCTGTGCCATTCTCCTCT<br>TCAACCTTCACTACCACTGATTCTTCAACCATCCCAGCCCTC<br>CATGAGATAACTTCCTCTTCAGCTACCCCATATAGAGTGGA<br>CACCAGTCTTGGGACAGAGAGCAGCACTACTGAAGGACGCT<br>TGGTTATGGTCAGTACTTTGGACACTTCAAGCCAACCAGGC<br>AGGACATCTTCATCACCCATTTTGGATACCAGAATGACAGA<br>GAGCGTTGAGCTGGGAACAGTGACAAGTGCTTATCAAGTTC<br>CTTCACTCTCAACACGGTTGACAAGAACTGATGGCATTATG<br>GAACACATCACAAAAATACCCAATGAAGCAGCACACAGAG<br>GTACCATAAGACCAGTCAAAGGCCCTCAGACATCCACTTCG<br>CCTGCCAGTCCTAAAGGACTACACACAGGAGGGACAAAAA<br>GAATGGAGACCACCACCACAGCTCTGAAGACCACCACCAC<br>AGCTCTGAAGACCACTTCCAGAGCCACCTTGACCACCAGTG<br>TCTATACTCCCACTTTGGGAACACTGACTCCCCTCAATGCAT<br>CAATGCAAATGGCCAGCACAATCCCCACAGAAATGATGATC<br>ACAACCCCATATGTTTTCCCTGATGTTCCAGAAACGACATCC<br>TCATTGGCTACCAGCCTGGGAGCAGAAACCAGCACAGCTCT<br>TCCCAGGACAACCCCATCTGTTTTCAATAGAGAATCAGAGA<br>CCACAGCCTCACTGGTCTCTCGTTCTGGGGCAGAGAGAAGT<br>CCGGTTATTCAAACTCTAGATGTTTCTTCTAGTGAGCCAGAT<br>ACAACAGCTTCATGGGTTATCCATCCTGCAGAGACCATCCC<br>AACTGTTTCCAAGACAACCCCCAATTTTTTCCACAGTGAATT<br>AGACACTGTATCTTCCACAGCCACCAGTCATGGGGCAGACG<br>TCAGCTCAGCCATTCCAACAAATATCTCACCTAGTGAACTA<br>GATGCACTGACCCCACTGGTCACTATTTCGGGGACAGATAC<br>TAGTACAACATTCCCAACACTGACTAAGTCCCCACATGAAA<br>CAGAGACAAGAACCACATGGCTCACTCATCCTGCAGAGACC<br>AGCTCAACTATTCCCAGAACAATCCCCAATTTTTCTCATCAT<br>GAATCAGATGCCACACCTTCAATAGCCACCAGTCCTGGGGC<br>AGAAACCAGTTCAGCTATTCCAATTATGACTGTCTCACCTG<br>GTGCAGAAGATCTGGTGACCTCACAGGTCACTAGTTCTGGG<br>ACAGACAGAAATATGACTATTCCAACTTTGACTCTTTCTCCT<br>GGTGAACCAAAGACGATAGCCTCATTAGTCACCCATCCTGA<br>AGCACAGACAAGTTCGGCCATTCCAACTTCAACTATCTCGC<br>CTGCTGTATCACGGTTGGTGACCTCAATGGTCACCAGTTTGG<br>CGGCAAAGACAAGTACAACTAATCGAGCTCTGACAAACTCC<br>CCTGGTGAACCAGCTACAACAGTTTCATTGGTCACGCATCC<br>TGCACAGACCAGCCCAACAGTTCCCTGGACAACTTCCATTT<br>TTTTCCATAGTAAATCAGACACCACACCTTCAATGACCACC<br>AGTCATGGGGCAGAATCCAGTTCAGCTGTTCCAACTCCAAC<br>TGTTTCAACTGAGGTACCAGGAGTAGTGACCCCTTTGGTCA<br>CCAGTTCTAGGGCAGTGATCAGTACAACTATTCCAATTCTG<br>ACTCTTTCTCCTGGTGAACCAGAGACCACACCTTCAATGGC<br>CACCAGTCATGGGGAAGAAGCCAGTTCTGCTATTCCAACTC<br>CAACTGTTTCACCTGGGGTACCAGGAGTGGTGACCTCTCTG<br>GTCACTAGTTCTAGGGCAGTGACTAGTACAACTATTCCAAT<br>TCTGACTTTTTCTCTTGGTGAACCAGAGACCACACCTTCAAT<br>GGCCACCAGTCATGGGACAGAAGCTGGCTCAGCTGTTCCAA<br>CTGTTTTACCTGAGGTACCAGGAATGGTGACCTCTCTGGTTG<br>CTAGTTCTAGGGCAGTAACCAGTACAACTCTTCCAACTCTG<br>ACTCTTTCTCCTGGTGAACCAGAGACCACACCTTCAATGGC<br>CACCAGTCATGGGGCAGAAGCCAGCTCAACTGTTCCAACTG<br>TTTCACCTGAGGTACCAGGAGTGGTGACCTCTCTGGTCACT<br>AGTTCTAGTGGAGTAAACAGTACAAGTATTCCAACTCTGAT<br>TCTTTCTCCTGGTGAACTAGAAACCACACCTTCAATGGCCAC<br>CAGTCATGGGGCAGAAGCCAGCTCAGCTGTTCCAACTCCAA<br>CTGTTTCACCTGGGGTATCAGGAGTGGTGACCCCTCTGGTC<br>ACTAGTTCCAGGGCAGTGACCAGTACAACTATTCCAATTCT<br>AACTCTTTCTTCTAGTGAGCCAGAGACCACACCTTCAATGG<br>CCACCAGTCATGGGGTAGAAGCCAGCTCAGCTGTTCTAACT<br>GTTTCACCTGAGGTACCAGGAATGGTGACCTCTCTGGTCAC<br>TAGTTCTAGAGCAGTAACCAGTACAACTATTCCAACTCTGA<br>CTATTTCTTCTGATGAACCAGAGACCACAACTTCATTGGTCA<br>CCCATTCTGAGGCAAAGATGATTTCAGCCATTCCAACTTTA<br>GCTGTCTCCCCTACTGTACAAGGGCTGGTGACTTCACTGGTC<br>ACTAGTTCTGGGTCAGAGACCAGTGCGTTTTCAAATCTAAC<br>TGTTGCCTCAAGTCAACCAGAGACCATAGACTCATGGGTCG<br>CTCATCCTGGGACAGAAGCAAGTTCTGTTGTTCCAACTTTGA<br>CTGTCTCCACTGGTGAGCCGTTTACAAATATCTCATTGGTCA<br>CCCATCCTGCAGAGAGTAGCTCAACTCTTCCCAGGACAACC<br>TCAAGGTTTTCCCACAGTGAATTAGACACTATGCCTTCTACA<br>GTCACCAGTCCTGAGGCAGAATCCAGCTCAGCCATTTCAAC<br>AACTATTTCACCTGGTATACCAGGTGTGCTGACATCACTGGT<br>CACTAGCTCTGGGAGAGACATCAGTGCAACTTTTCCAACAG |

TABLE 13-continued

| SEQ ID NO | NAME | SEQ |
|---|---|---|
| | | TGCCTGAGTCCCCACATGAATCAGAGGCAACAGCCTCATGG GTTACTCATCCTGCAGTCACCAGCACAACAGTTCCCAGGAC AACCCCTAATTATTCTCATAGTGAACCAGACACCACACCAT CAATAGCCACCAGTCCTGGGGCAGAAGCCACTTCAGATTTT CCAACAATAACTGTCTCACCTGATGTACCAGATATGGTAAC CTCACAGGTCACTAGTTCTGGGACAGACACCAGTATAACTA TTCCAACTCTGACTCTTTCTTCTGGTGAGCCAGAGACCACAA CCTCATTTATCACCTATTCTGAGACACACACAAGTTCAGCCA TTCCAACTCTCCCTGTCTCCCCTGGTGCATCAAAGATGCTGA CCTCACTGGTCATCAGTTCTGGGACAGACAGCACTACAACT TTCCCAACACTGACGGAGACCCCATATGAACCAGAGACAAC AGCCATACAGCTCATTCATCCTGCAGAGACCAACACAATGG TTCCCAGGACAACTCCCAAGTTTTCCCATAGTAAGTCAGAC ACCACACTCCCAGTAGCCATCACCAGTCCTGGGCCAGAAGC CAGTTCAGCTGTTTCAACGACAACTATCTCACCTGATATGTC AGATCTGGTGACCTCACTGGTCCCTAGTTCTGGGACAGACA CCAGTACAACCTTCCCAACATTGAGTGAGACCCCATATGAA CCAGAGACTACAGCCACGTGGCTCACTCATCCTGCAGAAAC CAGCACAACGGTTTCTGGGACAATTCCCAACTTTTCCCATA GGGGATCAGACACTGCACCCTCAATGGTCACCAGTCCTGGA GTAGACACGAGGTCAGGTGTTCCAACTACAACCATCCCACC CAGTATACCAGGGGTAGTGACCTCACAGGTCACTAGTTCTG CAACAGACACTAGTACAGCTATTCCAACTTTGACTCCTTCTC CTGGTGAACCAGAGACCACAGCCTCATCAGCTACCCATCCT GGGACACAGACTGGCTTCACTGTTCCAATTCGGACTGTTCC CTCTAGTGAGCCAGATACAATGGCTTCCTGGGTCACTCATC CTCCACAGACCAGCACACCTGTTTCCAGAACAACCTCCAGT TTTTCCCATAGTAGTCCAGATGCCACACCTGTAATGGCCACC AGTCCTAGGACAGAAGCCAGTTCAGCTGTACTGACAACAAT CTCACCTGGTGCACCAGAGATGGTGACTTCACAGATCACTA GTTCTGGGGCAGCAACCAGTACAACTGTTCCAACTTTGACT CATTCTCCTGGTATGCCAGAGACCACAGCCTTATTGAGCAC CCATCCCAGAACAGAGACAAGTAAAACATTTCCTGCTTCAA CTGTGTTTCCTCAAGTATCAGAGACCACAGCCTCACTCACC ATTAGACCTGGTGCAGAGACTAGCACAGCTCTCCCAACTCA GACAACATCCTCTCTCTTCACCCTACTTGTAACTGGAACCAG CAGAGTTGATCTAAGTCCAACTGCTTCACCTGGTGTTTCTGC AAAAACAGCCCCACTTTCCACCCATCCAGGGACAGAAACCA GCACAATGATTCCAACTTCAACTCTTTCCCTTGGTTTACTAG AGACTACAGGCTTACTGGCCACCAGCTCTTCAGCAGAGACC AGCACGAGTACTCTAACTCTGACTGTTTCCCCTGCTGTCTCT GGGCTTTCCAGTGCCTCTATAACAACTGATAAGCCCCAAAC TGTGACCTCCTGGAACACAGAAACCTCACCATCTGTAACTT CAGTTGGACCCCCAGAATTTTCCAGGACTGTCACAGGCACC ACTATGACCTTGATACCATCAGAGATGCCAACACCACCTAA AACCAGTCATGGAGAAGGAGTGAGTCCAACCACTATCTTGA GAACTACAATGGTTGAAGCCACTAATTTAGCTACCACAGGT TCCAGTCCCACTGTGGCCAAGACAACAACCACCTTCAATAC ACTGGCTGGAAGCCTCTTTACTCCTCTGACCACACCTGGGAT GTCCACCTTGGCCTCTGAGAGTGTGACCTCAAGAACAAGTT ATAACCATCGGTCCTGGATCTCCACCACCAGCAGTTATAAC CGTCGGTACTGGACCCCTGCCACCAGCACTCCAGTGACTTC TACATTCTCCCCAGGGATTTCCACATCCTCCATCCCCAGCTC CACAGCAGCCACAGTCCCATTCATGGTGCCATTCACCCTCA ACTTCACCATCACCAACCTGCAGTACGAGGAGGACATGCGG CACCCTGGTTCCAGGAAGTTCAACGCCACAGAGAGAGAACT GCAGGGTCTGCTCAAACCCTTGTTCAGGAATAGCAGTCTGG AATACCTCTATTCAGGCTGCAGACTAGCCTCACTCAGGCCA GAGAAGGATAGCTCAGCCACGGCAGTGGATGCCATCTGCAC ACATCGCCCTGACCCTGAAGACCTCGGACTGGACAGAGAGC GACTGTACTGGGAGCTGAGCAATCTGACAAATGGCATCCAG GAGCTGGGCCCCTACACCCTGGACCGGAACAGTCTCTATGT CAATGGTTTCACCCATCGAAGCTCTATGCCCACCACCAGCA CTCCTGGGACCTCCACAGTGGATGTGGGAACCTCAGGGACT CCATCCTCCAGCCCCAGCCCCACGACTGCTGGCCCTCTCCTG ATGCCGTTCACCCTCAACTTCACCATCACCAACCTGCAGTAC GAGGAGGACATGCGTCGCACTGGCTCCAGGAAGTTCAACAC CATGGAGAGTGTCCTGCAGGGTCTGCTCAAGCCCTTGTTCA AGAACACCAGTGTTGGCCCTCTGTACTCTGGCTGCAGATTG ACCTTGCTCAGGCCCGAGAAAGATGGGGCAGCCACTGGAGT GGATGCCATCTGCACCCACCGCCTTGACCCCAAAAGCCCTG GACTCAACAGGGAGCAGCTGTACTGGGAGCTAAGCAAACT GACCAATGACATTGAAGAGCTGGGCCCCTACACCCTGGACA GGAACAGTCTCTATGTCAATGGTTTCACCCATCAGAGCTCT |

TABLE 13-continued

| SEQ ID NO | NAME | SEQ |
|---|---|---|
| | | GTGTCCACCACCAGCACTCCTGGGACCTCCACAGTGGATCT CAGAACCTCAGGGACTCCATCCTCCCTCTCCAGCCCCACAA TTATGGCTGCTGGCCCTCTCCTGGTACCATTCACCCTCAACT TCACCATCACCAACCTGCAGTATGGGGAGGACATGGGTCAC CCTGGCTCCAGGAAGTTCAACACCACAGAGAGGGTCCTGCA GGGTCTGCTTGGTCCCATATTCAAGAACACCAGTGTTGGCC CTCTGTACTCTGGCTGCAGACTGACCTCTCTCAGGTCTGAGA AGGATGGAGCAGCCACTGGAGTGGATGCCATCTGCATCCAT CATCTTGACCCCAAAAGCCCTGGACTCAACAGAGAGCGGCT GTACTGGGAGCTGAGCCAACTGACCAATGGCATCAAAGAG CTGGGCCCCTACACCCTGGACAGGAACAGTCTCTATGTCAA TGGTTTCACCCATCGGACCTCTGTGCCCACCAGCAGCACTCC TGGGACCTCCACAGTGGACCTTGGAACCTCAGGGACTCCAT TCTCCCTCCCAAGCCCCGCAACTGCTGGCCCTCTCCTGGTGC TGTTCACCCTCAACTTCACCATCACCAACCTGAAGTATGAG GAGGACATGCATCGCCCTGGCTCCAGGAAGTTCAACACCAC TGAGAGGGTCCTGCAGACTCTGCTTGGTCCTATGTTCAAGA ACACCAGTGTTGGCCTTCTGTACTCTGGCTGCAGACTGACCT TGCTCAGGTCCGAGAAGGATGGAGCAGCCACTGGAGTGGA TGCCATCTGCACCCACCGTCTTGACCCCAAAAGCCCTGGAG TGGACAGGGAGCAGCTATACTGGGAGCTGAGCCAGCTGAC CAATGGCATCAAAGAGCTGGGCCCCTACACCCTGGACAGGA ACAGTCTCTATGTCAATGGTTTCACCCATTGGATCCCTGTGC CCACCAGCAGCACTCCTGGGACCTCCACAGTGGACCTTGGG TCAGGGACTCCATCCTCCCTCCCCAGCCCCACAACTGCTGG CCCTCTCCTGGTGCCGTTCACCCTCAACTTCACCATCACCAA CCTGAAGTACGAGGAGGACATGCATTGCCCTGGCTCCAGGA AGTTCAACACCACAGAGAGAGTCCTGCAGAGTCTGCTTGGT CCCATGTTCAAGAACACCAGTGTTGGCCCTCTGTACTCTGGC TGCAGACTGACCTTGCTCAGGTCCGAGAAGGATGGAGCAGC CACTGGAGTGGATGCCATCTGCACCCACCGTCTTGACCCCA AAAGCCCTGGAGTGGACAGGGAGCAGCTATACTGGGAGCT GAGCCAGCTGACCAATGGCATCAAAGAGCTGGGTCCCTACA CCCTGGACAGAAACAGTCTCTATGTCAATGGTTTCACCCAT CAGACCTCTGCGCCCAACACCAGCACTCCTGGGACCTCCAC AGTGGACCTTGGGACCTCAGGGACTCCATCCTCCCTCCCCA GCCCTACATCTGCTGGCCCTCTCCTGGTGCCATTCACCCTCA ACTTCACCATCACCAACCTGCAGTACGAGGAGGACATGCAT CACCCAGGCTCCAGGAAGTTCAACACCACGGAGCGGGTCCT GCAGGGTCTGCTTGGTCCCATGTTCAAGAACACCAGTGTCG GCCTTCTGTACTCTGGCTGCAGACTGACCTTGCTCAGGCCTG AGAAGAATGGGGCAGCCACTGGAATGGATGCCATCTGCAG CCACCGTCTTGACCCCAAAAGCCCTGGACTCAACAGAGAGC AGCTGTACTGGGAGCTGAGCCAGCTGACCCATGGCATCAAA GAGCTGGGCCCCTACACCCTGGACAGGAACAGTCTCTATGT CAATGGTTTCACCCATCGGAGCTCTGTGGCCCCCACCAGCA CTCCTGGGACCTCCACAGTGGACCTTGGGACCTCAGGGACT CCATCCTCCCTCCCCAGCCCCACAACAGCTGTTCCTCTCCTG GTGCCGTTCACCCTCAACTTTACCATCACCAATCTGCAGTAT GGGGAGGACATGCGTCACCCTGGCTCCAGGAAGTTCAACAC CACAGAGAGGGTCCTGCAGGGTCTGCTTGGTCCCTTGTTCA AGAACTCCAGTGTCGGCCCTCTGTACTCTGGCTGCAGACTG ATCTCTCTCAGGTCTGAGAAGGATGGGGCAGCCACTGGAGT GGATGCCATCTGCACCCACCACCTTAACCCTCAAAGCCCTG GACTGGACAGGGAGCAGCTGTACTGGCAGCTGAGCCAGAT GACCAATGGCATCAAAGAGCTGGGCCCCTACACCCTGGACC GGAACAGTCTCTACGTCAATGGTTTCACCCATCGGAGCTCT GGGCTCACCACCAGCACTCCTTGGACTTCCACAGTTGACCTT GGAACCTCAGGGACTCCATCCCCCGTCCCCAGCCCCACAAC CACCGGCCCTCTCCTGGTGCCATTCACACTCAACTTCACCAT CACTAACCTACAGTATGAGGAGAACATGGGTCACCCTGGCT CCAGGAAGTTCAACATCACGGAGAGTGTTCTGCAGGGTCTG CTCAAGCCCTTGTTCAAGAGCACCAGTGTTGGCCCTCTGTAT TCTGGCTGCAGACTGACCTTGCTCAGGCCTGAGAAGGATGG AGTAGCCACCAGAGTGGACGCCATCTGCACCCACCGCCCTG ACCCCAAAATCCCTGGGCTAGACAGACAGCAGCTATACTGG GAGCTGAGCCAGCTGACCCACAGCATCACTGAGCTGGGACC CTACACCCTGGATAGGGACAGTCTCTATGTCAATGGTTTCA CCCAGCGGAGCTCTGTGCCCACCACCAGCACTCCTGGGACT TTCACAGTACAGCCGGAAACCTCTGAGACTCCATCATCCCT CCCTGGCCCCACAGCCACTGGCCCTGTCCTGCTGCCATTCAC CCTCAATTTTACCATCACTAACCTGCAGTATGAGGAGGACA TGCGTCGCCCTGGCTCCAGGAAGTTCAACACCACGGAGAGG GTCCTTCAGGGTCTGCTTATGCCCTTGTTCAAGAACACCAGT |

TABLE 13-continued

Table of Sequences.

| SEQ ID NO | NAME | SEQ |
|---|---|---|
| | | GTCAGCTCTCTGTACTCTGGTTGCAGACTGACCTTGCTCAGG<br>CCTGAGAAGGATGGGGCAGCCACCAGAGTGGATGCTGTCTG<br>CACCCATCGTCCTGACCCCAAAAGCCCTGGACTGGACAGAG<br>AGCGGCTGTACTGGAAGCTGAGCCAGCTGACCCACGGCATC<br>ACTGAGCTGGGCCCCTACACCCTGGACAGGCACAGTCTCTA<br>TGTCAATGGTTTCACCCATCAGAGCTCTATGACGACCACCA<br>GAACTCCTGATACCTCCACAATGCACCTGGCAACCTCGAGA<br>ACTCCAGCCTCCCTGTCTGGACCCATGACCGCCAGCCCTCTC<br>CTGGTGCTATTCACAATTAACTTCACCATCACTAACCTGCGG<br>TATGAGGAGAACATGCATCACCCTGGCTCTAGAAAGTTTAA<br>CACCACGGAGAGAGTCCTTCAGGGTCTGCTCAGGCCTGTGT<br>TCAAGAACACCAGTGTTGGCCCTCTGTACTCTGGCTGCAGA<br>CTGACCTTGCTCAGGCCCAAGAAGGATGGGGCAGCCACCAA<br>AGTGGATGCCATCTGCACCTACCGCCCTGATCCCAAAAGCC<br>CTGGACTGGACAGAGAGCAGCTATACTGGGAGCTGAGCCA<br>GCTGACCCACAGCATCACTGAGCTGGGCCCCTACACCCTGG<br>ACAGGGACAGTCTCTATGTCAATGGTTTCACACAGCGGAGC<br>TCTGTGCCCACCACTAGCATTCCTGGGACCCCCACAGTGGA<br>CCTGGGAACATCTGGGACTCCAGTTTCTAAACCTGGTCCCTC<br>GGCTGCCAGCCCTCTCCTGGTGCTATTCACTCTCAACTTCAC<br>CATCACCAACCTGCGGTATGAGGAGAACATGCAGCACCCTG<br>GCTCCAGGAAGTTCAACACCACGGAGAGGGTCCTTCAGGGC<br>CTGCTCAGGTCCCTGTTCAAGAGCACCAGTGTTGGCCCTCTG<br>TACTCTGGCTGCAGACTGACTTTGCTCAGGCCTGAAAAGGA<br>TGGGACAGCCACTGGAGTGGATGCCATCTGCACCCACCACC<br>CTGACCCCAAAAGCCCTAGGCTGGACAGAGAGCAGCTGTAT<br>TGGGAGCTGAGCCAGCTGACCCACAATATCACTGAGCTGGG<br>CCCCTATGCCCTGGACAACGACAGCCTCTTTGTCAATGGTTT<br>CACTCATCGGAGCTCTGTGTCCACCACCAGCACTCCTGGGA<br>CCCCCACAGTGTATCTGGGAGCATCTAAGACTCCAGCCTCG<br>ATATTTGGCCCTTCAGCTGCCAGCCATCTCCTGATACTATTC<br>ACCCTCAACTTCACCATCACTAACCTGCGGTATGAGGAGAA<br>CATGTGGCCTGGCTCCAGGAAGTTCAACACTACAGAGAGGG<br>TCCTTCAGGGCCTGCTAAGGCCCTTGTTCAAGAACACCAGT<br>GTTGGCCCTCTGTACTCTGGCTGCAGGCTGACCTTGCTCAGG<br>CCAGAGAAAGATGGGGAAGCCACCGGAGTGGATGCCATCT<br>GCACCCACCGCCCTGACCCCACAGGCCCTGGGCTGGACAGA<br>GAGCAGCTGTATTTGGAGCTGAGCCAGCTGACCCACAGCAT<br>CACTGAGCTGGGCCCCTACACACTGGACAGGGACAGTCTCT<br>ATGTCAATGGTTTCACCCATCGGAGCTCTGTACCCACCACC<br>AGCACCGGGGTGGTCAGCGAGGAGCCATTCACACTGAACTT<br>CACCATCAACAACCTGCGCTACATGGCGGACATGGGCCAAC<br>CCGGCTCCCTCAAGTTCAACATCACAGACAACGTCATGCAG<br>CACCTGCTCAGTCCTTTGTTCCAGAGGAGCAGCCTGGGTGC<br>ACGGTACACAGGCTGCAGGGTCATCGCACTAAGGTCTGTGA<br>AGAACGGTGCTGAGACACGGGTGGACCTCCTCTGCACCTAC<br>CTGCAGCCCCTCAGCGGCCCAGGTCTGCCTATCAAGCAGGT<br>GTTCCATGAGCTGAGCCAGCAGACCCATGGCATCACCCGGC<br>TGGGCCCCTACTCTCTGGACAAAGACAGCCTCTACCTTAAC<br>GGTTACAATGAACCTGGTCCAGATGAGCCTCCTACAACTCC<br>CAAGCCAGCCACCACATTCCTGCCTCCTCTGTCAGAAGCCA<br>CAACAGCCATGGGGTACCACCTGAAGACCCTCACACTCAAC<br>TTCACCATCTCCAATCTCCAGTATTCACCAGATATGGGCAA<br>GGGCTCAGCTACATTCAACTCCACCGAGGGGGTCCTTCAGC<br>ACCTGCTCAGACCCTTGTTCCAGAAGAGCAGCATGGGCCCC<br>TTCTACTTGGGTTGCCAACTGATCTCCCTCAGGCCTGAGAAG<br>GATGGGGCAGCCACTGGTGTGGACACCACCTGCACCTACCA<br>CCCTGACCCTGTGGGCCCCGGGCTGGACATACAGCAGCTTT<br>ACTGGGAGCTGAGTCAGCTGACCCATGGTGTCACCCAACTG<br>GGCTTCTATGTCCTGGACAGGGATAGCCTCTTCATCAATGG<br>CTATGCACCCCAGAATTTATCAATCCGGGGCGAGTACCAGA<br>TAAATTTCCACATTGTCAACTGGAACCTCAGTAATCCAGAC<br>CCCACATCCTCAGAGTACATCACCCTGCTGAGGGACATCCA<br>GGACAAGGTCACCACACTCTACAAAGGCAGTCAACTACATG<br>ACACATTCCGCTTCTGCCTGGTCACCAACTTGACGATGGACT<br>CCGTGTTGGTCACTGTCAAGGCATTGTTCTCCTCCAATTTGG<br>ACCCCAGCCTGGTGGAGCAAGTCTTTCTAGATAAGACCCTG<br>AATGCCTCATTCCATTGGCTGGGCTCCACCTACCAGTTGGTG<br>GACATCCATGTGACAGAAATGGAGTCATCAGTTTATCAACC<br>AACAAGCAGCTCCAGCACCCAGCACTTCTACCTGAATTTCA<br>CCATCACCAACCTACCATATTCCCAGGACAAAGCCCAGCCA<br>GGCACCACCAATTACCAGAGGAACAAAAGGAATATTGAGG<br>ATGCGCTCAACCAACTCTTCCGAAACAGCAGCATCAAGAGT<br>TATTTTTCTGACTGTCAAGTTTCAACATTCAGGTCTGTCCCC |

TABLE 13-continued

Table of Sequences.

| SEQ ID NO | NAME | SEQ |
|---|---|---|
| | | AACAGGCACCACACCGGGGTGGACTCCCTGTGTAACTTCTC GCCACTGGCTCGGAGAGTAGACAGAGTTGCCATCTATGAGG AATTTCTGCGGATGACCCGGAATGGTACCCAGCTGCAGAAC TTCACCCTGGACAGGAGCAGTGTCCTTGTGGATGGGTATTC TCCCAACAGAAATGAGCCCTTAACTGGGAATTCTGACCTTC CCTTCTGGGCTGTCATCCTCATCGGCTTGGCAGGACTCCTGG GAGTCATCACATGCCTGATCTGCGGTGTCCTGGTGACCACC CGCCGGCGGAAGAAGGAAGGAGAATACAACGTCCAGCAAC AGTGCCCAGGCTACTACCAGTCACACCTAGACCTGGAGGAT CTGCAATGACTGGAACTTGCCGGTGCCTGGGGTGCCTTTCC CCCAGCCAGGGTCCAAAGAAGCTTGGCTGGGGCAGAAATA AACCATATTGGTCGGA |
| 138 | Bispecific | EIVMTQTPATLSVSAGERVTITCKASQSVSNDVTWYQQKPGQ APRLLIYSASNRYSGVPARFSGSGYGTEFTFTISSVQSEDFAVYF CQQDYSSFGQGTKLEIKRTVAAPSVFIFPPSDEQLKSGTASVVC LLNNFYPREAKVQWKVDNALQSGNSQESVTEQDSKDSTYSLS STLTLSKADYEKHKVYACEVTHQGLSSPVTKSFNRGECGGGG SGGGGSQVQLVQSGGGLTLSKADYEKHKVYACEVTHQGLSSP VTKSFNRGECGGGGSGGGGSQVQLVQSGGGVVQPGRSLRLSC KASGYTFTRYTMHWVRQAPGKCLEWIGYINPSRGYTNYNQKF KDRFTISRDNSKNTAFLQMDSLRPEDTGVYFCARYYDDHYCL DYWGQGTPVTVSSGGGGSGGGGSGGGGSDIQMTQSPSSLSAS VGDRVTITCSASSSVSYMNWYQQTPGKAPKRWIYDTSKLASG VPSRFSGSGSGTDYTFTISSLQPEDIATYYCQQWSSNPFTFGCG TKLQITR |
| 139 | MUC16c114-N3 | NFSPLARRVDRVAIYEEFLRMTRNGTQLQAFTLDRSSVLVDGY SPNRNEPLTGNSDLPFWAVILIGLAGLLGLITCLICGVLVTTRRR KKEGEYNVQQQCPGYYQSHLDLEDLQ |
| 140 | 10C6 VH NUCLEIC ACID | CAGGTAACTCTGAAAGAGTCTGGCCCTGGGATATTGCAGCC CTCCCAGACCCTCAGTCTGACTTGTTCTTTCTCTGGGTTTTC ACTGAACACTCTTGGTATGGGTGTAGGCTGGATTCGGCAGC CTTCAGGGAAGGGTCTGGAGTGGCTGGCACACATTTGGTGG GATGATGATAAGTACTATAACCCAGCCCTGAAGAGTCGGCT CACAATCTCCAAGGATTCCTCCAAAAACCAGGTTTTCCTCA AGATCGCCAATGTGGACACTGCAGATATTGCCACATACTAC TGTTCTCGAATCGGGACAGCTCAGGCTACGGATGCTCTGGA CTACTGGGGTCAAGGAACCTCAGTCACCGTCTCCTCA |
| 141 | 10C6 VL NUCLEIC ACID | GACATTGTGCTGACACAGTCTCCTGCTTCCTTAGCTGTATCT CTGGGGCAGAGGGCCACCATCTCATACAGGGCCAGCAAAA GTGTCAGTACATCTGGCTATAGTTATATGCACTGGAACCAA CAGAAACCAGGACAGCCACCCAGACTCCTCATCTATCTTGT ATCCAACCTAGAATCTGGGGTCCCTGCCAGGTTCAGTGGCA GTGGGTCTGGGACAGACTTCACCCTCAACATCCATCCTGTG GAGGAGGAGGATGCTGCAACCTATTACTGTCAGCACATTAG GGAGCTTACACGTTCGGAGGGGGGACCAAGCTGGAAATAA AAC |
| 142 | 7B12 VH NUCLEIC ACID | CAGGTTACTCTGAAAGAGTCTGGCCCTGGGATATTGCAGCC CTCCCAGACCCTCAGTCTGACTTGTTCTTTCTCTGGGTTTTC ACTGAGCACTGTTGGTATGGGTGTAGGCTGGAGTCGTCAGC CCTCAGGGAAGGGTCTGGAGTGGCTGGCACACATCTGGTGG GATGATGAAGATAAGTATTATAATCCAGCCCTGAAGAGTCG GCTCACAATCTCCAAGGATACCTCCAAAAACCAGGTCTTCC TCAAGATCGCCAATGTGGACACTGCAGATAGTGCCACATAC TACTGTACTCGAATCGGGACAGCTCAGGCTACGGATGCTTT GGACTACTGGGGTCAAGGAACCTCAGTCACCGTCTCCTCA |
| 143 | 7B12 VL NUCLEIC ACID | GATATTGTGATGACTCAGGCTGCACCCTCTGTATCTGTCACT CCTGGAGAGTCAGTATCCATCTCCTGCAGGTCTAGTAAGAG TCTTCGGAAAAGTAATGGCAACACTTACTTGTATTGGTTCCT GCAGAGGCCAGGCCAGTCTCCTCAGCGCCTGATATATTATA TGTCCAACCTTGCCTCAGGAGTCCCAGACAGGTTCAGTGGC AGAGGGTCAGGAACTGATTTCACACTGAGAATCAGTAGAGT GGAGGCTGAAGATGTGGGTGTTTATTACTGTATGCAAAGTC TAGAATATCCTCTCACGTTCGGAGGGGGGACTAAGCTAAAA ATAAAA |
| 144 | 19C11 VH NUCLEIC ACID | CAGGTTAATCTGAAAGAGTCTGGCCCTGGGAAATTGCAGCC CTCCCAGACCCTCAGTCTGACTTGTTCTTTCTCTGGGTTTTC ACTGAGCACTCTTGGTATGGGTGTAGGTTGGATTCGTCAGT |

TABLE 13-continued

Table of Sequences.

| SEQ ID NO | NAME | SEQ |
|---|---|---|
| | | CTTCAGGGAAGGGTCTGGAGTGGCTGGCACACATTTGGTGG GATGATGATAAGTACTATAACCCAGCCCTGAAGAGTCGGCT CACAATCTCCAGGGCTACCTCCAAAAACCAGGTTTTCCTCA AGATCGTCAATGTGGGCACTGCAGATACTGCCACATATTAC TGTGCTCGAATCGGGACAGCTCAGGCTACGGATGCTTTGGA CTATTGGGGTCAGGGAACCTCAGTCACCGTTTCCTCA |
| 145 | 19C11 VL NUCLEIC ACID | GATATTGTGATGACTCAGGCTGCACCCTCTATCCCTGTCACT CCTGGAGAGTCAGTATCCATCTCCTGCAGGTCTAGTAAGAG TCTTCTGCATAGTAATGGCAACACTTATTTGTATTGGTTCCT GCAGAGGCCAGGCCAGTCTCCTCAGCGCCTGATATATTATA TGTCCAACCTTGCCTCAGGAGTCCCAGACAGGTTCAGTGGC AGAGGGTCAGGAACTGATTTCACACTGAAAATCAGTAGAGT GGAGGCTGGGGATGTGGGTGTTTATTACTGTATGCAGGGTC TAGAGCATCCTCTCACGTTCGGAGGGGGGACCAAGCTGGAA ATAAAA |
| 146 | 16C5 VH NUCLEIC ACID | CAGGTTACTCTGAAAGAGTCTGGCCCTGGAATATTGCAGCC CTCCCAGACCCTCAGTCTGACTTGTTCTTTCTCTGGGTTTTC ACTGAACACTCTTGGTATGGGTGTAGGCTGGATTCGTCAGC CTTCAGGGAAGGGTCTGGAGTGGCTGGCACACATTTGGTGG GATGATGATAAGTACTATTACCCAGCCCTGAAGAGTCGGCT CACAATCTCCAGGGATACCTCCAAAAACCAGGTATTCCTCA AGATCGCCAATGTGGACACTGCAGATACTGCCACATACTAC TGTGCTCGAATCGGGACAGCTCAGGCTACGGATGCTCTGGA CTACTGGGGTCAAGGAACCTCAGTCACCGTCTCCTCA |
| 147 | 16C5 VL NUCLEIC ACID | GAGCTCGATATGACCCAGACTCCACCCTCCCTGTCTGCATCT GTGGGAGAAACTGTCAGGATTAGGTGCCTGGCCAGTGAGG ACATTTATAGTGGTATATCCTGGTATCAACAGAAGCCAGGG AAACCTCCTACACTCCTGATCTATGGTGCATCCAATTTAGAA TCTGGGGTCCCACCACGGTTCAGTGGCAGTGGATCTGGGAC AGATTACACCCTCACCATTGGCGGCGTGCAGGCTGAAGATG CTGCCACCTACTACTGTCTAGGCGGTTATAGTTATAGTAGTA CCTTGACTTTTGGAGCTGGCACCAATGTGGAAATCAAA |
| 148 | 18C6 VH NUCLEIC ACID | CAGGTTACTCTGAAAGAGTCTGGCCCTGGGATATTGCAGCC CTCCCAGACCCTCAGTCTGACTTGTTCTTTCTCTGGGTTTTC ACTGAGCACTGTTGGTATGGGTGTAGGCTGGAGTCGTCAGC CTTCAGGGAAGGGTCTGGAGTGGCTGGCACACATTTGGTGG GATGATGAGGATAAGTATTATAACCCAGCCCTGAAGAGTCG GCTCACAATCTCCAAGGATACCTCCAAAAACCAGGTATTCC TCAAGATCGCCAATGTGGACACTGCAGATACTGCCACATAC TACTGTACTCGAATCGGGACAGCTCAGGCTACGGATGCTTT GGACTACTGGGGTCAAGGAACCTCAGTCACCGTCTCCTCA |
| 149 | 18C6 VL NUCLEIC ACID | GATATTGTGATGACTCAGGCTGCACCCTCTGTACCTGTCACT CCTGGAGAGTCAGTATCCATCTCCTGCAGGTCTAGTAAGAG TCTTCTGCATAGTAATGGCAACACTTACTTGTATTGGTTCCT GCAGAGGCCAGGCCAGTCTCCTCAGCGCCTGATATATTATA TGTCCAACCTTGCCTCAGGAGTCCCAGACAGGTTCAGTGGC AGAGGGTCAGGAACTGATTTCACACTGAGAATCAGTAGAGT GGAGGCTGAGGATGTGGGTGTTTATTACTGTATGCAAAGTC TAGAATATCCTCTCACGTTCGGAGGGGGGACCAAGCTGGAA ATAAAA |
| 150 | Mature Human MUC 16 amino acid sequence | DKTLASPTSSVVGRTTQSLGVMSSALPESTSRGMTHSEQRTSPS LSPQVNGTPSRNYPATSMVSGLSSPRTRTSSTEGNFTKEASTYT LTVETTSGPVTEKYTVPTETSTTEGDSTETPWDTRYIPVKITSP MKTFADSTASKENAPVSMTPAETTVTDSHTPGRTNPSFGTLYS SFLDLSPKGTPNSRGETSLELILSTTGYPFSSPEPGSAGHSRISTS APLSSSASVLDNKISETSIFSGQSLTSPLSPGVPEARASTMPNSAI PFSMTLSNAETSAERVRSTISSLGTPSISTKQTAETILTFHAFAET MDIPSTHIAKTLASEWLGSPGTLGGTSTSALTTTSPSTTLVSEET NTHHSTSGKETEGTLNTSMTPLETSAPGEESEMTATLVPTLGFT TLDSKIRSPSQVSSSHPTRELRTTGSTSGRQSSSTAAHGSSDILR ATTSSTSKASSWTSESTAQQFSEPQHTQWVETSPSMKTERPPAS TSVAAPITTSVPSVVSGFTTLKTSSTKGIWLEETSADTLIGESTA GPTTHQFAVPTGISMTGGSSTRGSQGTTHLLTRATASSETSADL TLATNGVPVSVSPAVSKTAAGSSPPGGTKPSYTMVSSVIPETSS LQSSAFREGTSLGLTPLNTRHPFSSPEPDSAGHTKISTSIPLLSSA SVLEDKVSATSTFSHHKATSSITTGTPEISTKTKPSSAVLSSMTL SNAATSPERVRNATSPLTHPSPSGEETAGSVLTLSTSAETTDSP NIHPTGTLTSESSESPSTLSLPSVSGVKTTFSSSTPSTHLFTSGEE |

TABLE 13-continued

Table of Sequences.

| SEQ ID NO | NAME | SEQ |
|---|---|---|
| | | TEETSNPSVSQPETSVSRVRTTLASTSVPTPVFPTMDTWPTRSA
QFSSSHLVSELRATSSTSVTNSTGSALPKISHLTGTATMSQTNR
DTFNDSAAPQSTTWPETSPRFKTGLPSATTTVSTSATSLSATVM
VSKFTSPATSSMEATSIREPSTTILTTETTNGPGSMAVASTNIPIG
KGYITEGRLDTSHLPIGTTASSETSMDFTMAKESVSMSVSPSQS
MDAAGSSTPGRTSQFVDTFSDDVYHLTSREITIPRDGTSSALTP
QMTATHPPSPDPGSARSTWLGILSSSPSSPTPKVTMSSTFSTQR
VTTSMIMDTVETSRWNMPNLPSTTSLTPSNIPTSGAIGKSTLVP
LDTPSPATSLEASEGGLPTLSTYPESTNTPSIHLGAHASSESPSTI
KLTMASVVKPGSYTPLTFPSIETHIHVSTARMAYSSGSSPEMTA
PGETNTGSTWDPTTYITTTDPKDTSSAQVSTPHSVRTLRTTENH
PKTESATPAAYSGSPKISSSPNLTSPATKAWTITDTTEHSTQLHY
TKLAEKSSGFETQSAPGPVSVVIPTSPTIGSSTLELTSDVPGEPL
VLAPSEQTTITLPMATWLSTSLTEEMASTDLDISSPSSPMSTFAI
FPPMSTPSHELSKSEADTSAIRNTDSTTLDQHLGIRSLGRTGDLT
TVPITPLTTTWTSVIEHSTQAQDTLSATMSPTHVTQSLKDQTSIP
ASASPSHLTEVYPELGTQGRSSSEATTFWKPSTDTLSREIETGPT
NIQSTPPMDNTTTGSSSSGVTLGIAHLPIGTSSPAETSTNMALER
RSSTATVSMAGTMGLLVTSAPGRSISQSLGRVSSVLSESTTEGV
TDSSKGSSPRLNTQGNTALSSSLEPSYAEGSQMSTSIPLTSSPTT
PDVEFIGGSTFWTKEVTTVMTSDISKSSARTESSSATLMSTALG
STENTGKEKLRTASMDLPSPTPSMEVTPWISLTLSNAPNTTDSL
DLSHGVHTSSAGTLATDRSLNTGVTRASRLENGSDTSSKSLSM
GNSTHTSMTYTEKSEVSSSIHPRPETSAPGAETTLTSTPGNRAIS
LTLPFSSIPVEEVISTGITSGPDINSAPMTHSPITPPTIVWTSTGTIE
QSTQPLHAVSSEKVSVQTQSTPYVNSVAVSASPTHENSVSSGSS
TSSPYSSASLESLDSTISRRNAITSWLWDLTTSLPTTTWPSTSLS
EALSSGHSGVSNPSSTTTEFPLFSAASTSAAKQRNPETETHGPQ
NTAASTLNTDASSVTGLSETPVGASISSEVPLPMAITSRSDVSGL
TSESTANPSLGTASSAGTKLTRTISLPTSESLVSFRMNKDPWTV
SIPLGSHPTTNTETSIPVNSAGPPGLSTVASDVIDTPSDGAESIPT
VSFSPSPDTEVTTISHFPEKTTHSFRTISSLTHELTSRVTPIPGDW
MSSAMSTKPTGASPSITLGERRTITSAAPTTSPIVLTASFTETSTV
SLDNETTVKTSDILDARKTNELPSDSSSSSDLINTSIASSTMDVT
KTASISPTSISGMTASSSPSLFSSDRPQVPTSTTETNTATSPSVSS
NTYSLDGGSNVGGTPSTLPPFTITHPVETSSALLAWSRPVRTFS
TMVSTDTASGENPTSSNSVVTSVPAPGTWTSVGSTTDLPAMGF
LKTSPAGEAHSLLASTIEPATAFTPHLSAAVVTGSSATSEASLLT
TSESKAIHSSPQTPTTPTSGANWETSATPESLLVVTETSDTTLTS
KILVTDTILFSTVSTPPSKFPSTGTLSGASEPTLLPDTPAIPLTATE
PTSSLATSFDSTPLVTIASDSLGTVPETTLTMSETSNGDALVLKT
VSNPDRSIPGITIQGVTESPLHPSSTSPSKIVAPRNTTYEGSITVA
LSTLPAGTTGSLVFSQSSENSETTALVDSSAGLERASVMPLTTG
SQGMASSGGIRSGSTHSTGTKTFSSLPLTMNPGEVTAMSEITTN
RLTATQSTAPKGIPVKPTSAESGLLTPVSASSSPSKAFASLTTAP
PTWGIPQSTLTFEFSEVPSLDTKSASLPTPGQSLNTIPDSDASTA
SSSLSKSPEKNPRARMMTSTKAISASSFQSTGFTETPEGSASPSM
AGHEPRVPTSGTGDPRYASESMSYPDPSKASSAMTSTSLASKL
TTLFSTGQAARSGSSSSPISLSTEKETSFLSPTASTSRKTSLFLGP
SMARQPNILVHLQTSALTLSPTSTLNMSQEEPPELTSSQTIAEEE
GTTAETQTLTFTPSETPTSLLPVSSPTEPTARRKSSPETWASSISV
PAKTSLVETTDGTLVTTIKMSSQAAQGNSTWPAPAEETGSSPA
GTSPGSPEMSTTLKIMSSKEPSISPEIRSTVRNSPWKTPETTVPM
ETTVEPVTLQSTALGSGSTSISHLPTGTTSPTKSPTENMLATERV
SLSPSPPEAWTNLYSGTPGGTRQSLATMSSVSLESPTARSITGT
GQQSSPELVSKTTGMEFSMWHGSTGGTTGDTHVSLSTSSNILE
DPVTSPNSVSSLTDKSKHKTETWVSTTAIPSTVLNNKIMAAEQ
QTSRSVDEAYSSTSSWSDQTSGSDITLGASPDVTNTLYITSTAQ
TTSLVSLPSGDQGITSLTNPSGGKTSSASSVTSPSIGLETLRANV
SAVKSDIAPTAGHLSQTSSPAEVSILDVTTAPTPGISTTITTMGT
NSISTTTPNPEVGMSTMDSTPATERRTTSTEHPSTWSSTAASDS
WTVTDMTSNLKVARSPGTISTMHTTSFLASSTELDSMSTPHGRI
TVIGTSLVTPSSDASAVKTETSTSERTLSPSDTTASTPISTFSRVQ
RMSISVPDILSTSWTPSSTEAEDVPVSMVSTDHASTKTDPNTPL
STFLFDSLSTLDWDTGRSLSSATATTSAPQGATTPQELTLETMI
SPATSQLPFSIGHITSAVTPAAMARSSGVTFSRPDPTSKKAEQTS
TQLPTTTSAHPGQVPRSAATTLDVIPHTAKTPDATFQRQGQTA
LTTEARATSDSWNEKEKSTPSAPWITEMMNSVSEDTIKEVTSSS
SVLRTLNTLDINLESGTTSSPSWKSSPYERIAPSESTTDKEAIHPS
TNTVETTGWVTSSEHASHSTIPAHSASSKLTSPVVTTSTREQAI
VSMSTTTWPESTRARTEPNSFLTIELRDVSPYMDTSSTTQTSIIS
SPGSTAITKGPRTEITSSKRISSSFLAQSMRSSDSPSEAITRLSNFP
AMTESGGMILAMQTSPPGATSLSAPTLDTSATASWTGTPLATT
QRFTYSEKTTLFSKGPEDTSQPSPPSVEETSSSSSLVPIHATTSPS |

TABLE 13-continued

Table of Sequences.

| SEQ ID NO | NAME | SEQ |
|---|---|---|
| | | NILLTSQGHSPSSTPPVTSVFLSETSGLGKTTDMSRISLEPGTSLP |
| | | PNLSSTAGEALSTYEASRDTKAIHHSADTAVTNMEATSSEYSPI |
| | | PGHTKPSKATSPLVTSHIMGDITSSTSVFGSSETTEIETVSSVNQ |
| | | GLQERSTSQVASSATETSTVITHVSSGDATTHVTKTQATFSSGT |
| | | SISSPHQFITSTNTFTDVSTNPSTSLIMTESSGVTITTQTGPTGAA |
| | | TQGPYLLDTSTMPYLTETPLAVTPDFMQSEKTTLISKGPKDVS |
| | | WTSPPSVAETSYPSSLTPFLVTTIPPATSTLQGQHTSSPVSATSV |
| | | LTSGLVKTTDMLNTSMEPVTNSPQNLNNPSNEILATLAATTDIE |
| | | TIHPSINKAVTNMGTASSAHVLHSTLPVSSEPSTATSPMVPASS |
| | | MGDALASISIPGSETTDIEGEPTSSLTAGRKENSTLQEMNSTTES |
| | | NIILSNVSVGAITEATKMEVPSFDATFIPTPAQSTKFPDIFSVASS |
| | | RLSNSPPMTISTHMTTTQTGSSGATSKIPLALDTSTLETSAGTPS |
| | | VVTEGFAHSKITTAMNNDVKDVSQTNPPFQDEASSPSSQAPVL |
| | | VTTLPSSVAFTPQWHSTSSPVSMSSVLTSSLVKTAGKVDTSLET |
| | | VTSSPQSMSNTLDDISVTSAATTDIETTHPSINTVVTNVGTTGS |
| | | AFESHSTVSAYPEPSKVTSPNVTTSTMEDTTISRSIPKSSKTTRT |
| | | ETETTSSLTPKLRETSISQEITSSTETSTVPYKELTGATTEVSRTD |
| | | VTSSSSTSFPGPDQSTVSLDISTETNTRLSTSPIMTESAEITITTQT |
| | | GPHGATSQDTFTMDPSNTTPQAGIHSAMTHGFSQLDVTTLMSR |
| | | IPQDVSWTSPPSVDKTSSPSSFLSSPAMTTPSLISSTLPEDKLSSP |
| | | MTSLLTSGLVKITDILRTRLEPVTSSLPNFSSTSDKILATSKDSK |
| | | DTKEIFPSINTEETNVKANNSGHESHSPALADSETPKATTQMVI |
| | | TTTVGDPAPSTSMPVHGSSETTNIKREPTYFLTPRLRETSTSQES |
| | | SFPTDTSFLLSKVPTGTITEVSSTGVNSSSKISTPDHDKSTVPPDT |
| | | FTGEIPRVFTSSIKTKSAEMTITTQASPPESASHSTLPLDTSTTLS |
| | | QGGTHSTVTQGFPYSEVTTLMGMGPGNVSWMTTPPVEETSSV |
| | | SSLMSSPAMTSPSPVSSTSPQSIPSSPLPVTALPTSVLVTTTDVLG |
| | | TTSPESVTSSPPNLSSITHERPATYKDTAHTEAAMHHSTNTAVT |
| | | NVGTSGSGHKSQSSVLADSETSKATPLMSTTSTLGDTSVSTSTP |
| | | NISQTNQIQTEPTASLSPRLRESSTSEKTSSTTETNTAFSYVPTG |
| | | AITQASRTEISSSRTSISDLDRPTIAPDISTGMITRLFTSPIMTKSA |
| | | EMTVTTQTTTPGATSQGILPWDTSTTLFQGGTHSTVSQGFPHSE |
| | | ITTLRSRTPGDVSWMTTPPVEETSSGFSLMSPSMTSPSPVSSTSP |
| | | ESIPSSPLPVTALLTSVLVTTTNVLGTTSPEPVTSSPPNLSSPTQE |
| | | RLTTYKDTAHTEAMHASMHTNTAVANVGTSISGHESQSSVPA |
| | | DSHTSKATSPMGITFAMGDTSVSTSTPAFFETRIQTESTSSLIPG |
| | | LRDTRTSEEINTVTETSTVLSEVPTTTTTEVSRTEVITSSRTTISG |
| | | PDHSKMSPYISTETITRLSTFPFVTGSTEMAITNQTGPIGTISQAT |
| | | LTLDTSSTASWEGTHSPVTQRFPHSEETTTMSRSTKGVSWQSP |
| | | PSVEETSSPSSPVPLPAITSHSSLYSAVSGSSPTSALPVTSLLTSG |
| | | RRKTIDMLDTHSELVTSSLPSASSFSGEILTSEASTNTETIHFSEN |
| | | TAETNMGTTNSMHKLHSSVSIHSQPSGHTPPKVTGSMMEDAIV |
| | | STSTPGSPETKNVDRDSTSPLTPELKEDSTALVMNSTTESNTVF |
| | | SSVSLDAATEVSRAEVTYYDPTFMPASAQSTKSPDISPEASSSH |
| | | SNSPPLTISTHKTIATQTGPSGVTSLGQLTLDTSTIATSAGTPSAR |
| | | TQDFVDSETTSVMNNDLNDVLKTSPFSAEEANSLSSQAPLLVT |
| | | TSPSPVTSTLQEHSTSSLVSVTSVPTPTLAKITDMDTNLEPVTRS |
| | | PQNLRNTLATSEATTDTHTMHPSINTAVANVGTTSSPNEFYFT |
| | | VSPDSDPYKATSAVVITSTSGDSIVSTSMPRSSAMKKIESETTFS |
| | | LIFRLRETSTSQKIGSSSDTSTVFDKAFTAATTEVSRTELTSSSRT |
| | | SIQGTEKPTMSPDTSTRSVTMLSTFAGLTKSEERTIATQTGPHR |
| | | ATSQGTLTWDTSITTSQAGTHSAMTHGFSQLDLSTLTSRVPEYI |
| | | SGTSPPSVEKTSSSSSLLSLPAITSPSPVPTTLPESRPSSPVHLTSL |
| | | PTSGLVKTTDMLASVASLPPNLGSTSHKIPTTSEDIKDTEKMYP |
| | | STNIAVTNVGTTTSEKESYSSVPAYSEPPKVTSPMVTSFNIRDTI |
| | | VSTSMPGSSEITRIEMESTFSLAHGLKGTSTSQDPIVSTEKSAVL |
| | | HKLTTGATETSRTEVASSRRTSIPGPDHSTESPDISTEVIPSLPISL |
| | | GITESSNMTIITRTGPPLGSTSQGTFTLDTPTTSSRAGTHSMATQ |
| | | EFPHSEMTTVMNKDPEILSWTIPPSIEKTSFSSSLMPSPAMTSPP |
| | | VSSTLPKTIHTTPSPMTSLLTPSLVMTTDTLGTSPEPTTSSPPNLS |
| | | STSHEILTTDEDTTAIEAMHPSTSTAATNVETTSSGHGSQSSVL |
| | | ADSEKTKATAPMDTTSTMGHTTVSTSMSVSSETTKIKRESTYS |
| | | LTPGLRETSISQNASFSTDTSIVLSEVPTGTTAEVSRTEVTSSGR |
| | | TSIPGPSQSTVLPEISTRTMTRLFASPTMTESAEMTIPTQTGPSGS |
| | | TSQDTLTLDTSTTKSQAKTHSTLTQRFPHSEMTTLMSRGPGDM |
| | | SWQSSPSLENPSSLPSLLSLPATTSPPPISSTLPVTISSSPLPVTSLL |
| | | TSSPVTTTDMLHTSPELVTSSPPKLSHTSDERLTTGKDTTNTEA |
| | | VHPSTNTAASNVEIPSSGHESPSSALADSETSKATSPMFITSTQE |
| | | DTTVAISTPHFLETSRIQKESISSLSPKLRETGSSVETSSAIETSAV |
| | | LSEVSIGATTEISRTEVTSSSRTSISGSAESTMLPEISTTRKIIKFPT |
| | | SPILAESSEMTIKTQTSPPGSTSESTFTLDTSTTPSLVITHSTMTQ |
| | | RLPHSEITTLVSRGAGDVPRPSSLPVEETSPPSSQLSLSAMISPSP |
| | | VSSTLPASSHSSSASVTSLLTPGQVKTTEVLDASAEPETSSPPSL |
| | | SSTSVEILATSEVTTDTEKIHPFSNTAVTKVGTSSSGHESPSSVL |

TABLE 13-continued

Table of Sequences.

| SEQ ID NO | NAME | SEQ |
|---|---|---|
| | | PDSETTKATSAMGTISIMGDTSVSTLTPALSNTRKIQSEPASSLT |
| | | TRLRETSTSEETSLATEANTVLSKVSTGATTEVSRTEAISFSRTS |
| | | MSGPEQSTMSQDISIGTIPRISASSVLTESAKMTITTQTGPSESTL |
| | | ESTLNLNTATTPSWVETHSIVIQGFPHPEMTTSMGRGPGGVSW |
| | | PSPPFVKETSPPSSPLSLPAVTSPHPVSTTFLAHIPPSPLPVTSLLT |
| | | SGPATTTDILGTSTEPGTSSSSSLSTTSHERLTTYKDTAHTEAVH |
| | | PSTNTGGTNVATTSSGYKSQSSVLADSSPMCTTSTMGDTSVLT |
| | | STPAFLETRRIQTELASSLTPGLRESSGSEGTSSGTKMSTVLSKV |
| | | PTGATTEISKEDVTSIPGPAQSTISPDISTRTVSWFSTSPVMTESA |
| | | EITMNTHTSPLGATTQGTSTLDTSSTTSLTMTHSTISQGFSHSQ |
| | | MSTLMRRGPEDVSWMSPPLLEKTRPSFSLMSSPATTSPSPVSST |
| | | LPESISSSPLPVTSLLTSGLAKTTDMLHKSSEPVTNSPANLSSTS |
| | | VEILATSEVTTDTEKTHPSSNRTVTDVGTSSSGHESTSFVLADS |
| | | QTSKVTSPMVITSTMEDTSVSTSTPGFFETSRIQTEPTSSLTLGL |
| | | RKTSSSEGTSLATEMSTVLSGVPTGATAEVSRTEVTSSSRTSISG |
| | | FAQLTVSPETSTETITRLPTSSIMTESAEMMIKTQTDPPGSTPEST |
| | | HTVDISTTPNWVETHSTVTQRFSHSEMTTLVSRSPGDMLWPSQ |
| | | SSVEETSSASSLLSLPATTSPSPVSSTLVEDFPSASLPVTSLLNPG |
| | | LVITTDRMGISREPGTSSTSNLSSTSHERLTTLEDTVDTEDMQPS |
| | | THTAVTNVRTSISGHESQSSVLSDSETPKATSPMGTTYTMGETS |
| | | VSISTSDFFETSRIQIEPTSSLTSGLRETSSSERISSATEGSTVLSEV |
| | | PSGATTEVSRTEVISSRGTSMSGPDQFTISPDISTEAITRLSTSPEVI |
| | | TESAESAITIETGSPGATSEGTLTLDTSTTTFWSGTHSTASPGFS |
| | | HSEMTTLMSRTPGDVPWPSLPSVEEASSVSSSLSSPAMTSTSFF |
| | | STLPESISSSPHPVTALLTLGPVKTTDMLRTSSEPETSSPPNLSST |
| | | SAEILATSEVTKDREKIHPSSNTPVVNVGTVIYKHLSPSSVLAD |
| | | LVTTKPTSPMATTSTLGNTSVSTSTPAFPETMMTQPTSSLTSGL |
| | | REISTSQETSSATERSASLSGMPTGATTKVSRTEALSLGRTSTPG |
| | | PAQSTISPEISTETITRISTPLTTTGSAEMTITPKTGHSGASSQGTF |
| | | TLDTSSRASWPGTHSAATHRSPHSGMTTPMSRGPEDVSWPSRP |
| | | SVEKTSPPSSLVSLSAVTSPSPLYSTPSESSHSSPLRVTSLFTPVM |
| | | MKTTDMLDTSLEPVTTSPPSMNITSDESLATSKATMETEAIQLS |
| | | ENTAVTQMGTISARQEFYSSYPGLPEPSKVTSPVVTSSTIKDIVS |
| | | TTIPASSEITRIEMESTSTLTPTPRETSTSQEIHSATKPSTVPYKAL |
| | | TSATIEDSMTQVMSSSRGPSPDQSTMSQDISTEVITRLSTSPIKT |
| | | ESTEMTITTQTGSPGATSRGTLTLDTSTTFMSGTHSTASQGFSH |
| | | SQMTALMSRTPGDVPWLSHPSVEEASSASFSLSSPVMTSSSPVS |
| | | STLPDSIHSSSLPVTSLLTSGLVKTTELLGTSSEPETSSPPNLSSTS |
| | | AEILAITEVTTDTEKLEMTNVVTSGYTHESPSSVLADSVTTKAT |
| | | SSMGITYPTGDTNVLTSTPAFSDTSRIQTKSKLSLTPGLMETSIS |
| | | EETSSATEKSTVLSSVPTGATTEVSRTEAISSSRTSIPGPAQSTMS |
| | | SDTSMETITRISTPLTRKESTDMAITPKTGPSGATSQGTFTLDSS |
| | | STASWPGTHSATTQRFPQSVVTTPMSRGPEDVSWPSPLSVEKN |
| | | SPPSSLVSSSSVTSPSPLYSTPSGSSHSSPVPVTSLFTSIMMKATD |
| | | MLDASLEPETTSAPNMNITSDESLAASKATTETEAIHVFENTAA |
| | | SHVETTSATEELYSSSPGFSEPTKVISPVVTSSSIRDNMVSTTMP |
| | | GSSGITRIEIESMSSLTPGLRETRTSQDITSSTETSTVLYKMPSGA |
| | | TPEVSRTEVMPSSRTSIPGPAQSTMSLDISDEVVTRLSTSPIMTE |
| | | SAEITITTQTGYSLATSQVTLPLGTSMTFLSGTHSTMSQGLSHSE |
| | | MTNLMSRGPESLSWTSPRFVETTRSSSSLTSLPLTTSLSPVSSTL |
| | | LDSSPSSPLPVTSLILPGLVKTTEVLDTSSEPKTSSSPNLSSTSVEI |
| | | PATSEIMTDTEKIHPSSNTAVAKVRTSSSVHESHSSVLADSETTI |
| | | TIPSMGITSAVDDTTVFTSNPAFSETRRIPTEPTFSLTPGFRETST |
| | | SEETTSITETSAVLYGVPTSATTEVSMTEIMSSNRIHIPDSDQST |
| | | MSPDIITEVITRLSSSSMMSESTQMTITTQKSSPGATAQSTLTLA |
| | | TTTAPLARTHSTVPPRFLHSEMTTLMSRSPENPSWKSSLFVEKT |
| | | SSSSSLLSLPVTTSPSVSSTLPQSIPSSSFSVTSLLTPGMVKTTDTS |
| | | TEPGTSLSPNLSGTSVEILAASEVTTDTEKIHPSSSMAVTNVGTT |
| | | SSGHELYSSVSIHSEPSKATYPVGTPSSMAETSISTSMPANFETT |
| | | GFEAEPFSHLTSGFRKTNMSLDTSSVTPTNTPSSPGSTHLLQSSK |
| | | TDFTSSAKTSSPDWPPASQYTEIPVDIITPFNASPSITESTGITSFP |
| | | ESRFTMSVTESTHHLSTDLLPSAETISTGTVMPSLSEAMTSFAT |
| | | TGVPRAISGSGSPFSRTESGPGDATLSTIAESLPSSTPVPFSSSTFT |
| | | TTDSSTIPALHEITSSSATPYRVDTSLGTESSTTEGRLVMVSTLD |
| | | TSSQPGRTSSSPILDTRMTESVELGTVTSAYQVPSLSTRLTRTD |
| | | GIMEHITKIPNEAAHRGTIRPVKGPQTSTSPASPKGLHTGGTKR |
| | | METTTTALKTTTTALKTTSRATLTTSVYTPTLGTLTPLNASMQ |
| | | MASTIPTEMMITTPYVFPDVPETTSSLATSLGAETSTALPRTTPS |
| | | VFNRESETTASLVSRSGAERSPVIQTLDVSSSEPDTTASWVIHP |
| | | AETIPTVSKTTPNFFHSELDTVSSTATSHGADVSSAIPTNISPSEL |
| | | DALTPLVTISGTDTSTTFPTLTKSPHETETRTTWLTHPAETSSTIP |
| | | RTIPNFSHHESDATPSIATSPGAETSSAIPEVITVSPGAEDLVTSQV |
| | | TSSGTDRNMTIPTLTLSPGEPKTIASLVTHPEAQTSSAIPTSTISP |
| | | AVSRLVTSMVTSLAAKTSTTNRALTNSPGEPATTVSLVTHPAQ |

TABLE 13-continued

Table of Sequences.

| SEQ ID NO | NAME | SEQ |
|---|---|---|
| | | TSPTVPWTTSIFFHSKSDTTPSMTTSHGAESSSAVPTPTVSTEVP<br>GVVTPLVTSSRAVISTTIPILTLSPGEPETTPSMATSHGEEASSAI<br>PTPTVSPGVPGVVTSLVTSSRAVTSTTIPILTFSLGEPETTPSMAT<br>SHGTEAGSAVPTVLPEVPGMVTSLVASSRAVTSTTLPTLTLSPG<br>EPETTPSMATSHGAEASSTVPTVSPEVPGVVTSLVTSSSGVNST<br>SIPTLILSPGELETTPSMATSHGAEASSAVPTPTVSPGVSGVVTP<br>LVTSSRAVTSTTIPILTLSSSEPETTPSMATSHGVEASSAVLTVSP<br>EVPGMVTSLVTSSRAVTSTTIPTLTISSDEPETTTSLVTHSEAKM<br>ISAIPTLAVSPTVQGLVTSLVTSSGSETSAFSNLTVASSQPETIDS<br>WVAHPGTEASSVVPTLTVSTGEPFTNISLVTHPAESSSTLPRTTS<br>RFSHSELDTMPSTVTSPEAESSSAISTTISPGIPGVLTSLVTSSGR<br>DISATFPTVPESPHESEATASWVTHPAVTSTTVPRTTPNYSHSEP<br>DTTPSIATSPGAEATSDFPTITVSPDVPDMVTSQVTSSGTDTSITI<br>PTLTLSSGEPETTTSFITYSETHTSSAIPTLPVSPGASKMLTSLVIS<br>SGTDSTTTFPTLTETPYEPETTAIQLIHPAETNTMVPRTTPKFSH<br>SKSDTTLPVAITSPGPEASSAVSTTTISPDMSDLVTSLVPSSGTD<br>TSTTFPTLSETPYEPETTATWLTHPAETSTTVSGTIPNFSHRGSD<br>TAPSMVTSPGVDTRSGVPTTTIPPSIPGVVTSQVTSSATDTSTAI<br>PTLTPSPGEPETTASSATHPGTQTGFTVPIRTVPSSEPDTMASW<br>VTHPPQTSTPVSRTTSSFSHSSPDATPVMATSPRTEASSAVLTTI<br>SPGAPEMVTSQITSSGAATSTTVPTLTHSPGMPETTALLSTHPR<br>TETSKTFPASTVFPQVSETTASLTIRPGAETSTALPTQTTSSLFTL<br>LVTGTSRVDLSPTASPGVSAKTAPLSTHPGTETSTMIPTSTLSLG<br>LLETTGLLATSSSAETSTSTLTLTVSPAVSGLSSASITTDKPQTV<br>TSWNTETSPSVTSVGPPEFSRTVTGTTMTLIPSEMPTPPKTSHGE<br>GVSPTTILRTTMVEATNLATTGSSPTVAKTTTTFNTLAGSLFTP<br>LTTPGMSTLASESVTSRTSYNHRSWISTTSSYNRRYWTPATSTP<br>VTSTFSPGISTSSIPSSTAATVPFMVPFTLNFTITNLQYEEDMRHP<br>GSRKFNATERELQGLLKPLFRNSSLEYLYSGCRLASLRPEKDSS<br>ATAVDAICTHRPDPEDLGLDRERLYWELSNLTNGIQELGPYTL<br>DRNSLYVNGFTHRSSMPTTSTPGTSTVDVGTSGTPSSSPSPTTA<br>GPLLMPFTLNETITNLQYEEDMRRTGSRKENTMESVLQGLLKP<br>LFKNTSVGPLYSGCRLTLLRPEKDGAATGVDAICTHRLDPKSP<br>GLNREQLYWELSKLTNDIEELGPYTLDRNSLYVNGFTHQSSVS<br>TTSTPGTSTVDLRTSGTPSSLSSPTIMAAGPLLVPFTLNFTITNLQ<br>YGEDMGHPGSRKENTTERVLQGLLGPIEKNTSVGPLYSGCRLT<br>SLRSEKDGAATGVDAICIHHLDPKSPGLNRERLYWELSQLTNG<br>IKELGPYTLDRNSLYVNGFTHRTSVPTSSTPGTSTVDLGTSGTP<br>FSLPSPATAGPLLVLFTLNFTITNLKYEEDMHRPGSRKFNTTER<br>VLQTLLGPMFKNTSVGLLYSGCRLTLLRSEKDGAATGVDAICT<br>HRLDPKSPGVDREQLYWELSQLTNGIKELGPYTLDRNSLYVN<br>GFTHWIPVPTSSTPGTSTVDLGSGTPSSLPSPTTAGPLLVPFTLN<br>FTITNLKYEEDMHCPGSRKFNTTERVLQSLLGPMFKNTSVGPL<br>YSGCRLTLLRSEKDGAATGVDAICTHRLDPKSPGVDREQLYW<br>ELSQLTNGIKELGPYTLDRNSLYVNGFTHQTSAPNTSTPGTSTV<br>DLGTSGTPSSLPSPTSAGPLLVPFTLNFTITNLQYEEDMHHPGSR<br>KFNTTERVLQGLLGPMFKNTSVGLLYSGCRLTLLRPEKNGAAT<br>GMDAICSHRLDPKSPGLNREQLYWELSQLTHGIKELGPYTLDR<br>NSLYVNGFTHRSSVAPTSTPGTSTVDLGTSGTPSSLPSPTTAVPL<br>LVPFTLNETITNLQYGEDMRHPGSRKENTTERVLQGLLGPLEK<br>NSSVGPLYSGCRLISLRSEKDGAATGVDAICTHHLNPQSPGLDR<br>EQLYWQLSQMTNGIKELGPYTLDRNSLYVNGFTHRSSGLTTST<br>PWTSTVDLGTSGTPSPVPSPTTTGPLLVPFTLNFTITNLQYEEN<br>MGHPGSRKFNITESVLQGLLKPLEKSTSVGPLYSGCRLTLLRPE<br>KDGVATRVDAICTHRPDPKIPGLDRQQLYWELSQLTHSITELG<br>PYTLDRDSLYVNGFTQRSSVPTTSTPGTFTVQPETSETPSSLPGP<br>TATGPVLLPFTLNETITNLQYEEDMRRPGSRKENTTERVLQGLL<br>MPLFKNTSVSSLYSGCRLTLLRPEKDGAATRVDAVCTHRPDPK<br>SPGLDRERLYWKLSQLTHGITELGPYTLDRHSLYVNGFTHQSS<br>MTTTRTPDTSTMEILATSRTPASLSGPMTASPLLVLFTINETITNL<br>RYEENMEMPGSRKENTTERVLQGLLRPVEKNTSVGPLYSGCRL<br>TLLRPKKDGAATKVDAICTYRPDPKSPGLDREQLYWELSQLTH<br>SITELGPYTLDRDSLYVNGFTQRSSVPTTSIPGTPTVDLGTSGTP<br>VSKPGPSAASPLLVLFTLNFTITNLRYEENMQHPGSRKFNTTER<br>VLQGLLRSLFKSTSVGPLYSGCRLTLLRPEKDGTATGVDAICT<br>HHPDPKSPRLDREQLYWELSQLTHNITELGPYALDNDSLFVNG<br>FTHRSSVSTTSTPGTPTVYLGASKTPASIFGPSAASHLLILFTLNF<br>TITNLRYEENMWPGSRKFNTTERVLQGLLRPLFKNTSVGPLYS<br>GCRLTLLRPEKDGEATGVDAICTHRPDPTGPGLDREQLYLELS<br>QLTHSITELGPYTLDRDSLYVNGFTHRSSVPTTSTGVVSEEPFT<br>LNFTINNLRYMADMGQPGSLKFNITDNVMQHLLSPLFQRSSLG<br>ARYTGCRVIALRSVKNGAETRVDLLCTYLQPLSGPGLPIKQVF<br>HELSQQTHGITRLGPYSLDKDSLYLNGYNEPGPDEPPTTPKPAT<br>TFLPPLSEATTAMGYHLKTLTLNFTISNLQYSPDMGKGSATFNS |

TABLE 13-continued

Table of Sequences.

| SEQ ID NO | NAME | SEQ |
|---|---|---|
| | | TEGVLQHLLRPLFQKSSMGPFYLGCQLISLRPEKDGAATGVDT TCTYHPDPVGPGLDIQQLYWELSQLTHGVTQLGFYVLDRDSLF INGYAPQNLSIRGEYQINFHIVNWNLSNPDPTSSEYITLLRDIQD KVTTLYKGSQLHDTFRFCLVTNLTMDSVLVTVKALFSSNLDPS LVEQVFLDKTLNASFHWLGSTYQLVDIHVTEMESSVYQPTSSS STQHFYLNFTITNLPYSQDKAQPGTTNYQRNKRNIEDALNQLF RNSSIKSYFSDCQVSTFRSVPNRHHTGVDSLCNFSPLARRVDRV AIYEEFLRMTRNGTQLQNFTLDRSSVLVDGYSPNRNEPLTGNS DLPFWAVILIGLAGLLGVITCLICGVLVTTRRRKKEGEYNVQQ QCPGYYQSHLDLEDLQ |
| 151 | MUC16c114-N1 | AFSPLARRVDRVAIYEEFLRMTRNGTQLQNFTLDRSSVLVDGY SPNRNEPLTGNSDLPFWAVILIGLAGLLGLITCLICGVLVTTRRR KKEGEYNVQQQCPGYYQSHLDLEDLQ |
| 152 | MUC16c114-N2 | NFSPLARRVDRVAIYEEFLRMTRAGTQLQNFTLDRSSVLVDGY SPNRNEPLTGNSDLPFWAVILIGLAGLLGLITCLICGVLVTTRRR KKEGEYNVQQQCPGYYQSHLDLEDLQ |
| 153 | MUC16c114-N12 | AFSPLARRVDRVAIYEEFLRMTRAGTQLQNFTLDRSSVLVDGY SPNRNEPLTGNSDLPFWAVILIGLAGLLGLITCLICGVLVTTRRR KKEGEYNVQQQCPGYYQSHLDLEDLQ |
| 154 | MUC16c114-N123 | AFSPLARRVDRVAIYEEFLRMTRAGTQLQAFTLDRSSVLVDGY SPNRNEPLTGNSDLPFWAVILIGLAGLLGLITCLICGVLVTTRRR KKEGEYNVQQQCPGYYQSHLDLEDLQ |
| 155 | MUC16c344 N-term of first tandem repeat | WELSQL |
| 156 | MUC16c344 C-term of first tandem repeat | TGVDSLC |
| 157 | MUC16c344 N-term of ectodomain | NFSPLAR |
| 158 | MUC16c344 C-term of ectodomain | TGNSDLP |
| 159 | Transmembrane | FWAVILIGLAGLLGLITCLICGVLV |
| 160 | Cytoplasmic tail | TTRRRKKEGEYNVQQQCPGYYQSHLDLEDLQ |
| 161 | MUC16c114 ectodomain | NFSPLARRVDRVAIYEEFLRMTRNGTQLQNFTLDRSSVLVDGY SPNRNEPLTGNSDLP |
| 162 | MUC16c80 ectodomain | NFSPLARRVDRVAIYEEFLRMDLP |
| 163 | MUC16c86 ectodomain | NFSPLARRVDRVAIYEEFLRMTRNGTQLQNFTLDRSSVLVDGY SPNRNEPLTGNSDLP |
| 164 | MUC16c86 transmembrane | FWAVILIGLAGLLGLITCLICG |
| 165 | MUC16c86 cytoplasmic | DLEDLQ |
| 166 | MUC 16 3(N to A)c114 ectodomain | AFSPLARRVDRVAIYEEFLRMTRAGTQLQAFTLDRSSVLVDGY SPNRNEPLTGNSDLP |
| 167 | LGAL S3 sugar binding domain | PYNLPLPGGVVPRMLITILGTVKPNANRIALDFQRGNDVAFHF NPRFNENNRRVIVCNTKLDNNWGREERQSVFPFESGKPFKIQV LVEPDHFKVAVNDAHLLQYNHRVKKLNEISKLGISGDIDLTS |
| 168 | MUC16 nonglycosylated peptide 2 | CTLDRSSVLVDGYSPNRNE |

TABLE 13-continued

| Table of Sequences. | | |
|---|---|---|
| SEQ ID NO | NAME | SEQ |
| 169 | MUC16 unrelated peptide 18mer | GAVPRSATINVSRIATGP |
| 170 | 18mer (no C) | TRNGTQLQNFTLDRSSV |
| 171 | 15mer (no C) | GTQLQNFTLDRSSV |
| 172 | MUC16c114-N23 | NFSPLARRVDRVAIYEEFLRMTRAGTQLQAFTLDRSSVLVDGY SPNRNEPLTGNSDLPFWAVILIGLAGLLGLITCLICGVLVTTRRR KKEGEYNVQQQCPGYYQSHLDLEDLQ |
| 173 | N24 mut c344 | WELSQLTHGVTQLGFYVLDRDSLFINGYAPQNLSIRGEYQINF HIVNQNLSNPDPTSSEYITLLRDIQDKVTTLYKGSQLHDTFRFC LVTNLTMDSVLVTVKALFSSNLDPSLVEQVFLDKTLNASFHQL GSTYQLVDIHVTEMESSVYQPTSSSSTQHFYLNFTITNLPYSQD KAQPGTTNYQRNKRNIEDALNQLFRNSSIKSYFSDCQVSTFRS VPNRHHTGVDSLCNFSPLARRVDRVAIYEEFLRMTRAGTQLQ NFTLDRSSVLVDGYSPNRNEPLTGNSDLPFWAVILIGLAGLLGL ITCLICGVLVTTRRRKKEGEYNVQQQCPGYYQSHLDLEDLQ |
| 174 | N30 mut c344 | WELSQLTHGVTQLGFYVLDRDSLFINGYAPQNLSIRGEYQINF HIVNQNLSNPDPTSSEYITLLRDIQDKVTTLYKGSQLHDTFRFC LVTNLTMDSVLVTVKALFSSNLDPSLVEQVFLDKTLNASFHQL GSTYQLVDIHVTEMESSVYQPTSSSSTQHFYLNFTITNLPYSQD KAQPGTTNYQRNKRNIEDALNQLFRNSSIKSYFSDCQVSTFRS VPNRHHTGVDSLCNFSPLARRVDRVAIYEEFLRMTRNGTQLQ AFTLDRSSVLVDGYSPNRNEPLTGNSDLPFWAVILIGLAGLLGL ITCLICGVLVTTRRRKKEGEYNVQQQCPGYYQSHLDLEDLQ |
| 175 | N24-N30 mut c344 | WELSQLTHGVTQLGFYVLDRDSLFINGYAPQNLSIRGEYQINF HIVNQNLSNPDPTSSEYITLLRDIQDKVTTLYKGSQLHDTFRFC LVTNLTMDSVLVTVKALFSSNLDPSLVEQVFLDKTLNASFHQL GSTYQLVDIHVTEMESSVYQPTSSSSTQHFYLNFTITNLPYSQD KAQPGTTNYQRNKRNIEDALNQLFRNSSIKSYFSDCQVSTFRS VPNRHHTGVDSLCNFSPLARRVDRVAIYEEFLRMTRAGTQLQ AFTLDRSSVLVDGYSPNRNEPLTGNSDLPFWAVILIGLAGLLGL ITCLICGVLVTTRRRKKEGEYNVQQQCPGYYQSHLDLEDLQ |

8. EQUIVALENTS

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed:

1. An antibody or antigen-binding fragment thereof that immunospecifically binds to MUC16, wherein the antibody or antigen-binding fragment thereof comprises:

(a) (i) a VH comprising a VH CDR1 comprising the amino acid sequence $TX_1GMGVG$ (SEQ ID NO:103), wherein $X_1$ is L or V; a VH CDR2 comprising the amino acid sequence $HIWWDDX_2DKYYX_3PALKS$ (SEQ ID NO:104), wherein $X_2$ is E or absent, and $X_3$ is Y or N; and a VH CDR3 comprising the amino acid sequence IGTAQATDALDY (SEQ ID NO:105); and (ii) a VL comprising a VL CDR1 comprising the amino acid sequence $RSSKSLX_4X_5SNGNTYLY$ (SEQ ID NO:106), wherein $X_4$ is R or L, and $X_5$ is K or H; a VL CDR2 comprising the amino acid sequence YMSNLAS (SEQ ID NO:107); and a VL CDR3 comprising the amino acid sequence $MQX_6LEX_7PLT$ (SEQ ID NO:108), wherein $X_6$ is G or S, and $X_7$ is H or Y; or (b) (i) a VH comprising a VH CDR1 comprising the amino acid sequence GFSLX8TX9GM (SEQ ID NO:109), wherein X8 is N or S, and wherein X9 is L or V; a VH CDR2 comprising the amino acid sequence WDDX10 (SEQ ID NO:110), wherein X10 is E or absent; and a VH CDR3 comprising the amino acid sequence GTAQATDALD (SEQ ID NO:111); and (ii) a VL comprising a VL CDR1 comprising the amino acid sequence SKSLX11X12SNGNTY (SEQ ID NO:112), wherein X11 is L or R, and X12 is H or K; a VL CDR2 comprising the amino acid sequence YMS (SEQ ID NO:113); and a VL CDR3 comprising the amino acid sequence X13LEX14PL (SEQ ID NO:114), wherein X13 is G or S, and X14 is H or Y; or (c) (i) a VH CDR1 comprising the amino acid sequence GFSLX15TX16GMG (SEQ ID NO:115), wherein X15 is N or S, and X16 is V or L; a VH CDR2 comprising the amino acid sequence IWWDDX17DK (SEQ ID NO:116), wherein X17 is E or absent; and a VH CDR3 comprising the amino acid sequence X18RIGTAQATDALDY (SEQ ID NO:117), wherein X18 is T, A, or S; and (ii) a VL comprising a VL CDR1 comprising the amino acid sequence KSLX19X20SNGNTY (SEQ ID NO:118), wherein X19 is V or L, and X20 is H or K; a VL CDR2 comprising the amino acid sequence YMS (SEQ ID NO:119); and a VL CDR3 comprising the amino acid sequence MQSLEYPLT (SEQ ID NO:120); or (d) (i) a VH comprising a VH CDR1 comprising the amino acid sequence of SEQ ID NO:83, a VH CDR2 comprising the amino acid sequence of SEQ ID NO:84, and a VH CDR3 comprising the amino acid sequence of SEQ ID NO:85; and (ii) a VL comprising a VL CDR1 comprising the amino acid sequence of SEQ ID NO:86, a VL CDR2 comprising the amino acid sequence of SEQ ID NO:87, and a VL CDR3 comprising the amino acid sequence of SEQ ID NO:88; or (e) (i) a VH comprising a VH CDR1 comprising the amino acid sequence of SEQ ID NO:89, a VH CDR2 comprising the amino acid sequence of SEQ ID NO:90, and a VH CDR3 comprising the amino acid sequence of SEQ ID NO:91; and (ii) a VL comprising a VL CDR1 comprising the amino acid sequence of SEQ ID NO:92, a VL CDR2 comprising the amino acid sequence of SEQ ID NO:93, and a VL CDR3 comprising the amino acid sequence of SEQ ID NO:94; or (f) (i) a VH comprising a VH CDR1 comprising the amino acid sequence of SEQ ID NO:95, a VH CDR2 comprising the amino acid sequence of SEQ ID NO:96, and a VH CDR3 comprising the amino acid sequence of SEQ ID NO:97 and (ii) a VL comprising a VL CDR1 comprising the amino acid sequence of SEQ ID NO:98, a VL CDR2 comprising the amino acid sequence of SEQ ID NO:99, and a VL CDR3 comprising the amino acid sequence of SEQ ID NO:100; or (g) (i) a VH comprising a VH CDR1 comprising the amino acid sequence of SEQ ID NO:23, a VH CDR2 comprising the amino acid sequence of SEQ ID NO:24, and a VH CDR3 comprising the amino acid sequence of SEQ ID NO:25; and (ii) a VL comprising a VL CDR1 comprising the amino acid sequence of SEQ ID NO:26, a VL CDR2 comprising the amino acid sequence of SEQ ID NO:27, and a VL CDR3 comprising the amino acid sequence of SEQ ID NO:28; or (h) (i) a VH comprising a VH CDR1 comprising the amino acid sequence of SEQ ID NO:29, a VH CDR2 comprising the amino acid sequence of SEQ ID NO:30, and a VH CDR3 comprising the amino acid sequence of SEQ ID NO:31; and (ii) a VL comprising a VL CDR1 comprising the amino acid sequence of SEQ ID NO:32, a VL CDR2 comprising the amino acid sequence of SEQ ID NO:33, and a VL CDR3 comprising the amino acid sequence of SEQ ID NO:34; or (i) (i) a VH comprising a VH CDR1 comprising the amino acid sequence of SEQ ID NO:35, a VH CDR2 comprising the amino acid sequence of SEQ ID NO:36, and a VH CDR3 comprising the amino acid sequence of SEQ ID NO:37; and (ii) a VL comprising a VL CDR1 comprising the amino acid sequence of SEQ ID NO:38, a VL CDR2 comprising the amino acid sequence of SEQ ID NO:39, and a VL CDR3 comprising the amino acid sequence of SEQ ID NO:40; or (j) (i) a VH comprising a VH CDR1 comprising the amino acid sequence of SEQ ID NO:43, a VH CDR2 comprising the amino acid sequence of SEQ ID NO:44, and a VH CDR3 comprising the amino acid sequence of SEQ ID NO:45; and (ii) a VL comprising a VL CDR1 comprising the amino acid sequence of SEQ ID NO:46, a VL CDR2 comprising the amino acid sequence of SEQ ID NO:47, and a VL CDR3 comprising the amino acid sequence of SEQ ID NO:48; or (k) (i) a VH comprising a VH CDR1 comprising the amino acid sequence of SEQ ID NO:49, a VH CDR2 comprising the amino acid sequence of SEQ ID NO:50, and a VH CDR3 comprising the amino acid sequence of SEQ ID NO:51; and (ii) a VL comprising a VL CDR1 comprising the amino acid sequence of SEQ ID NO:52, a VL CDR2 comprising the amino acid sequence of SEQ ID NO:53, and a VL CDR3 comprising the amino acid sequence of SEQ ID NO:54; or (l) (i) a VH comprising a VH CDR1 comprising the amino acid sequence of SEQ ID NO:55, a VH CDR2 comprising the amino acid sequence of SEQ ID NO:56, and a VH CDR3 comprising the amino acid sequence of SEQ ID NO:57; and (ii) a VL comprising a VL CDR1 comprising the amino acid sequence of SEQ ID NO:58, a VL CDR2 comprising the amino acid sequence of SEQ ID NO:59, and a VL CDR3 comprising the amino acid sequence of SEQ ID NO:60; or (m) (i) a VH comprising a VH CDR1 comprising the amino acid sequence of SEQ ID NO:3, a VH CDR2 comprising the amino acid sequence of SEQ ID NO:4, and a VH CDR3 comprising the amino acid sequence of SEQ ID NO:5; and (ii) a VL comprising a VL CDR1 comprising the amino acid sequence of SEQ ID NO:6, a VL CDR2 comprising the amino acid sequence of SEQ ID NO:7, and a VL CDR3 comprising the amino acid sequence of SEQ ID NO:8; or (n) (i) a VH comprising a VH CDR1 comprising the amino acid sequence of SEQ ID NO:9, a VH CDR2 comprising the amino acid sequence of SEQ ID NO:10, and a VH CDR3 comprising the amino acid sequence of SEQ ID NO:11; and (ii) a VL comprising a VL CDR1 comprising the amino acid sequence of SEQ ID NO:12, a VL CDR2 comprising the amino acid sequence of SEQ ID NO:13, and a VL CDR3 comprising the amino acid sequence of SEQ ID NO:14; or (o) (i) a VH comprising a VH CDR1 comprising the amino acid sequence of SEQ ID NO:15, a VH CDR2 comprising the amino acid sequence of SEQ ID NO:16, and a VH CDR3 comprising the amino acid sequence of SEQ ID NO:17; and (ii) a VL comprising a VL CDR1 comprising the amino acid sequence of SEQ ID NO:18, a VL CDR2 comprising the amino acid sequence of SEQ ID NO:19, and a VL CDR3 comprising the amino acid sequence of SEQ ID NO:20; or (p) (i) a VH comprising a VH CDR1 comprising the amino acid sequence of SEQ ID NO:63, a VH CDR2 comprising the amino acid sequence of SEQ ID NO:64, and a VH CDR3 comprising the amino acid sequence of SEQ ID NO:65; and (ii) a VL comprising a VL CDR1 comprising the amino acid sequence of SEQ ID NO:66, a VL CDR2 comprising the amino acid sequence of SEQ ID NO:67, and a VL CDR3 comprising the amino acid sequence of SEQ ID NO:68; or (q) (i) a VH comprising a VH CDR1 comprising the amino acid sequence of SEQ ID NO:69, a VH CDR2 comprising the amino acid sequence of SEQ ID NO:70, and a VH CDR3 comprising the amino acid sequence of SEQ ID NO:71; and (ii) a VL comprising a VL CDR1 comprising the amino acid sequence of SEQ ID NO:72, a VL CDR2 comprising the amino acid sequence of SEQ ID NO:73, and a VL CDR3 comprising the amino acid sequence of SEQ ID NO:74; or (r) (i) a VH comprising a VH CDR1 comprising the amino acid sequence of SEQ ID NO:75, a VH CDR2 comprising the amino acid sequence of SEQ ID NO:76, and a VH CDR3 comprising the amino acid sequence of SEQ ID NO:77; and (ii) a VL comprising a VL CDR1 comprising the amino acid sequence of SEQ ID NO:78, a VL CDR2 comprising the amino acid sequence of SEQ ID NO:79, and a VL CDR3 comprising the amino acid sequence of SEQ ID NO:80.

2. The antibody or antigen-binding fragment thereof of claim 1, wherein the antibody or antigen-binding fragment thereof is humanized.

3. The antibody or antigen-binding fragment thereof of claim 1, wherein the antibody or antigen-binding fragment thereof is a bispecific antibody.

4. The antibody or antigen-binding fragment thereof of claim 1, wherein the antigen-binding fragment thereof is a scFv.

5. A pharmaceutical composition comprising a therapeutically effective amount of the antibody or antigen-binding fragment thereof of claim 1 and a pharmaceutically acceptable carrier.

6. A method of treating a MUC16-positive cancer in a patient in need thereof, comprising administering to said patient the pharmaceutical composition of claim 5.

7. The antibody or antigen-binding fragment thereof of claim 1, wherein the antibody or antigen-binding fragment thereof comprises:

(a) (i) a VH comprising a VH CDR1 comprising the amino acid sequence of SEQ ID NO:83, a VH CDR2 comprising the amino acid sequence of SEQ ID NO:84, and a VH CDR3 comprising the amino acid sequence of SEQ ID NO:85; and (ii) a VL comprising a VL CDR1 comprising the amino acid sequence of SEQ ID NO:86, a VL CDR2 comprising the amino acid sequence of SEQ ID NO:87, and a VL CDR3 comprising the amino acid sequence of SEQ ID NO:88; or (b) (i) a VH comprising a VH CDR1 comprising the amino acid sequence of SEQ ID NO:89, a VH CDR2 comprising the amino acid sequence of SEQ ID NO:90, and a VH CDR3 comprising the amino acid sequence of SEQ ID NO:91; and (ii) a VL comprising a VL CDR1 comprising the amino acid sequence of SEQ ID NO:92, a VL CDR2 comprising the amino acid sequence of SEQ ID NO:93, and a VL CDR3 comprising the amino acid sequence of SEQ ID NO:94; or (c) (i) a VH comprising a VH CDR1 comprising the amino acid sequence of SEQ ID NO:95, a VH CDR2 comprising the amino acid sequence of SEQ ID NO:96, and a VH CDR3 comprising the amino acid sequence of SEQ ID NO:97; and (ii) a VL comprising a VL CDR1 comprising the amino acid sequence of SEQ ID NO:98, a VL CDR2 comprising the amino acid sequence of SEQ ID NO:99, and a VL CDR3 comprising the amino acid sequence of SEQ ID NO:100.

8. The antibody or antigen-binding fragment thereof of claim 7, wherein the antibody or antigen-binding fragment thereof comprises (i) a VH comprising a VH CDR1 comprising the amino acid sequence of SEQ ID NO:83, a VH CDR2 comprising the amino acid sequence of SEQ ID NO:84, and a VH CDR3 comprising the amino acid sequence of SEQ ID NO:85; and (ii) a VL comprising a VL CDR1 comprising the amino acid sequence of SEQ ID NO:86, a VL CDR2 comprising the amino acid sequence of SEQ ID NO:87, and a VL CDR3 comprising the amino acid sequence of SEQ ID NO:88.

9. The antibody or antigen-binding fragment thereof of claim 7, wherein the antibody or antigen-binding fragment thereof comprises: (i) a VH comprising the amino acid sequence of SEQ ID NO:81; and (ii) a VL comprising the amino acid sequence of SEQ ID NO:82.

10. The antibody or antigen-binding fragment thereof of claim 1, wherein the antibody or antigen-binding fragment thereof comprises (i) a VH comprising the amino acid sequence of QVX21LKESGPGX22LQPSQTLSLTCSFSG-FSLX23TX24GMGVGWX25RQX26SGKGLEW LAHI-WWDDX27DKYYX28PALKSRLTISX29X30X31SKN-QVFLKIX32NVX33TADX34AT YYCX35RIGTAQA-TDALDYWGQGTSVTVSS (SEQ ID NO:101), wherein X21 is T or N, X22 is I or K, X23 is N or S, X24 is V or L, X25 is S or I, X26 is P or S, X27 is E or absent, X28 is N or Y, X29 is K or R, X30 is A or D, X31 is T or S, X32 is V or A, X33 is G or D, X34 is T, I, or S, and X35 is T, S, or A; and (ii) a VL comprising the amino acid sequence of DIVMTQAAPSX36X37VTPGESVSISCRSSKSLX38X-39SNGNTYLYWFLQRPGQSPQRLIY YMSNLASG-VPDRFSGRGSGTDFTLX40ISRVEAX41DVGVYYC-MQX42LEX43PLTFGGG TKLEIK (SEQ ID NO:102), wherein X36 is I or V, X37 is P or S, X38 is R or L, X39 is K or H, X40 is R or K, X41 is E or G, X42 is S or G, and X43 is Y or H.

11. An antibody or antigen-binding fragment thereof of claim 1, wherein the antibody or antigen-binding fragment thereof comprises:

(a) (i) a VH comprising: a VH CDR1 comprising the amino acid sequence TX1GMGVG (SEQ ID NO:103), wherein X1 is L or V; a VH CDR2 comprising the amino acid sequence HIWWDDX2DKYYX3PALKS (SEQ ID NO:104), wherein X2 is E or absent, and X3 is Y or N; and a VH CD3 comprising the amino acid sequence IGTAQATDALDY (SEQ ID NO:105); and (ii) a VL comprising: a VL CDR1 comprising the amino acid sequence RSSKSLX4X5SNGNTYLY (SEQ ID NO:106), wherein X4 is R or L, and X5 is K or H; a VL CDR2 comprising the amino acid sequence YMSNLAS (SEQ ID NO:107); and a VL CDR3 comprising the amino acid sequence MQX6LEX7PLT (SEQ ID NO:108), wherein X6 is G or S, and X7 is H or Y; or (b) (i) a VH comprising: a VH CDR1 comprising the amino acid sequence GFSLX8TX9GM (SEQ ID NO:109), wherein X8 is N or S, and wherein X9 is L or V; a VH CDR2 comprising the amino acid sequence WDDX10 (SEQ ID NO:110), wherein X10 is E or absent; and a VH CDR3 comprising the amino acid sequence GTAQATDALD (SEQ ID NO:111); and (ii) a VL comprising: a VL CDR1 comprising the amino acid sequence SKSLX11X12SNGNTY (SEQ ID NO:112), wherein X11 is L or R, and X12 is H or K; a VL CDR2 comprising the amino acid sequence YMS (SEQ ID NO:113); and a VL CDR3 comprising the amino acid sequence X13LEX14PL (SEQ ID NO:114), wherein X13 is G or S, and X14 is H or Y; or (c) (i) a VH comprising: a VH CDR1 comprising the amino acid sequence GFSLX15TX16GMG (SEQ ID NO:115), wherein X15 is N or S, and X16 is V or L; a VH CDR2 comprising the amino acid sequence IWWDDX17DK (SEQ ID NO:116), wherein X17 is E or absent; and a VH CDR3 comprising the amino acid sequence X18RIGTAQATDALDY (SEQ ID NO:117), wherein X18 is T, A, or S; and (ii) a VL comprising: a VL CDR1 comprising the amino acid sequence KSLX19X20SNGNTY (SEQ ID NO:118), wherein X19 is V or L, and X20 is H or K; a VL CDR2 comprising the amino acid sequence YMS (SEQ ID NO:119); and a VL CDR3 comprising the amino acid sequence MQSLEYPLT (SEQ ID NO:120).

12. A pharmaceutical composition comprising a therapeutically effective amount of the antibody or antigen-binding fragment thereof of claim 9 and a pharmaceutically acceptable carrier.

13. A method of treating a MUC16-positive cancer in a patient in need thereof, comprising administering to said patient the pharmaceutical composition of claim 12.

14. A pharmaceutical composition comprising a therapeutically effective amount of the antibody or antigen-binding fragment thereof of claim 10 and a pharmaceutically acceptable carrier.

15. A method of treating a MUC16-positive cancer in a patient in need thereof, comprising administering to said patient the pharmaceutical composition of claim 14.

16. A pharmaceutical composition comprising a therapeutically effective amount of the antibody or antigen-binding fragment thereof of claim 11 and a pharmaceutically acceptable carrier.

17. A method of treating a MUC16-positive cancer in a patient in need thereof, comprising administering to said patient the pharmaceutical composition of claim 16.

18. A pharmaceutical composition comprising a therapeutically effective amount of the antibody or antigen-binding fragment thereof of claim 7 and a pharmaceutically acceptable carrier.

19. A method of treating a MUC16-positive cancer in a patient in need thereof, comprising administering to said patient the pharmaceutical composition of claim 18.

20. A pharmaceutical composition comprising a therapeutically effective amount of the antibody or antigen-binding fragment thereof of claim 8 and a pharmaceutically acceptable carrier.

21. A method of treating a MUC16-positive cancer in a patient in need thereof, comprising administering to said patient the pharmaceutical composition of claim 20.

22. The antibody or antigen-binding fragment thereof of claim 1, wherein the antibody or antigen-binding fragment thereof (a) immunospecifically binds to a cell recombinantly expressing a first form of MUC16, which first form is glycosylated, and wherein the amino acid sequence of the first form is SEQ ID NO:133, (b) lacks immunospecific binding to a cell recombinantly expressing a second form of MUC16, which second form is unglycosylated, and wherein the amino acid sequence of the second form is SEQ ID NO:139; and (c) inhibits matrigel invasion in vitro of cells recombinantly expressing said first form of MUC16.

23. The antibody or antigen-binding fragment thereof of claim 7, wherein the antibody or antigen-binding fragment thereof (a) immunospecifically binds to a cell recombinantly expressing a first form of MUC16, which first form is glycosylated, and wherein the amino acid sequence of the first form is SEQ ID NO:133, (b) lacks immunospecific binding to a cell recombinantly expressing a second form of MUC16, which second form is unglycosylated, and wherein the amino acid sequence of the second form is SEQ ID NO:139; and (c) inhibits matrigel invasion in vitro of cells recombinantly expressing said first form of MUC16.

24. A pharmaceutical composition comprising a therapeutically effective amount of the antibody or antigen-binding fragment thereof of claim 23 and a pharmaceutically acceptable carrier.

25. A method of treating a MUC16-positive cancer in a patient in need thereof, comprising administering to said patient the pharmaceutical composition of claim 24.

26. The antibody or antigen-binding fragment thereof of claim 7, wherein the antibody or antigen-binding fragment thereof is humanized.

27. The antibody or antigen-binding fragment thereof of claim 7, wherein the antibody or antigen-binding fragment thereof is a bispecific antibody.

28. The antibody or antigen-binding fragment thereof of claim 7, wherein the antigen-binding fragment thereof is a scFv.

29. The antibody or antigen-binding fragment thereof of claim 1, wherein the antibody or antigen-binding fragment thereof comprises:

(a) (i) a VH comprising a VH CDR1 comprising the amino acid sequence of SEQ ID NO:23, a VH CDR2 comprising the amino acid sequence of SEQ ID NO:24, and a VH CDR3 comprising the amino acid sequence of SEQ ID NO:25; and (ii) a VL comprising a VL CDR1 comprising the amino acid sequence of SEQ ID NO:26, a VL CDR2 comprising the amino acid sequence of SEQ ID NO:27, and a VL CDR3 comprising the amino acid sequence of SEQ ID NO:28; or (b) (i) a VH comprising a VH CDR1 comprising the amino acid sequence of SEQ ID NO:29, a VH CDR2 comprising the amino acid sequence of SEQ ID NO:30, and a VH CDR3 comprising the amino acid sequence of SEQ ID NO:31; and (ii) a VL comprising a VL CDR1 comprising the amino acid sequence of SEQ ID NO:32, a VL CDR2 comprising the amino acid sequence of SEQ ID NO:33, and a VL CDR3 comprising the amino acid sequence of SEQ ID NO:34; or (c) (i) a VH comprising a VH CDR1 comprising the amino acid sequence of SEQ ID NO:35, a VH CDR2 comprising the amino acid sequence of SEQ ID NO:36, and a VH CDR3 comprising the amino acid sequence of SEQ ID NO:37; and (ii) a VL comprising a VL CDR1 comprising the amino acid sequence of SEQ ID NO:38, a VL CDR2 comprising the amino acid sequence of SEQ ID NO:39, and a VL CDR3 comprising the amino acid sequence of SEQ ID NO:40.

30. The antibody or antigen-binding fragment thereof of claim 1, wherein the antibody or antigen-binding fragment thereof comprises:

(a) (i) a VH comprising a VH CDR1 comprising the amino acid sequence of SEQ ID NO:43, a VH CDR2 comprising the amino acid sequence of SEQ ID NO:44, and a VH CDR3 comprising the amino acid sequence of SEQ ID NO:45; and (ii) a VL comprising a VL CDR1 comprising the amino acid sequence of SEQ ID NO:46, a VL CDR2 comprising the amino acid sequence of SEQ ID NO:47, and a VL CDR3 comprising the amino acid sequence of SEQ ID NO:48; or (b) (i) a VH comprising a VH CDR1 comprising the amino acid sequence of SEQ ID NO:49, a VH CDR2 comprising the amino acid sequence of SEQ ID NO:50, and a VH CDR3 comprising the amino acid sequence of SEQ ID NO:51; and (ii) a VL comprising a VL CDR1 comprising the amino acid sequence of SEQ ID NO:52, a VL CDR2 comprising the amino acid sequence of SEQ ID NO:53, and a VL CDR3 comprising the amino acid sequence of SEQ ID NO:54; or (c) (i) a VH comprising a VH CDR1 comprising the amino acid sequence of SEQ ID NO:55, a VH CDR2 comprising the amino acid sequence of SEQ ID NO:56, and a VH CDR3 comprising the amino acid sequence of SEQ ID NO:57; and (ii) a VL comprising a VL CDR1 comprising the amino acid sequence of SEQ ID NO:58, a VL CDR2 comprising the amino acid sequence of SEQ ID NO:59, and a VL CDR3 comprising the amino acid sequence of SEQ ID NO:60.

31. The antibody or antigen-binding fragment thereof of claim 1, wherein the antibody or antigen-binding fragment thereof comprises:

(a) (i) a VH comprising a VH CDR1 comprising the amino acid sequence of SEQ ID NO:3, a VH CDR2 comprising the amino acid sequence of SEQ ID NO:4, and a VH CDR3 comprising the amino acid sequence of SEQ ID NO:5; and (ii) a VL comprising a VL CDR1 comprising the amino acid sequence of SEQ ID NO:6, a VL CDR2 comprising the amino acid sequence of SEQ ID NO:7, and a VL CDR3 comprising the amino acid sequence of SEQ ID NO:8; or (b) (i) a VH comprising a VH CDR1 comprising the amino acid sequence of SEQ ID NO:9, a VH CDR2 comprising the amino acid sequence of SEQ ID NO:10, and a VH CDR3 comprising the amino acid sequence of SEQ ID NO:11; and (ii) a VL comprising a VL CDR1 comprising the amino acid sequence of SEQ ID NO:12, a VL CDR2 comprising the amino acid sequence of SEQ ID NO:13, and a VL CDR3 comprising the amino acid sequence of SEQ ID NO:14; or (c) (i) a VH comprising a VH CDR1 comprising the amino acid sequence of SEQ ID NO:15, a VH CDR2 comprising the amino acid sequence of SEQ ID NO:16, and a VH CDR3 comprising the amino acid sequence of SEQ ID NO:17; and (ii) a VL comprising a VL CDR1 comprising the amino acid sequence of SEQ ID NO: 18, a VL CDR2 comprising the amino acid sequence of SEQ ID NO: 19, and a VL CDR3 comprising the amino acid sequence of SEQ ID NO: 20.

32. A pharmaceutical composition comprising a therapeutically effective amount of the antibody or antigen-binding fragment thereof of claim 2 and a pharmaceutically acceptable carrier.

33. A method of treating a MUC16-positive cancer in a patient in need thereof, comprising administering to said patient the pharmaceutical composition of claim 32.

34. A pharmaceutical composition comprising a therapeutically effective amount of the antibody or antigen-binding fragment thereof of claim 3 and a pharmaceutically acceptable carrier.

35. A method of treating a MUC16-positive cancer in a patient in need thereof, comprising administering to said patient the pharmaceutical composition of claim 34.

36. A pharmaceutical composition comprising a therapeutically effective amount of the antibody or antigen-binding fragment thereof of claim 4 and a pharmaceutically acceptable carrier.

37. A method of treating a MUC16-positive cancer in a patient in need thereof, comprising administering to said patient the pharmaceutical composition of claim 36.

38. A pharmaceutical composition comprising a therapeutically effective amount of the antibody or antigen-binding fragment thereof of claim 22 and a pharmaceutically acceptable carrier.

39. A method of treating a MUC16-positive cancer in a patient in need thereof, comprising administering to said patient the pharmaceutical composition of claim 38.

40. A pharmaceutical composition comprising a therapeutically effective amount of the antibody or antigen-binding fragment thereof of claim 39 and a pharmaceutically acceptable carrier.

41. A method of treating a MUC16-positive cancer in a patient in need thereof, comprising administering to said patient the pharmaceutical composition of claim 40.

42. A pharmaceutical composition comprising a therapeutically effective amount of the antibody or antigen-binding fragment thereof of claim 27 and a pharmaceutically acceptable carrier.

43. A method of treating a MUC16-positive cancer in a patient in need thereof, comprising administering to said patient the pharmaceutical composition of claim 42.

44. A pharmaceutical composition comprising a therapeutically effective amount of the antibody or antigen-binding fragment thereof of claim 28 and a pharmaceutically acceptable carrier.

45. A method of treating a MUC16-positive cancer in a patient in need thereof, comprising administering to said patient the pharmaceutical composition of claim 44.

46. A pharmaceutical composition comprising a therapeutically effective amount of the antibody or antigen-binding fragment thereof of claim 29 and a pharmaceutically acceptable carrier.

47. A method of treating a MUC16-positive cancer in a patient in need thereof, comprising administering to said patient the pharmaceutical composition of claim 46.

48. A pharmaceutical composition comprising a therapeutically effective amount of the antibody or antigen-binding fragment thereof of claim 30 and a pharmaceutically acceptable carrier.

49. A method of treating a MUC16-positive cancer in a patient in need thereof, comprising administering to said patient the pharmaceutical composition of claim 48.

50. A pharmaceutical composition comprising a therapeutically effective amount of the antibody or antigen-binding fragment thereof of claim 31 and a pharmaceutically acceptable carrier.

51. A method of treating a MUC16-positive cancer in a patient in need thereof, comprising administering to said patient the pharmaceutical composition of claim 50.

* * * * *

SEQUENCE LISTING

<160> NUMBER OF SEQ ID NOS: 175

<210> SEQ ID NO 1
<211> LENGTH: 122
<212> TYPE: PRT
<213> ORGANISM: Artificial Sequence
<220> FEATURE:
<223> OTHER INFORMATION: 10C6 VH

<400> SEQUENCE: 1

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Asn Thr Leu
            20                  25                  30
```

```
Gly Met Gly Val Gly Trp Ile Arg Gln Pro Ser Gly Lys Gly Leu Glu
        35                  40                  45

Trp Leu Ala His Ile Trp Trp Asp Asp Asp Lys Tyr Tyr Asn Pro Ala
    50                  55                  60

Leu Lys Ser Arg Leu Thr Ile Ser Lys Asp Ser Ser Lys Asn Gln Val
65                  70                  75                  80

Phe Leu Lys Ile Ala Asn Val Asp Thr Ala Asp Ile Ala Thr Tyr Tyr
                85                  90                  95

Cys Ser Arg Ile Gly Thr Ala Gln Ala Thr Asp Ala Leu Asp Tyr Trp
            100                 105                 110

Gly Gln Gly Thr Ser Val Thr Val Ser Ser
        115                 120


<210> SEQ ID NO 2
<211> LENGTH: 109
<212> TYPE: PRT
<213> ORGANISM: Artificial Sequence
<220> FEATURE:
<223> OTHER INFORMATION: 10C6 VL

<400> SEQUENCE: 2

Asp Ile Val Leu Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Ser Trp Lys Asn
            100                 105


<210> SEQ ID NO 3
<211> LENGTH: 7
<212> TYPE: PRT
<213> ORGANISM: Artificial Sequence
<220> FEATURE:
<223> OTHER INFORMATION: 10C6 HCDR1 (KABAT)

<400> SEQUENCE: 3

Thr Leu Gly Met Gly Val Gly
1               5


<210> SEQ ID NO 4
<211> LENGTH: 16
<212> TYPE: PRT
<213> ORGANISM: Artificial Sequence
<220> FEATURE:
<223> OTHER INFORMATION: 10C6 HCDR2 (KABAT)

<400> SEQUENCE: 4

His Ile Trp Trp Asp Asp Asp Lys Tyr Tyr Asn Pro Ala Leu Lys Ser
1               5                   10                  15


<210> SEQ ID NO 5
<211> LENGTH: 12
<212> TYPE: PRT
```

<213> ORGANISM: Artificial Sequence
<220> FEATURE:
<223> OTHER INFORMATION: 10C6 HCDR3 (KABAT)

<400> SEQUENCE: 5

Ile Gly Thr Ala Gln Ala Thr Asp Ala Leu Asp Tyr
1 5 10

<210> SEQ ID NO 6
<211> LENGTH: 15
<212> TYPE: PRT
<213> ORGANISM: Artificial Sequence
<220> FEATURE:
<223> OTHER INFORMATION: 10C6 LCDR1 (KABAT)

<400> SEQUENCE: 6

Arg Ala Ser Lys Ser Val Ser Thr Ser Gly Tyr Ser Tyr Met His
1 5 10 15

<210> SEQ ID NO 7
<211> LENGTH: 7
<212> TYPE: PRT
<213> ORGANISM: Artificial Sequence
<220> FEATURE:
<223> OTHER INFORMATION: 10C6 LCDR2 (KABAT)

<400> SEQUENCE: 7

Leu Val Ser Asn Leu Glu Ser
1 5

<210> SEQ ID NO 8
<211> LENGTH: 9
<212> TYPE: PRT
<213> ORGANISM: Artificial Sequence
<220> FEATURE:
<223> OTHER INFORMATION: 10C6 LCDR3 (KABAT)

<400> SEQUENCE: 8

Gln His Ile Arg Glu Leu Thr Arg Ser
1 5

<210> SEQ ID NO 9
<211> LENGTH: 9
<212> TYPE: PRT
<213> ORGANISM: Artificial Sequence
<220> FEATURE:
<223> OTHER INFORMATION: 10C6 HCDR1 (CHOTHIA)

<400> SEQUENCE: 9

Gly Phe Ser Leu Asn Thr Leu Gly Met
1 5

<210> SEQ ID NO 10
<211> LENGTH: 3
<212> TYPE: PRT
<213> ORGANISM: Artificial Sequence
<220> FEATURE:
<223> OTHER INFORMATION: 10C6 HCDR2 (CHOTHIA)

<400> SEQUENCE: 10

Trp Asp Asp
1

<210> SEQ ID NO 11
<211> LENGTH: 10
<212> TYPE: PRT
<213> ORGANISM: Artificial Sequence

<220> FEATURE:
<223> OTHER INFORMATION: 10C6 HCDR3 (CHOTHIA)

<400> SEQUENCE: 11

Gly Thr Ala Gln Ala Thr Asp Ala Leu Asp
1 5 10

<210> SEQ ID NO 12
<211> LENGTH: 11
<212> TYPE: PRT
<213> ORGANISM: Artificial Sequence
<220> FEATURE:
<223> OTHER INFORMATION: 10C6 LCDR1 (CHOTHIA)

<400> SEQUENCE: 12

Ser Lys Ser Val Ser Thr Ser Gly Tyr Ser Tyr
1 5 10

<210> SEQ ID NO 13
<211> LENGTH: 3
<212> TYPE: PRT
<213> ORGANISM: Artificial Sequence
<220> FEATURE:
<223> OTHER INFORMATION: 10C6 LCDR2 (CHOTHIA)

<400> SEQUENCE: 13

Leu Val Ser
1

<210> SEQ ID NO 14
<211> LENGTH: 6
<212> TYPE: PRT
<213> ORGANISM: Artificial Sequence
<220> FEATURE:
<223> OTHER INFORMATION: 10C6 LCDR3 (CHOTHIA)

<400> SEQUENCE: 14

Ile Arg Glu Leu Thr Arg
1 5

<210> SEQ ID NO 15
<211> LENGTH: 10
<212> TYPE: PRT
<213> ORGANISM: Artificial Sequence
<220> FEATURE:
<223> OTHER INFORMATION: 10C6 HCDR1 (IMGT)

<400> SEQUENCE: 15

Gly Phe Ser Leu Asn Thr Leu Gly Met Gly
1 5 10

<210> SEQ ID NO 16
<211> LENGTH: 7
<212> TYPE: PRT
<213> ORGANISM: Artificial Sequence
<220> FEATURE:
<223> OTHER INFORMATION: 10C6 HCDR2 (IMGT)

<400> SEQUENCE: 16

Ile Trp Trp Asp Asp Asp Lys
1 5

<210> SEQ ID NO 17
<211> LENGTH: 14
<212> TYPE: PRT
<213> ORGANISM: Artificial Sequence
<220> FEATURE:

<223> OTHER INFORMATION: 10C6 HCDR3 (IMGT)

<400> SEQUENCE: 17

Ser Arg Ile Gly Thr Ala Gln Ala Thr Asp Ala Leu Asp Tyr
1 5 10

<210> SEQ ID NO 18
<211> LENGTH: 10
<212> TYPE: PRT
<213> ORGANISM: Artificial Sequence
<220> FEATURE:
<223> OTHER INFORMATION: 10C6 LCDR1 (IMGT)

<400> SEQUENCE: 18

Lys Ser Val Ser Thr Ser Gly Tyr Ser Tyr
1 5 10

<210> SEQ ID NO 19
<211> LENGTH: 3
<212> TYPE: PRT
<213> ORGANISM: Artificial Sequence
<220> FEATURE:
<223> OTHER INFORMATION: 10C6 LCDR2 (IMGT)

<400> SEQUENCE: 19

Leu Val Ser
1

<210> SEQ ID NO 20
<211> LENGTH: 9
<212> TYPE: PRT
<213> ORGANISM: Artificial Sequence
<220> FEATURE:
<223> OTHER INFORMATION: 10C6 LCDR3 (IMGT)

<400> SEQUENCE: 20

Gln His Ile Arg Glu Leu Thr Arg Ser
1 5

<210> SEQ ID NO 21
<211> LENGTH: 123
<212> TYPE: PRT
<213> ORGANISM: Artificial Sequence
<220> FEATURE:
<223> OTHER INFORMATION: 7B12 VH

<400> SEQUENCE: 21

Gln Val Thr Leu Lys Glu Ser Gly Pro Gly Ile Leu Gln Pro Ser Gln
1 5 10 15

Thr Leu Ser Leu Thr Cys Ser Phe Ser Gly Phe Ser Leu Ser Thr Val
20 25 30

Gly Met Gly Val Gly Trp Ser Arg Gln Pro Ser Gly Lys Gly Leu Glu
35 40 45

Trp Leu Ala His Ile Trp Trp Asp Asp Glu Asp Lys Tyr Tyr Asn Pro
50 55 60

Ala Leu Lys Ser Arg Leu Thr Ile Ser Lys Asp Thr Ser Lys Asn Gln
65 70 75 80

Val Phe Leu Lys Ile Ala Asn Val Asp Thr Ala Asp Ser Ala Thr Tyr
85 90 95

Tyr Cys Thr Arg Ile Gly Thr Ala Gln Ala Thr Asp Ala Leu Asp Tyr
100 105 110

Trp Gly Gln Gly Thr Ser Val Thr Val Ser Ser
115 120

<210> SEQ ID NO 22
<211> LENGTH: 112
<212> TYPE: PRT
<213> ORGANISM: Artificial Sequence
<220> FEATURE:
<223> OTHER INFORMATION: 7B12 VL

<400> SEQUENCE: 22

Asp Ile Val Met Thr Gln Ala Ala Pro Ser Val Ser Val Thr Pro Gly
1 5 10 15

Glu Ser Val Ser Ile Ser Cys Arg Ser Ser Lys Ser Leu Arg Lys Ser
20 25 30

Asn Gly Asn Thr Tyr Leu Tyr Trp Phe Leu Gln Arg Pro Gly Gln Ser
35 40 45

Pro Gln Arg Leu Ile Tyr Tyr Met Ser Asn Leu Ala Ser Gly Val Pro
50 55 60

Asp Arg Phe Ser Gly Arg Gly Ser Gly Thr Asp Phe Thr Leu Arg Ile
65 70 75 80

Ser Arg Val Glu Ala Glu Asp Val Gly Val Tyr Tyr Cys Met Gln Ser
85 90 95

Leu Glu Tyr Pro Leu Thr Phe Gly Gly Gly Thr Lys Leu Lys Ile Lys
100 105 110

<210> SEQ ID NO 23
<211> LENGTH: 7
<212> TYPE: PRT
<213> ORGANISM: Artificial Sequence
<220> FEATURE:
<223> OTHER INFORMATION: 7B12 HCDR1 (KABAT)

<400> SEQUENCE: 23

Thr Val Gly Met Gly Val Gly
1 5

<210> SEQ ID NO 24
<211> LENGTH: 17
<212> TYPE: PRT
<213> ORGANISM: Artificial Sequence
<220> FEATURE:
<223> OTHER INFORMATION: 7B12 HCDR2 (KABAT)

<400> SEQUENCE: 24

His Ile Trp Trp Asp Asp Glu Asp Lys Tyr Tyr Asn Pro Ala Leu Lys
1 5 10 15

Ser

<210> SEQ ID NO 25
<211> LENGTH: 12
<212> TYPE: PRT
<213> ORGANISM: Artificial Sequence
<220> FEATURE:
<223> OTHER INFORMATION: 7B12 HCDR3 (KABAT)

<400> SEQUENCE: 25

Ile Gly Thr Ala Gln Ala Thr Asp Ala Leu Asp Tyr
1 5 10

<210> SEQ ID NO 26
<211> LENGTH: 16
<212> TYPE: PRT
<213> ORGANISM: Artificial Sequence
<220> FEATURE:

<223> OTHER INFORMATION: 7B12 LCDR1 (KABAT)

<400> SEQUENCE: 26

Arg Ser Ser Lys Ser Leu Arg Lys Ser Asn Gly Asn Thr Tyr Leu Tyr
1 5 10 15

<210> SEQ ID NO 27
<211> LENGTH: 7
<212> TYPE: PRT
<213> ORGANISM: Artificial Sequence
<220> FEATURE:
<223> OTHER INFORMATION: 7B12 LCDR2 (KABAT)

<400> SEQUENCE: 27

Tyr Met Ser Asn Leu Ala Ser
1 5

<210> SEQ ID NO 28
<211> LENGTH: 9
<212> TYPE: PRT
<213> ORGANISM: Artificial Sequence
<220> FEATURE:
<223> OTHER INFORMATION: 7B12 LCDR3 (KABAT)

<400> SEQUENCE: 28

Met Gln Ser Leu Glu Tyr Pro Leu Thr
1 5

<210> SEQ ID NO 29
<211> LENGTH: 9
<212> TYPE: PRT
<213> ORGANISM: Artificial Sequence
<220> FEATURE:
<223> OTHER INFORMATION: 7B12 HCDR1 (CHOTHIA)

<400> SEQUENCE: 29

Gly Phe Ser Leu Ser Thr Val Gly Met
1 5

<210> SEQ ID NO 30
<211> LENGTH: 4
<212> TYPE: PRT
<213> ORGANISM: Artificial Sequence
<220> FEATURE:
<223> OTHER INFORMATION: 7B12 HCDR2 (CHOTHIA)

<400> SEQUENCE: 30

Trp Asp Asp Glu
1

<210> SEQ ID NO 31
<211> LENGTH: 10
<212> TYPE: PRT
<213> ORGANISM: Artificial Sequence
<220> FEATURE:
<223> OTHER INFORMATION: 7B12 HCDR3 (CHOTHIA)

<400> SEQUENCE: 31

Gly Thr Ala Gln Ala Thr Asp Ala Leu Asp
1 5 10

<210> SEQ ID NO 32
<211> LENGTH: 12
<212> TYPE: PRT
<213> ORGANISM: Artificial Sequence
<220> FEATURE:
<223> OTHER INFORMATION: 7B12 LCDR1 (CHOTHIA)

<400> SEQUENCE: 32

Ser Lys Ser Leu Arg Lys Ser Asn Gly Asn Thr Tyr
1 5 10

<210> SEQ ID NO 33
<211> LENGTH: 3
<212> TYPE: PRT
<213> ORGANISM: Artificial Sequence
<220> FEATURE:
<223> OTHER INFORMATION: 7B12 LCDR2 (CHOTHIA)

<400> SEQUENCE: 33

Tyr Met Ser
1

<210> SEQ ID NO 34
<211> LENGTH: 6
<212> TYPE: PRT
<213> ORGANISM: Artificial Sequence
<220> FEATURE:
<223> OTHER INFORMATION: 7B12 LCDR3 (CHOTHIA)

<400> SEQUENCE: 34

Ser Leu Glu Tyr Pro Leu
1 5

<210> SEQ ID NO 35
<211> LENGTH: 10
<212> TYPE: PRT
<213> ORGANISM: Artificial Sequence
<220> FEATURE:
<223> OTHER INFORMATION: 7B12 HCDR1 (IMGT)

<400> SEQUENCE: 35

Gly Phe Ser Leu Ser Thr Val Gly Met Gly
1 5 10

<210> SEQ ID NO 36
<211> LENGTH: 8
<212> TYPE: PRT
<213> ORGANISM: Artificial Sequence
<220> FEATURE:
<223> OTHER INFORMATION: 7B12 HCDR2 (IMGT)

<400> SEQUENCE: 36

Ile Trp Trp Asp Asp Glu Asp Lys
1 5

<210> SEQ ID NO 37
<211> LENGTH: 14
<212> TYPE: PRT
<213> ORGANISM: Artificial Sequence
<220> FEATURE:
<223> OTHER INFORMATION: 7B12 HCDR3 (IMGT)

<400> SEQUENCE: 37

Thr Arg Ile Gly Thr Ala Gln Ala Thr Asp Ala Leu Asp Tyr
1 5 10

<210> SEQ ID NO 38
<211> LENGTH: 11
<212> TYPE: PRT
<213> ORGANISM: Artificial Sequence
<220> FEATURE:
<223> OTHER INFORMATION: 7B12 LCDR1 (IMGT)

<400> SEQUENCE: 38

Lys Ser Leu Arg Lys Ser Asn Gly Asn Thr Tyr
1 5 10

<210> SEQ ID NO 39
<211> LENGTH: 3
<212> TYPE: PRT
<213> ORGANISM: Artificial Sequence
<220> FEATURE:
<223> OTHER INFORMATION: 7B12 LCDR2 (IMGT)

<400> SEQUENCE: 39

Tyr Met Ser
1

<210> SEQ ID NO 40
<211> LENGTH: 9
<212> TYPE: PRT
<213> ORGANISM: Artificial Sequence
<220> FEATURE:
<223> OTHER INFORMATION: 7B12 LCDR3 (IMGT)

<400> SEQUENCE: 40

Met Gln Ser Leu Glu Tyr Pro Leu Thr
1 5

<210> SEQ ID NO 41
<211> LENGTH: 122
<212> TYPE: PRT
<213> ORGANISM: Artificial Sequence
<220> FEATURE:
<223> OTHER INFORMATION: 19C11 VH

<400> SEQUENCE: 41

Gln Val Asn Leu Lys Glu Ser Gly Pro Gly Lys Leu Gln Pro Ser Gln
1 5 10 15

Thr Leu Ser Leu Thr Cys Ser Phe Ser Gly Phe Ser Leu Ser Thr Leu
20 25 30

Gly Met Gly Val Gly Trp Ile Arg Gln Ser Ser Gly Lys Gly Leu Glu
35 40 45

Trp Leu Ala His Ile Trp Trp Asp Asp Asp Lys Tyr Tyr Asn Pro Ala
50 55 60

Leu Lys Ser Arg Leu Thr Ile Ser Arg Ala Thr Ser Lys Asn Gln Val
65 70 75 80

Phe Leu Lys Ile Val Asn Val Gly Thr Ala Asp Thr Ala Thr Tyr Tyr
85 90 95

Cys Ala Arg Ile Gly Thr Ala Gln Ala Thr Asp Ala Leu Asp Tyr Trp
100 105 110

Gly Gln Gly Thr Ser Val Thr Val Ser Ser
115 120

<210> SEQ ID NO 42
<211> LENGTH: 112
<212> TYPE: PRT
<213> ORGANISM: Artificial Sequence
<220> FEATURE:
<223> OTHER INFORMATION: 19C11 VL

<400> SEQUENCE: 42

Asp Ile Val Met Thr Gln Ala Ala Pro Ser Ile Pro Val Thr Pro Gly
1 5 10 15

Glu Ser Val Ser Ile Ser Cys Arg Ser Ser Lys Ser Leu Leu His Ser

```
            20                  25                  30

Asn Gly Asn Thr Tyr Leu Tyr Trp Phe Leu Gln Arg Pro Gly Gln Ser
        35                  40                  45

Pro Gln Arg Leu Ile Tyr Tyr Met Ser Asn Leu Ala Ser Gly Val Pro
    50                  55                  60

Asp Arg Phe Ser Gly Arg Gly Ser Gly Thr Asp Phe Thr Leu Lys Ile
65                  70                  75                  80

Ser Arg Val Glu Ala Gly Asp Val Gly Val Tyr Tyr Cys Met Gln Gly
                85                  90                  95

Leu Glu His Pro Leu Thr Phe Gly Gly Gly Thr Lys Leu Glu Ile Lys
            100                 105                 110


<210> SEQ ID NO 43
<211> LENGTH: 7
<212> TYPE: PRT
<213> ORGANISM: Artificial Sequence
<220> FEATURE:
<223> OTHER INFORMATION: 19C11 HCDR1 (KABAT)

<400> SEQUENCE: 43

Thr Leu Gly Met Gly Val Gly
1               5


<210> SEQ ID NO 44
<211> LENGTH: 16
<212> TYPE: PRT
<213> ORGANISM: Artificial Sequence
<220> FEATURE:
<223> OTHER INFORMATION: 19C11 HCDR2 (KABAT)

<400> SEQUENCE: 44

His Ile Trp Trp Asp Asp Asp Lys Tyr Tyr Asn Pro Ala Leu Lys Ser
1               5                   10                  15


<210> SEQ ID NO 45
<211> LENGTH: 12
<212> TYPE: PRT
<213> ORGANISM: Artificial Sequence
<220> FEATURE:
<223> OTHER INFORMATION: 19C11 HCDR3 (KABAT)

<400> SEQUENCE: 45

Ile Gly Thr Ala Gln Ala Thr Asp Ala Leu Asp Tyr
1               5                   10


<210> SEQ ID NO 46
<211> LENGTH: 16
<212> TYPE: PRT
<213> ORGANISM: Artificial Sequence
<220> FEATURE:
<223> OTHER INFORMATION: 19C11 LCDR1 (KABAT)

<400> SEQUENCE: 46

Arg Ser Ser Lys Ser Leu Leu His Ser Asn Gly Asn Thr Tyr Leu Tyr
1               5                   10                  15


<210> SEQ ID NO 47
<211> LENGTH: 7
<212> TYPE: PRT
<213> ORGANISM: Artificial Sequence
<220> FEATURE:
<223> OTHER INFORMATION: 19C11 LCDR2 (KABAT)

<400> SEQUENCE: 47
```

Tyr Met Ser Asn Leu Ala Ser
1               5

<210> SEQ ID NO 48
<211> LENGTH: 9
<212> TYPE: PRT
<213> ORGANISM: Artificial Sequence
<220> FEATURE:
<223> OTHER INFORMATION: 19C11 LCDR3 (KABAT)

<400> SEQUENCE: 48

Met Gln Gly Leu Glu His Pro Leu Thr
1               5

<210> SEQ ID NO 49
<211> LENGTH: 9
<212> TYPE: PRT
<213> ORGANISM: Artificial Sequence
<220> FEATURE:
<223> OTHER INFORMATION: 19C11 HCDR1 (CHOTHIA)

<400> SEQUENCE: 49

Gly Phe Ser Leu Ser Thr Leu Gly Met
1               5

<210> SEQ ID NO 50
<211> LENGTH: 3
<212> TYPE: PRT
<213> ORGANISM: Artificial Sequence
<220> FEATURE:
<223> OTHER INFORMATION: 19C11 HCDR2 (CHOTHIA)

<400> SEQUENCE: 50

Trp Asp Asp
1

<210> SEQ ID NO 51
<211> LENGTH: 10
<212> TYPE: PRT
<213> ORGANISM: Artificial Sequence
<220> FEATURE:
<223> OTHER INFORMATION: 19C11 HCDR3 (CHOTHIA)

<400> SEQUENCE: 51

Gly Thr Ala Gln Ala Thr Asp Ala Leu Asp
1               5                   10

<210> SEQ ID NO 52
<211> LENGTH: 12
<212> TYPE: PRT
<213> ORGANISM: Artificial Sequence
<220> FEATURE:
<223> OTHER INFORMATION: 19C11 LCDR1 (CHOTHIA)

<400> SEQUENCE: 52

Ser Lys Ser Leu Leu His Ser Asn Gly Asn Thr Tyr
1               5                   10

<210> SEQ ID NO 53
<211> LENGTH: 3
<212> TYPE: PRT
<213> ORGANISM: Artificial Sequence
<220> FEATURE:
<223> OTHER INFORMATION: 19C11 LCDR2 (CHOTHIA)

<400> SEQUENCE: 53

Tyr Met Ser

1

<210> SEQ ID NO 54
<211> LENGTH: 6
<212> TYPE: PRT
<213> ORGANISM: Artificial Sequence
<220> FEATURE:
<223> OTHER INFORMATION: 19C11 LCDR3 (CHOTHIA)

<400> SEQUENCE: 54

Gly Leu Glu His Pro Leu
1 5

<210> SEQ ID NO 55
<211> LENGTH: 10
<212> TYPE: PRT
<213> ORGANISM: Artificial Sequence
<220> FEATURE:
<223> OTHER INFORMATION: 19C11 HCDR1 (IMGT)

<400> SEQUENCE: 55

Gly Phe Ser Leu Ser Thr Leu Gly Met Gly
1 5 10

<210> SEQ ID NO 56
<211> LENGTH: 7
<212> TYPE: PRT
<213> ORGANISM: Artificial Sequence
<220> FEATURE:
<223> OTHER INFORMATION: 19C11 HCDR2 (IMGT)

<400> SEQUENCE: 56

Ile Trp Trp Asp Asp Asp Lys
1 5

<210> SEQ ID NO 57
<211> LENGTH: 14
<212> TYPE: PRT
<213> ORGANISM: Artificial Sequence
<220> FEATURE:
<223> OTHER INFORMATION: 19C11 HCDR3 (IMGT)

<400> SEQUENCE: 57

Ala Arg Ile Gly Thr Ala Gln Ala Thr Asp Ala Leu Asp Tyr
1 5 10

<210> SEQ ID NO 58
<211> LENGTH: 11
<212> TYPE: PRT
<213> ORGANISM: Artificial Sequence
<220> FEATURE:
<223> OTHER INFORMATION: 19C11 LCDR1 (IMGT)

<400> SEQUENCE: 58

Lys Ser Leu Leu His Ser Asn Gly Asn Thr Tyr
1 5 10

<210> SEQ ID NO 59
<211> LENGTH: 3
<212> TYPE: PRT
<213> ORGANISM: Artificial Sequence
<220> FEATURE:
<223> OTHER INFORMATION: 19C11 LCDR2 (IMGT)

<400> SEQUENCE: 59

Tyr Met Ser
1

<210> SEQ ID NO 60
<211> LENGTH: 9
<212> TYPE: PRT
<213> ORGANISM: Artificial Sequence
<220> FEATURE:
<223> OTHER INFORMATION: 19C11 LCDR3 (IMGT)

<400> SEQUENCE: 60

```
Met Gln Gly Leu Glu His Pro Leu Thr
1               5
```

<210> SEQ ID NO 61
<211> LENGTH: 122
<212> TYPE: PRT
<213> ORGANISM: Artificial Sequence
<220> FEATURE:
<223> OTHER INFORMATION: 16C5 VH

<400> SEQUENCE: 61

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Asn Thr Leu
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Asp Lys Tyr Tyr Tyr Pro Ala
    50                  55                  60

Leu Lys Ser Arg Leu Thr Ile Ser Arg Asp Thr Ser Lys Asn Gln Val
65                  70                  75                  80

Phe Leu Lys Ile Ala Asn Val Asp Thr Ala Asp Thr Ala Thr Tyr Tyr
                85                  90                  95

Cys Ala Arg Ile Gly Thr Ala Gln Ala Thr Asp Ala Leu Asp Tyr Trp
            100                 105                 110

Gly Gln Gly Thr Ser Val Thr Val Ser Ser
        115                 120
```

<210> SEQ ID NO 62
<211> LENGTH: 109
<212> TYPE: PRT
<213> ORGANISM: Artificial Sequence
<220> FEATURE:
<223> OTHER INFORMATION: 16C5 VL

<400> SEQUENCE: 62

```
Glu Leu Asp Met Thr Gln Thr Pro Pro Ser Leu Ser Ala Ser Val Gly
1               5                   10                  15

Glu Thr Val Arg Ile Arg Cys Leu Ala Ser Glu Asp Ile Tyr Ser Gly
            20                  25                  30

Ile Ser Trp Tyr Gln Gln Lys Pro Gly Lys Pro Pro Thr Leu Leu Ile
        35                  40                  45

Tyr Gly Ala Ser Asn Leu Glu Ser Gly Val Pro Pro Arg Phe Ser Gly
    50                  55                  60

Ser Gly Ser Gly Thr Asp Tyr Thr Leu Thr Ile Gly Gly Val Gln Ala
65                  70                  75                  80

Glu Asp Ala Ala Thr Tyr Tyr Cys Leu Gly Gly Tyr Ser Tyr Ser Ser
                85                  90                  95

Thr Leu Thr Phe Gly Ala Gly Thr Asn Val Glu Ile Lys
            100                 105
```

<210> SEQ ID NO 63
<211> LENGTH: 7
<212> TYPE: PRT
<213> ORGANISM: Artificial Sequence
<220> FEATURE:
<223> OTHER INFORMATION: 16C5 HCDR1 (KABAT)

<400> SEQUENCE: 63

Thr Leu Gly Met Gly Val Gly
1 5

<210> SEQ ID NO 64
<211> LENGTH: 16
<212> TYPE: PRT
<213> ORGANISM: Artificial Sequence
<220> FEATURE:
<223> OTHER INFORMATION: 16C5 HCDR2 (KABAT)

<400> SEQUENCE: 64

His Ile Trp Trp Asp Asp Asp Lys Tyr Tyr Tyr Pro Ala Leu Lys Ser
1 5 10 15

<210> SEQ ID NO 65
<211> LENGTH: 12
<212> TYPE: PRT
<213> ORGANISM: Artificial Sequence
<220> FEATURE:
<223> OTHER INFORMATION: 16C5 HCDR3 (KABAT)

<400> SEQUENCE: 65

Ile Gly Thr Ala Gln Ala Thr Asp Ala Leu Asp Tyr
1 5 10

<210> SEQ ID NO 66
<211> LENGTH: 11
<212> TYPE: PRT
<213> ORGANISM: Artificial Sequence
<220> FEATURE:
<223> OTHER INFORMATION: 16C5 LCDR1 (KABAT)

<400> SEQUENCE: 66

Leu Ala Ser Glu Asp Ile Tyr Ser Gly Ile Ser
1 5 10

<210> SEQ ID NO 67
<211> LENGTH: 7
<212> TYPE: PRT
<213> ORGANISM: Artificial Sequence
<220> FEATURE:
<223> OTHER INFORMATION: 16C5 LCDR2 (KABAT)

<400> SEQUENCE: 67

Gly Ala Ser Asn Leu Glu Ser
1 5

<210> SEQ ID NO 68
<211> LENGTH: 11
<212> TYPE: PRT
<213> ORGANISM: Artificial Sequence
<220> FEATURE:
<223> OTHER INFORMATION: 16C5 LCDR3 (KABAT)

<400> SEQUENCE: 68

Leu Gly Gly Tyr Ser Tyr Ser Ser Thr Leu Thr
1 5 10

<210> SEQ ID NO 69
<211> LENGTH: 9
<212> TYPE: PRT
<213> ORGANISM: Artificial Sequence
<220> FEATURE:
<223> OTHER INFORMATION: 16C5 HCDR1 (CHOTHIA)

<400> SEQUENCE: 69

Gly Phe Ser Leu Asn Thr Leu Gly Met
1               5

<210> SEQ ID NO 70
<211> LENGTH: 3
<212> TYPE: PRT
<213> ORGANISM: Artificial Sequence
<220> FEATURE:
<223> OTHER INFORMATION: 16C5 HCDR2 (CHOTHIA)

<400> SEQUENCE: 70

Trp Asp Asp
1

<210> SEQ ID NO 71
<211> LENGTH: 10
<212> TYPE: PRT
<213> ORGANISM: Artificial Sequence
<220> FEATURE:
<223> OTHER INFORMATION: 16C5 HCDR3 (CHOTHIA)

<400> SEQUENCE: 71

Gly Thr Ala Gln Ala Thr Asp Ala Leu Asp
1               5                   10

<210> SEQ ID NO 72
<211> LENGTH: 7
<212> TYPE: PRT
<213> ORGANISM: Artificial Sequence
<220> FEATURE:
<223> OTHER INFORMATION: 16C5 LCDR1 (CHOTHIA)

<400> SEQUENCE: 72

Ser Glu Asp Ile Tyr Ser Gly
1               5

<210> SEQ ID NO 73
<211> LENGTH: 3
<212> TYPE: PRT
<213> ORGANISM: Artificial Sequence
<220> FEATURE:
<223> OTHER INFORMATION: 16C5 LCDR2 (CHOTHIA)

<400> SEQUENCE: 73

Gly Ala Ser
1

<210> SEQ ID NO 74
<211> LENGTH: 8
<212> TYPE: PRT
<213> ORGANISM: Artificial Sequence
<220> FEATURE:
<223> OTHER INFORMATION: 16C5 LCDR3 (CHOTHIA)

<400> SEQUENCE: 74

Gly Tyr Ser Tyr Ser Ser Thr Leu
1               5

<210> SEQ ID NO 75

<211> LENGTH: 10
<212> TYPE: PRT
<213> ORGANISM: Artificial Sequence
<220> FEATURE:
<223> OTHER INFORMATION: 16C5 HCDR1 (IMGT)

<400> SEQUENCE: 75

Gly Phe Ser Leu Asn Thr Leu Gly Met Gly
1 5 10

<210> SEQ ID NO 76
<211> LENGTH: 7
<212> TYPE: PRT
<213> ORGANISM: Artificial Sequence
<220> FEATURE:
<223> OTHER INFORMATION: 16C5 HCDR2 (IMGT)

<400> SEQUENCE: 76

Ile Trp Trp Asp Asp Asp Lys
1 5

<210> SEQ ID NO 77
<211> LENGTH: 14
<212> TYPE: PRT
<213> ORGANISM: Artificial Sequence
<220> FEATURE:
<223> OTHER INFORMATION: 16C5 HCDR3 (IMGT)

<400> SEQUENCE: 77

Ala Arg Ile Gly Thr Ala Gln Ala Thr Asp Ala Leu Asp Tyr
1 5 10

<210> SEQ ID NO 78
<211> LENGTH: 6
<212> TYPE: PRT
<213> ORGANISM: Artificial Sequence
<220> FEATURE:
<223> OTHER INFORMATION: 16C5 LCDR1 (IMGT)

<400> SEQUENCE: 78

Glu Asp Ile Tyr Ser Gly
1 5

<210> SEQ ID NO 79
<211> LENGTH: 3
<212> TYPE: PRT
<213> ORGANISM: Artificial Sequence
<220> FEATURE:
<223> OTHER INFORMATION: 16C5 LCDR2 (IMGT)

<400> SEQUENCE: 79

Gly Ala Ser
1

<210> SEQ ID NO 80
<211> LENGTH: 11
<212> TYPE: PRT
<213> ORGANISM: Artificial Sequence
<220> FEATURE:
<223> OTHER INFORMATION: 16C5 LCDR3 (IMGT)

<400> SEQUENCE: 80

Leu Gly Gly Tyr Ser Tyr Ser Ser Thr Leu Thr
1 5 10

<210> SEQ ID NO 81
<211> LENGTH: 123

<212> TYPE: PRT
<213> ORGANISM: Artificial Sequence
<220> FEATURE:
<223> OTHER INFORMATION: 18C6 VH

<400> SEQUENCE: 81

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Val
            20                  25                  30

Gly Met Gly Val Gly Trp Ser Arg Gln Pro Ser Gly Lys Gly Leu Glu
        35                  40                  45

Trp Leu Ala His Ile Trp Trp Asp Asp Glu Asp Lys Tyr Tyr Asn Pro
    50                  55                  60

Ala Leu Lys Ser Arg Leu Thr Ile Ser Lys Asp Thr Ser Lys Asn Gln
65                  70                  75                  80

Val Phe Leu Lys Ile Ala Asn Val Asp Thr Ala Asp Thr Ala Thr Tyr
                85                  90                  95

Tyr Cys Thr Arg Ile Gly Thr Ala Gln Ala Thr Asp Ala Leu Asp Tyr
            100                 105                 110

Trp Gly Gln Gly Thr Ser Val Thr Val Ser Ser
        115                 120

<210> SEQ ID NO 82
<211> LENGTH: 112
<212> TYPE: PRT
<213> ORGANISM: Artificial Sequence
<220> FEATURE:
<223> OTHER INFORMATION: 18C6 VL

<400> SEQUENCE: 82

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Arg Leu Ile Tyr Tyr Met Ser Asn Leu Ala Ser Gly Val Pro
    50                  55                  60

Asp Arg Phe Ser Gly Arg Gly Ser Gly Thr Asp Phe Thr Leu Arg Ile
65                  70                  75                  80

Ser Arg Val Glu Ala Glu Asp Val Gly Val Tyr Tyr Cys Met Gln Ser
                85                  90                  95

Leu Glu Tyr Pro Leu Thr Phe Gly Gly Gly Thr Lys Leu Glu Ile Lys
            100                 105                 110

<210> SEQ ID NO 83
<211> LENGTH: 7
<212> TYPE: PRT
<213> ORGANISM: Artificial Sequence
<220> FEATURE:
<223> OTHER INFORMATION: 18C6 HCDR1 (KABAT)

<400> SEQUENCE: 83

Thr Val Gly Met Gly Val Gly
1               5

<210> SEQ ID NO 84
<211> LENGTH: 17
<212> TYPE: PRT

<213> ORGANISM: Artificial Sequence
<220> FEATURE:
<223> OTHER INFORMATION: 18C6 HCDR2 (KABAT)

<400> SEQUENCE: 84

His Ile Trp Trp Asp Asp Glu Asp Lys Tyr Tyr Asn Pro Ala Leu Lys
1 5 10 15

Ser

<210> SEQ ID NO 85
<211> LENGTH: 12
<212> TYPE: PRT
<213> ORGANISM: Artificial Sequence
<220> FEATURE:
<223> OTHER INFORMATION: 18C6 HCDR3 (KABAT)

<400> SEQUENCE: 85

Ile Gly Thr Ala Gln Ala Thr Asp Ala Leu Asp Tyr
1 5 10

<210> SEQ ID NO 86
<211> LENGTH: 16
<212> TYPE: PRT
<213> ORGANISM: Artificial Sequence
<220> FEATURE:
<223> OTHER INFORMATION: 18C6 LCDR1 (KABAT)

<400> SEQUENCE: 86

Arg Ser Ser Lys Ser Leu Leu His Ser Asn Gly Asn Thr Tyr Leu Tyr
1 5 10 15

<210> SEQ ID NO 87
<211> LENGTH: 7
<212> TYPE: PRT
<213> ORGANISM: Artificial Sequence
<220> FEATURE:
<223> OTHER INFORMATION: 18C6 LCDR2 (KABAT)

<400> SEQUENCE: 87

Tyr Met Ser Asn Leu Ala Ser
1 5

<210> SEQ ID NO 88
<211> LENGTH: 9
<212> TYPE: PRT
<213> ORGANISM: Artificial Sequence
<220> FEATURE:
<223> OTHER INFORMATION: 18C6 LCDR3 (KABAT)

<400> SEQUENCE: 88

Met Gln Ser Leu Glu Tyr Pro Leu Thr
1 5

<210> SEQ ID NO 89
<211> LENGTH: 9
<212> TYPE: PRT
<213> ORGANISM: Artificial Sequence
<220> FEATURE:
<223> OTHER INFORMATION: 18C6 HCDR1 (CHOTHIA)

<400> SEQUENCE: 89

Gly Phe Ser Leu Ser Thr Val Gly Met
1 5

<210> SEQ ID NO 90
<211> LENGTH: 4

<212> TYPE: PRT
<213> ORGANISM: Artificial Sequence
<220> FEATURE:
<223> OTHER INFORMATION: 18C6 HCDR2 (CHOTHIA)

<400> SEQUENCE: 90

Trp Asp Asp Glu
1

<210> SEQ ID NO 91
<211> LENGTH: 10
<212> TYPE: PRT
<213> ORGANISM: Artificial Sequence
<220> FEATURE:
<223> OTHER INFORMATION: 18C6 HCDR3 (CHOTHIA)

<400> SEQUENCE: 91

Gly Thr Ala Gln Ala Thr Asp Ala Leu Asp
1 5 10

<210> SEQ ID NO 92
<211> LENGTH: 12
<212> TYPE: PRT
<213> ORGANISM: Artificial Sequence
<220> FEATURE:
<223> OTHER INFORMATION: 18C6 LCDR1 (CHOTHIA)

<400> SEQUENCE: 92

Ser Lys Ser Leu Leu His Ser Asn Gly Asn Thr Tyr
1 5 10

<210> SEQ ID NO 93
<211> LENGTH: 3
<212> TYPE: PRT
<213> ORGANISM: Artificial Sequence
<220> FEATURE:
<223> OTHER INFORMATION: 18C6 LCDR2 (CHOTHIA)

<400> SEQUENCE: 93

Tyr Met Ser
1

<210> SEQ ID NO 94
<211> LENGTH: 6
<212> TYPE: PRT
<213> ORGANISM: Artificial Sequence
<220> FEATURE:
<223> OTHER INFORMATION: 18C6 LCDR3 (CHOTHIA)

<400> SEQUENCE: 94

Ser Leu Glu Tyr Pro Leu
1 5

<210> SEQ ID NO 95
<211> LENGTH: 10
<212> TYPE: PRT
<213> ORGANISM: Artificial Sequence
<220> FEATURE:
<223> OTHER INFORMATION: 18C6 HCDR1 (IMGT)

<400> SEQUENCE: 95

Gly Phe Ser Leu Ser Thr Val Gly Met Gly
1 5 10

<210> SEQ ID NO 96
<211> LENGTH: 8
<212> TYPE: PRT

<213> ORGANISM: Artificial Sequence
<220> FEATURE:
<223> OTHER INFORMATION: 18C6 HCDR2 (IMGT)

<400> SEQUENCE: 96

Ile Trp Trp Asp Asp Glu Asp Lys
1 5

<210> SEQ ID NO 97
<211> LENGTH: 14
<212> TYPE: PRT
<213> ORGANISM: Artificial Sequence
<220> FEATURE:
<223> OTHER INFORMATION: 18C6 HCDR3 (IMGT)

<400> SEQUENCE: 97

Thr Arg Ile Gly Thr Ala Gln Ala Thr Asp Ala Leu Asp Tyr
1 5 10

<210> SEQ ID NO 98
<211> LENGTH: 11
<212> TYPE: PRT
<213> ORGANISM: Artificial Sequence
<220> FEATURE:
<223> OTHER INFORMATION: 18C6 LCDR1 (IMGT)

<400> SEQUENCE: 98

Lys Ser Leu Leu His Ser Asn Gly Asn Thr Tyr
1 5 10

<210> SEQ ID NO 99
<211> LENGTH: 3
<212> TYPE: PRT
<213> ORGANISM: Artificial Sequence
<220> FEATURE:
<223> OTHER INFORMATION: 18C6 LCDR2 (IMGT)

<400> SEQUENCE: 99

Tyr Met Ser
1

<210> SEQ ID NO 100
<211> LENGTH: 9
<212> TYPE: PRT
<213> ORGANISM: Artificial Sequence
<220> FEATURE:
<223> OTHER INFORMATION: 18C6 LCDR3 (IMGT)

<400> SEQUENCE: 100

Met Gln Ser Leu Glu Tyr Pro Leu Thr
1 5

<210> SEQ ID NO 101
<211> LENGTH: 123
<212> TYPE: PRT
<213> ORGANISM: Artificial Sequence
<220> FEATURE:
<223> OTHER INFORMATION: 10C6-18C6 VH consensus
<220> FEATURE:
<221> NAME/KEY: VARIANT
<222> LOCATION: 3
<223> OTHER INFORMATION: Xaa = Thr or Asn
<220> FEATURE:
<221> NAME/KEY: VARIANT
<222> LOCATION: 11
<223> OTHER INFORMATION: Xaa = Ile or Lys
<220> FEATURE:
<221> NAME/KEY: VARIANT
<222> LOCATION: 30

```
<223> OTHER INFORMATION: Xaa = Asn or Ser
<220> FEATURE:
<221> NAME/KEY: VARIANT
<222> LOCATION: 32
<223> OTHER INFORMATION: Xaa = Val or Leu
<220> FEATURE:
<221> NAME/KEY: VARIANT
<222> LOCATION: 39
<223> OTHER INFORMATION: Xaa = Ser or Ile
<220> FEATURE:
<221> NAME/KEY: VARIANT
<222> LOCATION: 42
<223> OTHER INFORMATION: Xaa = Pro or Ser
<220> FEATURE:
<221> NAME/KEY: VARIANT
<222> LOCATION: 58
<223> OTHER INFORMATION: Xaa = Glu or absent
<220> FEATURE:
<221> NAME/KEY: VARIANT
<222> LOCATION: 63
<223> OTHER INFORMATION: Xaa = Asn or Tyr
<220> FEATURE:
<221> NAME/KEY: VARIANT
<222> LOCATION: 74
<223> OTHER INFORMATION: Xaa = Lys or Arg
<220> FEATURE:
<221> NAME/KEY: VARIANT
<222> LOCATION: 75
<223> OTHER INFORMATION: Xaa = Ala or Asp
<220> FEATURE:
<221> NAME/KEY: VARIANT
<222> LOCATION: 76
<223> OTHER INFORMATION: Xaa = Thr or Ser
<220> FEATURE:
<221> NAME/KEY: VARIANT
<222> LOCATION: 86
<223> OTHER INFORMATION: Xaa = Val or Ala
<220> FEATURE:
<221> NAME/KEY: VARIANT
<222> LOCATION: 89
<223> OTHER INFORMATION: Xaa = Gly or Asp
<220> FEATURE:
<221> NAME/KEY: VARIANT
<222> LOCATION: 93
<223> OTHER INFORMATION: Xaa = Thr, Ile or Ser
<220> FEATURE:
<221> NAME/KEY: VARIANT
<222> LOCATION: 99
<223> OTHER INFORMATION: Xaa = Thr, Ser or Ala

<400> SEQUENCE: 101

Gln Val Xaa Leu Lys Glu Ser Gly Pro Gly Xaa Leu Gln Pro Ser Gln
1               5                   10                  15

Thr Leu Ser Leu Thr Cys Ser Phe Ser Gly Phe Ser Leu Xaa Thr Xaa
            20                  25                  30

Gly Met Gly Val Gly Trp Xaa Arg Gln Xaa Ser Gly Lys Gly Leu Glu
        35                  40                  45

Trp Leu Ala His Ile Trp Trp Asp Asp Xaa Asp Lys Tyr Tyr Xaa Pro
    50                  55                  60

Ala Leu Lys Ser Arg Leu Thr Ile Ser Xaa Xaa Xaa Ser Lys Asn Gln
65                  70                  75                  80

Val Phe Leu Lys Ile Xaa Asn Val Xaa Thr Ala Asp Xaa Ala Thr Tyr
                85                  90                  95

Tyr Cys Xaa Arg Ile Gly Thr Ala Gln Ala Thr Asp Ala Leu Asp Tyr
            100                 105                 110

Trp Gly Gln Gly Thr Ser Val Thr Val Ser Ser
        115                 120


<210> SEQ ID NO 102
<211> LENGTH: 112
```

<212> TYPE: PRT
<213> ORGANISM: Artificial Sequence
<220> FEATURE:
<223> OTHER INFORMATION: 7B12, 19C11, 18C6 VL consensus
<220> FEATURE:
<221> NAME/KEY: VARIANT
<222> LOCATION: 11
<223> OTHER INFORMATION: Xaa = Ile or Val
<220> FEATURE:
<221> NAME/KEY: VARIANT
<222> LOCATION: 12
<223> OTHER INFORMATION: Xaa = Pro or Ser
<220> FEATURE:
<221> NAME/KEY: VARIANT
<222> LOCATION: 30
<223> OTHER INFORMATION: Xaa = Arg or Leu
<220> FEATURE:
<221> NAME/KEY: VARIANT
<222> LOCATION: 31
<223> OTHER INFORMATION: Xaa = Lys or His
<220> FEATURE:
<221> NAME/KEY: VARIANT
<222> LOCATION: 79
<223> OTHER INFORMATION: Xaa = Arg or Lys
<220> FEATURE:
<221> NAME/KEY: VARIANT
<222> LOCATION: 86
<223> OTHER INFORMATION: Xaa = Glu or Gly
<220> FEATURE:
<221> NAME/KEY: VARIANT
<222> LOCATION: 96
<223> OTHER INFORMATION: Xaa = Ser or Gly
<220> FEATURE:
<221> NAME/KEY: VARIANT
<222> LOCATION: 99
<223> OTHER INFORMATION: Xaa = Tyr or His

<400> SEQUENCE: 102

```
Asp Ile Val Met Thr Gln Ala Ala Pro Ser Xaa Xaa Val Thr Pro Gly
1               5                   10                  15

Glu Ser Val Ser Ile Ser Cys Arg Ser Ser Lys Ser Leu Xaa Xaa Ser
            20                  25                  30

Asn Gly Asn Thr Tyr Leu Tyr Trp Phe Leu Gln Arg Pro Gly Gln Ser
        35                  40                  45

Pro Gln Arg Leu Ile Tyr Tyr Met Ser Asn Leu Ala Ser Gly Val Pro
    50                  55                  60

Asp Arg Phe Ser Gly Arg Gly Ser Gly Thr Asp Phe Thr Leu Xaa Ile
65                  70                  75                  80

Ser Arg Val Glu Ala Xaa Asp Val Gly Val Tyr Tyr Cys Met Gln Xaa
                85                  90                  95

Leu Glu Xaa Pro Leu Thr Phe Gly Gly Gly Thr Lys Leu Glu Ile Lys
            100                 105                 110
```

<210> SEQ ID NO 103
<211> LENGTH: 7
<212> TYPE: PRT
<213> ORGANISM: Artificial Sequence
<220> FEATURE:
<223> OTHER INFORMATION: HCDR1 KABAT CONSENSUS
<220> FEATURE:
<221> NAME/KEY: VARIANT
<222> LOCATION: 2
<223> OTHER INFORMATION: Xaa = Lue or Val

<400> SEQUENCE: 103

```
Thr Xaa Gly Met Gly Val Gly
1               5
```

<210> SEQ ID NO 104

<211> LENGTH: 17
<212> TYPE: PRT
<213> ORGANISM: Artificial Sequence
<220> FEATURE:
<223> OTHER INFORMATION: HCDR2 KABAT CONSENSUS
<220> FEATURE:
<221> NAME/KEY: VARIANT
<222> LOCATION: 7
<223> OTHER INFORMATION: Xaa = Glu or Absent
<220> FEATURE:
<221> NAME/KEY: VARIANT
<222> LOCATION: 12
<223> OTHER INFORMATION: Xaa = Tyr or Asn

<400> SEQUENCE: 104

His Ile Trp Trp Asp Asp Xaa Asp Lys Tyr Tyr Xaa Pro Ala Leu Lys
1 5 10 15

Ser

<210> SEQ ID NO 105
<211> LENGTH: 12
<212> TYPE: PRT
<213> ORGANISM: Artificial Sequence
<220> FEATURE:
<223> OTHER INFORMATION: HCDR3 KABAT CONSENSUS

<400> SEQUENCE: 105

Ile Gly Thr Ala Gln Ala Thr Asp Ala Leu Asp Tyr
1 5 10

<210> SEQ ID NO 106
<211> LENGTH: 16
<212> TYPE: PRT
<213> ORGANISM: Artificial Sequence
<220> FEATURE:
<223> OTHER INFORMATION: 7B12, 19C11, 18C6 LCDR2 KABAT CONSENSUS
<220> FEATURE:
<221> NAME/KEY: VARIANT
<222> LOCATION: 7
<223> OTHER INFORMATION: Xaa = Arg or Leu
<220> FEATURE:
<221> NAME/KEY: VARIANT
<222> LOCATION: 8
<223> OTHER INFORMATION: Xaa = Lys or His

<400> SEQUENCE: 106

Arg Ser Ser Lys Ser Leu Xaa Xaa Ser Asn Gly Asn Thr Tyr Leu Tyr
1 5 10 15

<210> SEQ ID NO 107
<211> LENGTH: 7
<212> TYPE: PRT
<213> ORGANISM: Artificial Sequence
<220> FEATURE:
<223> OTHER INFORMATION: 7B12, 19C11, 18C6 LCDR2 KABAT CONSENSUS

<400> SEQUENCE: 107

Tyr Met Ser Asn Leu Ala Ser
1 5

<210> SEQ ID NO 108
<211> LENGTH: 9
<212> TYPE: PRT
<213> ORGANISM: Artificial Sequence
<220> FEATURE:
<223> OTHER INFORMATION: 7B12, 19C11, 18C6 LCDR3 KABAT CONSENSUS
<220> FEATURE:
<221> NAME/KEY: VARIANT
<222> LOCATION: 3
<223> OTHER INFORMATION: Xaa = Gly or Ser
<220> FEATURE:
<221> NAME/KEY: VARIANT
<222> LOCATION: 6
<223> OTHER INFORMATION: Xaa = His or Tyr

<400> SEQUENCE: 108

Met Gln Xaa Leu Glu Xaa Pro Leu Thr
1 5

<210> SEQ ID NO 109
<211> LENGTH: 9
<212> TYPE: PRT
<213> ORGANISM: Artificial Sequence
<220> FEATURE:
<223> OTHER INFORMATION: 10C6-18C6 HCDR1 CHOTHIA CONSENSUS
<220> FEATURE:
<221> NAME/KEY: VARIANT
<222> LOCATION: 5
<223> OTHER INFORMATION: Xaa = Asn or Ser
<220> FEATURE:
<221> NAME/KEY: VARIANT
<222> LOCATION: 7
<223> OTHER INFORMATION: Xaa = Leu or Val

<400> SEQUENCE: 109

Gly Phe Ser Leu Xaa Thr Xaa Gly Met
1 5

<210> SEQ ID NO 110
<211> LENGTH: 4
<212> TYPE: PRT
<213> ORGANISM: Artificial Sequence
<220> FEATURE:
<223> OTHER INFORMATION: 10C6-18C6 HCDR2 CHOTHIA CONSENSUS
<220> FEATURE:
<221> NAME/KEY: VARIANT
<222> LOCATION: 4
<223> OTHER INFORMATION: Xaa = Glu or Absent

<400> SEQUENCE: 110

Trp Asp Asp Xaa
1

<210> SEQ ID NO 111
<211> LENGTH: 10
<212> TYPE: PRT
<213> ORGANISM: Artificial Sequence
<220> FEATURE:
<223> OTHER INFORMATION: 10C6-18C6 HCDR3 CHOTHIA CONSENSUS

<400> SEQUENCE: 111

Gly Thr Ala Gln Ala Thr Asp Ala Leu Asp
1 5 10

<210> SEQ ID NO 112
<211> LENGTH: 12
<212> TYPE: PRT
<213> ORGANISM: Artificial Sequence
<220> FEATURE:
<223> OTHER INFORMATION: 7B12, 19C11, 18C6 LCDR1 CHOTHIA CONSENSUS
<220> FEATURE:
<221> NAME/KEY: VARIANT
<222> LOCATION: 5
<223> OTHER INFORMATION: Xaa = Leu or Arg
<220> FEATURE:
<221> NAME/KEY: VARIANT
<222> LOCATION: 6
<223> OTHER INFORMATION: Xaa = His or Lys

<400> SEQUENCE: 112

-continued

```
Ser Lys Ser Leu Xaa Xaa Ser Asn Gly Asn Thr Tyr
1               5                   10


<210> SEQ ID NO 113
<211> LENGTH: 3
<212> TYPE: PRT
<213> ORGANISM: Artificial Sequence
<220> FEATURE:
<223> OTHER INFORMATION: 7B12, 19C11, 18C6 LCDR2 CHOTHIA CONSENSUS

<400> SEQUENCE: 113

Tyr Met Ser
1


<210> SEQ ID NO 114
<211> LENGTH: 6
<212> TYPE: PRT
<213> ORGANISM: Artificial Sequence
<220> FEATURE:
<223> OTHER INFORMATION: 7B12, 19C11, 18C6 LCDR3 CHOTHIA CONSENSUS
<220> FEATURE:
<221> NAME/KEY: VARIANT
<222> LOCATION: 1
<223> OTHER INFORMATION: Xaa = Gly or Ser
<220> FEATURE:
<221> NAME/KEY: VARIANT
<222> LOCATION: 4
<223> OTHER INFORMATION: Xaa = His or Tyr

<400> SEQUENCE: 114

Xaa Leu Glu Xaa Pro Leu
1               5


<210> SEQ ID NO 115
<211> LENGTH: 10
<212> TYPE: PRT
<213> ORGANISM: Artificial Sequence
<220> FEATURE:
<223> OTHER INFORMATION: 10C6-18C6 HCDR1 IMGT CONSENSUS
<220> FEATURE:
<221> NAME/KEY: VARIANT
<222> LOCATION: 5
<223> OTHER INFORMATION: Xaa = Asn or Ser
<220> FEATURE:
<221> NAME/KEY: VARIANT
<222> LOCATION: 7
<223> OTHER INFORMATION: Xaa = Val or Leu

<400> SEQUENCE: 115

Gly Phe Ser Leu Xaa Thr Xaa Gly Met Gly
1               5                   10


<210> SEQ ID NO 116
<211> LENGTH: 8
<212> TYPE: PRT
<213> ORGANISM: Artificial Sequence
<220> FEATURE:
<223> OTHER INFORMATION: 10C6-18C6 HCDR2 IMGT CONSENSUS
<220> FEATURE:
<221> NAME/KEY: VARIANT
<222> LOCATION: 6
<223> OTHER INFORMATION: Xaa = Glu or Absent

<400> SEQUENCE: 116

Ile Trp Trp Asp Asp Xaa Asp Lys
1               5


<210> SEQ ID NO 117
<211> LENGTH: 14
<212> TYPE: PRT
```

<213> ORGANISM: Artificial Sequence
<220> FEATURE:
<223> OTHER INFORMATION: 10C6-18C6 HCDR3 IMGT CONSENSUS
<220> FEATURE:
<221> NAME/KEY: VARIANT
<222> LOCATION: 1
<223> OTHER INFORMATION: Xaa = Thr, Ala or Ser

<400> SEQUENCE: 117

Xaa Arg Ile Gly Thr Ala Gln Ala Thr Asp Ala Leu Asp Tyr
1 5 10

<210> SEQ ID NO 118
<211> LENGTH: 11
<212> TYPE: PRT
<213> ORGANISM: Artificial Sequence
<220> FEATURE:
<223> OTHER INFORMATION: 7B12, 19C11, 18C6 LCDR1 IMGT CONSENSUS
<220> FEATURE:
<221> NAME/KEY: VARIANT
<222> LOCATION: 4
<223> OTHER INFORMATION: Xaa = Val or Leu
<220> FEATURE:
<221> NAME/KEY: VARIANT
<222> LOCATION: 5
<223> OTHER INFORMATION: Xaa = His or Lys

<400> SEQUENCE: 118

Lys Ser Leu Xaa Xaa Ser Asn Gly Asn Thr Tyr
1 5 10

<210> SEQ ID NO 119
<211> LENGTH: 3
<212> TYPE: PRT
<213> ORGANISM: Artificial Sequence
<220> FEATURE:
<223> OTHER INFORMATION: 7B12, 19C11, 18C6 LCDR2 IMGT CONSENSUS

<400> SEQUENCE: 119

Tyr Met Ser
1

<210> SEQ ID NO 120
<211> LENGTH: 9
<212> TYPE: PRT
<213> ORGANISM: Artificial Sequence
<220> FEATURE:
<223> OTHER INFORMATION: 7B12, 19C11, 18C6 LCDR3 IMGT CONSENSUS

<400> SEQUENCE: 120

Met Gln Ser Leu Glu Tyr Pro Leu Thr
1 5

<210> SEQ ID NO 121
<211> LENGTH: 42
<212> TYPE: PRT
<213> ORGANISM: Artificial Sequence
<220> FEATURE:
<223> OTHER INFORMATION: MUC16c114 F primer

<400> SEQUENCE: 121

Cys Cys Ala Thr Gly Cys Gly Ala Thr Ala Thr Cys Gly Cys Cys Ala
1 5 10 15

Cys Cys Ala Thr Gly Gly Thr Gly Ala Ala Cys Thr Thr Cys Thr Cys
20 25 30

Gly Cys Cys Ala Cys Thr Gly Gly Cys Thr
35 40

<210> SEQ ID NO 122
<211> LENGTH: 34
<212> TYPE: PRT
<213> ORGANISM: Artificial Sequence
<220> FEATURE:
<223> OTHER INFORMATION: MUC16c114 R primer

<400> SEQUENCE: 122

Thr Ala Cys Gly Gly Cys Gly Gly Cys Cys Gly Cys Thr Thr Gly Cys
1 5 10 15

Ala Gly Ala Thr Cys Cys Thr Cys Cys Ala Gly Gly Thr Cys Thr Ala
20 25 30

Gly Gly

<210> SEQ ID NO 123
<211> LENGTH: 45
<212> TYPE: PRT
<213> ORGANISM: Artificial Sequence
<220> FEATURE:
<223> OTHER INFORMATION: MUC16c344 F primer

<400> SEQUENCE: 123

Cys Cys Ala Thr Gly Cys Gly Ala Thr Ala Thr Cys Gly Cys Cys Ala
1 5 10 15

Cys Cys Ala Thr Gly Gly Thr Gly Ala Cys Ala Gly Gly Cys Cys Cys
20 25 30

Thr Gly Gly Gly Cys Thr Gly Gly Ala Cys Ala Gly Ala
35 40 45

<210> SEQ ID NO 124
<211> LENGTH: 34
<212> TYPE: PRT
<213> ORGANISM: Artificial Sequence
<220> FEATURE:
<223> OTHER INFORMATION: MUC16c344 R primer

<400> SEQUENCE: 124

Thr Ala Cys Gly Gly Cys Gly Gly Cys Cys Gly Cys Thr Thr Gly Cys
1 5 10 15

Ala Gly Ala Thr Cys Cys Thr Cys Cys Ala Gly Gly Thr Cys Thr Ala
20 25 30

Gly Gly

<210> SEQ ID NO 125
<211> LENGTH: 31
<212> TYPE: PRT
<213> ORGANISM: Artificial Sequence
<220> FEATURE:
<223> OTHER INFORMATION: MUC16c57-114 F primer

<400> SEQUENCE: 125

Cys Cys Ala Thr Gly Cys Gly Ala Thr Ala Thr Cys Ala Ala Ala Cys
1 5 10 15

Thr Thr Cys Thr Cys Gly Cys Cys Ala Cys Thr Gly Gly Cys Thr
20 25 30

<210> SEQ ID NO 126
<211> LENGTH: 33
<212> TYPE: PRT
<213> ORGANISM: Artificial Sequence
<220> FEATURE:
<223> OTHER INFORMATION: MUC16c57-114 R primer

<400> SEQUENCE: 126

Ala Gly Ala Thr Cys Thr Ala Ala Cys Cys Ala Thr Gly Gly Gly Ala
1 5 10 15

Ala Gly Gly Thr Cys Ala Gly Ala Ala Thr Thr Cys Cys Cys Ala Gly
20 25 30

Thr

<210> SEQ ID NO 127
<211> LENGTH: 31
<212> TYPE: PRT
<213> ORGANISM: Artificial Sequence
<220> FEATURE:
<223> OTHER INFORMATION: 117-244LGALS3 F primer

<400> SEQUENCE: 127

Cys Cys Ala Thr Gly Cys Gly Ala Thr Ala Thr Cys Ala Cys Cys Thr
1 5 10 15

Thr Ala Thr Ala Ala Cys Cys Thr Gly Cys Cys Thr Thr Thr Gly
20 25 30

<210> SEQ ID NO 128
<211> LENGTH: 30
<212> TYPE: PRT
<213> ORGANISM: Artificial Sequence
<220> FEATURE:
<223> OTHER INFORMATION: 117-244LGALS3 R primer

<400> SEQUENCE: 128

Ala Gly Ala Thr Cys Thr Ala Ala Cys Cys Ala Thr Gly Gly Thr Ala
1 5 10 15

Thr Ala Thr Gly Ala Ala Gly Cys Ala Cys Thr Gly Gly Thr
20 25 30

<210> SEQ ID NO 129
<211> LENGTH: 55
<212> TYPE: PRT
<213> ORGANISM: Artificial Sequence
<220> FEATURE:
<223> OTHER INFORMATION: 55mer immunizing peptide

<400> SEQUENCE: 129

Asn Phe Ser Pro Leu Ala Arg Arg Val Asp Arg Val Ala Ile Tyr Glu
1 5 10 15

Glu Phe Leu Arg Met Thr Arg Asn Gly Thr Gln Leu Gln Asn Phe Thr
20 25 30

Leu Asp Arg Ser Ser Val Leu Val Asp Gly Tyr Ser Pro Asn Arg Asn
35 40 45

Glu Pro Leu Thr Gly Asn Ser
50 55

<210> SEQ ID NO 130
<211> LENGTH: 18
<212> TYPE: PRT
<213> ORGANISM: Artificial Sequence
<220> FEATURE:
<223> OTHER INFORMATION: 18mer immunizing peptide

<400> SEQUENCE: 130

Cys Thr Arg Asn Gly Thr Gln Leu Gln Asn Phe Thr Leu Asp Arg Ser
1 5 10 15

Ser Val

<210> SEQ ID NO 131
<211> LENGTH: 15
<212> TYPE: PRT
<213> ORGANISM: Artificial Sequence
<220> FEATURE:
<223> OTHER INFORMATION: 15mer immunizing peptide

<400> SEQUENCE: 131

Cys Gly Thr Gln Leu Gln Asn Phe Thr Leu Asp Arg Ser Ser Val
1 5 10 15

<210> SEQ ID NO 132
<211> LENGTH: 344
<212> TYPE: PRT
<213> ORGANISM: Artificial Sequence
<220> FEATURE:
<223> OTHER INFORMATION: MUC16c344

<400> SEQUENCE: 132

Trp Glu Leu Ser Gln Leu Thr His Gly Val Thr Gln Leu Gly Phe Tyr
1 5 10 15

Val Leu Asp Arg Asp Ser Leu Phe Ile Asn Gly Tyr Ala Pro Gln Asn
20 25 30

Leu Ser Ile Arg Gly Glu Tyr Gln Ile Asn Phe His Ile Val Asn Gln
35 40 45

Asn Leu Ser Asn Pro Asp Pro Thr Ser Ser Glu Tyr Ile Thr Leu Leu
50 55 60

Arg Asp Ile Gln Asp Lys Val Thr Thr Leu Tyr Lys Gly Ser Gln Leu
65 70 75 80

His Asp Thr Phe Arg Phe Cys Leu Val Thr Asn Leu Thr Met Asp Ser
85 90 95

Val Leu Val Thr Val Lys Ala Leu Phe Ser Ser Asn Leu Asp Pro Ser
100 105 110

Leu Val Glu Gln Val Phe Leu Asp Lys Thr Leu Asn Ala Ser Phe His
115 120 125

Gln Leu Gly Ser Thr Tyr Gln Leu Val Asp Ile His Val Thr Glu Met
130 135 140

Glu Ser Ser Val Tyr Gln Pro Thr Ser Ser Ser Ser Thr Gln His Phe
145 150 155 160

Tyr Leu Asn Phe Thr Ile Thr Asn Leu Pro Tyr Ser Gln Asp Lys Ala
165 170 175

Gln Pro Gly Thr Thr Asn Tyr Gln Arg Asn Lys Arg Asn Ile Glu Asp
180 185 190

Ala Leu Asn Gln Leu Phe Arg Asn Ser Ser Ile Lys Ser Tyr Phe Ser
195 200 205

Asp Cys Gln Val Ser Thr Phe Arg Ser Val Pro Asn Arg His His Thr
210 215 220

Gly Val Asp Ser Leu Cys Asn Phe Ser Pro Leu Ala Arg Arg Val Asp
225 230 235 240

Arg Val Ala Ile Tyr Glu Glu Phe Leu Arg Met Thr Arg Asn Gly Thr
245 250 255

Gln Leu Gln Asn Phe Thr Leu Asp Arg Ser Ser Val Leu Val Asp Gly
260 265 270

Tyr Ser Pro Asn Arg Asn Glu Pro Leu Thr Gly Asn Ser Asp Leu Pro
275 280 285

Phe Trp Ala Val Ile Leu Ile Gly Leu Ala Gly Leu Leu Gly Leu Ile
290 295 300

Thr Cys Leu Ile Cys Gly Val Leu Val Thr Thr Arg Arg Arg Lys Lys
305 310 315 320

Glu Gly Glu Tyr Asn Val Gln Gln Gln Cys Pro Gly Tyr Tyr Gln Ser
325 330 335

His Leu Asp Leu Glu Asp Leu Gln
340

<210> SEQ ID NO 133
<211> LENGTH: 114
<212> TYPE: PRT
<213> ORGANISM: Artificial Sequence
<220> FEATURE:
<223> OTHER INFORMATION: MUC16c114

<400> SEQUENCE: 133

Asn Phe Ser Pro Leu Ala Arg Arg Val Asp Arg Val Ala Ile Tyr Glu
1 5 10 15

Glu Phe Leu Arg Met Thr Arg Asn Gly Thr Gln Leu Gln Asn Phe Thr
20 25 30

Leu Asp Arg Ser Ser Val Leu Val Asp Gly Tyr Ser Pro Asn Arg Asn
35 40 45

Glu Pro Leu Thr Gly Asn Ser Asp Leu Pro Phe Trp Ala Val Ile Leu
50 55 60

Ile Gly Leu Ala Gly Leu Leu Gly Leu Ile Thr Cys Leu Ile Cys Gly
65 70 75 80

Val Leu Val Thr Thr Arg Arg Arg Lys Lys Glu Gly Glu Tyr Asn Val
85 90 95

Gln Gln Gln Cys Pro Gly Tyr Tyr Gln Ser His Leu Asp Leu Glu Asp
100 105 110

Leu Gln

<210> SEQ ID NO 134
<211> LENGTH: 80
<212> TYPE: PRT
<213> ORGANISM: Artificial Sequence
<220> FEATURE:
<223> OTHER INFORMATION: MUC16c86

<400> SEQUENCE: 134

Asn Phe Ser Pro Leu Ala Arg Arg Val Asp Arg Val Ala Ile Tyr Glu
1 5 10 15

Glu Phe Leu Arg Met Asp Leu Pro Phe Trp Ala Val Ile Leu Ile Gly
20 25 30

Leu Ala Gly Leu Leu Gly Leu Ile Thr Cys Leu Ile Cys Gly Val Leu
35 40 45

Val Thr Thr Arg Arg Arg Lys Lys Glu Gly Glu Tyr Asn Val Gln Gln
50 55 60

Gln Cys Pro Gly Tyr Tyr Gln Ser His Leu Asp Leu Glu Asp Leu Gln
65 70 75 80

<210> SEQ ID NO 135
<211> LENGTH: 86
<212> TYPE: PRT
<213> ORGANISM: Artificial Sequence
<220> FEATURE:
<223> OTHER INFORMATION: MUC16c80

<400> SEQUENCE: 135

Asn Phe Ser Pro Leu Ala Arg Arg Val Asp Arg Val Ala Ile Tyr Glu

```
1               5                   10                  15

Glu Phe Leu Arg Met Thr Arg Asn Gly Thr Gln Leu Gln Asn Phe Thr
            20                  25                  30

Leu Asp Arg Ser Ser Val Leu Val Asp Gly Tyr Ser Pro Asn Arg Asn
        35                  40                  45

Glu Pro Leu Thr Gly Asn Ser Asp Leu Pro Phe Trp Ala Val Ile Leu
    50                  55                  60

Ile Gly Leu Ala Gly Leu Leu Gly Leu Ile Thr Cys Leu Ile Cys Gly
65                  70                  75                  80

Asp Leu Glu Asp Leu Gln
                85


<210> SEQ ID NO 136
<211> LENGTH: 14507
<212> TYPE: PRT
<213> ORGANISM: Homo sapiens
<220> FEATURE:
<223> OTHER INFORMATION: Immature Human MUC16 amino acid sequence
      (NP_078966.2)

<400> SEQUENCE: 136

Met Leu Lys Pro Ser Gly Leu Pro Gly Ser Ser Ser Pro Thr Arg Ser
1               5                   10                  15

Leu Met Thr Gly Ser Arg Ser Thr Lys Ala Thr Pro Glu Met Asp Ser
            20                  25                  30

Gly Leu Thr Gly Ala Thr Leu Ser Pro Lys Thr Ser Thr Gly Ala Ile
        35                  40                  45

Val Val Thr Glu His Thr Leu Pro Phe Thr Ser Pro Asp Lys Thr Leu
    50                  55                  60

Ala Ser Pro Thr Ser Ser Val Val Gly Arg Thr Thr Gln Ser Leu Gly
65                  70                  75                  80

Val Met Ser Ser Ala Leu Pro Glu Ser Thr Ser Arg Gly Met Thr His
                85                  90                  95

Ser Glu Gln Arg Thr Ser Pro Ser Leu Ser Pro Gln Val Asn Gly Thr
            100                 105                 110

Pro Ser Arg Asn Tyr Pro Ala Thr Ser Met Val Ser Gly Leu Ser Ser
        115                 120                 125

Pro Arg Thr Arg Thr Ser Ser Thr Glu Gly Asn Phe Thr Lys Glu Ala
    130                 135                 140

Ser Thr Tyr Thr Leu Thr Val Glu Thr Thr Ser Gly Pro Val Thr Glu
145                 150                 155                 160

Lys Tyr Thr Val Pro Thr Glu Thr Ser Thr Thr Glu Gly Asp Ser Thr
                165                 170                 175

Glu Thr Pro Trp Asp Thr Arg Tyr Ile Pro Val Lys Ile Thr Ser Pro
            180                 185                 190

Met Lys Thr Phe Ala Asp Ser Thr Ala Ser Lys Glu Asn Ala Pro Val
        195                 200                 205

Ser Met Thr Pro Ala Glu Thr Thr Val Thr Asp Ser His Thr Pro Gly
    210                 215                 220

Arg Thr Asn Pro Ser Phe Gly Thr Leu Tyr Ser Ser Phe Leu Asp Leu
225                 230                 235                 240

Ser Pro Lys Gly Thr Pro Asn Ser Arg Gly Glu Thr Ser Leu Glu Leu
                245                 250                 255

Ile Leu Ser Thr Thr Gly Tyr Pro Phe Ser Ser Pro Glu Pro Gly Ser
            260                 265                 270
```

Ala Gly His Ser Arg Ile Ser Thr Ser Ala Pro Leu Ser Ser Ser Ala
        275                 280                 285

Ser Val Leu Asp Asn Lys Ile Ser Glu Thr Ser Ile Phe Ser Gly Gln
    290                 295                 300

Ser Leu Thr Ser Pro Leu Ser Pro Gly Val Pro Glu Ala Arg Ala Ser
305                 310                 315                 320

Thr Met Pro Asn Ser Ala Ile Pro Phe Ser Met Thr Leu Ser Asn Ala
                325                 330                 335

Glu Thr Ser Ala Glu Arg Val Arg Ser Thr Ile Ser Ser Leu Gly Thr
            340                 345                 350

Pro Ser Ile Ser Thr Lys Gln Thr Ala Glu Thr Ile Leu Thr Phe His
        355                 360                 365

Ala Phe Ala Glu Thr Met Asp Ile Pro Ser Thr His Ile Ala Lys Thr
    370                 375                 380

Leu Ala Ser Glu Trp Leu Gly Ser Pro Gly Thr Leu Gly Gly Thr Ser
385                 390                 395                 400

Thr Ser Ala Leu Thr Thr Thr Ser Pro Ser Thr Thr Leu Val Ser Glu
                405                 410                 415

Glu Thr Asn Thr His His Ser Thr Ser Gly Lys Glu Thr Glu Gly Thr
            420                 425                 430

Leu Asn Thr Ser Met Thr Pro Leu Glu Thr Ser Ala Pro Gly Glu Glu
        435                 440                 445

Ser Glu Met Thr Ala Thr Leu Val Pro Thr Leu Gly Phe Thr Thr Leu
    450                 455                 460

Asp Ser Lys Ile Arg Ser Pro Ser Gln Val Ser Ser Ser His Pro Thr
465                 470                 475                 480

Arg Glu Leu Arg Thr Thr Gly Ser Thr Ser Gly Arg Gln Ser Ser Ser
                485                 490                 495

Thr Ala Ala His Gly Ser Ser Asp Ile Leu Arg Ala Thr Thr Ser Ser
            500                 505                 510

Thr Ser Lys Ala Ser Ser Trp Thr Ser Glu Ser Thr Ala Gln Gln Phe
        515                 520                 525

Ser Glu Pro Gln His Thr Gln Trp Val Glu Thr Ser Pro Ser Met Lys
    530                 535                 540

Thr Glu Arg Pro Pro Ala Ser Thr Ser Val Ala Ala Pro Ile Thr Thr
545                 550                 555                 560

Ser Val Pro Ser Val Val Ser Gly Phe Thr Thr Leu Lys Thr Ser Ser
                565                 570                 575

Thr Lys Gly Ile Trp Leu Glu Glu Thr Ser Ala Asp Thr Leu Ile Gly
            580                 585                 590

Glu Ser Thr Ala Gly Pro Thr Thr His Gln Phe Ala Val Pro Thr Gly
        595                 600                 605

Ile Ser Met Thr Gly Gly Ser Ser Thr Arg Gly Ser Gln Gly Thr Thr
    610                 615                 620

His Leu Leu Thr Arg Ala Thr Ala Ser Ser Glu Thr Ser Ala Asp Leu
625                 630                 635                 640

Thr Leu Ala Thr Asn Gly Val Pro Val Ser Val Ser Pro Ala Val Ser
                645                 650                 655

Lys Thr Ala Ala Gly Ser Ser Pro Pro Gly Gly Thr Lys Pro Ser Tyr
            660                 665                 670

Thr Met Val Ser Ser Val Ile Pro Glu Thr Ser Ser Leu Gln Ser Ser
        675                 680                 685

Ala Phe Arg Glu Gly Thr Ser Leu Gly Leu Thr Pro Leu Asn Thr Arg

```
    690                 695                 700

His Pro Phe Ser Ser Pro Glu Pro Asp Ser Ala Gly His Thr Lys Ile
705                 710                 715                 720

Ser Thr Ser Ile Pro Leu Leu Ser Ser Ala Ser Val Leu Glu Asp Lys
                725                 730                 735

Val Ser Ala Thr Ser Thr Phe Ser His His Lys Ala Thr Ser Ser Ile
            740                 745                 750

Thr Thr Gly Thr Pro Glu Ile Ser Thr Lys Thr Lys Pro Ser Ser Ala
        755                 760                 765

Val Leu Ser Ser Met Thr Leu Ser Asn Ala Ala Thr Ser Pro Glu Arg
    770                 775                 780

Val Arg Asn Ala Thr Ser Pro Leu Thr His Pro Ser Pro Ser Gly Glu
785                 790                 795                 800

Glu Thr Ala Gly Ser Val Leu Thr Leu Ser Thr Ser Ala Glu Thr Thr
                805                 810                 815

Asp Ser Pro Asn Ile His Pro Thr Gly Thr Leu Thr Ser Glu Ser Ser
            820                 825                 830

Glu Ser Pro Ser Thr Leu Ser Leu Pro Ser Val Ser Gly Val Lys Thr
        835                 840                 845

Thr Phe Ser Ser Ser Thr Pro Ser Thr His Leu Phe Thr Ser Gly Glu
    850                 855                 860

Glu Thr Glu Glu Thr Ser Asn Pro Ser Val Ser Gln Pro Glu Thr Ser
865                 870                 875                 880

Val Ser Arg Val Arg Thr Thr Leu Ala Ser Thr Ser Val Pro Thr Pro
                885                 890                 895

Val Phe Pro Thr Met Asp Thr Trp Pro Thr Arg Ser Ala Gln Phe Ser
            900                 905                 910

Ser Ser His Leu Val Ser Glu Leu Arg Ala Thr Ser Ser Thr Ser Val
        915                 920                 925

Thr Asn Ser Thr Gly Ser Ala Leu Pro Lys Ile Ser His Leu Thr Gly
    930                 935                 940

Thr Ala Thr Met Ser Gln Thr Asn Arg Asp Thr Phe Asn Asp Ser Ala
945                 950                 955                 960

Ala Pro Gln Ser Thr Thr Trp Pro Glu Thr Ser Pro Arg Phe Lys Thr
                965                 970                 975

Gly Leu Pro Ser Ala Thr Thr Thr Val Ser Thr Ser Ala Thr Ser Leu
            980                 985                 990

Ser Ala Thr Val Met Val Ser Lys  Phe Thr Ser Pro Ala  Thr Ser Ser
        995                 1000                1005

Met Glu  Ala Thr Ser Ile Arg  Glu Pro Ser Thr Thr  Ile Leu Thr
    1010                1015                1020

Thr Glu  Thr Thr Asn Gly Pro  Gly Ser Met Ala Val  Ala Ser Thr
    1025                1030                1035

Asn Ile  Pro Ile Gly Lys Gly  Tyr Ile Thr Glu Gly  Arg Leu Asp
    1040                1045                1050

Thr Ser  His Leu Pro Ile Gly  Thr Thr Ala Ser Ser  Glu Thr Ser
    1055                1060                1065

Met Asp  Phe Thr Met Ala Lys  Glu Ser Val Ser Met  Ser Val Ser
    1070                1075                1080

Pro Ser  Gln Ser Met Asp Ala  Ala Gly Ser Ser Thr  Pro Gly Arg
    1085                1090                1095

Thr Ser  Gln Phe Val Asp Thr  Phe Ser Asp Asp Val  Tyr His Leu
    1100                1105                1110
```

Thr Ser Arg Glu Ile Thr Ile Pro Arg Asp Gly Thr Ser Ser Ala
1115 1120 1125

Leu Thr Pro Gln Met Thr Ala Thr His Pro Pro Ser Pro Asp Pro
1130 1135 1140

Gly Ser Ala Arg Ser Thr Trp Leu Gly Ile Leu Ser Ser Ser Pro
1145 1150 1155

Ser Ser Pro Thr Pro Lys Val Thr Met Ser Ser Thr Phe Ser Thr
1160 1165 1170

Gln Arg Val Thr Thr Ser Met Ile Met Asp Thr Val Glu Thr Ser
1175 1180 1185

Arg Trp Asn Met Pro Asn Leu Pro Ser Thr Thr Ser Leu Thr Pro
1190 1195 1200

Ser Asn Ile Pro Thr Ser Gly Ala Ile Gly Lys Ser Thr Leu Val
1205 1210 1215

Pro Leu Asp Thr Pro Ser Pro Ala Thr Ser Leu Glu Ala Ser Glu
1220 1225 1230

Gly Gly Leu Pro Thr Leu Ser Thr Tyr Pro Glu Ser Thr Asn Thr
1235 1240 1245

Pro Ser Ile His Leu Gly Ala His Ala Ser Ser Glu Ser Pro Ser
1250 1255 1260

Thr Ile Lys Leu Thr Met Ala Ser Val Val Lys Pro Gly Ser Tyr
1265 1270 1275

Thr Pro Leu Thr Phe Pro Ser Ile Glu Thr His Ile His Val Ser
1280 1285 1290

Thr Ala Arg Met Ala Tyr Ser Ser Gly Ser Ser Pro Glu Met Thr
1295 1300 1305

Ala Pro Gly Glu Thr Asn Thr Gly Ser Thr Trp Asp Pro Thr Thr
1310 1315 1320

Tyr Ile Thr Thr Thr Asp Pro Lys Asp Thr Ser Ser Ala Gln Val
1325 1330 1335

Ser Thr Pro His Ser Val Arg Thr Leu Arg Thr Thr Glu Asn His
1340 1345 1350

Pro Lys Thr Glu Ser Ala Thr Pro Ala Ala Tyr Ser Gly Ser Pro
1355 1360 1365

Lys Ile Ser Ser Ser Pro Asn Leu Thr Ser Pro Ala Thr Lys Ala
1370 1375 1380

Trp Thr Ile Thr Asp Thr Thr Glu His Ser Thr Gln Leu His Tyr
1385 1390 1395

Thr Lys Leu Ala Glu Lys Ser Ser Gly Phe Glu Thr Gln Ser Ala
1400 1405 1410

Pro Gly Pro Val Ser Val Val Ile Pro Thr Ser Pro Thr Ile Gly
1415 1420 1425

Ser Ser Thr Leu Glu Leu Thr Ser Asp Val Pro Gly Glu Pro Leu
1430 1435 1440

Val Leu Ala Pro Ser Glu Gln Thr Thr Ile Thr Leu Pro Met Ala
1445 1450 1455

Thr Trp Leu Ser Thr Ser Leu Thr Glu Glu Met Ala Ser Thr Asp
1460 1465 1470

Leu Asp Ile Ser Ser Pro Ser Ser Pro Met Ser Thr Phe Ala Ile
1475 1480 1485

Phe Pro Pro Met Ser Thr Pro Ser His Glu Leu Ser Lys Ser Glu
1490 1495 1500

```
Ala Asp  Thr Ser Ala Ile Arg  Asn Thr Asp Ser Thr  Thr Leu Asp
    1505                 1510                 1515

Gln His  Leu Gly Ile Arg Ser  Leu Gly Arg Thr Gly  Asp Leu Thr
    1520                 1525                 1530

Thr Val  Pro Ile Thr Pro Leu  Thr Thr Thr Trp Thr  Ser Val Ile
    1535                 1540                 1545

Glu His  Ser Thr Gln Ala Gln  Asp Thr Leu Ser Ala  Thr Met Ser
    1550                 1555                 1560

Pro Thr  His Val Thr Gln Ser  Leu Lys Asp Gln Thr  Ser Ile Pro
    1565                 1570                 1575

Ala Ser  Ala Ser Pro Ser His  Leu Thr Glu Val Tyr  Pro Glu Leu
    1580                 1585                 1590

Gly Thr  Gln Gly Arg Ser Ser  Ser Glu Ala Thr Thr  Phe Trp Lys
    1595                 1600                 1605

Pro Ser  Thr Asp Thr Leu Ser  Arg Glu Ile Glu Thr  Gly Pro Thr
    1610                 1615                 1620

Asn Ile  Gln Ser Thr Pro Pro  Met Asp Asn Thr Thr  Thr Gly Ser
    1625                 1630                 1635

Ser Ser  Ser Gly Val Thr Leu  Gly Ile Ala His Leu  Pro Ile Gly
    1640                 1645                 1650

Thr Ser  Ser Pro Ala Glu Thr  Ser Thr Asn Met Ala  Leu Glu Arg
    1655                 1660                 1665

Arg Ser  Ser Thr Ala Thr Val  Ser Met Ala Gly Thr  Met Gly Leu
    1670                 1675                 1680

Leu Val  Thr Ser Ala Pro Gly  Arg Ser Ile Ser Gln  Ser Leu Gly
    1685                 1690                 1695

Arg Val  Ser Ser Val Leu Ser  Glu Ser Thr Thr Glu  Gly Val Thr
    1700                 1705                 1710

Asp Ser  Ser Lys Gly Ser Ser  Pro Arg Leu Asn Thr  Gln Gly Asn
    1715                 1720                 1725

Thr Ala  Leu Ser Ser Ser Leu  Glu Pro Ser Tyr Ala  Glu Gly Ser
    1730                 1735                 1740

Gln Met  Ser Thr Ser Ile Pro  Leu Thr Ser Ser Pro  Thr Thr Pro
    1745                 1750                 1755

Asp Val  Glu Phe Ile Gly Gly  Ser Thr Phe Trp Thr  Lys Glu Val
    1760                 1765                 1770

Thr Thr  Val Met Thr Ser Asp  Ile Ser Lys Ser Ser  Ala Arg Thr
    1775                 1780                 1785

Glu Ser  Ser Ser Ala Thr Leu  Met Ser Thr Ala Leu  Gly Ser Thr
    1790                 1795                 1800

Glu Asn  Thr Gly Lys Glu Lys  Leu Arg Thr Ala Ser  Met Asp Leu
    1805                 1810                 1815

Pro Ser  Pro Thr Pro Ser Met  Glu Val Thr Pro Trp  Ile Ser Leu
    1820                 1825                 1830

Thr Leu  Ser Asn Ala Pro Asn  Thr Thr Asp Ser Leu  Asp Leu Ser
    1835                 1840                 1845

His Gly  Val His Thr Ser Ser  Ala Gly Thr Leu Ala  Thr Asp Arg
    1850                 1855                 1860

Ser Leu  Asn Thr Gly Val Thr  Arg Ala Ser Arg Leu  Glu Asn Gly
    1865                 1870                 1875

Ser Asp  Thr Ser Ser Lys Ser  Leu Ser Met Gly Asn  Ser Thr His
    1880                 1885                 1890

Thr Ser  Met Thr Tyr Thr Glu  Lys Ser Glu Val Ser  Ser Ser Ile
```

1895 1900 1905

His Pro Arg Pro Glu Thr Ser Ala Pro Gly Ala Glu Thr Thr Leu
1910 1915 1920

Thr Ser Thr Pro Gly Asn Arg Ala Ile Ser Leu Thr Leu Pro Phe
1925 1930 1935

Ser Ser Ile Pro Val Glu Glu Val Ile Ser Thr Gly Ile Thr Ser
1940 1945 1950

Gly Pro Asp Ile Asn Ser Ala Pro Met Thr His Ser Pro Ile Thr
1955 1960 1965

Pro Pro Thr Ile Val Trp Thr Ser Thr Gly Thr Ile Glu Gln Ser
1970 1975 1980

Thr Gln Pro Leu His Ala Val Ser Ser Glu Lys Val Ser Val Gln
1985 1990 1995

Thr Gln Ser Thr Pro Tyr Val Asn Ser Val Ala Val Ser Ala Ser
2000 2005 2010

Pro Thr His Glu Asn Ser Val Ser Ser Gly Ser Ser Thr Ser Ser
2015 2020 2025

Pro Tyr Ser Ser Ala Ser Leu Glu Ser Leu Asp Ser Thr Ile Ser
2030 2035 2040

Arg Arg Asn Ala Ile Thr Ser Trp Leu Trp Asp Leu Thr Thr Ser
2045 2050 2055

Leu Pro Thr Thr Thr Trp Pro Ser Thr Ser Leu Ser Glu Ala Leu
2060 2065 2070

Ser Ser Gly His Ser Gly Val Ser Asn Pro Ser Ser Thr Thr Thr
2075 2080 2085

Glu Phe Pro Leu Phe Ser Ala Ala Ser Thr Ser Ala Ala Lys Gln
2090 2095 2100

Arg Asn Pro Glu Thr Glu Thr His Gly Pro Gln Asn Thr Ala Ala
2105 2110 2115

Ser Thr Leu Asn Thr Asp Ala Ser Ser Val Thr Gly Leu Ser Glu
2120 2125 2130

Thr Pro Val Gly Ala Ser Ile Ser Ser Glu Val Pro Leu Pro Met
2135 2140 2145

Ala Ile Thr Ser Arg Ser Asp Val Ser Gly Leu Thr Ser Glu Ser
2150 2155 2160

Thr Ala Asn Pro Ser Leu Gly Thr Ala Ser Ser Ala Gly Thr Lys
2165 2170 2175

Leu Thr Arg Thr Ile Ser Leu Pro Thr Ser Glu Ser Leu Val Ser
2180 2185 2190

Phe Arg Met Asn Lys Asp Pro Trp Thr Val Ser Ile Pro Leu Gly
2195 2200 2205

Ser His Pro Thr Thr Asn Thr Glu Thr Ser Ile Pro Val Asn Ser
2210 2215 2220

Ala Gly Pro Pro Gly Leu Ser Thr Val Ala Ser Asp Val Ile Asp
2225 2230 2235

Thr Pro Ser Asp Gly Ala Glu Ser Ile Pro Thr Val Ser Phe Ser
2240 2245 2250

Pro Ser Pro Asp Thr Glu Val Thr Thr Ile Ser His Phe Pro Glu
2255 2260 2265

Lys Thr Thr His Ser Phe Arg Thr Ile Ser Ser Leu Thr His Glu
2270 2275 2280

Leu Thr Ser Arg Val Thr Pro Ile Pro Gly Asp Trp Met Ser Ser
2285 2290 2295

```
Ala Met  Ser Thr Lys Pro Thr  Gly Ala Ser Pro Ser  Ile Thr Leu
    2300                 2305                 2310

Gly Glu  Arg Arg Thr Ile Thr  Ser Ala Ala Pro Thr  Thr Ser Pro
    2315                 2320                 2325

Ile Val  Leu Thr Ala Ser Phe  Thr Glu Thr Ser Thr  Val Ser Leu
    2330                 2335                 2340

Asp Asn  Glu Thr Thr Val Lys  Thr Ser Asp Ile Leu  Asp Ala Arg
    2345                 2350                 2355

Lys Thr  Asn Glu Leu Pro Ser  Asp Ser Ser Ser Ser  Ser Asp Leu
    2360                 2365                 2370

Ile Asn  Thr Ser Ile Ala Ser  Ser Thr Met Asp Val  Thr Lys Thr
    2375                 2380                 2385

Ala Ser  Ile Ser Pro Thr Ser  Ile Ser Gly Met Thr  Ala Ser Ser
    2390                 2395                 2400

Ser Pro  Ser Leu Phe Ser Ser  Asp Arg Pro Gln Val  Pro Thr Ser
    2405                 2410                 2415

Thr Thr  Glu Thr Asn Thr Ala  Thr Ser Pro Ser Val  Ser Ser Asn
    2420                 2425                 2430

Thr Tyr  Ser Leu Asp Gly Gly  Ser Asn Val Gly Gly  Thr Pro Ser
    2435                 2440                 2445

Thr Leu  Pro Pro Phe Thr Ile  Thr His Pro Val Glu  Thr Ser Ser
    2450                 2455                 2460

Ala Leu  Leu Ala Trp Ser Arg  Pro Val Arg Thr Phe  Ser Thr Met
    2465                 2470                 2475

Val Ser  Thr Asp Thr Ala Ser  Gly Glu Asn Pro Thr  Ser Ser Asn
    2480                 2485                 2490

Ser Val  Val Thr Ser Val Pro  Ala Pro Gly Thr Trp  Thr Ser Val
    2495                 2500                 2505

Gly Ser  Thr Thr Asp Leu Pro  Ala Met Gly Phe Leu  Lys Thr Ser
    2510                 2515                 2520

Pro Ala  Gly Glu Ala His Ser  Leu Leu Ala Ser Thr  Ile Glu Pro
    2525                 2530                 2535

Ala Thr  Ala Phe Thr Pro His  Leu Ser Ala Ala Val  Val Thr Gly
    2540                 2545                 2550

Ser Ser  Ala Thr Ser Glu Ala  Ser Leu Leu Thr Thr  Ser Glu Ser
    2555                 2560                 2565

Lys Ala  Ile His Ser Ser Pro  Gln Thr Pro Thr Thr  Pro Thr Ser
    2570                 2575                 2580

Gly Ala  Asn Trp Glu Thr Ser  Ala Thr Pro Glu Ser  Leu Leu Val
    2585                 2590                 2595

Val Thr  Glu Thr Ser Asp Thr  Thr Leu Thr Ser Lys  Ile Leu Val
    2600                 2605                 2610

Thr Asp  Thr Ile Leu Phe Ser  Thr Val Ser Thr Pro  Pro Ser Lys
    2615                 2620                 2625

Phe Pro  Ser Thr Gly Thr Leu  Ser Gly Ala Ser Phe  Pro Thr Leu
    2630                 2635                 2640

Leu Pro  Asp Thr Pro Ala Ile  Pro Leu Thr Ala Thr  Glu Pro Thr
    2645                 2650                 2655

Ser Ser  Leu Ala Thr Ser Phe  Asp Ser Thr Pro Leu  Val Thr Ile
    2660                 2665                 2670

Ala Ser  Asp Ser Leu Gly Thr  Val Pro Glu Thr Thr  Leu Thr Met
    2675                 2680                 2685
```

```
Ser Glu  Thr Ser Asn Gly Asp  Ala Leu Val Leu Lys  Thr Val Ser
    2690                2695                2700

Asn Pro  Asp Arg Ser Ile Pro  Gly Ile Thr Ile Gln  Gly Val Thr
    2705                2710                2715

Glu Ser  Pro Leu His Pro Ser  Ser Thr Ser Pro Ser  Lys Ile Val
    2720                2725                2730

Ala Pro  Arg Asn Thr Thr Tyr  Glu Gly Ser Ile Thr  Val Ala Leu
    2735                2740                2745

Ser Thr  Leu Pro Ala Gly Thr  Thr Gly Ser Leu Val  Phe Ser Gln
    2750                2755                2760

Ser Ser  Glu Asn Ser Glu Thr  Thr Ala Leu Val Asp  Ser Ser Ala
    2765                2770                2775

Gly Leu  Glu Arg Ala Ser Val  Met Pro Leu Thr Thr  Gly Ser Gln
    2780                2785                2790

Gly Met  Ala Ser Ser Gly Gly  Ile Arg Ser Gly Ser  Thr His Ser
    2795                2800                2805

Thr Gly  Thr Lys Thr Phe Ser  Ser Leu Pro Leu Thr  Met Asn Pro
    2810                2815                2820

Gly Glu  Val Thr Ala Met Ser  Glu Ile Thr Thr Asn  Arg Leu Thr
    2825                2830                2835

Ala Thr  Gln Ser Thr Ala Pro  Lys Gly Ile Pro Val  Lys Pro Thr
    2840                2845                2850

Ser Ala  Glu Ser Gly Leu Leu  Thr Pro Val Ser Ala  Ser Ser Ser
    2855                2860                2865

Pro Ser  Lys Ala Phe Ala Ser  Leu Thr Thr Ala Pro  Pro Thr Trp
    2870                2875                2880

Gly Ile  Pro Gln Ser Thr Leu  Thr Phe Glu Phe Ser  Glu Val Pro
    2885                2890                2895

Ser Leu  Asp Thr Lys Ser Ala  Ser Leu Pro Thr Pro  Gly Gln Ser
    2900                2905                2910

Leu Asn  Thr Ile Pro Asp Ser  Asp Ala Ser Thr Ala  Ser Ser Ser
    2915                2920                2925

Leu Ser  Lys Ser Pro Glu Lys  Asn Pro Arg Ala Arg  Met Met Thr
    2930                2935                2940

Ser Thr  Lys Ala Ile Ser Ala  Ser Ser Phe Gln Ser  Thr Gly Phe
    2945                2950                2955

Thr Glu  Thr Pro Glu Gly Ser  Ala Ser Pro Ser Met  Ala Gly His
    2960                2965                2970

Glu Pro  Arg Val Pro Thr Ser  Gly Thr Gly Asp Pro  Arg Tyr Ala
    2975                2980                2985

Ser Glu  Ser Met Ser Tyr Pro  Asp Pro Ser Lys Ala  Ser Ser Ala
    2990                2995                3000

Met Thr  Ser Thr Ser Leu Ala  Ser Lys Leu Thr Thr  Leu Phe Ser
    3005                3010                3015

Thr Gly  Gln Ala Ala Arg Ser  Gly Ser Ser Ser Ser  Pro Ile Ser
    3020                3025                3030

Leu Ser  Thr Glu Lys Glu Thr  Ser Phe Leu Ser Pro  Thr Ala Ser
    3035                3040                3045

Thr Ser  Arg Lys Thr Ser Leu  Phe Leu Gly Pro Ser  Met Ala Arg
    3050                3055                3060

Gln Pro  Asn Ile Leu Val His  Leu Gln Thr Ser Ala  Leu Thr Leu
    3065                3070                3075

Ser Pro  Thr Ser Thr Leu Asn  Met Ser Gln Glu Glu  Pro Pro Glu
```

3080 3085 3090

Leu Thr Ser Ser Gln Thr Ile Ala Glu Glu Glu Gly Thr Thr Ala
3095 3100 3105

Glu Thr Gln Thr Leu Thr Phe Thr Pro Ser Glu Thr Pro Thr Ser
3110 3115 3120

Leu Leu Pro Val Ser Ser Pro Thr Glu Pro Thr Ala Arg Arg Lys
3125 3130 3135

Ser Ser Pro Glu Thr Trp Ala Ser Ser Ile Ser Val Pro Ala Lys
3140 3145 3150

Thr Ser Leu Val Glu Thr Thr Asp Gly Thr Leu Val Thr Thr Ile
3155 3160 3165

Lys Met Ser Ser Gln Ala Ala Gln Gly Asn Ser Thr Trp Pro Ala
3170 3175 3180

Pro Ala Glu Glu Thr Gly Ser Ser Pro Ala Gly Thr Ser Pro Gly
3185 3190 3195

Ser Pro Glu Met Ser Thr Thr Leu Lys Ile Met Ser Ser Lys Glu
3200 3205 3210

Pro Ser Ile Ser Pro Glu Ile Arg Ser Thr Val Arg Asn Ser Pro
3215 3220 3225

Trp Lys Thr Pro Glu Thr Thr Val Pro Met Glu Thr Thr Val Glu
3230 3235 3240

Pro Val Thr Leu Gln Ser Thr Ala Leu Gly Ser Gly Ser Thr Ser
3245 3250 3255

Ile Ser His Leu Pro Thr Gly Thr Thr Ser Pro Thr Lys Ser Pro
3260 3265 3270

Thr Glu Asn Met Leu Ala Thr Glu Arg Val Ser Leu Ser Pro Ser
3275 3280 3285

Pro Pro Glu Ala Trp Thr Asn Leu Tyr Ser Gly Thr Pro Gly Gly
3290 3295 3300

Thr Arg Gln Ser Leu Ala Thr Met Ser Ser Val Ser Leu Glu Ser
3305 3310 3315

Pro Thr Ala Arg Ser Ile Thr Gly Thr Gly Gln Gln Ser Ser Pro
3320 3325 3330

Glu Leu Val Ser Lys Thr Thr Gly Met Glu Phe Ser Met Trp His
3335 3340 3345

Gly Ser Thr Gly Gly Thr Thr Gly Asp Thr His Val Ser Leu Ser
3350 3355 3360

Thr Ser Ser Asn Ile Leu Glu Asp Pro Val Thr Ser Pro Asn Ser
3365 3370 3375

Val Ser Ser Leu Thr Asp Lys Ser Lys His Lys Thr Glu Thr Trp
3380 3385 3390

Val Ser Thr Thr Ala Ile Pro Ser Thr Val Leu Asn Asn Lys Ile
3395 3400 3405

Met Ala Ala Glu Gln Gln Thr Ser Arg Ser Val Asp Glu Ala Tyr
3410 3415 3420

Ser Ser Thr Ser Ser Trp Ser Asp Gln Thr Ser Gly Ser Asp Ile
3425 3430 3435

Thr Leu Gly Ala Ser Pro Asp Val Thr Asn Thr Leu Tyr Ile Thr
3440 3445 3450

Ser Thr Ala Gln Thr Thr Ser Leu Val Ser Leu Pro Ser Gly Asp
3455 3460 3465

Gln Gly Ile Thr Ser Leu Thr Asn Pro Ser Gly Gly Lys Thr Ser
3470 3475 3480

Ser Ala Ser Ser Val Thr Ser Pro Ser Ile Gly Leu Glu Thr Leu
3485 3490 3495

Arg Ala Asn Val Ser Ala Val Lys Ser Asp Ile Ala Pro Thr Ala
3500 3505 3510

Gly His Leu Ser Gln Thr Ser Ser Pro Ala Glu Val Ser Ile Leu
3515 3520 3525

Asp Val Thr Thr Ala Pro Thr Pro Gly Ile Ser Thr Thr Ile Thr
3530 3535 3540

Thr Met Gly Thr Asn Ser Ile Ser Thr Thr Thr Pro Asn Pro Glu
3545 3550 3555

Val Gly Met Ser Thr Met Asp Ser Thr Pro Ala Thr Glu Arg Arg
3560 3565 3570

Thr Thr Ser Thr Glu His Pro Ser Thr Trp Ser Ser Thr Ala Ala
3575 3580 3585

Ser Asp Ser Trp Thr Val Thr Asp Met Thr Ser Asn Leu Lys Val
3590 3595 3600

Ala Arg Ser Pro Gly Thr Ile Ser Thr Met His Thr Thr Ser Phe
3605 3610 3615

Leu Ala Ser Ser Thr Glu Leu Asp Ser Met Ser Thr Pro His Gly
3620 3625 3630

Arg Ile Thr Val Ile Gly Thr Ser Leu Val Thr Pro Ser Ser Asp
3635 3640 3645

Ala Ser Ala Val Lys Thr Glu Thr Ser Thr Ser Glu Arg Thr Leu
3650 3655 3660

Ser Pro Ser Asp Thr Thr Ala Ser Thr Pro Ile Ser Thr Phe Ser
3665 3670 3675

Arg Val Gln Arg Met Ser Ile Ser Val Pro Asp Ile Leu Ser Thr
3680 3685 3690

Ser Trp Thr Pro Ser Ser Thr Glu Ala Glu Asp Val Pro Val Ser
3695 3700 3705

Met Val Ser Thr Asp His Ala Ser Thr Lys Thr Asp Pro Asn Thr
3710 3715 3720

Pro Leu Ser Thr Phe Leu Phe Asp Ser Leu Ser Thr Leu Asp Trp
3725 3730 3735

Asp Thr Gly Arg Ser Leu Ser Ser Ala Thr Ala Thr Thr Ser Ala
3740 3745 3750

Pro Gln Gly Ala Thr Thr Pro Gln Glu Leu Thr Leu Glu Thr Met
3755 3760 3765

Ile Ser Pro Ala Thr Ser Gln Leu Pro Phe Ser Ile Gly His Ile
3770 3775 3780

Thr Ser Ala Val Thr Pro Ala Ala Met Ala Arg Ser Ser Gly Val
3785 3790 3795

Thr Phe Ser Arg Pro Asp Pro Thr Ser Lys Lys Ala Glu Gln Thr
3800 3805 3810

Ser Thr Gln Leu Pro Thr Thr Thr Ser Ala His Pro Gly Gln Val
3815 3820 3825

Pro Arg Ser Ala Ala Thr Thr Leu Asp Val Ile Pro His Thr Ala
3830 3835 3840

Lys Thr Pro Asp Ala Thr Phe Gln Arg Gln Gly Gln Thr Ala Leu
3845 3850 3855

Thr Thr Glu Ala Arg Ala Thr Ser Asp Ser Trp Asn Glu Lys Glu
3860 3865 3870

```
Lys Ser Thr Pro Ser Ala Pro Trp Ile Thr Glu Met Met Asn Ser
    3875                3880                3885

Val Ser Glu Asp Thr Ile Lys Glu Val Thr Ser Ser Ser Ser Val
    3890                3895                3900

Leu Arg Thr Leu Asn Thr Leu Asp Ile Asn Leu Glu Ser Gly Thr
    3905                3910                3915

Thr Ser Ser Pro Ser Trp Lys Ser Ser Pro Tyr Glu Arg Ile Ala
    3920                3925                3930

Pro Ser Glu Ser Thr Thr Asp Lys Glu Ala Ile His Pro Ser Thr
    3935                3940                3945

Asn Thr Val Glu Thr Thr Gly Trp Val Thr Ser Ser Glu His Ala
    3950                3955                3960

Ser His Ser Thr Ile Pro Ala His Ser Ala Ser Ser Lys Leu Thr
    3965                3970                3975

Ser Pro Val Val Thr Thr Ser Thr Arg Glu Gln Ala Ile Val Ser
    3980                3985                3990

Met Ser Thr Thr Thr Trp Pro Glu Ser Thr Arg Ala Arg Thr Glu
    3995                4000                4005

Pro Asn Ser Phe Leu Thr Ile Glu Leu Arg Asp Val Ser Pro Tyr
    4010                4015                4020

Met Asp Thr Ser Ser Thr Thr Gln Thr Ser Ile Ile Ser Ser Pro
    4025                4030                4035

Gly Ser Thr Ala Ile Thr Lys Gly Pro Arg Thr Glu Ile Thr Ser
    4040                4045                4050

Ser Lys Arg Ile Ser Ser Ser Phe Leu Ala Gln Ser Met Arg Ser
    4055                4060                4065

Ser Asp Ser Pro Ser Glu Ala Ile Thr Arg Leu Ser Asn Phe Pro
    4070                4075                4080

Ala Met Thr Glu Ser Gly Gly Met Ile Leu Ala Met Gln Thr Ser
    4085                4090                4095

Pro Pro Gly Ala Thr Ser Leu Ser Ala Pro Thr Leu Asp Thr Ser
    4100                4105                4110

Ala Thr Ala Ser Trp Thr Gly Thr Pro Leu Ala Thr Thr Gln Arg
    4115                4120                4125

Phe Thr Tyr Ser Glu Lys Thr Thr Leu Phe Ser Lys Gly Pro Glu
    4130                4135                4140

Asp Thr Ser Gln Pro Ser Pro Pro Ser Val Glu Glu Thr Ser Ser
    4145                4150                4155

Ser Ser Ser Leu Val Pro Ile His Ala Thr Thr Ser Pro Ser Asn
    4160                4165                4170

Ile Leu Leu Thr Ser Gln Gly His Ser Pro Ser Ser Thr Pro Pro
    4175                4180                4185

Val Thr Ser Val Phe Leu Ser Glu Thr Ser Gly Leu Gly Lys Thr
    4190                4195                4200

Thr Asp Met Ser Arg Ile Ser Leu Glu Pro Gly Thr Ser Leu Pro
    4205                4210                4215

Pro Asn Leu Ser Ser Thr Ala Gly Glu Ala Leu Ser Thr Tyr Glu
    4220                4225                4230

Ala Ser Arg Asp Thr Lys Ala Ile His His Ser Ala Asp Thr Ala
    4235                4240                4245

Val Thr Asn Met Glu Ala Thr Ser Ser Glu Tyr Ser Pro Ile Pro
    4250                4255                4260

Gly His Thr Lys Pro Ser Lys Ala Thr Ser Pro Leu Val Thr Ser
```

```
    4265                4270                4275

His Ile Met Gly Asp Ile Thr Ser Ser Thr Ser Val Phe Gly Ser
    4280                4285                4290

Ser Glu Thr Thr Glu Ile Glu Thr Val Ser Ser Val Asn Gln Gly
    4295                4300                4305

Leu Gln Glu Arg Ser Thr Ser Gln Val Ala Ser Ser Ala Thr Glu
    4310                4315                4320

Thr Ser Thr Val Ile Thr His Val Ser Ser Gly Asp Ala Thr Thr
    4325                4330                4335

His Val Thr Lys Thr Gln Ala Thr Phe Ser Ser Gly Thr Ser Ile
    4340                4345                4350

Ser Ser Pro His Gln Phe Ile Thr Ser Thr Asn Thr Phe Thr Asp
    4355                4360                4365

Val Ser Thr Asn Pro Ser Thr Ser Leu Ile Met Thr Glu Ser Ser
    4370                4375                4380

Gly Val Thr Ile Thr Thr Gln Thr Gly Pro Thr Gly Ala Ala Thr
    4385                4390                4395

Gln Gly Pro Tyr Leu Leu Asp Thr Ser Thr Met Pro Tyr Leu Thr
    4400                4405                4410

Glu Thr Pro Leu Ala Val Thr Pro Asp Phe Met Gln Ser Glu Lys
    4415                4420                4425

Thr Thr Leu Ile Ser Lys Gly Pro Lys Asp Val Ser Trp Thr Ser
    4430                4435                4440

Pro Pro Ser Val Ala Glu Thr Ser Tyr Pro Ser Ser Leu Thr Pro
    4445                4450                4455

Phe Leu Val Thr Thr Ile Pro Pro Ala Thr Ser Thr Leu Gln Gly
    4460                4465                4470

Gln His Thr Ser Ser Pro Val Ser Ala Thr Ser Val Leu Thr Ser
    4475                4480                4485

Gly Leu Val Lys Thr Thr Asp Met Leu Asn Thr Ser Met Glu Pro
    4490                4495                4500

Val Thr Asn Ser Pro Gln Asn Leu Asn Asn Pro Ser Asn Glu Ile
    4505                4510                4515

Leu Ala Thr Leu Ala Ala Thr Thr Asp Ile Glu Thr Ile His Pro
    4520                4525                4530

Ser Ile Asn Lys Ala Val Thr Asn Met Gly Thr Ala Ser Ser Ala
    4535                4540                4545

His Val Leu His Ser Thr Leu Pro Val Ser Ser Glu Pro Ser Thr
    4550                4555                4560

Ala Thr Ser Pro Met Val Pro Ala Ser Ser Met Gly Asp Ala Leu
    4565                4570                4575

Ala Ser Ile Ser Ile Pro Gly Ser Glu Thr Thr Asp Ile Glu Gly
    4580                4585                4590

Glu Pro Thr Ser Ser Leu Thr Ala Gly Arg Lys Glu Asn Ser Thr
    4595                4600                4605

Leu Gln Glu Met Asn Ser Thr Thr Glu Ser Asn Ile Ile Leu Ser
    4610                4615                4620

Asn Val Ser Val Gly Ala Ile Thr Glu Ala Thr Lys Met Glu Val
    4625                4630                4635

Pro Ser Phe Asp Ala Thr Phe Ile Pro Thr Pro Ala Gln Ser Thr
    4640                4645                4650

Lys Phe Pro Asp Ile Phe Ser Val Ala Ser Ser Arg Leu Ser Asn
    4655                4660                4665
```

-continued

```
Ser Pro  Pro Met Thr Ile Ser  Thr His Met Thr Thr  Thr Gln Thr
    4670                 4675                 4680

Gly Ser  Ser Gly Ala Thr Ser  Lys Ile Pro Leu Ala  Leu Asp Thr
    4685                 4690                 4695

Ser Thr  Leu Glu Thr Ser Ala  Gly Thr Pro Ser Val  Val Thr Glu
    4700                 4705                 4710

Gly Phe  Ala His Ser Lys Ile  Thr Thr Ala Met Asn  Asn Asp Val
    4715                 4720                 4725

Lys Asp  Val Ser Gln Thr Asn  Pro Pro Phe Gln Asp  Glu Ala Ser
    4730                 4735                 4740

Ser Pro  Ser Ser Gln Ala Pro  Val Leu Val Thr Thr  Leu Pro Ser
    4745                 4750                 4755

Ser Val  Ala Phe Thr Pro Gln  Trp His Ser Thr Ser  Ser Pro Val
    4760                 4765                 4770

Ser Met  Ser Ser Val Leu Thr  Ser Ser Leu Val Lys  Thr Ala Gly
    4775                 4780                 4785

Lys Val  Asp Thr Ser Leu Glu  Thr Val Thr Ser Ser  Pro Gln Ser
    4790                 4795                 4800

Met Ser  Asn Thr Leu Asp Asp  Ile Ser Val Thr Ser  Ala Ala Thr
    4805                 4810                 4815

Thr Asp  Ile Glu Thr Thr His  Pro Ser Ile Asn Thr  Val Val Thr
    4820                 4825                 4830

Asn Val  Gly Thr Thr Gly Ser  Ala Phe Glu Ser His  Ser Thr Val
    4835                 4840                 4845

Ser Ala  Tyr Pro Glu Pro Ser  Lys Val Thr Ser Pro  Asn Val Thr
    4850                 4855                 4860

Thr Ser  Thr Met Glu Asp Thr  Thr Ile Ser Arg Ser  Ile Pro Lys
    4865                 4870                 4875

Ser Ser  Lys Thr Thr Arg Thr  Glu Thr Glu Thr Thr  Ser Ser Leu
    4880                 4885                 4890

Thr Pro  Lys Leu Arg Glu Thr  Ser Ile Ser Gln Glu  Ile Thr Ser
    4895                 4900                 4905

Ser Thr  Glu Thr Ser Thr Val  Pro Tyr Lys Glu Leu  Thr Gly Ala
    4910                 4915                 4920

Thr Thr  Glu Val Ser Arg Thr  Asp Val Thr Ser Ser  Ser Ser Thr
    4925                 4930                 4935

Ser Phe  Pro Gly Pro Asp Gln  Ser Thr Val Ser Leu  Asp Ile Ser
    4940                 4945                 4950

Thr Glu  Thr Asn Thr Arg Leu  Ser Thr Ser Pro Ile  Met Thr Glu
    4955                 4960                 4965

Ser Ala  Glu Ile Thr Ile Thr  Thr Gln Thr Gly Pro  His Gly Ala
    4970                 4975                 4980

Thr Ser  Gln Asp Thr Phe Thr  Met Asp Pro Ser Asn  Thr Thr Pro
    4985                 4990                 4995

Gln Ala  Gly Ile His Ser Ala  Met Thr His Gly Phe  Ser Gln Leu
    5000                 5005                 5010

Asp Val  Thr Thr Leu Met Ser  Arg Ile Pro Gln Asp  Val Ser Trp
    5015                 5020                 5025

Thr Ser  Pro Pro Ser Val Asp  Lys Thr Ser Ser Pro  Ser Ser Phe
    5030                 5035                 5040

Leu Ser  Ser Pro Ala Met Thr  Thr Pro Ser Leu Ile  Ser Ser Thr
    5045                 5050                 5055
```

```
Leu Pro  Glu Asp Lys Leu Ser  Ser Pro Met Thr Ser  Leu Leu Thr
    5060                5065                5070

Ser Gly  Leu Val Lys Ile Thr  Asp Ile Leu Arg Thr  Arg Leu Glu
    5075                5080                5085

Pro Val  Thr Ser Ser Leu Pro  Asn Phe Ser Ser Thr  Ser Asp Lys
    5090                5095                5100

Ile Leu  Ala Thr Ser Lys Asp  Ser Lys Asp Thr Lys  Glu Ile Phe
    5105                5110                5115

Pro Ser  Ile Asn Thr Glu Glu  Thr Asn Val Lys Ala  Asn Asn Ser
    5120                5125                5130

Gly His  Glu Ser His Ser Pro  Ala Leu Ala Asp Ser  Glu Thr Pro
    5135                5140                5145

Lys Ala  Thr Thr Gln Met Val  Ile Thr Thr Thr Val  Gly Asp Pro
    5150                5155                5160

Ala Pro  Ser Thr Ser Met Pro  Val His Gly Ser Ser  Glu Thr Thr
    5165                5170                5175

Asn Ile  Lys Arg Glu Pro Thr  Tyr Phe Leu Thr Pro  Arg Leu Arg
    5180                5185                5190

Glu Thr  Ser Thr Ser Gln Glu  Ser Ser Phe Pro Thr  Asp Thr Ser
    5195                5200                5205

Phe Leu  Leu Ser Lys Val Pro  Thr Gly Thr Ile Thr  Glu Val Ser
    5210                5215                5220

Ser Thr  Gly Val Asn Ser Ser  Ser Lys Ile Ser Thr  Pro Asp His
    5225                5230                5235

Asp Lys  Ser Thr Val Pro Pro  Asp Thr Phe Thr Gly  Glu Ile Pro
    5240                5245                5250

Arg Val  Phe Thr Ser Ser Ile  Lys Thr Lys Ser Ala  Glu Met Thr
    5255                5260                5265

Ile Thr  Thr Gln Ala Ser Pro  Pro Glu Ser Ala Ser  His Ser Thr
    5270                5275                5280

Leu Pro  Leu Asp Thr Ser Thr  Thr Leu Ser Gln Gly  Gly Thr His
    5285                5290                5295

Ser Thr  Val Thr Gln Gly Phe  Pro Tyr Ser Glu Val  Thr Thr Leu
    5300                5305                5310

Met Gly  Met Gly Pro Gly Asn  Val Ser Trp Met Thr  Thr Pro Pro
    5315                5320                5325

Val Glu  Glu Thr Ser Ser Val  Ser Ser Leu Met Ser  Ser Pro Ala
    5330                5335                5340

Met Thr  Ser Pro Ser Pro Val  Ser Ser Thr Ser Pro  Gln Ser Ile
    5345                5350                5355

Pro Ser  Ser Pro Leu Pro Val  Thr Ala Leu Pro Thr  Ser Val Leu
    5360                5365                5370

Val Thr  Thr Thr Asp Val Leu  Gly Thr Thr Ser Pro  Glu Ser Val
    5375                5380                5385

Thr Ser  Ser Pro Pro Asn Leu  Ser Ser Ile Thr His  Glu Arg Pro
    5390                5395                5400

Ala Thr  Tyr Lys Asp Thr Ala  His Thr Glu Ala Ala  Met His His
    5405                5410                5415

Ser Thr  Asn Thr Ala Val Thr  Asn Val Gly Thr Ser  Gly Ser Gly
    5420                5425                5430

His Lys  Ser Gln Ser Ser Val  Leu Ala Asp Ser Glu  Thr Ser Lys
    5435                5440                5445

Ala Thr  Pro Leu Met Ser Thr  Thr Ser Thr Leu Gly  Asp Thr Ser
```

-continued

```
    5450                5455                5460

Val Ser Thr Ser Thr Pro Asn Ile Ser Gln Thr Asn Gln Ile Gln
    5465                5470                5475

Thr Glu Pro Thr Ala Ser Leu Ser Pro Arg Leu Arg Glu Ser Ser
    5480                5485                5490

Thr Ser Glu Lys Thr Ser Ser Thr Thr Glu Thr Asn Thr Ala Phe
    5495                5500                5505

Ser Tyr Val Pro Thr Gly Ala Ile Thr Gln Ala Ser Arg Thr Glu
    5510                5515                5520

Ile Ser Ser Ser Arg Thr Ser Ile Ser Asp Leu Asp Arg Pro Thr
    5525                5530                5535

Ile Ala Pro Asp Ile Ser Thr Gly Met Ile Thr Arg Leu Phe Thr
    5540                5545                5550

Ser Pro Ile Met Thr Lys Ser Ala Glu Met Thr Val Thr Thr Gln
    5555                5560                5565

Thr Thr Thr Pro Gly Ala Thr Ser Gln Gly Ile Leu Pro Trp Asp
    5570                5575                5580

Thr Ser Thr Thr Leu Phe Gln Gly Gly Thr His Ser Thr Val Ser
    5585                5590                5595

Gln Gly Phe Pro His Ser Glu Ile Thr Thr Leu Arg Ser Arg Thr
    5600                5605                5610

Pro Gly Asp Val Ser Trp Met Thr Thr Pro Pro Val Glu Glu Thr
    5615                5620                5625

Ser Ser Gly Phe Ser Leu Met Ser Pro Ser Met Thr Ser Pro Ser
    5630                5635                5640

Pro Val Ser Ser Thr Ser Pro Glu Ser Ile Pro Ser Ser Pro Leu
    5645                5650                5655

Pro Val Thr Ala Leu Leu Thr Ser Val Leu Val Thr Thr Thr Asn
    5660                5665                5670

Val Leu Gly Thr Thr Ser Pro Glu Pro Val Thr Ser Ser Pro Pro
    5675                5680                5685

Asn Leu Ser Ser Pro Thr Gln Glu Arg Leu Thr Thr Tyr Lys Asp
    5690                5695                5700

Thr Ala His Thr Glu Ala Met His Ala Ser Met His Thr Asn Thr
    5705                5710                5715

Ala Val Ala Asn Val Gly Thr Ser Ile Ser Gly His Glu Ser Gln
    5720                5725                5730

Ser Ser Val Pro Ala Asp Ser His Thr Ser Lys Ala Thr Ser Pro
    5735                5740                5745

Met Gly Ile Thr Phe Ala Met Gly Asp Thr Ser Val Ser Thr Ser
    5750                5755                5760

Thr Pro Ala Phe Phe Glu Thr Arg Ile Gln Thr Glu Ser Thr Ser
    5765                5770                5775

Ser Leu Ile Pro Gly Leu Arg Asp Thr Arg Thr Ser Glu Glu Ile
    5780                5785                5790

Asn Thr Val Thr Glu Thr Ser Thr Val Leu Ser Glu Val Pro Thr
    5795                5800                5805

Thr Thr Thr Thr Glu Val Ser Arg Thr Glu Val Ile Thr Ser Ser
    5810                5815                5820

Arg Thr Thr Ile Ser Gly Pro Asp His Ser Lys Met Ser Pro Tyr
    5825                5830                5835

Ile Ser Thr Glu Thr Ile Thr Arg Leu Ser Thr Phe Pro Phe Val
    5840                5845                5850
```

```
Thr Gly Ser Thr Glu Met Ala Ile Thr Asn Gln Thr Gly Pro Ile
    5855                5860                5865

Gly Thr Ile Ser Gln Ala Thr Leu Thr Leu Asp Thr Ser Ser Thr
    5870                5875                5880

Ala Ser Trp Glu Gly Thr His Ser Pro Val Thr Gln Arg Phe Pro
    5885                5890                5895

His Ser Glu Glu Thr Thr Thr Met Ser Arg Ser Thr Lys Gly Val
    5900                5905                5910

Ser Trp Gln Ser Pro Pro Ser Val Glu Glu Thr Ser Ser Pro Ser
    5915                5920                5925

Ser Pro Val Pro Leu Pro Ala Ile Thr Ser His Ser Ser Leu Tyr
    5930                5935                5940

Ser Ala Val Ser Gly Ser Ser Pro Thr Ser Ala Leu Pro Val Thr
    5945                5950                5955

Ser Leu Leu Thr Ser Gly Arg Arg Lys Thr Ile Asp Met Leu Asp
    5960                5965                5970

Thr His Ser Glu Leu Val Thr Ser Ser Leu Pro Ser Ala Ser Ser
    5975                5980                5985

Phe Ser Gly Glu Ile Leu Thr Ser Glu Ala Ser Thr Asn Thr Glu
    5990                5995                6000

Thr Ile His Phe Ser Glu Asn Thr Ala Glu Thr Asn Met Gly Thr
    6005                6010                6015

Thr Asn Ser Met His Lys Leu His Ser Ser Val Ser Ile His Ser
    6020                6025                6030

Gln Pro Ser Gly His Thr Pro Pro Lys Val Thr Gly Ser Met Met
    6035                6040                6045

Glu Asp Ala Ile Val Ser Thr Ser Thr Pro Gly Ser Pro Glu Thr
    6050                6055                6060

Lys Asn Val Asp Arg Asp Ser Thr Ser Pro Leu Thr Pro Glu Leu
    6065                6070                6075

Lys Glu Asp Ser Thr Ala Leu Val Met Asn Ser Thr Thr Glu Ser
    6080                6085                6090

Asn Thr Val Phe Ser Ser Val Ser Leu Asp Ala Ala Thr Glu Val
    6095                6100                6105

Ser Arg Ala Glu Val Thr Tyr Tyr Asp Pro Thr Phe Met Pro Ala
    6110                6115                6120

Ser Ala Gln Ser Thr Lys Ser Pro Asp Ile Ser Pro Glu Ala Ser
    6125                6130                6135

Ser Ser His Ser Asn Ser Pro Pro Leu Thr Ile Ser Thr His Lys
    6140                6145                6150

Thr Ile Ala Thr Gln Thr Gly Pro Ser Gly Val Thr Ser Leu Gly
    6155                6160                6165

Gln Leu Thr Leu Asp Thr Ser Thr Ile Ala Thr Ser Ala Gly Thr
    6170                6175                6180

Pro Ser Ala Arg Thr Gln Asp Phe Val Asp Ser Glu Thr Thr Ser
    6185                6190                6195

Val Met Asn Asn Asp Leu Asn Asp Val Leu Lys Thr Ser Pro Phe
    6200                6205                6210

Ser Ala Glu Glu Ala Asn Ser Leu Ser Ser Gln Ala Pro Leu Leu
    6215                6220                6225

Val Thr Thr Ser Pro Ser Pro Val Thr Ser Thr Leu Gln Glu His
    6230                6235                6240
```

Ser Thr Ser Ser Leu Val Ser Val Thr Ser Val Pro Thr Pro Thr
6245 6250 6255

Leu Ala Lys Ile Thr Asp Met Asp Thr Asn Leu Glu Pro Val Thr
6260 6265 6270

Arg Ser Pro Gln Asn Leu Arg Asn Thr Leu Ala Thr Ser Glu Ala
6275 6280 6285

Thr Thr Asp Thr His Thr Met His Pro Ser Ile Asn Thr Ala Val
6290 6295 6300

Ala Asn Val Gly Thr Thr Ser Ser Pro Asn Glu Phe Tyr Phe Thr
6305 6310 6315

Val Ser Pro Asp Ser Asp Pro Tyr Lys Ala Thr Ser Ala Val Val
6320 6325 6330

Ile Thr Ser Thr Ser Gly Asp Ser Ile Val Ser Thr Ser Met Pro
6335 6340 6345

Arg Ser Ser Ala Met Lys Lys Ile Glu Ser Glu Thr Thr Phe Ser
6350 6355 6360

Leu Ile Phe Arg Leu Arg Glu Thr Ser Thr Ser Gln Lys Ile Gly
6365 6370 6375

Ser Ser Ser Asp Thr Ser Thr Val Phe Asp Lys Ala Phe Thr Ala
6380 6385 6390

Ala Thr Thr Glu Val Ser Arg Thr Glu Leu Thr Ser Ser Ser Arg
6395 6400 6405

Thr Ser Ile Gln Gly Thr Glu Lys Pro Thr Met Ser Pro Asp Thr
6410 6415 6420

Ser Thr Arg Ser Val Thr Met Leu Ser Thr Phe Ala Gly Leu Thr
6425 6430 6435

Lys Ser Glu Glu Arg Thr Ile Ala Thr Gln Thr Gly Pro His Arg
6440 6445 6450

Ala Thr Ser Gln Gly Thr Leu Thr Trp Asp Thr Ser Ile Thr Thr
6455 6460 6465

Ser Gln Ala Gly Thr His Ser Ala Met Thr His Gly Phe Ser Gln
6470 6475 6480

Leu Asp Leu Ser Thr Leu Thr Ser Arg Val Pro Glu Tyr Ile Ser
6485 6490 6495

Gly Thr Ser Pro Pro Ser Val Glu Lys Thr Ser Ser Ser Ser Ser
6500 6505 6510

Leu Leu Ser Leu Pro Ala Ile Thr Ser Pro Ser Pro Val Pro Thr
6515 6520 6525

Thr Leu Pro Glu Ser Arg Pro Ser Ser Pro Val His Leu Thr Ser
6530 6535 6540

Leu Pro Thr Ser Gly Leu Val Lys Thr Thr Asp Met Leu Ala Ser
6545 6550 6555

Val Ala Ser Leu Pro Pro Asn Leu Gly Ser Thr Ser His Lys Ile
6560 6565 6570

Pro Thr Thr Ser Glu Asp Ile Lys Asp Thr Glu Lys Met Tyr Pro
6575 6580 6585

Ser Thr Asn Ile Ala Val Thr Asn Val Gly Thr Thr Thr Ser Glu
6590 6595 6600

Lys Glu Ser Tyr Ser Ser Val Pro Ala Tyr Ser Glu Pro Pro Lys
6605 6610 6615

Val Thr Ser Pro Met Val Thr Ser Phe Asn Ile Arg Asp Thr Ile
6620 6625 6630

Val Ser Thr Ser Met Pro Gly Ser Ser Glu Ile Thr Arg Ile Glu

-continued

```
    6635                6640                6645

Met Glu  Ser Thr Phe Ser Leu  Ala His Gly Leu Lys  Gly Thr Ser
    6650                6655                6660

Thr Ser  Gln Asp Pro Ile Val  Ser Thr Glu Lys Ser  Ala Val Leu
    6665                6670                6675

His Lys  Leu Thr Thr Gly Ala  Thr Glu Thr Ser Arg  Thr Glu Val
    6680                6685                6690

Ala Ser  Ser Arg Arg Thr Ser  Ile Pro Gly Pro Asp  His Ser Thr
    6695                6700                6705

Glu Ser  Pro Asp Ile Ser Thr  Glu Val Ile Pro Ser  Leu Pro Ile
    6710                6715                6720

Ser Leu  Gly Ile Thr Glu Ser  Ser Asn Met Thr Ile  Ile Thr Arg
    6725                6730                6735

Thr Gly  Pro Pro Leu Gly Ser  Thr Ser Gln Gly Thr  Phe Thr Leu
    6740                6745                6750

Asp Thr  Pro Thr Thr Ser Ser  Arg Ala Gly Thr His  Ser Met Ala
    6755                6760                6765

Thr Gln  Glu Phe Pro His Ser  Glu Met Thr Thr Val  Met Asn Lys
    6770                6775                6780

Asp Pro  Glu Ile Leu Ser Trp  Thr Ile Pro Pro Ser  Ile Glu Lys
    6785                6790                6795

Thr Ser  Phe Ser Ser Ser Leu  Met Pro Ser Pro Ala  Met Thr Ser
    6800                6805                6810

Pro Pro  Val Ser Ser Thr Leu  Pro Lys Thr Ile His  Thr Thr Pro
    6815                6820                6825

Ser Pro  Met Thr Ser Leu Leu  Thr Pro Ser Leu Val  Met Thr Thr
    6830                6835                6840

Asp Thr  Leu Gly Thr Ser Pro  Glu Pro Thr Thr Ser  Ser Pro Pro
    6845                6850                6855

Asn Leu  Ser Ser Thr Ser His  Glu Ile Leu Thr Thr  Asp Glu Asp
    6860                6865                6870

Thr Thr  Ala Ile Glu Ala Met  His Pro Ser Thr Ser  Thr Ala Ala
    6875                6880                6885

Thr Asn  Val Glu Thr Thr Ser  Ser Gly His Gly Ser  Gln Ser Ser
    6890                6895                6900

Val Leu  Ala Asp Ser Glu Lys  Thr Lys Ala Thr Ala  Pro Met Asp
    6905                6910                6915

Thr Thr  Ser Thr Met Gly His  Thr Thr Val Ser Thr  Ser Met Ser
    6920                6925                6930

Val Ser  Ser Glu Thr Thr Lys  Ile Lys Arg Glu Ser  Thr Tyr Ser
    6935                6940                6945

Leu Thr  Pro Gly Leu Arg Glu  Thr Ser Ile Ser Gln  Asn Ala Ser
    6950                6955                6960

Phe Ser  Thr Asp Thr Ser Ile  Val Leu Ser Glu Val  Pro Thr Gly
    6965                6970                6975

Thr Thr  Ala Glu Val Ser Arg  Thr Glu Val Thr Ser  Ser Gly Arg
    6980                6985                6990

Thr Ser  Ile Pro Gly Pro Ser  Gln Ser Thr Val Leu  Pro Glu Ile
    6995                7000                7005

Ser Thr  Arg Thr Met Thr Arg  Leu Phe Ala Ser Pro  Thr Met Thr
    7010                7015                7020

Glu Ser  Ala Glu Met Thr Ile  Pro Thr Gln Thr Gly  Pro Ser Gly
    7025                7030                7035
```

-continued

Ser Thr Ser Gln Asp Thr Leu Thr Leu Asp Thr Ser Thr Thr Lys
7040 7045 7050

Ser Gln Ala Lys Thr His Ser Thr Leu Thr Gln Arg Phe Pro His
7055 7060 7065

Ser Glu Met Thr Thr Leu Met Ser Arg Gly Pro Gly Asp Met Ser
7070 7075 7080

Trp Gln Ser Ser Pro Ser Leu Glu Asn Pro Ser Ser Leu Pro Ser
7085 7090 7095

Leu Leu Ser Leu Pro Ala Thr Thr Ser Pro Pro Pro Ile Ser Ser
7100 7105 7110

Thr Leu Pro Val Thr Ile Ser Ser Ser Pro Leu Pro Val Thr Ser
7115 7120 7125

Leu Leu Thr Ser Ser Pro Val Thr Thr Thr Asp Met Leu His Thr
7130 7135 7140

Ser Pro Glu Leu Val Thr Ser Ser Pro Pro Lys Leu Ser His Thr
7145 7150 7155

Ser Asp Glu Arg Leu Thr Thr Gly Lys Asp Thr Thr Asn Thr Glu
7160 7165 7170

Ala Val His Pro Ser Thr Asn Thr Ala Ala Ser Asn Val Glu Ile
7175 7180 7185

Pro Ser Ser Gly His Glu Ser Pro Ser Ser Ala Leu Ala Asp Ser
7190 7195 7200

Glu Thr Ser Lys Ala Thr Ser Pro Met Phe Ile Thr Ser Thr Gln
7205 7210 7215

Glu Asp Thr Thr Val Ala Ile Ser Thr Pro His Phe Leu Glu Thr
7220 7225 7230

Ser Arg Ile Gln Lys Glu Ser Ile Ser Ser Leu Ser Pro Lys Leu
7235 7240 7245

Arg Glu Thr Gly Ser Ser Val Glu Thr Ser Ser Ala Ile Glu Thr
7250 7255 7260

Ser Ala Val Leu Ser Glu Val Ser Ile Gly Ala Thr Thr Glu Ile
7265 7270 7275

Ser Arg Thr Glu Val Thr Ser Ser Ser Arg Thr Ser Ile Ser Gly
7280 7285 7290

Ser Ala Glu Ser Thr Met Leu Pro Glu Ile Ser Thr Thr Arg Lys
7295 7300 7305

Ile Ile Lys Phe Pro Thr Ser Pro Ile Leu Ala Glu Ser Ser Glu
7310 7315 7320

Met Thr Ile Lys Thr Gln Thr Ser Pro Pro Gly Ser Thr Ser Glu
7325 7330 7335

Ser Thr Phe Thr Leu Asp Thr Ser Thr Thr Pro Ser Leu Val Ile
7340 7345 7350

Thr His Ser Thr Met Thr Gln Arg Leu Pro His Ser Glu Ile Thr
7355 7360 7365

Thr Leu Val Ser Arg Gly Ala Gly Asp Val Pro Arg Pro Ser Ser
7370 7375 7380

Leu Pro Val Glu Glu Thr Ser Pro Pro Ser Ser Gln Leu Ser Leu
7385 7390 7395

Ser Ala Met Ile Ser Pro Ser Pro Val Ser Ser Thr Leu Pro Ala
7400 7405 7410

Ser Ser His Ser Ser Ser Ala Ser Val Thr Ser Leu Leu Thr Pro
7415 7420 7425

-continued

```
Gly Gln  Val Lys Thr Thr Glu  Val Leu Asp Ala Ser  Ala Glu Pro
    7430                 7435                 7440

Glu Thr  Ser Ser Pro Pro Ser  Leu Ser Ser Thr Ser  Val Glu Ile
    7445                 7450                 7455

Leu Ala  Thr Ser Glu Val Thr  Thr Asp Thr Glu Lys  Ile His Pro
    7460                 7465                 7470

Phe Ser  Asn Thr Ala Val Thr  Lys Val Gly Thr Ser  Ser Ser Gly
    7475                 7480                 7485

His Glu  Ser Pro Ser Ser Val  Leu Pro Asp Ser Glu  Thr Thr Lys
    7490                 7495                 7500

Ala Thr  Ser Ala Met Gly Thr  Ile Ser Ile Met Gly  Asp Thr Ser
    7505                 7510                 7515

Val Ser  Thr Leu Thr Pro Ala  Leu Ser Asn Thr Arg  Lys Ile Gln
    7520                 7525                 7530

Ser Glu  Pro Ala Ser Ser Leu  Thr Thr Arg Leu Arg  Glu Thr Ser
    7535                 7540                 7545

Thr Ser  Glu Glu Thr Ser Leu  Ala Thr Glu Ala Asn  Thr Val Leu
    7550                 7555                 7560

Ser Lys  Val Ser Thr Gly Ala  Thr Thr Glu Val Ser  Arg Thr Glu
    7565                 7570                 7575

Ala Ile  Ser Phe Ser Arg Thr  Ser Met Ser Gly Pro  Glu Gln Ser
    7580                 7585                 7590

Thr Met  Ser Gln Asp Ile Ser  Ile Gly Thr Ile Pro  Arg Ile Ser
    7595                 7600                 7605

Ala Ser  Ser Val Leu Thr Glu  Ser Ala Lys Met Thr  Ile Thr Thr
    7610                 7615                 7620

Gln Thr  Gly Pro Ser Glu Ser  Thr Leu Glu Ser Thr  Leu Asn Leu
    7625                 7630                 7635

Asn Thr  Ala Thr Thr Pro Ser  Trp Val Glu Thr His  Ser Ile Val
    7640                 7645                 7650

Ile Gln  Gly Phe Pro His Pro  Glu Met Thr Thr Ser  Met Gly Arg
    7655                 7660                 7665

Gly Pro  Gly Gly Val Ser Trp  Pro Ser Pro Pro Phe  Val Lys Glu
    7670                 7675                 7680

Thr Ser  Pro Pro Ser Ser Pro  Leu Ser Leu Pro Ala  Val Thr Ser
    7685                 7690                 7695

Pro His  Pro Val Ser Thr Thr  Phe Leu Ala His Ile  Pro Pro Ser
    7700                 7705                 7710

Pro Leu  Pro Val Thr Ser Leu  Leu Thr Ser Gly Pro  Ala Thr Thr
    7715                 7720                 7725

Thr Asp  Ile Leu Gly Thr Ser  Thr Glu Pro Gly Thr  Ser Ser Ser
    7730                 7735                 7740

Ser Ser  Leu Ser Thr Thr Ser  His Glu Arg Leu Thr  Thr Tyr Lys
    7745                 7750                 7755

Asp Thr  Ala His Thr Glu Ala  Val His Pro Ser Thr  Asn Thr Gly
    7760                 7765                 7770

Gly Thr  Asn Val Ala Thr Thr  Ser Ser Gly Tyr Lys  Ser Gln Ser
    7775                 7780                 7785

Ser Val  Leu Ala Asp Ser Ser  Pro Met Cys Thr Thr  Ser Thr Met
    7790                 7795                 7800

Gly Asp  Thr Ser Val Leu Thr  Ser Thr Pro Ala Phe  Leu Glu Thr
    7805                 7810                 7815

Arg Arg  Ile Gln Thr Glu Leu  Ala Ser Ser Leu Thr  Pro Gly Leu
```

7820 7825 7830

Arg Glu Ser Ser Gly Ser Glu Gly Thr Ser Ser Gly Thr Lys Met
7835 7840 7845

Ser Thr Val Leu Ser Lys Val Pro Thr Gly Ala Thr Thr Glu Ile
7850 7855 7860

Ser Lys Glu Asp Val Thr Ser Ile Pro Gly Pro Ala Gln Ser Thr
7865 7870 7875

Ile Ser Pro Asp Ile Ser Thr Arg Thr Val Ser Trp Phe Ser Thr
7880 7885 7890

Ser Pro Val Met Thr Glu Ser Ala Glu Ile Thr Met Asn Thr His
7895 7900 7905

Thr Ser Pro Leu Gly Ala Thr Thr Gln Gly Thr Ser Thr Leu Asp
7910 7915 7920

Thr Ser Ser Thr Thr Ser Leu Thr Met Thr His Ser Thr Ile Ser
7925 7930 7935

Gln Gly Phe Ser His Ser Gln Met Ser Thr Leu Met Arg Arg Gly
7940 7945 7950

Pro Glu Asp Val Ser Trp Met Ser Pro Pro Leu Leu Glu Lys Thr
7955 7960 7965

Arg Pro Ser Phe Ser Leu Met Ser Ser Pro Ala Thr Thr Ser Pro
7970 7975 7980

Ser Pro Val Ser Ser Thr Leu Pro Glu Ser Ile Ser Ser Ser Pro
7985 7990 7995

Leu Pro Val Thr Ser Leu Leu Thr Ser Gly Leu Ala Lys Thr Thr
8000 8005 8010

Asp Met Leu His Lys Ser Ser Glu Pro Val Thr Asn Ser Pro Ala
8015 8020 8025

Asn Leu Ser Ser Thr Ser Val Glu Ile Leu Ala Thr Ser Glu Val
8030 8035 8040

Thr Thr Asp Thr Glu Lys Thr His Pro Ser Ser Asn Arg Thr Val
8045 8050 8055

Thr Asp Val Gly Thr Ser Ser Ser Gly His Glu Ser Thr Ser Phe
8060 8065 8070

Val Leu Ala Asp Ser Gln Thr Ser Lys Val Thr Ser Pro Met Val
8075 8080 8085

Ile Thr Ser Thr Met Glu Asp Thr Ser Val Ser Thr Ser Thr Pro
8090 8095 8100

Gly Phe Phe Glu Thr Ser Arg Ile Gln Thr Glu Pro Thr Ser Ser
8105 8110 8115

Leu Thr Leu Gly Leu Arg Lys Thr Ser Ser Ser Glu Gly Thr Ser
8120 8125 8130

Leu Ala Thr Glu Met Ser Thr Val Leu Ser Gly Val Pro Thr Gly
8135 8140 8145

Ala Thr Ala Glu Val Ser Arg Thr Glu Val Thr Ser Ser Ser Arg
8150 8155 8160

Thr Ser Ile Ser Gly Phe Ala Gln Leu Thr Val Ser Pro Glu Thr
8165 8170 8175

Ser Thr Glu Thr Ile Thr Arg Leu Pro Thr Ser Ser Ile Met Thr
8180 8185 8190

Glu Ser Ala Glu Met Met Ile Lys Thr Gln Thr Asp Pro Pro Gly
8195 8200 8205

Ser Thr Pro Glu Ser Thr His Thr Val Asp Ile Ser Thr Thr Pro
8210 8215 8220

```
Asn Trp Val Glu Thr His Ser Thr Val Thr Gln Arg Phe Ser His
    8225                8230                8235

Ser Glu Met Thr Thr Leu Val Ser Arg Ser Pro Gly Asp Met Leu
    8240                8245                8250

Trp Pro Ser Gln Ser Ser Val Glu Glu Thr Ser Ser Ala Ser Ser
    8255                8260                8265

Leu Leu Ser Leu Pro Ala Thr Thr Ser Pro Ser Pro Val Ser Ser
    8270                8275                8280

Thr Leu Val Glu Asp Phe Pro Ser Ala Ser Leu Pro Val Thr Ser
    8285                8290                8295

Leu Leu Asn Pro Gly Leu Val Ile Thr Thr Asp Arg Met Gly Ile
    8300                8305                8310

Ser Arg Glu Pro Gly Thr Ser Ser Thr Ser Asn Leu Ser Ser Thr
    8315                8320                8325

Ser His Glu Arg Leu Thr Thr Leu Glu Asp Thr Val Asp Thr Glu
    8330                8335                8340

Asp Met Gln Pro Ser Thr His Thr Ala Val Thr Asn Val Arg Thr
    8345                8350                8355

Ser Ile Ser Gly His Glu Ser Gln Ser Ser Val Leu Ser Asp Ser
    8360                8365                8370

Glu Thr Pro Lys Ala Thr Ser Pro Met Gly Thr Thr Tyr Thr Met
    8375                8380                8385

Gly Glu Thr Ser Val Ser Ile Ser Thr Ser Asp Phe Phe Glu Thr
    8390                8395                8400

Ser Arg Ile Gln Ile Glu Pro Thr Ser Ser Leu Thr Ser Gly Leu
    8405                8410                8415

Arg Glu Thr Ser Ser Ser Glu Arg Ile Ser Ser Ala Thr Glu Gly
    8420                8425                8430

Ser Thr Val Leu Ser Glu Val Pro Ser Gly Ala Thr Thr Glu Val
    8435                8440                8445

Ser Arg Thr Glu Val Ile Ser Ser Arg Gly Thr Ser Met Ser Gly
    8450                8455                8460

Pro Asp Gln Phe Thr Ile Ser Pro Asp Ile Ser Thr Glu Ala Ile
    8465                8470                8475

Thr Arg Leu Ser Thr Ser Pro Ile Met Thr Glu Ser Ala Glu Ser
    8480                8485                8490

Ala Ile Thr Ile Glu Thr Gly Ser Pro Gly Ala Thr Ser Glu Gly
    8495                8500                8505

Thr Leu Thr Leu Asp Thr Ser Thr Thr Thr Phe Trp Ser Gly Thr
    8510                8515                8520

His Ser Thr Ala Ser Pro Gly Phe Ser His Ser Glu Met Thr Thr
    8525                8530                8535

Leu Met Ser Arg Thr Pro Gly Asp Val Pro Trp Pro Ser Leu Pro
    8540                8545                8550

Ser Val Glu Glu Ala Ser Ser Val Ser Ser Ser Leu Ser Ser Pro
    8555                8560                8565

Ala Met Thr Ser Thr Ser Phe Phe Ser Thr Leu Pro Glu Ser Ile
    8570                8575                8580

Ser Ser Ser Pro His Pro Val Thr Ala Leu Leu Thr Leu Gly Pro
    8585                8590                8595

Val Lys Thr Thr Asp Met Leu Arg Thr Ser Ser Glu Pro Glu Thr
    8600                8605                8610
```

```
Ser Ser Pro Pro Asn Leu Ser Ser Thr Ser Ala Glu Ile Leu Ala
    8615                8620                8625

Thr Ser Glu Val Thr Lys Asp Arg Glu Lys Ile His Pro Ser Ser
    8630                8635                8640

Asn Thr Pro Val Val Asn Val Gly Thr Val Ile Tyr Lys His Leu
    8645                8650                8655

Ser Pro Ser Ser Val Leu Ala Asp Leu Val Thr Thr Lys Pro Thr
    8660                8665                8670

Ser Pro Met Ala Thr Thr Ser Thr Leu Gly Asn Thr Ser Val Ser
    8675                8680                8685

Thr Ser Thr Pro Ala Phe Pro Glu Thr Met Met Thr Gln Pro Thr
    8690                8695                8700

Ser Ser Leu Thr Ser Gly Leu Arg Glu Ile Ser Thr Ser Gln Glu
    8705                8710                8715

Thr Ser Ser Ala Thr Glu Arg Ser Ala Ser Leu Ser Gly Met Pro
    8720                8725                8730

Thr Gly Ala Thr Thr Lys Val Ser Arg Thr Glu Ala Leu Ser Leu
    8735                8740                8745

Gly Arg Thr Ser Thr Pro Gly Pro Ala Gln Ser Thr Ile Ser Pro
    8750                8755                8760

Glu Ile Ser Thr Glu Thr Ile Thr Arg Ile Ser Thr Pro Leu Thr
    8765                8770                8775

Thr Thr Gly Ser Ala Glu Met Thr Ile Thr Pro Lys Thr Gly His
    8780                8785                8790

Ser Gly Ala Ser Ser Gln Gly Thr Phe Thr Leu Asp Thr Ser Ser
    8795                8800                8805

Arg Ala Ser Trp Pro Gly Thr His Ser Ala Ala Thr His Arg Ser
    8810                8815                8820

Pro His Ser Gly Met Thr Thr Pro Met Ser Arg Gly Pro Glu Asp
    8825                8830                8835

Val Ser Trp Pro Ser Arg Pro Ser Val Glu Lys Thr Ser Pro Pro
    8840                8845                8850

Ser Ser Leu Val Ser Leu Ser Ala Val Thr Ser Pro Ser Pro Leu
    8855                8860                8865

Tyr Ser Thr Pro Ser Glu Ser Ser His Ser Ser Pro Leu Arg Val
    8870                8875                8880

Thr Ser Leu Phe Thr Pro Val Met Met Lys Thr Thr Asp Met Leu
    8885                8890                8895

Asp Thr Ser Leu Glu Pro Val Thr Thr Ser Pro Pro Ser Met Asn
    8900                8905                8910

Ile Thr Ser Asp Glu Ser Leu Ala Thr Ser Lys Ala Thr Met Glu
    8915                8920                8925

Thr Glu Ala Ile Gln Leu Ser Glu Asn Thr Ala Val Thr Gln Met
    8930                8935                8940

Gly Thr Ile Ser Ala Arg Gln Glu Phe Tyr Ser Ser Tyr Pro Gly
    8945                8950                8955

Leu Pro Glu Pro Ser Lys Val Thr Ser Pro Val Val Thr Ser Ser
    8960                8965                8970

Thr Ile Lys Asp Ile Val Ser Thr Thr Ile Pro Ala Ser Ser Glu
    8975                8980                8985

Ile Thr Arg Ile Glu Met Glu Ser Thr Ser Thr Leu Thr Pro Thr
    8990                8995                9000

Pro Arg Glu Thr Ser Thr Ser Gln Glu Ile His Ser Ala Thr Lys
```

```
    9005                9010                9015

Pro Ser  Thr Val Pro Tyr Lys  Ala Leu Thr Ser Ala  Thr Ile Glu
    9020                9025                9030

Asp Ser  Met Thr Gln Val Met  Ser Ser Ser Arg Gly  Pro Ser Pro
    9035                9040                9045

Asp Gln  Ser Thr Met Ser Gln  Asp Ile Ser Thr Glu  Val Ile Thr
    9050                9055                9060

Arg Leu  Ser Thr Ser Pro Ile  Lys Thr Glu Ser Thr  Glu Met Thr
    9065                9070                9075

Ile Thr  Thr Gln Thr Gly Ser  Pro Gly Ala Thr Ser  Arg Gly Thr
    9080                9085                9090

Leu Thr  Leu Asp Thr Ser Thr  Thr Phe Met Ser Gly  Thr His Ser
    9095                9100                9105

Thr Ala  Ser Gln Gly Phe Ser  His Ser Gln Met Thr  Ala Leu Met
    9110                9115                9120

Ser Arg  Thr Pro Gly Asp Val  Pro Trp Leu Ser His  Pro Ser Val
    9125                9130                9135

Glu Glu  Ala Ser Ser Ala Ser  Phe Ser Leu Ser Ser  Pro Val Met
    9140                9145                9150

Thr Ser  Ser Ser Pro Val Ser  Ser Thr Leu Pro Asp  Ser Ile His
    9155                9160                9165

Ser Ser  Ser Leu Pro Val Thr  Ser Leu Leu Thr Ser  Gly Leu Val
    9170                9175                9180

Lys Thr  Thr Glu Leu Leu Gly  Thr Ser Ser Glu Pro  Glu Thr Ser
    9185                9190                9195

Ser Pro  Pro Asn Leu Ser Ser  Thr Ser Ala Glu Ile  Leu Ala Ile
    9200                9205                9210

Thr Glu  Val Thr Thr Asp Thr  Glu Lys Leu Glu Met  Thr Asn Val
    9215                9220                9225

Val Thr  Ser Gly Tyr Thr His  Glu Ser Pro Ser Ser  Val Leu Ala
    9230                9235                9240

Asp Ser  Val Thr Thr Lys Ala  Thr Ser Ser Met Gly  Ile Thr Tyr
    9245                9250                9255

Pro Thr  Gly Asp Thr Asn Val  Leu Thr Ser Thr Pro  Ala Phe Ser
    9260                9265                9270

Asp Thr  Ser Arg Ile Gln Thr  Lys Ser Lys Leu Ser  Leu Thr Pro
    9275                9280                9285

Gly Leu  Met Glu Thr Ser Ile  Ser Glu Glu Thr Ser  Ser Ala Thr
    9290                9295                9300

Glu Lys  Ser Thr Val Leu Ser  Ser Val Pro Thr Gly  Ala Thr Thr
    9305                9310                9315

Glu Val  Ser Arg Thr Glu Ala  Ile Ser Ser Ser Arg  Thr Ser Ile
    9320                9325                9330

Pro Gly  Pro Ala Gln Ser Thr  Met Ser Ser Asp Thr  Ser Met Glu
    9335                9340                9345

Thr Ile  Thr Arg Ile Ser Thr  Pro Leu Thr Arg Lys  Glu Ser Thr
    9350                9355                9360

Asp Met  Ala Ile Thr Pro Lys  Thr Gly Pro Ser Gly  Ala Thr Ser
    9365                9370                9375

Gln Gly  Thr Phe Thr Leu Asp  Ser Ser Ser Thr Ala  Ser Trp Pro
    9380                9385                9390

Gly Thr  His Ser Ala Thr Thr  Gln Arg Phe Pro Gln  Ser Val Val
    9395                9400                9405
```

```
Thr Thr Pro Met Ser Arg Gly Pro Glu Asp Val Ser Trp Pro Ser
    9410                9415                9420

Pro Leu Ser Val Glu Lys Asn Ser Pro Pro Ser Ser Leu Val Ser
    9425                9430                9435

Ser Ser Ser Val Thr Ser Pro Ser Pro Leu Tyr Ser Thr Pro Ser
    9440                9445                9450

Gly Ser Ser His Ser Ser Pro Val Pro Val Thr Ser Leu Phe Thr
    9455                9460                9465

Ser Ile Met Met Lys Ala Thr Asp Met Leu Asp Ala Ser Leu Glu
    9470                9475                9480

Pro Glu Thr Thr Ser Ala Pro Asn Met Asn Ile Thr Ser Asp Glu
    9485                9490                9495

Ser Leu Ala Ala Ser Lys Ala Thr Thr Glu Thr Glu Ala Ile His
    9500                9505                9510

Val Phe Glu Asn Thr Ala Ala Ser His Val Glu Thr Thr Ser Ala
    9515                9520                9525

Thr Glu Glu Leu Tyr Ser Ser Ser Pro Gly Phe Ser Glu Pro Thr
    9530                9535                9540

Lys Val Ile Ser Pro Val Val Thr Ser Ser Ser Ile Arg Asp Asn
    9545                9550                9555

Met Val Ser Thr Thr Met Pro Gly Ser Ser Gly Ile Thr Arg Ile
    9560                9565                9570

Glu Ile Glu Ser Met Ser Ser Leu Thr Pro Gly Leu Arg Glu Thr
    9575                9580                9585

Arg Thr Ser Gln Asp Ile Thr Ser Ser Thr Glu Thr Ser Thr Val
    9590                9595                9600

Leu Tyr Lys Met Pro Ser Gly Ala Thr Pro Glu Val Ser Arg Thr
    9605                9610                9615

Glu Val Met Pro Ser Ser Arg Thr Ser Ile Pro Gly Pro Ala Gln
    9620                9625                9630

Ser Thr Met Ser Leu Asp Ile Ser Asp Glu Val Val Thr Arg Leu
    9635                9640                9645

Ser Thr Ser Pro Ile Met Thr Glu Ser Ala Glu Ile Thr Ile Thr
    9650                9655                9660

Thr Gln Thr Gly Tyr Ser Leu Ala Thr Ser Gln Val Thr Leu Pro
    9665                9670                9675

Leu Gly Thr Ser Met Thr Phe Leu Ser Gly Thr His Ser Thr Met
    9680                9685                9690

Ser Gln Gly Leu Ser His Ser Glu Met Thr Asn Leu Met Ser Arg
    9695                9700                9705

Gly Pro Glu Ser Leu Ser Trp Thr Ser Pro Arg Phe Val Glu Thr
    9710                9715                9720

Thr Arg Ser Ser Ser Ser Leu Thr Ser Leu Pro Leu Thr Thr Ser
    9725                9730                9735

Leu Ser Pro Val Ser Ser Thr Leu Leu Asp Ser Ser Pro Ser Ser
    9740                9745                9750

Pro Leu Pro Val Thr Ser Leu Ile Leu Pro Gly Leu Val Lys Thr
    9755                9760                9765

Thr Glu Val Leu Asp Thr Ser Ser Glu Pro Lys Thr Ser Ser Ser
    9770                9775                9780

Pro Asn Leu Ser Ser Thr Ser Val Glu Ile Pro Ala Thr Ser Glu
    9785                9790                9795
```

```
Ile Met Thr Asp Thr Glu Lys Ile His Pro Ser Ser Asn Thr Ala
    9800                9805                9810

Val Ala Lys Val Arg Thr Ser Ser Ser Val His Glu Ser His Ser
    9815                9820                9825

Ser Val Leu Ala Asp Ser Glu Thr Thr Ile Thr Ile Pro Ser Met
    9830                9835                9840

Gly Ile Thr Ser Ala Val Asp Asp Thr Thr Val Phe Thr Ser Asn
    9845                9850                9855

Pro Ala Phe Ser Glu Thr Arg Arg Ile Pro Thr Glu Pro Thr Phe
    9860                9865                9870

Ser Leu Thr Pro Gly Phe Arg Glu Thr Ser Thr Ser Glu Glu Thr
    9875                9880                9885

Thr Ser Ile Thr Glu Thr Ser Ala Val Leu Tyr Gly Val Pro Thr
    9890                9895                9900

Ser Ala Thr Thr Glu Val Ser Met Thr Glu Ile Met Ser Ser Asn
    9905                9910                9915

Arg Ile His Ile Pro Asp Ser Asp Gln Ser Thr Met Ser Pro Asp
    9920                9925                9930

Ile Ile Thr Glu Val Ile Thr Arg Leu Ser Ser Ser Ser Met Met
    9935                9940                9945

Ser Glu Ser Thr Gln Met Thr Ile Thr Thr Gln Lys Ser Ser Pro
    9950                9955                9960

Gly Ala Thr Ala Gln Ser Thr Leu Thr Leu Ala Thr Thr Thr Ala
    9965                9970                9975

Pro Leu Ala Arg Thr His Ser Thr Val Pro Pro Arg Phe Leu His
    9980                9985                9990

Ser Glu Met Thr Thr Leu Met Ser Arg Ser Pro Glu Asn Pro Ser
    9995                10000               10005

Trp Lys Ser Ser Leu Phe Val Glu Lys Thr Ser Ser Ser Ser Ser
    10010               10015               10020

Leu Leu Ser Leu Pro Val Thr Thr Ser Pro Ser Val Ser Ser Thr
    10025               10030               10035

Leu Pro Gln Ser Ile Pro Ser Ser Ser Phe Ser Val Thr Ser Leu
    10040               10045               10050

Leu Thr Pro Gly Met Val Lys Thr Thr Asp Thr Ser Thr Glu Pro
    10055               10060               10065

Gly Thr Ser Leu Ser Pro Asn Leu Ser Gly Thr Ser Val Glu Ile
    10070               10075               10080

Leu Ala Ala Ser Glu Val Thr Thr Asp Thr Glu Lys Ile His Pro
    10085               10090               10095

Ser Ser Ser Met Ala Val Thr Asn Val Gly Thr Thr Ser Ser Gly
    10100               10105               10110

His Glu Leu Tyr Ser Ser Val Ser Ile His Ser Glu Pro Ser Lys
    10115               10120               10125

Ala Thr Tyr Pro Val Gly Thr Pro Ser Ser Met Ala Glu Thr Ser
    10130               10135               10140

Ile Ser Thr Ser Met Pro Ala Asn Phe Glu Thr Thr Gly Phe Glu
    10145               10150               10155

Ala Glu Pro Phe Ser His Leu Thr Ser Gly Phe Arg Lys Thr Asn
    10160               10165               10170

Met Ser Leu Asp Thr Ser Ser Val Thr Pro Thr Asn Thr Pro Ser
    10175               10180               10185

Ser Pro Gly Ser Thr His Leu Leu Gln Ser Ser Lys Thr Asp Phe
```

10190 10195 10200

Thr Ser Ser Ala Lys Thr Ser Ser Pro Asp Trp Pro Pro Ala Ser
10205 10210 10215

Gln Tyr Thr Glu Ile Pro Val Asp Ile Ile Thr Pro Phe Asn Ala
10220 10225 10230

Ser Pro Ser Ile Thr Glu Ser Thr Gly Ile Thr Ser Phe Pro Glu
10235 10240 10245

Ser Arg Phe Thr Met Ser Val Thr Glu Ser Thr His His Leu Ser
10250 10255 10260

Thr Asp Leu Leu Pro Ser Ala Glu Thr Ile Ser Thr Gly Thr Val
10265 10270 10275

Met Pro Ser Leu Ser Glu Ala Met Thr Ser Phe Ala Thr Thr Gly
10280 10285 10290

Val Pro Arg Ala Ile Ser Gly Ser Gly Ser Pro Phe Ser Arg Thr
10295 10300 10305

Glu Ser Gly Pro Gly Asp Ala Thr Leu Ser Thr Ile Ala Glu Ser
10310 10315 10320

Leu Pro Ser Ser Thr Pro Val Pro Phe Ser Ser Ser Thr Phe Thr
10325 10330 10335

Thr Thr Asp Ser Ser Thr Ile Pro Ala Leu His Glu Ile Thr Ser
10340 10345 10350

Ser Ser Ala Thr Pro Tyr Arg Val Asp Thr Ser Leu Gly Thr Glu
10355 10360 10365

Ser Ser Thr Thr Glu Gly Arg Leu Val Met Val Ser Thr Leu Asp
10370 10375 10380

Thr Ser Ser Gln Pro Gly Arg Thr Ser Ser Ser Pro Ile Leu Asp
10385 10390 10395

Thr Arg Met Thr Glu Ser Val Glu Leu Gly Thr Val Thr Ser Ala
10400 10405 10410

Tyr Gln Val Pro Ser Leu Ser Thr Arg Leu Thr Arg Thr Asp Gly
10415 10420 10425

Ile Met Glu His Ile Thr Lys Ile Pro Asn Glu Ala Ala His Arg
10430 10435 10440

Gly Thr Ile Arg Pro Val Lys Gly Pro Gln Thr Ser Thr Ser Pro
10445 10450 10455

Ala Ser Pro Lys Gly Leu His Thr Gly Gly Thr Lys Arg Met Glu
10460 10465 10470

Thr Thr Thr Thr Ala Leu Lys Thr Thr Thr Thr Ala Leu Lys Thr
10475 10480 10485

Thr Ser Arg Ala Thr Leu Thr Thr Ser Val Tyr Thr Pro Thr Leu
10490 10495 10500

Gly Thr Leu Thr Pro Leu Asn Ala Ser Met Gln Met Ala Ser Thr
10505 10510 10515

Ile Pro Thr Glu Met Met Ile Thr Thr Pro Tyr Val Phe Pro Asp
10520 10525 10530

Val Pro Glu Thr Thr Ser Ser Leu Ala Thr Ser Leu Gly Ala Glu
10535 10540 10545

Thr Ser Thr Ala Leu Pro Arg Thr Thr Pro Ser Val Phe Asn Arg
10550 10555 10560

Glu Ser Glu Thr Thr Ala Ser Leu Val Ser Arg Ser Gly Ala Glu
10565 10570 10575

Arg Ser Pro Val Ile Gln Thr Leu Asp Val Ser Ser Ser Glu Pro
10580 10585 10590

```
Asp Thr Thr Ala Ser Trp Val Ile His Pro Ala Glu Thr Ile Pro
    10595               10600               10605

Thr Val Ser Lys Thr Thr Pro Asn Phe Phe His Ser Glu Leu Asp
    10610               10615               10620

Thr Val Ser Ser Thr Ala Thr Ser His Gly Ala Asp Val Ser Ser
    10625               10630               10635

Ala Ile Pro Thr Asn Ile Ser Pro Ser Glu Leu Asp Ala Leu Thr
    10640               10645               10650

Pro Leu Val Thr Ile Ser Gly Thr Asp Thr Ser Thr Thr Phe Pro
    10655               10660               10665

Thr Leu Thr Lys Ser Pro His Glu Thr Glu Thr Arg Thr Thr Trp
    10670               10675               10680

Leu Thr His Pro Ala Glu Thr Ser Ser Thr Ile Pro Arg Thr Ile
    10685               10690               10695

Pro Asn Phe Ser His His Glu Ser Asp Ala Thr Pro Ser Ile Ala
    10700               10705               10710

Thr Ser Pro Gly Ala Glu Thr Ser Ser Ala Ile Pro Ile Met Thr
    10715               10720               10725

Val Ser Pro Gly Ala Glu Asp Leu Val Thr Ser Gln Val Thr Ser
    10730               10735               10740

Ser Gly Thr Asp Arg Asn Met Thr Ile Pro Thr Leu Thr Leu Ser
    10745               10750               10755

Pro Gly Glu Pro Lys Thr Ile Ala Ser Leu Val Thr His Pro Glu
    10760               10765               10770

Ala Gln Thr Ser Ser Ala Ile Pro Thr Ser Thr Ile Ser Pro Ala
    10775               10780               10785

Val Ser Arg Leu Val Thr Ser Met Val Thr Ser Leu Ala Ala Lys
    10790               10795               10800

Thr Ser Thr Thr Asn Arg Ala Leu Thr Asn Ser Pro Gly Glu Pro
    10805               10810               10815

Ala Thr Thr Val Ser Leu Val Thr His Pro Ala Gln Thr Ser Pro
    10820               10825               10830

Thr Val Pro Trp Thr Thr Ser Ile Phe Phe His Ser Lys Ser Asp
    10835               10840               10845

Thr Thr Pro Ser Met Thr Thr Ser His Gly Ala Glu Ser Ser Ser
    10850               10855               10860

Ala Val Pro Thr Pro Thr Val Ser Thr Glu Val Pro Gly Val Val
    10865               10870               10875

Thr Pro Leu Val Thr Ser Ser Arg Ala Val Ile Ser Thr Thr Ile
    10880               10885               10890

Pro Ile Leu Thr Leu Ser Pro Gly Glu Pro Glu Thr Thr Pro Ser
    10895               10900               10905

Met Ala Thr Ser His Gly Glu Glu Ala Ser Ser Ala Ile Pro Thr
    10910               10915               10920

Pro Thr Val Ser Pro Gly Val Pro Gly Val Val Thr Ser Leu Val
    10925               10930               10935

Thr Ser Ser Arg Ala Val Thr Ser Thr Thr Ile Pro Ile Leu Thr
    10940               10945               10950

Phe Ser Leu Gly Glu Pro Glu Thr Thr Pro Ser Met Ala Thr Ser
    10955               10960               10965

His Gly Thr Glu Ala Gly Ser Ala Val Pro Thr Val Leu Pro Glu
    10970               10975               10980
```

-continued

```
Val Pro Gly Met Val Thr Ser Leu Val Ala Ser Ser Arg Ala Val
    10985               10990               10995

Thr Ser Thr Thr Leu Pro Thr Leu Thr Leu Ser Pro Gly Glu Pro
    11000               11005               11010

Glu Thr Thr Pro Ser Met Ala Thr Ser His Gly Ala Glu Ala Ser
    11015               11020               11025

Ser Thr Val Pro Thr Val Ser Pro Glu Val Pro Gly Val Val Thr
    11030               11035               11040

Ser Leu Val Thr Ser Ser Ser Gly Val Asn Ser Thr Ser Ile Pro
    11045               11050               11055

Thr Leu Ile Leu Ser Pro Gly Glu Leu Glu Thr Thr Pro Ser Met
    11060               11065               11070

Ala Thr Ser His Gly Ala Glu Ala Ser Ser Ala Val Pro Thr Pro
    11075               11080               11085

Thr Val Ser Pro Gly Val Ser Gly Val Val Thr Pro Leu Val Thr
    11090               11095               11100

Ser Ser Arg Ala Val Thr Ser Thr Thr Ile Pro Ile Leu Thr Leu
    11105               11110               11115

Ser Ser Ser Glu Pro Glu Thr Thr Pro Ser Met Ala Thr Ser His
    11120               11125               11130

Gly Val Glu Ala Ser Ser Ala Val Leu Thr Val Ser Pro Glu Val
    11135               11140               11145

Pro Gly Met Val Thr Ser Leu Val Thr Ser Ser Arg Ala Val Thr
    11150               11155               11160

Ser Thr Thr Ile Pro Thr Leu Thr Ile Ser Ser Asp Glu Pro Glu
    11165               11170               11175

Thr Thr Thr Ser Leu Val Thr His Ser Glu Ala Lys Met Ile Ser
    11180               11185               11190

Ala Ile Pro Thr Leu Ala Val Ser Pro Thr Val Gln Gly Leu Val
    11195               11200               11205

Thr Ser Leu Val Thr Ser Ser Gly Ser Glu Thr Ser Ala Phe Ser
    11210               11215               11220

Asn Leu Thr Val Ala Ser Ser Gln Pro Glu Thr Ile Asp Ser Trp
    11225               11230               11235

Val Ala His Pro Gly Thr Glu Ala Ser Ser Val Val Pro Thr Leu
    11240               11245               11250

Thr Val Ser Thr Gly Glu Pro Phe Thr Asn Ile Ser Leu Val Thr
    11255               11260               11265

His Pro Ala Glu Ser Ser Ser Thr Leu Pro Arg Thr Thr Ser Arg
    11270               11275               11280

Phe Ser His Ser Glu Leu Asp Thr Met Pro Ser Thr Val Thr Ser
    11285               11290               11295

Pro Glu Ala Glu Ser Ser Ser Ala Ile Ser Thr Thr Ile Ser Pro
    11300               11305               11310

Gly Ile Pro Gly Val Leu Thr Ser Leu Val Thr Ser Ser Gly Arg
    11315               11320               11325

Asp Ile Ser Ala Thr Phe Pro Thr Val Pro Glu Ser Pro His Glu
    11330               11335               11340

Ser Glu Ala Thr Ala Ser Trp Val Thr His Pro Ala Val Thr Ser
    11345               11350               11355

Thr Thr Val Pro Arg Thr Thr Pro Asn Tyr Ser His Ser Glu Pro
    11360               11365               11370

Asp Thr Thr Pro Ser Ile Ala Thr Ser Pro Gly Ala Glu Ala Thr
```

-continued

```
    11375               11380               11385

Ser Asp Phe Pro Thr Ile Thr Val Ser Pro Asp Val Pro Asp Met
    11390               11395               11400

Val Thr Ser Gln Val Thr Ser Ser Gly Thr Asp Thr Ser Ile Thr
    11405               11410               11415

Ile Pro Thr Leu Thr Leu Ser Ser Gly Glu Pro Glu Thr Thr Thr
    11420               11425               11430

Ser Phe Ile Thr Tyr Ser Glu Thr His Thr Ser Ser Ala Ile Pro
    11435               11440               11445

Thr Leu Pro Val Ser Pro Gly Ala Ser Lys Met Leu Thr Ser Leu
    11450               11455               11460

Val Ile Ser Ser Gly Thr Asp Ser Thr Thr Thr Phe Pro Thr Leu
    11465               11470               11475

Thr Glu Thr Pro Tyr Glu Pro Glu Thr Thr Ala Ile Gln Leu Ile
    11480               11485               11490

His Pro Ala Glu Thr Asn Thr Met Val Pro Arg Thr Thr Pro Lys
    11495               11500               11505

Phe Ser His Ser Lys Ser Asp Thr Thr Leu Pro Val Ala Ile Thr
    11510               11515               11520

Ser Pro Gly Pro Glu Ala Ser Ser Ala Val Ser Thr Thr Thr Ile
    11525               11530               11535

Ser Pro Asp Met Ser Asp Leu Val Thr Ser Leu Val Pro Ser Ser
    11540               11545               11550

Gly Thr Asp Thr Ser Thr Thr Phe Pro Thr Leu Ser Glu Thr Pro
    11555               11560               11565

Tyr Glu Pro Glu Thr Thr Ala Thr Trp Leu Thr His Pro Ala Glu
    11570               11575               11580

Thr Ser Thr Thr Val Ser Gly Thr Ile Pro Asn Phe Ser His Arg
    11585               11590               11595

Gly Ser Asp Thr Ala Pro Ser Met Val Thr Ser Pro Gly Val Asp
    11600               11605               11610

Thr Arg Ser Gly Val Pro Thr Thr Thr Ile Pro Pro Ser Ile Pro
    11615               11620               11625

Gly Val Val Thr Ser Gln Val Thr Ser Ser Ala Thr Asp Thr Ser
    11630               11635               11640

Thr Ala Ile Pro Thr Leu Thr Pro Ser Pro Gly Glu Pro Glu Thr
    11645               11650               11655

Thr Ala Ser Ser Ala Thr His Pro Gly Thr Gln Thr Gly Phe Thr
    11660               11665               11670

Val Pro Ile Arg Thr Val Pro Ser Ser Glu Pro Asp Thr Met Ala
    11675               11680               11685

Ser Trp Val Thr His Pro Pro Gln Thr Ser Thr Pro Val Ser Arg
    11690               11695               11700

Thr Thr Ser Ser Phe Ser His Ser Ser Pro Asp Ala Thr Pro Val
    11705               11710               11715

Met Ala Thr Ser Pro Arg Thr Glu Ala Ser Ser Ala Val Leu Thr
    11720               11725               11730

Thr Ile Ser Pro Gly Ala Pro Glu Met Val Thr Ser Gln Ile Thr
    11735               11740               11745

Ser Ser Gly Ala Ala Thr Ser Thr Thr Val Pro Thr Leu Thr His
    11750               11755               11760

Ser Pro Gly Met Pro Glu Thr Thr Ala Leu Leu Ser Thr His Pro
    11765               11770               11775
```

Arg Thr Glu Thr Ser Lys Thr Phe Pro Ala Ser Thr Val Phe Pro
11780 11785 11790

Gln Val Ser Glu Thr Thr Ala Ser Leu Thr Ile Arg Pro Gly Ala
11795 11800 11805

Glu Thr Ser Thr Ala Leu Pro Thr Gln Thr Thr Ser Ser Leu Phe
11810 11815 11820

Thr Leu Leu Val Thr Gly Thr Ser Arg Val Asp Leu Ser Pro Thr
11825 11830 11835

Ala Ser Pro Gly Val Ser Ala Lys Thr Ala Pro Leu Ser Thr His
11840 11845 11850

Pro Gly Thr Glu Thr Ser Thr Met Ile Pro Thr Ser Thr Leu Ser
11855 11860 11865

Leu Gly Leu Leu Glu Thr Thr Gly Leu Leu Ala Thr Ser Ser Ser
11870 11875 11880

Ala Glu Thr Ser Thr Ser Thr Leu Thr Leu Thr Val Ser Pro Ala
11885 11890 11895

Val Ser Gly Leu Ser Ser Ala Ser Ile Thr Thr Asp Lys Pro Gln
11900 11905 11910

Thr Val Thr Ser Trp Asn Thr Glu Thr Ser Pro Ser Val Thr Ser
11915 11920 11925

Val Gly Pro Pro Glu Phe Ser Arg Thr Val Thr Gly Thr Thr Met
11930 11935 11940

Thr Leu Ile Pro Ser Glu Met Pro Thr Pro Pro Lys Thr Ser His
11945 11950 11955

Gly Glu Gly Val Ser Pro Thr Thr Ile Leu Arg Thr Thr Met Val
11960 11965 11970

Glu Ala Thr Asn Leu Ala Thr Thr Gly Ser Ser Pro Thr Val Ala
11975 11980 11985

Lys Thr Thr Thr Thr Phe Asn Thr Leu Ala Gly Ser Leu Phe Thr
11990 11995 12000

Pro Leu Thr Thr Pro Gly Met Ser Thr Leu Ala Ser Glu Ser Val
12005 12010 12015

Thr Ser Arg Thr Ser Tyr Asn His Arg Ser Trp Ile Ser Thr Thr
12020 12025 12030

Ser Ser Tyr Asn Arg Arg Tyr Trp Thr Pro Ala Thr Ser Thr Pro
12035 12040 12045

Val Thr Ser Thr Phe Ser Pro Gly Ile Ser Thr Ser Ser Ile Pro
12050 12055 12060

Ser Ser Thr Ala Ala Thr Val Pro Phe Met Val Pro Phe Thr Leu
12065 12070 12075

Asn Phe Thr Ile Thr Asn Leu Gln Tyr Glu Glu Asp Met Arg His
12080 12085 12090

Pro Gly Ser Arg Lys Phe Asn Ala Thr Glu Arg Glu Leu Gln Gly
12095 12100 12105

Leu Leu Lys Pro Leu Phe Arg Asn Ser Ser Leu Glu Tyr Leu Tyr
12110 12115 12120

Ser Gly Cys Arg Leu Ala Ser Leu Arg Pro Glu Lys Asp Ser Ser
12125 12130 12135

Ala Thr Ala Val Asp Ala Ile Cys Thr His Arg Pro Asp Pro Glu
12140 12145 12150

Asp Leu Gly Leu Asp Arg Glu Arg Leu Tyr Trp Glu Leu Ser Asn
12155 12160 12165

-continued

```
Leu Thr Asn Gly Ile Gln Glu Leu Gly Pro Tyr Thr Leu Asp Arg
    12170               12175               12180

Asn Ser Leu Tyr Val Asn Gly Phe Thr His Arg Ser Ser Met Pro
    12185               12190               12195

Thr Thr Ser Thr Pro Gly Thr Ser Thr Val Asp Val Gly Thr Ser
    12200               12205               12210

Gly Thr Pro Ser Ser Ser Pro Ser Pro Thr Thr Ala Gly Pro Leu
    12215               12220               12225

Leu Met Pro Phe Thr Leu Asn Phe Thr Ile Thr Asn Leu Gln Tyr
    12230               12235               12240

Glu Glu Asp Met Arg Arg Thr Gly Ser Arg Lys Phe Asn Thr Met
    12245               12250               12255

Glu Ser Val Leu Gln Gly Leu Leu Lys Pro Leu Phe Lys Asn Thr
    12260               12265               12270

Ser Val Gly Pro Leu Tyr Ser Gly Cys Arg Leu Thr Leu Leu Arg
    12275               12280               12285

Pro Glu Lys Asp Gly Ala Ala Thr Gly Val Asp Ala Ile Cys Thr
    12290               12295               12300

His Arg Leu Asp Pro Lys Ser Pro Gly Leu Asn Arg Glu Gln Leu
    12305               12310               12315

Tyr Trp Glu Leu Ser Lys Leu Thr Asn Asp Ile Glu Glu Leu Gly
    12320               12325               12330

Pro Tyr Thr Leu Asp Arg Asn Ser Leu Tyr Val Asn Gly Phe Thr
    12335               12340               12345

His Gln Ser Ser Val Ser Thr Thr Ser Thr Pro Gly Thr Ser Thr
    12350               12355               12360

Val Asp Leu Arg Thr Ser Gly Thr Pro Ser Ser Leu Ser Ser Pro
    12365               12370               12375

Thr Ile Met Ala Ala Gly Pro Leu Leu Val Pro Phe Thr Leu Asn
    12380               12385               12390

Phe Thr Ile Thr Asn Leu Gln Tyr Gly Glu Asp Met Gly His Pro
    12395               12400               12405

Gly Ser Arg Lys Phe Asn Thr Thr Glu Arg Val Leu Gln Gly Leu
    12410               12415               12420

Leu Gly Pro Ile Phe Lys Asn Thr Ser Val Gly Pro Leu Tyr Ser
    12425               12430               12435

Gly Cys Arg Leu Thr Ser Leu Arg Ser Glu Lys Asp Gly Ala Ala
    12440               12445               12450

Thr Gly Val Asp Ala Ile Cys Ile His His Leu Asp Pro Lys Ser
    12455               12460               12465

Pro Gly Leu Asn Arg Glu Arg Leu Tyr Trp Glu Leu Ser Gln Leu
    12470               12475               12480

Thr Asn Gly Ile Lys Glu Leu Gly Pro Tyr Thr Leu Asp Arg Asn
    12485               12490               12495

Ser Leu Tyr Val Asn Gly Phe Thr His Arg Thr Ser Val Pro Thr
    12500               12505               12510

Ser Ser Thr Pro Gly Thr Ser Thr Val Asp Leu Gly Thr Ser Gly
    12515               12520               12525

Thr Pro Phe Ser Leu Pro Ser Pro Ala Thr Ala Gly Pro Leu Leu
    12530               12535               12540

Val Leu Phe Thr Leu Asn Phe Thr Ile Thr Asn Leu Lys Tyr Glu
    12545               12550               12555

Glu Asp Met His Arg Pro Gly Ser Arg Lys Phe Asn Thr Thr Glu
```

```
    12560               12565               12570

Arg Val Leu Gln Thr Leu Leu Gly Pro Met Phe Lys Asn Thr Ser
    12575               12580               12585

Val Gly Leu Leu Tyr Ser Gly Cys Arg Leu Thr Leu Leu Arg Ser
    12590               12595               12600

Glu Lys Asp Gly Ala Ala Thr Gly Val Asp Ala Ile Cys Thr His
    12605               12610               12615

Arg Leu Asp Pro Lys Ser Pro Gly Val Asp Arg Glu Gln Leu Tyr
    12620               12625               12630

Trp Glu Leu Ser Gln Leu Thr Asn Gly Ile Lys Glu Leu Gly Pro
    12635               12640               12645

Tyr Thr Leu Asp Arg Asn Ser Leu Tyr Val Asn Gly Phe Thr His
    12650               12655               12660

Trp Ile Pro Val Pro Thr Ser Ser Thr Pro Gly Thr Ser Thr Val
    12665               12670               12675

Asp Leu Gly Ser Gly Thr Pro Ser Ser Leu Pro Ser Pro Thr Thr
    12680               12685               12690

Ala Gly Pro Leu Leu Val Pro Phe Thr Leu Asn Phe Thr Ile Thr
    12695               12700               12705

Asn Leu Lys Tyr Glu Glu Asp Met His Cys Pro Gly Ser Arg Lys
    12710               12715               12720

Phe Asn Thr Thr Glu Arg Val Leu Gln Ser Leu Leu Gly Pro Met
    12725               12730               12735

Phe Lys Asn Thr Ser Val Gly Pro Leu Tyr Ser Gly Cys Arg Leu
    12740               12745               12750

Thr Leu Leu Arg Ser Glu Lys Asp Gly Ala Ala Thr Gly Val Asp
    12755               12760               12765

Ala Ile Cys Thr His Arg Leu Asp Pro Lys Ser Pro Gly Val Asp
    12770               12775               12780

Arg Glu Gln Leu Tyr Trp Glu Leu Ser Gln Leu Thr Asn Gly Ile
    12785               12790               12795

Lys Glu Leu Gly Pro Tyr Thr Leu Asp Arg Asn Ser Leu Tyr Val
    12800               12805               12810

Asn Gly Phe Thr His Gln Thr Ser Ala Pro Asn Thr Ser Thr Pro
    12815               12820               12825

Gly Thr Ser Thr Val Asp Leu Gly Thr Ser Gly Thr Pro Ser Ser
    12830               12835               12840

Leu Pro Ser Pro Thr Ser Ala Gly Pro Leu Leu Val Pro Phe Thr
    12845               12850               12855

Leu Asn Phe Thr Ile Thr Asn Leu Gln Tyr Glu Glu Asp Met His
    12860               12865               12870

His Pro Gly Ser Arg Lys Phe Asn Thr Thr Glu Arg Val Leu Gln
    12875               12880               12885

Gly Leu Leu Gly Pro Met Phe Lys Asn Thr Ser Val Gly Leu Leu
    12890               12895               12900

Tyr Ser Gly Cys Arg Leu Thr Leu Leu Arg Pro Glu Lys Asn Gly
    12905               12910               12915

Ala Ala Thr Gly Met Asp Ala Ile Cys Ser His Arg Leu Asp Pro
    12920               12925               12930

Lys Ser Pro Gly Leu Asn Arg Glu Gln Leu Tyr Trp Glu Leu Ser
    12935               12940               12945

Gln Leu Thr His Gly Ile Lys Glu Leu Gly Pro Tyr Thr Leu Asp
    12950               12955               12960
```

```
Arg Asn Ser Leu Tyr Val Asn Gly Phe Thr His Arg Ser Ser Val
    12965               12970               12975

Ala Pro Thr Ser Thr Pro Gly Thr Ser Thr Val Asp Leu Gly Thr
    12980               12985               12990

Ser Gly Thr Pro Ser Ser Leu Pro Ser Pro Thr Thr Ala Val Pro
    12995               13000               13005

Leu Leu Val Pro Phe Thr Leu Asn Phe Thr Ile Thr Asn Leu Gln
    13010               13015               13020

Tyr Gly Glu Asp Met Arg His Pro Gly Ser Arg Lys Phe Asn Thr
    13025               13030               13035

Thr Glu Arg Val Leu Gln Gly Leu Leu Gly Pro Leu Phe Lys Asn
    13040               13045               13050

Ser Ser Val Gly Pro Leu Tyr Ser Gly Cys Arg Leu Ile Ser Leu
    13055               13060               13065

Arg Ser Glu Lys Asp Gly Ala Ala Thr Gly Val Asp Ala Ile Cys
    13070               13075               13080

Thr His His Leu Asn Pro Gln Ser Pro Gly Leu Asp Arg Glu Gln
    13085               13090               13095

Leu Tyr Trp Gln Leu Ser Gln Met Thr Asn Gly Ile Lys Glu Leu
    13100               13105               13110

Gly Pro Tyr Thr Leu Asp Arg Asn Ser Leu Tyr Val Asn Gly Phe
    13115               13120               13125

Thr His Arg Ser Ser Gly Leu Thr Thr Ser Thr Pro Trp Thr Ser
    13130               13135               13140

Thr Val Asp Leu Gly Thr Ser Gly Thr Pro Ser Pro Val Pro Ser
    13145               13150               13155

Pro Thr Thr Thr Gly Pro Leu Leu Val Pro Phe Thr Leu Asn Phe
    13160               13165               13170

Thr Ile Thr Asn Leu Gln Tyr Glu Glu Asn Met Gly His Pro Gly
    13175               13180               13185

Ser Arg Lys Phe Asn Ile Thr Glu Ser Val Leu Gln Gly Leu Leu
    13190               13195               13200

Lys Pro Leu Phe Lys Ser Thr Ser Val Gly Pro Leu Tyr Ser Gly
    13205               13210               13215

Cys Arg Leu Thr Leu Leu Arg Pro Glu Lys Asp Gly Val Ala Thr
    13220               13225               13230

Arg Val Asp Ala Ile Cys Thr His Arg Pro Asp Pro Lys Ile Pro
    13235               13240               13245

Gly Leu Asp Arg Gln Gln Leu Tyr Trp Glu Leu Ser Gln Leu Thr
    13250               13255               13260

His Ser Ile Thr Glu Leu Gly Pro Tyr Thr Leu Asp Arg Asp Ser
    13265               13270               13275

Leu Tyr Val Asn Gly Phe Thr Gln Arg Ser Ser Val Pro Thr Thr
    13280               13285               13290

Ser Thr Pro Gly Thr Phe Thr Val Gln Pro Glu Thr Ser Glu Thr
    13295               13300               13305

Pro Ser Ser Leu Pro Gly Pro Thr Ala Thr Gly Pro Val Leu Leu
    13310               13315               13320

Pro Phe Thr Leu Asn Phe Thr Ile Thr Asn Leu Gln Tyr Glu Glu
    13325               13330               13335

Asp Met Arg Arg Pro Gly Ser Arg Lys Phe Asn Thr Thr Glu Arg
    13340               13345               13350
```

```
Val Leu Gln Gly Leu Leu Met Pro Leu Phe Lys Asn Thr Ser Val
    13355                  13360                  13365

Ser Ser Leu Tyr Ser Gly Cys Arg Leu Thr Leu Leu Arg Pro Glu
    13370                  13375                  13380

Lys Asp Gly Ala Ala Thr Arg Val Asp Ala Val Cys Thr His Arg
    13385                  13390                  13395

Pro Asp Pro Lys Ser Pro Gly Leu Asp Arg Glu Arg Leu Tyr Trp
    13400                  13405                  13410

Lys Leu Ser Gln Leu Thr His Gly Ile Thr Glu Leu Gly Pro Tyr
    13415                  13420                  13425

Thr Leu Asp Arg His Ser Leu Tyr Val Asn Gly Phe Thr His Gln
    13430                  13435                  13440

Ser Ser Met Thr Thr Thr Arg Thr Pro Asp Thr Ser Thr Met His
    13445                  13450                  13455

Leu Ala Thr Ser Arg Thr Pro Ala Ser Leu Ser Gly Pro Met Thr
    13460                  13465                  13470

Ala Ser Pro Leu Leu Val Leu Phe Thr Ile Asn Phe Thr Ile Thr
    13475                  13480                  13485

Asn Leu Arg Tyr Glu Glu Asn Met His His Pro Gly Ser Arg Lys
    13490                  13495                  13500

Phe Asn Thr Thr Glu Arg Val Leu Gln Gly Leu Leu Arg Pro Val
    13505                  13510                  13515

Phe Lys Asn Thr Ser Val Gly Pro Leu Tyr Ser Gly Cys Arg Leu
    13520                  13525                  13530

Thr Leu Leu Arg Pro Lys Lys Asp Gly Ala Ala Thr Lys Val Asp
    13535                  13540                  13545

Ala Ile Cys Thr Tyr Arg Pro Asp Pro Lys Ser Pro Gly Leu Asp
    13550                  13555                  13560

Arg Glu Gln Leu Tyr Trp Glu Leu Ser Gln Leu Thr His Ser Ile
    13565                  13570                  13575

Thr Glu Leu Gly Pro Tyr Thr Leu Asp Arg Asp Ser Leu Tyr Val
    13580                  13585                  13590

Asn Gly Phe Thr Gln Arg Ser Ser Val Pro Thr Thr Ser Ile Pro
    13595                  13600                  13605

Gly Thr Pro Thr Val Asp Leu Gly Thr Ser Gly Thr Pro Val Ser
    13610                  13615                  13620

Lys Pro Gly Pro Ser Ala Ala Ser Pro Leu Leu Val Leu Phe Thr
    13625                  13630                  13635

Leu Asn Phe Thr Ile Thr Asn Leu Arg Tyr Glu Glu Asn Met Gln
    13640                  13645                  13650

His Pro Gly Ser Arg Lys Phe Asn Thr Thr Glu Arg Val Leu Gln
    13655                  13660                  13665

Gly Leu Leu Arg Ser Leu Phe Lys Ser Thr Ser Val Gly Pro Leu
    13670                  13675                  13680

Tyr Ser Gly Cys Arg Leu Thr Leu Leu Arg Pro Glu Lys Asp Gly
    13685                  13690                  13695

Thr Ala Thr Gly Val Asp Ala Ile Cys Thr His His Pro Asp Pro
    13700                  13705                  13710

Lys Ser Pro Arg Leu Asp Arg Glu Gln Leu Tyr Trp Glu Leu Ser
    13715                  13720                  13725

Gln Leu Thr His Asn Ile Thr Glu Leu Gly Pro Tyr Ala Leu Asp
    13730                  13735                  13740

Asn Asp Ser Leu Phe Val Asn Gly Phe Thr His Arg Ser Ser Val
```

-continued 13745 13750 13755

Ser Thr Thr Ser Thr Pro Gly Thr Pro Thr Val Tyr Leu Gly Ala
13760 13765 13770

Ser Lys Thr Pro Ala Ser Ile Phe Gly Pro Ser Ala Ala Ser His
13775 13780 13785

Leu Leu Ile Leu Phe Thr Leu Asn Phe Thr Ile Thr Asn Leu Arg
13790 13795 13800

Tyr Glu Glu Asn Met Trp Pro Gly Ser Arg Lys Phe Asn Thr Thr
13805 13810 13815

Glu Arg Val Leu Gln Gly Leu Leu Arg Pro Leu Phe Lys Asn Thr
13820 13825 13830

Ser Val Gly Pro Leu Tyr Ser Gly Cys Arg Leu Thr Leu Leu Arg
13835 13840 13845

Pro Glu Lys Asp Gly Glu Ala Thr Gly Val Asp Ala Ile Cys Thr
13850 13855 13860

His Arg Pro Asp Pro Thr Gly Pro Gly Leu Asp Arg Glu Gln Leu
13865 13870 13875

Tyr Leu Glu Leu Ser Gln Leu Thr His Ser Ile Thr Glu Leu Gly
13880 13885 13890

Pro Tyr Thr Leu Asp Arg Asp Ser Leu Tyr Val Asn Gly Phe Thr
13895 13900 13905

His Arg Ser Ser Val Pro Thr Thr Ser Thr Gly Val Val Ser Glu
13910 13915 13920

Glu Pro Phe Thr Leu Asn Phe Thr Ile Asn Asn Leu Arg Tyr Met
13925 13930 13935

Ala Asp Met Gly Gln Pro Gly Ser Leu Lys Phe Asn Ile Thr Asp
13940 13945 13950

Asn Val Met Gln His Leu Leu Ser Pro Leu Phe Gln Arg Ser Ser
13955 13960 13965

Leu Gly Ala Arg Tyr Thr Gly Cys Arg Val Ile Ala Leu Arg Ser
13970 13975 13980

Val Lys Asn Gly Ala Glu Thr Arg Val Asp Leu Leu Cys Thr Tyr
13985 13990 13995

Leu Gln Pro Leu Ser Gly Pro Gly Leu Pro Ile Lys Gln Val Phe
14000 14005 14010

His Glu Leu Ser Gln Gln Thr His Gly Ile Thr Arg Leu Gly Pro
14015 14020 14025

Tyr Ser Leu Asp Lys Asp Ser Leu Tyr Leu Asn Gly Tyr Asn Glu
14030 14035 14040

Pro Gly Pro Asp Glu Pro Pro Thr Thr Pro Lys Pro Ala Thr Thr
14045 14050 14055

Phe Leu Pro Pro Leu Ser Glu Ala Thr Thr Ala Met Gly Tyr His
14060 14065 14070

Leu Lys Thr Leu Thr Leu Asn Phe Thr Ile Ser Asn Leu Gln Tyr
14075 14080 14085

Ser Pro Asp Met Gly Lys Gly Ser Ala Thr Phe Asn Ser Thr Glu
14090 14095 14100

Gly Val Leu Gln His Leu Leu Arg Pro Leu Phe Gln Lys Ser Ser
14105 14110 14115

Met Gly Pro Phe Tyr Leu Gly Cys Gln Leu Ile Ser Leu Arg Pro
14120 14125 14130

Glu Lys Asp Gly Ala Ala Thr Gly Val Asp Thr Thr Cys Thr Tyr
14135 14140 14145

His Pro Asp Pro Val Gly Pro Gly Leu Asp Ile Gln Gln Leu Tyr
14150 14155 14160

Trp Glu Leu Ser Gln Leu Thr His Gly Val Thr Gln Leu Gly Phe
14165 14170 14175

Tyr Val Leu Asp Arg Asp Ser Leu Phe Ile Asn Gly Tyr Ala Pro
14180 14185 14190

Gln Asn Leu Ser Ile Arg Gly Glu Tyr Gln Ile Asn Phe His Ile
14195 14200 14205

Val Asn Trp Asn Leu Ser Asn Pro Asp Pro Thr Ser Ser Glu Tyr
14210 14215 14220

Ile Thr Leu Leu Arg Asp Ile Gln Asp Lys Val Thr Thr Leu Tyr
14225 14230 14235

Lys Gly Ser Gln Leu His Asp Thr Phe Arg Phe Cys Leu Val Thr
14240 14245 14250

Asn Leu Thr Met Asp Ser Val Leu Val Thr Val Lys Ala Leu Phe
14255 14260 14265

Ser Ser Asn Leu Asp Pro Ser Leu Val Glu Gln Val Phe Leu Asp
14270 14275 14280

Lys Thr Leu Asn Ala Ser Phe His Trp Leu Gly Ser Thr Tyr Gln
14285 14290 14295

Leu Val Asp Ile His Val Thr Glu Met Glu Ser Ser Val Tyr Gln
14300 14305 14310

Pro Thr Ser Ser Ser Ser Thr Gln His Phe Tyr Leu Asn Phe Thr
14315 14320 14325

Ile Thr Asn Leu Pro Tyr Ser Gln Asp Lys Ala Gln Pro Gly Thr
14330 14335 14340

Thr Asn Tyr Gln Arg Asn Lys Arg Asn Ile Glu Asp Ala Leu Asn
14345 14350 14355

Gln Leu Phe Arg Asn Ser Ser Ile Lys Ser Tyr Phe Ser Asp Cys
14360 14365 14370

Gln Val Ser Thr Phe Arg Ser Val Pro Asn Arg His His Thr Gly
14375 14380 14385

Val Asp Ser Leu Cys Asn Phe Ser Pro Leu Ala Arg Arg Val Asp
14390 14395 14400

Arg Val Ala Ile Tyr Glu Glu Phe Leu Arg Met Thr Arg Asn Gly
14405 14410 14415

Thr Gln Leu Gln Asn Phe Thr Leu Asp Arg Ser Ser Val Leu Val
14420 14425 14430

Asp Gly Tyr Ser Pro Asn Arg Asn Glu Pro Leu Thr Gly Asn Ser
14435 14440 14445

Asp Leu Pro Phe Trp Ala Val Ile Leu Ile Gly Leu Ala Gly Leu
14450 14455 14460

Leu Gly Val Ile Thr Cys Leu Ile Cys Gly Val Leu Val Thr Thr
14465 14470 14475

Arg Arg Arg Lys Lys Glu Gly Glu Tyr Asn Val Gln Gln Gln Cys
14480 14485 14490

Pro Gly Tyr Tyr Gln Ser His Leu Asp Leu Glu Asp Leu Gln
14495 14500 14505

<210> SEQ ID NO 137
<211> LENGTH: 43815
<212> TYPE: DNA
<213> ORGANISM: Homo sapiens
<220> FEATURE:

<223> OTHER INFORMATION: Immature Human MUC16 nucleic acid sequence (NM_024690.2)

<400> SEQUENCE: 137

```
agcgttgcac aattccccca acctccatac atacggcagc tcttctagac acaggttttc     60
ccaggtcaaa tgcggggacc ccagccatat ctcccaccct gagaaatttt ggagtttcag    120
ggagctcaga agctctgcag aggccaccct ctctgagggg attcttctta gacctccatc    180
cagaggcaaa tgttgacctg tccatgctga aaccctcagg ccttcctggg tcatcttctc    240
ccacccgctc cttgatgaca gggagcagga gcactaaagc cacaccagaa atggattcag    300
gactgacagg agccaccttg tcacctaaga catctacagg tgcaatcgtg gtgacagaac    360
atactctgcc ctttacttcc ccagataaga ccttggccag tcctacatct tcggttgtgg    420
gaagaaccac ccagtctttg gggtgatgt cctctgctct ccctgagtca acctctagag    480
gaatgacaca ctccgagcaa agaaccagcc catcgctgag tccccaggtc aatggaactc    540
cctctaggaa ctaccctgct acaagcatgg tttcaggatt gagttcccca aggaccagga    600
ccagttccac agaaggaaat tttaccaaag aagcatctac atacacactc actgtagaga    660
ccacaagtgg cccagtcact gagaagtaca cagtccccac tgagacctca acaactgaag    720
gtgacagcac agagaccccc tgggacacaa gatatattcc tgtaaaaatc acatctccaa    780
tgaaaacatt tgcagattca actgcatcca aggaaaatgc cccagtgtct atgactccag    840
ctgagaccac agttactgac tcacatactc caggaaggac aaacccatca tttgggacac    900
tttattcttc cttccttgac ctatcaccta aagggacccc aaattccaga ggtgaaacaa    960
gcctggaact gattctatca accactggat atcccttctc ctctcctgaa cctggctctg   1020
caggacacag cagaataagt accagtgcgc ctttgtcatc atctgcttca gttctcgata   1080
ataaaatatc agagaccagc atattctcag gccagagtct cacctcccct ctgtctcctg   1140
gggtgcccga ggccagagcc agcacaatgc ccaactcagc tatccctttt tccatgacac   1200
taagcaatgc agaaacaagt gccgaaaggg tcagaagcac aatttcctct ctggggactc   1260
catcaatatc cacaaagcag acagcagaga ctatccttac cttccatgcc ttcgctgaga   1320
ccatggatat acccagcacc cacatagcca agactttggc ttcagaatgg ttgggaagtc   1380
caggtaccct tggtggcacc agcacttcag cgctgacaac cacatctcca tctaccactt   1440
tagtctcaga ggagaccaac acccatcact ccacgagtgg aaaggaaaca gaaggaactt   1500
tgaatacatc tatgactcca cttgagacct ctgctcctgg agaagagtcc gaaatgactg   1560
ccaccttggt ccccactcta ggttttacaa ctcttgacag caagatcaga agtccatctc   1620
aggtctcttc atcccaccca acaagagagc tcagaaccac aggcagcacc tctgggaggc   1680
agagttccag cacagctgcc cacgggagct ctgacatcct gagggcaacc acttccagca   1740
cctcaaaagc atcatcatgg accagtgaaa gcacagctca gcaatttagt gaaccccagc   1800
acacacagtg ggtggagaca agtcctagca tgaaaacaga gagaccccca gcatcaacca   1860
gtgtggcagc ccctatcacc acttctgttc cctcagtggt ctctggcttc accaccctga   1920
agaccagctc cacaaaaggg atttggcttg aagaaacatc tgcagacaca ctcatcggag   1980
aatccacagc tggcccaacc acccatcagt ttgctgttcc cactgggatt tcaatgacag   2040
gaggcagcag caccagggga agccagggca caacccacct actcaccaga gccacagcat   2100
catctgagac atccgcagat ttgactctgg ccacgaacgg tgtcccagtc tccgtgtctc   2160
cagcagtgag caagacggct gctggctcaa gtcctccagg agggacaaag ccatcatata   2220
```

```
caatggtttc ttctgtcatc cctgagacat catctctaca gtcctcagct ttcagggaag   2280
gaaccagcct gggactgact ccattaaaca ctagacatcc cttctcttcc cctgaaccag   2340
actctgcagg acacaccaag ataagcacca gcattcctct gttgtcatct gcttcagttc   2400
ttgaggataa agtgtcagcg accagcacat tctcacacca caaagccacc tcatctatta   2460
ccacagggac tcctgaaatc tcaacaaaga caaagcccag ctcagccgtt ctttcctcca   2520
tgaccctaag caatgcagca acaagtcctg aaagagtcag aaatgcaact tcccctctga   2580
ctcatccatc tccatcaggg gaagagacag cagggagtgt cctcactctc agcacctctg   2640
ctgagactac agactcacct aacatccacc caactgggac actgacttca gaatcgtcag   2700
agagtcctag cactctcagc ctcccaagtg tctctggagt caaaaccaca ttttcttcat   2760
ctactccttc cactcatcta tttactagtg gagaagaaac agaggaaact tcgaatccat   2820
ctgtgtctca acctgagact tctgtttcca gagtaaggac caccttggcc agcacctctg   2880
tccctacccc agtattcccc accatggaca cctggcctac acgttcagct cagttctctt   2940
catcccacct agtgagtgag ctcagagcta cgagcagtac ctcagttaca aactcaactg   3000
gttcagctct tcctaaaata tctcacctca ctgggacggc aacaatgtca cagaccaata   3060
gagacacgtt taatgactct gctgcacccc aaagcacaac ttggccagag actagtccca   3120
gattcaagac agggttacct tcagcaacaa ccactgtttc aacctctgcc acttctctct   3180
ctgctactgt aatggtctct aaattcactt ctccagcaac tagttccatg gaagcaactt   3240
ctatcaggga accatcaaca accatcctca caacagagac cacgaatggc ccaggctcta   3300
tggctgtggc ttctaccaac atcccaattg gaaagggcta cattactgaa ggaagattgg   3360
acacaagcca tctgcccatt ggaaccacag cttcctctga gacatctatg gattttacca   3420
tggccaaaga aagtgtctca atgtcagtat ctccatctca gtccatggat gctgctggct   3480
caagcactcc aggaaggaca agccaattcg ttgacacatt ttctgatgat gtctatcatt   3540
taacatccag agaaattaca atacctagag atggaacaag ctcagctctg actccacaaa   3600
tgactgcaac tcaccctcca tctcctgatc ctggctctgc tagaagcacc tggcttggca   3660
tcttgtcctc atctccttct tctcctactc ccaaagtcac aatgagctcc acattttcaa   3720
ctcagagagt caccacaagc atgataatgg acacagttga aactagtcgg tggaacatgc   3780
ccaacttacc ttccacgact tccttgacac caagtaatat tccaacaagt ggtgccatag   3840
gaaaaagcac cctggttccc ttggacactc catctccagc cacatcattg gaggcatcag   3900
aagggggact tccaaccctc agcacctacc ctgaatcaac aaacacaccc agcatccacc   3960
tcggagcaca cgctagttca gaaagtccaa gcaccatcaa acttaccatg gcttcagtag   4020
taaaacctgg ctcttacaca cctctcacct tcccctcaat agagacccac attcatgtat   4080
caacagccag aatggcttac tcttctgggt cttcacctga gatgacagct cctggagaga   4140
ctaacactgg tagtacctgg gaccccacca cctacatcac cactacggat cctaaggata   4200
caagttcagc tcaggtctct acaccccact cagtgaggac actcagaacc acagaaaacc   4260
atccaaagac agagtccgcc accccagctg cttactctgg aagtcctaaa atctcaagtt   4320
cacccaatct caccagtccg gccacaaaag catggaccat cacagacaca actgaacact   4380
ccactcaatt acattacaca aaattggcag aaaaatcatc tggatttgag acacagtcag   4440
ctccaggacc tgtctctgta gtaatcccta cctcccctac cattggaagc agcacattgg   4500
aactaacttc tgatgtccca ggggaacccc tggtccttgc tcccagtgag cagaccacaa   4560
tcactctccc catggcaaca tggctgagta ccagtttgac agaggaaatg gcttcaacag   4620
```

```
accttgatat ttcaagtcca agttcaccca tgagtacatt tgctattttt ccacctatgt   4680
ccacaccttc tcatgaactt tcaaagtcag aggcagatac cagtgccatt agaaatacag   4740
attcaacaac gttggatcag cacctaggaa tcaggagttt gggcagaact ggggacttaa   4800
caactgttcc tatcacccca ctgacaacca cgtggaccag tgtgattgaa cactcaacac   4860
aagcacagga caccctttct gcaacgatga gtcctactca cgtgacacag tcactcaaag   4920
atcaaacatc tataccagcc tcagcatccc cttcccatct tactgaagtc taccctgagc   4980
tcgggacaca agggagaagc tcctctgagg caaccacttt ttggaaacca tctacagaca   5040
cactgtccag agagattgag actggcccaa caaacattca atccactcca cccatggaca   5100
acacaacaac agggagcagt agtagtggag tcaccctggg catagcccac cttcccatag   5160
gaacatcctc cccagctgag acatccacaa acatggcact ggaaagaaga agttctacag   5220
ccactgtctc tatggctggg acaatgggac tccttgttac tagtgctcca ggaagaagca   5280
tcagccagtc attaggaaga gtttcctctg tcctttctga gtcaactact gaaggagtca   5340
cagattctag taagggaagc agcccaaggc tgaacacaca gggaaataca gctctctcct   5400
cctctcttga acccagctat gctgaaggaa gccagatgag cacaagcatc cctctaacct   5460
catctcctac aactcctgat gtggaattca tagggggcag cacattttgg accaaggagg   5520
tcaccacagt tatgacctca gacatctcca agtcttcagc aaggacagag tccagctcag   5580
ctacccttat gtccacagct ttgggaagca ctgaaaatac aggaaaagaa aaactcagaa   5640
ctgcctctat ggatcttcca tctccaactc catcaatgga ggtgacacca tggatttctc   5700
tcactctcag taatgccccc aataccacag attcacttga cctcagccat ggggtgcaca   5760
ccagctctgc agggactttg gccactgaca ggtcattgaa tactggtgtc actagagcct   5820
ccagattgga aaacggctct gatacctctt ctaagtccct gtctatggga aacagcactc   5880
acacttccat gacttacaca gagaagagtg aagtgtcttc ttcaatccat ccccgacctg   5940
agacctcagc tcctggagca gagaccactt tgacttccac tcctggaaac agggccataa   6000
gcttaacatt gcctttttca tccattccag tggaagaagt catttctaca ggcataacct   6060
caggaccaga catcaactca gcacccatga cacattctcc catcacccca ccaacaattg   6120
tatggaccag tacaggcaca attgaacagt ccactcaacc actacatgca gtttcttcag   6180
aaaaagtttc tgtgcagaca cagtcaactc catatgtcaa ctctgtggca gtgtctgctt   6240
cccctaccca tgagaattca gtctcttctg gaagcagcac atcctctcca tattcctcag   6300
cctcacttga atccttggat tccacaatca gtaggaggaa tgcaatcact tcctggctat   6360
gggacctcac tacatctctc cccactacaa cttggccaag tactagttta tctgaggcac   6420
tgtcctcagg ccattctggg gtttcaaacc caagttcaac tacgactgaa tttccactct   6480
tttcagctgc atccacatct gctgctaagc aaagaaatcc agaaacagag acccatggtc   6540
cccagaatac agccgcgagt actttgaaca ctgatgcatc ctcggtcaca ggtctttctg   6600
agactcctgt gggggcaagt atcagctctg aagtccctct tccaatggcc ataacttcta   6660
gatcagatgt ttctggcctt acatctgaga gtactgctaa cccgagttta ggcacagcct   6720
cttcagcagg gaccaaatta actaggacaa tatccctgcc cacttcagag tctttggttt   6780
cctttagaat gaacaaggat ccatggacag tgtcaatccc tttggggtcc catccaacta   6840
ctaatacaga aacaagcatc ccagtaaaca gcgcaggtcc acctggcttg tccacagtag   6900
catcagatgt aattgacaca ccttcagatg ggctgagag tattcccact gtctcctttt   6960
```

```
ccccctcccc tgatactgaa gtgacaacta tctcacattt cccagaaaag acaactcatt   7020
catttagaac catttcatct ctcactcatg agttgacttc aagagtgaca cctattcctg   7080
gggattggat gagttcagct atgtctacaa agcccacagg agccagtccc tccattacac   7140
tgggagagag aaggacaatc acctctgctg ctccaaccac ttcccccata gttctcactg   7200
ctagtttcac agagaccagc acagtttcac tggataatga aactacagta aaaacctcag   7260
atatccttga cgcacggaaa acaaatgagc tcccctcaga tagcagttct tcttctgatc   7320
tgatcaacac ctccatagct tcttcaacta tggatgtcac taaaacagcc tccatcagtc   7380
ccactagcat ctcaggaatg acagcaagtt cctccccatc tctcttctct tcagatagac   7440
cccaggttcc cacatctaca acagagacaa atacagccac ctctccatct gtttccagta   7500
acacctattc tcttgatggg ggctccaatg tgggtggcac tccatccact ttaccaccct   7560
ttacaatcac ccaccctgtc gagacaagct cggccctatt agcctggtct agaccagtaa   7620
gaactttcag caccatggtc agcactgaca ctgcctccgg agaaaatcct acctctagca   7680
attctgtggt gacttctgtt ccagcaccag gtacatggac cagtgtaggc agtactactg   7740
acttacctgc catgggcttt ctcaagacaa gtcctgcagg agaggcacac tcacttctag   7800
catcaactat tgaaccagcc actgccttca ctccccatct ctcagcagca gtggtcactg   7860
gatccagtgc tacatcagaa gccagtcttc tcactacgag tgaaagcaaa gccattcatt   7920
cttcaccaca gaccccaact acacccacct ctggagcaaa ctgggaaact tcagctactc   7980
ctgagagcct tttggtagtc actgagactt cagacacaac acttacctca aagattttgg   8040
tcacagatac catcttgttt tcaactgtgt ccacgccacc ttctaaattt ccaagtacgg   8100
ggactctgtc tggagcttcc ttccctactt tactcccgga cactccagcc atccctctca   8160
ctgccactga gccaacaagt tcattagcta catcctttga ttccacccca ctggtgacta   8220
tagcttcgga tagtcttggc acagtcccag agactaccct gaccatgtca gagacctcaa   8280
atggtgatgc actggttctt aagacagtaa gtaacccaga taggagcatc cctggaatca   8340
ctatccaagg agtaacagaa agtccactcc atccttcttc cacttccccc tctaagattg   8400
ttgctccacg gaatacaacc tatgaaggtt cgatcacagt ggcactttct actttgcctg   8460
cgggaactac tggttccctt gtattcagtc agagttctga aaactcagag acaacggctt   8520
tggtagactc atcagctggg cttgagaggg catctgtgat gccactaacc acaggaagcc   8580
agggtatggc tagctctgga ggaatcagaa gtgggtccac tcactcaact ggaaccaaaa   8640
cattttcttc tctccctctg accatgaacc caggtgaggt tacagccatg tctgaaatca   8700
ccacgaacag actgacagct actcaatcaa cagcacccaa agggatacct gtgaagccca   8760
ccagtgctga gtcaggcctc ctaacacctg tctctgcctc ctcaagccca tcaaaggcct   8820
ttgcctcact gactacagct cccccaactt gggggatccc acagtctacc ttgacatttg   8880
agttttctga ggtcccaagt ttggatacta agtccgcttc tttaccaact cctggacagt   8940
ccctgaacac cattccagac tcagatgcaa gcacagcatc ttcctcactg tccaagtctc   9000
cagaaaaaaa cccaagggca aggatgatga cttccacaaa ggccataagt gcaagctcat   9060
ttcaatcaac aggttttact gaaacccctg agggatctgc ctccccttct atggcagggc   9120
atgaacccag agtccccact tcaggaacag gggaccctag atatgcctca gagagcatgt   9180
cttatccaga cccaagcaag gcatcatcag ctatgacatc gacctctctt gcatcaaaac   9240
tcacaactct cttcagcaca ggtcaagcag caaggtctgg ttctagttcc tctcccataa   9300
gcctatccac tgagaaagaa acaagcttcc tttcccccac tgcatccacc tccagaaaga   9360
```

```
cttcactatt tcttgggcct tccatggcaa ggcagcccaa catattggtg catcttcaga   9420
cttcagctct gacactttct ccaacatcca ctctaaatat gtcccaggag gagcctcctg   9480
agttaacctc aagccagacc attgcagaag aagagggaac aacagctgaa acacagacgt   9540
taaccttcac accatctgag accccaacat ccttgttacc tgtctcttct cccacagaac   9600
ccacagccag aagaaagagt tctccagaaa catgggcaag ctctatttca gttcctgcca   9660
agacctcctt ggttgaaaca actgatggaa cgctagtgac caccataaag atgtcaagcc   9720
aggcagcaca aggaaattcc acgtggcctg ccccagcaga ggagacgggg agcagtccag   9780
caggcacatc cccaggaagc ccagaaatgt ctaccactct caaaatcatg agctccaagg   9840
aacccagcat cagcccagag atcaggtcca ctgtgagaaa ttctccttgg aagactccag   9900
aaacaactgt tcccatggag accacagtgg aaccagtcac ccttcagtcc acagccctag   9960
gaagtggcag caccagcatc tctcacctgc ccacaggaac cacatcacca accaagtcac  10020
caacagaaaa tatgttggct acagaaaggg tctccctctc ccccatcccca cctgaggctt  10080
ggaccaacct ttattctgga actccaggag ggaccaggca gtcactggcc acaatgtcct  10140
ctgtctccct agagtcacca actgctagaa gcatcacagg gactggtcag caaagcagtc  10200
cagaactggt ttcaaagaca actggaatgg aattctctat gtggcatggc tctactggag  10260
ggaccacagg ggacacacat gtctctctga gcacatcttc caatatcctt gaagaccctg  10320
taaccagccc aaactctgtg agctcattga cagataaatc caaacataaa accgagacat  10380
gggtaagcac cacagccatt ccctccactg tcctgaataa taagataatg gcagctgaac  10440
aacagacaag tcgatctgtg gatgaggctt attcatcaac tagttcttgg tcagatcaga  10500
catctgggag tgacatcacc cttggtgcat ctcctgatgt cacaaacaca ttatacatca  10560
cctccacagc acaaaccacc tcactagtgt ctctgccctc tggagaccaa ggcattacaa  10620
gcctcaccaa tccctcagga ggaaaaacaa gctctgcgtc atctgtcaca tctccttcaa  10680
tagggcttga gactctgagg gccaatgtaa gtgcagtgaa aagtgacatt gcccctactg  10740
ctgggcatct atctcagact tcatctcctg cggaagtgag catcctggac gtaaccacag  10800
ctcctactcc aggtatctcc accaccatca ccaccatggg aaccaactca atctcaacta  10860
ccacacccaa cccagaagtg ggtatgagta ccatggacag caccccggcc acagagaggc  10920
gcacaacttc tacagaacac ccttccacct ggtcttccac agctgcatca gattcctgga  10980
ctgtcacaga catgacttca aacttgaaag ttgcaagatc tcctggaaca atttccacaa  11040
tgcatacaac ttcattctta gcctcaagca ctgaattaga ctccatgtct actccccatg  11100
gccgtataac tgtcattgga accagcctgg tcactccatc ctctgatgct tcagctgtaa  11160
agacagagac cagtacaagt gaaagaacat tgagtccttc agacacaact gcatctactc  11220
ccatctcaac tttttctcgt gtccagagga tgagcatctc agttcctgac attttaagta  11280
caagttggac tcccagtagt acagaagcag aagatgtgcc tgtttcaatg gtttctacag  11340
atcatgctag tacaaagact gacccaaata cgcccctgtc cacttttctg tttgattctc  11400
tgtccactct tgactgggac actgggagat ctctgtcatc agccacagcc actacctcag  11460
ctcctcaggg ggccacaact ccccaggaac tcactttgga aaccatgatc agcccagcta  11520
cctcacagtt gcccttctct atagggcaca ttacaagtgc agtcacacca gctgcaatgg  11580
caaggagctc tggagttact ttttcaagac cagatcccac aagcaaaaag gcagagcaga  11640
cttccactca gcttcccacc accacttctg cacatccagg gcaggtgccc agatcagcag  11700
```

-continued

```
caacaactct ggatgtgatc ccacacacag caaaaactcc agatgcaact tttcagagac  11760
aagggcagac agctcttaca acagaggcaa gagctacatc tgactcctgg aatgagaaag  11820
aaaaatcaac cccaagtgca ccttggatca ctgagatgat gaattctgtc tcagaagata  11880
ccatcaagga ggttaccagc tcctccagtg tattaaggac cctgaatacg ctggacataa  11940
acttggaatc tgggacgact tcatccccaa gttggaaaag cagcccatat gagagaattg  12000
ccccttctga gtccaccaca gacaaagagg caattcaccc ttctacaaac acagtagaga  12060
ccacaggctg ggtcacaagt tccgaacatg cttctcattc cactatccca gcccactcag  12120
cgtcatccaa actcacatct ccagtggtta caacctccac cagggaacaa gcaatagttt  12180
ctatgtcaac aaccacatgg ccagagtcta caagggctag aacagagcct aattccttct  12240
tgactattga actgagggac gtcagccctt acatggacac cagctcaacc acacaaacaa  12300
gtattatctc ttccccaggt tccactgcga tcaccaaggg gcctagaaca gaaattacct  12360
cctctaagag aatatccagc tcattccttg cccagtctat gaggtcgtca gacagcccct  12420
cagaagccat caccaggctg tctaactttc ctgccatgac agaatctgga ggaatgatcc  12480
ttgctatgca aacaagtcca cctggcgcta catcactaag tgcacctact ttggatacat  12540
cagccacagc ctcctggaca gggactccac tggctacgac tcagagattt acatactcag  12600
agaagaccac tctctttagc aaaggtcctg aggatacatc acagccaagc cctccctctg  12660
tggaagaaac cagctcttcc tcttccctgg tacctatcca tgctacaacc tcgccttcca  12720
atattttgtt gacatcacaa gggcacagtc cctcctctac tccacctgtg acctcagttt  12780
tcttgtctga gacctctggc ctggggaaga ccacagacat gtcgaggata agcttggaac  12840
ctggcacaag tttacctccc aatttgagca gtacagcagg tgaggcgtta tccacttatg  12900
aagcctccag agatacaaag gcaattcatc attctgcaga cacagcagtg acgaatatgg  12960
aggcaaccag ttctgaatat tctcctatcc caggccatac aaagccatcc aaagccacat  13020
ctccattggt tacctcccac atcatggggg acatcacttc ttccacatca gtatttggct  13080
cctccgagac cacagagatt gagacagtgt cctctgtgaa ccagggactt caggagagaa  13140
gcacatccca ggtggccagc tctgctacag agacaagcac tgtcattacc catgtgtcta  13200
gtggtgatgc tactactcat gtcaccaaga cacaagccac tttctctagc ggaacatcca  13260
tctcaagccc tcatcagttt ataacttcta ccaacacatt tacagatgtg agcaccaacc  13320
cctccacctc tctgataatg acagaatctt caggagtgac catcaccacc caaacaggtc  13380
ctactggagc tgcaacacag ggtccatatc tcttggacac atcaaccatg ccttacttga  13440
cagagactcc attagctgtg actccagatt ttatgcaatc agagaagacc actctcataa  13500
gcaaaggtcc caaggatgtg tcctggacaa gccctccctc tgtggcagaa accagctatc  13560
cctcttccct gacacctttc ttggtcacaa ccatacctcc tgccacttcc acgttacaag  13620
ggcaacatac atcctctcct gtttctgcga cttcagttct tacctctgga ctggtgaaga  13680
ccacagatat gttgaacaca agcatggaac ctgtgaccaa ttcacctcaa aatttgaaca  13740
atccatcaaa tgagatactg gccactttgg cagccaccac agatatagag actattcatc  13800
cttccataaa caaagcagtg accaatatgg ggactgccag ttcagcacat gtactgcatt  13860
ccactctccc agtcagctca gaaccatcta cagccacatc tccaatggtt cctgcctcca  13920
gcatggggga cgctcttgct tctatatcaa tacctggttc tgagaccaca gacattgagg  13980
gagagccaac atcctccctg actgctggac gaaaagagaa cagcaccctc caggagatga  14040
actcaactac agagtcaaac atcatcctct ccaatgtgtc tgtgggggct attactgaag  14100
```

```
ccacaaaaat ggaagtcccc tcttttgatg caacattcat accaactcct gctcagtcaa  14160
caaagttccc agatattttc tcagtagcca gcagtagact ttcaaactct cctcccatga  14220
caatatctac ccacatgacc accacccaga cagggtcttc tggagctaca tcaaagattc  14280
cacttgcctt agacacatca accttggaaa cctcagcagg gactccatca gtggtgactg  14340
aggggtttgc ccactcaaaa ataaccactg caatgaacaa tgatgtcaag gacgtgtcac  14400
agacaaaccc tccctttcag gatgaagcca gctctccctc ttctcaagca cctgtccttg  14460
tcacaacctt accttcttct gttgctttca caccgcaatg gcacagtacc tcctctcctg  14520
tttctatgtc ctcagttctt acttcttcac tggtaaagac cgcaggcaag gtggatacaa  14580
gcttagaaac agtgaccagt tcacctcaaa gtatgagcaa cactttggat gacatatcgg  14640
tcacttcagc agccaccaca gatatagaga caacgcatcc ttccataaac acagtagtta  14700
ccaatgtggg gaccaccggt tcagcatttg aatcacattc tactgtctca gcttacccag  14760
agccatctaa agtcacatct ccaaatgtta ccacctccac catggaagac accacaattt  14820
ccagatcaat acctaaatcc tctaagacta caagaactga gactgagaca acttcctccc  14880
tgactcctaa actgagggag accagcatct cccaggagat cacctcgtcc acagagacaa  14940
gcactgttcc ttacaaagag ctcactggtg ccactaccga ggtatccagg acagatgtca  15000
cttcctctag cagtacatcc ttccctggcc ctgatcagtc cacagtgtca ctagacatct  15060
ccacagaaac caacaccagg ctgtctacct ccccaataat gacagaatct gcagaaataa  15120
ccatcaccac ccaaacaggt cctcatgggg ctacatcaca ggatactttt accatggacc  15180
catcaaatac aacccccag gcagggatcc actcagctat gactcatgga ttttcacaat  15240
tggatgtgac cactcttatg agcagaattc cacaggatgt atcatggaca agtcctccct  15300
ctgtggataa aaccagctcc ccctcttcct ttctgtcctc acctgcaatg accacacctt  15360
ccctgatttc ttctacctta ccagaggata agctctcctc tcctatgact tcacttctca  15420
cctctggcct agtgaagatt acagacatat tacgtacacg cttggaacct gtgaccagct  15480
cacttccaaa tttcagcagc acctcagata agatactggc cacttctaaa gacagtaaag  15540
acacaaagga atttttcct tctataaaca cagaagagac caatgtgaaa gccaacaact  15600
ctggacatga atcccattcc cctgcactgg ctgactcaga gacacccaaa gccacaactc  15660
aaatggttat caccaccact gtgggagatc cagctccttc cacatcaatg ccagtgcatg  15720
gttcctctga gactacaaac attaagagag agccaacata tttcttgact cctagactga  15780
gagagaccag tacctctcag gagtccagct ttcccacgga cacaagtttt ctactttcca  15840
aagtccccac tggtactatt actgaggtct ccagtacagg ggtcaactct tctagcaaaa  15900
tttccacccc agaccatgat aagtccacag tgccacctga caccttcaca ggagagatcc  15960
ccagggtctt cacctcctct attaagacaa aatctgcaga aatgacgatc accacccaag  16020
caagtcctcc tgagtctgca tcgcacagta cccttccctt ggacacatca accacacttt  16080
cccagggagg gactcattca actgtgactc agggattccc atactcagag gtgaccactc  16140
tcatgggcat gggtcctggg aatgtgtcat ggatgacaac tccccctgtg gaagaaacca  16200
gctctgtgtc ttccctgatg tcttcacctg ccatgacatc cccttctcct gtttcctcca  16260
catcaccaca gagcatcccc tcctctcctc ttcctgtgac tgcacttcct acttctgttc  16320
tggtgacaac cacagatgtg ttgggcacaa caagcccaga gtctgtaacc agttcacctc  16380
caaatttgag cagcatcact catgagagac cggccactta caaagacact gcacacacag  16440
```

aagccgccat gcatcattcc acaaacaccg cagtgaccaa tgtagggact tccgggtctg 16500
gacataaatc acaatcctct gtcctagctg actcagagac atcgaaagcc acacctctga 16560
tgagtaccac ctccaccctg ggggacacaa gtgtttccac atcaactcct aatatctctc 16620
agactaacca aattcaaaca gagccaacag catccctgag ccctagactg agggagagca 16680
gcacgtctga gaagaccagc tcaacaacag agacaaatac tgccttttct tatgtgccca 16740
caggtgctat tactcaggcc tccagaacag aaatctcctc tagcagaaca tccatctcag 16800
accttgatcg gcccacaata gcacccgaca tctccacagg aatgatcacc aggctcttca 16860
cctcccccat catgacaaaa tctgcagaaa tgaccgtcac cactcaaaca actactcctg 16920
gggctacatc acagggtatc cttccctggg acacatcaac cacacttttc cagggaggga 16980
ctcattcaac cgtgtctcag ggattcccac actcagagat aaccactctt cggagcagaa 17040
cccctggaga tgtgtcatgg atgacaactc cccctgtgga agaaaccagc tctgggtttt 17100
ccctgatgtc accttccatg acatcccctt ctcctgtttc ctccacatca ccagagagca 17160
tcccctcctc tcctctccct gtgactgcac ttcttacttc tgttctggtg acaaccacaa 17220
atgtattggg cacaacaagc ccagagcccg taacgagttc acctccaaat ttaagcagcc 17280
ccacacagga gagactgacc acttacaaag acactgcgca cacagaagcc atgcatgctt 17340
ccatgcatac aaacactgca gtggccaacg tggggacctc catttctgga catgaatcac 17400
aatcttctgt cccagctgat tcacacacat ccaaagccac atctccaatg ggtatcacct 17460
tcgccatggg ggatacaagt gtttctacat caactcctgc cttctttgag actagaattc 17520
agactgaatc aacatcctct ttgattcctg gattaaggga caccaggacg tctgaggaga 17580
tcaacactgt gacagagacc agcactgtcc tttcagaagt gcccactact actactactg 17640
aggtctccag gacagaagtt atcacttcca gcagaacaac catctcaggg cctgatcatt 17700
ccaaaatgtc accctacatc tccacagaaa ccatcaccag gctctccact tttccttttg 17760
taacaggatc cacagaaatg gccatcacca accaaacagg tcctataggg actatctcac 17820
aggctaccct taccctggac acatcaagca cagcttcctg ggaagggact cactcacctg 17880
tgactcagag atttccacac tcagaggaga ccactactat gagcagaagt actaagggcg 17940
tgtcatggca aagccctccc tctgtggaag aaaccagttc tccttcttcc ccagtgcctt 18000
tacctgcaat aacctcacat tcatctcttt attccgcagt atcaggaagt agccccactt 18060
ctgctctccc tgtgacttcc cttctcacct ctggcaggag gaagaccata gacatgttgg 18120
acacacactc agaacttgtg accagctcct taccaagtgc aagtagcttc tcaggtgaga 18180
tactcacttc tgaagcctcc acaaatacag agacaattca cttttcagag aacacagcag 18240
aaaccaatat ggggaccacc aattctatgc ataaactaca ttcctctgtc tcaatccact 18300
cccagccatc cggacacaca cctccaaagg ttactggatc tatgatggag gacgctattg 18360
tttccacatc aacacctggt tctcctgaga ctaaaaatgt tgacagagac tcaacatccc 18420
ctctgactcc tgaactgaaa gaggacagca ccgccctggt gatgaactca actacagagt 18480
caaacactgt tttctccagt gtgtccctgg atgctgctac tgaggtctcc agggcagaag 18540
tcacctacta tgatcctaca ttcatgccag cttctgctca gtcaacaaag tccccagaca 18600
tttcacctga agccagcagc agtcattcta actctcctcc cttgacaata tctacacaca 18660
agaccatcgc cacacaaaca ggtccttctg ggtgacatc tcttggccaa ctgaccctgg 18720
acacatcaac catagccacc tcagcaggaa ctccatcagc cagaactcag gattttgtag 18780
attcagaaac aaccagtgtc atgaacaatg atctcaatga tgtgttgaag acaagccctt 18840
tctctgcaga agaagccaac tctctctctt ctcaggcacc tctccttgtg acaacctcac 18900
cttctcctgt aacttccaca ttgcaagagc acagtacctc ctctcttgtt tctgtgacct 18960
cagtacccac ccctacactg gcgaagatca cagacatgga cacaaactta gaacctgtga 19020
ctcgttcacc tcaaaattta aggaacacct tggccacttc agaagccacc acagatacac 19080
acacaatgca tccttctata aacacagcag tggccaatgt ggggaccacc agttcaccaa 19140
atgaattcta ttttactgtc tcacctgact cagacccata taaagccaca tccgcagtag 19200
ttatcacttc cacctcgggg gactcaatag tttccacatc aatgcctaga tcctctgcga 19260
tgaaaaagat tgagtctgag acaactttct ccctgatatt tagactgagg gagactagca 19320
cctcccagaa aattggctca tcctcagaca caagcacggt ctttgacaaa gcattcactg 19380
ctgctactac tgaggtctcc agaacagaac tcacctcctc tagcagaaca tccatccaag 19440
gcactgaaaa gcccacaatg tcaccggaca cctccacaag atctgtcacc atgctttcta 19500
cttttgctgg cctgacaaaa tccgaagaaa ggaccattgc cacccaaaca ggtcctcata 19560
gggcgacatc acagggtacc cttacctggg acacatcaat cacaacctca caggcaggga 19620
cccactcagc tatgactcat ggattttcac aattagattt gtccactctt acgagtagag 19680
ttcctgagta catatcaggg acaagcccac cctctgtgga aaaaaccagc tcttcctctt 19740
cccttctgtc tttaccagca ataacctcac cgtcccctgt acctactaca ttaccagaaa 19800
gtaggccgtc ttctcctgtt catctgactt cactccccac ctctggccta gtgaagacca 19860
cagatatgct ggcatctgtg gccagtttac ctccaaactt gggcagcacc tcacataaga 19920
taccgactac ttcagaagac attaaagata cagagaaaat gtatccttcc acaaacatag 19980
cagtaaccaa tgtggggacc accacttctg aaaaggaatc ttattcgtct gtcccagcct 20040
actcagaacc acccaaagtc acctctccaa tggttacctc tttcaacata agggacacca 20100
ttgtttccac atccatgcct ggctcctctg agattacaag gattgagatg gagtcaacat 20160
tctccctggc tcatgggctg aagggaacca gcacctccca ggaccccatc gtatccacag 20220
agaaaagtgc tgtccttcac aagttgacca ctggtgctac tgagacctct aggacagaag 20280
ttgcctcttc tagaagaaca tccattccag gccctgatca ttccacagag tcaccagaca 20340
tctccactga agtgatcccc agcctgccta tctcccttgg cattacagaa tcttcaaata 20400
tgaccatcat cactcgaaca ggtcctcctc ttggctctac atcacagggc acatttacct 20460
tggacacacc aactacatcc tccagggcag gaacacactc gatggcgact caggaatttc 20520
cacactcaga aatgaccact gtcatgaaca aggaccctga gattctatca tggacaatcc 20580
ctccttctat agagaaaacc agcttctcct cttccctgat gccttcacca gccatgactt 20640
cacctcctgt ttcctcaaca ttaccaaaga ccattcacac cactccttct cctatgacct 20700
cactgctcac ccctagccta gtgatgacca cagacacatt gggcacaagc ccagaaccta 20760
caaccagttc acctccaaat ttgagcagta cctcacatga gatactgaca acagatgaag 20820
acaccacagc tatagaagcc atgcatcctt ccacaagcac agcagcgact aatgtggaaa 20880
ccaccagttc tggacatggg tcacaatcct ctgtcctagc tgactcagaa aaaaccaagg 20940
ccacagctcc aatggatacc acctccacca tggggcatac aactgtttcc acatcaatgt 21000
ctgtttcctc tgagactaca aaaattaaga gagagtcaac atattccttg actcctggac 21060
tgagagagac cagcatttcc caaaatgcca gcttttccac tgacacaagt attgttcttt 21120
cagaagtccc cactggtact actgctgagg tctccaggac agaagtcacc tcctctggta 21180
gaacatccat ccctggccct tctcagtcca cagttttgcc agaaatatcc acaagaacaa 21240
tgacaaggct ctttgcctcg cccaccatga cagaatcagc agaaatgacc atccccactc 21300
aaacaggtcc ttctgggtct acctcacagg ataccottac cttggacaca tccaccacaa 21360
agtcccaggc aaagactcat tcaactttga ctcagagatt tccacactca gagatgacca 21420
ctctcatgag cagaggtcct ggagatatgt catggcaaag ctctccctct ctggaaaatc 21480
ccagctctct cccttccctg ctgtctttac ctgccacaac ctcacctcct cccatttcct 21540
ccacattacc agtgactatc tcctcctctc ctcttcctgt gacttcactt ctcacctcta 21600
gcccggtaac gaccacagac atgttacaca caagcccaga acttgtaacc agttcacctc 21660
caaagctgag ccacacttca gatgagagac tgaccactgg caaggacacc acaaatacag 21720
aagctgtgca tccttccaca aacacagcag cgtccaatgt ggagattccc agctctggac 21780
atgaatcccc ttcctctgcc ttagctgact cagagacatc caaagccaca tcaccaatgt 21840
ttattacctc cacccaggag gatacaactg ttgccatatc aacccctcac ttcttggaga 21900
ctagcagaat tcagaaagag tcaatttcct ccctgagccc taaattgagg gagacaggca 21960
gttctgtgga gacaagctca gccatagaga caagtgctgt cctttctgaa gtgtccattg 22020
gtgctactac tgagatctcc aggacagaag tcacctcctc tagcagaaca tccatctctg 22080
gttctgctga gtccacaatg ttgccagaaa tatccaccac aagaaaaatc attaagttcc 22140
ctacttcccc catcctggca gaatcatcag aaatgaccat caagacccaa acaagtcctc 22200
ctgggtctac atcagagagt acctttacat tagacacatc aaccactccc tccttggtaa 22260
taacccattc gactatgact cagagattgc cacactcaga gataaccact cttgtgagta 22320
gaggtgctgg ggatgtgcca cggcccagct ctctccctgt ggaagaaaca agccctccat 22380
cttcccagct gtctttatct gccatgatct caccttctcc tgtttcttcc acattaccag 22440
caagtagcca ctcctcttct gcttctgtga cttcacttct cacaccaggc caagtgaaga 22500
ctactgaggt gttggacgca agtgcagaac ctgaaaccag ttcacctcca agtttgagca 22560
gcacctcagt tgaaatactg gccacctctg aagtcaccac agatacggag aaaattcatc 22620
ctttctcaaa cacggcagta accaaagttg gaacttccag ttctggacat gaatcccctt 22680
cctctgtcct acctgactca gagacaacca aagccacatc ggcaatgggt accatctcca 22740
ttatggggga tacaagtgtt tctacattaa ctcctgcctt atctaacact aggaaaattc 22800
agtcagagcc agcttcctca ctgaccacca gattgaggga gaccagcacc tctgaagaga 22860
ccagcttagc cacagaagca aacactgttc tttctaaagt gtccactggt gctactactg 22920
aggtctccag gacagaagcc atctccttta gcagaacatc catgtcaggc cctgagcagt 22980
ccacaatgtc acaagacatc tccataggaa ccatccccag gatttctgcc tcctctgtcc 23040
tgacagaatc tgcaaaaatg accatcacaa cccaaacagg tccttcggag tctacactag 23100
aaagtaccct taatttgaac acagcaacca caccctcttg ggtggaaacc cactctatag 23160
taattcaggg atttccacac ccagagatga ccacttccat gggcagaggt cctggaggtg 23220
tgtcatggcc tagccctccc tttgtgaaag aaaccagccc tccatcctcc ccgctgtctt 23280
tacctgccgt gacctcacct catcctgttt ccaccacatt cctagcacat atcccccccct 23340
ctccccttcc tgtgacttca cttctcacct ctggcccggc gacaaccaca gatatcttgg 23400
gtacaagcac agaacctgga accagttcat cttcaagttt gagcaccacc tcccatgaga 23460
gactgaccac ttacaaagac actgcacata cagaagccgt gcatccttcc acaaacacag 23520
gagggaccaa tgtggcaacc accagctctg gatataaatc acagtcctct gtcctagctg 23580

-continued

```
actcatctcc aatgtgtacc acctccacca tgggggatac aagtgttctc acatcaactc  23640
ctgccttcct tgagactagg aggattcaga cagagctagc ttcctccctg acccctggat  23700
tgagggagtc cagcggctct gaagggacca gctcaggcac caagatgagc actgtcctct  23760
ctaaagtgcc cactggtgct actactgaga tctccaagga agacgtcacc tccatcccag  23820
gtcccgctca atccacaata tcaccagaca tctccacaag aaccgtcagc tggttctcta  23880
catcccctgt catgacagaa tcagcagaaa taaccatgaa cacccataca agtcctttag  23940
gggccacaac acaaggcacc agtactttgg acacgtcaag cacaacctct ttgacaatga  24000
cacactcaac tatatctcaa ggattttcac actcacagat gagcactctt atgaggaggg  24060
gtcctgagga tgtatcatgg atgagccctc cccttctgga aaaaactaga ccttcctttt  24120
ctctgatgtc ttcaccagcc acaacttcac cttctcctgt ttcctccaca ttaccagaga  24180
gcatctcttc ctctcctctt cctgtgactt cactcctcac gtctggcttg gcaaaaacta  24240
cagatatgtt gcacaaaagc tcagaacctg taaccaactc acctgcaaat ttgagcagca  24300
cctcagttga aatactggcc acctctgaag tcaccacaga tacagagaaa actcatcctt  24360
cttcaaacag aacagtgacc gatgtgggga cctccagttc tggacatgaa tccacttcct  24420
ttgtcctagc tgactcacag acatccaaag tcacatctcc aatggttatt acctccacca  24480
tggaggatac gagtgtctcc acatcaactc ctggcttttt tgagactagc agaattcaga  24540
cagaaccaac atcctccctg acccttggac tgagaaagac cagcagctct gaggggacca  24600
gcttagccac agagatgagc actgtccttt ctggagtgcc cactggtgcc actgctgaag  24660
tctccaggac agaagtcacc tcctctagca gaacatccat ctcaggcttt gctcagctca  24720
cagtgtcacc agagacttcc acagaaacca tcaccagact ccctacctcc agcataatga  24780
cagaatcagc agaaatgatg atcaagacac aaacagatcc tcctgggtct acaccagaga  24840
gtactcatac tgtggacata tcaacaacac ccaactgggt agaaacccac tcgactgtga  24900
ctcagagatt ttcacactca gagatgacca ctcttgtgag cagaagccct ggtgatatgt  24960
tatggcctag tcaatcctct gtggaagaaa ccagctctgc ctcttccctg ctgtctctgc  25020
ctgccacgac ctcaccttct cctgtttcct ctacattagt agaggatttc ccttccgctt  25080
ctcttcctgt gacttctctt ctcaaccctg gcctggtgat aaccacagac aggatgggca  25140
taagcagaga acctggaacc agttccactt caaatttgag cagcacctcc catgagagac  25200
tgaccacttt ggaagacact gtagatacag aagacatgca gccttccaca cacacagcag  25260
tgaccaacgt gaggacctcc atttctggac atgaatcaca atcttctgtc ctatctgact  25320
cagagacacc caaagccaca tctccaatgg gtaccaccta caccatgggg gaaacgagtg  25380
tttccatatc cacttctgac ttctttgaga ccagcagaat tcagatagaa ccaacatcct  25440
ccctgacttc tggattgagg gagaccagca gctctgagag gatcagctca gccacagagg  25500
gaagcactgt cctttctgaa gtgcccagtg gtgctaccac tgaggtctcc aggacagaag  25560
tgatatcctc taggggaaca tccatgtcag ggcctgatca gttcaccata tcaccagaca  25620
tctctactga agcgatcacc aggctttcta cttcccccat tatgacagaa tcagcagaaa  25680
gtgccatcac tattgagaca ggttctcctg gggctacatc agagggtacc ctcaccttgg  25740
acacctcaac aacaaccttt tggtcaggga cccactcaac tgcatctcca ggattttcac  25800
actcagagat gaccactctt atgagtagaa ctcctggaga tgtgccatgg ccgagccttc  25860
cctctgtgga agaagccagc tctgtctctt cctcactgtc ttcacctgcc atgacctcaa  25920
```

```
cttctttttt ctccacatta ccagagagca tctcctcctc tcctcatcct gtgactgcac  25980
ttctcaccct tggcccagtg aagaccacag acatgttgcg cacaagctca gaacctgaaa  26040
ccagttcacc tccaaatttg agcagcacct cagctgaaat attagccacg tctgaagtca  26100
ccaaagatag agagaaaatt catccctcct caaacacacc tgtagtcaat gtagggactg  26160
tgatttataa acatctatcc ccttcctctg ttttggctga cttagtgaca acaaaaccca  26220
catctccaat ggctaccacc tccactctgg ggaatacaag tgtttccaca tcaactcctg  26280
ccttcccaga aactatgatg acacagccaa cttcctccct gacttctgga ttaagggaga  26340
tcagtacctc tcaagagacc agctcagcaa cagagagaag tgcttctctt tctggaatgc  26400
ccactggtgc tactactaag gtctccagaa cagaagccct ctccttaggc agaacatcca  26460
ccccaggtcc tgctcaatcc acaatatcac cagaaatctc cacggaaacc atcactagaa  26520
tttctactcc cctcaccacg acaggatcag cagaaatgac catcaccccc aaaacaggtc  26580
attctggggc atcctcacaa ggtaccttta ccttggacac atcaagcaga gcctcctggc  26640
caggaactca ctcagctgca actcacagat ctccacactc agggatgacc actcctatga  26700
gcagaggtcc tgaggatgtg tcatggccaa gccgcccatc agtggaaaaa actagccctc  26760
catcttccct ggtgtcttta tctgcagtaa cctcaccttc gccactttat tccacaccat  26820
ctgagagtag ccactcatct cctctccggg tgacttctct tttcacccct gtcatgatga  26880
agaccacaga catgttggac acaagcttgg aacctgtgac cacttcacct cccagtatga  26940
atatcacctc agatgagagt ctggccactt ctaaagccac catggagaca gaggcaattc  27000
agctttcaga aaacacagct gtgactcaga tgggcaccat cagcgctaga caagaattct  27060
attcctctta tccaggcctc ccagagccat ccaaagtgac atctccagtg gtcacctctt  27120
ccaccataaa agacattgtt tctacaacca tacctgcttc ctctgagata acaagaattg  27180
agatggagtc aacatccacc ctgaccccca caccaaggga gaccagcacc tcccaggaga  27240
tccactcagc cacaaagcca agcactgttc cttacaaggc actcactagt gccacgattg  27300
aggactccat gacacaagtc atgtcctcta gcagaggacc tagccctgat cagtccacaa  27360
tgtcacaaga catatccact gaagtgatca ccaggctctc tacctccccc atcaagacag  27420
aatctacaga aatgaccatt accacccaaa caggttctcc tggggctaca tcaaggggta  27480
cccttacctt ggacacttca acaactttta tgtcagggac ccactcaact gcatctcaag  27540
gattttcaca ctcacagatg accgctctta tgagtagaac tcctggagat gtgccatggc  27600
taagccatcc ctctgtggaa gaagccagct ctgcctcttt ctcactgtct tcacctgtca  27660
tgacctcatc ttctcccgtt tcttccacat taccagacag catccactct tcttcgcttc  27720
ctgtgacatc acttctcacc tcagggctgg tgaagaccac agagctgttg ggcacaagct  27780
cagaacctga aaccagttca cccccaaatt tgagcagcac ctcagctgaa atactggcca  27840
tcactgaagt cactacagat acagagaaac tggagatgac caatgtggta acctcaggtt  27900
atacacatga atctccttcc tctgtcctag ctgactcagt gacaacaaag gccacatctt  27960
caatgggtat cacctacccc acaggagata caaatgttct cacatcaacc cctgccttct  28020
ctgacaccag taggattcaa acaaagtcaa agctctcact gactcctggg ttgatggaga  28080
ccagcatctc tgaagagacc agctctgcca cagaaaaaag cactgtcctt tctagtgtgc  28140
ccactggtgc tactactgag gtctccagga cagaagccat ctcttctagc agaacatcca  28200
tcccaggccc tgctcaatcc acaatgtcat cagacacctc catggaaacc atcactagaa  28260
tttctacccc cctcacaagg aaagaatcaa cagacatggc catcaccccc aaaacaggtc  28320
```

-continued

```
cttctggggc tacctcgcag ggtaccttta ccttggactc atcaagcaca gcctcctggc  28380
caggaactca ctcagctaca actcagagat ttccacagtc agtggtgaca actcctatga  28440
gcagaggtcc tgaggatgtg tcatggccaa gcccgctgtc tgtggaaaaa aacagccctc  28500
catcttccct ggtatcttca tcttcagtaa cctcaccttc gccactttat tccacaccat  28560
ctgggagtag ccactcctct cctgtccctg tcacttctct tttcacctct atcatgatga  28620
aggccacaga catgttggat gcaagtttgg aacctgagac cacttcagct cccaatatga  28680
atatcacctc agatgagagt ctggccgctt ctaaagccac cacggagaca gaggcaattc  28740
acgtttttga aaatacagca gcgtcccatg tggaaaccac cagtgctaca gaggaactct  28800
attcctcttc cccaggcttc tcagagccaa caaaagtgat atctccagtg gtcacctctt  28860
cctctataag agacaacatg gtttccacaa caatgcctgg ctcctctggc attacaagga  28920
ttgagataga gtcaatgtca tctctgaccc ctggactgag ggagaccaga acctcccagg  28980
acatcacctc atccacagag acaagcactg tcctttacaa gatgccctct ggtgccactc  29040
ctgaggtctc caggacagaa gttatgccct ctagcagaac atccattcct ggccctgctc  29100
agtccacaat gtcactagac atctccgatg aagttgtcac caggctgtct acctctccca  29160
tcatgacaga atctgcagaa ataaccatca ccacccaaac aggttattct ctggctacat  29220
cccaggttac ccttcccttg ggcacctcaa tgaccttttt gtcagggacc cactcaacta  29280
tgtctcaagg actttcacac tcagagatga ccaatcttat gagcaggggt cctgaaagtc  29340
tgtcatggac gagccctcgc tttgtggaaa caactagatc ttcctcttct ctgacatcat  29400
tacctctcac gacctcactt tctcctgtgt cctccacatt actagacagt agcccctcct  29460
ctcctcttcc tgtgacttca cttatcctcc caggcctggt gaagactaca gaagtgttgg  29520
atacaagctc agagcctaaa accagttcat ctccaaattt gagcagcacc tcagttgaaa  29580
taccggccac ctctgaaatc atgacagata cagagaaaat tcatccttcc tcaaacacag  29640
cggtggccaa agtgaggacc tccagttctg ttcatgaatc tcattcctct gtcctagctg  29700
actcagaaac aaccataacc ataccttcaa tgggtatcac ctccgctgtg gacgatacca  29760
ctgttttcac atcaaatcct gccttctctg agactaggag gattccgaca gagccaacat  29820
tctcattgac tcctggattc agggagacta gcacctctga agagaccacc tcaatcacag  29880
aaacaagtgc agtcctttat ggagtgccca ctagtgctac tactgaagtc tccatgacag  29940
aaatcatgtc ctctaataga atacacatcc ctgactctga tcagtccacg atgtctccag  30000
acatcatcac tgaagtgatc accaggctct cttcctcatc catgatgtca gaatcaacac  30060
aaatgaccat caccacccaa aaaagttctc ctggggctac agcacagagt actcttacct  30120
tggccacaac aacagccccc ttggcaagga cccactcaac tgttcctcct agatttttac  30180
actcagagat gacaactctt atgagtagga gtcctgaaaa tccatcatgg aagagctctc  30240
tctttgtgga aaaaactagc tcttcatctt ctctgttgtc cttacctgtc acgacctcac  30300
cttctgtttc ttccacatta ccgcagagta tcccttcctc ctctttttct gtgacttcac  30360
tcctcacccc aggcatggtg aagactacag acacaagcac agaacctgga accagtttat  30420
ctccaaatct gagtggcacc tcagttgaaa tactggctgc ctctgaagtc accacagata  30480
cagagaaaat tcatccttct tcaagcatgg cagtgaccaa tgtgggaacc accagttctg  30540
gacatgaact atattcctct gtttcaatcc actcggagcc atccaaggct acataccag  30600
tgggtactcc ctcttccatg gctgaaacct ctatttccac atcaatgcct gctaattttg  30660
```

-continued agaccacagg atttgaggct gagccatttt ctcatttgac ttctggattt aggaagacaa 30720
acatgtccct ggacaccagc tcagtcacac caacaaatac accttcttct cctgggtcca 30780
ctcacctttt acagagttcc aagactgatt tcacctcttc tgcaaaaaca tcatccccag 30840
actggcctcc agcctcacag tatactgaaa ttccagtgga cataatcacc ccctttaatg 30900
cttctccatc tattacggag tccactggga taacctcctt cccagaatcc aggtttacta 30960
tgtctgtaac agaaagtact catcatctga gtacagattt gctgccttca gctgagacta 31020
tttccactgg cacagtgatg ccttctctat cagaggccat gacttcattt gccaccactg 31080
gagttccacg agccatctca ggttcaggta gtccattctc taggacagag tcaggccctg 31140
gggatgctac tctgtccacc attgcagaga gcctgccttc atccactcct gtgccattct 31200
cctcttcaac cttcactacc actgattctt caaccatccc agccctccat gagataactt 31260
cctcttcagc taccccatat agagtggaca ccagtcttgg gacagagagc agcactactg 31320
aaggacgctt ggttatggtc agtactttgg acacttcaag ccaaccaggc aggacatctt 31380
catcacccat tttggatacc agaatgacag agagcgttga gctgggaaca gtgacaagtg 31440
cttatcaagt tccttcactc tcaacacggt tgacaagaac tgatggcatt atggaacaca 31500
tcacaaaaat acccaatgaa gcagcacaca gaggtaccat aagaccagtc aaaggccctc 31560
agacatccac ttcgcctgcc agtcctaaag gactacacac aggagggaca aaaagaatgg 31620
agaccaccac cacagctctg aagaccacca ccacagctct gaagaccact tccagagcca 31680
ccttgaccac cagtgtctat actcccactt tgggaacact gactcccctc aatgcatcaa 31740
tgcaaatggc cagcacaatc cccacagaaa tgatgatcac aaccccatat gttttccctg 31800
atgttccaga aacgacatcc tcattggcta ccagcctggg agcagaaacc agcacagctc 31860
ttcccaggac aaccccatct gttttcaata gagaatcaga gaccacagcc tcactggtct 31920
ctcgttctgg ggcagagaga agtccggtta ttcaaactct agatgtttct tctagtgagc 31980
cagatacaac agcttcatgg gttatccatc ctgcagagac catcccaact gtttccaaga 32040
caacccccaa tttttttccac agtgaattag acactgtatc ttccacagcc accagtcatg 32100
gggcagacgt cagctcagcc attccaacaa atatctcacc tagtgaacta gatgcactga 32160
ccccactggt cactatttcg gggacagata ctagtacaac attcccaaca ctgactaagt 32220
ccccacatga aacagagaca agaaccacat ggctcactca tcctgcagag accagctcaa 32280
ctattcccag aacaatcccc aatttttctc atcatgaatc agatgccaca ccttcaatag 32340
ccaccagtcc tggggcagaa accagttcag ctattccaat tatgactgtc tcacctggtg 32400
cagaagatct ggtgacctca caggtcacta gttctgggac agacagaaat atgactattc 32460
caactttgac tctttctcct ggtgaaccaa agacgatagc ctcattagtc acccatcctg 32520
aagcacagac aagttcggcc attccaactt caactatctc gcctgctgta tcacggttgg 32580
tgacctcaat ggtcaccagt ttggcggcaa agacaagtac aactaatcga gctctgacaa 32640
actcccctgg tgaaccagct acaacagttt cattggtcac gcatcctgca cagaccagcc 32700
caacagttcc ctggacaact tccatttttt tccatagtaa atcagacacc acaccttcaa 32760
tgaccaccag tcatggggca gaatccagtt cagctgttcc aactccaact gtttcaactg 32820
aggtaccagg agtagtgacc cctttggtca ccagttctag ggcagtgatc agtacaacta 32880
ttccaattct gactctttct cctggtgaac cagagaccac accttcaatg gccaccagtc 32940
atggggaaga agccagttct gctattccaa ctccaactgt ttcacctggg gtaccaggag 33000
tggtgacctc tctggtcact agttctaggg cagtgactag tacaactatt ccaattctga 33060

```
cttttctct tggtgaacca gagaccacac cttcaatggc caccagtcat gggacagaag 33120
ctggctcagc tgttccaact gttttacctg aggtaccagg aatggtgacc tctctggttg 33180
ctagttctag ggcagtaacc agtacaactc ttccaactct gactctttct cctggtgaac 33240
cagagaccac accttcaatg gccaccagtc atggggcaga agccagctca actgttccaa 33300
ctgtttcacc tgaggtacca ggagtggtga cctctctggt cactagttct agtggagtaa 33360
acagtacaag tattccaact ctgattcttt ctcctggtga actagaaacc acaccttcaa 33420
tggccaccag tcatggggca gaagccagct cagctgttcc aactccaact gtttcacctg 33480
gggtatcagg agtggtgacc cctctggtca ctagttccag ggcagtgacc agtacaacta 33540
ttccaattct aactctttct tctagtgagc cagagaccac accttcaatg gccaccagtc 33600
atggggtaga agccagctca gctgttctaa ctgtttcacc tgaggtacca ggaatggtga 33660
cctctctggt cactagttct agagcagtaa ccagtacaac tattccaact ctgactattt 33720
cttctgatga accagagacc acaacttcat tggtcaccca ttctgaggca aagatgattt 33780
cagccattcc aactttagct gtctccccta ctgtacaagg gctggtgact tcactggtca 33840
ctagttctgg gtcagagacc agtgcgtttt caaatctaac tgttgcctca agtcaaccag 33900
agaccataga ctcatgggtc gctcatcctg ggacagaagc aagttctgtt gttccaactt 33960
tgactgtctc cactggtgag ccgtttacaa atatctcatt ggtcacccat cctgcagaga 34020
gtagctcaac tcttcccagg acaacctcaa ggttttccca cagtgaatta gacactatgc 34080
cttctacagt caccagtcct gaggcagaat ccagctcagc catttcaaca actatttcac 34140
ctggtatacc aggtgtgctg acatcactgg tcactagctc tgggagagac atcagtgcaa 34200
cttttccaac agtgcctgag tccccacatg aatcagaggc aacagcctca tgggttactc 34260
atcctgcagt caccagcaca acagttccca ggacaacccc taattattct catagtgaac 34320
cagacaccac accatcaata gccaccagtc ctggggcaga agccacttca gattttccaa 34380
caataactgt ctcacctgat gtaccagata tggtaacctc acaggtcact agttctggga 34440
cagacaccag tataactatt ccaactctga ctctttcttc tggtgagcca gagaccacaa 34500
cctcatttat cacctattct gagacacaca caagttcagc cattccaact ctccctgtct 34560
cccctggtgc atcaaagatg ctgacctcac tggtcatcag ttctgggaca gacagcacta 34620
caactttccc aacactgacg gagaccccat atgaaccaga gacaacagcc atacagctca 34680
ttcatcctgc agagaccaac acaatggttc ccaggacaac tcccaagttt tcccatagta 34740
agtcagacac cacactccca gtagccatca ccagtcctgg gccagaagcc agttcagctg 34800
tttcaacgac aactatctca cctgatatgt cagatctggt gacctcactg gtccctagtt 34860
ctgggacaga caccagtaca accttcccaa cattgagtga gaccccatat gaaccagaga 34920
ctacagccac gtggctcact catcctgcag aaaccagcac aacggtttct gggacaattc 34980
ccaacttttc ccatagggga tcagacactg caccctcaat ggtcaccagt cctggagtag 35040
acacgaggtc aggtgttcca actacaacca tcccacccag tataccaggg gtagtgacct 35100
cacaggtcac tagttctgca acagacacta gtacagctat tccaactttg actccttctc 35160
ctggtgaacc agagaccaca gcctcatcag ctacccatcc tgggacacag actggcttca 35220
ctgttccaat tcggactgtt ccctctagtg agccagatac aatggcttcc tgggtcactc 35280
atcctccaca gaccagcaca cctgtttcca gaacaacctc cagtttttcc catagtagtc 35340
cagatgccac acctgtaatg gccaccagtc ctaggacaga agccagttca gctgtactga 35400
```

```
caacaatctc acctggtgca ccagagatgg tgacttcaca gatcactagt tctggggcag  35460
caaccagtac aactgttcca actttgactc attctcctgg tatgccagag accacagcct  35520
tattgagcac ccatcccaga acagagacaa gtaaaacatt tcctgcttca actgtgtttc  35580
ctcaagtatc agagaccaca gcctcactca ccattagacc tggtgcagag actagcacag  35640
ctctcccaac tcagacaaca tcctctctct tcaccctact tgtaactgga accagcagag  35700
ttgatctaag tccaactgct tcacctggtg tttctgcaaa aacagcccca ctttccaccc  35760
atccagggac agaaaccagc acaatgattc caacttcaac tctttccctt ggtttactag  35820
agactacagg cttactggcc accagctctt cagcagagac cagcacgagt actctaactc  35880
tgactgtttc ccctgctgtc tctgggcttt ccagtgcctc tataacaact gataagcccc  35940
aaactgtgac ctcctggaac acagaaacct caccatctgt aacttcagtt ggacccccag  36000
aattttccag gactgtcaca ggcaccacta tgaccttgat accatcagag atgccaacac  36060
cacctaaaac cagtcatgga gaaggagtga gtccaaccac tatcttgaga actacaatgg  36120
ttgaagccac taatttagct accacaggtt ccagtcccac tgtggccaag acaacaacca  36180
ccttcaatac actggctgga agcctcttta ctcctctgac cacacctggg atgtccacct  36240
tggcctctga gagtgtgacc tcaagaacaa gttataacca tcggtcctgg atctccacca  36300
ccagcagtta taaccgtcgg tactggaccc ctgccaccag cactccagtg acttctacat  36360
tctccccagg gatttccaca tcctccatcc ccagctccac agcagccaca gtcccattca  36420
tggtgccatt caccctcaac ttcaccatca ccaacctgca gtacgaggag gacatgcggc  36480
accctggttc caggaagttc aacgccacag agagagaact gcagggtctg ctcaaaccct  36540
tgttcaggaa tagcagtctg gaatacctct attcaggctg cagactagcc tcactcaggc  36600
cagagaagga tagctcagcc acggcagtgg atgccatctg cacacatcgc cctgaccctg  36660
aagacctcgg actggacaga gagcgactgt actgggagct gagcaatctg acaaatggca  36720
tccaggagct gggcccctac accctggacc ggaacagtct ctatgtcaat ggtttcaccc  36780
atcgaagctc tatgcccacc accagcactc ctgggacctc cacagtggat gtgggaacct  36840
cagggactcc atcctccagc cccagcccca cgactgctgg ccctctcctg atgccgttca  36900
ccctcaactt caccatcacc aacctgcagt acgaggagga catgcgtcgc actggctcca  36960
ggaagttcaa caccatggag agtgtcctgc agggtctgct caagcccttg ttcaagaaca  37020
ccagtgttgg ccctctgtac tctggctgca gattgacctt gctcaggccc gagaaagatg  37080
gggcagccac tggagtggat gccatctgca cccaccgcct tgaccccaaa agccctggac  37140
tcaacaggga gcagctgtac tgggagctaa gcaaactgac caatgacatt gaagagctgg  37200
gcccctacac cctggacagg aacagtctct atgtcaatgg tttcacccat cagagctctg  37260
tgtccaccac cagcactcct gggacctcca cagtggatct cagaacctca gggactccat  37320
cctccctctc cagccccaca attatggctg ctggccctct cctggtacca ttcaccctca  37380
acttcaccat caccaacctg cagtatgggg aggacatggg tcaccctggc tccaggaagt  37440
tcaacaccac agagagggtc ctgcagggtc tgcttggtcc catattcaag aacaccagtg  37500
ttggccctct gtactctggc tgcagactga cctctctcag gtctgagaag gatggagcag  37560
ccactggagt ggatgccatc tgcatccatc atcttgaccc caaaagccct ggactcaaca  37620
gagagcggct gtactgggag ctgagccaac tgaccaatgg catcaaagag ctgggcccct  37680
acaccctgga caggaacagt ctctatgtca atggtttcac ccatcggacc tctgtgccca  37740
ccagcagcac tcctgggacc tccacagtgg accttggaac ctcagggact ccattctccc  37800
```

```
tcccaagccc cgcaactgct ggccctctcc tggtgctgtt caccctcaac ttcaccatca  37860
ccaacctgaa gtatgaggag gacatgcatc gccctggctc caggaagttc aacaccactg  37920
agagggtcct gcagactctg cttggtccta tgttcaagaa caccagtgtt ggccttctgt  37980
actctggctg cagactgacc ttgctcaggt ccgagaagga tggagcagcc actggagtgg  38040
atgccatctg cacccaccgt cttgacccca aaagccctgg agtggacagg gagcagctat  38100
actgggagct gagccagctg accaatggca tcaaagagct gggcccctac accctggaca  38160
ggaacagtct ctatgtcaat ggtttcaccc attggatccc tgtgcccacc agcagcactc  38220
ctgggacctc cacagtggac cttgggtcag ggactccatc ctccctcccc agccccacaa  38280
ctgctggccc tctcctggtg ccgttcaccc tcaacttcac catcaccaac ctgaagtacg  38340
aggaggacat gcattgccct ggctccagga agttcaacac cacagagaga gtcctgcaga  38400
gtctgcttgg tcccatgttc aagaacacca gtgttggccc tctgtactct ggctgcagac  38460
tgaccttgct caggtccgag aaggatggag cagccactgg agtggatgcc atctgcaccc  38520
accgtcttga ccccaaaagc cctggagtgg acagggagca gctatactgg gagctgagcc  38580
agctgaccaa tggcatcaaa gagctgggtc cctacaccct ggacagaaac agtctctatg  38640
tcaatggttt cacccatcag acctctgcgc ccaacaccag cactcctggg acctccacag  38700
tggaccttgg gacctcaggg actccatcct ccctccccag ccctacatct gctggccctc  38760
tcctggtgcc attcaccctc aacttcacca tcaccaacct gcagtacgag gaggacatgc  38820
atcacccagg ctccaggaag ttcaacacca cggagcgggt cctgcagggt ctgcttggtc  38880
ccatgttcaa gaacaccagt gtcggccttc tgtactctgg ctgcagactg accttgctca  38940
ggcctgagaa gaatggggca gccactggaa tggatgccat ctgcagccac cgtcttgacc  39000
ccaaaagccc tggactcaac agagagcagc tgtactggga gctgagccag ctgacccatg  39060
gcatcaaaga gctgggcccc tacaccctgg acaggaacag tctctatgtc aatggtttca  39120
cccatcggag ctctgtggcc cccaccagca ctcctgggac ctccacagtg gaccttggga  39180
cctcagggac tccatcctcc ctccccagcc ccacaacagc tgttcctctc ctggtgccgt  39240
tcaccctcaa ctttaccatc accaatctgc agtatgggga ggacatgcgt caccctggct  39300
ccaggaagtt caacaccaca gagagggtcc tgcagggtct gcttggtccc ttgttcaaga  39360
actccagtgt cggccctctg tactctggct gcagactgat ctctctcagg tctgagaagg  39420
atggggcagc cactggagtg gatgccatct gcacccacca ccttaaccct caaagccctg  39480
gactggacag ggagcagctg tactggcagc tgagccagat gaccaatggc atcaaagagc  39540
tgggccccta caccctggac cggaacagtc tctacgtcaa tggtttcacc catcggagct  39600
ctgggctcac caccagcact ccttggactt ccacagttga ccttggaacc tcagggactc  39660
catcccccgt ccccagcccc acaaccaccg gccctctcct ggtgccattc acactcaact  39720
tcaccatcac taacctacag tatgaggaga acatgggtca ccctggctcc aggaagttca  39780
acatcacgga gagtgttctg cagggtctgc tcaagccctt gttcaagagc accagtgttg  39840
gccctctgta ttctggctgc agactgacct tgctcaggcc tgagaaggat ggagtagcca  39900
ccagagtgga cgccatctgc acccaccgcc ctgaccccaa aatccctggg ctagacagac  39960
agcagctata ctgggagctg agccagctga cccacagcat cactgagctg ggaccctaca  40020
ccctggatag ggacagtctc tatgtcaatg gtttcaccca gcggagctct gtgcccacca  40080
ccagcactcc tgggactttc acagtacagc cggaaacctc tgagactcca tcatccctcc  40140
```

-continued

```
ctggccccac agccactggc cctgtcctgc tgccattcac cctcaatttt accatcacta  40200
acctgcagta tgaggaggac atgcgtcgcc ctggctccag gaagttcaac accacggaga  40260
gggtccttca gggtctgctt atgcccttgt tcaagaacac cagtgtcagc tctctgtact  40320
ctggttgcag actgaccttg ctcaggcctg agaaggatgg ggcagccacc agagtggatg  40380
ctgtctgcac ccatcgtcct gaccccaaaa gccctggact ggacagagag cggctgtact  40440
ggaagctgag ccagctgacc cacggcatca ctgagctggg cccctacacc ctggacaggc  40500
acagtctcta tgtcaatggt ttcacccatc agagctctat gacgaccacc agaactcctg  40560
atacctccac aatgcacctg gcaacctcga gaactccagc ctccctgtct ggacccatga  40620
ccgccagccc tctcctggtg ctattcacaa ttaacttcac catcactaac ctgcggtatg  40680
aggagaacat gcatcaccct ggctctagaa agtttaacac cacggagaga gtccttcagg  40740
gtctgctcag gcctgtgttc aagaacacca gtgttggccc tctgtactct ggctgcagac  40800
tgaccttgct caggcccaag aaggatgggg cagccaccaa agtggatgcc atctgcacct  40860
accgccctga tcccaaaagc cctggactgg acagagagca gctatactgg gagctgagcc  40920
agctgaccca cagcatcact gagctgggcc cctacaccct ggacagggac agtctctatg  40980
tcaatggttt cacacagcgg agctctgtgc ccaccactag cattcctggg acccccacag  41040
tggacctggg aacatctggg actccagttt ctaaacctgg tccctcggct gccagccctc  41100
tcctggtgct attcactctc aacttcacca tcaccaacct gcggtatgag gagaacatgc  41160
agcaccctgg ctccaggaag ttcaacacca cggagagggt ccttcagggc ctgctcaggt  41220
ccctgttcaa gagcaccagt gttggccctc tgtactctgg ctgcagactg actttgctca  41280
ggcctgaaaa ggatgggaca gccactggag tggatgccat ctgcacccac caccctgacc  41340
ccaaaagccc taggctggac agagagcagc tgtattggga gctgagccag ctgacccaca  41400
atatcactga gctgggcccc tatgccctgg acaacgacag cctctttgtc aatggtttca  41460
ctcatcggag ctctgtgtcc accaccagca ctcctgggac ccccacagtg tatctgggag  41520
catctaagac tccagcctcg atatttggcc cttcagctgc cagccatctc ctgatactat  41580
tcaccctcaa cttcaccatc actaacctgc ggtatgagga gaacatgtgg cctggctcca  41640
ggaagttcaa cactacagag agggtccttc agggcctgct aaggcccttg ttcaagaaca  41700
ccagtgttgg ccctctgtac tctggctgca ggctgacctt gctcaggcca gagaaagatg  41760
gggaagccac cggagtggat gccatctgca cccaccgccc tgaccccaca ggccctgggc  41820
tggacagaga gcagctgtat ttggagctga gccagctgac ccacagcatc actgagctgg  41880
gcccctacac actggacagg gacagtctct atgtcaatgg tttcacccat cggagctctg  41940
tacccaccac cagcaccggg gtggtcagcg aggagccatt cacactgaac ttcaccatca  42000
acaacctgcg ctacatggcg gacatgggcc aacccggctc cctcaagttc aacatcacag  42060
acaacgtcat gcagcacctg ctcagtcctt tgttccagag gagcagcctg ggtgcacggt  42120
acacaggctg cagggtcatc gcactaaggt ctgtgaagaa cggtgctgag acacgggtgg  42180
acctcctctg cacctacctg cagcccctca gcggcccagg tctgcctatc aagcaggtgt  42240
tccatgagct gagccagcag acccatggca tcacccggct gggcccctac tctctggaca  42300
aagacagcct ctaccttaac ggttacaatg aacctggtcc agatgagcct cctacaactc  42360
ccaagccagc caccacattc ctgcctcctc tgtcagaagc cacaacagcc atggggtacc  42420
acctgaagac cctcacactc aacttcacca tctccaatct ccagtattca ccagatatgg  42480
gcaagggctc agctacattc aactccaccg agggggtcct tcagcacctg ctcagaccct  42540
```

```
tgttccagaa gagcagcatg ggccccttct acttgggttg ccaactgatc tccctcaggc  42600
ctgagaagga tggggcagcc actggtgtgg acaccacctg cacctaccac cctgaccctg  42660
tgggccccgg gctggacata cagcagcttt actgggagct gagtcagctg acccatggtg  42720
tcacccaact gggcttctat gtcctggaca gggatagcct cttcatcaat ggctatgcac  42780
cccagaattt atcaatccgg ggcgagtacc agataaattt ccacattgtc aactggaacc  42840
tcagtaatcc agaccccaca tcctcagagt acatcaccct gctgagggac atccaggaca  42900
aggtcaccac actctacaaa ggcagtcaac tacatgacac attccgcttc tgcctggtca  42960
ccaacttgac gatggactcc gtgttggtca ctgtcaaggc attgttctcc tccaatttgg  43020
accccagcct ggtggagcaa gtctttctag ataagaccct gaatgcctca ttccattggc  43080
tgggctccac ctaccagttg gtggacatcc atgtgacaga aatggagtca tcagtttatc  43140
aaccaacaag cagctccagc acccagcact tctacctgaa tttcaccatc accaacctac  43200
catattccca ggacaaagcc cagccaggca ccaccaatta ccagaggaac aaaaggaata  43260
ttgaggatgc gctcaaccaa ctcttccgaa acagcagcat caagagttat ttttctgact  43320
gtcaagtttc aacattcagg tctgtcccca acaggcacca caccggggtg gactccctgt  43380
gtaacttctc gccactggct cggagagtag acagagttgc catctatgag gaatttctgc  43440
ggatgacccg gaatggtacc cagctgcaga acttcaccct ggacaggagc agtgtccttg  43500
tggatgggta ttctcccaac agaaatgagc ccttaactgg gaattctgac cttcccttct  43560
gggctgtcat cctcatcggc ttggcaggac tcctgggagt catcacatgc ctgatctgcg  43620
gtgtcctggt gaccacccgc cggcggaaga aggaaggaga atacaacgtc cagcaacagt  43680
gcccaggcta ctaccagtca cacctagacc tggaggatct gcaatgactg gaacttgccg  43740
gtgcctgggg tgcctttccc ccagccaggg tccaaagaag cttggctggg gcagaaataa  43800
accatattgg tcgga                                                    43815
```

```
<210> SEQ ID NO 138
<211> LENGTH: 518
<212> TYPE: PRT
<213> ORGANISM: Artificial Sequence
<220> FEATURE:
<223> OTHER INFORMATION: Bispecific

<400> SEQUENCE: 138

Glu Ile Val Met Thr Gln Thr Pro Ala Thr Leu Ser Val Ser Ala Gly
1               5                   10                  15

Glu Arg Val Thr Ile Thr Cys Lys Ala Ser Gln Ser Val Ser Asn Asp
            20                  25                  30

Val Thr Trp Tyr Gln Gln Lys Pro Gly Gln Ala Pro Arg Leu Leu Ile
        35                  40                  45

Tyr Ser Ala Ser Asn Arg Tyr Ser Gly Val Pro Ala Arg Phe Ser Gly
    50                  55                  60

Ser Gly Tyr Gly Thr Glu Phe Thr Phe Thr Ile Ser Ser Val Gln Ser
65                  70                  75                  80

Glu Asp Phe Ala Val Tyr Phe Cys Gln Gln Asp Tyr Ser Ser Phe Gly
                85                  90                  95

Gln Gly Thr Lys Leu Glu Ile Lys Arg Thr Val Ala Ala Pro Ser Val
            100                 105                 110

Phe Ile Phe Pro Pro Ser Asp Glu Gln Leu Lys Ser Gly Thr Ala Ser
        115                 120                 125
```

-continued

```
Val Val Cys Leu Leu Asn Asn Phe Tyr Pro Arg Glu Ala Lys Val Gln
    130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu Cys Gly Gly Gly Gly Ser Gly Gly Gly Gly Ser Gln Val Gln
    210                 215                 220

Leu Val Gln Ser Gly Gly Gly Leu Thr Leu Ser Lys Ala Asp Tyr Glu
225                 230                 235                 240

Lys His Lys Val Tyr Ala Cys Glu Val Thr His Gln Gly Leu Ser Ser
                245                 250                 255

Pro Val Thr Lys Ser Phe Asn Arg Gly Glu Cys Gly Gly Gly Gly Ser
            260                 265                 270

Gly Gly Gly Gly Ser Gln Val Gln Leu Val Gln Ser Gly Gly Gly Val
        275                 280                 285

Val Gln Pro Gly Arg Ser Leu Arg Leu Ser Cys Lys Ala Ser Gly Tyr
    290                 295                 300

Thr Phe Thr Arg Tyr Thr Met His Trp Val Arg Gln Ala Pro Gly Lys
305                 310                 315                 320

Cys Leu Glu Trp Ile Gly Tyr Ile Asn Pro Ser Arg Gly Tyr Thr Asn
                325                 330                 335

Tyr Asn Gln Lys Phe Lys Asp Arg Phe Thr Ile Ser Arg Asp Asn Ser
            340                 345                 350

Lys Asn Thr Ala Phe Leu Gln Met Asp Ser Leu Arg Pro Glu Asp Thr
        355                 360                 365

Gly Val Tyr Phe Cys Ala Arg Tyr Tyr Asp Asp His Tyr Cys Leu Asp
    370                 375                 380

Tyr Trp Gly Gln Gly Thr Pro Val Thr Val Ser Ser Gly Gly Gly Gly
385                 390                 395                 400

Ser Gly Gly Gly Gly Ser Gly Gly Gly Gly Ser Asp Ile Gln Met Thr
                405                 410                 415

Gln Ser Pro Ser Ser Leu Ser Ala Ser Val Gly Asp Arg Val Thr Ile
            420                 425                 430

Thr Cys Ser Ala Ser Ser Ser Val Ser Tyr Met Asn Trp Tyr Gln Gln
        435                 440                 445

Thr Pro Gly Lys Ala Pro Lys Arg Trp Ile Tyr Asp Thr Ser Lys Leu
    450                 455                 460

Ala Ser Gly Val Pro Ser Arg Phe Ser Gly Ser Gly Ser Gly Thr Asp
465                 470                 475                 480

Tyr Thr Phe Thr Ile Ser Ser Leu Gln Pro Glu Asp Ile Ala Thr Tyr
                485                 490                 495

Tyr Cys Gln Gln Trp Ser Ser Asn Pro Phe Thr Phe Gly Cys Gly Thr
            500                 505                 510

Lys Leu Gln Ile Thr Arg
        515
```

<210> SEQ ID NO 139
<211> LENGTH: 114
<212> TYPE: PRT

<213> ORGANISM: Artificial Sequence
<220> FEATURE:
<223> OTHER INFORMATION: MUC16c114-N3

<400> SEQUENCE: 139

Asn Phe Ser Pro Leu Ala Arg Arg Val Asp Arg Val Ala Ile Tyr Glu
1               5                   10                  15

Glu Phe Leu Arg Met Thr Arg Asn Gly Thr Gln Leu Gln Ala Phe Thr
            20                  25                  30

Leu Asp Arg Ser Ser Val Leu Val Asp Gly Tyr Ser Pro Asn Arg Asn
        35                  40                  45

Glu Pro Leu Thr Gly Asn Ser Asp Leu Pro Phe Trp Ala Val Ile Leu
    50                  55                  60

Ile Gly Leu Ala Gly Leu Leu Gly Leu Ile Thr Cys Leu Ile Cys Gly
65                  70                  75                  80

Val Leu Val Thr Thr Arg Arg Arg Lys Lys Glu Gly Glu Tyr Asn Val
                85                  90                  95

Gln Gln Gln Cys Pro Gly Tyr Tyr Gln Ser His Leu Asp Leu Glu Asp
            100                 105                 110

Leu Gln

<210> SEQ ID NO 140
<211> LENGTH: 366
<212> TYPE: DNA
<213> ORGANISM: Artificial Sequence
<220> FEATURE:
<223> OTHER INFORMATION: 10C6 VH NUCLEIC ACID

<400> SEQUENCE: 140
caggtaactc tgaaagagtc tggccctggg atattgcagc cctcccagac cctcagtctg 60
acttgttctt tctctgggtt ttcactgaac actcttggta tgggtgtagg ctggattcgg 120
cagccttcag ggaagggtct ggagtggctg gcacacattt ggtgggatga tgataagtac 180
tataacccag ccctgaagag tcggctcaca atctccaagg attcctccaa aaaccaggtt 240
ttcctcaaga tcgccaatgt ggacactgca gatattgcca catactactg ttctcgaatc 300
gggacagctc aggctacgga tgctctggac tactggggtc aaggaacctc agtcaccgtc 360
tcctca 366

<210> SEQ ID NO 141
<211> LENGTH: 330
<212> TYPE: DNA
<213> ORGANISM: Artificial Sequence
<220> FEATURE:
<223> OTHER INFORMATION: 10C6 VL NUCLEIC ACID

<400> SEQUENCE: 141
gacattgtgc tgacacagtc tcctgcttcc ttagctgtat ctctggggca gagggccacc 60
atctcataca gggccagcaa aagtgtcagt acatctggct atagttatat gcactggaac 120
caacagaaac caggacagcc acccagactc ctcatctatc ttgtatccaa cctagaatct 180
ggggtccctg ccaggttcag tggcagtggg tctgggacag acttcaccct caacatccat 240
cctgtggagg aggaggatgc tgcaacctat tactgtcagc acattaggga gcttacacgt 300
tcggaggggg gaccaagctg gaaataaaac 330

<210> SEQ ID NO 142
<211> LENGTH: 369
<212> TYPE: DNA

<213> ORGANISM: Artificial Sequence
<220> FEATURE:
<223> OTHER INFORMATION: 7B12 VH NUCLEIC ACID

<400> SEQUENCE: 142
caggttactc tgaaagagtc tggccctggg atattgcagc cctcccagac cctcagtctg 60
acttgttctt tctctgggtt ttcactgagc actgttggta tgggtgtagg ctggagtcgt 120
cagccctcag ggaagggtct ggagtggctg gcacacatct ggtgggatga tgaagataag 180
tattataatc cagccctgaa gagtcggctc acaatctcca aggatacctc caaaaaccag 240
gtcttcctca agatcgccaa tgtggacact gcagatagtg ccacatacta ctgtactcga 300
atcgggacag ctcaggctac ggatgctttg gactactggg gtcaaggaac ctcagtcacc 360
gtctcctca 369

<210> SEQ ID NO 143
<211> LENGTH: 336
<212> TYPE: DNA
<213> ORGANISM: Artificial Sequence
<220> FEATURE:
<223> OTHER INFORMATION: 7B12 VL NUCLEIC ACID

<400> SEQUENCE: 143
gatattgtga tgactcaggc tgcaccctct gtatctgtca ctcctggaga gtcagtatcc 60
atctcctgca ggtctagtaa gagtcttcgg aaaagtaatg gcaacactta cttgtattgg 120
ttcctgcaga ggccaggcca gtctcctcag cgcctgatat attatatgtc caaccttgcc 180
tcaggagtcc cagacaggtt cagtggcaga gggtcaggaa ctgatttcac actgagaatc 240
agtagagtgg aggctgaaga tgtgggtgtt tattactgta tgcaaagtct agaatatcct 300
ctcacgttcg gagggggggac taagctaaaa ataaaa 336

<210> SEQ ID NO 144
<211> LENGTH: 366
<212> TYPE: DNA
<213> ORGANISM: Artificial Sequence
<220> FEATURE:
<223> OTHER INFORMATION: 19C11 VH NUCLEIC ACID

<400> SEQUENCE: 144
caggttaatc tgaaagagtc tggccctggg aaattgcagc cctcccagac cctcagtctg 60
acttgttctt tctctgggtt ttcactgagc actcttggta tgggtgtagg ttggattcgt 120
cagtcttcag ggaagggtct ggagtggctg gcacacattt ggtgggatga tgataagtac 180
tataacccag ccctgaagag tcggctcaca atctccaggg ctacctccaa aaaccaggtt 240
ttcctcaaga tcgtcaatgt gggcactgca gatactgcca catattactg tgctcgaatc 300
gggacagctc aggctacgga tgctttggac tattggggtc agggaacctc agtcaccgtt 360
tcctca 366

<210> SEQ ID NO 145
<211> LENGTH: 336
<212> TYPE: DNA
<213> ORGANISM: Artificial Sequence
<220> FEATURE:
<223> OTHER INFORMATION: 19C11 VL NUCLEIC ACID

<400> SEQUENCE: 145
gatattgtga tgactcaggc tgcaccctct atccctgtca ctcctggaga gtcagtatcc 60
atctcctgca ggtctagtaa gagtcttctg catagtaatg gcaacactta tttgtattgg 120
ttcctgcaga ggccaggcca gtctcctcag cgcctgatat attatatgtc caaccttgcc 180
tcaggagtcc cagacaggtt cagtggcaga gggtcaggaa ctgatttcac actgaaaatc 240
agtagagtgg aggctgggga tgtgggtgtt tattactgta tgcagggtct agagcatcct 300
ctcacgttcg gagggggggac caagctggaa ataaaa 336

<210> SEQ ID NO 146
<211> LENGTH: 366
<212> TYPE: DNA
<213> ORGANISM: Artificial Sequence
<220> FEATURE:
<223> OTHER INFORMATION: 16C5 VH NUCLEIC ACID

<400> SEQUENCE: 146
caggttactc tgaaagagtc tggccctgga atattgcagc cctcccagac cctcagtctg 60
acttgttctt tctctgggtt ttcactgaac actcttggta tgggtgtagg ctggattcgt 120
cagccttcag ggaagggtct ggagtggctg gcacacattt ggtgggatga tgataagtac 180
tattacccag ccctgaagag tcggctcaca atctccaggg atacctccaa aaaccaggta 240
ttcctcaaga tcgccaatgt ggacactgca gatactgcca catactactg tgctcgaatc 300
gggacagctc aggctacgga tgctctggac tactggggtc aaggaacctc agtcaccgtc 360
tcctca 366

<210> SEQ ID NO 147
<211> LENGTH: 327
<212> TYPE: DNA
<213> ORGANISM: Artificial Sequence
<220> FEATURE:
<223> OTHER INFORMATION: 16C5 VL NUCLEIC ACID

<400> SEQUENCE: 147
gagctcgata tgacccagac tccaccctcc ctgtctgcat ctgtgggaga aactgtcagg 60
attaggtgcc tggccagtga ggacatttat agtggtatat cctggtatca acagaagcca 120
gggaaacctc ctacactcct gatctatggt gcatccaatt tagaatctgg ggtcccacca 180
cggttcagtg gcagtggatc tgggacagat tacaccctca ccattggcgg cgtgcaggct 240
gaagatgctg ccacctacta ctgtctaggc ggttatagtt atagtagtac cttgactttt 300
ggagctggca ccaatgtgga aatcaaa 327

<210> SEQ ID NO 148
<211> LENGTH: 369
<212> TYPE: DNA
<213> ORGANISM: Artificial Sequence
<220> FEATURE:
<223> OTHER INFORMATION: 18C6 VH NUCLEIC ACID

<400> SEQUENCE: 148
caggttactc tgaaagagtc tggccctggg atattgcagc cctcccagac cctcagtctg 60
acttgttctt tctctgggtt ttcactgagc actgttggta tgggtgtagg ctggagtcgt 120
cagccttcag ggaagggtct ggagtggctg gcacacattt ggtgggatga tgaggataag 180
tattataacc cagccctgaa gagtcggctc acaatctcca aggatacctc caaaaaccag 240
gtattcctca agatcgccaa tgtggacact gcagatactg ccacatacta ctgtactcga 300
atcgggacag ctcaggctac ggatgctttg gactactggg gtcaaggaac ctcagtcacc 360
gtctcctca 369

<210> SEQ ID NO 149
<211> LENGTH: 336
<212> TYPE: DNA
<213> ORGANISM: Artificial Sequence
<220> FEATURE:
<223> OTHER INFORMATION: 18C6 VL NUCLEIC ACID

<400> SEQUENCE: 149
gatattgtga tgactcaggc tgcaccctct gtacctgtca ctcctggaga gtcagtatcc 60
atctcctgca ggtctagtaa gagtcttctg catagtaatg gcaacactta cttgtattgg 120
ttcctgcaga ggccaggcca gtctcctcag cgcctgatat attatatgtc caaccttgcc 180
tcaggagtcc cagacaggtt cagtggcaga gggtcaggaa ctgatttcac actgagaatc 240
agtagagtgg aggctgagga tgtgggtgtt tattactgta tgcaaagtct agaatatcct 300
ctcacgttcg gagggggac caagctggaa ataaaa 336

<210> SEQ ID NO 150
<211> LENGTH: 14447
<212> TYPE: PRT
<213> ORGANISM: Homo sapiens
<220> FEATURE:
<223> OTHER INFORMATION: Mature Human MUC16 amino acid sequence

<400> SEQUENCE: 150

Asp Lys Thr Leu Ala Ser Pro Thr Ser Ser Val Val Gly Arg Thr Thr
1 5 10 15

Gln Ser Leu Gly Val Met Ser Ser Ala Leu Pro Glu Ser Thr Ser Arg
20 25 30

Gly Met Thr His Ser Glu Gln Arg Thr Ser Pro Ser Leu Ser Pro Gln
35 40 45

Val Asn Gly Thr Pro Ser Arg Asn Tyr Pro Ala Thr Ser Met Val Ser
50 55 60

Gly Leu Ser Ser Pro Arg Thr Arg Thr Ser Ser Thr Glu Gly Asn Phe
65 70 75 80

Thr Lys Glu Ala Ser Thr Tyr Thr Leu Thr Val Glu Thr Thr Ser Gly
85 90 95

Pro Val Thr Glu Lys Tyr Thr Val Pro Thr Glu Thr Ser Thr Thr Glu
100 105 110

Gly Asp Ser Thr Glu Thr Pro Trp Asp Thr Arg Tyr Ile Pro Val Lys
115 120 125

Ile Thr Ser Pro Met Lys Thr Phe Ala Asp Ser Thr Ala Ser Lys Glu
130 135 140

Asn Ala Pro Val Ser Met Thr Pro Ala Glu Thr Thr Val Thr Asp Ser
145 150 155 160

His Thr Pro Gly Arg Thr Asn Pro Ser Phe Gly Thr Leu Tyr Ser Ser
165 170 175

Phe Leu Asp Leu Ser Pro Lys Gly Thr Pro Asn Ser Arg Gly Glu Thr
180 185 190

Ser Leu Glu Leu Ile Leu Ser Thr Thr Gly Tyr Pro Phe Ser Ser Pro
195 200 205

Glu Pro Gly Ser Ala Gly His Ser Arg Ile Ser Thr Ser Ala Pro Leu
210 215 220

Ser Ser Ser Ala Ser Val Leu Asp Asn Lys Ile Ser Glu Thr Ser Ile
225 230 235 240

Phe Ser Gly Gln Ser Leu Thr Ser Pro Leu Ser Pro Gly Val Pro Glu
245 250 255

```
Ala Arg Ala Ser Thr Met Pro Asn Ser Ala Ile Pro Phe Ser Met Thr
            260                 265                 270

Leu Ser Asn Ala Glu Thr Ser Ala Glu Arg Val Arg Ser Thr Ile Ser
        275                 280                 285

Ser Leu Gly Thr Pro Ser Ile Ser Thr Lys Gln Thr Ala Glu Thr Ile
    290                 295                 300

Leu Thr Phe His Ala Phe Ala Glu Thr Met Asp Ile Pro Ser Thr His
305                 310                 315                 320

Ile Ala Lys Thr Leu Ala Ser Glu Trp Leu Gly Ser Pro Gly Thr Leu
                325                 330                 335

Gly Gly Thr Ser Thr Ser Ala Leu Thr Thr Thr Ser Pro Ser Thr Thr
            340                 345                 350

Leu Val Ser Glu Glu Thr Asn Thr His His Ser Thr Ser Gly Lys Glu
        355                 360                 365

Thr Glu Gly Thr Leu Asn Thr Ser Met Thr Pro Leu Glu Thr Ser Ala
    370                 375                 380

Pro Gly Glu Glu Ser Glu Met Thr Ala Thr Leu Val Pro Thr Leu Gly
385                 390                 395                 400

Phe Thr Thr Leu Asp Ser Lys Ile Arg Ser Pro Ser Gln Val Ser Ser
                405                 410                 415

Ser His Pro Thr Arg Glu Leu Arg Thr Thr Gly Ser Thr Ser Gly Arg
            420                 425                 430

Gln Ser Ser Ser Thr Ala Ala His Gly Ser Ser Asp Ile Leu Arg Ala
        435                 440                 445

Thr Thr Ser Ser Thr Ser Lys Ala Ser Ser Trp Thr Ser Glu Ser Thr
    450                 455                 460

Ala Gln Gln Phe Ser Glu Pro Gln His Thr Gln Trp Val Glu Thr Ser
465                 470                 475                 480

Pro Ser Met Lys Thr Glu Arg Pro Pro Ala Ser Thr Ser Val Ala Ala
                485                 490                 495

Pro Ile Thr Thr Ser Val Pro Ser Val Val Ser Gly Phe Thr Thr Leu
            500                 505                 510

Lys Thr Ser Ser Thr Lys Gly Ile Trp Leu Glu Glu Thr Ser Ala Asp
        515                 520                 525

Thr Leu Ile Gly Glu Ser Thr Ala Gly Pro Thr Thr His Gln Phe Ala
    530                 535                 540

Val Pro Thr Gly Ile Ser Met Thr Gly Gly Ser Ser Thr Arg Gly Ser
545                 550                 555                 560

Gln Gly Thr Thr His Leu Leu Thr Arg Ala Thr Ala Ser Ser Glu Thr
                565                 570                 575

Ser Ala Asp Leu Thr Leu Ala Thr Asn Gly Val Pro Val Ser Val Ser
            580                 585                 590

Pro Ala Val Ser Lys Thr Ala Ala Gly Ser Ser Pro Pro Gly Gly Thr
        595                 600                 605

Lys Pro Ser Tyr Thr Met Val Ser Ser Val Ile Pro Glu Thr Ser Ser
    610                 615                 620

Leu Gln Ser Ser Ala Phe Arg Glu Gly Thr Ser Leu Gly Leu Thr Pro
625                 630                 635                 640

Leu Asn Thr Arg His Pro Phe Ser Ser Pro Glu Pro Asp Ser Ala Gly
                645                 650                 655

His Thr Lys Ile Ser Thr Ser Ile Pro Leu Leu Ser Ser Ala Ser Val
            660                 665                 670
```

```
Leu Glu Asp Lys Val Ser Ala Thr Ser Thr Phe Ser His His Lys Ala
        675                 680                 685

Thr Ser Ser Ile Thr Thr Gly Thr Pro Glu Ile Ser Thr Lys Thr Lys
    690                 695                 700

Pro Ser Ser Ala Val Leu Ser Ser Met Thr Leu Ser Asn Ala Ala Thr
705                 710                 715                 720

Ser Pro Glu Arg Val Arg Asn Ala Thr Ser Pro Leu Thr His Pro Ser
                725                 730                 735

Pro Ser Gly Glu Glu Thr Ala Gly Ser Val Leu Thr Leu Ser Thr Ser
            740                 745                 750

Ala Glu Thr Thr Asp Ser Pro Asn Ile His Pro Thr Gly Thr Leu Thr
        755                 760                 765

Ser Glu Ser Ser Glu Ser Pro Ser Thr Leu Ser Leu Pro Ser Val Ser
    770                 775                 780

Gly Val Lys Thr Thr Phe Ser Ser Ser Thr Pro Ser Thr His Leu Phe
785                 790                 795                 800

Thr Ser Gly Glu Glu Thr Glu Glu Thr Ser Asn Pro Ser Val Ser Gln
                805                 810                 815

Pro Glu Thr Ser Val Ser Arg Val Arg Thr Thr Leu Ala Ser Thr Ser
            820                 825                 830

Val Pro Thr Pro Val Phe Pro Thr Met Asp Thr Trp Pro Thr Arg Ser
        835                 840                 845

Ala Gln Phe Ser Ser Ser His Leu Val Ser Glu Leu Arg Ala Thr Ser
    850                 855                 860

Ser Thr Ser Val Thr Asn Ser Thr Gly Ser Ala Leu Pro Lys Ile Ser
865                 870                 875                 880

His Leu Thr Gly Thr Ala Thr Met Ser Gln Thr Asn Arg Asp Thr Phe
                885                 890                 895

Asn Asp Ser Ala Ala Pro Gln Ser Thr Thr Trp Pro Glu Thr Ser Pro
            900                 905                 910

Arg Phe Lys Thr Gly Leu Pro Ser Ala Thr Thr Thr Val Ser Thr Ser
        915                 920                 925

Ala Thr Ser Leu Ser Ala Thr Val Met Val Ser Lys Phe Thr Ser Pro
    930                 935                 940

Ala Thr Ser Ser Met Glu Ala Thr Ser Ile Arg Glu Pro Ser Thr Thr
945                 950                 955                 960

Ile Leu Thr Thr Glu Thr Thr Asn Gly Pro Gly Ser Met Ala Val Ala
                965                 970                 975

Ser Thr Asn Ile Pro Ile Gly Lys Gly Tyr Ile Thr Glu Gly Arg Leu
            980                 985                 990

Asp Thr Ser His Leu Pro Ile Gly  Thr Thr Ala Ser Ser  Glu Thr Ser
        995                 1000                 1005

Met Asp  Phe Thr Met Ala Lys  Glu Ser Val Ser Met  Ser Val Ser
    1010                 1015                 1020

Pro Ser  Gln Ser Met Asp Ala  Ala Gly Ser Ser Thr  Pro Gly Arg
    1025                 1030                 1035

Thr Ser  Gln Phe Val Asp Thr  Phe Ser Asp Asp Val  Tyr His Leu
    1040                 1045                 1050

Thr Ser  Arg Glu Ile Thr Ile  Pro Arg Asp Gly Thr  Ser Ser Ala
    1055                 1060                 1065

Leu Thr  Pro Gln Met Thr Ala  Thr His Pro Pro Ser  Pro Asp Pro
    1070                 1075                 1080

Gly Ser  Ala Arg Ser Thr Trp  Leu Gly Ile Leu Ser  Ser Ser Pro
```

1085 1090 1095

Ser Ser Pro Thr Pro Lys Val Thr Met Ser Ser Thr Phe Ser Thr
1100 1105 1110

Gln Arg Val Thr Thr Ser Met Ile Met Asp Thr Val Glu Thr Ser
1115 1120 1125

Arg Trp Asn Met Pro Asn Leu Pro Ser Thr Thr Ser Leu Thr Pro
1130 1135 1140

Ser Asn Ile Pro Thr Ser Gly Ala Ile Gly Lys Ser Thr Leu Val
1145 1150 1155

Pro Leu Asp Thr Pro Ser Pro Ala Thr Ser Leu Glu Ala Ser Glu
1160 1165 1170

Gly Gly Leu Pro Thr Leu Ser Thr Tyr Pro Glu Ser Thr Asn Thr
1175 1180 1185

Pro Ser Ile His Leu Gly Ala His Ala Ser Ser Glu Ser Pro Ser
1190 1195 1200

Thr Ile Lys Leu Thr Met Ala Ser Val Val Lys Pro Gly Ser Tyr
1205 1210 1215

Thr Pro Leu Thr Phe Pro Ser Ile Glu Thr His Ile His Val Ser
1220 1225 1230

Thr Ala Arg Met Ala Tyr Ser Ser Gly Ser Ser Pro Glu Met Thr
1235 1240 1245

Ala Pro Gly Glu Thr Asn Thr Gly Ser Thr Trp Asp Pro Thr Thr
1250 1255 1260

Tyr Ile Thr Thr Thr Asp Pro Lys Asp Thr Ser Ser Ala Gln Val
1265 1270 1275

Ser Thr Pro His Ser Val Arg Thr Leu Arg Thr Thr Glu Asn His
1280 1285 1290

Pro Lys Thr Glu Ser Ala Thr Pro Ala Ala Tyr Ser Gly Ser Pro
1295 1300 1305

Lys Ile Ser Ser Ser Pro Asn Leu Thr Ser Pro Ala Thr Lys Ala
1310 1315 1320

Trp Thr Ile Thr Asp Thr Thr Glu His Ser Thr Gln Leu His Tyr
1325 1330 1335

Thr Lys Leu Ala Glu Lys Ser Ser Gly Phe Glu Thr Gln Ser Ala
1340 1345 1350

Pro Gly Pro Val Ser Val Val Ile Pro Thr Ser Pro Thr Ile Gly
1355 1360 1365

Ser Ser Thr Leu Glu Leu Thr Ser Asp Val Pro Gly Glu Pro Leu
1370 1375 1380

Val Leu Ala Pro Ser Glu Gln Thr Thr Ile Thr Leu Pro Met Ala
1385 1390 1395

Thr Trp Leu Ser Thr Ser Leu Thr Glu Glu Met Ala Ser Thr Asp
1400 1405 1410

Leu Asp Ile Ser Ser Pro Ser Ser Pro Met Ser Thr Phe Ala Ile
1415 1420 1425

Phe Pro Pro Met Ser Thr Pro Ser His Glu Leu Ser Lys Ser Glu
1430 1435 1440

Ala Asp Thr Ser Ala Ile Arg Asn Thr Asp Ser Thr Thr Leu Asp
1445 1450 1455

Gln His Leu Gly Ile Arg Ser Leu Gly Arg Thr Gly Asp Leu Thr
1460 1465 1470

Thr Val Pro Ile Thr Pro Leu Thr Thr Thr Trp Thr Ser Val Ile
1475 1480 1485

```
Glu His Ser Thr Gln Ala Gln Asp Thr Leu Ser Ala Thr Met Ser
    1490                1495                1500

Pro Thr His Val Thr Gln Ser Leu Lys Asp Gln Thr Ser Ile Pro
    1505                1510                1515

Ala Ser Ala Ser Pro Ser His Leu Thr Glu Val Tyr Pro Glu Leu
    1520                1525                1530

Gly Thr Gln Gly Arg Ser Ser Ser Glu Ala Thr Thr Phe Trp Lys
    1535                1540                1545

Pro Ser Thr Asp Thr Leu Ser Arg Glu Ile Glu Thr Gly Pro Thr
    1550                1555                1560

Asn Ile Gln Ser Thr Pro Pro Met Asp Asn Thr Thr Thr Gly Ser
    1565                1570                1575

Ser Ser Ser Gly Val Thr Leu Gly Ile Ala His Leu Pro Ile Gly
    1580                1585                1590

Thr Ser Ser Pro Ala Glu Thr Ser Thr Asn Met Ala Leu Glu Arg
    1595                1600                1605

Arg Ser Ser Thr Ala Thr Val Ser Met Ala Gly Thr Met Gly Leu
    1610                1615                1620

Leu Val Thr Ser Ala Pro Gly Arg Ser Ile Ser Gln Ser Leu Gly
    1625                1630                1635

Arg Val Ser Ser Val Leu Ser Glu Ser Thr Thr Glu Gly Val Thr
    1640                1645                1650

Asp Ser Ser Lys Gly Ser Ser Pro Arg Leu Asn Thr Gln Gly Asn
    1655                1660                1665

Thr Ala Leu Ser Ser Ser Leu Glu Pro Ser Tyr Ala Glu Gly Ser
    1670                1675                1680

Gln Met Ser Thr Ser Ile Pro Leu Thr Ser Ser Pro Thr Thr Pro
    1685                1690                1695

Asp Val Glu Phe Ile Gly Gly Ser Thr Phe Trp Thr Lys Glu Val
    1700                1705                1710

Thr Thr Val Met Thr Ser Asp Ile Ser Lys Ser Ser Ala Arg Thr
    1715                1720                1725

Glu Ser Ser Ser Ala Thr Leu Met Ser Thr Ala Leu Gly Ser Thr
    1730                1735                1740

Glu Asn Thr Gly Lys Glu Lys Leu Arg Thr Ala Ser Met Asp Leu
    1745                1750                1755

Pro Ser Pro Thr Pro Ser Met Glu Val Thr Pro Trp Ile Ser Leu
    1760                1765                1770

Thr Leu Ser Asn Ala Pro Asn Thr Thr Asp Ser Leu Asp Leu Ser
    1775                1780                1785

His Gly Val His Thr Ser Ser Ala Gly Thr Leu Ala Thr Asp Arg
    1790                1795                1800

Ser Leu Asn Thr Gly Val Thr Arg Ala Ser Arg Leu Glu Asn Gly
    1805                1810                1815

Ser Asp Thr Ser Ser Lys Ser Leu Ser Met Gly Asn Ser Thr His
    1820                1825                1830

Thr Ser Met Thr Tyr Thr Glu Lys Ser Glu Val Ser Ser Ser Ile
    1835                1840                1845

His Pro Arg Pro Glu Thr Ser Ala Pro Gly Ala Glu Thr Thr Leu
    1850                1855                1860

Thr Ser Thr Pro Gly Asn Arg Ala Ile Ser Leu Thr Leu Pro Phe
    1865                1870                1875
```

```
Ser Ser  Ile Pro Val Glu Glu  Val Ile Ser Thr Gly  Ile Thr Ser
    1880                 1885                 1890

Gly Pro  Asp Ile Asn Ser Ala  Pro Met Thr His Ser  Pro Ile Thr
    1895                 1900                 1905

Pro Pro  Thr Ile Val Trp Thr  Ser Thr Gly Thr Ile  Glu Gln Ser
    1910                 1915                 1920

Thr Gln  Pro Leu His Ala Val  Ser Ser Glu Lys Val  Ser Val Gln
    1925                 1930                 1935

Thr Gln  Ser Thr Pro Tyr Val  Asn Ser Val Ala Val  Ser Ala Ser
    1940                 1945                 1950

Pro Thr  His Glu Asn Ser Val  Ser Ser Gly Ser Ser  Thr Ser Ser
    1955                 1960                 1965

Pro Tyr  Ser Ser Ala Ser Leu  Glu Ser Leu Asp Ser  Thr Ile Ser
    1970                 1975                 1980

Arg Arg  Asn Ala Ile Thr Ser  Trp Leu Trp Asp Leu  Thr Thr Ser
    1985                 1990                 1995

Leu Pro  Thr Thr Thr Trp Pro  Ser Thr Ser Leu Ser  Glu Ala Leu
    2000                 2005                 2010

Ser Ser  Gly His Ser Gly Val  Ser Asn Pro Ser Ser  Thr Thr Thr
    2015                 2020                 2025

Glu Phe  Pro Leu Phe Ser Ala  Ala Ser Thr Ser Ala  Ala Lys Gln
    2030                 2035                 2040

Arg Asn  Pro Glu Thr Glu Thr  His Gly Pro Gln Asn  Thr Ala Ala
    2045                 2050                 2055

Ser Thr  Leu Asn Thr Asp Ala  Ser Ser Val Thr Gly  Leu Ser Glu
    2060                 2065                 2070

Thr Pro  Val Gly Ala Ser Ile  Ser Ser Glu Val Pro  Leu Pro Met
    2075                 2080                 2085

Ala Ile  Thr Ser Arg Ser Asp  Val Ser Gly Leu Thr  Ser Glu Ser
    2090                 2095                 2100

Thr Ala  Asn Pro Ser Leu Gly  Thr Ala Ser Ser Ala  Gly Thr Lys
    2105                 2110                 2115

Leu Thr  Arg Thr Ile Ser Leu  Pro Thr Ser Glu Ser  Leu Val Ser
    2120                 2125                 2130

Phe Arg  Met Asn Lys Asp Pro  Trp Thr Val Ser Ile  Pro Leu Gly
    2135                 2140                 2145

Ser His  Pro Thr Thr Asn Thr  Glu Thr Ser Ile Pro  Val Asn Ser
    2150                 2155                 2160

Ala Gly  Pro Pro Gly Leu Ser  Thr Val Ala Ser Asp  Val Ile Asp
    2165                 2170                 2175

Thr Pro  Ser Asp Gly Ala Glu  Ser Ile Pro Thr Val  Ser Phe Ser
    2180                 2185                 2190

Pro Ser  Pro Asp Thr Glu Val  Thr Thr Ile Ser His  Phe Pro Glu
    2195                 2200                 2205

Lys Thr  Thr His Ser Phe Arg  Thr Ile Ser Ser Leu  Thr His Glu
    2210                 2215                 2220

Leu Thr  Ser Arg Val Thr Pro  Ile Pro Gly Asp Trp  Met Ser Ser
    2225                 2230                 2235

Ala Met  Ser Thr Lys Pro Thr  Gly Ala Ser Pro Ser  Ile Thr Leu
    2240                 2245                 2250

Gly Glu  Arg Arg Thr Ile Thr  Ser Ala Ala Pro Thr  Thr Ser Pro
    2255                 2260                 2265

Ile Val  Leu Thr Ala Ser Phe  Thr Glu Thr Ser Thr  Val Ser Leu
```

2270 2275 2280

Asp Asn Glu Thr Thr Val Lys Thr Ser Asp Ile Leu Asp Ala Arg
2285 2290 2295

Lys Thr Asn Glu Leu Pro Ser Asp Ser Ser Ser Ser Ser Asp Leu
2300 2305 2310

Ile Asn Thr Ser Ile Ala Ser Ser Thr Met Asp Val Thr Lys Thr
2315 2320 2325

Ala Ser Ile Ser Pro Thr Ser Ile Ser Gly Met Thr Ala Ser Ser
2330 2335 2340

Ser Pro Ser Leu Phe Ser Ser Asp Arg Pro Gln Val Pro Thr Ser
2345 2350 2355

Thr Thr Glu Thr Asn Thr Ala Thr Ser Pro Ser Val Ser Ser Asn
2360 2365 2370

Thr Tyr Ser Leu Asp Gly Gly Ser Asn Val Gly Gly Thr Pro Ser
2375 2380 2385

Thr Leu Pro Pro Phe Thr Ile Thr His Pro Val Glu Thr Ser Ser
2390 2395 2400

Ala Leu Leu Ala Trp Ser Arg Pro Val Arg Thr Phe Ser Thr Met
2405 2410 2415

Val Ser Thr Asp Thr Ala Ser Gly Glu Asn Pro Thr Ser Ser Asn
2420 2425 2430

Ser Val Val Thr Ser Val Pro Ala Pro Gly Thr Trp Thr Ser Val
2435 2440 2445

Gly Ser Thr Thr Asp Leu Pro Ala Met Gly Phe Leu Lys Thr Ser
2450 2455 2460

Pro Ala Gly Glu Ala His Ser Leu Leu Ala Ser Thr Ile Glu Pro
2465 2470 2475

Ala Thr Ala Phe Thr Pro His Leu Ser Ala Ala Val Val Thr Gly
2480 2485 2490

Ser Ser Ala Thr Ser Glu Ala Ser Leu Leu Thr Thr Ser Glu Ser
2495 2500 2505

Lys Ala Ile His Ser Ser Pro Gln Thr Pro Thr Thr Pro Thr Ser
2510 2515 2520

Gly Ala Asn Trp Glu Thr Ser Ala Thr Pro Glu Ser Leu Leu Val
2525 2530 2535

Val Thr Glu Thr Ser Asp Thr Thr Leu Thr Ser Lys Ile Leu Val
2540 2545 2550

Thr Asp Thr Ile Leu Phe Ser Thr Val Ser Thr Pro Pro Ser Lys
2555 2560 2565

Phe Pro Ser Thr Gly Thr Leu Ser Gly Ala Ser Phe Pro Thr Leu
2570 2575 2580

Leu Pro Asp Thr Pro Ala Ile Pro Leu Thr Ala Thr Glu Pro Thr
2585 2590 2595

Ser Ser Leu Ala Thr Ser Phe Asp Ser Thr Pro Leu Val Thr Ile
2600 2605 2610

Ala Ser Asp Ser Leu Gly Thr Val Pro Glu Thr Thr Leu Thr Met
2615 2620 2625

Ser Glu Thr Ser Asn Gly Asp Ala Leu Val Leu Lys Thr Val Ser
2630 2635 2640

Asn Pro Asp Arg Ser Ile Pro Gly Ile Thr Ile Gln Gly Val Thr
2645 2650 2655

Glu Ser Pro Leu His Pro Ser Ser Thr Ser Pro Ser Lys Ile Val
2660 2665 2670

Ala Pro Arg Asn Thr Thr Tyr Glu Gly Ser Ile Thr Val Ala Leu
2675 2680 2685

Ser Thr Leu Pro Ala Gly Thr Thr Gly Ser Leu Val Phe Ser Gln
2690 2695 2700

Ser Ser Glu Asn Ser Glu Thr Thr Ala Leu Val Asp Ser Ser Ala
2705 2710 2715

Gly Leu Glu Arg Ala Ser Val Met Pro Leu Thr Thr Gly Ser Gln
2720 2725 2730

Gly Met Ala Ser Ser Gly Gly Ile Arg Ser Gly Ser Thr His Ser
2735 2740 2745

Thr Gly Thr Lys Thr Phe Ser Ser Leu Pro Leu Thr Met Asn Pro
2750 2755 2760

Gly Glu Val Thr Ala Met Ser Glu Ile Thr Thr Asn Arg Leu Thr
2765 2770 2775

Ala Thr Gln Ser Thr Ala Pro Lys Gly Ile Pro Val Lys Pro Thr
2780 2785 2790

Ser Ala Glu Ser Gly Leu Leu Thr Pro Val Ser Ala Ser Ser Ser
2795 2800 2805

Pro Ser Lys Ala Phe Ala Ser Leu Thr Thr Ala Pro Pro Thr Trp
2810 2815 2820

Gly Ile Pro Gln Ser Thr Leu Thr Phe Glu Phe Ser Glu Val Pro
2825 2830 2835

Ser Leu Asp Thr Lys Ser Ala Ser Leu Pro Thr Pro Gly Gln Ser
2840 2845 2850

Leu Asn Thr Ile Pro Asp Ser Asp Ala Ser Thr Ala Ser Ser Ser
2855 2860 2865

Leu Ser Lys Ser Pro Glu Lys Asn Pro Arg Ala Arg Met Met Thr
2870 2875 2880

Ser Thr Lys Ala Ile Ser Ala Ser Ser Phe Gln Ser Thr Gly Phe
2885 2890 2895

Thr Glu Thr Pro Glu Gly Ser Ala Ser Pro Ser Met Ala Gly His
2900 2905 2910

Glu Pro Arg Val Pro Thr Ser Gly Thr Gly Asp Pro Arg Tyr Ala
2915 2920 2925

Ser Glu Ser Met Ser Tyr Pro Asp Pro Ser Lys Ala Ser Ser Ala
2930 2935 2940

Met Thr Ser Thr Ser Leu Ala Ser Lys Leu Thr Thr Leu Phe Ser
2945 2950 2955

Thr Gly Gln Ala Ala Arg Ser Gly Ser Ser Ser Ser Pro Ile Ser
2960 2965 2970

Leu Ser Thr Glu Lys Glu Thr Ser Phe Leu Ser Pro Thr Ala Ser
2975 2980 2985

Thr Ser Arg Lys Thr Ser Leu Phe Leu Gly Pro Ser Met Ala Arg
2990 2995 3000

Gln Pro Asn Ile Leu Val His Leu Gln Thr Ser Ala Leu Thr Leu
3005 3010 3015

Ser Pro Thr Ser Thr Leu Asn Met Ser Gln Glu Glu Pro Pro Glu
3020 3025 3030

Leu Thr Ser Ser Gln Thr Ile Ala Glu Glu Glu Gly Thr Thr Ala
3035 3040 3045

Glu Thr Gln Thr Leu Thr Phe Thr Pro Ser Glu Thr Pro Thr Ser
3050 3055 3060

Leu Leu Pro Val Ser Ser Pro Thr Glu Pro Thr Ala Arg Arg Lys
3065 3070 3075

Ser Ser Pro Glu Thr Trp Ala Ser Ser Ile Ser Val Pro Ala Lys
3080 3085 3090

Thr Ser Leu Val Glu Thr Thr Asp Gly Thr Leu Val Thr Thr Ile
3095 3100 3105

Lys Met Ser Ser Gln Ala Ala Gln Gly Asn Ser Thr Trp Pro Ala
3110 3115 3120

Pro Ala Glu Glu Thr Gly Ser Ser Pro Ala Gly Thr Ser Pro Gly
3125 3130 3135

Ser Pro Glu Met Ser Thr Thr Leu Lys Ile Met Ser Ser Lys Glu
3140 3145 3150

Pro Ser Ile Ser Pro Glu Ile Arg Ser Thr Val Arg Asn Ser Pro
3155 3160 3165

Trp Lys Thr Pro Glu Thr Thr Val Pro Met Glu Thr Thr Val Glu
3170 3175 3180

Pro Val Thr Leu Gln Ser Thr Ala Leu Gly Ser Gly Ser Thr Ser
3185 3190 3195

Ile Ser His Leu Pro Thr Gly Thr Thr Ser Pro Thr Lys Ser Pro
3200 3205 3210

Thr Glu Asn Met Leu Ala Thr Glu Arg Val Ser Leu Ser Pro Ser
3215 3220 3225

Pro Pro Glu Ala Trp Thr Asn Leu Tyr Ser Gly Thr Pro Gly Gly
3230 3235 3240

Thr Arg Gln Ser Leu Ala Thr Met Ser Ser Val Ser Leu Glu Ser
3245 3250 3255

Pro Thr Ala Arg Ser Ile Thr Gly Thr Gly Gln Gln Ser Ser Pro
3260 3265 3270

Glu Leu Val Ser Lys Thr Thr Gly Met Glu Phe Ser Met Trp His
3275 3280 3285

Gly Ser Thr Gly Gly Thr Thr Gly Asp Thr His Val Ser Leu Ser
3290 3295 3300

Thr Ser Ser Asn Ile Leu Glu Asp Pro Val Thr Ser Pro Asn Ser
3305 3310 3315

Val Ser Ser Leu Thr Asp Lys Ser Lys His Lys Thr Glu Thr Trp
3320 3325 3330

Val Ser Thr Thr Ala Ile Pro Ser Thr Val Leu Asn Asn Lys Ile
3335 3340 3345

Met Ala Ala Glu Gln Gln Thr Ser Arg Ser Val Asp Glu Ala Tyr
3350 3355 3360

Ser Ser Thr Ser Ser Trp Ser Asp Gln Thr Ser Gly Ser Asp Ile
3365 3370 3375

Thr Leu Gly Ala Ser Pro Asp Val Thr Asn Thr Leu Tyr Ile Thr
3380 3385 3390

Ser Thr Ala Gln Thr Thr Ser Leu Val Ser Leu Pro Ser Gly Asp
3395 3400 3405

Gln Gly Ile Thr Ser Leu Thr Asn Pro Ser Gly Gly Lys Thr Ser
3410 3415 3420

Ser Ala Ser Ser Val Thr Ser Pro Ser Ile Gly Leu Glu Thr Leu
3425 3430 3435

Arg Ala Asn Val Ser Ala Val Lys Ser Asp Ile Ala Pro Thr Ala
3440 3445 3450

Gly His Leu Ser Gln Thr Ser Ser Pro Ala Glu Val Ser Ile Leu

```
    3455                3460                3465

Asp Val  Thr Thr Ala Pro Thr  Pro Gly Ile Ser Thr  Thr Ile Thr
    3470                3475                3480

Thr Met  Gly Thr Asn Ser Ile  Ser Thr Thr Thr Pro  Asn Pro Glu
    3485                3490                3495

Val Gly  Met Ser Thr Met Asp  Ser Thr Pro Ala Thr  Glu Arg Arg
    3500                3505                3510

Thr Thr  Ser Thr Glu His Pro  Ser Thr Trp Ser Ser  Thr Ala Ala
    3515                3520                3525

Ser Asp  Ser Trp Thr Val Thr  Asp Met Thr Ser Asn  Leu Lys Val
    3530                3535                3540

Ala Arg  Ser Pro Gly Thr Ile  Ser Thr Met His Thr  Thr Ser Phe
    3545                3550                3555

Leu Ala  Ser Ser Thr Glu Leu  Asp Ser Met Ser Thr  Pro His Gly
    3560                3565                3570

Arg Ile  Thr Val Ile Gly Thr  Ser Leu Val Thr Pro  Ser Ser Asp
    3575                3580                3585

Ala Ser  Ala Val Lys Thr Glu  Thr Ser Thr Ser Glu  Arg Thr Leu
    3590                3595                3600

Ser Pro  Ser Asp Thr Thr Ala  Ser Thr Pro Ile Ser  Thr Phe Ser
    3605                3610                3615

Arg Val  Gln Arg Met Ser Ile  Ser Val Pro Asp Ile  Leu Ser Thr
    3620                3625                3630

Ser Trp  Thr Pro Ser Ser Thr  Glu Ala Glu Asp Val  Pro Val Ser
    3635                3640                3645

Met Val  Ser Thr Asp His Ala  Ser Thr Lys Thr Asp  Pro Asn Thr
    3650                3655                3660

Pro Leu  Ser Thr Phe Leu Phe  Asp Ser Leu Ser Thr  Leu Asp Trp
    3665                3670                3675

Asp Thr  Gly Arg Ser Leu Ser  Ser Ala Thr Ala Thr  Thr Ser Ala
    3680                3685                3690

Pro Gln  Gly Ala Thr Thr Pro  Gln Glu Leu Thr Leu  Glu Thr Met
    3695                3700                3705

Ile Ser  Pro Ala Thr Ser Gln  Leu Pro Phe Ser Ile  Gly His Ile
    3710                3715                3720

Thr Ser  Ala Val Thr Pro Ala  Ala Met Ala Arg Ser  Ser Gly Val
    3725                3730                3735

Thr Phe  Ser Arg Pro Asp Pro  Thr Ser Lys Lys Ala  Glu Gln Thr
    3740                3745                3750

Ser Thr  Gln Leu Pro Thr Thr  Thr Ser Ala His Pro  Gly Gln Val
    3755                3760                3765

Pro Arg  Ser Ala Ala Thr Thr  Leu Asp Val Ile Pro  His Thr Ala
    3770                3775                3780

Lys Thr  Pro Asp Ala Thr Phe  Gln Arg Gln Gly Gln  Thr Ala Leu
    3785                3790                3795

Thr Thr  Glu Ala Arg Ala Thr  Ser Asp Ser Trp Asn  Glu Lys Glu
    3800                3805                3810

Lys Ser  Thr Pro Ser Ala Pro  Trp Ile Thr Glu Met  Met Asn Ser
    3815                3820                3825

Val Ser  Glu Asp Thr Ile Lys  Glu Val Thr Ser Ser  Ser Ser Val
    3830                3835                3840

Leu Arg  Thr Leu Asn Thr Leu  Asp Ile Asn Leu Glu  Ser Gly Thr
    3845                3850                3855
```

Thr Ser Ser Pro Ser Trp Lys Ser Ser Pro Tyr Glu Arg Ile Ala
3860 3865 3870

Pro Ser Glu Ser Thr Thr Asp Lys Glu Ala Ile His Pro Ser Thr
3875 3880 3885

Asn Thr Val Glu Thr Thr Gly Trp Val Thr Ser Ser Glu His Ala
3890 3895 3900

Ser His Ser Thr Ile Pro Ala His Ser Ala Ser Ser Lys Leu Thr
3905 3910 3915

Ser Pro Val Val Thr Thr Ser Thr Arg Glu Gln Ala Ile Val Ser
3920 3925 3930

Met Ser Thr Thr Thr Trp Pro Glu Ser Thr Arg Ala Arg Thr Glu
3935 3940 3945

Pro Asn Ser Phe Leu Thr Ile Glu Leu Arg Asp Val Ser Pro Tyr
3950 3955 3960

Met Asp Thr Ser Ser Thr Thr Gln Thr Ser Ile Ile Ser Ser Pro
3965 3970 3975

Gly Ser Thr Ala Ile Thr Lys Gly Pro Arg Thr Glu Ile Thr Ser
3980 3985 3990

Ser Lys Arg Ile Ser Ser Ser Phe Leu Ala Gln Ser Met Arg Ser
3995 4000 4005

Ser Asp Ser Pro Ser Glu Ala Ile Thr Arg Leu Ser Asn Phe Pro
4010 4015 4020

Ala Met Thr Glu Ser Gly Gly Met Ile Leu Ala Met Gln Thr Ser
4025 4030 4035

Pro Pro Gly Ala Thr Ser Leu Ser Ala Pro Thr Leu Asp Thr Ser
4040 4045 4050

Ala Thr Ala Ser Trp Thr Gly Thr Pro Leu Ala Thr Thr Gln Arg
4055 4060 4065

Phe Thr Tyr Ser Glu Lys Thr Thr Leu Phe Ser Lys Gly Pro Glu
4070 4075 4080

Asp Thr Ser Gln Pro Ser Pro Pro Ser Val Glu Glu Thr Ser Ser
4085 4090 4095

Ser Ser Ser Leu Val Pro Ile His Ala Thr Thr Ser Pro Ser Asn
4100 4105 4110

Ile Leu Leu Thr Ser Gln Gly His Ser Pro Ser Ser Thr Pro Pro
4115 4120 4125

Val Thr Ser Val Phe Leu Ser Glu Thr Ser Gly Leu Gly Lys Thr
4130 4135 4140

Thr Asp Met Ser Arg Ile Ser Leu Glu Pro Gly Thr Ser Leu Pro
4145 4150 4155

Pro Asn Leu Ser Ser Thr Ala Gly Glu Ala Leu Ser Thr Tyr Glu
4160 4165 4170

Ala Ser Arg Asp Thr Lys Ala Ile His His Ser Ala Asp Thr Ala
4175 4180 4185

Val Thr Asn Met Glu Ala Thr Ser Ser Glu Tyr Ser Pro Ile Pro
4190 4195 4200

Gly His Thr Lys Pro Ser Lys Ala Thr Ser Pro Leu Val Thr Ser
4205 4210 4215

His Ile Met Gly Asp Ile Thr Ser Ser Thr Ser Val Phe Gly Ser
4220 4225 4230

Ser Glu Thr Thr Glu Ile Glu Thr Val Ser Ser Val Asn Gln Gly
4235 4240 4245

```
Leu Gln  Glu Arg Ser Thr Ser  Gln Val Ala Ser Ser  Ala Thr Glu
    4250                 4255                 4260

Thr Ser  Thr Val Ile Thr His  Val Ser Ser Gly Asp  Ala Thr Thr
    4265                 4270                 4275

His Val  Thr Lys Thr Gln Ala  Thr Phe Ser Ser Gly  Thr Ser Ile
    4280                 4285                 4290

Ser Ser  Pro His Gln Phe Ile  Thr Ser Thr Asn Thr  Phe Thr Asp
    4295                 4300                 4305

Val Ser  Thr Asn Pro Ser Thr  Ser Leu Ile Met Thr  Glu Ser Ser
    4310                 4315                 4320

Gly Val  Thr Ile Thr Thr Gln  Thr Gly Pro Thr Gly  Ala Ala Thr
    4325                 4330                 4335

Gln Gly  Pro Tyr Leu Leu Asp  Thr Ser Thr Met Pro  Tyr Leu Thr
    4340                 4345                 4350

Glu Thr  Pro Leu Ala Val Thr  Pro Asp Phe Met Gln  Ser Glu Lys
    4355                 4360                 4365

Thr Thr  Leu Ile Ser Lys Gly  Pro Lys Asp Val Ser  Trp Thr Ser
    4370                 4375                 4380

Pro Pro  Ser Val Ala Glu Thr  Ser Tyr Pro Ser Ser  Leu Thr Pro
    4385                 4390                 4395

Phe Leu  Val Thr Thr Ile Pro  Pro Ala Thr Ser Thr  Leu Gln Gly
    4400                 4405                 4410

Gln His  Thr Ser Ser Pro Val  Ser Ala Thr Ser Val  Leu Thr Ser
    4415                 4420                 4425

Gly Leu  Val Lys Thr Thr Asp  Met Leu Asn Thr Ser  Met Glu Pro
    4430                 4435                 4440

Val Thr  Asn Ser Pro Gln Asn  Leu Asn Asn Pro Ser  Asn Glu Ile
    4445                 4450                 4455

Leu Ala  Thr Leu Ala Ala Thr  Thr Asp Ile Glu Thr  Ile His Pro
    4460                 4465                 4470

Ser Ile  Asn Lys Ala Val Thr  Asn Met Gly Thr Ala  Ser Ser Ala
    4475                 4480                 4485

His Val  Leu His Ser Thr Leu  Pro Val Ser Ser Glu  Pro Ser Thr
    4490                 4495                 4500

Ala Thr  Ser Pro Met Val Pro  Ala Ser Ser Met Gly  Asp Ala Leu
    4505                 4510                 4515

Ala Ser  Ile Ser Ile Pro Gly  Ser Glu Thr Thr Asp  Ile Glu Gly
    4520                 4525                 4530

Glu Pro  Thr Ser Ser Leu Thr  Ala Gly Arg Lys Glu  Asn Ser Thr
    4535                 4540                 4545

Leu Gln  Glu Met Asn Ser Thr  Thr Glu Ser Asn Ile  Ile Leu Ser
    4550                 4555                 4560

Asn Val  Ser Val Gly Ala Ile  Thr Glu Ala Thr Lys  Met Glu Val
    4565                 4570                 4575

Pro Ser  Phe Asp Ala Thr Phe  Ile Pro Thr Pro Ala  Gln Ser Thr
    4580                 4585                 4590

Lys Phe  Pro Asp Ile Phe Ser  Val Ala Ser Ser Arg  Leu Ser Asn
    4595                 4600                 4605

Ser Pro  Pro Met Thr Ile Ser  Thr His Met Thr Thr  Thr Gln Thr
    4610                 4615                 4620

Gly Ser  Ser Gly Ala Thr Ser  Lys Ile Pro Leu Ala  Leu Asp Thr
    4625                 4630                 4635

Ser Thr  Leu Glu Thr Ser Ala  Gly Thr Pro Ser Val  Val Thr Glu
```

```
    4640                4645                4650

Gly Phe Ala His Ser Lys Ile Thr Thr Ala Met Asn Asn Asp Val
    4655                4660                4665

Lys Asp Val Ser Gln Thr Asn Pro Pro Phe Gln Asp Glu Ala Ser
    4670                4675                4680

Ser Pro Ser Ser Gln Ala Pro Val Leu Val Thr Thr Leu Pro Ser
    4685                4690                4695

Ser Val Ala Phe Thr Pro Gln Trp His Ser Thr Ser Ser Pro Val
    4700                4705                4710

Ser Met Ser Ser Val Leu Thr Ser Ser Leu Val Lys Thr Ala Gly
    4715                4720                4725

Lys Val Asp Thr Ser Leu Glu Thr Val Thr Ser Ser Pro Gln Ser
    4730                4735                4740

Met Ser Asn Thr Leu Asp Asp Ile Ser Val Thr Ser Ala Ala Thr
    4745                4750                4755

Thr Asp Ile Glu Thr Thr His Pro Ser Ile Asn Thr Val Val Thr
    4760                4765                4770

Asn Val Gly Thr Thr Gly Ser Ala Phe Glu Ser His Ser Thr Val
    4775                4780                4785

Ser Ala Tyr Pro Glu Pro Ser Lys Val Thr Ser Pro Asn Val Thr
    4790                4795                4800

Thr Ser Thr Met Glu Asp Thr Thr Ile Ser Arg Ser Ile Pro Lys
    4805                4810                4815

Ser Ser Lys Thr Thr Arg Thr Glu Thr Glu Thr Thr Ser Ser Leu
    4820                4825                4830

Thr Pro Lys Leu Arg Glu Thr Ser Ile Ser Gln Glu Ile Thr Ser
    4835                4840                4845

Ser Thr Glu Thr Ser Thr Val Pro Tyr Lys Glu Leu Thr Gly Ala
    4850                4855                4860

Thr Thr Glu Val Ser Arg Thr Asp Val Thr Ser Ser Ser Ser Thr
    4865                4870                4875

Ser Phe Pro Gly Pro Asp Gln Ser Thr Val Ser Leu Asp Ile Ser
    4880                4885                4890

Thr Glu Thr Asn Thr Arg Leu Ser Thr Ser Pro Ile Met Thr Glu
    4895                4900                4905

Ser Ala Glu Ile Thr Ile Thr Thr Gln Thr Gly Pro His Gly Ala
    4910                4915                4920

Thr Ser Gln Asp Thr Phe Thr Met Asp Pro Ser Asn Thr Thr Pro
    4925                4930                4935

Gln Ala Gly Ile His Ser Ala Met Thr His Gly Phe Ser Gln Leu
    4940                4945                4950

Asp Val Thr Thr Leu Met Ser Arg Ile Pro Gln Asp Val Ser Trp
    4955                4960                4965

Thr Ser Pro Pro Ser Val Asp Lys Thr Ser Ser Pro Ser Ser Phe
    4970                4975                4980

Leu Ser Ser Pro Ala Met Thr Thr Pro Ser Leu Ile Ser Ser Thr
    4985                4990                4995

Leu Pro Glu Asp Lys Leu Ser Ser Pro Met Thr Ser Leu Leu Thr
    5000                5005                5010

Ser Gly Leu Val Lys Ile Thr Asp Ile Leu Arg Thr Arg Leu Glu
    5015                5020                5025

Pro Val Thr Ser Ser Leu Pro Asn Phe Ser Ser Thr Ser Asp Lys
    5030                5035                5040
```

```
Ile Leu Ala Thr Ser Lys Asp Ser Lys Asp Thr Lys Glu Ile Phe
    5045                5050                5055

Pro Ser Ile Asn Thr Glu Glu Thr Asn Val Lys Ala Asn Asn Ser
    5060                5065                5070

Gly His Glu Ser His Ser Pro Ala Leu Ala Asp Ser Glu Thr Pro
    5075                5080                5085

Lys Ala Thr Thr Gln Met Val Ile Thr Thr Thr Val Gly Asp Pro
    5090                5095                5100

Ala Pro Ser Thr Ser Met Pro Val His Gly Ser Ser Glu Thr Thr
    5105                5110                5115

Asn Ile Lys Arg Glu Pro Thr Tyr Phe Leu Thr Pro Arg Leu Arg
    5120                5125                5130

Glu Thr Ser Thr Ser Gln Glu Ser Ser Phe Pro Thr Asp Thr Ser
    5135                5140                5145

Phe Leu Leu Ser Lys Val Pro Thr Gly Thr Ile Thr Glu Val Ser
    5150                5155                5160

Ser Thr Gly Val Asn Ser Ser Ser Lys Ile Ser Thr Pro Asp His
    5165                5170                5175

Asp Lys Ser Thr Val Pro Pro Asp Thr Phe Thr Gly Glu Ile Pro
    5180                5185                5190

Arg Val Phe Thr Ser Ser Ile Lys Thr Lys Ser Ala Glu Met Thr
    5195                5200                5205

Ile Thr Thr Gln Ala Ser Pro Pro Glu Ser Ala Ser His Ser Thr
    5210                5215                5220

Leu Pro Leu Asp Thr Ser Thr Thr Leu Ser Gln Gly Gly Thr His
    5225                5230                5235

Ser Thr Val Thr Gln Gly Phe Pro Tyr Ser Glu Val Thr Thr Leu
    5240                5245                5250

Met Gly Met Gly Pro Gly Asn Val Ser Trp Met Thr Thr Pro Pro
    5255                5260                5265

Val Glu Glu Thr Ser Ser Val Ser Ser Leu Met Ser Ser Pro Ala
    5270                5275                5280

Met Thr Ser Pro Ser Pro Val Ser Ser Thr Ser Pro Gln Ser Ile
    5285                5290                5295

Pro Ser Ser Pro Leu Pro Val Thr Ala Leu Pro Thr Ser Val Leu
    5300                5305                5310

Val Thr Thr Thr Asp Val Leu Gly Thr Thr Ser Pro Glu Ser Val
    5315                5320                5325

Thr Ser Ser Pro Pro Asn Leu Ser Ser Ile Thr His Glu Arg Pro
    5330                5335                5340

Ala Thr Tyr Lys Asp Thr Ala His Thr Glu Ala Ala Met His His
    5345                5350                5355

Ser Thr Asn Thr Ala Val Thr Asn Val Gly Thr Ser Gly Ser Gly
    5360                5365                5370

His Lys Ser Gln Ser Ser Val Leu Ala Asp Ser Glu Thr Ser Lys
    5375                5380                5385

Ala Thr Pro Leu Met Ser Thr Thr Ser Thr Leu Gly Asp Thr Ser
    5390                5395                5400

Val Ser Thr Ser Thr Pro Asn Ile Ser Gln Thr Asn Gln Ile Gln
    5405                5410                5415

Thr Glu Pro Thr Ala Ser Leu Ser Pro Arg Leu Arg Glu Ser Ser
    5420                5425                5430
```

Thr Ser Glu Lys Thr Ser Ser Thr Thr Glu Thr Asn Thr Ala Phe
5435 5440 5445

Ser Tyr Val Pro Thr Gly Ala Ile Thr Gln Ala Ser Arg Thr Glu
5450 5455 5460

Ile Ser Ser Ser Arg Thr Ser Ile Ser Asp Leu Asp Arg Pro Thr
5465 5470 5475

Ile Ala Pro Asp Ile Ser Thr Gly Met Ile Thr Arg Leu Phe Thr
5480 5485 5490

Ser Pro Ile Met Thr Lys Ser Ala Glu Met Thr Val Thr Thr Gln
5495 5500 5505

Thr Thr Thr Pro Gly Ala Thr Ser Gln Gly Ile Leu Pro Trp Asp
5510 5515 5520

Thr Ser Thr Thr Leu Phe Gln Gly Gly Thr His Ser Thr Val Ser
5525 5530 5535

Gln Gly Phe Pro His Ser Glu Ile Thr Thr Leu Arg Ser Arg Thr
5540 5545 5550

Pro Gly Asp Val Ser Trp Met Thr Thr Pro Pro Val Glu Glu Thr
5555 5560 5565

Ser Ser Gly Phe Ser Leu Met Ser Pro Ser Met Thr Ser Pro Ser
5570 5575 5580

Pro Val Ser Ser Thr Ser Pro Glu Ser Ile Pro Ser Ser Pro Leu
5585 5590 5595

Pro Val Thr Ala Leu Leu Thr Ser Val Leu Val Thr Thr Thr Asn
5600 5605 5610

Val Leu Gly Thr Thr Ser Pro Glu Pro Val Thr Ser Ser Pro Pro
5615 5620 5625

Asn Leu Ser Ser Pro Thr Gln Glu Arg Leu Thr Thr Tyr Lys Asp
5630 5635 5640

Thr Ala His Thr Glu Ala Met His Ala Ser Met His Thr Asn Thr
5645 5650 5655

Ala Val Ala Asn Val Gly Thr Ser Ile Ser Gly His Glu Ser Gln
5660 5665 5670

Ser Ser Val Pro Ala Asp Ser His Thr Ser Lys Ala Thr Ser Pro
5675 5680 5685

Met Gly Ile Thr Phe Ala Met Gly Asp Thr Ser Val Ser Thr Ser
5690 5695 5700

Thr Pro Ala Phe Phe Glu Thr Arg Ile Gln Thr Glu Ser Thr Ser
5705 5710 5715

Ser Leu Ile Pro Gly Leu Arg Asp Thr Arg Thr Ser Glu Glu Ile
5720 5725 5730

Asn Thr Val Thr Glu Thr Ser Thr Val Leu Ser Glu Val Pro Thr
5735 5740 5745

Thr Thr Thr Thr Glu Val Ser Arg Thr Glu Val Ile Thr Ser Ser
5750 5755 5760

Arg Thr Thr Ile Ser Gly Pro Asp His Ser Lys Met Ser Pro Tyr
5765 5770 5775

Ile Ser Thr Glu Thr Ile Thr Arg Leu Ser Thr Phe Pro Phe Val
5780 5785 5790

Thr Gly Ser Thr Glu Met Ala Ile Thr Asn Gln Thr Gly Pro Ile
5795 5800 5805

Gly Thr Ile Ser Gln Ala Thr Leu Thr Leu Asp Thr Ser Ser Thr
5810 5815 5820

Ala Ser Trp Glu Gly Thr His Ser Pro Val Thr Gln Arg Phe Pro

-continued

```
    5825                5830                5835

His Ser  Glu Glu Thr Thr Thr  Met Ser Arg Ser Thr  Lys Gly Val
    5840                5845                5850

Ser Trp  Gln Ser Pro Pro Ser  Val Glu Glu Thr Ser  Ser Pro Ser
    5855                5860                5865

Ser Pro  Val Pro Leu Pro Ala  Ile Thr Ser His Ser  Ser Leu Tyr
    5870                5875                5880

Ser Ala  Val Ser Gly Ser Ser  Pro Thr Ser Ala Leu  Pro Val Thr
    5885                5890                5895

Ser Leu  Leu Thr Ser Gly Arg  Arg Lys Thr Ile Asp  Met Leu Asp
    5900                5905                5910

Thr His  Ser Glu Leu Val Thr  Ser Ser Leu Pro Ser  Ala Ser Ser
    5915                5920                5925

Phe Ser  Gly Glu Ile Leu Thr  Ser Glu Ala Ser Thr  Asn Thr Glu
    5930                5935                5940

Thr Ile  His Phe Ser Glu Asn  Thr Ala Glu Thr Asn  Met Gly Thr
    5945                5950                5955

Thr Asn  Ser Met His Lys Leu  His Ser Ser Val Ser  Ile His Ser
    5960                5965                5970

Gln Pro  Ser Gly His Thr Pro  Pro Lys Val Thr Gly  Ser Met Met
    5975                5980                5985

Glu Asp  Ala Ile Val Ser Thr  Ser Thr Pro Gly Ser  Pro Glu Thr
    5990                5995                6000

Lys Asn  Val Asp Arg Asp Ser  Thr Ser Pro Leu Thr  Pro Glu Leu
    6005                6010                6015

Lys Glu  Asp Ser Thr Ala Leu  Val Met Asn Ser Thr  Thr Glu Ser
    6020                6025                6030

Asn Thr  Val Phe Ser Ser Val  Ser Leu Asp Ala Ala  Thr Glu Val
    6035                6040                6045

Ser Arg  Ala Glu Val Thr Tyr  Tyr Asp Pro Thr Phe  Met Pro Ala
    6050                6055                6060

Ser Ala  Gln Ser Thr Lys Ser  Pro Asp Ile Ser Pro  Glu Ala Ser
    6065                6070                6075

Ser Ser  His Ser Asn Ser Pro  Pro Leu Thr Ile Ser  Thr His Lys
    6080                6085                6090

Thr Ile  Ala Thr Gln Thr Gly  Pro Ser Gly Val Thr  Ser Leu Gly
    6095                6100                6105

Gln Leu  Thr Leu Asp Thr Ser  Thr Ile Ala Thr Ser  Ala Gly Thr
    6110                6115                6120

Pro Ser  Ala Arg Thr Gln Asp  Phe Val Asp Ser Glu  Thr Thr Ser
    6125                6130                6135

Val Met  Asn Asn Asp Leu Asn  Asp Val Leu Lys Thr  Ser Pro Phe
    6140                6145                6150

Ser Ala  Glu Glu Ala Asn Ser  Leu Ser Ser Gln Ala  Pro Leu Leu
    6155                6160                6165

Val Thr  Thr Ser Pro Ser Pro  Val Thr Ser Thr Leu  Gln Glu His
    6170                6175                6180

Ser Thr  Ser Ser Leu Val Ser  Val Thr Ser Val Pro  Thr Pro Thr
    6185                6190                6195

Leu Ala  Lys Ile Thr Asp Met  Asp Thr Asn Leu Glu  Pro Val Thr
    6200                6205                6210

Arg Ser  Pro Gln Asn Leu Arg  Asn Thr Leu Ala Thr  Ser Glu Ala
    6215                6220                6225
```

```
Thr Thr Asp Thr His Thr Met His Pro Ser Ile Asn Thr Ala Val
    6230                6235                6240

Ala Asn Val Gly Thr Thr Ser Ser Pro Asn Glu Phe Tyr Phe Thr
    6245                6250                6255

Val Ser Pro Asp Ser Asp Pro Tyr Lys Ala Thr Ser Ala Val Val
    6260                6265                6270

Ile Thr Ser Thr Ser Gly Asp Ser Ile Val Ser Thr Ser Met Pro
    6275                6280                6285

Arg Ser Ser Ala Met Lys Lys Ile Glu Ser Glu Thr Thr Phe Ser
    6290                6295                6300

Leu Ile Phe Arg Leu Arg Glu Thr Ser Thr Ser Gln Lys Ile Gly
    6305                6310                6315

Ser Ser Ser Asp Thr Ser Thr Val Phe Asp Lys Ala Phe Thr Ala
    6320                6325                6330

Ala Thr Thr Glu Val Ser Arg Thr Glu Leu Thr Ser Ser Ser Arg
    6335                6340                6345

Thr Ser Ile Gln Gly Thr Glu Lys Pro Thr Met Ser Pro Asp Thr
    6350                6355                6360

Ser Thr Arg Ser Val Thr Met Leu Ser Thr Phe Ala Gly Leu Thr
    6365                6370                6375

Lys Ser Glu Glu Arg Thr Ile Ala Thr Gln Thr Gly Pro His Arg
    6380                6385                6390

Ala Thr Ser Gln Gly Thr Leu Thr Trp Asp Thr Ser Ile Thr Thr
    6395                6400                6405

Ser Gln Ala Gly Thr His Ser Ala Met Thr His Gly Phe Ser Gln
    6410                6415                6420

Leu Asp Leu Ser Thr Leu Thr Ser Arg Val Pro Glu Tyr Ile Ser
    6425                6430                6435

Gly Thr Ser Pro Pro Ser Val Glu Lys Thr Ser Ser Ser Ser Ser
    6440                6445                6450

Leu Leu Ser Leu Pro Ala Ile Thr Ser Pro Ser Pro Val Pro Thr
    6455                6460                6465

Thr Leu Pro Glu Ser Arg Pro Ser Ser Pro Val His Leu Thr Ser
    6470                6475                6480

Leu Pro Thr Ser Gly Leu Val Lys Thr Thr Asp Met Leu Ala Ser
    6485                6490                6495

Val Ala Ser Leu Pro Pro Asn Leu Gly Ser Thr Ser His Lys Ile
    6500                6505                6510

Pro Thr Thr Ser Glu Asp Ile Lys Asp Thr Glu Lys Met Tyr Pro
    6515                6520                6525

Ser Thr Asn Ile Ala Val Thr Asn Val Gly Thr Thr Thr Ser Glu
    6530                6535                6540

Lys Glu Ser Tyr Ser Ser Val Pro Ala Tyr Ser Glu Pro Pro Lys
    6545                6550                6555

Val Thr Ser Pro Met Val Thr Ser Phe Asn Ile Arg Asp Thr Ile
    6560                6565                6570

Val Ser Thr Ser Met Pro Gly Ser Ser Glu Ile Thr Arg Ile Glu
    6575                6580                6585

Met Glu Ser Thr Phe Ser Leu Ala His Gly Leu Lys Gly Thr Ser
    6590                6595                6600

Thr Ser Gln Asp Pro Ile Val Ser Thr Glu Lys Ser Ala Val Leu
    6605                6610                6615
```

His Lys Leu Thr Thr Gly Ala Thr Glu Thr Ser Arg Thr Glu Val
6620 6625 6630

Ala Ser Ser Arg Arg Thr Ser Ile Pro Gly Pro Asp His Ser Thr
6635 6640 6645

Glu Ser Pro Asp Ile Ser Thr Glu Val Ile Pro Ser Leu Pro Ile
6650 6655 6660

Ser Leu Gly Ile Thr Glu Ser Ser Asn Met Thr Ile Ile Thr Arg
6665 6670 6675

Thr Gly Pro Pro Leu Gly Ser Thr Ser Gln Gly Thr Phe Thr Leu
6680 6685 6690

Asp Thr Pro Thr Thr Ser Ser Arg Ala Gly Thr His Ser Met Ala
6695 6700 6705

Thr Gln Glu Phe Pro His Ser Glu Met Thr Thr Val Met Asn Lys
6710 6715 6720

Asp Pro Glu Ile Leu Ser Trp Thr Ile Pro Pro Ser Ile Glu Lys
6725 6730 6735

Thr Ser Phe Ser Ser Ser Leu Met Pro Ser Pro Ala Met Thr Ser
6740 6745 6750

Pro Pro Val Ser Ser Thr Leu Pro Lys Thr Ile His Thr Thr Pro
6755 6760 6765

Ser Pro Met Thr Ser Leu Leu Thr Pro Ser Leu Val Met Thr Thr
6770 6775 6780

Asp Thr Leu Gly Thr Ser Pro Glu Pro Thr Thr Ser Ser Pro Pro
6785 6790 6795

Asn Leu Ser Ser Thr Ser His Glu Ile Leu Thr Thr Asp Glu Asp
6800 6805 6810

Thr Thr Ala Ile Glu Ala Met His Pro Ser Thr Ser Thr Ala Ala
6815 6820 6825

Thr Asn Val Glu Thr Thr Ser Ser Gly His Gly Ser Gln Ser Ser
6830 6835 6840

Val Leu Ala Asp Ser Glu Lys Thr Lys Ala Thr Ala Pro Met Asp
6845 6850 6855

Thr Thr Ser Thr Met Gly His Thr Thr Val Ser Thr Ser Met Ser
6860 6865 6870

Val Ser Ser Glu Thr Thr Lys Ile Lys Arg Glu Ser Thr Tyr Ser
6875 6880 6885

Leu Thr Pro Gly Leu Arg Glu Thr Ser Ile Ser Gln Asn Ala Ser
6890 6895 6900

Phe Ser Thr Asp Thr Ser Ile Val Leu Ser Glu Val Pro Thr Gly
6905 6910 6915

Thr Thr Ala Glu Val Ser Arg Thr Glu Val Thr Ser Ser Gly Arg
6920 6925 6930

Thr Ser Ile Pro Gly Pro Ser Gln Ser Thr Val Leu Pro Glu Ile
6935 6940 6945

Ser Thr Arg Thr Met Thr Arg Leu Phe Ala Ser Pro Thr Met Thr
6950 6955 6960

Glu Ser Ala Glu Met Thr Ile Pro Thr Gln Thr Gly Pro Ser Gly
6965 6970 6975

Ser Thr Ser Gln Asp Thr Leu Thr Leu Asp Thr Ser Thr Thr Lys
6980 6985 6990

Ser Gln Ala Lys Thr His Ser Thr Leu Thr Gln Arg Phe Pro His
6995 7000 7005

Ser Glu Met Thr Thr Leu Met Ser Arg Gly Pro Gly Asp Met Ser

```
    7010                7015                7020

Trp Gln  Ser Ser Pro Ser Leu  Glu Asn Pro Ser Ser  Leu Pro Ser
    7025                7030                7035

Leu Leu  Ser Leu Pro Ala Thr  Thr Ser Pro Pro Pro  Ile Ser Ser
    7040                7045                7050

Thr Leu  Pro Val Thr Ile Ser  Ser Ser Pro Leu Pro  Val Thr Ser
    7055                7060                7065

Leu Leu  Thr Ser Ser Pro Val  Thr Thr Thr Asp Met  Leu His Thr
    7070                7075                7080

Ser Pro  Glu Leu Val Thr Ser  Ser Pro Pro Lys Leu  Ser His Thr
    7085                7090                7095

Ser Asp  Glu Arg Leu Thr Thr  Gly Lys Asp Thr Thr  Asn Thr Glu
    7100                7105                7110

Ala Val  His Pro Ser Thr Asn  Thr Ala Ala Ser Asn  Val Glu Ile
    7115                7120                7125

Pro Ser  Ser Gly His Glu Ser  Pro Ser Ser Ala Leu  Ala Asp Ser
    7130                7135                7140

Glu Thr  Ser Lys Ala Thr Ser  Pro Met Phe Ile Thr  Ser Thr Gln
    7145                7150                7155

Glu Asp  Thr Thr Val Ala Ile  Ser Thr Pro His Phe  Leu Glu Thr
    7160                7165                7170

Ser Arg  Ile Gln Lys Glu Ser  Ile Ser Ser Leu Ser  Pro Lys Leu
    7175                7180                7185

Arg Glu  Thr Gly Ser Ser Val  Glu Thr Ser Ser Ala  Ile Glu Thr
    7190                7195                7200

Ser Ala  Val Leu Ser Glu Val  Ser Ile Gly Ala Thr  Thr Glu Ile
    7205                7210                7215

Ser Arg  Thr Glu Val Thr Ser  Ser Ser Arg Thr Ser  Ile Ser Gly
    7220                7225                7230

Ser Ala  Glu Ser Thr Met Leu  Pro Glu Ile Ser Thr  Thr Arg Lys
    7235                7240                7245

Ile Ile  Lys Phe Pro Thr Ser  Pro Ile Leu Ala Glu  Ser Ser Glu
    7250                7255                7260

Met Thr  Ile Lys Thr Gln Thr  Ser Pro Pro Gly Ser  Thr Ser Glu
    7265                7270                7275

Ser Thr  Phe Thr Leu Asp Thr  Ser Thr Thr Pro Ser  Leu Val Ile
    7280                7285                7290

Thr His  Ser Thr Met Thr Gln  Arg Leu Pro His Ser  Glu Ile Thr
    7295                7300                7305

Thr Leu  Val Ser Arg Gly Ala  Gly Asp Val Pro Arg  Pro Ser Ser
    7310                7315                7320

Leu Pro  Val Glu Glu Thr Ser  Pro Pro Ser Ser Gln  Leu Ser Leu
    7325                7330                7335

Ser Ala  Met Ile Ser Pro Ser  Pro Val Ser Ser Thr  Leu Pro Ala
    7340                7345                7350

Ser Ser  His Ser Ser Ser Ala  Ser Val Thr Ser Leu  Leu Thr Pro
    7355                7360                7365

Gly Gln  Val Lys Thr Thr Glu  Val Leu Asp Ala Ser  Ala Glu Pro
    7370                7375                7380

Glu Thr  Ser Ser Pro Pro Ser  Leu Ser Ser Thr Ser  Val Glu Ile
    7385                7390                7395

Leu Ala  Thr Ser Glu Val Thr  Thr Asp Thr Glu Lys  Ile His Pro
    7400                7405                7410
```

-continued

```
Phe Ser Asn Thr Ala Val Thr Lys Val Gly Thr Ser Ser Ser Gly
    7415                7420                7425

His Glu Ser Pro Ser Ser Val Leu Pro Asp Ser Glu Thr Thr Lys
    7430                7435                7440

Ala Thr Ser Ala Met Gly Thr Ile Ser Ile Met Gly Asp Thr Ser
    7445                7450                7455

Val Ser Thr Leu Thr Pro Ala Leu Ser Asn Thr Arg Lys Ile Gln
    7460                7465                7470

Ser Glu Pro Ala Ser Ser Leu Thr Thr Arg Leu Arg Glu Thr Ser
    7475                7480                7485

Thr Ser Glu Glu Thr Ser Leu Ala Thr Glu Ala Asn Thr Val Leu
    7490                7495                7500

Ser Lys Val Ser Thr Gly Ala Thr Thr Glu Val Ser Arg Thr Glu
    7505                7510                7515

Ala Ile Ser Phe Ser Arg Thr Ser Met Ser Gly Pro Glu Gln Ser
    7520                7525                7530

Thr Met Ser Gln Asp Ile Ser Ile Gly Thr Ile Pro Arg Ile Ser
    7535                7540                7545

Ala Ser Ser Val Leu Thr Glu Ser Ala Lys Met Thr Ile Thr Thr
    7550                7555                7560

Gln Thr Gly Pro Ser Glu Ser Thr Leu Glu Ser Thr Leu Asn Leu
    7565                7570                7575

Asn Thr Ala Thr Thr Pro Ser Trp Val Glu Thr His Ser Ile Val
    7580                7585                7590

Ile Gln Gly Phe Pro His Pro Glu Met Thr Thr Ser Met Gly Arg
    7595                7600                7605

Gly Pro Gly Gly Val Ser Trp Pro Ser Pro Pro Phe Val Lys Glu
    7610                7615                7620

Thr Ser Pro Pro Ser Ser Pro Leu Ser Leu Pro Ala Val Thr Ser
    7625                7630                7635

Pro His Pro Val Ser Thr Thr Phe Leu Ala His Ile Pro Pro Ser
    7640                7645                7650

Pro Leu Pro Val Thr Ser Leu Leu Thr Ser Gly Pro Ala Thr Thr
    7655                7660                7665

Thr Asp Ile Leu Gly Thr Ser Thr Glu Pro Gly Thr Ser Ser Ser
    7670                7675                7680

Ser Ser Leu Ser Thr Thr Ser His Glu Arg Leu Thr Thr Tyr Lys
    7685                7690                7695

Asp Thr Ala His Thr Glu Ala Val His Pro Ser Thr Asn Thr Gly
    7700                7705                7710

Gly Thr Asn Val Ala Thr Thr Ser Ser Gly Tyr Lys Ser Gln Ser
    7715                7720                7725

Ser Val Leu Ala Asp Ser Ser Pro Met Cys Thr Thr Ser Thr Met
    7730                7735                7740

Gly Asp Thr Ser Val Leu Thr Ser Thr Pro Ala Phe Leu Glu Thr
    7745                7750                7755

Arg Arg Ile Gln Thr Glu Leu Ala Ser Ser Leu Thr Pro Gly Leu
    7760                7765                7770

Arg Glu Ser Ser Gly Ser Glu Gly Thr Ser Ser Gly Thr Lys Met
    7775                7780                7785

Ser Thr Val Leu Ser Lys Val Pro Thr Gly Ala Thr Thr Glu Ile
    7790                7795                7800
```

Ser Lys Glu Asp Val Thr Ser Ile Pro Gly Pro Ala Gln Ser Thr
7805 7810 7815

Ile Ser Pro Asp Ile Ser Thr Arg Thr Val Ser Trp Phe Ser Thr
7820 7825 7830

Ser Pro Val Met Thr Glu Ser Ala Glu Ile Thr Met Asn Thr His
7835 7840 7845

Thr Ser Pro Leu Gly Ala Thr Thr Gln Gly Thr Ser Thr Leu Asp
7850 7855 7860

Thr Ser Ser Thr Thr Ser Leu Thr Met Thr His Ser Thr Ile Ser
7865 7870 7875

Gln Gly Phe Ser His Ser Gln Met Ser Thr Leu Met Arg Arg Gly
7880 7885 7890

Pro Glu Asp Val Ser Trp Met Ser Pro Pro Leu Leu Glu Lys Thr
7895 7900 7905

Arg Pro Ser Phe Ser Leu Met Ser Ser Pro Ala Thr Thr Ser Pro
7910 7915 7920

Ser Pro Val Ser Ser Thr Leu Pro Glu Ser Ile Ser Ser Ser Pro
7925 7930 7935

Leu Pro Val Thr Ser Leu Leu Thr Ser Gly Leu Ala Lys Thr Thr
7940 7945 7950

Asp Met Leu His Lys Ser Ser Glu Pro Val Thr Asn Ser Pro Ala
7955 7960 7965

Asn Leu Ser Ser Thr Ser Val Glu Ile Leu Ala Thr Ser Glu Val
7970 7975 7980

Thr Thr Asp Thr Glu Lys Thr His Pro Ser Ser Asn Arg Thr Val
7985 7990 7995

Thr Asp Val Gly Thr Ser Ser Ser Gly His Glu Ser Thr Ser Phe
8000 8005 8010

Val Leu Ala Asp Ser Gln Thr Ser Lys Val Thr Ser Pro Met Val
8015 8020 8025

Ile Thr Ser Thr Met Glu Asp Thr Ser Val Ser Thr Ser Thr Pro
8030 8035 8040

Gly Phe Phe Glu Thr Ser Arg Ile Gln Thr Glu Pro Thr Ser Ser
8045 8050 8055

Leu Thr Leu Gly Leu Arg Lys Thr Ser Ser Ser Glu Gly Thr Ser
8060 8065 8070

Leu Ala Thr Glu Met Ser Thr Val Leu Ser Gly Val Pro Thr Gly
8075 8080 8085

Ala Thr Ala Glu Val Ser Arg Thr Glu Val Thr Ser Ser Ser Arg
8090 8095 8100

Thr Ser Ile Ser Gly Phe Ala Gln Leu Thr Val Ser Pro Glu Thr
8105 8110 8115

Ser Thr Glu Thr Ile Thr Arg Leu Pro Thr Ser Ser Ile Met Thr
8120 8125 8130

Glu Ser Ala Glu Met Met Ile Lys Thr Gln Thr Asp Pro Pro Gly
8135 8140 8145

Ser Thr Pro Glu Ser Thr His Thr Val Asp Ile Ser Thr Thr Pro
8150 8155 8160

Asn Trp Val Glu Thr His Ser Thr Val Thr Gln Arg Phe Ser His
8165 8170 8175

Ser Glu Met Thr Thr Leu Val Ser Arg Ser Pro Gly Asp Met Leu
8180 8185 8190

Trp Pro Ser Gln Ser Ser Val Glu Glu Thr Ser Ser Ala Ser Ser

```
    8195                8200                8205

Leu Leu  Ser Leu Pro Ala Thr  Thr Ser Pro Ser Pro  Val Ser Ser
    8210                8215                8220

Thr Leu  Val Glu Asp Phe Pro  Ser Ala Ser Leu Pro  Val Thr Ser
    8225                8230                8235

Leu Leu  Asn Pro Gly Leu Val  Ile Thr Thr Asp Arg  Met Gly Ile
    8240                8245                8250

Ser Arg  Glu Pro Gly Thr Ser  Ser Thr Ser Asn Leu  Ser Ser Thr
    8255                8260                8265

Ser His  Glu Arg Leu Thr Thr  Leu Glu Asp Thr Val  Asp Thr Glu
    8270                8275                8280

Asp Met  Gln Pro Ser Thr His  Thr Ala Val Thr Asn  Val Arg Thr
    8285                8290                8295

Ser Ile  Ser Gly His Glu Ser  Gln Ser Ser Val Leu  Ser Asp Ser
    8300                8305                8310

Glu Thr  Pro Lys Ala Thr Ser  Pro Met Gly Thr Thr  Tyr Thr Met
    8315                8320                8325

Gly Glu  Thr Ser Val Ser Ile  Ser Thr Ser Asp Phe  Phe Glu Thr
    8330                8335                8340

Ser Arg  Ile Gln Ile Glu Pro  Thr Ser Ser Leu Thr  Ser Gly Leu
    8345                8350                8355

Arg Glu  Thr Ser Ser Ser Glu  Arg Ile Ser Ser Ala  Thr Glu Gly
    8360                8365                8370

Ser Thr  Val Leu Ser Glu Val  Pro Ser Gly Ala Thr  Thr Glu Val
    8375                8380                8385

Ser Arg  Thr Glu Val Ile Ser  Ser Arg Gly Thr Ser  Met Ser Gly
    8390                8395                8400

Pro Asp  Gln Phe Thr Ile Ser  Pro Asp Ile Ser Thr  Glu Ala Ile
    8405                8410                8415

Thr Arg  Leu Ser Thr Ser Pro  Ile Met Thr Glu Ser  Ala Glu Ser
    8420                8425                8430

Ala Ile  Thr Ile Glu Thr Gly  Ser Pro Gly Ala Thr  Ser Glu Gly
    8435                8440                8445

Thr Leu  Thr Leu Asp Thr Ser  Thr Thr Thr Phe Trp  Ser Gly Thr
    8450                8455                8460

His Ser  Thr Ala Ser Pro Gly  Phe Ser His Ser Glu  Met Thr Thr
    8465                8470                8475

Leu Met  Ser Arg Thr Pro Gly  Asp Val Pro Trp Pro  Ser Leu Pro
    8480                8485                8490

Ser Val  Glu Glu Ala Ser Ser  Val Ser Ser Ser Leu  Ser Ser Pro
    8495                8500                8505

Ala Met  Thr Ser Thr Ser Phe  Phe Ser Thr Leu Pro  Glu Ser Ile
    8510                8515                8520

Ser Ser  Ser Pro His Pro Val  Thr Ala Leu Leu Thr  Leu Gly Pro
    8525                8530                8535

Val Lys  Thr Thr Asp Met Leu  Arg Thr Ser Ser Glu  Pro Glu Thr
    8540                8545                8550

Ser Ser  Pro Pro Asn Leu Ser  Ser Thr Ser Ala Glu  Ile Leu Ala
    8555                8560                8565

Thr Ser  Glu Val Thr Lys Asp  Arg Glu Lys Ile His  Pro Ser Ser
    8570                8575                8580

Asn Thr  Pro Val Val Asn Val  Gly Thr Val Ile Tyr  Lys His Leu
    8585                8590                8595
```

Ser Pro Ser Ser Val Leu Ala Asp Leu Val Thr Thr Lys Pro Thr
8600 8605 8610

Ser Pro Met Ala Thr Thr Ser Thr Leu Gly Asn Thr Ser Val Ser
8615 8620 8625

Thr Ser Thr Pro Ala Phe Pro Glu Thr Met Met Thr Gln Pro Thr
8630 8635 8640

Ser Ser Leu Thr Ser Gly Leu Arg Glu Ile Ser Thr Ser Gln Glu
8645 8650 8655

Thr Ser Ser Ala Thr Glu Arg Ser Ala Ser Leu Ser Gly Met Pro
8660 8665 8670

Thr Gly Ala Thr Thr Lys Val Ser Arg Thr Glu Ala Leu Ser Leu
8675 8680 8685

Gly Arg Thr Ser Thr Pro Gly Pro Ala Gln Ser Thr Ile Ser Pro
8690 8695 8700

Glu Ile Ser Thr Glu Thr Ile Thr Arg Ile Ser Thr Pro Leu Thr
8705 8710 8715

Thr Thr Gly Ser Ala Glu Met Thr Ile Thr Pro Lys Thr Gly His
8720 8725 8730

Ser Gly Ala Ser Ser Gln Gly Thr Phe Thr Leu Asp Thr Ser Ser
8735 8740 8745

Arg Ala Ser Trp Pro Gly Thr His Ser Ala Ala Thr His Arg Ser
8750 8755 8760

Pro His Ser Gly Met Thr Thr Pro Met Ser Arg Gly Pro Glu Asp
8765 8770 8775

Val Ser Trp Pro Ser Arg Pro Ser Val Glu Lys Thr Ser Pro Pro
8780 8785 8790

Ser Ser Leu Val Ser Leu Ser Ala Val Thr Ser Pro Ser Pro Leu
8795 8800 8805

Tyr Ser Thr Pro Ser Glu Ser Ser His Ser Ser Pro Leu Arg Val
8810 8815 8820

Thr Ser Leu Phe Thr Pro Val Met Met Lys Thr Thr Asp Met Leu
8825 8830 8835

Asp Thr Ser Leu Glu Pro Val Thr Thr Ser Pro Pro Ser Met Asn
8840 8845 8850

Ile Thr Ser Asp Glu Ser Leu Ala Thr Ser Lys Ala Thr Met Glu
8855 8860 8865

Thr Glu Ala Ile Gln Leu Ser Glu Asn Thr Ala Val Thr Gln Met
8870 8875 8880

Gly Thr Ile Ser Ala Arg Gln Glu Phe Tyr Ser Ser Tyr Pro Gly
8885 8890 8895

Leu Pro Glu Pro Ser Lys Val Thr Ser Pro Val Val Thr Ser Ser
8900 8905 8910

Thr Ile Lys Asp Ile Val Ser Thr Thr Ile Pro Ala Ser Ser Glu
8915 8920 8925

Ile Thr Arg Ile Glu Met Glu Ser Thr Ser Thr Leu Thr Pro Thr
8930 8935 8940

Pro Arg Glu Thr Ser Thr Ser Gln Glu Ile His Ser Ala Thr Lys
8945 8950 8955

Pro Ser Thr Val Pro Tyr Lys Ala Leu Thr Ser Ala Thr Ile Glu
8960 8965 8970

Asp Ser Met Thr Gln Val Met Ser Ser Ser Arg Gly Pro Ser Pro
8975 8980 8985

Asp Gln Ser Thr Met Ser Gln Asp Ile Ser Thr Glu Val Ile Thr
8990 8995 9000

Arg Leu Ser Thr Ser Pro Ile Lys Thr Glu Ser Thr Glu Met Thr
9005 9010 9015

Ile Thr Thr Gln Thr Gly Ser Pro Gly Ala Thr Ser Arg Gly Thr
9020 9025 9030

Leu Thr Leu Asp Thr Ser Thr Thr Phe Met Ser Gly Thr His Ser
9035 9040 9045

Thr Ala Ser Gln Gly Phe Ser His Ser Gln Met Thr Ala Leu Met
9050 9055 9060

Ser Arg Thr Pro Gly Asp Val Pro Trp Leu Ser His Pro Ser Val
9065 9070 9075

Glu Glu Ala Ser Ser Ala Ser Phe Ser Leu Ser Ser Pro Val Met
9080 9085 9090

Thr Ser Ser Ser Pro Val Ser Ser Thr Leu Pro Asp Ser Ile His
9095 9100 9105

Ser Ser Ser Leu Pro Val Thr Ser Leu Leu Thr Ser Gly Leu Val
9110 9115 9120

Lys Thr Thr Glu Leu Leu Gly Thr Ser Ser Glu Pro Glu Thr Ser
9125 9130 9135

Ser Pro Pro Asn Leu Ser Ser Thr Ser Ala Glu Ile Leu Ala Ile
9140 9145 9150

Thr Glu Val Thr Thr Asp Thr Glu Lys Leu Glu Met Thr Asn Val
9155 9160 9165

Val Thr Ser Gly Tyr Thr His Glu Ser Pro Ser Ser Val Leu Ala
9170 9175 9180

Asp Ser Val Thr Thr Lys Ala Thr Ser Ser Met Gly Ile Thr Tyr
9185 9190 9195

Pro Thr Gly Asp Thr Asn Val Leu Thr Ser Thr Pro Ala Phe Ser
9200 9205 9210

Asp Thr Ser Arg Ile Gln Thr Lys Ser Lys Leu Ser Leu Thr Pro
9215 9220 9225

Gly Leu Met Glu Thr Ser Ile Ser Glu Glu Thr Ser Ser Ala Thr
9230 9235 9240

Glu Lys Ser Thr Val Leu Ser Ser Val Pro Thr Gly Ala Thr Thr
9245 9250 9255

Glu Val Ser Arg Thr Glu Ala Ile Ser Ser Ser Arg Thr Ser Ile
9260 9265 9270

Pro Gly Pro Ala Gln Ser Thr Met Ser Ser Asp Thr Ser Met Glu
9275 9280 9285

Thr Ile Thr Arg Ile Ser Thr Pro Leu Thr Arg Lys Glu Ser Thr
9290 9295 9300

Asp Met Ala Ile Thr Pro Lys Thr Gly Pro Ser Gly Ala Thr Ser
9305 9310 9315

Gln Gly Thr Phe Thr Leu Asp Ser Ser Ser Thr Ala Ser Trp Pro
9320 9325 9330

Gly Thr His Ser Ala Thr Thr Gln Arg Phe Pro Gln Ser Val Val
9335 9340 9345

Thr Thr Pro Met Ser Arg Gly Pro Glu Asp Val Ser Trp Pro Ser
9350 9355 9360

Pro Leu Ser Val Glu Lys Asn Ser Pro Pro Ser Ser Leu Val Ser
9365 9370 9375

Ser Ser Ser Val Thr Ser Pro Ser Pro Leu Tyr Ser Thr Pro Ser 9380 9385 9390

Gly Ser Ser His Ser Ser Pro Val Pro Val Thr Ser Leu Phe Thr
9395 9400 9405

Ser Ile Met Met Lys Ala Thr Asp Met Leu Asp Ala Ser Leu Glu
9410 9415 9420

Pro Glu Thr Thr Ser Ala Pro Asn Met Asn Ile Thr Ser Asp Glu
9425 9430 9435

Ser Leu Ala Ala Ser Lys Ala Thr Thr Glu Thr Glu Ala Ile His
9440 9445 9450

Val Phe Glu Asn Thr Ala Ala Ser His Val Glu Thr Thr Ser Ala
9455 9460 9465

Thr Glu Glu Leu Tyr Ser Ser Ser Pro Gly Phe Ser Glu Pro Thr
9470 9475 9480

Lys Val Ile Ser Pro Val Val Thr Ser Ser Ser Ile Arg Asp Asn
9485 9490 9495

Met Val Ser Thr Thr Met Pro Gly Ser Ser Gly Ile Thr Arg Ile
9500 9505 9510

Glu Ile Glu Ser Met Ser Ser Leu Thr Pro Gly Leu Arg Glu Thr
9515 9520 9525

Arg Thr Ser Gln Asp Ile Thr Ser Ser Thr Glu Thr Ser Thr Val
9530 9535 9540

Leu Tyr Lys Met Pro Ser Gly Ala Thr Pro Glu Val Ser Arg Thr
9545 9550 9555

Glu Val Met Pro Ser Ser Arg Thr Ser Ile Pro Gly Pro Ala Gln
9560 9565 9570

Ser Thr Met Ser Leu Asp Ile Ser Asp Glu Val Val Thr Arg Leu
9575 9580 9585

Ser Thr Ser Pro Ile Met Thr Glu Ser Ala Glu Ile Thr Ile Thr
9590 9595 9600

Thr Gln Thr Gly Tyr Ser Leu Ala Thr Ser Gln Val Thr Leu Pro
9605 9610 9615

Leu Gly Thr Ser Met Thr Phe Leu Ser Gly Thr His Ser Thr Met
9620 9625 9630

Ser Gln Gly Leu Ser His Ser Glu Met Thr Asn Leu Met Ser Arg
9635 9640 9645

Gly Pro Glu Ser Leu Ser Trp Thr Ser Pro Arg Phe Val Glu Thr
9650 9655 9660

Thr Arg Ser Ser Ser Ser Leu Thr Ser Leu Pro Leu Thr Thr Ser
9665 9670 9675

Leu Ser Pro Val Ser Ser Thr Leu Leu Asp Ser Ser Pro Ser Ser
9680 9685 9690

Pro Leu Pro Val Thr Ser Leu Ile Leu Pro Gly Leu Val Lys Thr
9695 9700 9705

Thr Glu Val Leu Asp Thr Ser Ser Glu Pro Lys Thr Ser Ser Ser
9710 9715 9720

Pro Asn Leu Ser Ser Thr Ser Val Glu Ile Pro Ala Thr Ser Glu
9725 9730 9735

Ile Met Thr Asp Thr Glu Lys Ile His Pro Ser Ser Asn Thr Ala
9740 9745 9750

Val Ala Lys Val Arg Thr Ser Ser Ser Val His Glu Ser His Ser
9755 9760 9765

Ser Val Leu Ala Asp Ser Glu Thr Thr Ile Thr Ile Pro Ser Met
9770 9775 9780

```
Gly Ile  Thr Ser Ala Val Asp  Asp Thr Thr Val Phe  Thr Ser Asn
    9785                 9790                 9795

Pro Ala  Phe Ser Glu Thr Arg  Arg Ile Pro Thr Glu  Pro Thr Phe
    9800                 9805                 9810

Ser Leu  Thr Pro Gly Phe Arg  Glu Thr Ser Thr Ser  Glu Glu Thr
    9815                 9820                 9825

Thr Ser  Ile Thr Glu Thr Ser  Ala Val Leu Tyr Gly  Val Pro Thr
    9830                 9835                 9840

Ser Ala  Thr Thr Glu Val Ser  Met Thr Glu Ile Met  Ser Ser Asn
    9845                 9850                 9855

Arg Ile  His Ile Pro Asp Ser  Asp Gln Ser Thr Met  Ser Pro Asp
    9860                 9865                 9870

Ile Ile  Thr Glu Val Ile Thr  Arg Leu Ser Ser Ser  Ser Met Met
    9875                 9880                 9885

Ser Glu  Ser Thr Gln Met Thr  Ile Thr Thr Gln Lys  Ser Ser Pro
    9890                 9895                 9900

Gly Ala  Thr Ala Gln Ser Thr  Leu Thr Leu Ala Thr  Thr Thr Ala
    9905                 9910                 9915

Pro Leu  Ala Arg Thr His Ser  Thr Val Pro Pro Arg  Phe Leu His
    9920                 9925                 9930

Ser Glu  Met Thr Thr Leu Met  Ser Arg Ser Pro Glu  Asn Pro Ser
    9935                 9940                 9945

Trp Lys  Ser Ser Leu Phe Val  Glu Lys Thr Ser Ser  Ser Ser Ser
    9950                 9955                 9960

Leu Leu  Ser Leu Pro Val Thr  Thr Ser Pro Ser Val  Ser Ser Thr
    9965                 9970                 9975

Leu Pro  Gln Ser Ile Pro Ser  Ser Ser Phe Ser Val  Thr Ser Leu
    9980                 9985                 9990

Leu Thr  Pro Gly Met Val Lys   Thr Thr Asp Thr Ser   Thr Glu Pro
    9995                 10000                 10005

Gly Thr   Ser Leu Ser Pro Asn   Leu Ser Gly Thr Ser   Val Glu Ile
    10010                 10015                 10020

Leu Ala   Ala Ser Glu Val Thr   Thr Asp Thr Glu Lys   Ile His Pro
    10025                 10030                 10035

Ser Ser   Ser Met Ala Val Thr   Asn Val Gly Thr Thr   Ser Ser Gly
    10040                 10045                 10050

His Glu   Leu Tyr Ser Ser Val   Ser Ile His Ser Glu   Pro Ser Lys
    10055                 10060                 10065

Ala Thr   Tyr Pro Val Gly Thr   Pro Ser Ser Met Ala   Glu Thr Ser
    10070                 10075                 10080

Ile Ser   Thr Ser Met Pro Ala   Asn Phe Glu Thr Thr   Gly Phe Glu
    10085                 10090                 10095

Ala Glu   Pro Phe Ser His Leu   Thr Ser Gly Phe Arg   Lys Thr Asn
    10100                 10105                 10110

Met Ser   Leu Asp Thr Ser Ser   Val Thr Pro Thr Asn   Thr Pro Ser
    10115                 10120                 10125

Ser Pro   Gly Ser Thr His Leu   Leu Gln Ser Ser Lys   Thr Asp Phe
    10130                 10135                 10140

Thr Ser   Ser Ala Lys Thr Ser   Ser Pro Asp Trp Pro   Pro Ala Ser
    10145                 10150                 10155

Gln Tyr   Thr Glu Ile Pro Val   Asp Ile Ile Thr Pro   Phe Asn Ala
    10160                 10165                 10170
```

```
Ser Pro   Ser Ile Thr Glu Ser   Thr Gly Ile Thr Ser   Phe Pro Glu
    10175                 10180                 10185

Ser Arg   Phe Thr Met Ser Val   Thr Glu Ser Thr His   His Leu Ser
    10190                 10195                 10200

Thr Asp   Leu Leu Pro Ser Ala   Glu Thr Ile Ser Thr   Gly Thr Val
    10205                 10210                 10215

Met Pro   Ser Leu Ser Glu Ala   Met Thr Ser Phe Ala   Thr Thr Gly
    10220                 10225                 10230

Val Pro   Arg Ala Ile Ser Gly   Ser Gly Ser Pro Phe   Ser Arg Thr
    10235                 10240                 10245

Glu Ser   Gly Pro Gly Asp Ala   Thr Leu Ser Thr Ile   Ala Glu Ser
    10250                 10255                 10260

Leu Pro   Ser Ser Thr Pro Val   Pro Phe Ser Ser Ser   Thr Phe Thr
    10265                 10270                 10275

Thr Thr   Asp Ser Ser Thr Ile   Pro Ala Leu His Glu   Ile Thr Ser
    10280                 10285                 10290

Ser Ser   Ala Thr Pro Tyr Arg   Val Asp Thr Ser Leu   Gly Thr Glu
    10295                 10300                 10305

Ser Ser   Thr Thr Glu Gly Arg   Leu Val Met Val Ser   Thr Leu Asp
    10310                 10315                 10320

Thr Ser   Ser Gln Pro Gly Arg   Thr Ser Ser Ser Pro   Ile Leu Asp
    10325                 10330                 10335

Thr Arg   Met Thr Glu Ser Val   Glu Leu Gly Thr Val   Thr Ser Ala
    10340                 10345                 10350

Tyr Gln   Val Pro Ser Leu Ser   Thr Arg Leu Thr Arg   Thr Asp Gly
    10355                 10360                 10365

Ile Met   Glu His Ile Thr Lys   Ile Pro Asn Glu Ala   Ala His Arg
    10370                 10375                 10380

Gly Thr   Ile Arg Pro Val Lys   Gly Pro Gln Thr Ser   Thr Ser Pro
    10385                 10390                 10395

Ala Ser   Pro Lys Gly Leu His   Thr Gly Gly Thr Lys   Arg Met Glu
    10400                 10405                 10410

Thr Thr   Thr Thr Ala Leu Lys   Thr Thr Thr Thr Ala   Leu Lys Thr
    10415                 10420                 10425

Thr Ser   Arg Ala Thr Leu Thr   Thr Ser Val Tyr Thr   Pro Thr Leu
    10430                 10435                 10440

Gly Thr   Leu Thr Pro Leu Asn   Ala Ser Met Gln Met   Ala Ser Thr
    10445                 10450                 10455

Ile Pro   Thr Glu Met Met Ile   Thr Thr Pro Tyr Val   Phe Pro Asp
    10460                 10465                 10470

Val Pro   Glu Thr Thr Ser Ser   Leu Ala Thr Ser Leu   Gly Ala Glu
    10475                 10480                 10485

Thr Ser   Thr Ala Leu Pro Arg   Thr Thr Pro Ser Val   Phe Asn Arg
    10490                 10495                 10500

Glu Ser   Glu Thr Thr Ala Ser   Leu Val Ser Arg Ser   Gly Ala Glu
    10505                 10510                 10515

Arg Ser   Pro Val Ile Gln Thr   Leu Asp Val Ser Ser   Ser Glu Pro
    10520                 10525                 10530

Asp Thr   Thr Ala Ser Trp Val   Ile His Pro Ala Glu   Thr Ile Pro
    10535                 10540                 10545

Thr Val   Ser Lys Thr Thr Pro   Asn Phe Phe His Ser   Glu Leu Asp
    10550                 10555                 10560

Thr Val   Ser Ser Thr Ala Thr   Ser His Gly Ala Asp   Val Ser Ser
```

```
    10565               10570               10575

Ala Ile   Pro Thr Asn Ile Ser   Pro Ser Glu Leu Asp   Ala Leu Thr
    10580               10585               10590

Pro Leu   Val Thr Ile Ser Gly   Thr Asp Thr Ser Thr   Thr Phe Pro
    10595               10600               10605

Thr Leu   Thr Lys Ser Pro His   Glu Thr Glu Thr Arg   Thr Thr Trp
    10610               10615               10620

Leu Thr   His Pro Ala Glu Thr   Ser Ser Thr Ile Pro   Arg Thr Ile
    10625               10630               10635

Pro Asn   Phe Ser His His Glu   Ser Asp Ala Thr Pro   Ser Ile Ala
    10640               10645               10650

Thr Ser   Pro Gly Ala Glu Thr   Ser Ser Ala Ile Pro   Ile Met Thr
    10655               10660               10665

Val Ser   Pro Gly Ala Glu Asp   Leu Val Thr Ser Gln   Val Thr Ser
    10670               10675               10680

Ser Gly   Thr Asp Arg Asn Met   Thr Ile Pro Thr Leu   Thr Leu Ser
    10685               10690               10695

Pro Gly   Glu Pro Lys Thr Ile   Ala Ser Leu Val Thr   His Pro Glu
    10700               10705               10710

Ala Gln   Thr Ser Ser Ala Ile   Pro Thr Ser Thr Ile   Ser Pro Ala
    10715               10720               10725

Val Ser   Arg Leu Val Thr Ser   Met Val Thr Ser Leu   Ala Ala Lys
    10730               10735               10740

Thr Ser   Thr Thr Asn Arg Ala   Leu Thr Asn Ser Pro   Gly Glu Pro
    10745               10750               10755

Ala Thr   Thr Val Ser Leu Val   Thr His Pro Ala Gln   Thr Ser Pro
    10760               10765               10770

Thr Val   Pro Trp Thr Thr Ser   Ile Phe Phe His Ser   Lys Ser Asp
    10775               10780               10785

Thr Thr   Pro Ser Met Thr Thr   Ser His Gly Ala Glu   Ser Ser Ser
    10790               10795               10800

Ala Val   Pro Thr Pro Thr Val   Ser Thr Glu Val Pro   Gly Val Val
    10805               10810               10815

Thr Pro   Leu Val Thr Ser Ser   Arg Ala Val Ile Ser   Thr Thr Ile
    10820               10825               10830

Pro Ile   Leu Thr Leu Ser Pro   Gly Glu Pro Glu Thr   Thr Pro Ser
    10835               10840               10845

Met Ala   Thr Ser His Gly Glu   Glu Ala Ser Ser Ala   Ile Pro Thr
    10850               10855               10860

Pro Thr   Val Ser Pro Gly Val   Pro Gly Val Val Thr   Ser Leu Val
    10865               10870               10875

Thr Ser   Ser Arg Ala Val Thr   Ser Thr Thr Ile Pro   Ile Leu Thr
    10880               10885               10890

Phe Ser   Leu Gly Glu Pro Glu   Thr Thr Pro Ser Met   Ala Thr Ser
    10895               10900               10905

His Gly   Thr Glu Ala Gly Ser   Ala Val Pro Thr Val   Leu Pro Glu
    10910               10915               10920

Val Pro   Gly Met Val Thr Ser   Leu Val Ala Ser Ser   Arg Ala Val
    10925               10930               10935

Thr Ser   Thr Thr Leu Pro Thr   Leu Thr Leu Ser Pro   Gly Glu Pro
    10940               10945               10950

Glu Thr   Thr Pro Ser Met Ala   Thr Ser His Gly Ala   Glu Ala Ser
    10955               10960               10965
```

-continued

```
Ser Thr Val Pro Thr Val Ser Pro Glu Val Pro Gly Val Val Thr
    10970               10975               10980

Ser Leu Val Thr Ser Ser Ser Gly Val Asn Ser Thr Ser Ile Pro
    10985               10990               10995

Thr Leu Ile Leu Ser Pro Gly Glu Leu Glu Thr Thr Pro Ser Met
    11000               11005               11010

Ala Thr Ser His Gly Ala Glu Ala Ser Ser Ala Val Pro Thr Pro
    11015               11020               11025

Thr Val Ser Pro Gly Val Ser Gly Val Val Thr Pro Leu Val Thr
    11030               11035               11040

Ser Ser Arg Ala Val Thr Ser Thr Thr Ile Pro Ile Leu Thr Leu
    11045               11050               11055

Ser Ser Ser Glu Pro Glu Thr Thr Pro Ser Met Ala Thr Ser His
    11060               11065               11070

Gly Val Glu Ala Ser Ser Ala Val Leu Thr Val Ser Pro Glu Val
    11075               11080               11085

Pro Gly Met Val Thr Ser Leu Val Thr Ser Ser Arg Ala Val Thr
    11090               11095               11100

Ser Thr Thr Ile Pro Thr Leu Thr Ile Ser Ser Asp Glu Pro Glu
    11105               11110               11115

Thr Thr Thr Ser Leu Val Thr His Ser Glu Ala Lys Met Ile Ser
    11120               11125               11130

Ala Ile Pro Thr Leu Ala Val Ser Pro Thr Val Gln Gly Leu Val
    11135               11140               11145

Thr Ser Leu Val Thr Ser Ser Gly Ser Glu Thr Ser Ala Phe Ser
    11150               11155               11160

Asn Leu Thr Val Ala Ser Ser Gln Pro Glu Thr Ile Asp Ser Trp
    11165               11170               11175

Val Ala His Pro Gly Thr Glu Ala Ser Ser Val Val Pro Thr Leu
    11180               11185               11190

Thr Val Ser Thr Gly Glu Pro Phe Thr Asn Ile Ser Leu Val Thr
    11195               11200               11205

His Pro Ala Glu Ser Ser Ser Thr Leu Pro Arg Thr Thr Ser Arg
    11210               11215               11220

Phe Ser His Ser Glu Leu Asp Thr Met Pro Ser Thr Val Thr Ser
    11225               11230               11235

Pro Glu Ala Glu Ser Ser Ser Ala Ile Ser Thr Thr Ile Ser Pro
    11240               11245               11250

Gly Ile Pro Gly Val Leu Thr Ser Leu Val Thr Ser Ser Gly Arg
    11255               11260               11265

Asp Ile Ser Ala Thr Phe Pro Thr Val Pro Glu Ser Pro His Glu
    11270               11275               11280

Ser Glu Ala Thr Ala Ser Trp Val Thr His Pro Ala Val Thr Ser
    11285               11290               11295

Thr Thr Val Pro Arg Thr Thr Pro Asn Tyr Ser His Ser Glu Pro
    11300               11305               11310

Asp Thr Thr Pro Ser Ile Ala Thr Ser Pro Gly Ala Glu Ala Thr
    11315               11320               11325

Ser Asp Phe Pro Thr Ile Thr Val Ser Pro Asp Val Pro Asp Met
    11330               11335               11340

Val Thr Ser Gln Val Thr Ser Ser Gly Thr Asp Thr Ser Ile Thr
    11345               11350               11355
```

```
Ile Pro Thr Leu Thr Leu Ser Ser Gly Glu Pro Glu Thr Thr Thr
    11360               11365               11370

Ser Phe Ile Thr Tyr Ser Glu Thr His Thr Ser Ser Ala Ile Pro
    11375               11380               11385

Thr Leu Pro Val Ser Pro Gly Ala Ser Lys Met Leu Thr Ser Leu
    11390               11395               11400

Val Ile Ser Ser Gly Thr Asp Ser Thr Thr Thr Phe Pro Thr Leu
    11405               11410               11415

Thr Glu Thr Pro Tyr Glu Pro Glu Thr Thr Ala Ile Gln Leu Ile
    11420               11425               11430

His Pro Ala Glu Thr Asn Thr Met Val Pro Arg Thr Thr Pro Lys
    11435               11440               11445

Phe Ser His Ser Lys Ser Asp Thr Thr Leu Pro Val Ala Ile Thr
    11450               11455               11460

Ser Pro Gly Pro Glu Ala Ser Ser Ala Val Ser Thr Thr Thr Ile
    11465               11470               11475

Ser Pro Asp Met Ser Asp Leu Val Thr Ser Leu Val Pro Ser Ser
    11480               11485               11490

Gly Thr Asp Thr Ser Thr Thr Phe Pro Thr Leu Ser Glu Thr Pro
    11495               11500               11505

Tyr Glu Pro Glu Thr Thr Ala Thr Trp Leu Thr His Pro Ala Glu
    11510               11515               11520

Thr Ser Thr Thr Val Ser Gly Thr Ile Pro Asn Phe Ser His Arg
    11525               11530               11535

Gly Ser Asp Thr Ala Pro Ser Met Val Thr Ser Pro Gly Val Asp
    11540               11545               11550

Thr Arg Ser Gly Val Pro Thr Thr Thr Ile Pro Pro Ser Ile Pro
    11555               11560               11565

Gly Val Val Thr Ser Gln Val Thr Ser Ser Ala Thr Asp Thr Ser
    11570               11575               11580

Thr Ala Ile Pro Thr Leu Thr Pro Ser Pro Gly Glu Pro Glu Thr
    11585               11590               11595

Thr Ala Ser Ser Ala Thr His Pro Gly Thr Gln Thr Gly Phe Thr
    11600               11605               11610

Val Pro Ile Arg Thr Val Pro Ser Ser Glu Pro Asp Thr Met Ala
    11615               11620               11625

Ser Trp Val Thr His Pro Pro Gln Thr Ser Thr Pro Val Ser Arg
    11630               11635               11640

Thr Thr Ser Ser Phe Ser His Ser Ser Pro Asp Ala Thr Pro Val
    11645               11650               11655

Met Ala Thr Ser Pro Arg Thr Glu Ala Ser Ser Ala Val Leu Thr
    11660               11665               11670

Thr Ile Ser Pro Gly Ala Pro Glu Met Val Thr Ser Gln Ile Thr
    11675               11680               11685

Ser Ser Gly Ala Ala Thr Ser Thr Thr Val Pro Thr Leu Thr His
    11690               11695               11700

Ser Pro Gly Met Pro Glu Thr Thr Ala Leu Leu Ser Thr His Pro
    11705               11710               11715

Arg Thr Glu Thr Ser Lys Thr Phe Pro Ala Ser Thr Val Phe Pro
    11720               11725               11730

Gln Val Ser Glu Thr Thr Ala Ser Leu Thr Ile Arg Pro Gly Ala
    11735               11740               11745

Glu Thr Ser Thr Ala Leu Pro Thr Gln Thr Thr Ser Ser Leu Phe
```

```
    11750               11755               11760

Thr Leu Leu Val Thr Gly Thr Ser Arg Val Asp Leu Ser Pro Thr
    11765               11770               11775

Ala Ser Pro Gly Val Ser Ala Lys Thr Ala Pro Leu Ser Thr His
    11780               11785               11790

Pro Gly Thr Glu Thr Ser Thr Met Ile Pro Thr Ser Thr Leu Ser
    11795               11800               11805

Leu Gly Leu Leu Glu Thr Thr Gly Leu Leu Ala Thr Ser Ser Ser
    11810               11815               11820

Ala Glu Thr Ser Thr Ser Thr Leu Thr Leu Thr Val Ser Pro Ala
    11825               11830               11835

Val Ser Gly Leu Ser Ser Ala Ser Ile Thr Thr Asp Lys Pro Gln
    11840               11845               11850

Thr Val Thr Ser Trp Asn Thr Glu Thr Ser Pro Ser Val Thr Ser
    11855               11860               11865

Val Gly Pro Pro Glu Phe Ser Arg Thr Val Thr Gly Thr Thr Met
    11870               11875               11880

Thr Leu Ile Pro Ser Glu Met Pro Thr Pro Pro Lys Thr Ser His
    11885               11890               11895

Gly Glu Gly Val Ser Pro Thr Thr Ile Leu Arg Thr Thr Met Val
    11900               11905               11910

Glu Ala Thr Asn Leu Ala Thr Thr Gly Ser Ser Pro Thr Val Ala
    11915               11920               11925

Lys Thr Thr Thr Thr Phe Asn Thr Leu Ala Gly Ser Leu Phe Thr
    11930               11935               11940

Pro Leu Thr Thr Pro Gly Met Ser Thr Leu Ala Ser Glu Ser Val
    11945               11950               11955

Thr Ser Arg Thr Ser Tyr Asn His Arg Ser Trp Ile Ser Thr Thr
    11960               11965               11970

Ser Ser Tyr Asn Arg Arg Tyr Trp Thr Pro Ala Thr Ser Thr Pro
    11975               11980               11985

Val Thr Ser Thr Phe Ser Pro Gly Ile Ser Thr Ser Ser Ile Pro
    11990               11995               12000

Ser Ser Thr Ala Ala Thr Val Pro Phe Met Val Pro Phe Thr Leu
    12005               12010               12015

Asn Phe Thr Ile Thr Asn Leu Gln Tyr Glu Glu Asp Met Arg His
    12020               12025               12030

Pro Gly Ser Arg Lys Phe Asn Ala Thr Glu Arg Glu Leu Gln Gly
    12035               12040               12045

Leu Leu Lys Pro Leu Phe Arg Asn Ser Ser Leu Glu Tyr Leu Tyr
    12050               12055               12060

Ser Gly Cys Arg Leu Ala Ser Leu Arg Pro Glu Lys Asp Ser Ser
    12065               12070               12075

Ala Thr Ala Val Asp Ala Ile Cys Thr His Arg Pro Asp Pro Glu
    12080               12085               12090

Asp Leu Gly Leu Asp Arg Glu Arg Leu Tyr Trp Glu Leu Ser Asn
    12095               12100               12105

Leu Thr Asn Gly Ile Gln Glu Leu Gly Pro Tyr Thr Leu Asp Arg
    12110               12115               12120

Asn Ser Leu Tyr Val Asn Gly Phe Thr His Arg Ser Ser Met Pro
    12125               12130               12135

Thr Thr Ser Thr Pro Gly Thr Ser Thr Val Asp Val Gly Thr Ser
    12140               12145               12150
```

```
Gly Thr Pro Ser Ser Ser Pro Ser Pro Thr Thr Ala Gly Pro Leu
    12155               12160               12165

Leu Met Pro Phe Thr Leu Asn Phe Thr Ile Thr Asn Leu Gln Tyr
    12170               12175               12180

Glu Glu Asp Met Arg Arg Thr Gly Ser Arg Lys Phe Asn Thr Met
    12185               12190               12195

Glu Ser Val Leu Gln Gly Leu Leu Lys Pro Leu Phe Lys Asn Thr
    12200               12205               12210

Ser Val Gly Pro Leu Tyr Ser Gly Cys Arg Leu Thr Leu Leu Arg
    12215               12220               12225

Pro Glu Lys Asp Gly Ala Ala Thr Gly Val Asp Ala Ile Cys Thr
    12230               12235               12240

His Arg Leu Asp Pro Lys Ser Pro Gly Leu Asn Arg Glu Gln Leu
    12245               12250               12255

Tyr Trp Glu Leu Ser Lys Leu Thr Asn Asp Ile Glu Glu Leu Gly
    12260               12265               12270

Pro Tyr Thr Leu Asp Arg Asn Ser Leu Tyr Val Asn Gly Phe Thr
    12275               12280               12285

His Gln Ser Ser Val Ser Thr Thr Ser Thr Pro Gly Thr Ser Thr
    12290               12295               12300

Val Asp Leu Arg Thr Ser Gly Thr Pro Ser Ser Leu Ser Ser Pro
    12305               12310               12315

Thr Ile Met Ala Ala Gly Pro Leu Leu Val Pro Phe Thr Leu Asn
    12320               12325               12330

Phe Thr Ile Thr Asn Leu Gln Tyr Gly Glu Asp Met Gly His Pro
    12335               12340               12345

Gly Ser Arg Lys Phe Asn Thr Thr Glu Arg Val Leu Gln Gly Leu
    12350               12355               12360

Leu Gly Pro Ile Phe Lys Asn Thr Ser Val Gly Pro Leu Tyr Ser
    12365               12370               12375

Gly Cys Arg Leu Thr Ser Leu Arg Ser Glu Lys Asp Gly Ala Ala
    12380               12385               12390

Thr Gly Val Asp Ala Ile Cys Ile His His Leu Asp Pro Lys Ser
    12395               12400               12405

Pro Gly Leu Asn Arg Glu Arg Leu Tyr Trp Glu Leu Ser Gln Leu
    12410               12415               12420

Thr Asn Gly Ile Lys Glu Leu Gly Pro Tyr Thr Leu Asp Arg Asn
    12425               12430               12435

Ser Leu Tyr Val Asn Gly Phe Thr His Arg Thr Ser Val Pro Thr
    12440               12445               12450

Ser Ser Thr Pro Gly Thr Ser Thr Val Asp Leu Gly Thr Ser Gly
    12455               12460               12465

Thr Pro Phe Ser Leu Pro Ser Pro Ala Thr Ala Gly Pro Leu Leu
    12470               12475               12480

Val Leu Phe Thr Leu Asn Phe Thr Ile Thr Asn Leu Lys Tyr Glu
    12485               12490               12495

Glu Asp Met His Arg Pro Gly Ser Arg Lys Phe Asn Thr Thr Glu
    12500               12505               12510

Arg Val Leu Gln Thr Leu Leu Gly Pro Met Phe Lys Asn Thr Ser
    12515               12520               12525

Val Gly Leu Leu Tyr Ser Gly Cys Arg Leu Thr Leu Leu Arg Ser
    12530               12535               12540
```

```
Glu Lys Asp Gly Ala Ala Thr Gly Val Asp Ala Ile Cys Thr His
    12545               12550               12555

Arg Leu Asp Pro Lys Ser Pro Gly Val Asp Arg Glu Gln Leu Tyr
    12560               12565               12570

Trp Glu Leu Ser Gln Leu Thr Asn Gly Ile Lys Glu Leu Gly Pro
    12575               12580               12585

Tyr Thr Leu Asp Arg Asn Ser Leu Tyr Val Asn Gly Phe Thr His
    12590               12595               12600

Trp Ile Pro Val Pro Thr Ser Ser Thr Pro Gly Thr Ser Thr Val
    12605               12610               12615

Asp Leu Gly Ser Gly Thr Pro Ser Ser Leu Pro Ser Pro Thr Thr
    12620               12625               12630

Ala Gly Pro Leu Leu Val Pro Phe Thr Leu Asn Phe Thr Ile Thr
    12635               12640               12645

Asn Leu Lys Tyr Glu Glu Asp Met His Cys Pro Gly Ser Arg Lys
    12650               12655               12660

Phe Asn Thr Thr Glu Arg Val Leu Gln Ser Leu Leu Gly Pro Met
    12665               12670               12675

Phe Lys Asn Thr Ser Val Gly Pro Leu Tyr Ser Gly Cys Arg Leu
    12680               12685               12690

Thr Leu Leu Arg Ser Glu Lys Asp Gly Ala Ala Thr Gly Val Asp
    12695               12700               12705

Ala Ile Cys Thr His Arg Leu Asp Pro Lys Ser Pro Gly Val Asp
    12710               12715               12720

Arg Glu Gln Leu Tyr Trp Glu Leu Ser Gln Leu Thr Asn Gly Ile
    12725               12730               12735

Lys Glu Leu Gly Pro Tyr Thr Leu Asp Arg Asn Ser Leu Tyr Val
    12740               12745               12750

Asn Gly Phe Thr His Gln Thr Ser Ala Pro Asn Thr Ser Thr Pro
    12755               12760               12765

Gly Thr Ser Thr Val Asp Leu Gly Thr Ser Gly Thr Pro Ser Ser
    12770               12775               12780

Leu Pro Ser Pro Thr Ser Ala Gly Pro Leu Leu Val Pro Phe Thr
    12785               12790               12795

Leu Asn Phe Thr Ile Thr Asn Leu Gln Tyr Glu Glu Asp Met His
    12800               12805               12810

His Pro Gly Ser Arg Lys Phe Asn Thr Thr Glu Arg Val Leu Gln
    12815               12820               12825

Gly Leu Leu Gly Pro Met Phe Lys Asn Thr Ser Val Gly Leu Leu
    12830               12835               12840

Tyr Ser Gly Cys Arg Leu Thr Leu Leu Arg Pro Glu Lys Asn Gly
    12845               12850               12855

Ala Ala Thr Gly Met Asp Ala Ile Cys Ser His Arg Leu Asp Pro
    12860               12865               12870

Lys Ser Pro Gly Leu Asn Arg Glu Gln Leu Tyr Trp Glu Leu Ser
    12875               12880               12885

Gln Leu Thr His Gly Ile Lys Glu Leu Gly Pro Tyr Thr Leu Asp
    12890               12895               12900

Arg Asn Ser Leu Tyr Val Asn Gly Phe Thr His Arg Ser Ser Val
    12905               12910               12915

Ala Pro Thr Ser Thr Pro Gly Thr Ser Thr Val Asp Leu Gly Thr
    12920               12925               12930

Ser Gly Thr Pro Ser Ser Leu Pro Ser Pro Thr Thr Ala Val Pro
```

```
    12935               12940               12945

Leu Leu Val Pro Phe Thr Leu Asn Phe Thr Ile Thr Asn Leu Gln
    12950               12955               12960

Tyr Gly Glu Asp Met Arg His Pro Gly Ser Arg Lys Phe Asn Thr
    12965               12970               12975

Thr Glu Arg Val Leu Gln Gly Leu Leu Gly Pro Leu Phe Lys Asn
    12980               12985               12990

Ser Ser Val Gly Pro Leu Tyr Ser Gly Cys Arg Leu Ile Ser Leu
    12995               13000               13005

Arg Ser Glu Lys Asp Gly Ala Ala Thr Gly Val Asp Ala Ile Cys
    13010               13015               13020

Thr His His Leu Asn Pro Gln Ser Pro Gly Leu Asp Arg Glu Gln
    13025               13030               13035

Leu Tyr Trp Gln Leu Ser Gln Met Thr Asn Gly Ile Lys Glu Leu
    13040               13045               13050

Gly Pro Tyr Thr Leu Asp Arg Asn Ser Leu Tyr Val Asn Gly Phe
    13055               13060               13065

Thr His Arg Ser Ser Gly Leu Thr Thr Ser Thr Pro Trp Thr Ser
    13070               13075               13080

Thr Val Asp Leu Gly Thr Ser Gly Thr Pro Ser Pro Val Pro Ser
    13085               13090               13095

Pro Thr Thr Thr Gly Pro Leu Leu Val Pro Phe Thr Leu Asn Phe
    13100               13105               13110

Thr Ile Thr Asn Leu Gln Tyr Glu Glu Asn Met Gly His Pro Gly
    13115               13120               13125

Ser Arg Lys Phe Asn Ile Thr Glu Ser Val Leu Gln Gly Leu Leu
    13130               13135               13140

Lys Pro Leu Phe Lys Ser Thr Ser Val Gly Pro Leu Tyr Ser Gly
    13145               13150               13155

Cys Arg Leu Thr Leu Leu Arg Pro Glu Lys Asp Gly Val Ala Thr
    13160               13165               13170

Arg Val Asp Ala Ile Cys Thr His Arg Pro Asp Pro Lys Ile Pro
    13175               13180               13185

Gly Leu Asp Arg Gln Gln Leu Tyr Trp Glu Leu Ser Gln Leu Thr
    13190               13195               13200

His Ser Ile Thr Glu Leu Gly Pro Tyr Thr Leu Asp Arg Asp Ser
    13205               13210               13215

Leu Tyr Val Asn Gly Phe Thr Gln Arg Ser Ser Val Pro Thr Thr
    13220               13225               13230

Ser Thr Pro Gly Thr Phe Thr Val Gln Pro Glu Thr Ser Glu Thr
    13235               13240               13245

Pro Ser Ser Leu Pro Gly Pro Thr Ala Thr Gly Pro Val Leu Leu
    13250               13255               13260

Pro Phe Thr Leu Asn Phe Thr Ile Thr Asn Leu Gln Tyr Glu Glu
    13265               13270               13275

Asp Met Arg Arg Pro Gly Ser Arg Lys Phe Asn Thr Thr Glu Arg
    13280               13285               13290

Val Leu Gln Gly Leu Leu Met Pro Leu Phe Lys Asn Thr Ser Val
    13295               13300               13305

Ser Ser Leu Tyr Ser Gly Cys Arg Leu Thr Leu Leu Arg Pro Glu
    13310               13315               13320

Lys Asp Gly Ala Ala Thr Arg Val Asp Ala Val Cys Thr His Arg
    13325               13330               13335
```

```
Pro Asp   Pro Lys Ser Pro Gly   Leu Asp Arg Glu Arg   Leu Tyr Trp
    13340                 13345                 13350

Lys Leu   Ser Gln Leu Thr His   Gly Ile Thr Glu Leu   Gly Pro Tyr
    13355                 13360                 13365

Thr Leu   Asp Arg His Ser Leu   Tyr Val Asn Gly Phe   Thr His Gln
    13370                 13375                 13380

Ser Ser   Met Thr Thr Thr Arg   Thr Pro Asp Thr Ser   Thr Met His
    13385                 13390                 13395

Leu Ala   Thr Ser Arg Thr Pro   Ala Ser Leu Ser Gly   Pro Met Thr
    13400                 13405                 13410

Ala Ser   Pro Leu Leu Val Leu   Phe Thr Ile Asn Phe   Thr Ile Thr
    13415                 13420                 13425

Asn Leu   Arg Tyr Glu Glu Asn   Met His His Pro Gly   Ser Arg Lys
    13430                 13435                 13440

Phe Asn   Thr Thr Glu Arg Val   Leu Gln Gly Leu Leu   Arg Pro Val
    13445                 13450                 13455

Phe Lys   Asn Thr Ser Val Gly   Pro Leu Tyr Ser Gly   Cys Arg Leu
    13460                 13465                 13470

Thr Leu   Leu Arg Pro Lys Lys   Asp Gly Ala Ala Thr   Lys Val Asp
    13475                 13480                 13485

Ala Ile   Cys Thr Tyr Arg Pro   Asp Pro Lys Ser Pro   Gly Leu Asp
    13490                 13495                 13500

Arg Glu   Gln Leu Tyr Trp Glu   Leu Ser Gln Leu Thr   His Ser Ile
    13505                 13510                 13515

Thr Glu   Leu Gly Pro Tyr Thr   Leu Asp Arg Asp Ser   Leu Tyr Val
    13520                 13525                 13530

Asn Gly   Phe Thr Gln Arg Ser   Ser Val Pro Thr Thr   Ser Ile Pro
    13535                 13540                 13545

Gly Thr   Pro Thr Val Asp Leu   Gly Thr Ser Gly Thr   Pro Val Ser
    13550                 13555                 13560

Lys Pro   Gly Pro Ser Ala Ala   Ser Pro Leu Leu Val   Leu Phe Thr
    13565                 13570                 13575

Leu Asn   Phe Thr Ile Thr Asn   Leu Arg Tyr Glu Glu   Asn Met Gln
    13580                 13585                 13590

His Pro   Gly Ser Arg Lys Phe   Asn Thr Thr Glu Arg   Val Leu Gln
    13595                 13600                 13605

Gly Leu   Leu Arg Ser Leu Phe   Lys Ser Thr Ser Val   Gly Pro Leu
    13610                 13615                 13620

Tyr Ser   Gly Cys Arg Leu Thr   Leu Leu Arg Pro Glu   Lys Asp Gly
    13625                 13630                 13635

Thr Ala   Thr Gly Val Asp Ala   Ile Cys Thr His His   Pro Asp Pro
    13640                 13645                 13650

Lys Ser   Pro Arg Leu Asp Arg   Glu Gln Leu Tyr Trp   Glu Leu Ser
    13655                 13660                 13665

Gln Leu   Thr His Asn Ile Thr   Glu Leu Gly Pro Tyr   Ala Leu Asp
    13670                 13675                 13680

Asn Asp   Ser Leu Phe Val Asn   Gly Phe Thr His Arg   Ser Ser Val
    13685                 13690                 13695

Ser Thr   Thr Ser Thr Pro Gly   Thr Pro Thr Val Tyr   Leu Gly Ala
    13700                 13705                 13710

Ser Lys   Thr Pro Ala Ser Ile   Phe Gly Pro Ser Ala   Ala Ser His
    13715                 13720                 13725
```

```
Leu Leu   Ile Leu Phe Thr Leu   Asn Phe Thr Ile Thr   Asn Leu Arg
    13730                 13735                 13740

Tyr Glu   Glu Asn Met Trp Pro   Gly Ser Arg Lys Phe   Asn Thr Thr
    13745                 13750                 13755

Glu Arg   Val Leu Gln Gly Leu   Leu Arg Pro Leu Phe   Lys Asn Thr
    13760                 13765                 13770

Ser Val   Gly Pro Leu Tyr Ser   Gly Cys Arg Leu Thr   Leu Leu Arg
    13775                 13780                 13785

Pro Glu   Lys Asp Gly Glu Ala   Thr Gly Val Asp Ala   Ile Cys Thr
    13790                 13795                 13800

His Arg   Pro Asp Pro Thr Gly   Pro Gly Leu Asp Arg   Glu Gln Leu
    13805                 13810                 13815

Tyr Leu   Glu Leu Ser Gln Leu   Thr His Ser Ile Thr   Glu Leu Gly
    13820                 13825                 13830

Pro Tyr   Thr Leu Asp Arg Asp   Ser Leu Tyr Val Asn   Gly Phe Thr
    13835                 13840                 13845

His Arg   Ser Ser Val Pro Thr   Thr Ser Thr Gly Val   Val Ser Glu
    13850                 13855                 13860

Glu Pro   Phe Thr Leu Asn Phe   Thr Ile Asn Asn Leu   Arg Tyr Met
    13865                 13870                 13875

Ala Asp   Met Gly Gln Pro Gly   Ser Leu Lys Phe Asn   Ile Thr Asp
    13880                 13885                 13890

Asn Val   Met Gln His Leu Leu   Ser Pro Leu Phe Gln   Arg Ser Ser
    13895                 13900                 13905

Leu Gly   Ala Arg Tyr Thr Gly   Cys Arg Val Ile Ala   Leu Arg Ser
    13910                 13915                 13920

Val Lys   Asn Gly Ala Glu Thr   Arg Val Asp Leu Leu   Cys Thr Tyr
    13925                 13930                 13935

Leu Gln   Pro Leu Ser Gly Pro   Gly Leu Pro Ile Lys   Gln Val Phe
    13940                 13945                 13950

His Glu   Leu Ser Gln Gln Thr   His Gly Ile Thr Arg   Leu Gly Pro
    13955                 13960                 13965

Tyr Ser   Leu Asp Lys Asp Ser   Leu Tyr Leu Asn Gly   Tyr Asn Glu
    13970                 13975                 13980

Pro Gly   Pro Asp Glu Pro Pro   Thr Thr Pro Lys Pro   Ala Thr Thr
    13985                 13990                 13995

Phe Leu   Pro Pro Leu Ser Glu   Ala Thr Thr Ala Met   Gly Tyr His
    14000                 14005                 14010

Leu Lys   Thr Leu Thr Leu Asn   Phe Thr Ile Ser Asn   Leu Gln Tyr
    14015                 14020                 14025

Ser Pro   Asp Met Gly Lys Gly   Ser Ala Thr Phe Asn   Ser Thr Glu
    14030                 14035                 14040

Gly Val   Leu Gln His Leu Leu   Arg Pro Leu Phe Gln   Lys Ser Ser
    14045                 14050                 14055

Met Gly   Pro Phe Tyr Leu Gly   Cys Gln Leu Ile Ser   Leu Arg Pro
    14060                 14065                 14070

Glu Lys   Asp Gly Ala Ala Thr   Gly Val Asp Thr Thr   Cys Thr Tyr
    14075                 14080                 14085

His Pro   Asp Pro Val Gly Pro   Gly Leu Asp Ile Gln   Gln Leu Tyr
    14090                 14095                 14100

Trp Glu   Leu Ser Gln Leu Thr   His Gly Val Thr Gln   Leu Gly Phe
    14105                 14110                 14115

Tyr Val   Leu Asp Arg Asp Ser   Leu Phe Ile Asn Gly   Tyr Ala Pro
```

14120 14125 14130

Gln Asn Leu Ser Ile Arg Gly Glu Tyr Gln Ile Asn Phe His Ile
14135 14140 14145

Val Asn Trp Asn Leu Ser Asn Pro Asp Pro Thr Ser Ser Glu Tyr
14150 14155 14160

Ile Thr Leu Leu Arg Asp Ile Gln Asp Lys Val Thr Thr Leu Tyr
14165 14170 14175

Lys Gly Ser Gln Leu His Asp Thr Phe Arg Phe Cys Leu Val Thr
14180 14185 14190

Asn Leu Thr Met Asp Ser Val Leu Val Thr Val Lys Ala Leu Phe
14195 14200 14205

Ser Ser Asn Leu Asp Pro Ser Leu Val Glu Gln Val Phe Leu Asp
14210 14215 14220

Lys Thr Leu Asn Ala Ser Phe His Trp Leu Gly Ser Thr Tyr Gln
14225 14230 14235

Leu Val Asp Ile His Val Thr Glu Met Glu Ser Ser Val Tyr Gln
14240 14245 14250

Pro Thr Ser Ser Ser Ser Thr Gln His Phe Tyr Leu Asn Phe Thr
14255 14260 14265

Ile Thr Asn Leu Pro Tyr Ser Gln Asp Lys Ala Gln Pro Gly Thr
14270 14275 14280

Thr Asn Tyr Gln Arg Asn Lys Arg Asn Ile Glu Asp Ala Leu Asn
14285 14290 14295

Gln Leu Phe Arg Asn Ser Ser Ile Lys Ser Tyr Phe Ser Asp Cys
14300 14305 14310

Gln Val Ser Thr Phe Arg Ser Val Pro Asn Arg His His Thr Gly
14315 14320 14325

Val Asp Ser Leu Cys Asn Phe Ser Pro Leu Ala Arg Arg Val Asp
14330 14335 14340

Arg Val Ala Ile Tyr Glu Glu Phe Leu Arg Met Thr Arg Asn Gly
14345 14350 14355

Thr Gln Leu Gln Asn Phe Thr Leu Asp Arg Ser Ser Val Leu Val
14360 14365 14370

Asp Gly Tyr Ser Pro Asn Arg Asn Glu Pro Leu Thr Gly Asn Ser
14375 14380 14385

Asp Leu Pro Phe Trp Ala Val Ile Leu Ile Gly Leu Ala Gly Leu
14390 14395 14400

Leu Gly Val Ile Thr Cys Leu Ile Cys Gly Val Leu Val Thr Thr
14405 14410 14415

Arg Arg Arg Lys Lys Glu Gly Glu Tyr Asn Val Gln Gln Gln Cys
14420 14425 14430

Pro Gly Tyr Tyr Gln Ser His Leu Asp Leu Glu Asp Leu Gln
14435 14440 14445

<210> SEQ ID NO 151
<211> LENGTH: 114
<212> TYPE: PRT
<213> ORGANISM: Artificial Sequence
<220> FEATURE:
<223> OTHER INFORMATION: MUC16c114-N1

<400> SEQUENCE: 151

Ala Phe Ser Pro Leu Ala Arg Arg Val Asp Arg Val Ala Ile Tyr Glu
1 5 10 15

Glu Phe Leu Arg Met Thr Arg Asn Gly Thr Gln Leu Gln Asn Phe Thr 20 25 30

Leu Asp Arg Ser Ser Val Leu Val Asp Gly Tyr Ser Pro Asn Arg Asn
35 40 45

Glu Pro Leu Thr Gly Asn Ser Asp Leu Pro Phe Trp Ala Val Ile Leu
50 55 60

Ile Gly Leu Ala Gly Leu Leu Gly Leu Ile Thr Cys Leu Ile Cys Gly
65 70 75 80

Val Leu Val Thr Thr Arg Arg Arg Lys Lys Glu Gly Glu Tyr Asn Val
85 90 95

Gln Gln Gln Cys Pro Gly Tyr Tyr Gln Ser His Leu Asp Leu Glu Asp
100 105 110

Leu Gln

<210> SEQ ID NO 152
<211> LENGTH: 114
<212> TYPE: PRT
<213> ORGANISM: Artificial Sequence
<220> FEATURE:
<223> OTHER INFORMATION: MUC16c114-N2

<400> SEQUENCE: 152

Asn Phe Ser Pro Leu Ala Arg Arg Val Asp Arg Val Ala Ile Tyr Glu
1 5 10 15

Glu Phe Leu Arg Met Thr Arg Ala Gly Thr Gln Leu Gln Asn Phe Thr
20 25 30

Leu Asp Arg Ser Ser Val Leu Val Asp Gly Tyr Ser Pro Asn Arg Asn
35 40 45

Glu Pro Leu Thr Gly Asn Ser Asp Leu Pro Phe Trp Ala Val Ile Leu
50 55 60

Ile Gly Leu Ala Gly Leu Leu Gly Leu Ile Thr Cys Leu Ile Cys Gly
65 70 75 80

Val Leu Val Thr Thr Arg Arg Arg Lys Lys Glu Gly Glu Tyr Asn Val
85 90 95

Gln Gln Gln Cys Pro Gly Tyr Tyr Gln Ser His Leu Asp Leu Glu Asp
100 105 110

Leu Gln

<210> SEQ ID NO 153
<211> LENGTH: 114
<212> TYPE: PRT
<213> ORGANISM: Artificial Sequence
<220> FEATURE:
<223> OTHER INFORMATION: MUC16c114-N12

<400> SEQUENCE: 153

Ala Phe Ser Pro Leu Ala Arg Arg Val Asp Arg Val Ala Ile Tyr Glu
1 5 10 15

Glu Phe Leu Arg Met Thr Arg Ala Gly Thr Gln Leu Gln Asn Phe Thr
20 25 30

Leu Asp Arg Ser Ser Val Leu Val Asp Gly Tyr Ser Pro Asn Arg Asn
35 40 45

Glu Pro Leu Thr Gly Asn Ser Asp Leu Pro Phe Trp Ala Val Ile Leu
50 55 60

Ile Gly Leu Ala Gly Leu Leu Gly Leu Ile Thr Cys Leu Ile Cys Gly
65 70 75 80

Val Leu Val Thr Thr Arg Arg Arg Lys Lys Glu Gly Glu Tyr Asn Val
85 90 95

Gln Gln Gln Cys Pro Gly Tyr Tyr Gln Ser His Leu Asp Leu Glu Asp
100 105 110

Leu Gln

<210> SEQ ID NO 154
<211> LENGTH: 114
<212> TYPE: PRT
<213> ORGANISM: Artificial Sequence
<220> FEATURE:
<223> OTHER INFORMATION: MUC16c114-N123

<400> SEQUENCE: 154

Ala Phe Ser Pro Leu Ala Arg Arg Val Asp Arg Val Ala Ile Tyr Glu
1 5 10 15

Glu Phe Leu Arg Met Thr Arg Ala Gly Thr Gln Leu Gln Ala Phe Thr
20 25 30

Leu Asp Arg Ser Ser Val Leu Val Asp Gly Tyr Ser Pro Asn Arg Asn
35 40 45

Glu Pro Leu Thr Gly Asn Ser Asp Leu Pro Phe Trp Ala Val Ile Leu
50 55 60

Ile Gly Leu Ala Gly Leu Leu Gly Leu Ile Thr Cys Leu Ile Cys Gly
65 70 75 80

Val Leu Val Thr Thr Arg Arg Arg Lys Lys Glu Gly Glu Tyr Asn Val
85 90 95

Gln Gln Gln Cys Pro Gly Tyr Tyr Gln Ser His Leu Asp Leu Glu Asp
100 105 110

Leu Gln

<210> SEQ ID NO 155
<211> LENGTH: 6
<212> TYPE: PRT
<213> ORGANISM: Artificial Sequence
<220> FEATURE:
<223> OTHER INFORMATION: MUC16c344 N-term of first tandem repeat

<400> SEQUENCE: 155

Trp Glu Leu Ser Gln Leu
1 5

<210> SEQ ID NO 156
<211> LENGTH: 7
<212> TYPE: PRT
<213> ORGANISM: Artificial Sequence
<220> FEATURE:
<223> OTHER INFORMATION: MUC16c344 C-term of first tandem repeat

<400> SEQUENCE: 156

Thr Gly Val Asp Ser Leu Cys
1 5

<210> SEQ ID NO 157
<211> LENGTH: 7
<212> TYPE: PRT
<213> ORGANISM: Artificial Sequence
<220> FEATURE:
<223> OTHER INFORMATION: MUC16c344 N-term of ectodomain

<400> SEQUENCE: 157

Asn Phe Ser Pro Leu Ala Arg
1 5

<210> SEQ ID NO 158
<211> LENGTH: 7
<212> TYPE: PRT
<213> ORGANISM: Artificial Sequence
<220> FEATURE:
<223> OTHER INFORMATION: MUC16c344 C-term of ectodomain

<400> SEQUENCE: 158

Thr Gly Asn Ser Asp Leu Pro
1               5

<210> SEQ ID NO 159
<211> LENGTH: 25
<212> TYPE: PRT
<213> ORGANISM: Artificial Sequence
<220> FEATURE:
<223> OTHER INFORMATION: Transmembrane

<400> SEQUENCE: 159

Phe Trp Ala Val Ile Leu Ile Gly Leu Ala Gly Leu Leu Gly Leu Ile
1               5                   10                  15

Thr Cys Leu Ile Cys Gly Val Leu Val
            20                  25

<210> SEQ ID NO 160
<211> LENGTH: 31
<212> TYPE: PRT
<213> ORGANISM: Artificial Sequence
<220> FEATURE:
<223> OTHER INFORMATION: Cytoplasmic tail

<400> SEQUENCE: 160

Thr Thr Arg Arg Arg Lys Lys Glu Gly Glu Tyr Asn Val Gln Gln Gln
1               5                   10                  15

Cys Pro Gly Tyr Tyr Gln Ser His Leu Asp Leu Glu Asp Leu Gln
            20                  25                  30

<210> SEQ ID NO 161
<211> LENGTH: 58
<212> TYPE: PRT
<213> ORGANISM: Artificial Sequence
<220> FEATURE:
<223> OTHER INFORMATION: MUC16c114 ectodomain

<400> SEQUENCE: 161

Asn Phe Ser Pro Leu Ala Arg Arg Val Asp Arg Val Ala Ile Tyr Glu
1               5                   10                  15

Glu Phe Leu Arg Met Thr Arg Asn Gly Thr Gln Leu Gln Asn Phe Thr
            20                  25                  30

Leu Asp Arg Ser Ser Val Leu Val Asp Gly Tyr Ser Pro Asn Arg Asn
        35                  40                  45

Glu Pro Leu Thr Gly Asn Ser Asp Leu Pro
    50                  55

<210> SEQ ID NO 162
<211> LENGTH: 24
<212> TYPE: PRT
<213> ORGANISM: Artificial Sequence
<220> FEATURE:
<223> OTHER INFORMATION: MUC16c80 ectodomain

<400> SEQUENCE: 162

Asn Phe Ser Pro Leu Ala Arg Arg Val Asp Arg Val Ala Ile Tyr Glu
1               5                   10                  15

```
Glu Phe Leu Arg Met Asp Leu Pro
            20


<210> SEQ ID NO 163
<211> LENGTH: 58
<212> TYPE: PRT
<213> ORGANISM: Artificial Sequence
<220> FEATURE:
<223> OTHER INFORMATION: MUC16c86 ectodomain

<400> SEQUENCE: 163

Asn Phe Ser Pro Leu Ala Arg Arg Val Asp Arg Val Ala Ile Tyr Glu
1               5                   10                  15

Glu Phe Leu Arg Met Thr Arg Asn Gly Thr Gln Leu Gln Asn Phe Thr
            20                  25                  30

Leu Asp Arg Ser Ser Val Leu Val Asp Gly Tyr Ser Pro Asn Arg Asn
        35                  40                  45

Glu Pro Leu Thr Gly Asn Ser Asp Leu Pro
    50                  55


<210> SEQ ID NO 164
<211> LENGTH: 22
<212> TYPE: PRT
<213> ORGANISM: Artificial Sequence
<220> FEATURE:
<223> OTHER INFORMATION: MUC16c86 transmembrane

<400> SEQUENCE: 164

Phe Trp Ala Val Ile Leu Ile Gly Leu Ala Gly Leu Leu Gly Leu Ile
1               5                   10                  15

Thr Cys Leu Ile Cys Gly
            20


<210> SEQ ID NO 165
<211> LENGTH: 6
<212> TYPE: PRT
<213> ORGANISM: Artificial Sequence
<220> FEATURE:
<223> OTHER INFORMATION: MUC16c86 cytoplasmic

<400> SEQUENCE: 165

Asp Leu Glu Asp Leu Gln
1               5


<210> SEQ ID NO 166
<211> LENGTH: 58
<212> TYPE: PRT
<213> ORGANISM: Artificial Sequence
<220> FEATURE:
<223> OTHER INFORMATION: MUC16 3(N to A)c114 ectodomain

<400> SEQUENCE: 166

Ala Phe Ser Pro Leu Ala Arg Arg Val Asp Arg Val Ala Ile Tyr Glu
1               5                   10                  15

Glu Phe Leu Arg Met Thr Arg Ala Gly Thr Gln Leu Gln Ala Phe Thr
            20                  25                  30

Leu Asp Arg Ser Ser Val Leu Val Asp Gly Tyr Ser Pro Asn Arg Asn
        35                  40                  45

Glu Pro Leu Thr Gly Asn Ser Asp Leu Pro
    50                  55


<210> SEQ ID NO 167
<211> LENGTH: 128
```

<212> TYPE: PRT
<213> ORGANISM: Artificial Sequence
<220> FEATURE:
<223> OTHER INFORMATION: LGALS3 sugar binding domain

<400> SEQUENCE: 167

```
Pro Tyr Asn Leu Pro Leu Pro Gly Gly Val Val Pro Arg Met Leu Ile
1               5                   10                  15

Thr Ile Leu Gly Thr Val Lys Pro Asn Ala Asn Arg Ile Ala Leu Asp
            20                  25                  30

Phe Gln Arg Gly Asn Asp Val Ala Phe His Phe Asn Pro Arg Phe Asn
        35                  40                  45

Glu Asn Asn Arg Arg Val Ile Val Cys Asn Thr Lys Leu Asp Asn Asn
    50                  55                  60

Trp Gly Arg Glu Glu Arg Gln Ser Val Phe Pro Phe Glu Ser Gly Lys
65                  70                  75                  80

Pro Phe Lys Ile Gln Val Leu Val Glu Pro Asp His Phe Lys Val Ala
                85                  90                  95

Val Asn Asp Ala His Leu Leu Gln Tyr Asn His Arg Val Lys Lys Leu
            100                 105                 110

Asn Glu Ile Ser Lys Leu Gly Ile Ser Gly Asp Ile Asp Leu Thr Ser
        115                 120                 125
```

<210> SEQ ID NO 168
<211> LENGTH: 19
<212> TYPE: PRT
<213> ORGANISM: Artificial Sequence
<220> FEATURE:
<223> OTHER INFORMATION: MUC16 nonglycosylated peptide 2

<400> SEQUENCE: 168

```
Cys Thr Leu Asp Arg Ser Ser Val Leu Val Asp Gly Tyr Ser Pro Asn
1               5                   10                  15

Arg Asn Glu
```

<210> SEQ ID NO 169
<211> LENGTH: 18
<212> TYPE: PRT
<213> ORGANISM: Artificial Sequence
<220> FEATURE:
<223> OTHER INFORMATION: MUC16 unrelated peptide 18mer

<400> SEQUENCE: 169

```
Gly Ala Val Pro Arg Ser Ala Thr Ile Asn Val Ser Arg Ile Ala Thr
1               5                   10                  15

Gly Pro
```

<210> SEQ ID NO 170
<211> LENGTH: 17
<212> TYPE: PRT
<213> ORGANISM: Artificial Sequence
<220> FEATURE:
<223> OTHER INFORMATION: 18mer (no C)

<400> SEQUENCE: 170

```
Thr Arg Asn Gly Thr Gln Leu Gln Asn Phe Thr Leu Asp Arg Ser Ser
1               5                   10                  15

Val
```

<210> SEQ ID NO 171
<211> LENGTH: 14

<212> TYPE: PRT
<213> ORGANISM: Artificial Sequence
<220> FEATURE:
<223> OTHER INFORMATION: 15mer (no C)

<400> SEQUENCE: 171

Gly Thr Gln Leu Gln Asn Phe Thr Leu Asp Arg Ser Ser Val
1               5                   10

<210> SEQ ID NO 172
<211> LENGTH: 114
<212> TYPE: PRT
<213> ORGANISM: Artificial Sequence
<220> FEATURE:
<223> OTHER INFORMATION: MUC16c114-N23

<400> SEQUENCE: 172

Asn Phe Ser Pro Leu Ala Arg Arg Val Asp Arg Val Ala Ile Tyr Glu
1               5                   10                  15

Glu Phe Leu Arg Met Thr Arg Ala Gly Thr Gln Leu Gln Ala Phe Thr
            20                  25                  30

Leu Asp Arg Ser Ser Val Leu Val Asp Gly Tyr Ser Pro Asn Arg Asn
        35                  40                  45

Glu Pro Leu Thr Gly Asn Ser Asp Leu Pro Phe Trp Ala Val Ile Leu
    50                  55                  60

Ile Gly Leu Ala Gly Leu Leu Gly Leu Ile Thr Cys Leu Ile Cys Gly
65                  70                  75                  80

Val Leu Val Thr Thr Arg Arg Arg Lys Lys Glu Gly Glu Tyr Asn Val
                85                  90                  95

Gln Gln Gln Cys Pro Gly Tyr Tyr Gln Ser His Leu Asp Leu Glu Asp
            100                 105                 110

Leu Gln

<210> SEQ ID NO 173
<211> LENGTH: 344
<212> TYPE: PRT
<213> ORGANISM: Artificial Sequence
<220> FEATURE:
<223> OTHER INFORMATION: N24 mut c344

<400> SEQUENCE: 173

Trp Glu Leu Ser Gln Leu Thr His Gly Val Thr Gln Leu Gly Phe Tyr
1               5                   10                  15

Val Leu Asp Arg Asp Ser Leu Phe Ile Asn Gly Tyr Ala Pro Gln Asn
            20                  25                  30

Leu Ser Ile Arg Gly Glu Tyr Gln Ile Asn Phe His Ile Val Asn Gln
        35                  40                  45

Asn Leu Ser Asn Pro Asp Pro Thr Ser Ser Glu Tyr Ile Thr Leu Leu
    50                  55                  60

Arg Asp Ile Gln Asp Lys Val Thr Thr Leu Tyr Lys Gly Ser Gln Leu
65                  70                  75                  80

His Asp Thr Phe Arg Phe Cys Leu Val Thr Asn Leu Thr Met Asp Ser
                85                  90                  95

Val Leu Val Thr Val Lys Ala Leu Phe Ser Ser Asn Leu Asp Pro Ser
            100                 105                 110

Leu Val Glu Gln Val Phe Leu Asp Lys Thr Leu Asn Ala Ser Phe His
        115                 120                 125

Gln Leu Gly Ser Thr Tyr Gln Leu Val Asp Ile His Val Thr Glu Met
    130                 135                 140

Glu Ser Ser Val Tyr Gln Pro Thr Ser Ser Ser Ser Thr Gln His Phe
145 150 155 160

Tyr Leu Asn Phe Thr Ile Thr Asn Leu Pro Tyr Ser Gln Asp Lys Ala
165 170 175

Gln Pro Gly Thr Thr Asn Tyr Gln Arg Asn Lys Arg Asn Ile Glu Asp
180 185 190

Ala Leu Asn Gln Leu Phe Arg Asn Ser Ser Ile Lys Ser Tyr Phe Ser
195 200 205

Asp Cys Gln Val Ser Thr Phe Arg Ser Val Pro Asn Arg His His Thr
210 215 220

Gly Val Asp Ser Leu Cys Asn Phe Ser Pro Leu Ala Arg Arg Val Asp
225 230 235 240

Arg Val Ala Ile Tyr Glu Glu Phe Leu Arg Met Thr Arg Ala Gly Thr
245 250 255

Gln Leu Gln Asn Phe Thr Leu Asp Arg Ser Ser Val Leu Val Asp Gly
260 265 270

Tyr Ser Pro Asn Arg Asn Glu Pro Leu Thr Gly Asn Ser Asp Leu Pro
275 280 285

Phe Trp Ala Val Ile Leu Ile Gly Leu Ala Gly Leu Leu Gly Leu Ile
290 295 300

Thr Cys Leu Ile Cys Gly Val Leu Val Thr Thr Arg Arg Arg Lys Lys
305 310 315 320

Glu Gly Glu Tyr Asn Val Gln Gln Gln Cys Pro Gly Tyr Tyr Gln Ser
325 330 335

His Leu Asp Leu Glu Asp Leu Gln
340

<210> SEQ ID NO 174
<211> LENGTH: 344
<212> TYPE: PRT
<213> ORGANISM: Artificial Sequence
<220> FEATURE:
<223> OTHER INFORMATION: N30 mut c344

<400> SEQUENCE: 174

Trp Glu Leu Ser Gln Leu Thr His Gly Val Thr Gln Leu Gly Phe Tyr
1 5 10 15

Val Leu Asp Arg Asp Ser Leu Phe Ile Asn Gly Tyr Ala Pro Gln Asn
20 25 30

Leu Ser Ile Arg Gly Glu Tyr Gln Ile Asn Phe His Ile Val Asn Gln
35 40 45

Asn Leu Ser Asn Pro Asp Pro Thr Ser Ser Glu Tyr Ile Thr Leu Leu
50 55 60

Arg Asp Ile Gln Asp Lys Val Thr Thr Leu Tyr Lys Gly Ser Gln Leu
65 70 75 80

His Asp Thr Phe Arg Phe Cys Leu Val Thr Asn Leu Thr Met Asp Ser
85 90 95

Val Leu Val Thr Val Lys Ala Leu Phe Ser Ser Asn Leu Asp Pro Ser
100 105 110

Leu Val Glu Gln Val Phe Leu Asp Lys Thr Leu Asn Ala Ser Phe His
115 120 125

Gln Leu Gly Ser Thr Tyr Gln Leu Val Asp Ile His Val Thr Glu Met
130 135 140

Glu Ser Ser Val Tyr Gln Pro Thr Ser Ser Ser Ser Thr Gln His Phe
145 150 155 160

```
Tyr Leu Asn Phe Thr Ile Thr Asn Leu Pro Tyr Ser Gln Asp Lys Ala
                165                 170                 175

Gln Pro Gly Thr Thr Asn Tyr Gln Arg Asn Lys Arg Asn Ile Glu Asp
            180                 185                 190

Ala Leu Asn Gln Leu Phe Arg Asn Ser Ser Ile Lys Ser Tyr Phe Ser
        195                 200                 205

Asp Cys Gln Val Ser Thr Phe Arg Ser Val Pro Asn Arg His His Thr
    210                 215                 220

Gly Val Asp Ser Leu Cys Asn Phe Ser Pro Leu Ala Arg Arg Val Asp
225                 230                 235                 240

Arg Val Ala Ile Tyr Glu Glu Phe Leu Arg Met Thr Arg Asn Gly Thr
                245                 250                 255

Gln Leu Gln Ala Phe Thr Leu Asp Arg Ser Ser Val Leu Val Asp Gly
            260                 265                 270

Tyr Ser Pro Asn Arg Asn Glu Pro Leu Thr Gly Asn Ser Asp Leu Pro
        275                 280                 285

Phe Trp Ala Val Ile Leu Ile Gly Leu Ala Gly Leu Leu Gly Leu Ile
    290                 295                 300

Thr Cys Leu Ile Cys Gly Val Leu Val Thr Thr Arg Arg Arg Lys Lys
305                 310                 315                 320

Glu Gly Glu Tyr Asn Val Gln Gln Gln Cys Pro Gly Tyr Tyr Gln Ser
                325                 330                 335

His Leu Asp Leu Glu Asp Leu Gln
            340


<210> SEQ ID NO 175
<211> LENGTH: 344
<212> TYPE: PRT
<213> ORGANISM: Artificial Sequence
<220> FEATURE:
<223> OTHER INFORMATION: N24-N30 mut c344

<400> SEQUENCE: 175

Trp Glu Leu Ser Gln Leu Thr His Gly Val Thr Gln Leu Gly Phe Tyr
1               5                   10                  15

Val Leu Asp Arg Asp Ser Leu Phe Ile Asn Gly Tyr Ala Pro Gln Asn
            20                  25                  30

Leu Ser Ile Arg Gly Glu Tyr Gln Ile Asn Phe His Ile Val Asn Gln
        35                  40                  45

Asn Leu Ser Asn Pro Asp Pro Thr Ser Ser Glu Tyr Ile Thr Leu Leu
    50                  55                  60

Arg Asp Ile Gln Asp Lys Val Thr Thr Leu Tyr Lys Gly Ser Gln Leu
65                  70                  75                  80

His Asp Thr Phe Arg Phe Cys Leu Val Thr Asn Leu Thr Met Asp Ser
                85                  90                  95

Val Leu Val Thr Val Lys Ala Leu Phe Ser Ser Asn Leu Asp Pro Ser
            100                 105                 110

Leu Val Glu Gln Val Phe Leu Asp Lys Thr Leu Asn Ala Ser Phe His
        115                 120                 125

Gln Leu Gly Ser Thr Tyr Gln Leu Val Asp Ile His Val Thr Glu Met
    130                 135                 140

Glu Ser Ser Val Tyr Gln Pro Thr Ser Ser Ser Ser Thr Gln His Phe
145                 150                 155                 160

Tyr Leu Asn Phe Thr Ile Thr Asn Leu Pro Tyr Ser Gln Asp Lys Ala
                165                 170                 175
```

-continued

```
Gln Pro Gly Thr Thr Asn Tyr Gln Arg Asn Lys Arg Asn Ile Glu Asp
            180                 185                 190

Ala Leu Asn Gln Leu Phe Arg Asn Ser Ser Ile Lys Ser Tyr Phe Ser
        195                 200                 205

Asp Cys Gln Val Ser Thr Phe Arg Ser Val Pro Asn Arg His His Thr
    210                 215                 220

Gly Val Asp Ser Leu Cys Asn Phe Ser Pro Leu Ala Arg Arg Val Asp
225                 230                 235                 240

Arg Val Ala Ile Tyr Glu Glu Phe Leu Arg Met Thr Arg Ala Gly Thr
                245                 250                 255

Gln Leu Gln Ala Phe Thr Leu Asp Arg Ser Ser Val Leu Val Asp Gly
            260                 265                 270

Tyr Ser Pro Asn Arg Asn Glu Pro Leu Thr Gly Asn Ser Asp Leu Pro
        275                 280                 285

Phe Trp Ala Val Ile Leu Ile Gly Leu Ala Gly Leu Leu Gly Leu Ile
    290                 295                 300

Thr Cys Leu Ile Cys Gly Val Leu Val Thr Thr Arg Arg Arg Lys Lys
305                 310                 315                 320

Glu Gly Glu Tyr Asn Val Gln Gln Gln Cys Pro Gly Tyr Tyr Gln Ser
                325                 330                 335

His Leu Asp Leu Glu Asp Leu Gln
            340
```